United States Patent
Holzer et al.

(10) Patent No.: US 10,883,084 B2
(45) Date of Patent: Jan. 5, 2021

(54) PERSONALIZED CELLS, TISSUES, AND ORGANS FOR TRANSPLANTATION FROM A HUMANIZED, BESPOKE, DESIGNATED-PATHOGEN FREE, (NON-HUMAN) DONOR AND METHODS AND PRODUCTS RELATING TO SAME

(71) Applicants: XENOTHERAPEUTICS, INC., Boston, MA (US); XENOTHERAPEUTICS CORPORATION, Enfield, NH (US)

(72) Inventors: Paul W. Holzer, Enfield, NH (US); Jon Adkins, Londonderry, NH (US); Rodney L. Monroy, North Fort Myers, FL (US); Elizabeth J. Chang, Pittsford, NY (US)

(73) Assignees: XENOTHERAPEUTICS, INC., Boston, MA (US); XENOTHERAPEUTICS CORPORATION, Enfield, NH (US)

( * ) Notice: Subject to any disclaimer, the term of this patent is extended or adjusted under 35 U.S.C. 154(b) by 0 days.

(21) Appl. No.: 16/830,213

(22) Filed: Mar. 25, 2020

(65) Prior Publication Data
US 2020/0283737 A1    Sep. 10, 2020

Related U.S. Application Data

(63) Continuation-in-part of application No. 16/593,785, filed on Oct. 4, 2019, now Pat. No. 10,799,614.

(60) Provisional application No. 62/848,272, filed on May 15, 2019, provisional application No. 62/823,455, filed on Mar. 25, 2019, provisional application No. 62/795,527, filed on Jan. 22, 2019, provisional application No. 62/792,282, filed on Jan. 14, 2019, provisional application No. 62/756,977, filed on Nov. 7, 2018, provisional application No. 62/756,955, filed on Nov. 7, 2018, provisional application No. 62/756,925, filed on Nov. 7, 2018, provisional application No. 62/756,993, filed on Nov. 7, 2018, provisional application No. 62/742,188, filed on Oct. 5, 2018, provisional application No. 62/964,397, filed on Jan. 22, 2020, provisional application No. 62/975,611, filed on Feb. 12, 2020.

(51) Int. Cl.
| | |
|---|---|
| *A01K 67/027* | (2006.01) |
| *C12N 5/071* | (2010.01) |
| *A61K 35/12* | (2015.01) |
| *C12N 15/10* | (2006.01) |
| *C12N 15/113* | (2010.01) |
| *C12Q 1/14* | (2006.01) |

(52) U.S. Cl.
CPC ........ *C12N 5/0697* (2013.01); *A01K 67/0278* (2013.01); *A61K 35/12* (2013.01); *C12N 15/102* (2013.01); *C12N 15/113* (2013.01); *C12Q 1/14* (2013.01); *A01K 2207/15* (2013.01); *A01K 2227/108* (2013.01); *A01K 2267/025* (2013.01); *C12N 2310/20* (2017.05); *C12N 2800/80* (2013.01)

(58) Field of Classification Search
None
See application file for complete search history.

(56) References Cited

U.S. PATENT DOCUMENTS

| | | |
|---|---|---|
| 5,964,096 A | 10/1999 | Watson et al. |
| 6,242,482 B1 | 6/2001 | Shorr et al. |
| 6,413,769 B1 | 7/2002 | Gustafsson et al. |
| 6,469,229 B1 | 10/2002 | Sachs et al. |
| 6,521,212 B1 | 2/2003 | Cloutier et al. |
| 6,558,663 B1 | 5/2003 | Seebach et al. |
| 6,610,288 B1 | 8/2003 | Edge et al. |
| 6,756,033 B2 | 6/2004 | Cloutier et al. |
| 6,867,347 B2 | 3/2005 | Patience |
| 7,128,719 B2 | 10/2006 | Rosenberg |
| 7,141,716 B2 | 11/2006 | Sachs et al. |
| 7,547,522 B2 | 6/2009 | Hawley |
| 7,547,816 B2 | 6/2009 | Day et al. |
| 7,794,709 B2 | 9/2010 | Rosenberg |

(Continued)

FOREIGN PATENT DOCUMENTS

| | | |
|---|---|---|
| WO | 98053850 | 12/1998 |
| WO | 2006006167 | 1/2006 |

(Continued)

OTHER PUBLICATIONS

Fishman et al., Xenotransplantation, 2020, 27: e12595, pp. 1-6 (Year: 2020).*

(Continued)

*Primary Examiner* — Scott Long
*Assistant Examiner* — Evelyn Y Pyla
(74) *Attorney, Agent, or Firm* — Rothwell, Figg, Ernst & Manbeck, P.C.

(57) ABSTRACT

A biological system for generating and preserving a repository of personalized, humanized transplantable cells, tissues, and organs for transplantation, wherein the biological system is biologically active and metabolically active, the biological system having genetically reprogrammed cells, tissues, and organs in a non-human animal for transplantation into a human recipient, wherein the non-human animal does not present one or more surface glycan epitopes and specific sequences from the wild-type swine's SLA is replaced with a synthetic nucleotides based on a human captured reference sequence from a human recipient's HLA.

20 Claims, 97 Drawing Sheets
Specification includes a Sequence Listing.

(56) References Cited

U.S. PATENT DOCUMENTS

| | | |
|---|---|---|
| 7,795,493 B2 | 9/2010 | Phelps et al. |
| 7,816,560 B1 | 10/2010 | Zitzmann et al. |
| 8,088,969 B2 | 1/2012 | Elliott et al. |
| 8,106,251 B2 | 1/2012 | Ayares et al. |
| 8,119,124 B2 | 2/2012 | Gorecki et al. |
| 8,540,983 B2 | 9/2013 | Gorecki et al. |
| 8,624,077 B2 | 1/2014 | Rosenberg |
| 9,089,515 B2 | 7/2015 | Zitzmann et al. |
| 9,326,992 B2 | 5/2016 | Kole et al. |
| 9,339,519 B2 | 5/2016 | Ayares |
| 9,420,770 B2 | 8/2016 | Tector, III |
| 9,585,374 B2 | 3/2017 | Wells et al. |
| 9,713,599 B2 | 7/2017 | Wade |
| 9,833,468 B2 | 12/2017 | Kole et al. |
| 9,834,791 B2 | 12/2017 | Zhang et al. |
| 9,883,939 B2 | 2/2018 | Yamada et al. |
| 9,888,673 B2 | 2/2018 | Hering et al. |
| 9,888,674 B2 | 2/2018 | Tector et al. |
| 10,016,463 B2 | 6/2018 | Jeffs |
| 10,071,123 B2 | 9/2018 | Jeffs et al. |
| 10,076,505 B2 | 9/2018 | Wade |
| 10,080,730 B2 | 9/2018 | Jeffs et al. |
| 10,130,737 B2 | 11/2018 | Ayares et al. |
| 10,149,461 B2 | 12/2018 | Ayares et al. |
| 10,278,372 B2 | 5/2019 | Hering et al. |
| 10,300,112 B2 | 5/2019 | Ayares et al. |
| 2001/0046965 A1 | 11/2001 | Ayares |
| 2001/0049827 A1 | 12/2001 | Hunter et al. |
| 2002/0012660 A1 | 1/2002 | Colman |
| 2003/0024002 A1 | 1/2003 | Colman |
| 2003/0053958 A1 | 3/2003 | Cloutier |
| 2003/0109480 A1 | 6/2003 | Corden |
| 2003/0192066 A1 | 10/2003 | Zhang |
| 2004/0208846 A1 | 10/2004 | Zhang |
| 2005/0260176 A1 | 11/2005 | Ayares et al. |
| 2005/0266561 A1 | 12/2005 | Wells et al. |
| 2006/0130157 A1 | 6/2006 | Wells |
| 2006/0147432 A1 | 7/2006 | Moore |
| 2008/0131398 A1 | 6/2008 | Jeffs |
| 2008/0250517 A1 | 10/2008 | Colman |
| 2009/0010910 A1 | 1/2009 | Toren et al. |
| 2009/0049562 A1 | 2/2009 | Koike |
| 2009/0124697 A1 | 5/2009 | Cloutier |
| 2009/0186097 A1 | 7/2009 | Ayares |
| 2010/0077494 A1 | 3/2010 | Wells |
| 2010/0137365 A1 | 6/2010 | Zitmann |
| 2011/0038841 A1 | 2/2011 | Ayares |
| 2011/0184019 A1 | 7/2011 | Zitmann |
| 2012/0090039 A1 | 4/2012 | Ayares |
| 2012/0255047 A1 | 10/2012 | Phelps |
| 2012/0282226 A1 | 11/2012 | Ayares |
| 2013/0024961 A1 | 1/2013 | Burlak |
| 2013/0083042 A1 | 4/2013 | Sagall |
| 2013/0195798 A1 | 8/2013 | Jeffs |
| 2013/0202569 A1 | 8/2013 | Ayares |
| 2014/0017215 A1 | 1/2014 | Ayares |
| 2014/0024698 A1 | 1/2014 | Kole |
| 2014/0115728 A1 | 4/2014 | Tector |
| 2014/0193379 A1 | 7/2014 | Jeffs |
| 2015/0106959 A1 | 4/2015 | Phelps |
| 2015/0135344 A1 | 5/2015 | Tector |
| 2015/0164834 A1 | 6/2015 | Wade |
| 2015/0182664 A1 | 7/2015 | Ayares |
| 2015/0216909 A1 | 8/2015 | Jeffs |
| 2015/0246078 A1 | 9/2015 | Jeffs |
| 2015/0264900 A1 | 9/2015 | Tector |
| 2016/0227750 A1 | 8/2016 | Harada et al. |
| 2016/0278349 A1 | 9/2016 | Ayares |
| 2016/0278350 A1 | 9/2016 | Ayares |
| 2016/0346498 A1 | 12/2016 | Tector |
| 2017/0183685 A1 | 6/2017 | Wells |
| 2017/0216358 A1 | 8/2017 | Gregory et al. |
| 2017/0251646 A1 | 9/2017 | Tector |
| 2017/0311579 A1 | 11/2017 | Tector |
| 2018/0042876 A1 | 2/2018 | Wade |
| 2018/0110807 A1 | 4/2018 | Ilagan |
| 2018/0153146 A1 | 6/2018 | Tector |
| 2018/0184630 A1 | 7/2018 | Tector, III |
| 2018/0228144 A1 | 8/2018 | Bonvillain |
| 2018/0249688 A1 | 9/2018 | Ayares |
| 2018/0332832 A1 | 11/2018 | Phelps et al. |
| 2019/0004063 A1 | 1/2019 | Tector |
| 2019/0008904 A1 | 1/2019 | Jeffs |
| 2019/0111180 A1 | 4/2019 | Ayares |
| 2020/0041512 A1 | 2/2020 | Hantash |

FOREIGN PATENT DOCUMENTS

| | | |
|---|---|---|
| WO | 2016210280 A1 | 12/2016 |
| WO | 2017044864 A1 | 3/2017 |
| WO | 2018195402 A1 | 10/2018 |
| WO | 2019018447 | 1/2019 |

OTHER PUBLICATIONS

Guell et al., Xenotransplantation, 2017; 24: e12366, pp. 1-4 (Year: 2017).*

Carey et al., "Factors affecting HLA expression: A review" International Journal of Immunogenetics. 2019, 14 pgs.

Carey et al., "Frequency of off-targeting in genome edited pigs produced via direct injection of the CRISPR/Cas9 system into developing embryos" BMC Biotechnology. 2019, 8pgs.

Chen et al., "Conserved Nature of the Antigen-Presenting of Bony Fishes Provides Insights into the the Structure of the MHC Class I Molecule System" Journal of Immunology. Oct. 20, 2017, 12 pgs.

Cole et al., "Modification of MHC Anchor Residues Generates Heteroclitic Peptides That Alter TCR Binding and T Cell Recognition" Journal of Immunology. Jul. 16, 2010, 12 pgs.

Cooper et al., "Perspectives on the Optimal Genetically Engineered Pig in 2018 for Initial Clinical Trials of Kidney or Heart Xenotransplantation" Transplantation. Dec. 2018, vol. 102, No. 12, 9 pgs.

Cooper et al., "Justification of specific genetic modifications in pigs for clinical organ xenotransplantation" Xenotransplantation. 2019, 12 pgs.

Guo et al., "Sequencing of the MHC region defines HLA-DQA1 as the major genetic risk for seropositive rheumatoid arthritis in Han Chinese population" Epidemiological Science. Ann Rheum Dis, 2019, vol. 78, 8 pgs.

Henneke et al., "T Cell Receptor—MHC Interactions up Close" Cell, vol. 104, Jan. 12, 2001, 4 pgs.

Iwase et al., "Regulation of Human Platelet Aggregation by Genetically Modified Pig Endothelial Cells and Thrombin Inhibition" Xenotransplantation. Jan. 2014, 21 pgs.

Jo et al., "Introns: The Functional Benefits of Introns in Genomes" Genomics and Informatics. 2015, vol. 13, Issue 4, 7 pgs.

Li et al., "Strict major histocompatibility complex molecule class-specific binding by co-receptors enforces MHC-restricted ab TCR recognition during T lineage subset commitment" Frontiers in Immunology. Nov. 22, 2013, 8 pgs.

Ogawa et al., "Next-generation sequencing identifies contribution of both class I and II HLA genes on susceptibility of multiple sclerosis in Japanese" Journal of Neuroinflammation. 2019, 9 pgs.

Van den Elsen, P.J. "Expression regulation of major histocompatibility complex class I and class II encoding genes" Frontiers in Immunology. Oct. 4, 2011, 9 pgs.

Reche et al., "Sequence Variability Analysis of Human Class I and Class II MHC Molecules: Functional and Structural Correlates of Amino Acid Polymorphisms" Journal of Molecular Biology, vol. 331, Issue 3, Aug. 15, 2003, pp. 623-641.

Renard et al., "Sequence of the pig major histocompatibility region containing the classical class I genes" Immunogenetics, 2001, 11 pgs.

Renard et al., "The genomic sequence and analysis of the swine major histocompatibility complex" Genomics. 1998, vol. 88, 12 pgs.

Sasazuki et al., "Effects of Matching of Class I HLA Alleles on Clinical Outcome after Transplantation of Hematopoietic Stem

(56) References Cited

OTHER PUBLICATIONS

Cells from an Unrelated Donor" The New England Journal of Medicine. Oct. 22, 1998, 17 pgs.
Shen et al., "The Utility of Supertype Clustering in Prediction for Class II MHC-Peptide Binding" Molecules. Nov. 20, 2018, 18 pgs.
Song et al., "Expression and Regulation Profile of Mature MicroRNA in the Pig: Relevance to Xenotransplantation" BioMed Research International. Mar. 21, 2018, 9 pgs.
Southwood et al., "Several Common HLA-DR Types Share Largely Overlapping Peptide Binding Repertoires" Journal of Immunology. 1998, 12 pgs.
Van Chanh Li et al., "Analysis of peptide-SLA binding by establishing immortalized porcine alveolar macrophage cells with di"erent SLA class II haplotypes" Veterinary Research, 2018, 10 pgs.
Whyte "Genetic Modifications of Pigs for Medicine and Agriculture" Molecular Reproduction & Development. 2011, 13 pgs.
Zavala-Ruiz "A Polymorphic Pocket at the P10 Position Contributes to Peptide Binding Specificity in Class II MHC Proteins" Chemistry & Biology. vol. 11, Oct. 2004, 8 pgs.
Gussow et al, "The human beta 2-microglobulin gene. Primary structure and definition of the transcriptional unit." Journal of Immunology. 1987, 8pgs.
Glimcher et al., "Sequences and Factors: A Guide to MHC Class-II Transcription" Annu. Rev. Immunol. 1992, 37 pgs.
Quatrini et al., "Endogenous glucocorticoids control host resistance to viral infection through the tissue-specific regulation of PD-1 expression on NK cells" Nature Immunology, vol. 19, Sep. 2018, 14 pgs.
Hull, "Genollle C,oinposition, Organization, and Expression" Plant Virology. 2014, 1 pg.
Sharp, "Splicing of Messenger RNA Precursors" Science, New Edition. Vo. 235, No. 4790, Feb. 13, 1987, 7 pgs.
Shiina et al., "The HLA genomic loci map: expression, interaction, diversity and disease" Journal of Human Genetics. 2009, vol. 54, 25 pgs.
Castelli et al., "Transcriptional and Posttranscriptional Regulations of the HLA-G Gene" Journal of Immunology Research. 2014, 15 pgs.
Dib et al., "Polymorphic sites preferentially avoid coevolving residues inMHC class I proteins" PLOS Computational Biology. May 21, 2018, 19 pgs.
Artyomov et al., "CD4 and CD8 binding to MHC molecules primarily acts to enhance Lck delivery" PNAS. Sep. 28, 2010, vol. 107, No. 39, 6 pgs.
Ting et al., "Genetic Control of MHC Class II Expression" Cell, vol. 109, Apr. 2002, 13 pgs.
Yamaguchi et al., "Major Histocompatibility Complex (MHC) Genes and Disease Resistance in Fish" Cells. 2019, 31 pgs.
Fisher et al., "Viable pigs after simultaneous inactivation of porcine MHC class I and three xenoreactive antigen genes GGTA1, CMAH and B4GALNT2" Xenotransplantation. 2019, 11 pgs.
Rosales et al., "Systematic pathological component scores for skin-containing vascularized composite allografts" Vascularized Composite Allotransplantation. 2017, 13 pgs.
Joly et al., "The orthology of HLA-E and H2-Qa1 is hidden by their concerted evolution with other MHC class I molecules" Biology Direct. Jan. 31, 2006, 18 pgs.
Reith et al., "Cloning of the Major Histocompatability Complex Class II Promoter Binding Protein Affected in a Hereditary defect in Class II Gene Regulation" Proc. Natl. Acad. Sci. USA. 1989, 5 pgs.
Chen et al., "Distribution Characteristics of Alleles of Classical SLA-I and II Genes and Bioinformatic Analysis of Novel Alleles in Guizhou Miniature Pigs" Pakistan J. Zool. 2014, vol. 46(3), 8 pgs.
Nakamura et al., "Liver Allograft Rejection in Sensitized Recipients Observations in a Clinically Relevant Small Animal Model" American Journal of Pathology. May 1993, vol. 142, No. 5.
Nariai et al., "HLA-VBSeq: accurate HLA typing at full resolution from whole-genome sequencing data" BMC Genomics. 2015, 6 pgs.

Shuurman, "Regulatory aspects of clinical xenotransplantation" International Journal of Surgery. 2015, 10 pgs.
Tector et al., "Rejection of Pig Liver Xenografts in Patients With Liver Failure: Implications for Xenotransplantation" Liver Transplantation, Feb. 2001, vol. 7, No. 2, 8 pgs.
Xie et al., "Fast and accurate HLA typing from short-read next-generation sequence data with xHLA" PNAS. Jul. 25, 2017, vol. 114, No. 30, 6 pgs.
Demetris et al., "Antibody Mediated Rejection of Human Liver Allografts: Transplantation Across ABO Blood Group Barriers" Transplant Proc. Feb. 1989, 8 pgs.
Dilthey et al., "High-Accuracy HLA Type Inference from Whole-Genome Sequencing Data Using Population Reference Graphs" PLOS Computational Biology. Oct. 28, 2016, 16 pgs.
Erlich et al., "Next-generation sequencing for HLA typing of class I loci" BMC Genomics. 2011, 13 pgs.
Furuya et al., "Preformed Lymphocytotoxic Antibodies: The Effects of Class, Titer and Specificity on Liver vs. Heart Allografts" Hepatology. Dec. 1992, 16 pgs.
Mezrich et al., "Histocompatible Miniature Swine: An Inbred Largeanimal Model1" Transplantation. Mar. 27, 2003, vol. 75, No. 6, 4 pgs.
Galili et al., Man, Apes, and Old World Monkeys Differ from Other Mammals in the Expression of a-Galactosyl Epitopes on Nucleated Cells* The Journal of Biological Chemistry. 1988, vol. 263, No. 33, 8 pgs.
Sachs et al., "Transplantation in Miniature Swine" Transplantation, 1976, vol. 22 No. 6, 9 pgs.
Tsururi et al., "Exhaustive Characterization of TCR—pMHC Binding Energy Estimated by the String Model and Miyazawa-Jernigan Matrix" General Medicine. 2013, 7 pgs.
Varela et al., "Cross-Reactivity between Swine Leukocyte Antigen and Human Anti-HLA-Specific Antibodies in Sensitized Patients Awaiting Renal Transplantation" Journal of the American Society of Nephrology. 2003, 7 pgs.
Ali et al., "Could Sentinel Skin Transplants Have Some Utility in Solid Organ Transplantation?" Elsevier. 2016, 6 pgs.
Cooper et al., "Genetically Engineered Pigs" The Lancet. Sep. 11, 1993, 2pgs.
Kemter, Elisabeth et al: "Will Genetic Engineering Carry Xenotransplantation of Pig Islets to the Clinic?", Current Diabetes Reports, Current Science, Philadelphia, VA, US, vol. 18, No. 11, Sep. 18, 2018, pp. 1-12, XP036595160.
Abicht, Jan-Michael et al: "Multiple genetically modified GTKO/hCD46/HLA-E/h[beta]2-mg porcine hearts are protected from complement activation and natural killer cell infiltration during ex vivo perfusion with human blood", Xenotransplantation, vol. 25, No. 5, Mar. 14, 2018, 11 pages, XP55710133.
Holzer, P. et al: "352 Cryopreserved Gal-Knockout Xenografts Provide Efficacious Temporary Coverage of Full-Thickness Wounds: Good Laboratory Practice-Compliant Studies in Non-Human Primates", Journal of Burn Care & Research, vol. 40, No. Supplement,1, Mar. 2019, pp. S153-S153, XP055653680.
Notification of Transmittal of the International Search Report and The Written Opinion issued in PCT/US2020/024780, dated Jul. 13, 2020, 17 pages.
Groenen, "A Decade of Pig Genome Sequencing: A Window on Pig Domestication and Evolution" Genetics, Selection, Evolution:GSE. Mar. 29, 2016, vol. 48, pp. 1-9.
Matczynska et al., "Analysis of swine leukocyte antigen class I gene profiles and porcine endogenous retrovirus viremia level in a transgenic porcine herd inbred for xenotransplantation research" Journal of Veterinary Science. 2018, vol. 19, Issue 3, pp. 384-392.
Tanaka-Matsuda et al., "Difference in number of loci of swine leukocyte antigen classical class I genes among haplotypes" Genomics. Mar. 1, 2009, vol. 93, Issue 3, pp. 261-273.
Dadi et al., "Genetic Diversity and mRNA Expression of Porcine MHC Class I Chain-Related 2 (SLA-MIC2) Gene and Development of a High-Resolution Typing Method" PLOS ONE. Aug. 25, 2015, vol. 10, Issue 8 pp. e0135922.
Warr et al., "Identification of Low-Confidence Regions in the Pig Reference Genome (Sscrofa10.2)" Frontiers in Genetics. 2015, vol. 6, pp. 1-8.

(56) References Cited

OTHER PUBLICATIONS

Yang et al., "Swine Leukocyte Antigen-DQA Gene Variation and Its Association with Piglet Diarrhea in Large White, Landrace and Duroc" Asian-Australasian Journal of Animal Sciences. Aug. 2013, vol. 26, Issue 8, pp. 1065-1071.
Le el al., "β2-microglobulin gene duplication in cetartiodactyla remains intact only in pigs and possibly confers selectives advantage to the species" PLoS ONE. 2017, vol. 12, Issue 8, pp. e0182322.
Reinoso-Barbero et al., "Anatomical comparison of sciatic nerves between adults and newborns: clinical implications for ultrasound guided block" Journal of Anatomy. Feb. 2014, vol. 224, Issue 2, pp. 108-112.
Sinis et al., "Bioartificial reconstruction of peripheral nerves using the rat median nerve model" Annals of Anatomy—Anatomischer Anzeiger. Jul. 2011, vol. 193, Issue 4, pp. 341-346.
Kelly et al., "End-to-side nerve coaptation: a qualitative and quantitative assessment in the primate" Journal of Plastic, Reconstructive & Aesthetic Surgery. Jan. 1, 2007. vol. 60, Issue 1, pp. 1-12.
Gao et al., "Nerve autografts and tissue-engineered materials for the repair of peripheral nerve injuries: a 5-year bibliometric analysis" Neural Regeneration Research. Jun. 2015, vol. 10, Issue 6, pp. 1003-1008.
Kornfeld et al., "Nerve grafting for peripheral nerve injuries with extended defect sizes" Wiener Medizinische Wochenschrift (1946). Nov. 21, 2018, vol. 169, Issue 9-10, pp. 240-251.
Kowalska et al., "Normal and sonographic anatomy of selected peripheral nerves. Part III: Peripheral nerves of the lower limb" Journal of Ultrasonography. Jun. 2012, vol. 12, Issue 49, pp. 48-163.
Kouyoumdjian et al., "Peripheral nerve injuries: A retrospective survey of 1124 cases" Neurology India. May 9, 2017. vol. 65, Issue 3, pp. 551-555.
Matsumoto et al., "Peripheral nerve regeneration across an 80-mm gap bridged by a polyglycolic acid (PGA)-collagen tube filled with laminin-coated collagen fibers: a histological and electrophysiological evaluation of regenerated nerves" Brain Research. Jun. 2013, vol. 868, Issue 2, pp. 315-328.
Stenberg et al., "Regeneration of long-distance peripheral nerve defects after delayed reconstruction in healthy and diabetic rats is supported by immunomodulatory chitosan nerve guides" BMC Neuroscience. Jul. 18, 2017, vol. 18.
Alshami et al., "Reliability and size of the measurement error when determining the cross-sectional area of the tibial nerve at the tarsal tunnel with ultrasonography" Ultrasound in Medicine & Biology. Jul. 2009, vol. 35, Issue 7, pp. 1098-1102.
Campana, "Schwann Cells: Activated Peripheral Glia and Their Role in Neuropathic Pain" Brain, behavior, and immunity. Jul. 2007, vol. 21, Issue 5, pp. 522-527.
Liu et al., "Specific Marker Expression and Cell State of Schwann Cells during Culture In Vitro" PLOS One. Apr. 10, 2015, vol. 10, Issue 4, pp. e0123278.
Koller et al., "The influence of the graft length on the functional and morphological result after nerve grafting: an experimental study in rabbits" British Journal of Plastic Surgery. Dec. 1, 1997, vol. 50, Issue 8, pp. 609-614.
Gaudet et al., "Wallerian degeneration: gaining perspective on inflammatory events after peripheral nerve injury" Journal of Neuroinflammation. Aug. 2011, vol. 8, pp. 1-13.
Esmaelli et al., "Frequencies of HLA-A, B and DRB1 alleles in a large normal population living in the city of Mashhad, Northeastern Iran" Iranian Journal of Basic Medical Sciences. Aug. 2017, vol. 20, Issue 8, pp. 940-943.
Aminikhah et al., "HLA Class I and Class II Genes Distribution of Sistanis in Iran" Iranian Journal of Immunology, Jun. 2016, vol. 15, Issue 2. pp. 97-111.
Atter et al., "HLA class I haplotype diversity is consistent with selection for frequent existing haplotypes" PLOS Computational Biology Aug. 28, 2017, vol. 13, Issue 8, pp. e1005693.
Kirijas et al., "HLA profile of the donors in Macedonian Bone Marrow Donor Registry" International Journal of Immunogenetics. Dec. 2018, vol. 45, Issue 6, pp. 337-346.
Jawdat et al., "HLA-A, B, C, DRB1 and DQB1 allele and haplotype frequencies in volunteer bone marrow donors from Eastern Region of Saudi Arabia" HLA. Jul. 2019, vol. 94, Issue 1, pp. 49-56.
Tshabalala et al., "HLA-A, B, C, DRB1 and DQB1 allele and haplotype frequencies in volunteer bone marrow donors from Eastern Region of Saudi Arabia" Journal of Immunology Research. 2018, vol. 2018, pp. 2031571.
Briata et al., "Alternative Splicing of HLA-DQB Transcripts and Secretion of HLA-DQ β-Chain Proteins: Allelic Polymorphism in Splicing and Polyadenylylation Sites" National Academy of Sciences. 1989, vol. 86, Issue 3, pp. 1003-1007.
Samandary et al., "Associations of HLA-A, HLA-B and HLA-C Alleles Frequency with Prevalence of Herpes Simplex Virus Infections and Diseases Across Global Populations: Implication for the Development of an Universal CD6+ T-Cell Epitope-Based Vaccines" Human Immunology. Aug. 2014, vol. 75, Issue 8, pp. 715-729.
Gomalusse et al., "HLA-E-expressing pluripotent stem cells escape allogeneic responses and lysis by NK cells" Nature Biotechnology. Aug. 2017, vol. 35. Issue 8, pp. 765-772.
Takahashi et al., "Exhaustive Characterization of TCR—pMHC Binding Energy Estimated by the String Model and Miyazawa-Jernigan Matrix" General Medicine. 2014, vol. 2, Issue 1.
Taxman et al., "Identification of Class II Transcriptional Activator-Induced Genes by Representational Difference Analysis: Discoordinate Regulation of the DNα/DOβ Heterodimer" The Journal of Immunology. Aug. 1, 2000, vol. 165. Issue 3, pp. 1410-1416.
Ouedemi et al., "Major histocompatibility complex class II expression deficiency caused by a RFXANK founder mutation: a survey of 35 patients" Blood. Nov. 10, 2011. vol. 118, Issue 19. pp. 5108-5118.
Hanna et al., "MHC class I and II deficiencies" Journal of Allergy and Clinical Immunology. Aug. 1, 2014, vol. 134, Issue 2, pp. 269-275.
Takeda et al., "MHC class II molecules are not required for survival of newly generated CD4+ T Cells, but affect their long-term life span" Immunity. Sep. 1996, vol. 5, Issue 3, pp. 217-228.
Grusby et al., "Mice lacking major histocompatibility complex class I and class II molecules" Proceedings of the National Academy of Sciences of the United States of America, May 1, 1993, vol. 90, Issue 9, pp. 3913-3917.
Cosgrove et. al., "Mice lacking MHC class II molecules." Cell. Sep. 6, 1991, vol. 66, Issue 5, pp. 1051-1056.
Reith et al., "The Bare Lymphocyte Syndrome and the Regulation of MHC Expression" Annual Review of Immunology. 2001, vol. 19, Issue 1, pp. 331-373.
International Search Report issued for PCT/US2019/054833. dated Jan. 17, 2020, 16 pgs.
World Health Organization, First WHO Global Consulation on Regulatory Requirements for Xenotransplantation Clinical Trials. Changsha, China. Nov. 2008.
Holzer et al., "352 Cryopreserved Gal-Knockout Xenografts Provide Efficacious Temporary Coverage of Full-Thickness Wounds: Good Laboratory Practice-Compliant Studies in Non-Human Primates." Journal of Burn Care and Research, 2019, vol. 40, Issue 1, 2 pgs.
Kemler et al., "Will Genetic Engineering Carry Xenotransplantation of Pig Islets to the Clinic?" Current Diabetes Reports. 2018, vol. 18, Issue 103, pp. 1-12.
Weiss, "Xenografts and Retroviruses" Perspective Biomedicine. Aug. 20, 1990, vol. 285, Issue 5431, pp. 1221-1222.
Lawrence et al., "HIV Transmission and Skin Grafts" The Lancet, Apr. 25, 1987, p. 983.
Hansmann, "The Economics and Ethics of Markets for Human Organs" Journal of Health Politics, Policy and Law. 1989, vol. 14 No. 1, pp. 57-85.
Fansa et al., "Stimulation of Schwann cell proliferation and axonal regeneration by FK 506" Restorative Neurology and Neuroscience. 2000, vol. 16, pp. 77-86.

(56) References Cited

OTHER PUBLICATIONS

Fansa et al., "Cryopreservation of Peripheral Nerve Grafts" Muscle Nerve. 2000, vol. 23, pp. 1227-1233.
Diaz-Siso et al., "Vascularized Composite Tissue Allotransplantation—State of the Art" Clinical Transplantation. May 2013, vol. 27, Issue 3, pp. 330-337.
Cooper et al., "Progress in pig-to-non-human primate transplantation models (1998-2013): a comprehensive review of the literature" Xenotransplantation. Sep. 2014, vol. 21, Issue 5, pp. 397-419.
Choukairi et al., "Letter to the Editor" Burns. Sep. 2008, vol. 34, Issue 6, p. 896.
Chiarini et al., "In vitro and in vivo characteristics of frozen/thawed neonatal pig split-skin strips: A novel biologically active dressing for areas of severe, acute or chronic skin loss" International Journal of Molecular Medicine. Feb. 1, 2007, vol. 19 pp. 245-255.
Cetrulo et al., "Penis Transplantation: First US Experience" Annals of Surgery. May 2018, vol. 267, Issue 5, pp. 983-988.
Boneva et al., "Xenotransplantation and risks of zoonotic infections" Annals of Medicine. Jan. 2004, vol. 36, Issue 7, pp. 504-517.
Kealey et al., "Cadaver skin allografts and transmission of human cytomegalovirus to burn patients." Journal of the American College of Surgeons. Mar. 1996. vol. 182, Issue 3, pp. 201-205.
Klein et al., "A reliable and cost-effective in vitro assay of skin viability for skin banks and burn centers" The Journal of Burn Care & Rehabilitation. Nov.-Dec. 1996, vol. 17, Issue 6 Pt 1, pp. 565-570.
Pegg, "Viability assays for preserved cells, tissues, and organss" Cryobiology, Jun. 1989, vol. 26, Issue 3, pp. 212-231.
Robson et al., "Factors in xenograft rejection." Annals of the New York Academy of Sciences. Jun. 18, 1999, vol. 875, pp. 261-276.
Merrell et al., "An in vivo test of viability for cryopreserved human skin" Current Surgery. Jul.-Aug. 1986, vol. 43, Issue 4, pp. 296-300.
Farley et al., "Cells, tissues, organs, and systems" Nursing Standard, Aug. 29-Sep. 4, 2012, vol. 26, Issue 52, pp. 40-45.
Ezzelarab et al., "Reducing Gal expression on the pig organ—a retrospective review" Xenotransplantation. Jul. 2005, vol. 12, Issue 4, pp. 278-285.
Scudiero et al., "Evaluation of a soluble tetrazolium/formazan assay for cell growth and drug sensitivity in culture using human and other tumor cell lines" Cancer Research. Sep. 1, 1988, vol. 48, Issue 17, pp. 4827-4833.
Marshall, "A critical assessment of the use of microculture tetrazolium assays to measure cell growth and function." Growth Regulation. Jun. 1995, vol. 5, Issue 2, pp. 69-84.
May et al., "Recent developments in skin banking and the clinical uses of cryopreserved skin" Journal of the Medical Association of Georgia. Apr. 1984, vol. 73, Issue 4, pp. 233-236, 57.
Vloemans et al., "Commentary on: "The effect of moist and moist exposed dressings on healing and barrier function restoration of partial thickness wounds" by Atiyeh et al." European Journal of Plastic Surgery. Apr. 1, 2003. vol. 26, Issue 1, pp. 12-12.
Vloemans et al., "The use of glycerol-preserved allografts in the Beverwijk Burn Centre: a restrospective study" Burns. Oct. 1, 2002, vol. 28, pp. 2-9.
Clavien et al., "Preservation and reperfusion injuries in liver allografts. An overview and synthesis of current studies" Transplantation. May 1992, vol. 53, Issue 5, pp. 957-978.
Koyama et al., "The role of oxygen free radicals in mediating the reperfusion injury of cold-preserved ischemic kidneys" Transplantation. Dec. 1985, vol. 40, Issue 6, pp. 590-595.
Riss et al., "Cell Viability Assays" Assay Guidance Manual. May 1, 2013, 31 pgs.
Lee et al., "High-resolution donor-recipient HLA matching contrbutes to the success of unrelated donor marrow transplantation" www.bloodjournal.org, Dec. 15, 2007, vol. 110, Issue 13, 28 pgs.
Fishman, "Screening of source animals and clinical monitoting for xenotransplantation" Xenotransplantation, Jul. 2007, vol. 14, Issue 4, pp. 349-352.
Murray, "Organ Transplantation (Skin, Kidney, Heart) and the Plastic Surgeon" Plastic and Reconstructive Surgery, May 1971, vol. 47, Issue 5, p. 425.
Kawai et al., "Tolerance—On Transplant for Life" Transplantation. Jul. 27, 2014, vol. 98, issue 2, pp. 117-121.
Barth et al., "Vascularized Bone Marrow-Based Immunosuppression Inhibits Rejection of Vascularized Composite Allografts in Nonhuman Primates" American Journal of Tranplantation. Jul. 1, 2011, vol. 11, Issue 7, pp. 1407-1416.
Wachtel et al., "Viability of frozen allografts" American Journal of Surgery. Dec. 1979, vol. 138, Issue 6, pp. 783-787.
Sokolic et al., "The use of heterograft skin as a biological dressing" Surgical Forum. 1960, vol. 10, pp. 847-849.
May et al. "Skin Banking.: Part III. Cadaveric Allograft Skin Viability" Journal of Burn Care & Research. May 1, 1981, vol. 2.
Levi et al., "Liver allotransplantation after extracorporeal hepatic support with transgenic (hCD55/hCD59) porcine livers: clinical results and lack of pig-to-human transmission of the porcine endogenous retrovirus" Transplantation. Jan. 27, 2000, vol. 69, Issue 2, pp. 272-280.
Ersek et al., "Porcine xenografts in the treatment of pressure ulcers." Annals of Plastic Surgery, Dec. 1980, vol. 5, Issue 6, pp. 464-470.
Ravindra et al., "The need for inducing tolerance in vascularized composite allotransplantation" Clinical and Developmental Immunology. vol. 2012, 11 pgs.
Morozov et al., "No PERV transmission during a clinical trial of pig islet cell transplantation" Virus Research. Jan. 2017, vol. 227, pp. 34-40.
Dheda et al., "Validation of housekeeping genes for normalizing RNA expression in real-time PCR" BioTechniques. Jul. 2004, vol. 37, Issue 1, pp. 112-114, 116, 118-119.
Shi et al., "Inhibition of porcine endogenous retrovirus (PERV) replication by HIV-1 gene expression inhibitors" Antiviral Research. Aug. 2009, vol. 83, Issue 2, pp. 201-204.
Teh, "Why do skin grafts fail?" Plastic and Reconstructive Surgery Mar. 1979, vol. 63, Issue3, pp. 323-332.
Cooper et al., "The role of genetically engineered pigs in xenotransplantation research: Genetically engineered pigs in xenotransplantation" The Journal of Pathology. Jan. 2016, vol. 238, Issue 2, pp. 288-299.
Denner, "Why was PERV not transmitted during preclinical and clinical xenotransplantation trials and after inoculation of animals?" Retrovirology. Dec. 2018, vol. 15, Issue, 1 p. 28.
Denner et al., "Is it currently possible to evaluate the risk posed by PERVs for clinical xenotransplantation?" Xenotransplantation. 2018, vol. 25, Issue 4, pp. e12403.
Yamamoto et al., "Skin xenotransplantation: Histroical review and clinical potential" Burns: Journal of the International Society for Burn Injuries. Nov. 2018, vol. 44, Issue 7. pp. 1738-1749.
Irgang, "Porcine endogenous retroviruses: no infection in patients treated with bioreactor based on porcine liver cells" Journal of Clinical Virology. Oct. 2003, vol. 28, Issue 2, pp. 141-154.
Di Nicuolo et al., "Long-term absence of porcine endogenous retrovirus infection in chronically immunosuppressed patients after treatment with the porcine cell-based Academic Medical Center bioartificial liver: Absence of PERV after BAL treatment" Xenotransplantation. Nov. 2010, vol. 17, Issue 6, pp. 431-439.
Zych et al., "Application of Genome Editing Techniques in Immunology" Archivum Immunologiae et Therapiae Experimentalis. Aug. 2018, vol. 66, Issue 4, pp. 289-298.
Issa et al., "Absence of Replication of Porcine Endogenous Retrovirus and Porcine Lymphotropic Herpesvirus Type 1 with Prolonged Pig Cell Microchimerism after Pig-to-Baboon Xenotransplantation" Journal of Virology. Dec. 12, 2008, vol. 82, Issue 24. pp. 12441-12448.
Holmes et al., "Anti-pig antibody levels in naive baboons and cynomolgus monkeys" Xenotransplantation. Mar. 2002, vol. 9, Issue 2, pp. 135-147.
Zhang et al., "Lamellar Keratoplasty Treatment of Fungal Corneal Ulcers With Acellular Porcine Corneal Stroma: Acellular Porcine Cornea in Keratoplasty" American Journal of Transplantation. Apr. 2015, vol. 15, Issue 4, pp. 1068-1075.
Turhan-Haktanir et al., "Evaluation of amniotic fluid as a skin graft storage media compared with RPMI and saline" Burns. Jun. 1, 2011, vol. 37, Issue 4, pp. 652-655.

(56) References Cited

OTHER PUBLICATIONS

Valdez-Gonzalez et al., "No evidence of porcine endogenous retrovirus in patients with type 1 diabetes after long-term porcine islet xenotransplantation" Journal of Medical Virology. 2010, vol. 82, Issue 2, pp. 331-334.
Vadori et al., "Immunological Challenges and Therapies in Xenotransplantation" Cold Spring Harbor Preservatives in Medicine. Apr. 2014. vol. 4, Issue 4.
Chardon et al., "Sequence of the swine major histocompatibility complex region containing all non-classical class I genes" Tissue Antigens. Jan. 2001, vol. 57, Issue 1, pp. 55-65.
Byrne et al., "Recent investigations into pig antigen and anti-pig antibody expression" International Journal of Surgery. Nov. 2015, vol. 23, pp. 223-228.
Buhler et al., "An investigation of the specificity of induced anti-pig antibodies in baboons," Xenotransplantion. Jan. 2003, vol. 10, Issue 1, pp. 88-93.
Floss et al., "Insights into IL-23 biology: From structure to function" Cytokine & Growth Factor Reviews, Oct. 1, 2015, vol. 26, Issue 5, pp. 569-578.
Patience et al., "No evidence of pig DNA or retroviral infection in patients with short-term extracorporeal connection to pig kidneys" The Lancet. Aug. 1998, vol. 352, Issue 9129, pp. 699-701.
Zhu et al., "Anti-N-glycolylneuraminic acid antibodies identified in healthy human serum" Xenotransplantation. Nov. 2002, vol. 9, Issue 6, pp. 376-381.
Morozov et al., "Islet cell transplantation from Göttingen minipigs to cynomolgus monkeys: analysis of virus safety" Xenotransplantation. Jul. 2016, vol. 23, Issue 4, pp. 320-327.
Choi et al., "Long-term safety from transmission of porcine endogenous retroviros after pig-to-non-human primate corneal transplantation" Xenotransplantation. Jul. 2017, vol. 24, Issue 4, 13 pgs.
Heneine et al., "No evidence of infection with porcine endogenous retrovirus in recipients of porcine islet-cell xenografts" The Lancet. Aug. 1998, vol. 352, Issue 9129, pp. 695-699.
Lin et al., "The role of antibodies in acute vascular rejection of pig-to-baboon cardiac transplants." Journal of Clinical Investigation. Apr. 15, 1998, vol. 101, Issue 8, pp. 1745-1756.
Varki, "Loss of N-glycolylneuraminic acid in humans: Mechanisms, consequences, and implications for hominid evolution" American Journal of Physical Anthropology, 2001, vol. Suppl 33, pp. 54-69.
Vimr et al., "Diversity of microbial sialic acid metabolism" Microbiology and Molecular Biology Reviews. Mar. 2004, vol. 68, Issue 1, pp. 132-153.
Diswall et al., "Structural characterization of alpha1,3-galactosyltransferase knockout pig heart and kidney glycolipids and their reactivity with human and baboon antibodies" Xenotransplantation. Jan.-Feb. 2010, vol. 17, Issue 1, pp. 48-60.
Brochner et al., "Pathophysiology of the systemic inflammatory response after major accidental trauma" Scandinavian Journal of Trama, Resusitation and Emergency Medicine. Sep. 15, 2009, vol. 17, p. 43.
Kravitz, "Immune consequences of burn injury" AACN Clinical Issues in Critical Care Nursing. May 1993, vol. 4. Issue 7, pp. 399-413.
Pavoni et al., "Outcome predictors and quality of life of severe burn patients admitted to intensive care unit" Scandinavian Journal of Trauma. Resuscitation and Emergency Medicine. Apr. 27, 2010, vol. 18, Issue 24, 8 pgs.
Bühler et al., "Pig kidney transplantation in baboons: anti-Gal(alpha)1-3Gal IgM alone is associated with acute humoral xenograft rejection and disseminated intravascular coagulation" Transplantation. Dec. 15, 2001, vol. 72, Issue 11, pp. 1743-1752.
Cendales et al., "The Banff 2007 Working Classification of Skin-Containing Composite Tissue Allogaft Pathology: Banff CTA Allograft Pathology Classification" American Journal of Transplantation. Jul. 2008, vol. 8, Issue 7, pp. 1396-1400.
Levy et al., "Liver allotransplantation after extracorporeal hepatic support with transgenic (hCD55/hCD59) porcine livers: clinical results and lack of pig-to-human transmission of the porcine endogenous retrovirus" Transplantation. Jan. 27, 2000. vol. 69, Issue 2, pp. 272-280.
Sharp, "Splicing of Messenger RNA Precursors" Science. 1987, vol. 235, Issue 4790, pp. 766-771.
Buermann et al., "Pigs expressing the human inhibitory ligand PD-L1 (CD 274) provide a new source of xenogeneic cells and tissues with low immunogenic properties" Xenotransplantation. Sep. 2018, vol. 25, Issue 5, pp. E12387.
Butler et al., "Recent advances in genome editing and creation of genetically modified pigs" International Journal of Surgery. Nov. 2015, vol. 23, pp. 217-222.
Hara et al., "Human dominant-negative class II transactivator trangenic pigs—effect on the human anti-pig T-cell immune response and immune status" Immunology, Sep. 2013. vol. 140, Issue 1, pp. 39-46.
Wang et al., "IL-36 promotes anti-viral immunity by boosting sensitivity to IFN-α/β in IRF1 dependent and independent manners" Nature Communications. Oct. 16, 2019, vol. 10, Issue 1, pp. 1-17.
Ohara, "From transcriptome analysis to immunogenomics: Current status and future direction" FEBS Letters. vol. 583, Issue 11, pp. 1662-1667.
Forte et al., "HLA-E Expression on Porcine Cells: Protection from Human NK Cytotoxicity Depends on Peptide Loading" American Journal of Transplantation. 2005, vol. 5, Issue 9, pp. 2085-2093.
Gupta et al., "Immunogenomics: recent discoveries" International Journal of Genetics. Dec. 30, 2009, vol. 1, Issue 2, pp. 1-5.
Greiff et al., "Learning the High-Dimensional Immunogenomic Features That Predict Public and Private Antibody Repertoires" The Journal of Immunology. Oct. 15, 2017, vol. 199, Issue 8, pp. 2985-2997.
Miretti et al., "Immunogenomics: Molecular hide and seek" Human Genomics. Jan. 1, 2006, vol. 2, Issue 4, pp. 244-251.
Holt, "Immunoogenomics: a foundation for intelligent immune design" Genome Medicine. Nov. 19, 2015, vol. 7, Issue 116, pp. 1-3.
Kralovic et al., "Position-Dependent Repression and Promotion of DQB1 Intron 3 Splicing by GGGG Motifs" The Journal of Immunology. Feb. 15, 2006. vol. 176, Issue 4, pp. 2381-2388.
Simmonds et al., "Structural and Functional Implications of the Intron/Exon Organization of the Human Endothelial Cell Protein C/Activated Protein C Receptor (EPCR) Gene: Comparison With the Structure of CD1/Major Histocompatibility Complex □1 and □2 Domains" Blood. Jul. 15, 1999, vol. 94, Issue 2, pp. 632-641.
Hughes, "Evolution of introns and exons of class II major histocompatibilty complex genes of vertebrates" Immunogenetics. 2000, vol. 51, Issue 6, pp. 473-486.
Mach et al., "Regulations of MHC Class II Genes: Lessons from a Diseases" Annual Review of Immunology. vol. 14, pp. 301-331.
Reith et al., "Regulation of MHC Class II gene expression by the class II transactivator" Nature Reviews Immuology. Oct. 2005, vol. 5, Issue 10, pp. 793-806.
Zachary et al., "HLA Mismatching Strategies for Solid Organ Transplantation—A Balancing Act" Frontiers in Immunology.
Figueiredo et al., "Immunoengineering of the Vascular Endothelium to Silence MHC Expression During Normothermic Ex Vivo Perfusion" Human Gene Therapy. Apr. 2019, vol. 30, Issue 4, pp. 485-496.
Deuse et al., "Hypoimmunogenic derivatives of induced pluripotent stem cells evade immune rejection in fully immunocompetent allogeneic recipients" Nature Biotechnology. Mar. 2019, vol. 37, pp. 252-258.
Harara et al., "Generation of a Novel HLA Class I Transgenic Mouse Model Carrying a Knock-in Mutation at the β$_{2}$-Micro-globulin Locus" The Journal of Immunology. Jan. 1, 2017, vol. 198, Issue 1, pp. 516-527.
Lanza et al., "Engineering universal cells that evade immune detection" Nature Reviews Immunology. Aug. 15, 2019, pp. 1-11.
Taneja et al., "HLA transgenic mice as humanized mouse models of disease and immunity." Journal of Clinical Investigation. Mar. 1, 1998, vol. 101, Issue 5, pp. 921-926.
Wolf et al., "Genetically modified pigs as donors of cells, tissues, and organs for xenotransplantation" Animal Frontiers. Jun. 25, 2019, vol. 9, Issue 3, pp. 13-20.

(56) References Cited

OTHER PUBLICATIONS

Gadola et al., "TAP deficiency syndrome" Clinical and Experimental Immunology. Aug. 2008, vol. 121, Issue 2, pp. 173-178.
Shimizu et al., "Thrombotic microangiopathy associated wnh humoral rejection of cardiac xenografts from alpha,3-galactosyltransferase gene-knockout pigs in baboons" The American Journal of Pathology. Jun. 2008, vol. 172, Issue 6, pp. 1471-1481.
Laird et al., "Transgenic expression of human leukocyte antigen-E attenuates GalKO.hCD46 porcine lung xenograft injury" Xenotransplantation. Mar. 2017, vol. 24, Issue 2.
Asako Ando et al., "Genomic sequence analysis of the 238-kb swine segment with a cluster of TRIM and olfactory receptor genes located, but with no class I genes, at the distal end of the SLA class I region", Immunogenetics, (2005) 57: 864-873.
G. Bentley et al., "High-resolution, high throughput HLA genotyping by next-generation sequencing", Tissue Antigens, 74, 393-403.
Caixia Gao et al., "Characterization of swine leukocyte antigen (SLA) polymorphismby sequence-based and PCR-SSP methods in Chinese Bama miniature pigs", Developmental and Comparative Immunology, 45 (2014) 87-96.
John K. Lunney et al., "Molecular genetics of the swine major histocompatibility complex, the SLA complex", Developmental and Comparative Immunology, 33 (2009) 362-374.
Atsuko Shigenari et al., "Nucleotide sequencing analysis of the swine 433-kb genomic segment located between the non-classical and classical SLA class I gene clusters", Immunogenetics, (2004) 55:695-705.
Kelton, Reprogramming MHC specificity by CRISPR-Cas9-assisted cassette exchange, Apr. 2017, Scientific Reports.
Sachs article (Jul. 2010), https://apps.dtic.mil/dtic/tr/fulltext/u2/a535275.pdf.
Tucker article (2002, Xenotransplantation 9: 191-202), https://www.ncbi.nlm.nih.gov/pubmed/11983017.
Zhu et al. Frontiers in Surgery, Mar. 2014, vol. 1, Art. 7, 1-8.
Stone et al., Advancements in Regenerative Strategies Through the Continuum of Burn Care, Frontiers in Pharm., Jul. 2018, vol. 9, Art. 62, pp. 1-33.
Klymiuk N, Aigner B, Brem G. Wolf E. Genetic modification of pigs as organ donors for xenotransplantation. Mol Reprod Dev. 2010;77:209-221.
Hryhorowicz M. Zeyland J, Stomski R. Lipinski D. Genetically mod-ified pigs as organ donors for xenotransplantation. Mol Biotechnol. 2017;59:435-444.
Yang L. Guell M, Niu D. et al. Genome-wide inactivation of porcine endogenous retroviruses (PERVs). Science. 2015,350:1101-1104.
Sachs DH, Galli C. Genetic manipulation in pigs. Curr Opin Organ Transplant. 2009;14:148-153.
Phelps CJ, Koike C, Vaught TD, et al. Production of alpha 1,3-galactosyltransferase-deficient pigs. Science. 2003;299:411-414.
Fishman JA, Xenosis and xenotransplantation: addressing the infectious risks posed by an emerging technology. Kidney Int—Suppl. 1997;58:S41-S45.
Fishman J, Patience C. Xenotransplantation: infectious risK revisited. Am J Transplantation. 2004;4:1383-1390.
Fishman JA, Infection in xenotransplantation. J Card Surg. 2001;16:363-373.
Fishman JA. Infection and xenotransplantation. Developing strategies to minimize risk. Ann NY Acad Sci. 1998;862:52-66.
Fishman JA. The risk of infection in xenotransplantation. Introduction. Ann N Y Acad Sci. 1998;862:45-51.
Moraes et al., Prediction of early kidney transplant rejection by a crossmatch with donor skin. Dec. 1989;48(6):951-2.
Ravi Starzl et al., Review of the Early Diagnoses and Assessment of Rejection in Vascularized Composite Allotransplantation. Hindawi Publishing Corporation Clinical and Developmental Immunology vol. 2013, Article ID 402980, 9 pages.
Shackman R, Castro JE. Prelusive skin grafts in live-donor kidney transplantation. Lancet. Sep. 20, 1975;2(7934)521-4.

Kelly et al, How many patients do we need for a clinical trial Demystifying sample size calculations Sample size estimatation in nephrology. Nephrology, vol. 15, Issue 8, Dec. 2010, pp. 725-731.
Villiger, et al., Getting Real About Valuations in Biotech, Nature Biotecnnology, vol. 23, Issue 4, Apr. 2005, pp. 423-428.
Booth et al., In defense of life sciences venture investing. Nature Biotechnology, vol. 29, 2011, pp. 579-583.
K. Paradis, Search for Cross-Species Transmission of Porcine Endogenous Retrovirus in Patients Treated wih Living Pig Tissue, Science, vol. 285, Issue 5431, pp. 1236-1241.
Fishman, Infectious disease risks in xenotransplantation. American Journal of Transplantation, Aug. 2008, vol. 18. Issue 8, pp. 1857-1864.
Nellore et al., Donor-derived infections and infectious risk in xenotransplantation and allotransplantation, Xenotransplantation, 2018, vol. 25, Issue 4, pp. e12423.
Fishman et al., Absence of interaction between porcine endogenous retrovirus and porcine cytomegalovirus in pig-to-baboon renal transplantation in vivo. Xenotransplantation, Sep. 2018, vol. 25, Issue 5, pp. e12395.
Schuurman, The International Xenotransplantation Association consensus statement on condititons for undertaking clinical trials of porcine islet products in type 1 diabetes—chapter 2: Source pigs. Xenotransplantation. Jul.-Aug. 2009. vol. 16, Issue 4, pp. 215-222.
Denner et al., The International Xenotransplantation Association consensus statement on conditions for undertaking clinical trials of porcine islet products in type 1 diabetes—chapter 5: Strategies to prevent transmission of porcine endogenous retroviruses. Xenotransplantation, Jul.-Aug. 2009. vol. 16, Issue 4, pp. 239-248.
Paradis et al., Search for cross-species transmission of porcine endogenous retrovirus in patients treated with living pig tissue. The Xen 111 Study Group. Science (New York, N.Y.), Aug. 20, 1999. vol. 285, Issue 5431, pp. 1236-1241.
Spizzo et al., First update of the International Xenotransplantation Association consensus statement on conditions for undertaking clinical trials of porcine islet products in type 1 diabetes—Chapter 2a source pigs—preventing xenozoonoses. Xenotransplantation. 2016. vol. 23, Issue 1, pp. 25-31.
Cooper et al., Joint FDA-IXA Symposium. Sep. 20, 2017, Xenotransplantation. Nov. 2017, vol. 24, Issue 6.
Fishman et al., Innovation in organ transplantation A meeting report. American Journal of Transplantation, 2018. vol. 18, Issue 8, pp. 1875-1878.
Fishman et al., Pneumocystis jiroveci in Solid Organ Transplantation—Guidelines from the American Society of Transplantation Infectious Diseases Community Practice. Clinical Transplantation. May 11, 2019. pp. e13587.
Fishman, *Myobacterium tuberculosis* in transplantation Immunity sufficient to perpetuate disease American Journal of Transplantation, 2019, vol. 19, Issue 5. pp. 1252-1263.
Hartline, Xenotranslantation panel for the detection of infectious agents in pigs, Xenotransplantation. 2018, vol. 25, Issue 4, pp. e12427.
Estrada, Evaluation of human and non-human primate antibody binding to pig cells lacking GGTA1CMAHβ4GaINT2 genes, Xenotransplantation, Jun. 2015, vol. 22, lssue3, pp. 194-202.
Adams e al., Xenoantigen Deletion and Chemical Immunosuppression Can Prolong Renal Xenograft Survival. Annals of Surgery, Oct. 2018, vol. 268. Issue 4, pp. 564-573.
Ladowski et al., The desirable donor pig to eliminate all xenoreactive antigens. Xenotransplantation, 2016. pp. e12504.
Ladowski et al., Swine Leukocyte Antigen Class II is a Xenoantigen. Transplantation, Feb. 2008, vol. 102, Issue 2, pp. 249-254.
Kim et al., Long-term survival of pig-to-rhesus macaque renal xenografts is dependent on CD4 T cell depletion. American Journal of Transplantation, 2019, vol. 19, Issue 8, pp. 2174-2185.
Martens et al., Humoral Reactivity of Renal Transplant-Waitlisted Patients to Cells From GGTA1CMAHB4GaINT2, and SLA Class I Knockout Pigs. Transpantation. Apr. 2017, vol. 101, Issue 4.
Ladowski et al., Examing the Biosynthesis and Xenoantigenicity of Class II Swine Leukocyte Antigen Proteins. Journal of Immunology (Baltimore, Md. 1950), Apr. 15, 2018, vol. 200, Issue 8, pp. 2957-2964.

(56) References Cited

OTHER PUBLICATIONS

Wang et al., Elliminating Xenoantigen Expression on Swine RBC. Transplantation, Mar. 2017. vol. 101, Issue 3, pp. 517-523.
Butler et al,. Efficient generation of targeted and controlled mutational events in porcine cells using nuclease-directed homologous recombination. Journal of Surgical Research, May 2017, vol. 212. pp. 238-245.
Yamamoto et al., Data on B cells phenotypes in baboons with pig artery patch grafts receiving conventional immunosupressive therapy. Sep. 13, 2018, vol. 20, pp. 1965-1974.
Nunes Dos Santos, CRISPRCas and recombinase-based human-to-pig orthotopic gene exchange for xenotransplantation. The Journal of Surgical Research, Sep. 2018, vol. 229, pp. 28-40.
Achauer et al., Long Term Skin Allograft Survival Aftet Short-Term Cyclosporin Treatment ina Patient with Massive Burns. The Lancet, Jan. 1986, vol. 327, Issue 8471, pp. 14-15.
Albritton et al., Lack of Cross-Sensitization Between α-1,3-Galactosyltransferase Knockout Porcine and Allogeneic Skin Grafts Permits Serial Grafting. Transplantation, Jun. 2014, vol. 97, Issue 12, pp. 1209-1215.
Ardehali, I. While millions and millions of lives have been saved, organ transplantation still faces massive problems after 50years; organ preservation is a big part of the solution. Cryobiology, Aug. 2015, vol. 71 Issue 1, pp. 164-165.
Argaw et al., Susceptibility of porcine endogenous retrovirus to anti-retroviral inhibitors. Xenotransplantation, Mar. 2016, vol. 23, issue 2, pp. 151-158.
Atiyeh et al., Military and Civilian Burn Injuries During Armed Conflicts. Annals of Burns and Fire Disasters, Dec. 31, 2007, vol. 20, Issue 4, pp. 203-215.
Banner et al., Effect of Heart Transplantation on Survival in Ambulatory and Decompensated Heart Failure:, Transplantation, Dec. 2008, vol. 86, Issue 11, pp. 1515-1522.
Barker et al., Historical overview of transplantation. Cold Spring Harbor Perspectives in Medicine, Apr. 1, 2013, vol. 3, Issue 4, pp. a014977.
Barone et al., Genetically modified porcine split-thickness skin grafts as an alternative to allograft for provision of temporary wound coverage: preliminary characterization. Burns, May 2015, vol. 41, Issue 3, pp. 565-574.
Barret et al., Cost-Efficacy of Cultured Epidermal Autografts in Massive Pediatric Burns:, Annals of Surgery, Jun. 2000, vol. 231, Issue 6, pp. 869-876.
Becker, Thomas Schlich, The Origins of Organ Transplantation: Surgery and Laboratory Science 1880-1930, Social History of Medicine, May 1, 2012, vol. 25, Issue 2, pp. 549-550.
Belzer et al., Principles of solid-organ preservation by cold storage. Transplantation, Apr. 1988,vol. 45, Issue 4, pp. 673-676.
Ben-Bassat et al., How long can cryopreserved skin be stored to maintain adequate graft performance. Burns, Aug. 2001, vol. 27, Issue 5, pp. 425-431.
Bender et al., Evaluation of demineralized bone matrix paste and putty in periodontal intraosseous defects. Journal of Periodontology, May 2005, vol. 76, Issue 5, pp. 768-777.
Benichou et al., Immune recognition and rejection of allogeneic skin grafts. Immunotherapy, Jun. 2011, vol. 3, Issue 6, pp. 757-770.
Benson et al., Burns. BJM, 2006, vol. 332, Issue 7542, pp. 649-652.
Beziat et al., NK cell responses to cytomegalovirus infection lead to stable imprints in the human KIR repertoire and involve activating KIRs, Blood, Apr. 4, 2013, vol. 121, Issue 14, pp. 2678-2688.
Boas, Where do human organs come from? Trends of generalized and restricted altruism in organ donations—ScienceDirect. Soc Sci Med, Nov. 2011, vol. 73, Issue 9, pp. 1378-1385.
Bramhall, Presumed consent for organ donation: a case against. Annals of The Royal College of Surgeons of England, May 2011, vol. 93, Issue 4, pp. 270-272.
Branski et al., Fibrin sealant improves graft adherence in a porcine full-thickness burn wound model. Burns, Dec. 2011, vol. 37, Issue 8, 1360-1366.

Braud, et al., HLA-E binds to natural killer cell receptors CD94/NKG2A, B and C. Nature, Feb. 1998, vol. 391, Issue 6669, pp. 795-799.
Bravo et al., Effect of storage and preservation methods on viability in transplantable human skin allografts, Burns, 2000, vol. 26, pp. 367-378.
Burd et al., Allogenic skin in the treatment of burns. Clinics in Dermatology, Jul. 2005, vol. 23, Issue 4, pp. 376-387.
Burke et al., Immunosuppression and temporary skin transplantation in the treatment of massive third degree burns. Annals of Surgery, Sep. 1975, vol. 182, Issue 3, pp. 183-197.
Burlak et al., N-linked glycan profiling of GGTA1/CMAH knockout pigs identifies new potential carbohydrate xenoantigens. Xenotransplantation, Sep.-Oct. 2013, vol. 20, Issue 5 pp. 277-291.
Burlak et al., Reduced binding of human antibodies to cells from GGTA1/CMAH knockout pigs. American Journal of Transplantation, Aug. 2014, vol. 14, Issue 8. pp. 1895-1900.
Butler et al., Silencing porcine CMAH and GGTA1 genes significantly reduces xenogeneic consumption of human platelets by porcine livers. Transplantation, Mar. 2016, vol. 100, Issue 3 pp. 571-576.
Butler et al., Silencing porcine genes significantly reduces human-anti-pig cytotoxicity profiles: an alternative to direct complement regulation. Transgenic Research, Oct. 2016, vol. 25, Issue 5, pp. 751-759.
Byrne et al., B4GALNT2 and xenotransplantation: A newly appreciated xenogeneic antigen, Xenotransplantation, Sep. 2018, vol. 25, Issue 5, pp. e12394.
Byrne et al., Cloning and expression of porcine β1,4 N-acetylgalactosaminyl transterase encoding a new xenoreactive antigen. Xenotransplantation, Nov. 2014, vol. 31, Issue 6, pp. 543-554.
Castagnoli et al., Evaluation of donor skin viability: fresh and cryopreserved skin using tetrazolioum salt assay. Burns, Dec. 2003, vol. 29, Issue 8, pp. 759-767.
Cetrulo et al., Vascularized Composite Allograft Transplant Survival in Miniature Swine: Is MGC Tolerance Sufficient for Acceptance of Epidermis? Transplantation, Dec. 15, 2013, vol. 96. Issue 11, 966-974.
Chambers et al., A band of surgeons, a long healing line: development of craniofacial surgery in response to armed conflict. The Journal of craniofacial surgery, 2010, vol. 21, Issue 4, pp. 991-997.
Chambers et al., Achieving Growth and Excellence in Medicine The Case History of Armed Conflict and Modern Reconstructive Surgery. Annals of plastic surgery, Nov. 1, 2009, vol. 63, pp. 473-478.
Chihara et al., Fibronectin from alpha 1,3-galactosyltransferase knockout pigs is a xenoantigen, Journal of Surgical Research, Oct. 2013, vol. 184, Issue 2 pp. 1123-1133.
Chiu et al., "Xenograft" dressing in the treatment of burns. Clinics in Dermatology, Jul. 2005, vol. 23, Issue 4, pp. 419-423.
Christiansen et al., Veterinarians' role in clients' decision-making regarding seriously ill companion animal patients, Acta Veterinaria Scandinavica, May 25, 2016, vol. 58, Issue 1, p. 30.
Church et al., Burn Wound Infections. Clinical Microbiology Reviews, Apr. 2006, vol. 19, Issue 2, pp. 403-434.
Cleland et al., Clinical application and viability at cryopreserved cadaveric skin allografts in severe burn: A retrospective analysis. Burns, Feb. 2014, vol. 40, Issue 1, pp. 61-66.
Cooper et al., A brief history of clinical xenotransplantation, International Journal of Surgery, Nov. 2015, vol. 21, pp. 205-210.
Cooper et al., Immunobiological barriers to xenotransplantation. International Journal of Surgery (London, England), Nov. 2015, vol. 23, Issue Pt B, pp. 211-216.
Cooper et al., Pig Liver Xenotransplantation: A Review of Progress Toward the Clinic Transplantation, Oct. 2016, vol. 100, Issue 10, pp. 2039-2047.
Cooper et al., Xenotransplantation—the current status and prospects. British Medical Bulletin, Mar. 1, 2018, vol. 125, Issue 1, pp. 5-14.
Cooper, A Brief History of Cross-Species Organ Transplantation. Baylor University Medical Center Proceedings, Jan. 2012, vol. 25, Issue 1, pp. 49-57.

(56) References Cited

OTHER PUBLICATIONS

Cowan et al., The Resurgence of Xenotransplantation. American Journal of Transplantation, Oct. 2017, vol. 17, Issue 10, pp. 2531-2536.
Dalal, Philosophy of organ donation: Review of ethical facets. World Journal of Transplantation, Jun. 24, 2015, vol. 5, Issue 2, pp. 44-51.
Demange et al., Porcine endogenous retrovirus—A/C: biochemical properties of its integrase and susceptibility to raltegravir. Journal of General Virology, 2015, vol. 96, Issue 10, pp. 3124-3130.
Denner et al., Infection Barriers to Successful Xenotransplantation Focusing on Porcine Endogenous Retroviruses. Clinical Microbiology Reviews, Apr. 2012, vol. 25, Issue 2, pp. 318-343.
Denner et al., Preventing transfer of infectious agents. Nov. 2015, vol. 23, pp. 306-311.
Denner, Can Antiretroviral Drugs Be Used to Treat Porcine Endogenous Retrovirus (PERV) Infection after Xenotransplantation? Viruses, Aug. 8, 2017, vol. 9, Issue 8.
Denner, Paving the Path toward Porcine Organs for Transplantation, New England Journal of Medicine, Nov. 9, 2017, vol. 377, Issue 19, pp. 1891-1893.
Denner, Reduction of the survival time of pig xenotransplants by porcine cytomegalovirus. Virology Journal, 2018, vol. 15, Issue 1, p. 171.
Denner, Xenotransplantation—Progress and Problems: A Review, Journal of Transplantation Technologies & Research. 2014, vol. 4, Issue 2.
Deschamps et al., History of xenotransplantation. Xenotransplantation, Mar. 2005, vol. 12, Issue 2, pp. 91-109.
Dickens, Morals and legal markets in transplantable organs. Health Law Journal, 1994, vol. 2, pp. 121-134.
Dor et al., ??1,3-Galactosyltransferase Gene-Knockout Miniature Swine Produce Natural Cytotoxic Anti-Gal Antibodies:, Transplantation, Jul. 2004, vol. 78, Issue 1, pp. 15-20.
Duncan et al., Transplant-related Immunosuppression. Proceedings of the American Thoracic Society. Dec. 2005, vol. 2, Issue 5, pp. 449-455.
Durand et al., How is organ transplantation depicted in internal medicine and transplantation journals. BMC Medical Ethics, Oct. 2, 2013, vol. 14, pp. 39.
Ekser et al., Current status of pig liver xenotransplantation. International Journal of Surgery, Nov. 2015, vol. 23, pp. 240-246.
Ekser et al., The Need for Xenotransplantation as a Source of Organs and Cells for Clinical Transplantation. International Journal of Surgery (London, England), Nov. 2015, vol. 23, Issue 0 0, pp. 199-204.
Ekser et al., Pig Liver Xenotransplantation as a Bridge to Allotransplantation: Which Patients Might Benefit? Transplantation, Nov. 15, 2009, vol. 88, Issue 9, pp. 1041-1049.
Ekser et al., Progress toward clinical xenotransplantation, International Journal of Surgery (London, England), Nov. 2015, vol. 23, Issue 23, Issue Pt B, pp. 197-198.
Ekser, et al., A Novel Approach in Combined Liver and Kidney Transplantation With Long-term Outcomes. Annals of Surgery, May 2017, vol. 265, Issue 5, pp. 1000-1008.
Ericsson et al., Identification of receptors for pig endogenous retrovirus. Proceedings of the National Academy of Sciences, May 27, 2003, vol. 100, Issue 11, pp. 6759-6764.
Favier, et al., Functions of HLA-G in the immune system. Tissue Antigens, Apr. 2007, vol. 69, pp. 150-152.
Fishman et al., Transmission of Infection with Human Allografts: Essential Considerations in Donor Screening. Clinical Infectious Diseases, Sep. 1, 2012, vol. 55, Issue 5, pp. 720-727.
Fishman et al., Xenotransplantation-associated infectious risk: a WHO consultation: Xenotransplantation-associated infectious risk. Xenotransplantation, Mar. 2012, vol. 19, Issue 2, pp. 72-81.
Food and Drug Administration, Source Animal, Product, Preclinical, and Clinical Issues Concerning the Use of Xenotransplantation Products in Humans; Guidance for Industry. Zotero, Dec. 2016.
Gala et al., HIV-1 detection by nested PCR and viral culture in fresh or cryopreserved postmortem skin: potential implications for skin handling and allografting. Journal of Clinical Pathology, Jun. 1, 1997, vol. 50, Issue 6, pp. 481-484.
Gao et al., Production of $\alpha$1,3-galactosyltransferase and cytidine monophosphatc-N-acetylneuraminie acid hydroxylase gene double-deficient pigs by CRISPR/Cas9 and handmade cloning. Journal of Reproduction and Development, 2017, vol. 63, Issue 1, pp. 17-26.
Ge et al., The viability change of pigskin in vitro. Burns, Jun. 2010, vol. 36, Issue 4, pp. 533-538.
Godehardt et al., Review on porcine endogenous retrovirus detection assays-impact on quality and safety of xenotransplants. Xenotransplantation, Mar. 2015, vol. 22, Issue 2, pp. 95-101.
Goodier et al., NKG2C+ NK Cells Are Enriched in AIDS Patients with Advanced-Stage Kaposi's Sarcoma. Journal of Virology, Jan. 2007, vol. 81, Issue 1, pp. 430-433.
Gore et al., Deceased donor skin allograll baking: Response and utilization, Indian Journal of Plastic Surgery: Official Publication of the Association of Plastic Surgeons of India, Sep. 2010, vol. 43, Issue Suppl, pp. S114-S120.
Greenwood et al., Real-Time Demonstration of Split Skin Graft Inosculation and Integra Dermal Matrix Neovascularization Using Confocal Laser Scanning Microscopy, Eplasty, Aug. 20, 2009, vol. 9, pp. 309-318.
Hawley, Genetic modification of pigs by nuclear transfer. Xenotransplantation, May 2002, vol. 9, Issue 3, pp. 159-160.
Hector et al., Pre-screening of miniature swine may reduce the risk of transmitting human tropic recombinant porcine endogenous retroviruses. Xenotransplantation, May 2007, vol. 14, Issue 3, pp. 222-226.
Heneine et al., Evidence of Porcine Endogenous Retroviruses in Porcine Factor VIII and Evaluation of Transmission to Recipients with Hemophilia. The Journal of Infectious Diseases, Feb. 15, 2001, vol. 183, Issue 4, pp. 648-652.
Hermans, Porcine xenograft vs. (cryopreserved) allografts in the management of partial thickness burns: Is there a clinical difference. Burns, May 2014, vol. 40, Issue 3, pp. 408-415.
Hermans, Results of an Internet Survey on the Treatment of Partial Thickness Burns, Full Thickness Burns, and Donor Sites. Journal of Burn Care & Research, Nov. 2007, vol. 28, Issue 6, pp. 835-847.
Higginbotham et al., Pre-transplant antibody screening and anti-CD154 costimulation blockade promote long-term xenograft survival in a pig-to-primate kidney transplant model. Xenotransplantation, 2015, vol. 2, Issue 3, pp. 221-230.
Holzer et al., A Comparative Examination of The Clinical Outcome and Histological Appearance of Cryopreserved and Fresh Split-Thickness Skin Grafts, Journal of Burn Care & Research: Official Publication of the American Burn Association, Jan.-Feb. 2017, vol. 38, Issue 1, pp. e55-e61.
Hosseini et al., Xenoderm dressing in the treatment of second degree burns. Burns, Sep. 2007, vol. 33, Issue 6, pp. 776-781.
Huang et al., Mechanochemical studies of enzymatic degradation of insoluble collagen fibers. Journal of Biomedical Materials Research, Jan. 1977, vol. 11, Issue 1, pp. 137-154.
Hunt et al., HLA-G and immune tolerance in pregnancy. The FASEB Journal, May 2005, vol. 19, Issue 7, pp. 681-693.
Hunter, One organ at a time: Research has been making much progress to create in vitro human tissues for transplantation but laboratory-grown complex organs still remain decades away. EMBO reports, Mar. 1, 2014, vol. 15, Issue 3, pp. 227-230.
Iop et al., Xenotransplantation: The Way beyond and Ahead toward Clinical Application. 2018, vol. 2018, pp. 6191359.
Jo et al,. The Unreliability of MTT Assay in the Cytotoxic Test of Primary Cultured Glioblastoma Cells. Experimental Neurobiology, 2015, vol. 24, Issue 3, p. 235.
Johnson et al., Partial-thickness burns: identification and management. Advances in Skin & Wound Care, 2003. vol. 16, Issue 4, pp. 178-187; quiz 188-189.
Jones et al., Skin grafting for venous leg ulcers. The Cochrane Database of Systematic Reviews, Jan. 31, 2013, Issue 1, pp. CD001737.
Jonsen, The Ethics of Organ Transplantation: A Brief History. AMA Journal of Ethics, Mar. 1, 2012, vol. 14, Issue 3, pp. 264-268.

(56) References Cited

OTHER PUBLICATIONS

Kallinen et al., Multiple Organ Failure as a Cause of Death in Patients With Severe Burns. Journal of Burn Care & Research, Mar. 1, 2012, vol. 33, Issue 2, pp. 206-211.

Kararoudi et al., Clustered Regularly Interspaced Short Palindromic Repeats/Cas9 Gene Editing Technique in Xenotransplantation. Frontiers in Immunology, Sep. 5, 2018, vol. 9.

Kaserman, "Should we sell human organs?" Correction of a faulty analysis. Int J of Social Economics, Oct. 1, 2005, vol. 12, Issue 10, pp. 893-898.

King et al., Evidence for the expression of HLA-C class I mRNA and protein by human first trimester trophoblast. Journal of Reproductive Immunology, Oct. 1996, vol. 31, Issue 3, pp. 232-233.

King et al., Uterine NK Cells and Trophoblast HLA Class I Molecules. American Journal of Reproductive Immunology, Jun. 1997, vol. 37, Issue 6, pp. 459-462.

King, French doctors on trial for manslaughter. The Lancet, Feb. 23, 2008, vol. 371, Issue 9613, p. 637.

Kirkeby et al., Binding of <i>Griftbnia simplicifolia</i> 1 isolectin B4 (GS1 B4) to α-galactose antigens. Immunology and Cell Biology, Apr. 2001, vol. 79, Issue 2, pp. 121-127.

Kitala et al., Allogeneic vs, Autologous Skin Grafts in the Therapy of Patients with Burn Injuries: A Restrospective, Open-label Clinical Study with Pair Matching. Advances in Clinical and Experimental Medicine, 2016, vol. 25, Issue 5, pp. 923-929.

Kobayashi et al., Cadaveric Skin Allograft-Associated Cytomegalovirus Transmission in a Mouse Model of Thermal Injury. Clinical Immunology, Aug. 1999, vol. 92, Issue 2, pp. 181-187.

Kolber-Simonds et al., Production of -1,3-galactosyltransferase null pigs by means of nuclear transfer with fibroblasts bearing loss of heterozygosity mutations. Proceedings of the National Academy of Sciences, May 11, 2004, vol. 101, Issue 19, pp. 7335-7340.

Kubal et al., Prospective Monitoring of Donor-specific Anti-HLA Antibodies After Intestine/Multivisceral Transplantation: Significance of De Novo Antibodies. Transplantation, Aug. 2015, vol. 99, Issue 8, pp. e49-e56.

Lai et al., Production of α-1,3-Galactosyltransferase Knockout Pigs by Nuclear Transfer of Nuclear Transfer Cloning. Science, New Series, 2002, vol. 295, Issue 5557, pp. 1089-1092.

Lee et al., Expression of NeuGc on Pig Corneas and Its Potential Significance in Pig Corneal Xenotransplantation. Cornea, Jan. 2016, vol. 35, Issue 1, pp. 105-113.

Lee et al., HLA-E is a major ligand for the natural killer inhibitory receptor CD94/NKG2A. Proceedings of the National Academy of Sciences, Apr. 28, 1998, vol. 95, Issue 9, pp. 5199-5204.

Lee et al., The physiochemical basis for thermal and non-thermal 'burn' injuries. Burns, 1996, vol. 22, Issue 7, pp. 509-519.

Leidig-Bruckner et al., Frequency and predictors of osteoporotic fractures after cardiac or liver transplantation: a follow-up study. The Lancet, Feb. 2001, vol. 357, Issue 9253, pp. 342-347.

Leonard et al., Skin grafts from genetically modified α-1,3-galactosyltransferase knockout miniature swine: A functional equivalent to allografts. Burns: Journal of the International Society for Burn Injuries. Dec. 2017, vol. 43, Issue 8, pp. 1717-1724.

Li et al., Efficient generation of genetically distinct pigs in a single pregnancy using multiplexed single-guide RNA and carbohydrate selection. Xenotransplantation, Jan. 2015, vol. 22, Issue 1, pp. 20-31.

Lutz et al., Double knockout pigs deficient in N-glycolylneuraminic acid and Galactose α-1,3-Galactose reduce the humoral barrier to xenotransplantation. Xenotransplantation, Jan. 2013, vol. 20, Issue 1, pp. 27-35.

Manara et al., Donation after circulatory death. British Journal of Anaesthesia, Jan. 1, 2012, vol. 108, pp. 108-121.

Martin et al., Genomic presence of recombinant porcine endogenous retrovirus in transmitting miniature swine. Virology Journal, 2006, p. 6.

McGregor et al., PERVading strategies and infectious risk for clinical xenotransplantation, Xentransplantation, Jul. 2018, vol. 25, Issue 4, pp. e12402.

McGregor et al., The angiosome—an in vim study by fluorescein angiography. British Journal of Plastic Surgery, , Apr. 1992, vol. 45. Issue 3, pp. 219-221.

McLafferty et al., The integumentary system: anatomy, physiology and function of skin. Nursing Standard (Royal College of Nursing (Great Britain): 1987), Sep. 19-25, 2012, vol. 27, Issue 3, pp. 35-42.

Mulder et al., Johann "Hans" Ehrenhaft (1915-2009): (The Ultimate) Renaissance Mentor. The Annals of Thoracic Surgery, vol. 89, Issue 4, pp. 1337-1338.

Nakajima et al., A New Concept of Vascular Supply to the Skin and Classification of Skin Flaps According to Their Vascularization. Annals of Plastic Surgery, Jan. 1986, vol. 16, Issue 1, pp. 1-19.

Nathan et al., Organ donation in the United States. American Journal of Transplantation, Apr. 2003, vol. 3, Issue S4, pp. 20-40.

Nekrep et al., When the Lymphocyte Loses its Clothes. Immunity, Apr. 2003, vol. 18, Issue 4, pp. 453-457.

Office of Regulatory Affairs, Expiration Dating and Stability Testing for Human Drug Products. FDA, Nov. 3, 2018.

Padler-Karavani et al., Potential impact of the non-human sialic acid N-glycolylneuraminic acid on transplant rejection risk: Invited Commentary. Xenotransplantation, Jan. 2011, vol. 18, Issue 1, pp. 1-5.

Paradis et al., Search tor cross-species transmission of porcine endogenous retrovirus in patients treated with living pig tissue. The XEN 111 Study Group, Science (New York, N.Y.), Aug. 20, 1999, vol. 285, Issue 5431, pp. 1236-1241.

Petitdemange et al., Unconventional Repetoire Profile Is Imprinted during Acute Chikungunya Infection for Natural Killer Cells Polarization toward Cytotoxicity, PLoS Pathogens, Sep. 22, 2011, vol. 7, Issue 9, pp. e1002268.

Petrini, Ethical and legal considerations regarding the ownership and commercial use of human biological materials and their derivatives. Journal of Blood Medicine, Aug. 7, 2012, vol. 3, pp. 87-96.

Petruzzo et al., Outcomes After Bilateral Hand Allotransplantation: A Risk/Benefit Ratio Analysis. Ann Surg, 2014.

Pfeiffer et al., Hyperacute lung rejection in the pig-to-human model. III. platelet receptor inhibitors synergistically modulate complement activation and lung injury;. Transplantation, Apr. 2003, pp. 953-959.

Pirnay et al., Beware of the commercialization of human cells and tissues: situation in the European Union. Cell and Tissue Banking, Aug. 2012, vol. 13, Issue 3, pp. 487-498.

Pirnay et al., HIV transmission by transplantation of allograft skin: a review of the literature. Burns: Journal of the International Society for Burn Injuries, Feb. 1997, vol. 23, Issue 1, pp. 1-5.

Platt et al., The Future Promises of Xenotransplantation a,b. Annals of the New York Academy of Sciences, Dec. 1998, vol. 862, Issue 1, pp. 5-18.

Powell et al., Creating effective biocontainment facilities and maintenance protocols for raising specific pathogen-free, severe combined immunodeficient (SCID) pigs. Laboratory Animals, Aug. 2018, vol. 52, Issue 4, pp. 402-412.

Rappaort et al., Early use of xenografts as a biologic dressing in burn trauma. The American Journal of Surgery, Aug. 1970, vol. 120, Issue 2, pp. 144-148.

Reyes et al., Charaterization of swine leucocyte antigen alleles in a crossbred pig to be used in xenotransplant studies. Tissue Antigens, 2014, vol. 84, Issue 5, pp. 484-488.

Reyes et al., Creating Class I MHC-Null Pigs Using Guide RNA and the Cas9 Endonuclease, The Journal of Immunology, Dec. 1, 2014, vol. 193, Issue 11, pp. 5751-5757.

Rheinwald et al., Serial Cultivation of Strains of Human Epidermal Keratinocytes: the Formation of Keratinizing Colonies from Single Cells. Cell, Nov. 1975, vol. 6, pp. 331-344.

Rithalia et al., Impact of presumed consent for organ donation on donation rates. A systematic review. BMJ, Jan. 15, 2009, vol. 338, pp. a3162.

Rubin, Impact of cytomegalovirus infection on organ transplant recipients. Reviews of Infectious Diseases, Sep. Oct. 1990, vol. 12. Suppl 7, pp. S754-S766.

Sachs et al., Induction of Tolerance through Mixed Chimerism. Cold Spring Harbor Perspectives in Medicine, Jan. 1, 2014, vol. 4, Issue 1, pp. a015529-a015329.

(56) References Cited

OTHER PUBLICATIONS

Sachs, The lure of transplantation. Clinical Transplants 2008 edition, 2008, pp. 287-305.
Saidi et al., Challenges of Organ Shortage for Transplantation: Solutions and Opportunities. International Journal of Organ Transplantation Medicine. 2014, vol. 5, Issue 3, pp. 87-96.
Schook et al., Unraveling the swine genome: implications for human health. Annual Review of Animal Biosciences, 2015, vol. 3, pp. 219-244.
Schulz, Necrotizing Fasciitis: Background, Pathophysiology, Etiology. eMedicine, Feb. 2, 2019, https://emedicine.medscape.com/article/2051157-overview.
Scobie et al., Long-Term 1gG Response to Porcine Neu5Gc Antigens without Transmission of PERV in Burn Patients Treated with Porcine Skin Xenografts. The Journal of Immunolology, Sep. 15, 2013, vol. 191, Issue 6, pp. 2907-2915.
Shafran et al., Organ Shortage: The Greatest Challenge Facing Transplant Medicine. World Journal of Surgery, Jul. 2014, vol. 38, Issue 7, pp. 1650-1657.
Shaw et al., Xenotransplantation: Steps toward Clinical Application. Clinical Journal of the American Society of Nephrology, Apr. 5, 2019, vol. 14, Issue 4, pp. 620-622.
Sheridan e al., Skin Substitutes in Burns, Burns, 1999, vol. 25, pp. 97-103.
Sheridan, Closure of the Excised Wound: Autografts, Semipermanent Skin Substitutes, and Permanent Skin Substitutes. Clinics in Plastic Surgery, Oct. 2009, vol. 36, Issue 4, pp. 643-651.
Shlobin et al., Persistent cytomegalovirus-specific memory responses in the lung allograft and blood following primary infection in lung transplant recipients. Journal of Immunology (Baltimore, Md.: 1950), Feb. 15, 2006, vol. 176, Issue 4, pp. 2625-2634.
Siemionow et al., Nerve Allograft Transplantation—A Review. Journal of Reconstructive Microsurgery, Nov. 2007, vol. 23, Issue 8, pp. 511-520.
Snyderman et al., Prolonged Skin Homograft and Heterograft Survival in Patients with Neoplastic Disease. Plastic and Reconstructive Surgery, Oct. 1960, vol. 26, Issue 4, p. 373.
Spurgeon, French doctors are tried for treating children with infected growth hormone. British Medical Journal, Feb. 16, 2008, vol. 336, Issue 7640, pp. 348-349.
Stewart, The fire at Cocoanut Grove. Journal of Burn Care & Research: Official Publication of the American Burn Association, Jan.-Feb. 2015, vol. 36, Issue 1, pp. 232-235.
Takefman et al., Detection and Characterization of Porcine Endogenous Retrovirus in Porcine Plasma and Porcine Factor VIII, Journal of Virology, May 15, 2001, vol. 75, Issue 10, pp. 4551-4557.
Takeo et al., Wound Healing and Skin Regeneration. Cold Spring Harbor Perspectives in Medicine, Jan. 1, 2015, vol. 5, Issue 1, pp. a023267-a023267.
Taniguchi et al., Clinical xenotransplantation: past, present and future. Annals of the Royal College of Surgeons of England. Jan. 1997, vol. 79, Issue 1, pp. 13-19.
Tavis et al., Graft Adherence to De-epithelialized Surfaces: A Comparative Study. Annals of Surgery, Nov. 1976, vol. 184, Issue 5, pp. 594-600.
Tector, New Hope for Liver Xenontransplantation. Annals of Surgery, Jun. 2016, vol. 263, Issue 6, pp. 1072.
Thornton et al., Skin Grafts and Skin Substitutes and Principles of Flaps. Selected Readings in Plastic Surgery, 2004, vol. 10, Issue 1, pp. 16-19.

Troöhler, Emil Theodor Kocher (1841-1917), Journal of the Royal Society of Medicine , Sep. 2014, vol. 107, Issue 9, pp. 376-377.
US Department of Health & Human Services FDA, Guidance for Industry, Current Good Tissue Practice (CGTP) and Additional Requirements for Manufacturers of Human Cells, Tissues, and Cellular and Tissue-Based Products (HCT/Ps). Zotero, Dec. 2011, p. 67.
Wadman, FDA 'fails to keep track of transplant patients'. Nature, Jan. 1998. vol. 391, Issue 5, p. 315.
Wang et al., Erythrocytes from GGTA1/CMAH knockout pigs: implications for xenotransfusion and testing in non-human primates. Xenotransplantation , Jul.-Aug. 2014, vol. 21, Issue 4, pp. 376-384.
Wang et al., Immunogenicity of Renal Microvascular Endothelial Cells From Genetically Modified Pigs. Transplantation, Jan. 30, 2016, vol. 100, Issue 3, pp. 533-537.
Warnecke et al., Normothermic perfusion of donor lungs for preservation and assessment with the Organ Care System Lung before bilateral transplantation: a pilot study of 12 patients. The Lancet, Nov. 2012, vol. 380, Issue 9856, pp. 1851-1858.
Watson et al., Organ transplantation: historical perspective and current practice. British Journal of Anaesthesia, Jan. 2012, vol. 108, pp. i29-i42.
Weathers et al., Full-Thickness Skin Grafting in Nasal Reconstruction. Seminars in Plastic Surgery, Aug. 14, 2013, vol. 27, Issue 2, pp. 090-095.
Weiner et al., Prolonged survival of GalT—KO swine on baboons. Xenotransplantation, Mar. 2010, vol. 17, Issue 2, pp. 147-152.
Wendler et al., The Consent Process for Cadaveric Organ Procurement: How Does it Work? How Can it Be Improved? JAMA, Jan. 17, 2001, vol. 285, Issue 3, pp. 329-333.
Wilhelm et al., Susceptibility of recombinant porcine endogenous retrovirus reverse transcriptase to nucleoside and non-nucleoside inhibitors. Cellular and Molecular Life Sciences (CMLS), Dec. 1, 2002, vol. 59, Issue 12, pp. 2184-2190.
Wojda et al., Keys to successful organ procurement: An experience-based review of clinical practices at a high-performing health-care organization. International Journal of Critical Illness and Injury Science, 2017, vol. 7, Issue 2, pp. 91-100.
Wolf et al., Comparison between civilian burns and combat burns from Operation Iraqi Freedom and Operation Enduring Freedom. Ann Surg, 2006, vol. 243, pp. 786.
Wood et al., The use of cultured epithelial autograft in the treatment of major burn injuries: A critical review of the literature, Burns, Jun. 2006, vol. 32, Issue 4, pp. 395-401.
Wood et al., The use of pigskin in the treatment of thermal burns. The American Journal of Surgery, Dec. 1972, vol. 124, Issue 6, pp. 720-723.
Wynyard et al., Microbiological safety of the first clinical pig islet xenotransplantation trial in New Zealand. Xenotransplantation,, Jul. 2014, vol. 21, Issue 4, pp. 309-323.
Yannas et al., Correlation of in vivo collagen degradation rate within vitro measurernents. Journal of Biomedical Materials Research, Nov. 1975, vol. 9, Issue 6, pp. 623-628
Yue et al., A study on the susceptibility of allogeneic human hepatocytes to porcine endogenous retrovirus. European review for medical and pharmacological sciences, Sep. 2015, vol. 19, Issue 18, pp. 3481-3491.
Zuo et al., Observation of viable alloskin vs xenoskin grafted onto subcutaneous tissue wounds after tangential excision in massive burns. Burns & Trauma, Dec. 2016, vol. 4, Issue 1.

* cited by examiner

| TABLE 1. | HLA: The Most Polymorphic (Diverse) Genes in the Human Genome | | |
|---|---|---|---|
| | Target of anti-HLA Antibodies | | |
| HLA Gene | Serological antigens[a] | Proteins | Alleles[b] |
| Class I | | | |
| A | 28 | 2703 | 3830 |
| B | 62 | 3408 | 4647 |
| C | 10 | 2391 | 3382 |
| Class II | | | |
| DRA | 24 | 2 | 7 |
| DRB1 | 24 | 1465 | 2011 |
| DQA1 | 9 | 34 | 77 |
| DQB1 | 9 | 727 | 1054 |
| DPA1 | Undefined | 22 | 44 |
| DPB1 | Undefined | 615 | 740 |

[a]Serological antigens according to the World Health Organization.
[b]Not including null alleles.

FIG. 7

Composite Genetic Alteration Design for "Humanization" of Extracellular Porcine Cell Expression
via Reprogramming at Endogenous Genetic Targets

| | HUMAN GENE | SWINE GENE | REPROGRAMMING EFFECT | SITE-DIRECTED MUTAGENIC SUBSTITUTION ACTION |
|---|---|---|---|---|
| 1. | HLA-A | SLA-1 | Silencing | Replacement with stop codon |
| 2. | HLA-B | SLA-2 | Silencing | Replacement with stop codon |
| 3. | HLA-C | SLA-3 | Humanizing | Replacement with "human-capture" reference sequence |
| 4. | HLA-E | SLA-6 | Humanizing | Replacement with "human-capture" reference sequence |
| 5. | HLA-F | SLA-7 | Humanizing | Replacement with "human-capture" reference sequence |
| 6. | HLA-G | SLA-8 | Humanizing | Replacement with "human-capture" reference sequence |
| 7. | MIC-A | MIC-2 | Humanizing | Replacement with "human-capture" reference sequence |
| 8. | HLA-DR HLA-DRA1 HLA-DRB1 | SLA-DR SLA-DRA SLA-DRB1 | Silencing | Replacement with stop codon |
| 9. | HLA-DQ HLA-DQA1 HLA-DQB1 | SLA-DQ SLA-DQA SLA-DQB1 | Humanizing | Replacement with "human-capture" reference sequence |
| 10. | B2M (Single Copy) | B2M (Copy 1) B2M (Copy 2) | Humanizing Silencing | Replacement with "human-capture" reference sequence Replacement with stop codon |

FIG. 14

| | | | |
|---|---|---|---|
| 11. | CTLA-4 | Humanizing/Upregulation | Replacement with "human-capture" reference sequence |
| 12. | PD-L1 (CD274) | Humanizing/Upregulation | Replacement with "human-capture" reference sequence |
| 13. | PROCR (CD201) | Humanizing | Replacement with "human-capture" reference sequence |
| 14. | THBD (CD141) | Humanizing | Replacement with "human-capture" reference sequence |
| 15. | TFPI | Humanizing | Replacement with "human-capture" reference sequence |
| 16. | GGTA1 | Silencing | Replacement with stop codon |
| 17. | CMAH | Silencing | Replacement with stop codon |
| 18. | B4GALNT2 | Silencing | Replacement with stop codon |

| | | Start | End | Start Phase | End Phase | Length | Sequence |
|---|---|---|---|---|---|---|---|
| (SEQ ID NO: 16)<br>(SEQ ID NO: 17) | 2 ENSSSSCE00045085054<br>Intron 2-3 | 763,484<br>763,754 | 763,753<br>767,861 | 1 | 1 | 270<br>4,108 | ACACAACTACCAGATAGAGGAAGGCACGACCCTGCAGCCGGCGAG<br>GTGAGTGCCTGCCCGCCCGCCCGGG..........TTTTCCGTCGTGTTACTCCCCCAG<br>TGCAACTGGCCAGAGCTGACTATCCCCATCCAAGGCAGAGGCTCTAAACCACCAACCTGGTGGCTTGTGCGGTGGTTGTGCGGGTGACAGATTTCTATCCAAGCCAGGTGAAAGTCCAGTGGTTCCG<br>GAATGGCCAGAGCAGACACCTGCCAGCACACTGCAGGAGCTCCACTCGGAATGGCAACTAGAGACTGGACCACCAGCTGCTGCTGTGCGGTGGATCGCTGATGCTAGAGATGAATCTCCAGCGACGAGAGTGCTGCAA |
| (SEQ ID NO: 18) | 3 ENSSSSCE00045085973<br>3' downstream sequence | 767,862<br>763,754 | 768,143 | 1 | 1 | 282 | CACCCTGGCCGCCTGCGAGCACTCCAGC CTCCAAGAGCCCCATCTTGGCTGGGAGTGGC<br>GT.... |
| SLA-DQB1-203 No Exon / Intron | | Start | End | Start Phase | End Phase | Length | Sequence |
| | 5' upstream sequence | | | | | | ...AG<br>AGGATTTCGTCTACCAGTTTAAGTTGAGTCAGTGCCTACTTCTCAACGGACGGCAGGGTGCGCTCTTGACCAGATACATCTACCAGGAGCAGCAGCCACGTCCCTCGCGTTGACAGCAA<br>CGTGGGGGAGTACCACCAGTTCCTGCAGGCGGTGACCCCGCGCCTGGGGCGGCCACTCCCAGAGGAGGAGCTCCTGGAAGGCAACCGCCAGCTACCTGGACTGGAACTCTGGACACTGTGCAGAA |
| (SEQ ID NO: 19)<br>(SEQ ID NO: 20) | 2 ENSSSSCE00045085054<br>Intron 2-3 | 763,484<br>763,754 | 763,753<br>767,861 | 1 | 1 | 270<br>4,108 | ACACAACTACCAGATAGAGGAAGGCACGACCCTGCAGCCGGCGAG<br>GTGAGTGCCTGCCTGCCTGTTACTCCCCCAG..........TTTTCCGTCGTGTTACTCCCCCAG<br>TGCAACTGGCCAGAGCTGACTATCCCCATCCAAGGCAGAGGCTCTAAACCACCAACCTGGTGGCTTGTGCGGTGGTTGTGCGGGTGACAGATTTCTATCCAAGCCAGGTGAAAGTCCAGTGGTTCCG<br>GAATGGCCAGAGCAGACACCTGCCAGCACACTGCAGGAGCTCCACTCGGAATGGCAACTAGAGACTGGACCACCAGCTGCTGCTGTGCGGTGGATCGCTGATGCTAGAGATGAATCTCCAGCGACGAGAGTGCTGCAA |
| (SEQ ID NO: 21) | 3 ENSSSSCE00045085973<br>3' downstream sequence | 767,862 | 768,143 | 1 | 1 | 282 | CACCCTGGCCGCCCGCTGCGAGC CTCCAAGAGCCCCATCTTGGCTGGGAGTGGC<br>GT.... |
| SLA-DQB1-204 No Exon / Intron | | Start | End | Start Phase | End Phase | Length | Sequence |
| | 5' upstream sequence | | | | | | ...AG<br>AGGATTTCGTCTACCAGTTTAAGTTGAGTCAGTGCCTACTTCTCAACGGACGGCAGGGTGCGCTCTTGACCAGATACATCTACCAGGAGCAGCAGCCACGTCCCTCGCGTTGACAGCAA<br>CGTGGGGGAGTACCACCAGTTCCTGCAGGCGGTGACCCCGCGCCTGGGGCGGCCACTCCCAGAGGAGGAGCTCCTGGAAGGCAACCGCCAGCTACCTGGACTGGAACTCTGGACACTGTGCAGAA |
| (SEQ ID NO: 22)<br>(SEQ ID NO: 23) | 2 ENSSSSCE00045085054<br>Intron 2-3 | 763,484<br>763,754 | 763,753<br>767,861 | 1 | 1 | 270<br>4,108 | ACACAACTACCAGATAGAGGAAGGCACGACCCTGCAGCCGGCGAG<br>GTGAGTGCCTGCCTGCCTGTTACTCCCCCAG..........TTTTCCGTCGTGTTACTCCCCCAG<br>TGCAACTGGCCAGAGCTGACTATCCCCATCCAAGGCAGAGGCTCTAAACCACCAACCTGGTGGCTTGTGCGGTGGTTGTGCGGGTGACAGATTTCTATCCAAGCCAGGTGAAAGTCCAGTGGTTCCG<br>GAATGGCCAGAGCAGACACCTGCCAGCACACTGCAGGAGCTCCACTCGGAATGGCAACTAGAGACTGGACCACCAGCTGCTGCTGTGCGGTGGATCGCTGATGCTAGAGATGAATCTCCAGCGACGAGAGTGCTGCAA |
| (SEQ ID NO: 24) | 3 ENSSSSCE00045085973<br>3' downstream sequence | 767,862 | 768,143 | 1 | 1 | 282 | CACCCTGGCCGCCCGCTGCGAGCACTCCAGC CTCCAAGAGCCCCATCTTGGCTGGGAGTGGC<br>GT.... |

| SLA-DQB1-205 | No. Exon / Intron | Start | End | Start Phase | End Phase | Length | Sequence |
|---|---|---|---|---|---|---|---|
| (SEQ ID NO: 120) | 5' upstream sequence | | | | | | ............CGGGGGCCGGCAGCGCCGGGCACCGGCCCGGCTTGGGGGCGGGGGTTTCAGTGCG |
| (SEQ ID NO: 121) | 1 ENSSSCE00045086917 | 763,384 | 763,753 | . | 1 | 370 | ATGGGCCCAGCTGGCCAGTTTAAGTTCGTGACCAGTTTCAGTGCACAGCGCCTACTTCTTCAACGGAACGTCCTGGGCGGCAGCTGGCCAGCCTGACGCCGAGCCTGAGGCCCTGAGCGCTGGGGCAGCCTGGCAGGGAGCCCAGGGAGCCCAGGGATCTCCCCCAGAG<br>GATTTCGTGACCAGTTAAGTTCGTGAGTTCGAGTTTGAGTTCGAGTTCGAGTTCAACGGAACGTCCTGGGCCGACATCTACAACAGGAGGAGCAGCACCTGCGCCTTC<br>GACAGCAACCTGGGGGAGTACCGGGCGGTACCCCGCTGGGCCGCCGGGACTACTGGAACGGCCAGAAGGGCAGGAGCTCCTGACTGGAACCTGGACAGAGCACCCCGGAGCCCGA<br>GCTGGACACTGTGTGCAAACACAACTACCAGATAGAGGAAGGCACGACGACCCCTGCAGGGGCGAG |
| (SEQ ID NO: 122) | Intron 1-2 | 763,754 | 767,881 | | | 4,108 | GTGAGTGCCTGCCCGCCCGCCTCAG............TTTTTCCCGTCCTGTTACTCCCCTCAG<br>TGCAACCTACAGTGACTACTCCCCATCCAGCCAGCAGGCCTCTAAACACCTCACACCTCTGCCTGCAGATTTCATCCAAGCCAGGTGAAAAGTCC<br>AGTGGTTCCGGAATGGCCAGGAGGAGACAGGCTGGCGTTGTGTCCACTCCTTATTAGGAATGGAGACTGGACCTACCAGGTGCTCGTAGCTAGAGATGAAT<br>CTTCAGCGCAGAGCGAGGCAGGCACTGGCCGCCGTCCCGGCGCAGAGCTCCAGCCATCCTGGTTGGTGGCGCAGCAGTCACTCAGCCCTGGACATACTCACTGGGCACTGAGTGCTG<br>GCCCTCGAGAACAGAGGCCATCAGCACAGGCAGCTTTCAGATCCTGGAGTGCCTGCCCAGAGCCCCAGGCCCCCCTGCCCCAGCGAGCCTCCCACTCGTCCAGGGAGCTATTTGGCT<br>TTCCCAATGCCCAGTTCCGGGGTGACAACAGGGGTTCCCTGGCCCCGGGCACACAGTCACAGAGGAGCAGGATCCATTTTCCTTCCTACCTGAAATCCAGCTAGCAACTTCAGGGCCTCATAAAGGAGCACCATGG<br>GGTCCCTGCTGGTGCTGACAAACCTGACATTTGGGCTTCCCAGGCCGCAGCACAGTGCTGAGCTCGAGGCAAGAGCGCGAGCGGTCTGGCAGCGCGGAACTCCCGGAGCCTCCCGCTCAGGG<br>TGATCTTCCCCGGGCTGCCCTGGGCTTTCATCCCCGCCACGAGGTCACAGAGGTAAGGACGCACAGAGCAACAAACAAAATAATCAGGGAGCAACAATGAGTGCTCGA<br>AGGCCTTGCTCTCCTAGAGAGGCTTCCTAGAGAGCCTTTCCTCAGTCAGACCCGTGACAGAGGTGAGTGAGGTTTATTTCAGGGCAGAACCTATTTGCATCAGTTGTGGGA<br>TTTCACTGATTGATTGAAAGCTAGCCCAGGCAGGAATATCAGCCTTGCCTTCCTTTGGGTAGCCGTGAGACACTGCCATGAGACACTCAGGAGGATTTATTTGTGGGA<br>CACTTAAGGGCCTTGTGGCTAGGAGGGAATAATTCACCTGAGGCTCCTTTGGGGTAGCCGTGAGACACTCAGGAGACGGCGAGCAGGCGAGGAGCCTCCTTGAGCT<br>CCTCCTGGGCAGCTAGTAATGTTTGTCAGCCTCTTGCATCAGCCTAGCAGCGCCATGAGCGCCATGAGCGGCCCTG |
| (SEQ ID NO: 123)<br>(SEQ ID NO: 124) | 2 ENSSSCE00045087028<br>3' downstream sequence | 767,882 | 769,302 | 1 | . | 1,441 | CATTCACGAGCCTATTTACTTCTTCGTGGGATCCAGACTTAGGGAGCAGCGAGTTGCTTCAGTTTGCACCACTCGAAGCTG<br>TTCCCCAGAACCAGGCCATAACTTGGTGGCACCTTTCTCGAAGCTGGG............ |

Transcript: SLA-DQB1-201 ENSSCT00045019436.1

Description Sus scrofa SLA-DQ beta1 domain (SLA-DQB1), mRNA, [Source:RefSeq mRNA;Acc:NM_001113694]

Gene Synonyms SLA-DQB,SLADQB

Location *Primary assembly LUXT01028933.1:761,972-770,496 forward stand.*

About this transcript This transcript has *4 exons* and is annotated with *14 domains and features.*

Gene This transcript is a product of gene ENSSSCG00045011379.1   Show transcript table

Summary ⓘ

Statistics Exons: 4, Coding exons: 3. Transcript length: 1,690 bps. Translation length: 255 residues
Version ENSSSCT00045019436.1
Type Protein coding
Annotation Method Annotation produced by the Ensembl *genebuild.*

FIG. 22

| Show All entries | | | Show/hide columns | | |
|---|---|---|---|---|---|
| No. | Exon / Intron | Start | End | Status Phase End Phase | Length |
| | 5' upstream sequence | | | | |
| 1 | ENSE00001766857 | 32,605,178 | 32,605,317 | - 1 | 140 |
| | Intron 1-2 | 32,605,318 | 32,609,086 | | 3,769 |
| 2 | ENSE00003527459 | 32,609,087 | 32,609,335 | 1 1 | 249 |
| | Intron 2-3 | 32,609,336 | 32,609,748 | | 413 |
| 3 | ENSE00003658074 | 32,609,749 | 32,610,030 | 1 1 | 282 |
| | Intron 3-4 | 32,610,031 | 32,610,386 | | 356 |
| 4 | ENSE00003566368 | 32,610,387 | 32,610,561 | 1 - | 175 |
| | Intron 4-5 | 32,610,562 | 32,611,069 | | 508 |
| 5 | ENSE00001802247 | 32,611,070 | 32,611,429 | - - | 360 |
| | 3' downstream sequence | | | | |

FIG. 24

HLA vs HLA (DQ-A, Exon 2) Nucleotide Sequence Library

| Source | Descriptor | Location | Allele Designator | 10 | 20 |
|---|---|---|---|---|---|
| HLAAlleles.Org | 9.05% USA | Exon 2 | DQA1*01:01:01:01 | CTGACCACGT | TGCCTCTTGT |
| HLAAlleles.Org | 14.17% USA | Exon 2 | DQA1*01:02:01:01 | CTGACCACGT | TGCCTCTTGT |
| HLAAlleles.Org | 13.14% USA | Exon 2 | DQA1*05:01:01:01 | CTGACCACGT | CGCCTCTTAT |
| HLAAlleles.Org | 11.08% USA | Exon 2 | DQA1*02:01:01:01 | CTGACCACGT | TGCCTCTTAC |
| | | | | | |
| Ubiguity_DQA1 | 19 (Allele 1), 57 (Allele 1) | Exon 2 | DQA1*01:01:01 | CTGACCACGT | TGCCTCTTGT |
| Ubiguity_DQA1 | 50 (Allele 1, 2) | Exon 2 | DQA1*01:02:01 | CTGACCACGT | TGCCTCTTGT |
| Ubiguity_DQA1 | 19 (Allele 2), 29 (Allele 1) | Exon 2 | DQA1*05:01:01 | CTGACCACGT | CGCCTCTTAT |
| Ubiguity_DQA1 | 11 (Allele 1 & 2) | Exon 2 | DQA1*05:05:01 | CTGACCACGT | CGCCTCTTAT |
| Ubiguity_DQA1 | 57 (Allele 2) | Exon 2 | DQA1*03:03:01 | CTGACCATGT | TGCCTCTTAC |

| Source | | | | 100 | 110 |
|---|---|---|---|---|---|
| HLAAlleles.Org | 9.05% USA | Exon 2 | DQA1*01:01:01:01 | TCTACGTGGA | CCTGGAGAGG |
| HLAAlleles.Org | 14.17% USA | Exon 2 | DQA1*01:02:01:01 | TCTACGTGGA | CCTGGAGAGG |
| HLAAlleles.Org | 13.14% USA | Exon 2 | DQA1*05:01:01:01 | TCTACGTGGA | CCTGGGGAGG |
| HLAAlleles.Org | 11.08% USA | Exon 2 | DQA1*02:01:01:01 | TCTATGTGGA | CCTGGAGAGG |
| | | | | | |
| Ubiguity_DQA1 | 19 (Allele 1), 57 (Allele 1) | Exon 2 | DQA1*01:01:01 | TCTACGTGGA | CCTGGAGAGG |
| Ubiguity_DQA1 | 50 (Allele 1, 2) | Exon 2 | DQA1*01:02:01 | TCTACGTGGA | CCTGGAGAGG |
| Ubiguity_DQA1 | 19 (Allele 2), 29 (Allele 1) | Exon 2 | DQA1*05:01:01 | TCTACGTGGA | CCTGGGGAGG |
| Ubiguity_DQA1 | 11 (Allele 1 & 2) | Exon 2 | DQA1*05:05:01 | TCTACGTGGA | CCTGGGGAGG |
| Ubiguity_DQA1 | 57 (Allele 2) | Exon 2 | DQA1*03:03:01 | TCTATGTGGA | CCTGGAGAGG |

| Source | | | | 190 | 200 |
|---|---|---|---|---|---|
| HLAAlleles.Org | 9.05% USA | Exon 2 | DQA1*01:01:01:01 | ACATGGCTGT | GGCAAAACAC |
| HLAAlleles.Org | 14.17% USA | Exon 2 | DQA1*01:02:01:01 | ACATGGCTGT | GGCAAAACAC |
| HLAAlleles.Org | 13.14% USA | Exon 2 | DQA1*05:01:01:01 | ACATCGCTGT | CCTAAAACAT |
| HLAAlleles.Org | 11.08% USA | Exon 2 | DQA1*02:01:01:01 | ACATCGCTGT | GCTAAAACAT |
| | | | | | |
| Ubiguity_DQA1 | 19 (Allele 1), 57 (Allele 1) | Exon 2 | DQA1*01:01:01 | ACATGGCTGT | GGCAAAACAC |
| Ubiguity_DQA1 | 50 (Allele 1, 2) | Exon 2 | DQA1*01:02:01 | ACATGGCTGT | GGCAAAACAC |
| Ubiguity_DQA1 | 19 (Allele 2), 29 (Allele 1) | Exon 2 | DQA1*05:01:01 | ACATCGCTGT | CCTAAAACAT |
| Ubiguity_DQA1 | 11 (Allele 1 & 2) | Exon 2 | DQA1*05:05:01 | ACATCGCTGT | CCTAAAACAT |
| Ubiguity_DQA1 | 57 (Allele 2) | Exon 2 | DQA1*03:03:01 | ACATCGCTGT | GCTAAAACAT |

FIG. 25A

```
           30         40         50         60        70         80         90
    GGTGTAAACT TGTACCAGTT TTACGGTCCC TCTGGCCAGT ACACCCATGA ATTTGATGGA GATGAGGAGT
    GGTGTAAACT TGTACCAGTT TTACGGTCCC TCTGGCCAGT ACACCCATGA ATTTGATGGA GATGAGCAGT
    GGTGTAAACT TGTACCAGTC TTACGGTCCC TCTGGCCAGT ACACCCATGA ATTTGATGGA GATGAGCAGT
    GGTGTAAACT TGTACCAGTC TTACGGTCCC TCTGGCCAGT TCACCCATGA ATTTGATGGA GATGAGGAGT

GGTGTAAACT TGTACCAGTT TTACGGTCCC TCTGGCCAGT ACACCCATGA ATTTGATGGA GATGAGGAGT
    GGTGTAAACT TGTACCAGTT TTACGGTCCC TCTGGCCAGT ACACCCATGA ATTTGATGGA GATGAGCAGT
    GGTGTAAACT TGTACCAGTC TTACGGTCCC TCTGGCCAGT ACACCCATGA ATTTGATGGA GATGAGCAGT
    GGTGTAAACT TGTACCAGTC TTACGGTCCC TCTGGCCAGT ACACCCATGA ATTTGATGGA GATGAGCAGT
    GGTGTAAACT TGTACCAGTC TTATGGTCCC TCTGGCCAGT ACAGCCATGA ATTTGATGGA GACGAGGAGT 120        130        140       150        160        170        180
    AAGGAGACTG CCTGGCGGTG GCCTGAGTTC AGCAAATTTG GAGGTTTTGA CCCGCAGGGT GCACTGAGAA
    AAGGAGACTG CCTGGCGGTG GCCTGAGTTC AGCAAATTTG GAGGTTTTGA CCCGCAGGGT GCACTGAGAA
    AAGGAGACTG TCTGGTGTTT GCCTGTTCTC AGACAATTTA GAT---TTGA CCCGCAATTT GCACTGACAA
    AAGGAGACTG TCTGGAAGTT GCCTCTGTTC CACAAATTTG GAT---TTGA CCCGCAATTT GCACTGACAA

AAGGAGACTG CCTGGCGGTG GCCTGAGTTC AGCAAATTTG GAGGTTTTGA CCCGCAGGGT GCACTGAGAA
    AAGGAGACTG CCTGGCGGTG GCCTGAGTTC AGCAAATTTG GAGGTTTTGA CCCGCAGGGT GCACTGAGAA
    AAGGAGACTG TCTGGTGTTT GCCTGTTCTC AGACAATTTA GAT---TTGA CCCGCAATTT GCACTGACAA
    AAGGAGACTG TCTGGTGTTT GCCTGTTCTC AGACAATTTA GAT---TTGA CCCGCAATTT GCACTGACAA
    AAGGAGACTG TCTGGCAGTT GCCTCTGTTC CGCAGATTTA GAAGATTTGA CCCGCAATTT GCACTGACAA 210        220        230        240        250
    AACTTGAACA TCATGATTAA ACGCTACAAC TCTACCGCTG CTACCAATG  (SEQ ID NO: 168)
    AACTTGAACA TCATGATTAA ACGCTACAAC TCTACCGCTG CTACCAATG  (SEQ ID NO: 169)
    AACTTGAACA GTCTGATTAA ACGCTCCAAC TCTACCGCTG CTACCAATG  (SEQ ID NO: 170)
    AACTTGAACA TCCTGATTAA ACGCTCCAAC TCTACCGCTG CTACCAATG  (SEQ ID NO: 171)

AACTTGAACA TCATGATTAA ACGCTACAAC TCTACCGCTG CTACCAATG  (SEQ ID NO: 136)
    AACTTGAACA TCATGATTAA ACGCTACAAC TCTACCGCTG CTACCAATG  (SEQ ID NO: 139)
    AACTTGAACA GTCTGATTAA ACGCTCCAAC TCTACCGCTG CTACCAATG  (SEQ ID NO: 138)
    AACTTGAACA GTCTGATTAA ACGCTCCAAC TCTACCGCTG CTACCAATG  (SEQ ID NO: 133)
    AACTTGAACA TCCTGATTAA ACGCTCCAAC TCTACCGCTG CTACCAATG  (SEQ ID NO: 137)
```

FIG. 25A (Cont.)

HLA vs SLA (DQ-A, Exon 2) Nucleotide Sequence Library with Complete Divergence

| Source | Descriptor | Location | Allele Designator | | | | | | | | | |
|---|---|---|---|---|---|---|---|---|---|---|---|---|
| | | | | 10 | 20 | 30 | 40 | 50 | 60 | 70 | 80 | 90 |
| HLAAlleles.Org | 9.05% USA | Exon 2 | DQA1*01:01:01:01 | CTGACCAGT | TGCCTCTTGT | GGTGTAAACT | TGTACCAGT | TTACGTCCC | TCTGGCCAGT | ACACCCATGA | ATTTGATGGA | GATGAGGAGT |
| HLAAlleles.Org | 14.17% USA | Exon 2 | DQA1*01:02:01:01 | CTGACCAGT | TGCCTCTTGT | GGTGTAAACT | TGTACCAGT | TTACGTCCC | TCTGGCCAGT | ACACCCATGA | ATTTGATGGA | GATGAGGAGT |
| HLAAlleles.Org | 13.14% USA | Exon 2 | DQA1*05:01:01:01 | CTGACCAGT | CGCCTCTTAT | GGTGTAAACT | TGTACCAGT | TTACGTCCC | TCTGGCCAGT | ACACCCATGA | ATTTGATGGA | GATGAGGAGT |
| HLAAlleles.Org | 11.08% USA | Exon 2 | DQA1*02:01:01:01 | CTGACCAGT | TGCCTCTTAC | GGTGTAAACT | TGTACCAGT | TTACGTCCC | TCACCCATGA | ATTTGATGGA | GACGAGGAGT | |
| Ubiquity_DQA1 | 19 (Allele 1), 57 (Allele 1) | Exon 2 | DQA1*01:01:01 | CTGACCAGT | TGCCTCTTGT | GGTGTAAACT | TGTACCAGT | TTACGTCCC | TCTGGCCAGT | ACACCCATGA | ATTTGATGGA | GATGAGGAGT |
| Ubiquity_DQA1 | 50 (Allele 1, 2) | Exon 2 | DQA1*01:02:01 | CTGACCAGT | TGCCTCTTGT | GGTGTAAACT | TGTACCAGT | TTACGTCCC | TCTGGCCAGT | ACACCCATGA | ATTTGATGGA | GATGAGGAGT |
| Ubiquity_DQA1 | 19 (Allele 2), 29 (Allele 1) | Exon 2 | DQA1*05:01:01 | CTGACCAGT | CGCCTCTTAT | GGTGTAAACT | TGTACCAGT | TTACGTCCC | TCTGGCCAGT | ACACCCATGA | ATTTGATGGA | GATGAGGAGT |
| Ubiquity_DQA1 | 11 (Allele 1 & 2) | Exon 2 | DQA1*05:05:01 | CTGACCAGT | CGCCTCTTAT | GGTGTAAACT | TGTACCAGT | TTACGTCCC | TCTGGCCAGT | ACACCCATGA | ATTTGATGGA | GATGAGGAGT |
| Ubiquity_DQA1 | 57 (Allele 2) | Exon 2 | DQA1*03:03:01 | CTGACCATGT | TGCCTCTTAC | GGTGTAAACT | TGTACCAGT | TTATGCCAGT | ACACCCATGA | ATTTGATGGA | GACGAGGAGT | |

| Source | | Location | Allele Designator | | | | | | | | | |
|---|---|---|---|---|---|---|---|---|---|---|---|---|
| | | | | 10 | 20 | 30 | 40 | 50 | 60 | 70 | 80 | 90 |
| Ensembl.org | ENSSSCE00045087536 | Exon 2 | SLA-201 | CCGACCATGT | TGGCTCCTAT | GGCTAAAATG | TCTACCAGTC | TTACGTCCC | AGCGGCTATT | ATACCCATGA | ATTTGATGGC | GACGAGGAAT |
| Ensembl.org | ENSSSCE00045087536 | Exon 2 | SLA-202 | CCGACCATGT | TGGCTCCTAT | GGCTAAAATG | TCTACCAGTC | TTACGTCCC | AGCGGCTATT | ATACCCATGA | ATTTGATGGC | GACGAGGAAT |
| Ensembl.org | ENSSSCE00045087536 | Exon 2 | SLA-203 | CCGACCATGT | TGGCTCCTAT | GGCTAAAATG | TCTACCAGTC | TTACGTCCC | AGCGGCTATT | ATACCCATGA | ATTTGATGGC | GACGAGGAAT |
| Ensembl.org | ENSSSCE00045087536 | Exon 2 | SLA-204 | CCGACCATGT | TGGCTCCTAT | GGCTAAAATG | TCTACCAGTC | TTACGTCCC | AGCGGCTATT | ATACCCATGA | ATTTGATGGC | GACGAGGAAT |

| Source | | Location | Allele Designator | | | | | | | | | |
|---|---|---|---|---|---|---|---|---|---|---|---|---|
| | | | | 100 | 110 | 120 | 130 | 140 | 150 | 160 | 170 | 180 |
| HLAAlleles.Org | 9.05% USA | Exon 2 | DQA1*01:01:01:01 | TCTACGTGGA | CCTGGAGAGG | AAGGAGACTG | CCTGGGGGTG | GCCTAGAGTC | AGCAAATTTG | GAGGTTTTGA | CCCGGAGGGT | GCACTGACAA |
| HLAAlleles.Org | 14.17% USA | Exon 2 | DQA1*01:02:01:01 | TCTACGTGGA | CCTGGAGAGG | AAGGAGACTG | CCTGGGGGTG | GCCTGAGTTC | AGCAAATTTG | GAGGTTTTGA | CCCGGAGGGT | GCACTGACAA |
| HLAAlleles.Org | 13.14% USA | Exon 2 | DQA1*05:01:01:01 | TCTACGTGGA | CCTGGGAGAGG | AAGGAGACTG | TCTGGGGTTT | GCCTGAGTTC | AGACAATTTA | GAT---TTGA | CCCGGAATTT | GCACTGACAA |
| HLAAlleles.Org | 11.08% USA | Exon 2 | DQA1*02:01:01:01 | TCTATGTGGA | CCTGGAGAGG | AAGGAGACTG | TCTGGAAGTT | GCCTCTGTTC | CACAAATTTG | GAT---TTGA | CCCGAAATTT | GCACTGACAA |

FIG. 25B

| Source | | | | | | | | | | |
|---|---|---|---|---|---|---|---|---|---|---|
| Ubiquity_DQA1 | 19 (Allele 1), 57 (Allele 1) | Exon 2 | DQA1*01:01:01 | TCTACGTGGA | CCTGGGAGAGG | AAGGAGACTG | GCCTGAGTTC | AGCAAATTTG | GAAGTTTGA | CCCGCAGGGT | GCACTGACAA |
| Ubiquity_DQA1 | 50 (Allele 1, 2) | Exon 2 | DQA1*01:02:01 | TCTACGTGGA | CCTGGGAGAGG | AAGGAGACTG | GCCTGAGTTC | AGCAAATTTG | GAAGTTTGA | CCCGCAGGGT | GCACTGACAA |
| Ubiquity_DQA1 | 19 (Allele 2), 29 (Allele 1) | Exon 2 | DQA1*05:01:01 | TCTACGTGGA | CCTGGGGAGG | AAGGAGACTG | GCCTGAGTTC | AGACAATTTA | GAT---TTGA | CCCGCAATTT | GCACTGACAA |
| Ubiquity_DQA1 | 11 (Allele 1 & 2) | Exon 2 | DQA1*05:05:01 | TCTACGTGGA | CCTGGGGAGG | AAGGAGACTG | GCCTGTCC | AGACAATTTA | GAT---TTGA | CCCGCAATTT | GCACTGACAA |
| Ubiquity_DQA1 | 57 (Allele 2) | Exon 2 | DQA1*03:03:01 | TCTACGTGGA | CCTGGGGAGG | AAGGAGACTG | GCCTGAGTT | CGCACGATTA | GAAGATTTGA | CCCGCAATTT | GCACTGACAA |

| Source | | | | 100 | 110 | 120 | 130 | 140 | 150 | 160 | 170 | 180 |
|---|---|---|---|---|---|---|---|---|---|---|---|---|
| Ensembl.org | ENSSSCE00045087536 | Exon 2 | SLA-201 | TCTACGTGGA | CCTGGGAGAAG | AAGGAGACTG | TCTGGCGGCT | GCCTCTGTTT | AGTGAATTTA | CAAGTTTGA | CCCGCAGGGT | GCACTGACGA |
| Ensembl.org | ENSSSCE00045087536 | Exon 2 | SLA-202 | TCTACGTGGA | CCTGGGAGAAG | AAGGAGACTG | TCTGGCGGCT | GCCTCTGTTT | AGTGAATTTA | CAAGTTTGA | CCCGCAGGGT | GCACTGACGA |
| Ensembl.org | ENSSSCE00045087536 | Exon 2 | SLA-203 | TCTACGTGGA | CCTGGGAGAAG | AAGGAGACTG | TCTGGCGGCT | GCCTCTGTTT | AGTGAATTTA | CAAGTTTGA | CCCGCAGGGT | GCACTGACGA |
| Ensembl.org | ENSSSCE00045087536 | Exon 2 | SLA-204 | TCTACGTGGA | CCTGGGAGAAG | AAGGAGACTG | TCTGGCGGCT | GCCTGTGTTT | AGTGAATTTA | CAAGTTTGA | CCCGCAGGGT | GCACTGACGA |

| Source | | | | 190 | 200 | 210 | 220 | 230 | 240 | 250 | | |
|---|---|---|---|---|---|---|---|---|---|---|---|---|
| HLAAlleles.Org | 9.05% USA | Exon 2 | DQA1*01:01:01:01 | ACATGGCTGT | GGCAAAACAC | AACTTGAACA | TCATGATTAA | ACGCTACAAC | TCTACCGCTG | CTACCAATG | (SEQ ID NO: 168) | |
| HLAAlleles.Org | 14.17% USA | Exon 2 | DQA1*01:02:01:01 | ACATGGCTGT | GGCAAAACAC | AACTTGAACA | TCATGATTAA | ACGCTACAAC | TCTACCGCTG | CTACCAATG | (SEQ ID NO: 169) | |
| HLAAlleles.Org | 13.14% USA | Exon 2 | DQA1*05:01:01:01 | ACATGGCTGT | CCTAAAACAT | AACTTGAACA | GTCTGATTAA | ACGCTCCAAC | TCTACCGCTG | CTACCAATG | (SEQ ID NO: 170) | |
| HLAAlleles.Org | 11.08% USA | Exon 2 | DQA1*02:01:01:01 | ACATGGCTGT | GCTAAAACAT | AACTTGAACA | TCCTGATTAA | ACGCTCCAAC | TCTACCGCTG | CTACCAATG | (SEQ ID NO: 171) | |

| | | | | | | | | | | | | |
|---|---|---|---|---|---|---|---|---|---|---|---|---|
| Ubiquity_DQA1 | 19 (Allele 1), 57 (Allele 1) | Exon 2 | DQA1*01:01:01 | ACATGGCTGT | GGCAAAACAC | AACTTGAACA | TCATGATTAA | ACGCTACAAC | TCTACCGCTG | CTACCAATG | (SEQ ID NO: 136) | |
| Ubiquity_DQA1 | 50 (Allele 1, 2) | Exon 2 | DQA1*01:02:01 | ACATGGCTGT | GGCAAAACAC | AACTTGAACA | TCATGATTAA | ACGCTACAAC | TCTACCGCTG | CTACCAATG | (SEQ ID NO: 139) | |
| Ubiquity_DQA1 | 19 (Allele 2), 29 (Allele 1) | Exon 2 | DQA1*05:01:01 | ACATGGCTGT | CCTAAAACAT | AACTTGAACA | GTCTGATTAA | ACGCTCCAAC | TCTACCGCTG | CTACCAATG | (SEQ ID NO: 138) | |
| Ubiquity_DQA1 | 11 (Allele 1 & 2) | Exon 2 | DQA1*05:05:01 | ACATGGCTGT | CCTAAAACAT | AACTTGAACA | GTCTGATTAA | GTCTCCAAC | TCTACCGCTG | CTACCAATG | (SEQ ID NO: 133) | |
| Ubiquity_DQA1 | 57 (Allele 2) | Exon 2 | DQA1*03:03:01 | ACATGGCTGT | GCTAAAACAT | AACTTGAACA | TCGTGATTAA | ACGCTCCAAC | TCTACCGCTG | CTACCAATG | (SEQ ID NO: 137) | |

FIG. 25B (Cont.)

| Source | | | | 190 | 200 | 210 | 220 | 230 | 240 | 250 | |
|---|---|---|---|---|---|---|---|---|---|---|---|
| Ensembl.org | ENSSSCE00045087536 | Exon 2 | SLA-201 | ATATAGCTAC | GTTAAAACAT | AACTTGAACA | TCGTGACTAA | ACGCTCCAAC | AACACCGCGG | CTGTCAATC | (SEQ ID NO: 140) |
| Ensembl.org | ENSSSCE00045087536 | Exon 2 | SLA-202 | ATATAGCTAC | GTTAAAACAT | AACTTGAACA | TCGTGACTAA | ACGCTCCAAC | AACACCGCGG | CTGTCAATC | (SEQ ID NO: 141) |
| Ensembl.org | ENSSSCE00045087536 | Exon 2 | SLA-203 | ATATAGCTAC | GTTAAAACAT | AACTTGAACA | TCGTGACTAA | ACGCTCCAAC | AACACCGCGG | CTGTCAATC | (SEQ ID NO: 142) |
| Ensembl.org | ENSSSCE00045087536 | Exon 2 | SLA-204 | ATATAGCTAC | GTTAAAACAT | AACTTGAACA | TCGTGACTAA | ACGCTCCAAC | AACACCGCGG | CTGTCAATC | (SEQ ID NO: 143) |

Complete Divergent Nucleotides
Total 27
Total Nucleotides 249

11% of the Aligned 249 Nucleotides Are Completely Divergent

Letter Shading Indicates Nucleotides Are Completely Divergent

FIG. 25B (Cont.)

DQ-A1 Human Capture Reference Sequence for Three Patients

| | Exon | Sequence | |
|---|---|---|---|
| HLA-DQA1-PT.11 05.05.01 | 1 | ATGATCCTAAACAAAGCTCTGATGCTGGGGACCCTGCCCTGACCACGTGATGAGCCCCTGTGGAGGTGAAGACATTGTGG | (SEQ ID NO: 144) |
| | 2 | CTGACCACGTGCCCTCTTATGGTGTAAACTTGTACCGTCACCCAGTAGCAAATTGATGAGAATGAGCAGTTCTACGTGGACCTGGGGAGGAGGAGAC TGTCTGGTGTTGCCCTGTTCAGCAATTAGATTTGACCCGGCAATTGCACTGAAAACATACGTGATCAGTCGTGATAAACGCTGATTAAACGCTACGGCTGC TACCAATG | (SEQ ID NO: 145) |
| | 3 | AGGTCCTGAGGTCACAGTGTTCCAAGTCCCGACACTGGGTCAGCCCAAACATCCTATCTGTCCCTGTGGACATCATCTCTGAGCAAT GGGCACTCAGTGACAGAAGGTGTTCTGAGACCAGCTTCCTCCAAGAGTGATCAATCCTTGTTCAAGATCAGTTACCAGTCATCAGAGAGTTAGACTGCAA GGTGGAGCACTGGGACTGGGGGCTGGACAAGCCTCTTCTGAAACACTGGG | (SEQ ID NO: 146) |
| | 4 | AGCCTGAGAATTCAGCCCCTATGCTCAGAGCTCAGAGAGCTCAGGGTCTCGGCCCTGGTCGTGGGGCACTGTCTTCATCATCCGAGGCCCTGC GTTCAGTTGGTGCTTCCAGACACCAAGGGCCTTGTGA | (SEQ ID NO: 147) |
| HLA-DQA1-PT.50 01.02.01 | 1 | ATGATCCTAAACAAAGCTCTGCTGCTGGGGGCCCTTCGCTCTGACCACGTGAGCCCCTGTGGAGGTGAAGACATTGTGG | (SEQ ID NO: 148) |
| | 2 | CTGACCACGTTCCCTCTGTGTGTGTAAACTTGTACCGGTTCAGTTTATGGATCAAATTTGACCCGAGCAATGAATTTGATGAGGAGGAGGAC TGCCTGGGTGCCAGTTCAGCAATTGACCCCCGCAGGTCACTGACTGAAACACAACTTGACACATCATGATTAAACGCTACAACTCTACC GCTGCTACCAATG | (SEQ ID NO: 149) |
| | 3 | AGGTTCCTGAGGTCACAGTGTTTCCAAGTCTCCGTGACACTGGGTCAGCCCAATGCCCAAACTCCTGTGGCAACATCACATGGCTGAGCAAT GGGCAGTGGCAGTCACAGAAGGTCACAGGTGGTTCTTGAGACCAGCCACTTCTCTCCAAGAGAGTCATCAATCCTTCACCTTCCCCCTTCTGCTGATGATTATGACTGCAA GGTGGAGCACTGGGCCCTGGGGGAGCCCTCTCTGAAACACTGGG | (SEQ ID NO: 150) |
| | 4 | AGCCTGAGATTCAGCCCCTATGTCAGAGCTCAGAGAGCTCAGGGTCTGGGGCCCCATGGCCTGGTTTGTCTGGGGACTGTCTTCATCATCCAAGGCCCTGC GTTCAGTTGGTGCTTCCAGACACCCAGGGGCCATTGTGA | (SEQ ID NO: 151) |

FIG. 25C

| HLA-DQA1-PT.57 | Exon | Sequence | |
|---|---|---|---|
| 03:03:01 | 1 | ATGATCCTAAACAAACTTCTGATGCTGGGGGCCCTCGGCCTCACCGTGATGGCTGTCAGCATTGTGG | (SEQ ID NO: 152) |
| | 2 | CTGACCATCTTCCCTCTTACGGCTGTAAACTTGTACCAGTCTTATGGTCCCTGGGCAGTAGCCATGAATTGATGGAGGACGAGGAGTTATGTGACCTGGAAGGAAGGAGAGACGTGTGCAGTTGCCTCTGTT CCGCAGAGATTTAGACCCGCCAATTTGACTGACTGAGATTGCTGCTAAAACATGAAGTTCAATAAACGCTCCAACTGTGATTAAACATGTGATTAAAGCTCCAACTGTGATTAAAGCTCCAACTGTGATTAAAGCCTACCAATG | (SEQ ID NO: 153) |
| | 3 | AGGTTCCTGAGGTCAGATCTTTTCCAAGTCTCCCGTGACACAGTTCAGGCTCAGCCTGAAGATCGTGTCCGTAAGATCCTTCACAGAGAAGTCACAGAGATCAGAAGTGAAGATGAGTTGCAGGTAGAGATCAGAAGTGAAGATGAGCTGCAGAGAAGGT GTTTCTGAGACCCAGTTCCTCCAAGAGTCGATCATTCCTTCAAGATCAGTTACCTCAGATCAGTTAGCCTTCAGAGACTGGGCACTGCAAGGTGGAGCACTGGGCCCTGGATGAGCCCTTCGAAACACTGG G | (SEQ ID NO: 154) |
| | 4 | AGCCTGAGATTCCAACACCTATGCAGAGTCACAGAGATGTGGTCTGCGCCCTGGGTTGCTGTGGGGACCGTCTGATCATCCGAGGCCTGGGTTAGTTGGTGTTCCAGACA CCAAGGGCCCCTTGTGA | (SEQ ID NO: 155) |

FIG. 25C (Cont.)

DQ-B1 Human Capture Reference Sequence for Three Patients

HLA-DQB1-PT.11
03:01:01

| Exon | Sequence | |
|---|---|---|
| 1 | ATGTCTTGGAAAAAGGCTTTGCGGATCCCCGGAGGCCTTCGGGCAGCAACTGTTACCTTGATGTGGCCATGCTGAGGCACCCAGTGCTGAGGGCAGAGACTCTCCCG | (SEQ ID NO: 156) |
| | AGGATTTCGTGTACCAGTTTAAGGGCATGTGCTACTTCACCAACGGGACGGAGCGGGTGCGTTATGTGACCAGATACATCTATAACCGAGAGGAGTACGCACGCTTCACACAGCGACGT | |
| 2 | GGAGTCTGTACCGGGGCGGTCGCGGGCTGACGGCCGCGGTGACAGCCAGAAGGAAGTCCTGGAAGAGACCCGGAGCGAGTTGGACACGGTGTGCAGACACAA | (SEQ ID NO: 157) |
| | CTACCAGTTGGAGCTCCGCACGACCTTGCAGCGGCGAG | |
| 3 | TGGACCCCACAGTGACCATCTCCCCATCCAGGACGAGGCCCTCAACCACCACAACCTCTGGTCTGCTCAGTGACAGATTTCTATCAGCCCAGATCAAAGTCCGGTGGTTCGGAA | (SEQ ID NO: 158) |
| | TGACCAGGAGGAGAGCAAACCCGGCTGACTGACTGAGGCGTGACTCCCACCCCCCTTATTAGGAAGGGTCGACCTCCCAGCATGCTGGAAATGACTCCCCAGCCATGGAGACGTCTACACCTG | (SEQ ID NO: 159) |
| | CCACAGTGGAGCACCCCAGCCTCCAGAGACCAAATGCTCAGTGGCATTGGAGGCTTCGTGCCTGGGAGTCAGCAGGAGTCAGAAAG | |
| 4 | GGGCTCAGTCTGAATCTGCCCAGACCAAATGCTCAGTGGCATTGGAGGCTTCGTGCCTGGGAGTCAGCAGGAGTCAGAAAG | |

HLA-DQB1-PT.50
06:02:01

| Exon | Sequence | |
|---|---|---|
| 1 | ATGTCTTGGAAGAAGGCTTTGCGGATCCCCGGAGACCCTCGGGGTAGCAACTGTCACCTTGATGTGGCCATGCTGAGCCTACTGGCTGAGGGCAGAGACTCTCCCG | (SEQ ID NO: 160) |
| | AGGATTCGTGTTCCAGTTTAAGGGCATGTGCTACTTCACCAACGGGACGGAGCGCGTGCGTCTTGTGACCAGATACATCTATAACCGAGAGGAGTACGCGCTTCACACAGCGACGT | |
| 2 | GGGGGTGTACCGGGGCGGTGACGGGCTGACCGCCCCCAGGGGCGGCTGATGCTGACTACTGGAACAGCCAGAAGGACCTCCTGGAGCAGAAGCGAGCAGTGCAGACACACAA | (SEQ ID NO: 161) |
| | CTACCAGGTGGCGTTCCCGGGGATCCTTGCAGAGGAGAG | |
| 3 | TGGACCCCACAGTGACCATCTCCCCATCCAGGACGAGGCCCTCAACCACCACAACCTCTGGTCTGCTCGGTGACAGATTTCATCAGGCCCAGATCAAAGTCCGGTGGTTCGGAA | (SEQ ID NO: 162) |
| | TGATCAGGAGGAGAGCAGCAGCCCGGCTGTCGTCCAGACCCCTGGTGACTTTCCAGATCCCTGGTGATGCTGGAAATGACTCCCCAGCTGGAGATGTCTACACTGC | |
| | CACGTGGAGCACCCCAGCCTCCAGAGACCAACGCTCAGTGGCGTTCCTGGGGAGTCTTGGGCTTATCATCCCTCAAAGGAGTCAGAAAG | (SEQ ID NO: 163) |
| 4 | GGGCTCAGTCTGAATCTGCCCAGACCAACGCTCAGTGGCGTTCCTGGGGAGTCTTGGGCTTATCATCCCTCAAAGGAGTCAGAAAG | |

FIG. 25D

| | Exon | Sequence | |
|---|---|---|---|
| HLA-DQB1-PT.57 03:01:01 | 1 | ATGTCTTGGAAAAGGCTTTGCGATCCCGGAGGCCTTCGGGCAGCAACTGTTACCTTGATGTGGCAGCCCAGTGGCTGAGGGCAGAGACTCCCTG AGGATTTCGTGTACCAGTTTAAGGCCATGTGCTACTTCACCAACGGGACGGAGAGGGTCCGTTATGTGACCAGATACATCTATAACCGAGAGGAGTACCACCGTTCGACAGGCGACGT | (SEQ ID NO: 164) |
| | 2 | GGAGTGTACCGGGGGTGACGCCGCTGGGGCTGCAGATGGCAGAAGTCCTGAGAGAAGAGTCCGGGCCAGTTGGACACGGTGTGCAGACACAA CTACCAGTTGGAGCTCCGCACGACCTTGCAGCGGCGAG | (SEQ ID NO: 165) |
| | 3 | TGGAGCCCACAGTGACCATCTCCCCATCCAGGACAGAGGCCCTCAACCACCACAACCTGCTGGTCTGCTCAGTGACAGATTTCTATCCAGCCCAGATCAAAGTCCGGTGGTTTCGGAA TGACCAGGAGGAGACAAACGGGCGTGTCCACCCCCTTATTAGGAATGGTGACTGGACCTTCCAGATCCTGGTGATGCTGGAAATGACTCCCCAGATGGGAGAGTCTACACCTG CCACGTGGGAGCACCCCAGCCTCCAGAACCCCATCACCGTGGAGTGGC | (SEQ ID NO: 166) |
| | 4 | GGGCTCAGTCTGAATCTGCCAGAGCAAGATGCTGAGTGGCAATGGCTCGCTGGGCTCATCTCCTGGGCTGGGCTTATTATCCATCAGGAGTCAGAAAG | (SEQ ID NO: 167) |

FIG. 25D (Cont.)

DR-A Human Capture Reference Sequence for Three Patients

HLA-DRA-PT. 11
01:01:01

| Exon | Sequence | |
|---|---|---|
| 1 | ATGGCCATAAGTGGAGTCCCTGCTAGGATTTTTCATCATAGCTGTGCTAGGATCATGAGCGCTCAGGAATCATGGGCTATCAAAG | (SEQ ID NO: 172) |
| | AAGAACAATGTGATCATCCAGGCCGAGTCTATACTGCAGCCAATCAGCGACTTTATGTTTGACTTTGATGGTGATGAGATTTTCCATGTGGATATGGCAAAGAAGGAGACGGTC | |
| 2 | TGGCGGCTTGAAGAATTTGGACGATTTGCCACAGCTTTGAGGGCTCAAGCTGCATTGGGACTCCAACATAGCTGTGACCAACTAGCTGTGAAACTGGAAATCATGACAAAGCGCTCCAACTATACTCCGA | (SEQ ID NO: 173) |
| | TCACCAATG | |
| 3 | TACCTCCAGAGTAACTGTGCTCACGAACAGCCCTGTGGAACTGAGAGCCTCATCGTTTCATCGACAAGTTCACCCACCAGTGCTCATTGTGGCTTCGAAA | (SEQ ID NO: 174) |
| | TGGAAAACCTGTCACCACAGGAGTGTCAGAGAGTGTCAGAGAGACAGTCTCCTGCCCAGGAACCACCCACCTTTTCCAAGTTCCACTATCTCCCCTTCCTGCCCTCAACTGAGGACGTTTACGACTGC | |
| | AGGGTGGAGCACTGGGGCTTGATGAGCCCTTCTCAAGCACTGGG | |
| 4 | AGTTTGATGCTCCAAGCCTCTACCAGAGCTACAAGACAACGAACGTGGTGTGCCCTGGGGCATCATTATTGGGGCATCATTATTGGGGACCATCTTCATCATCAAGGGAGT | (SEQ ID NO: 175) |
| | GCAAAAGCAATGCAGCAGAACGCAGGGGCCCTCTGTAA | |

HLA-DRA-PT. 50
01:02:03

| Exon | Sequence | |
|---|---|---|
| 1 | ATGGCCATAAGTGGAGTCCCTGCTAGGATTTTTCATCATAGCTGTGCTAGGATCATGAGCGCTCAGGAATCATGGGCTATCAAAG | (SEQ ID NO: 176) |
| | AAGAACAATGTGATCATCCAGGCCGAGTCTATACTGCAGCCAATCAGCGACTTTATGTTTGACTTTGATGGTGATGAGATTTTCCATGTGGATATGGCAAAGAAGGAGACGGTC | |
| 2 | TGGCGGCTTGAAGAATTTGGACGATTTGCCACAGCTTTGAGGGCTCAAGCTGCATTGGGACTCCAACATAGCTGTGACCAACTAGCTGTGAAACTGGAAATCATGACAAAGCGCTCCAACTATACTCCGA | (SEQ ID NO: 177) |
| | TCACCAATG | |
| 3 | TACCTCCAGAGTAACTGTGCTCACGAACAGCCCTGTGGAACTGAGAGCCTCATCGTTTCATCGACAAGTTCACCCACCAGTGCTCATTGTGGCTTCGAAA | (SEQ ID NO: 178) |
| | TGGAAAACCTGTCACCACAGGAGTGTCAGAGAGTGTCAGAGAGACAGTCTCCTGCCCAGGAACCACCCACCTTTTCCAAGTTCCACTATCTCCCCTTCCTGCCCTCAACTGAGGACGTTTACGACTGC | |
| | AGGGTGGAGCACTGGGGCTTGATGAGCCCTTCTCAAGCACTGGG | |
| 4 | AGTTTGATGCTCCAAGCCTCTACCAGAGCTACAAGACAACGAACGTGGTGTGCCCTGGGGCATCATTATTGGGGCATCATTATTGGGGACCATCTTCATCATCAAGGGAGT | (SEQ ID NO: 179) |
| | GCAAAAGCAATGCAGCAGAACGCAGGGGCCCTCTGTAA | |

HLA-DRA-PT. 57
01:01:01

| Exon | Sequence | |
|---|---|---|
| 1 | ATGGCCATAAGTGGAGTCCCTGCTAGGATTTTTCATCATAGCTGTGCTAGGATCATGAGCGCTCAGGAATCATGGGCTATCAAAG | (SEQ ID NO: 180) |
| | AAGAACAATGTGATCATCCAGGCCGAGTCTATACTGCAGCCAATCAGCGACTTTATGTTTGACTTTGATGGTGATGAGATTTTCCATGTGGATATGGCAAAGAAGGAGACGGTC | |
| 2 | TGGCGGCTTGAAGAATTTGGACGATTTGCCACAGCTTTGAGGGCTCAAGCTGCATTGGGACTCCAACATAGCTGTGACCAACTAGCTGTGAAACTGGAAATCATGACAAAGCGCTCCAACTATACTCCGA | (SEQ ID NO: 181) |
| | TCACCAATG | |
| 3 | TACCTCCAGAGTAACTGTGCTCACGAACAGCCCTGTGGAACTGAGAGCCTCATCGTTTCATCGACAAGTTCACCCACCAGTGCTCATTGTGGCTTCGAAA | (SEQ ID NO: 182) |
| | TGGAAAACCTGTCACCACAGGAGTGTCAGAGAGTGTCAGAGAGACAGTCTCCTGCCCAGGAACCACCCACCTTTTCCAAGTTCCACTATCTCCCCTTCCTGCCCTCAACTGAGGACGTTTACGACTGC | |
| | AGGGTGGAGCACTGGGGCTTGATGAGCCCTTCTCAAGCACTGGG | |
| 4 | AGTTTGATGCTCCAAGCCTCTACCAGAGCTACAAGACAACGAACGTGGTGTGCCCTGGGGCATCATTATTGGGGCATCATTATTGGGGACCATCTTCATCATCAAGGGAGTGC | (SEQ ID NO: 183) |
| | GCAAAAGCAATGCAGCAGAACGCAGGGGCCCTCTGTAA | |

FIG. 25E

DR-B1 Human Capture Reference Sequence for Three Patients

| | Exon | Sequence | |
|---|---|---|---|
| HLA-DRB1-PT.11 11:01:01 | 1 | ATGGTGTGTCTGAGGCTCCCTGAGTGCAGTTCTGACAGTGACACTGATGGTGCTGAGTGCTCCCACTGGCTTGGCTGGGACACCAGAC | (SEQ ID NO: 184) |
| | 2 | CAGTTCCTTCTGGAGTACTACTGCAGTCTGACTGTCATTTCTTCAATGACGGAGGGCCGGTTCCTGGACAGATACTTCTATAACCAAGAGGAGTACGTGCGCTTCGACAGCGACGT | |
| | | GGGGGAGTTCCGGGCCGTGACCGAGCTGGGGCGGCCTGATGAGGAGTACTGGAACAGCCAGAAGGACCTCCTGGAACAGACAGGCGGCGGCCGTGACACTACTGCAGACACAC | |
| | | TACGGGGTTGGTGAGAGCTTCACAGTGCAGCGGCGAG | |
| | 3 | TCCATCCTAAGGTGACTGTGTATCCTGCAAAGACCCAGCCCCTGCAGCACCACAACCTCCTGGTCTGCTCTGTGAGTGGTTTCTATCCAGGCAGCATTGAAGTCAGGTGGTTCCGGAAT | |
| | | GGCCAGGAAGAGAAGACTGGGGTTGTGTCCACAGGCCTGATCCACAATGGAGACTGGACCTTCCAGACCCTGGTGATGCTGGAAACAGTTCCTCGAGTGGAGAGTTTACACCTGC | |
| | 4 | CAAGTGGAGCACCCAAGCGTGACAAGCCCTCTCACAGTGGAATGGA | (SEQ ID NO: 185) |
| | | GAGCACGGTCTGAATCTGCACAGAGCAAGATGCTGAGTGGAGTCGGGGGCTTTGTCCTGGGCCTGCTCTTCCTTCATCTACTTCAGGAATCAGAAAG | (SEQ ID NO: 186) (SEQ ID NO: 187) |
| HLA-DRB1-PT.50 15:01:01 | 1 | ATGGTGTGTCTGAAGCTCCCTGGAGCCTCCTGCCATGACAGCTCCTGCATGACAGCTGACACTGATGGTGCTGAGCTCCCCACTGGCTTTGTCTGGGGACACCCGAC | (SEQ ID NO: 188) |
| | 2 | CAGTTCCTGTGCAGCACAGGAGTGGAGTCATTCTTCAATGGGACGGAGCGGGTGCGGTTCCTGGACAGATACTTCTATAACCAAGAGGAGAGTGTCCGTTCGACACG | |
| | | TGGGGGAGTTCCGGGCGGTGACGGAGCTGGGGCGGCCTGATGCCGAGTACTGGAACAGCCAGAAGGACCTCCTGGAGCAGAGGCGGGCCGAGGTGGACACCTACTGCAGACACA | |
| | | ACTACGGGGTTGGTGAGAGCTTCACAGTGCAGCGGCGAC | |
| | 3 | TCCAACCTAAGGTGACTGTATATCCTTCAAAGACCCAGCCCCTGCAGCACCACAACCTCCTGGTCTGCTCTGTGAGTGGTTTCTATCCAGGCAGCATTGAAGTCAGGTGGTTCCTGAAC | (SEQ ID NO: 189) |
| | | GGCCAGGAAGAGAAGACTGGAGGTTGTCCACAGCCCTGATCAAGAATGGAGACTGGACCTTCCAGACCCTGGTGATGCTGGAAACAGTTCCTCGAAGTGGAGAGTTCTACTTCCTGC | |
| | 4 | CAACTGGAGCACCCAAGCGTGACAAGCCCTCTCACAGTGGAATGGA | (SEQ ID NO: 190) (SEQ ID NO: 191) |
| | | GAGCACGGTCTGAATCTGCACAGAGCAAGATGCTGAGTGGAGTCGGGGGCTTTGTGCTGGGCCTGCTCTTCCTTGGGCCCTCGTTCATCTACTTCAGGAATCAGAAAG | |
| HLA-DRB1-PT.57 04:01:01 | 1 | ATGGTGTGTCTGAAGTTCCCTGGAGGCCTGAGTGCCATGACTGCAGTTCTGACGCTGACTGATGGTGCTGAGCTCCCCACTGGCTTTGTCTGGGACACCCGAC | (SEQ ID NO: 192) |
| | | CACGTTTCTTGGAGCAGTTAAACATGAGTGCATTTTCTTCAATGGGACGGAGCGGGTGCGGTTCCTGGACAGATACTTCTATAACCAAGAGGAGTACGTGCGCTTCGACAGCGACGT | |
| | 2 | GGGGGAGTACCGGGCGGTGACGGAGCTGGGGCGGCCTGATGAGGAGTACTGGAACAGCCAGAAGGACCTCCTGGAGCAGAGGCGGGCCGAAGTGGACACCTACTGCAGACACACA | (SEQ ID NO: 193) (SEQ ID NO: 194) |
| | | CTACGGGGTTGGTGAGAGCTTCACAGTGCAGCGGCGAG | |
| | 3 | TCTATCCTGAGGTGACTGTGTATCCTGCAAAGACCCAGCCCCTGCAGCACCACAACCTCCTGGTCTGCTCTGTGAATGGTTTCTATCCAGGCAGCATTGAAGTCAGGTGGTTCCGGAA | |
| | | CGGCCAAGAAGAGAAGACAGGGGTGGTGTCCACAGGCCTGATCCAGAATGGAGATTGGACCTTCCAGACCCTGGTGATGCTGGAAACAGTTCCTCGGAGTGGAGAGTTCTACTTCAG | |
| | | GCCAAGTGGAGCACCCAAGCGCACCGAGCCCTCTCACAGTGGAATGGA | |
| | 4 | GAGCACGGTCTGAATCTGCACAGAGCAAGATGCTGAGTGGAGTCGGGGGCGTTCGTGCTGGGCCTGCTCTTCCTTCGTGCGCCCTCTCTTCATCTACTTCAGGAATCAGAAAG | (SEQ ID NO: 195) |

FIG. 25F

DQ-A1 Humanization of a Porcine Cell Line
Example of Human Capture Reference Sequence for Three Patients

| HLA-DQA1-PT.11 | Exon | Sequence |
|---|---|---|
| 05:05:01 | 2 | CTGACCACGTCGCCTCTTATGGTGTAAACTTGTACCAGTCTCCTCTGGCCAGTACACCCATGAATTTGATGGAGATGAGCAGTTCTACGTGGACCTGGGGAGGAAGGAG ACTGTCTCGGTGTTTGCCTGTGTTCCCAGCAGTTTAGACGAATTTGACCCGCAATTTGCACTGACAACATAGCTGTCCTAAAACATAACTTGATTAAACGCTCAACTCTACCGC TGCTACCAATG (SEQ ID NO: 196) |

| HLA-DQA1-PT.50 | Exon | Sequence |
|---|---|---|
| 01:02:01 | 2 | CTGACCACGTTGCCTCTTGCTGTGTAAACTTGTACCAGTTTTACGGTCCCTCTGGCCAGTACACCCATGAATTTGATGGAGATGAGCAGTTCTACGTGGACCTGGAGAGGAAGGAGA CTGCCCTGGGGGTGGCCTGAGTTCAGCAAATTTGAGGTTTTGACCCGAGGGTGTGGCAAACAACATGGCTGTGGCAAAACAACATCATGATTAAACGCTACAACTCTA CCGCTGCTACCAATG (SEQ ID NO: 197) |

| HLA-DQA1-PT.57 | Exon | Sequence |
|---|---|---|
| 03:03:01 | 2 | CTGACCACTGTTGCCTTACGGTGTAAACTTGTACCAGTCTTATGGTGCCCTCTGGGCAGTACAGCCACCATGAATTTGATGGAGACGAGGAGTTCTATGTGACCTGAGAGGAAGGAGA CTGTCTCGGCAGTTCCCCTGTTCCGCAGATTTACGAAGATTGACCCGCAATTTGCACTGACAAACATCGCTGTGCTAAAACATAACTTGAACATCGTGATTAAACGTCCAACTCTAC CGCTGCTACCAATG (SEQ ID NO: 198) |

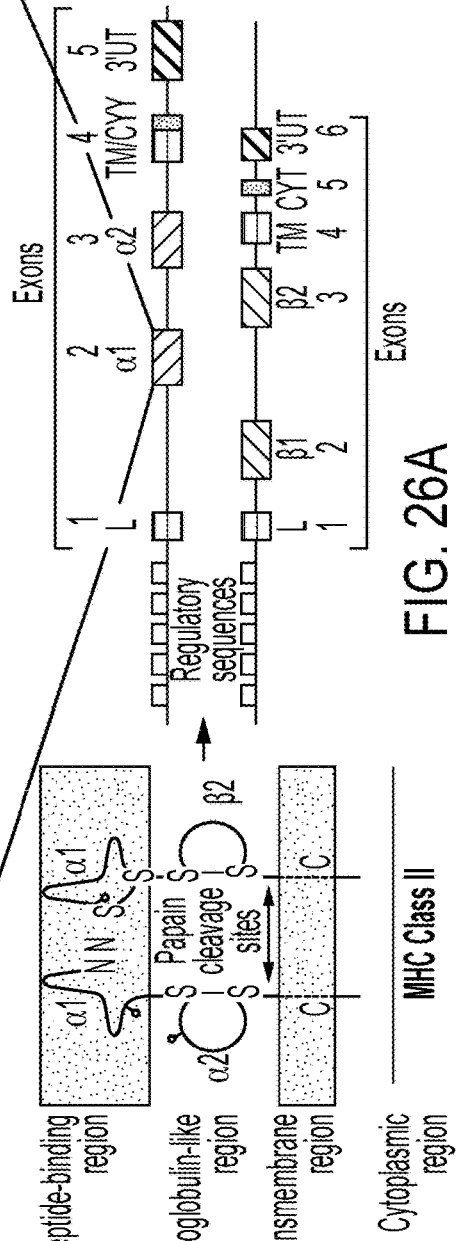

FIG. 26A

EXON 2

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|---|
| SLA B2M-208 | ENSSSCE00000185155 | R | P | P | K | V | Q | V | Y | S | R | H | P | A | E | N | G | K | P | N | Y | L | N | C | Y | V | S | G | F | H | P |
| Research Gate WT hB2M | | R | T | P | K | I | Q | V | Y | S | R | H | P | A | E | N | G | K | S | N | F | L | N | C | Y | V | S | G | F | H | P |
| HLA B2M-207 | ENSE00003659794 | R | T | P | K | I | Q | V | Y | S | R | H | P | A | E | N | G | K | S | N | F | L | N | C | Y | V | S | G | F | H | P |
| HLA B2M-214 | ENSE00003659794 | R | T | P | K | I | Q | V | Y | S | R | H | P | A | E | N | G | K | S | N | F | L | N | C | Y | V | S | G | F | H | P |

EXON 2

| | | 31 | 32 | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|---|---|---|---|---|---|---|---|---|---|---|---|---|---|---|
| SLA B2M-208 | ENSSSCE00000185155 | P | Q | E | I | D | L | L | K | N | G | E | K | M | N | A | E | Q | ■ | S | D | L | S | F | S | K | D | W | S | F |
| HLA B2M-202 | ENSE00003751577 | S | D | F | V | E | D | L | L | K | N | G | E | R | I | E | K | V | E | H | S | D | L | S | F | S | K | D | W | S | F |
| HLA B2M-207 | ENSE00003659794 | S | D | V | V | E | D | L | L | K | N | G | E | R | I | E | K | V | E | H | S | D | L | S | F | S | K | D | W | S | F |
| HLA B2M-214 | ENSE00003659794 | S | D | V | V | E | D | L | L | K | N | G | E | R | I | E | K | V | E | H | S | D | L | S | F | S | K | D | W | S | F |

EXON 2

| | | 61 | 62 | 63 | 64 | 65 | 66 | 67 | 68 | 69 | 70 | 71 | 72 | 73 | 74 | 75 | 76 | 77 | 78 | 79 | 80 | 81 | 82 | 83 | 84 | 85 | 86 | 87 | 88 | 89 | 90 |
|---|---|---|---|---|---|---|---|---|---|---|---|---|---|---|---|---|---|---|---|---|---|---|---|---|---|---|---|---|---|---|---|
| SLA B2M-208 | ENSSSCE00000185155 | Y | L | L | V | H | T | E | F | T | P | N | A | V | D | Q | Y | S | C | R | V | K | H | V | T | L | D | K | P | K | I |
| HLA B2M-202 | ENSE00003751577 | Y | L | L | Y | Y | T | E | F | T | P | T | E | K | D | E | Y | A | C | R | V | N | H | V | T | L | S | Q | P | K | I |
| HLA B2M-207 | ENSE00003659794 | Y | L | L | Y | Y | T | E | F | T | P | T | E | K | D | E | Y | A | C | R | V | N | H | V | T | L | S | Q | P | K | I |
| HLA B2M-214 | ENSE00003659794 | Y | L | L | Y | Y | T | E | F | T | P | T | E | K | D | E | Y | A | C | R | V | N | H | V | T | L | S | Q | P | K | I |

EXON 2

| | | 91 | 92 | 93 | | |
|---|---|---|---|---|---|---|
| SLA B2M-208 | ENSSSCE00000185155 | V | K | W | SEQ ID NO: 208 |
| HLA B2M-202 | ENSE00003751577 | V | K | W | SEQ ID NO: 209 |
| HLA B2M-207 | ENSE00003659794 | V | K | W | SEQ ID NO: 210 |
| HLA B2M-214 | ENSE00003659794 | V | K | W | SEQ ID NO: 211 |

FIG. 28

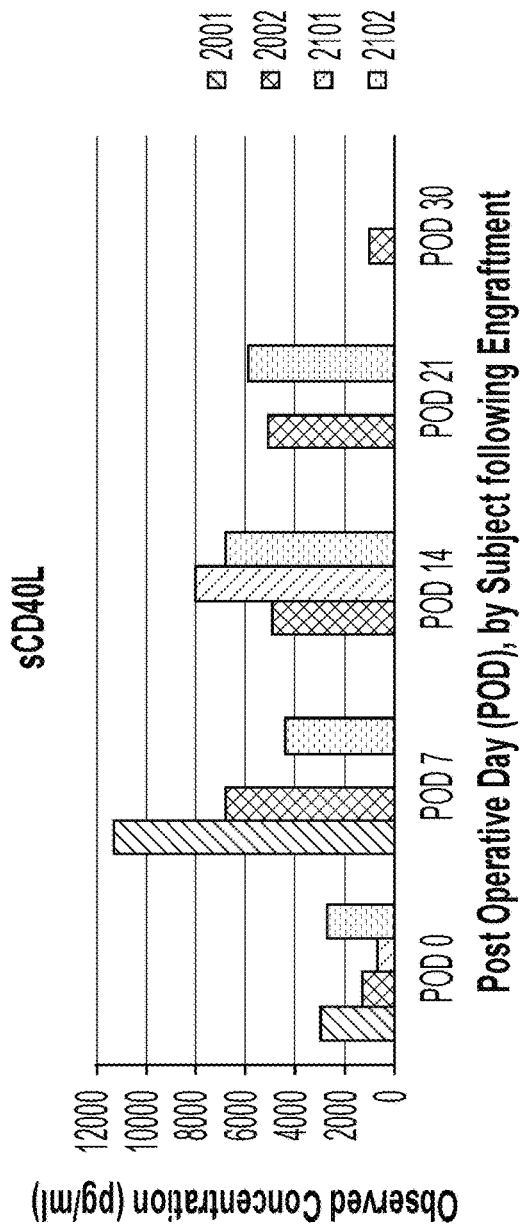
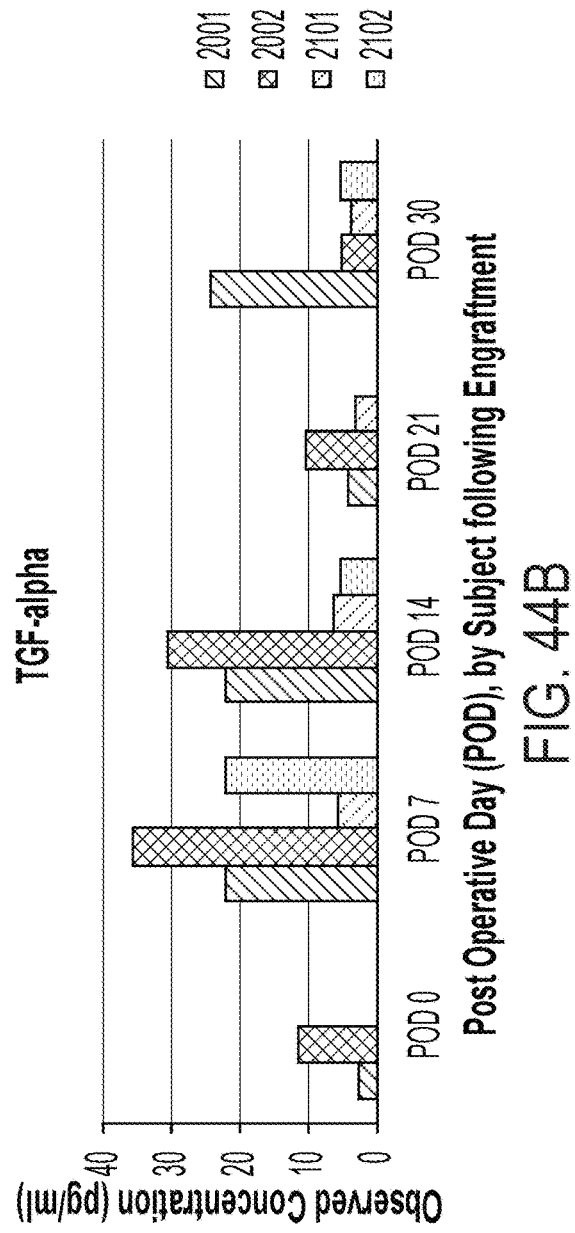

| Process resource | Process step | Process description | Process duration |
|---|---|---|---|
| Cryovial | Pre-labeling of Cyrovial | Pre-labeling of the cryovials reduces processing time and unnecessary material exposure to DMSO prior to cryopreservation | N/a |
| Drug Substance & Antimicrobial Solution | Drug Substance Sterilization | Under ISO 5 hood, remove xenotransplantation product from RPMI bath & place into antimicrobial solution | Not less than 30 minutes |
| Drug Substance & Packaging Component | Placement of Nylon Mesh Packaging Component | Under ISO 5 hood, placement of xenotransplantation product from the antimicrobial solution onto nylon mesh packaging component using sterile technique | 1 Minute Each |
| Cryovial | Packaging into Primary Container Closure System | Under ISO 5 hood, operator will then place the drug substance and nylon mesh packaging component and place the combination within the primary container closure system | 1 Minute Each |
| Cryostor CS5 | Addition of Cryoprotectant Media | Under ISO 5 hood, each Cryovial is filled with 5-7ml of Cryostor CS5 until the xenotransplantation product is fully immersed and then the primary containment closure system is sealed | 1 Minute Each |
| Control Rate Freezer | Cryopreservation | Drug Product is placed in Certified, Q-A control Rate-Freezer per SOP | 40 Minutes per Batch time elapse From room temp to -80 °C |
| -80 °C Freezer | Storage | Transfer Drug Product To a Q/A certified, -80 °C Freezer until use. | 1 Minute |

FIG. 45

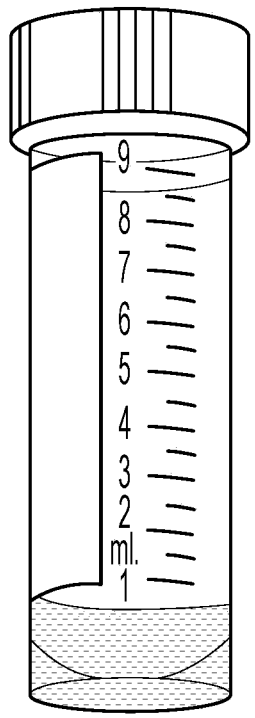

Cryovial

Vertical ribs facilitate cap removal

Silicone washer

Both cap and tube are made of same polypropylene material, therefore same coefficient of expansion ensures secure seal at all temperatures Super fast 1¼ turn thread design Thick wall makes vial almost unbreakable Large white marking area Excellent clarity makes sample easy to see Round bottom / Very easy to empty contents completely

FIG. 46

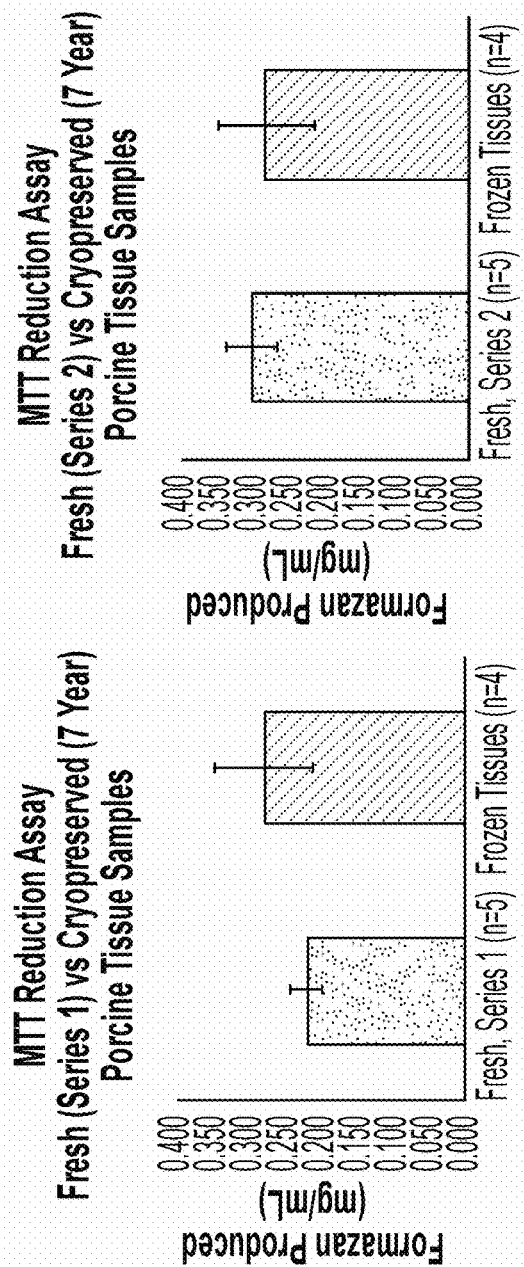
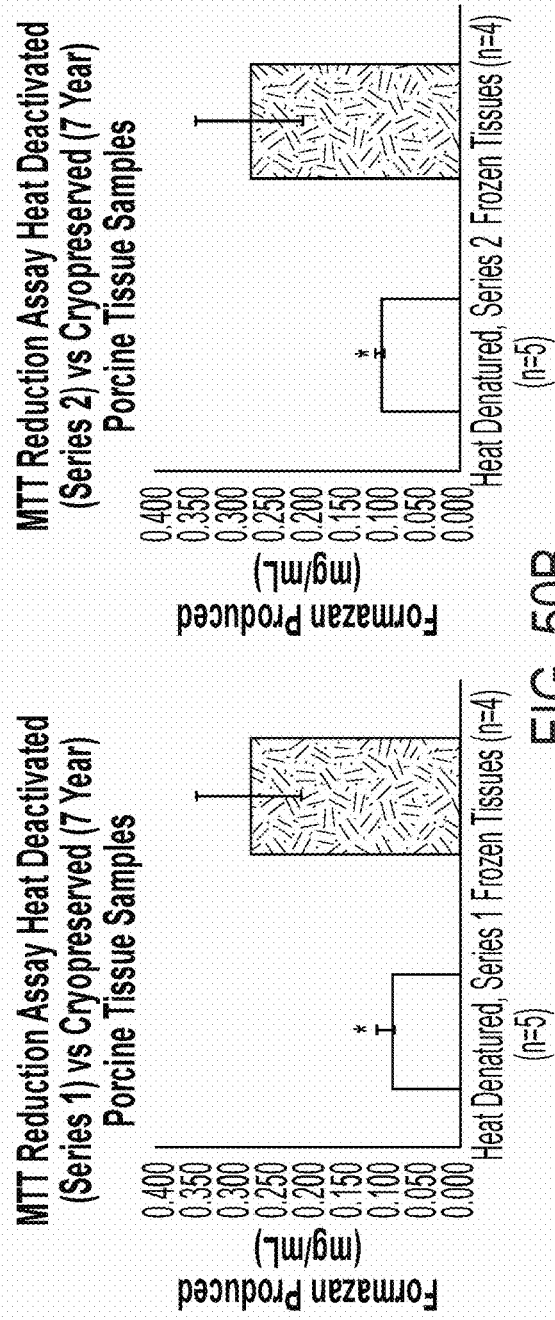
FIG. 50A
FIG. 50B

PERSONALIZED CELLS, TISSUES, AND ORGANS FOR TRANSPLANTATION FROM A HUMANIZED, BESPOKE, DESIGNATED-PATHOGEN FREE, (NON-HUMAN) DONOR AND METHODS AND PRODUCTS RELATING TO SAME

CROSS-REFERENCE TO RELATED APPLICATIONS

This application claims priority of U.S. provisional patent application No. 62/975,611, filed Feb. 12, 2020, U.S. provisional patent application No. 62/964,397, filed Jan. 22, 2020, U.S. provisional patent application No. 62/848,272, filed May 15, 2019, U.S. provisional patent application No. 62/823,455, filed Mar. 25, 2019, and U.S. non-provisional patent application Ser. No. 16/59378, filed Oct. 4, 2019, which claims priority benefit of U.S. provisional application No. 62/742,188, filed Oct. 5, 2018; 62/756,925, filed Nov. 7, 2018; U.S. 62/756,955 filed Nov. 7, 2018; U.S. 62/756,977, filed Nov. 7, 2018; U.S. 62/756,993, filed Nov. 7, 2018; U.S. 62/792,282, filed Jan. 14, 2019; U.S. 62/795,527, filed Jan. 22, 2019; U.S. 62/823,455, filed Mar. 25, 2019; and U.S. 62/848,272, filed May 15, 2019, the disclosures of all of which are incorporated herein by reference in their entireties. The instant application contains a Sequence Listing which has been submitted on the filing date of Mar. 25, 2020 via EFS-Web and is incorporated by reference in its entirety. Said Sequence Listing, created on Mar. 25, 2020, is named 4772-108_ST25.TXT and is 87 kilobytes in size.

BACKGROUND OF THE INVENTION

According to the United Network for Organ Sharing ("UNOS"), every ten minutes, someone is added to the national transplant waiting list, and nearly 20 people die each day waiting for a transplant. As of March 2020, there were about 112,385 people in need of a lifesaving organ transplant in the United States, with only about 19,000 donors identified and about 39,000 transplants performed in 2019 (data from the United Network for Organ Sharing (UNOS)). The need for specific organs in the United States is as follows:

| Organ | Candidates in Need |
|---|---|
| Kidney | 102,730 |
| Liver | 12,926 |
| Pancreas | 879 |
| Kidney/Pancreas | 1,820 |
| Heart | 3,702 |
| Lung | 1,283 |
| Heart/Lung | 52 |
| Intestine | 238 |
| Total | 124,630 |

Over the past 5 years, from 2014 through 2019, an average of about 6,400 candidates died each year while on the waiting list and without receiving an organ transplant. About the same number were not able to receive a long-awaited transplant because they were too sick to receive a transplant for the requisite surgery. While the rate of divergence between available donors and unmet need of recipients has been improved marginally, this disparity has continued to present day and remains considerable; the supply remains disastrously inadequate. Of course, the patients in need are awaiting for organs from human donors, which would represent the transplantation of organs from one species to another (allotransplantation).

Allotransplantation presents many significant multifaceted problems, involving safety, ethical, legal, institutional, and cultural complications. From a safety perspective, allogeneic tissues from human donors carry significant infectious disease risks. For example some in the transplantation field have report that "[human] cytomegalovirus (CMV) is the single most important infectious agent affecting recipients of organ transplants, with at least two-thirds of these patients having CMV infection after transplantation." Denner J (2018) Reduction of the survival time of pig xenotransplants by porcine cytomegalovirus. Virology Journal, 15(1): 171; Rubin R H (1990) Impact of cytomegalovirus infection on organ transplant recipients. Reviews of Infectious Diseases, 12 Suppl 7:S754-766.

Regulations regarding tissue transplants include criteria for donor screening and testing for adventitious agents, as well as strict regulations that govern the processing and distribution of tissue grafts. The transmission of viruses has occurred as a result of allotransplantation. Exogenous retroviruses (Human T-cell leukemia virus type 1 (HTLV-1), Human T-cell leukemia virus type 2 (HTLV-2), and Human immunodeficiency virus (HIV) have been transmitted by human tissues during organ and cell transplantation, as have viruses such as human cytomegalovirus, and even rabies. Due to technical and timing constraints surrounding organ viability and post-mortem screening, absolute testing is hindered, and this risk cannot be eliminated.

Immunological disparities between recipient and donor prevent graft-survival for extended durations, without immunosuppressive regimens that pose their own set of complications and additional risks. When a patient receives an organ from a (non-self) donor (living or deceased), the recipient's immune system will recognize the transplant as foreign. This recognition will cause their immune system to mobilize and "reject" the organ unless concomitant medications that suppress the immune system's natural processes are utilized. The response to an allogeneic skin graft is a potent immune response involving engagement of both the innate and adaptive immune systems. Abbas A K, Lichtman A H H, Pillai S (2017) Cellular and Molecular Immunology.

With regard to the use of immunosuppressants, immunosuppressive drugs prolong survival of the transplanted graft in acute and chronic rejection schemas. However, they leave patients vulnerable to infections from even the most routine of pathogens and require continued use for life but expose the patient to an increased risk of infection, even cancer. immunosuppressant can blunt the natural immunological processes; unfortunately, these medications are often a lifelong requirement after organ transplantation and increase recipient susceptibility to otherwise routine pathogens. While these drugs allow transplant recipients to tolerate the presence of foreign organs, they also increase the risk of infectious disease and symptoms associated with a compromised immune system, as a broad array of organisms may be transmitted with human allografts." Fishman J A, Greenwald M A, Grossi P A (2012) Transmission of Infection With Human Allografts: Essential Considerations in Donor Screening. Clinical Infectious Diseases, 55(5):720-727.

Logistically, numerous factors must be considered prior to a successful organ donation and transplant procedure. Blood type and other medical factors must be evaluated for every donated organ, but further, each organ type presents unique characteristics that also must be weighed, such as post-mortem ischemia, immunological compatibility, patient location, and institutional capabilities.

For these patients, and the millions not included in these statistics who also would benefit significantly from tissue transplants such as cornea or pancreatic islet cells, some in the field have confirmed that "allotransplantation will never prove to be a sufficient source." Ekser B, Cooper D K C, Tector A J (2015) The Need for Xenotransplantation as a Source of Organs and Cells for Clinical Transplantation. International journal of surgery (London, England), 23(0 0): 199-204.

Despite such drawbacks, organ transplantation is unquestionably the preferred therapy for most patients with end stage organ failure, in large part due to a lack of viable alternatives. However, the advent of organ transplantation as a successful life-saving therapeutic intervention, juxtaposed against the paucity of organs available to transplant, unfortunately places medical professionals in an ideologically vexing position of having to decide who lives and who dies. Ultimately, alternative and adjunct treatment options that would minimize the severe shortcomings of allotransplant materials while providing the same mechanism of action that makes them so effective would be of enormous benefit to patients worldwide.

The urgent need for organs and other transplantation tissue generally, including for temporary therapies while more permanent organs or other tissue are located and utilized, has led to investigation into utilization of organs, cells and tissue from non-human sources, including other animals for temporary and/or permanent xenotransplantation.

Xenotransplantation, such as the transplantation of a non-human animal organ into a human recipient, has the potential to reduce the shortage of organs available for transplant, potentially helping thousands of people worldwide. Swine have been considered a potential non-human source of organs, tissue and/or cells for use in human xenotransplantation given that their size and physiology are compatible with humans. However, xenotransplantation using standard, unmodified pig tissue into a human or other primate is accompanied by rejection of the transplanted tissue.

Wild type swine organs would evoke rejection by the human immune system upon transplantation into a human where natural human antibodies target epitopes on the swine cells, causing rejection and failure of the transplanted organs, cells or tissue. The rejection may be a cellular rejection (lymphocyte mediated) or humoral (antibody mediated) rejection including but not limited to hyperacute rejection, an acute rejection, a chronic rejection, may involve survival limiting thrombocytopenia coagulopathy and an acute humoral xenograft reaction (AHXR). Other roadblocks with respect to swine to human xenotransplantation include risks of cross-species transmission of disease or parasites.

One cause of hyperacute rejection results from the expression of alpha-1,3-galactosyltransferase ("alpha-1,3-GT") in porcine cells, which causes the synthesis of alpha-1,3-galactose epitopes. Except for humans, apes and Old World monkeys, most mammals carry glycoproteins on their cell surfaces that contain galactose alpha 1,3-galactose (see, e.g., Galili et al., "Man, apes, and old world monkeys differ from other mammals in the expression of α-galactosyl epitopes on nucleated cells," *J. Biol. Chem.* 263: 17755-17762 (1988). Humans, apes and Old World monkeys have a naturally occurring anti-alpha gal antibody that is produced and binds to glycoproteins and glycolipids having galactose alpha-1,3 galactose (see, e.g., Cooper et al., "Genetically engineered pigs," *Lancet* 342:682-683 (1993)).

Accordingly, when natural type swine products are utilized in xenotransplantation, human antibodies will be invoked to confront the foreign alpha-1,3-galactose epitopes, and hyperacute rejection normally follows. Beyond alpha-1,3-GT, swine cells express multiple genes which are not found in human cells. These include, but are not limited to, Neu5GC, and β1,4-N-acetylgalactosaminyltransferase (B4GALNT2). Antibodies to the α-Gal, Neu5GC, β1,4-N and Sda-like antigens are present in human blood prior to implantation of xeno-tissue, and are involved in the intense and immediate antibody-mediated rejection of implanted tissue.

Additionally pig cells express Class I and Class II SLAs on endothelial cells. The SLA cross-reacting antibodies contribute to the intense and immediate rejection of the implanted porcine tissue. SLA antigens may also be involved with the recipient's T-cell mediated immune response. Porcine SLAs may include, but are not limited to, antigens encoded by the SLA-1, SLA-2, SLA-3, SLA-4, SLA-5, SLA-6, SLA-8, SLA-9, SLA-11 and SLA-12 loci. Porcine Class II SLAs include antigens encoded by the SLA-DQ and SLA-DR loci.

Many attempts have been made by others to modify swine to serve as a source for xenotransplantation products, however such attempts have not yielded a successful swine model to date. Such commercial, academic and other groups have focused on interventions, gene alterations, efforts to induce tolerance through chimerism, inclusion of transgenes, concomitant use of exogenous immunosuppressive medications aimed to reduce the recipients' natural immunologic response(s) and other approaches. These groups have sought to create a "one size fits all" source animal aiming to create one, standardized source animal for all recipients.

Specifically, certain groups have focused on creating transgenic swine free of PERV and utilizing transgenic bone marrow for therapy (see, e.g., eGenesis, Inc. PCT/US2018/028539); creating transgenic swine utilizing stem cell scaffolding (see, e.g. United Therapeutics/Revivicor [US20190111180A1]); mixed chimerism and utilizing transgenic bone marrow for therapy to tolerize patient T-cells (see, e.g. Columbia University [US20180070564A1]). These "downstream" approaches—post recognition by the human immune system—have not succeeded in producing swine that produce products suitable for prolonged use in xenotransplantation or that survive the above-referenced transgenic and other alterations.

In contrast to the above-referenced approaches, the present invention achieves a "patient-specific" solution by modifying the genome of donor swine cells to escape detection from the human immune system in the first instance, avoiding the immune cascade that follows when a patient's T-cells and antibodies are primed to destroy foreign material. This "upstream" approach is achieved through, in one aspect, specific combinations of minimal genetic alterations that render the donor animal's cells, tissues, and organs tolerogenic when transplanted into a human without sacrificing the animal's immune function. The present invention therefore addresses long-felt but unmet need for translating the science of xenotransplantation into a clinical reality.

This "upstream" approach is achieved through, in one aspect, specific combinations of minimal genetic alterations that render the donor animal's cells, tissues, and organs tolerogenic when transplanted into a human without sacrificing the animal's immune function. The present invention therefore addresses long-felt but unmet need for translating the science of xenotransplantation into a clinical reality.

SUMMARY OF THE INVENTION

In one aspect, the present disclosure includes a biological system for generating and preserving a repository of personalized, humanized transplantable cells, tissues, and organs for transplantation, wherein the biological system is biologically active and metabolically active, the biological system comprising genetically reprogrammed cells, tissues, and organs in a non-human animal for transplantation into a human recipient. For example, the non-human animal is a genetically reprogrammed swine for xenotransplantation of cells, tissue, and/or an organ isolated from the genetically reprogrammed swine, the genetically reprogrammed swine comprising a nuclear genome that has been reprogrammed to replace a plurality of nucleotides in a plurality of exon regions of a major histocompatibility complex of a wild-type swine with a plurality of synthesized nucleotides from a human captured reference sequence. In one aspect, cells of said genetically reprogrammed swine do not present one or more surface glycan epitopes selected from alpha-Gal, Neu5Gc, and $SD^a$. Further, genes encoding alpha-1,3 galactosyltransferase, cytidine monophosphate-N-acetylneuraminic acid hydroxylase (CMAH), and β1,4-N-acetylgalactosaminyltransferase are altered such that the genetically reprogrammed swine lacks functional expression of surface glycan epitopes encoded by those genes. In some aspects, the reprogrammed genome comprises site-directed mutagenic substitutions of nucleotides at exon regions of: i) at least one of the wild-type swine's SLA-1, SLA-2, and SLA-3 with nucleotides from an orthologous exon region of HLA-A, HLA-B, and HLA-C, respectively, of the human captured reference sequence; and ii) at least one the wild-type swine's SLA-6, SLA-7, and SLA-8 with nucleotides from an orthologous exon region of HLA-E, HLA-F, and HLA-G, respectively, of the human captured reference sequence; and iii) at least one of the wild-type swine's SLA-DR and SLA-DQ with nucleotides from an orthologous exon region of HLA-DR and HLA-DQ, respectively, of the human captured reference sequence. In some aspects, the reprogrammed genome comprises at least one of A-C:

- A) wherein the reprogrammed swine nuclear genome comprises site-directed mutagenic substitutions of nucleotides at exon regions of the wild-type swine's β2-microglobulin with nucleotides from orthologous exons of a known human β2-microglobulin from the human captured reference sequence;
- B) wherein the reprogrammed swine nuclear genome comprises a polynucleotide that encodes a polypeptide that is a humanized beta 2 microglobulin (hB2M) polypeptide sequence that is at least 95% identical to the amino acid sequence of beta 2 microglobulin glycoprotein expressed by the human captured reference genome;
- C) wherein the reprogrammed swine nuclear genome has been reprogrammed such that, at the swine's endogenous β2-microglobulin locus, the nuclear genome has been reprogrammed to comprise a nucleotide sequence encoding β2-microglobulin polypeptide of the human recipient. Further, in some aspects, the reprogrammed swine nuclear genome has been reprogrammed such that the genetically reprogrammed swine lacks functional expression of the wild-type swine's endogenous β2-microglobulin polypeptides. Further, the reprogramming does not introduce any frameshifts or frame disruptions.

In other aspects, the present disclosure includes a method of preparing a genetically reprogrammed swine comprising a nuclear genome that lacks functional expression of surface glycan epitopes selected from alpha-Gal, Neu5Gc, and $SD^a$ and is genetically reprogrammed to express a humanized phenotype of a human captured reference sequence comprising:

- a. obtaining a porcine fetal fibroblast cell, a porcine zygote, a porcine Induced Pluripotent Stem Cells (IPSC), or a porcine germ-line cell;
- b. genetically altering said cell in a) to lack functional alpha-1,3 galactosyltransferase, cytidine monophosphate-N-acetylneuraminic acid hydroxylase (CMAH), and β1,4-N-acetylgalactosaminyltransferase;
- c. genetically reprogramming said cell in b) using clustered regularly interspaced short palindromic repeats (CRISPR)/Cas for site-directed mutagenic substitutions of nucleotides at exon regions of: i) at least one of the wild-type swine's SLA-1, SLA-2, and SLA-3 with nucleotides from an orthologous exon region of HLA-A, HLA-B, and HLA-C, respectively, of the human captured reference sequence; and ii) at least one the wild-type swine's SLA-6, SLA-7, and SLA-8 with nucleotides from an orthologous exon region of HLA-E, HLA-F, and HLA-G, respectively, of the human captured reference sequence; and iii) at least one of the wild-type swine's SLA-DR and SLA-DQ with nucleotides from an orthologous exon region of HLA-DR and HLA-DQ, respectively, of the human captured reference sequence, wherein intron regions of the wild-type swine's genome are not reprogrammed, and
wherein the reprogrammed genome comprises at least one of A-C:
A) wherein the reprogrammed swine nuclear genome comprises site-directed mutagenic substitutions of nucleotides at exon regions of the wild-type swine's β2-microglobulin with nucleotides from orthologous exons of a known human β2-microglobulin from the human captured reference sequence;
B) wherein the reprogrammed swine nuclear genome comprises a polynucleotide that encodes a polypeptide that is a humanized beta 2 microglobulin (hB2M) polypeptide sequence that is at least 95% identical to beta 2 microglobulin expressed by the human captured reference genome;
C) wherein the reprogrammed swine nuclear genome has been reprogrammed such that the genetically reprogrammed swine lacks functional expression of the wild-type swine's endogenous β2-microglobulin polypeptides, wherein the reprogrammed swine nuclear genome has been reprogrammed such that, at the swine's endogenous β2-microglobulin locus, the nuclear genome has been reprogrammed to comprise a nucleotide sequence encoding β2-microglobulin polypeptide of the human recipient, wherein said reprogramming does not introduce any frameshifts or frame disruptions,

- d. generating an embryo from the genetically reprogrammed cell in c); and
- e. transferring the embryo into a surrogate pig and growing the transferred embryo in the surrogate pig.

In another aspect, the present disclosure includes a method of producing a donor swine tissue or organ for xenotransplantation, wherein cells of said donor swine tissue or organ are genetically reprogrammed to be characterized by a recipient-specific surface phenotype comprising:

- a. obtaining a biological sample containing DNA from a prospective human transplant recipient;
- b. performing whole genome sequencing of the biological sample to obtain a human capture reference sequence;

c. comparing the human capture reference sequence with the wild-type genome of the donor swine at loci (i)-(v):
   (i) exon regions encoding at least one of SLA-1, SLA-2, and SLA-3;
   (ii) exon regions encoding at least one of SLA-6, SLA-7, and SLA-8;
   (iii) exon regions encoding at least one of SLA-DR and SLA-DQ;
   (iv) one or more exons encoding beta 2 microglobulin (B2M);
   (v) exon regions of SLA-MIC-2 gene and a gene encoding at least one of PD-L1, CTLA-4, EPCR, TBM, and TFPI,
d. creating synthetic donor swine nucleotide sequences of 10 to 350 basepairs in length for one or more of said loci (i)-(v), wherein said synthetic donor swine nucleotide sequences are at least 95% identical to the human capture reference sequence at orthologous loci (vi)-(x) corresponding to swine loci (i)-(vi), respectively:
   (vi) exon regions encoding at least one of HLA-A, HLA-B, and HLA-C;
   (vii) exon regions encoding at least one of HLA-E, HLA-F, and HLA-G;
   (viii) exon regions encoding at least one of HLA-DR and HLA-DQ;
   (ix) one or more exons encoding human beta 2 microglobulin (hB2M);
   (x) exon regions encoding at least one of MIC-A, MIC-B, PD-L1, CTLA-4, EPCR, TBM, and TFPI from the human capture reference sequence,
e. replacing nucleotide sequences in (i)-(v) with said synthetic donor swine nucleotide sequences; and
f. obtaining the swine tissue or organ for xenotransplantation from a genetically reprogrammed swine having said synthetic donor swine nucleotide sequences.

In another aspect, the present disclosure includes a method of screening for off target edits or genome alterations in the genetically reprogrammed swine comprising a nuclear genome of the present disclosure including:
a. performing whole genome sequencing on a biological sample containing DNA from a donor swine before performing genetic reprogramming of the donor swine nuclear genome, thereby obtaining a first whole genome sequence;
b. after reprogramming of the donor swine nuclear genome, performing whole genome sequencing to obtain a second whole genome sequence;
c. aligning the first whole genome sequence and the second whole genome sequence to obtain a sequence alignment;
d. analyzing the sequence alignment to identify any mismatches to the swine's genome at off-target sites.

In another aspect, the present disclosure includes a synthetic nucleotide sequence having wild-type swine intron regions from a wild-type swine MHC Class Ia, and reprogrammed at exon regions encoding the wild-type swine's SLA-3 with codons of HLA-C from a human capture reference sequence that encode amino acids that are not conserved between the SLA-3 and the HLA-C from the human capture reference sequence. In some aspects, the wild-type swine's SLA-1 and SLA-2 each comprise a stop codon.

In another aspect, the present disclosure includes a synthetic nucleotide sequence having wild-type swine intron regions from a wild-type swine MHC Class Ib, and reprogrammed at exon regions encoding the wild-type swine's SLA-6, SLA-7, and SLA-8 with codons of HLA-E, HLA-F, and HLA-G, respectively, from a human capture reference sequence that encode amino acids that are not conserved between the SLA-6, SLA-7, and SLA-8 and the HLA-E, HLA-F, and HLA-G, respectively, from the human capture reference sequence.

In another aspect, the present disclosure includes a synthetic nucleotide sequence having wild-type swine intron regions from a wild-type swine MHC Class II, and reprogrammed at exon regions encoding the wild-type swine's SLA-DQ with codons of HLA-DQ, respectively, from a human capture reference sequence that encode amino acids that are not conserved between the SLA-DQ and the HLA-DQ, respectively, from the human capture reference sequence, and wherein the wild-type swine's SLA-DR comprises a stop codon.

In another aspect, the present disclosure includes a synthetic nucleotide sequence having wild-type swine intron regions from a wild-type swine beta-2-microglobulin and reprogrammed at exon regions encoding the wild-type swine's beta-2-microglobulin with codons of beta-2-microglobulin from a human capture reference sequence that encode amino acids that are not conserved between the wild-type swine's beta-2-microglobulin and the beta-2-microglobulin from the human capture reference sequence, wherein the synthetic nucleotide sequence comprises at least one stop codon in an exon region such that the synthetic nucleotide sequence lacks functional expression of the wild-type swine's β2-microglobulin polypeptides.

In another aspect, the present disclosure includes a synthetic nucleotide sequence having wild-type swine intron regions from a wild-type swine MIC-2, and reprogrammed at exon regions of the wild-type swine's MIC-2 with codons of MIC-A or MIC-B from a human capture reference sequence that encode amino acids that are not conserved between the MIC-2 and the MIC-A or the MIC-B from the human capture reference sequence.

In another aspect, the present disclosure includes a synthetic nucleotide sequence having wild-type swine intron regions from a wild-type swine CTLA-4, and reprogrammed at exon regions encoding the wild-type swine's CTLA-4 with codons of CTLA-4 from a human capture reference sequence that encode amino acids that are not conserved between the wild-type swine's CTLA-4 and the CTLA-4 from the human capture reference sequence.

In another aspect, the present disclosure includes a synthetic nucleotide sequence having wild-type swine intron regions from a wild-type swine PD-L1 and reprogrammed at exon regions encoding the wild-type swine's PD-L1 with codons of PD-L1 from a human capture reference sequence that encode amino acids that are not conserved between the wild-type swine's PD-L1 and the PD-L1 from the human capture reference sequence.

In another aspect, the present disclosure includes a synthetic nucleotide sequence having wild-type swine intron regions from a wild-type swine EPCR and reprogrammed at exon regions encoding the wild-type swine's EPCR with codons of EPCR from a human capture reference sequence that encode amino acids that are not conserved between the wild-type swine's EPCR and the EPCR from the human capture reference sequence.

In another aspect, the present disclosure includes a synthetic nucleotide sequence having wild-type swine intron regions from a wild-type swine TBM and reprogrammed at exon regions encoding the wild-type swine's TBM with codons of TBM from a human capture reference sequence that encode amino acids that are not conserved between the wild-type swine's TBM and the TBM from the human capture reference sequence.

In another aspect, the present disclosure includes a synthetic nucleotide sequence having wild-type swine intron regions from a wild-type swine TFPI and reprogrammed at exon regions encoding the wild-type swine's TFPI with codons of TFPI from a human capture reference sequence that encode amino acids that are not conserved between the wild-type swine's TFPI and the TFPI from the human capture reference sequence.

In contrast to the above-referenced approaches, the present invention achieves a "patient-specific" solution by modifying the genome of donor swine cells to escape detection from the human immune system in the first instance, avoiding the immune cascade that follows when a patient's T-cells and antibodies are primed to destroy foreign material. This "upstream" approach is achieved through, in one aspect, minimal, modifications to the swine genome involving distinct combinations of disruptions (such as knocking out α1,3-galactosyltransferase (αGal), cytidine monophosphate-N-acetylneuraminic acid hydroxylase (CMAH) and/or β1-4 N-acetylgalactosaminyltransferase such that the donor swine cells do not express such on its cell surfaces), regulation of expression of certain genes (for example, CTLA-4 and PD-1), and replacement of specific sections of the swine genome with synthetically engineered sections based upon recipient human capture sequences (for example, in certain SLA sequences to regulate the swine's expression of, for example, MHC-I and MHC-II). The present invention therefore addresses long-felt but unmet need for translating the science of xenotransplantation into a clinical reality.

Such modifications result in the reduce the extent of, the causative, immunological disparities and associated, deleterious immune processes that result from the recognition of "non-self", by selectively altering the extracellular antigens of the donor to increase the likelihood of acceptance of the transplant.

In certain aspects, the present disclosure centralizes (predicates) the creation of hypoimmunogenic and/or tolerogenic cells, tissues, and organs that does not necessitate the transplant recipients' prevalent and deleterious use of exogenous immunosuppressive drugs (or prolonged immunosuppressive regimens) following the transplant procedure to prolong the life-saving graft. This approach is countervailing to the existing and previous dogmatic approaches; instead of accepting that innate and immovable disparity between donor and recipient, and thus focusing on interventions, gene alterations, and/or concomitant exogenous immunosuppressive medications used as a method of reducing/eliminating/negatively-altering the recipients' naturally resulting immunologic response, shifting (if not reversing) the focus of the otherwise area of fundamental scientific dogma.

In certain other aspects, the present disclosure provides genetically modified, non-transgenic swine that are minimally altered. For example, in the present invention, certain distinct sequences appearing on the donor swine SLA comprising native base pairs are removed and replaced with a synthetic sequence comprising the same number of base pairs but reprogrammed based on the recipient's human capture sequence. This minimal alteration keeps other aspects of the native swine genome in place and does not disturb, for example, introns and other codons naturally existing in the swine genome.

In certain other aspects, the present invention provides swine with such and other modifications, created in a designated pathogen environment in accordance with the processes and methods provided herein.

In certain other aspects the products derived from such swine for xenotransplantation are minimally manipulated, viable, live cell, and capable of making an organic union with the transplant recipient, including, but not limited to, inducing vascularization and/or collagen generation in the transplant recipient.

In certain other aspects products derived from such source animals are preserved, including, but not limited to, through cryopreservation, in a manner that maintains viability and live cell characteristics of such products.

In certain other aspects, such products are for homologous use, i.e., the repair, reconstruction, replacement or supplementation of a recipient's organ, cell and/or tissue with a corresponding organ, cell and/or tissue that performs the same basic function or functions as the donor (e.g., swine skin is used as a transplant for human skin, swine kidney is used as a transplant for human kidney, swine liver is used as a transplant for human liver, swine nerve is used as a transplant for human nerve and so forth).

In certain other aspects, the present invention that the utilization of such products in xenotransplantation be performed with or without the need to use immunosuppressant drugs or therapies which inhibit or interfere with normal immune function.

BRIEF DESCRIPTION OF THE DRAWINGS

The accompanying drawings, which are incorporated herein and form part of the disclosure, help illustrate various aspects of the present invention and, together with the description, further serve to describe the invention to enable a person skilled in the pertinent art to make and use the aspects disclosed herein. In the drawings, like reference numbers indicate identical or functionally similar elements.

FIG. 7 is a table listing numbers of serological antigens, proteins, and alleles for human MHC Class I and Class II isotypes.

FIG. 14 showing composite genetic alteration design for "humanization" of extracellular porcine cell expression

Figure 21:
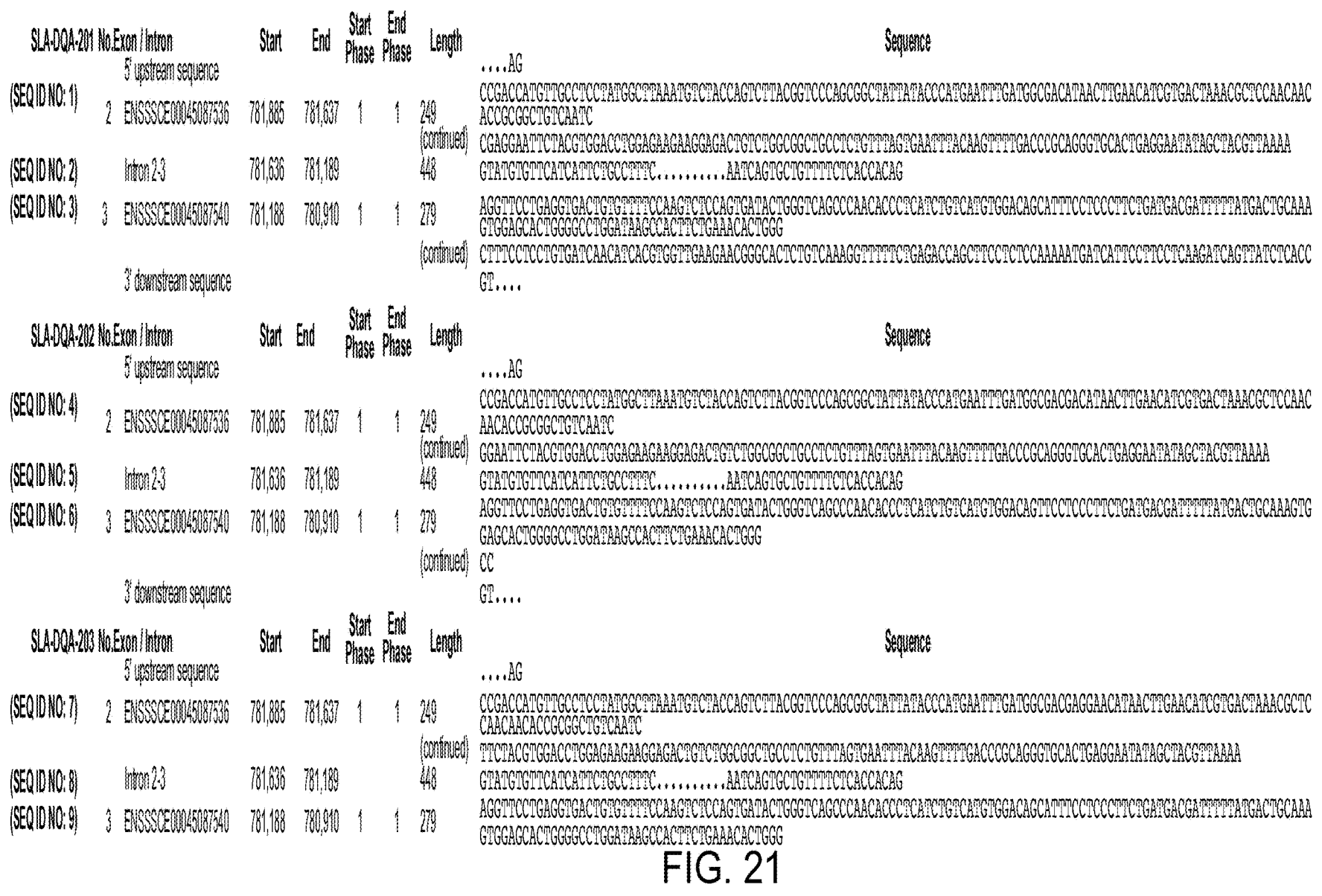
Figure 21:
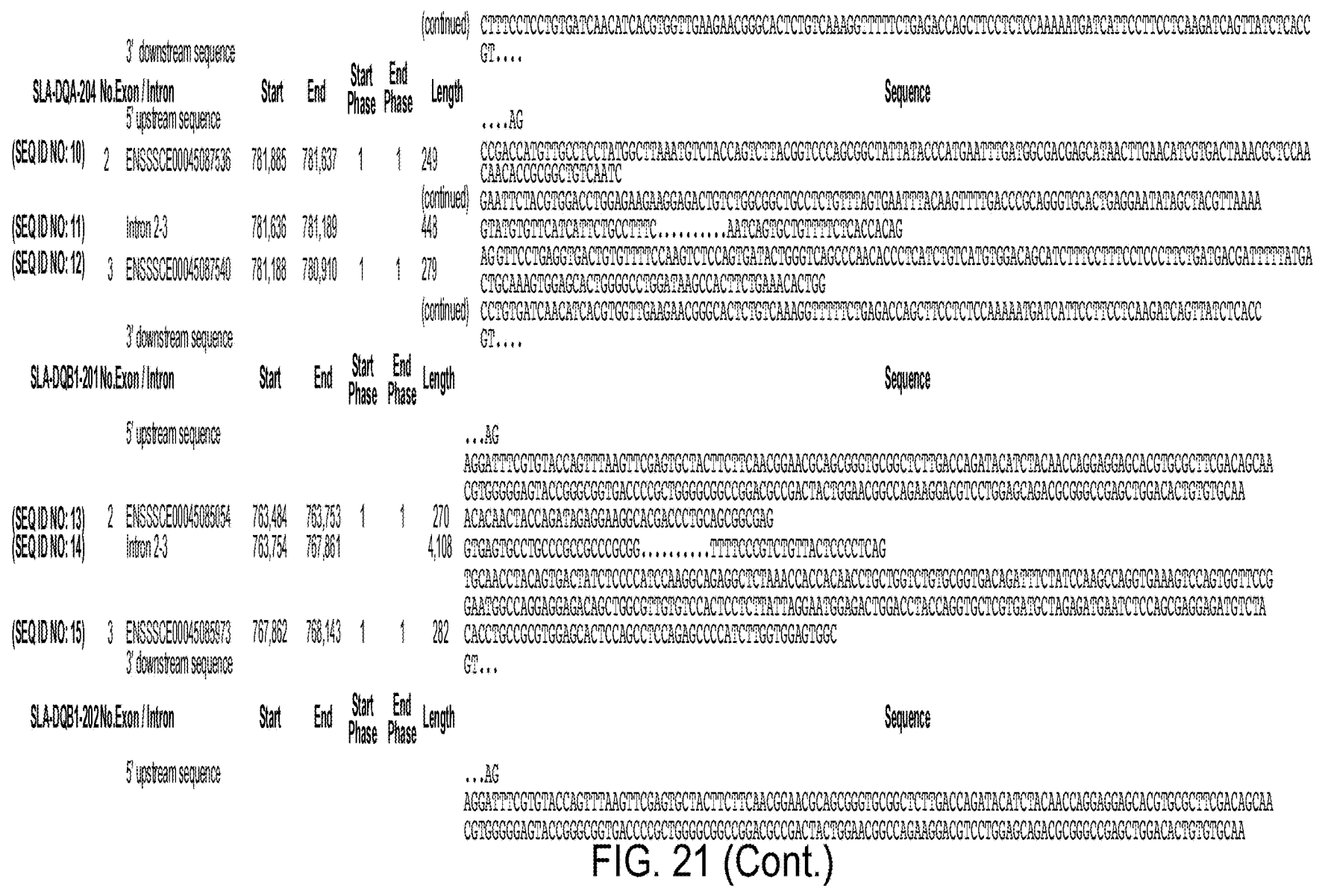
Figure 21:
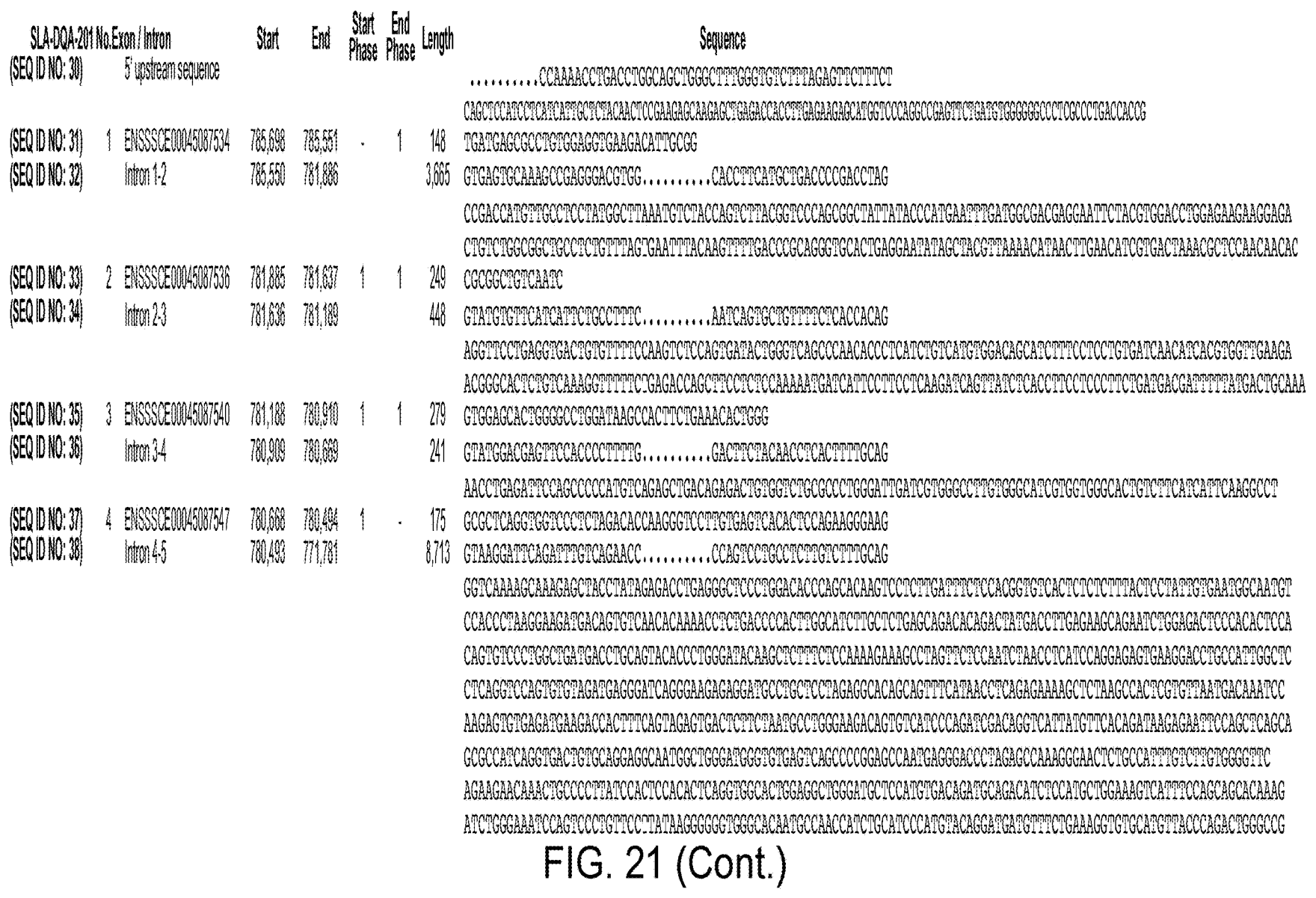
Figure 21:
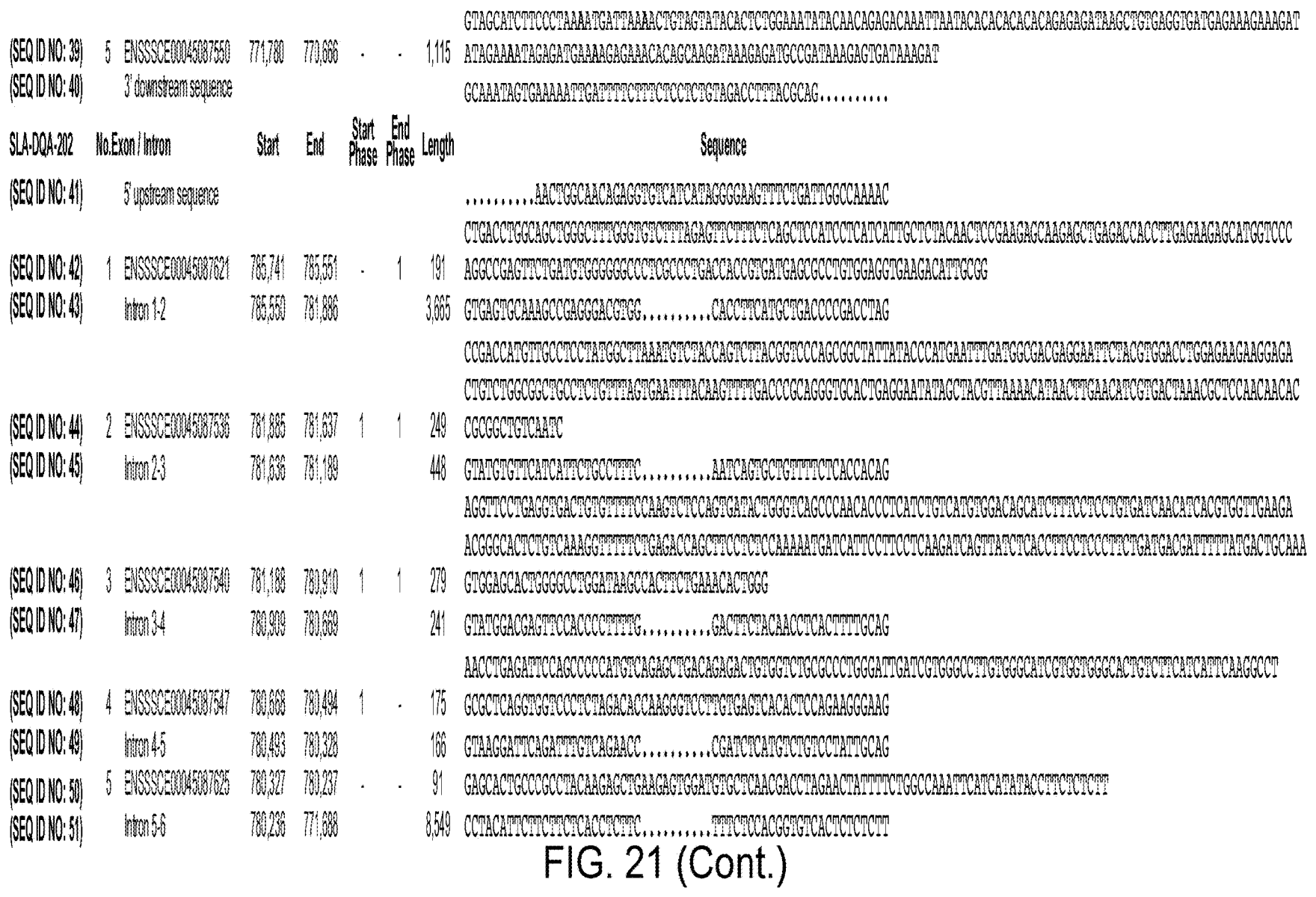
Figure 21:
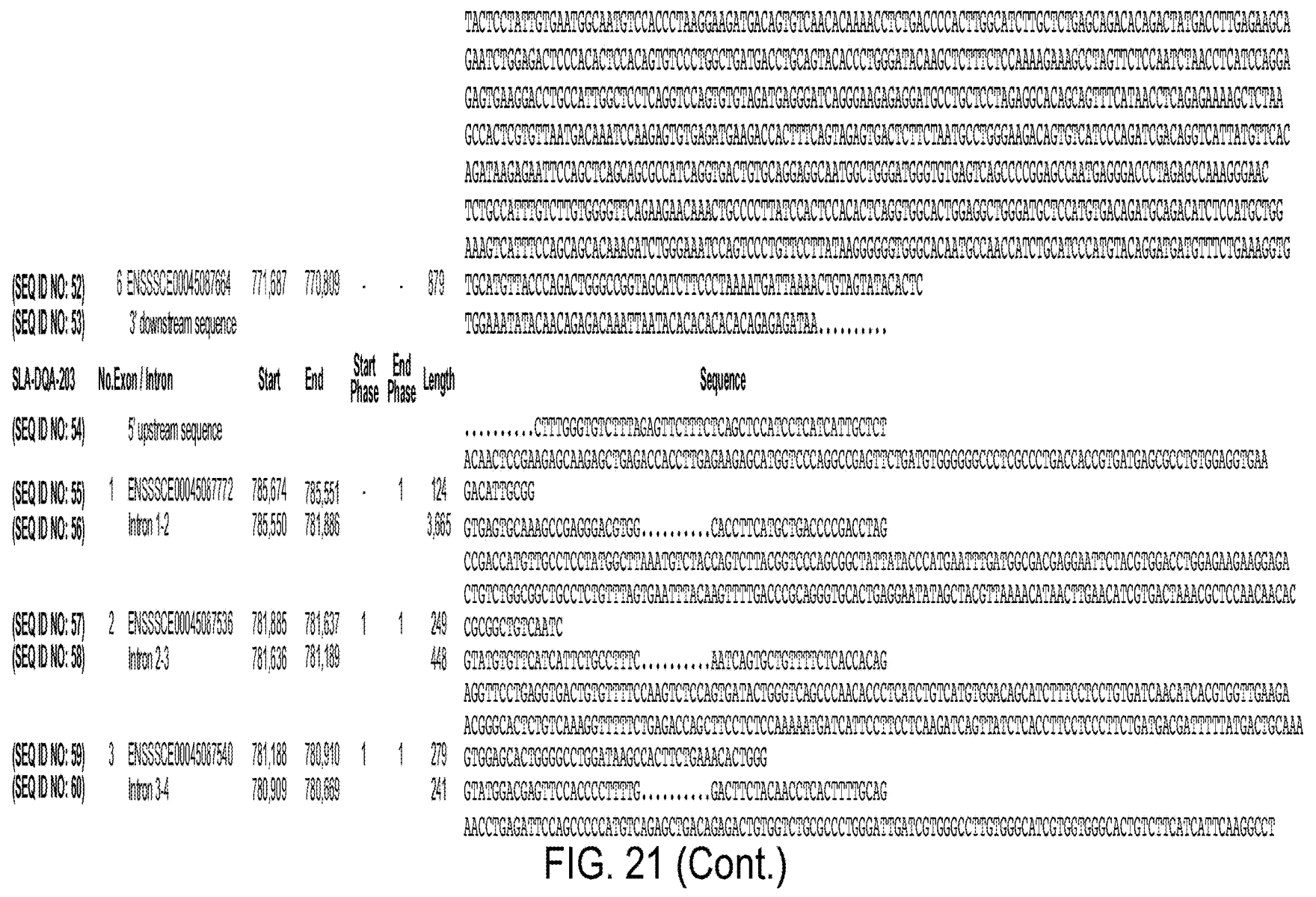
Figure 21:
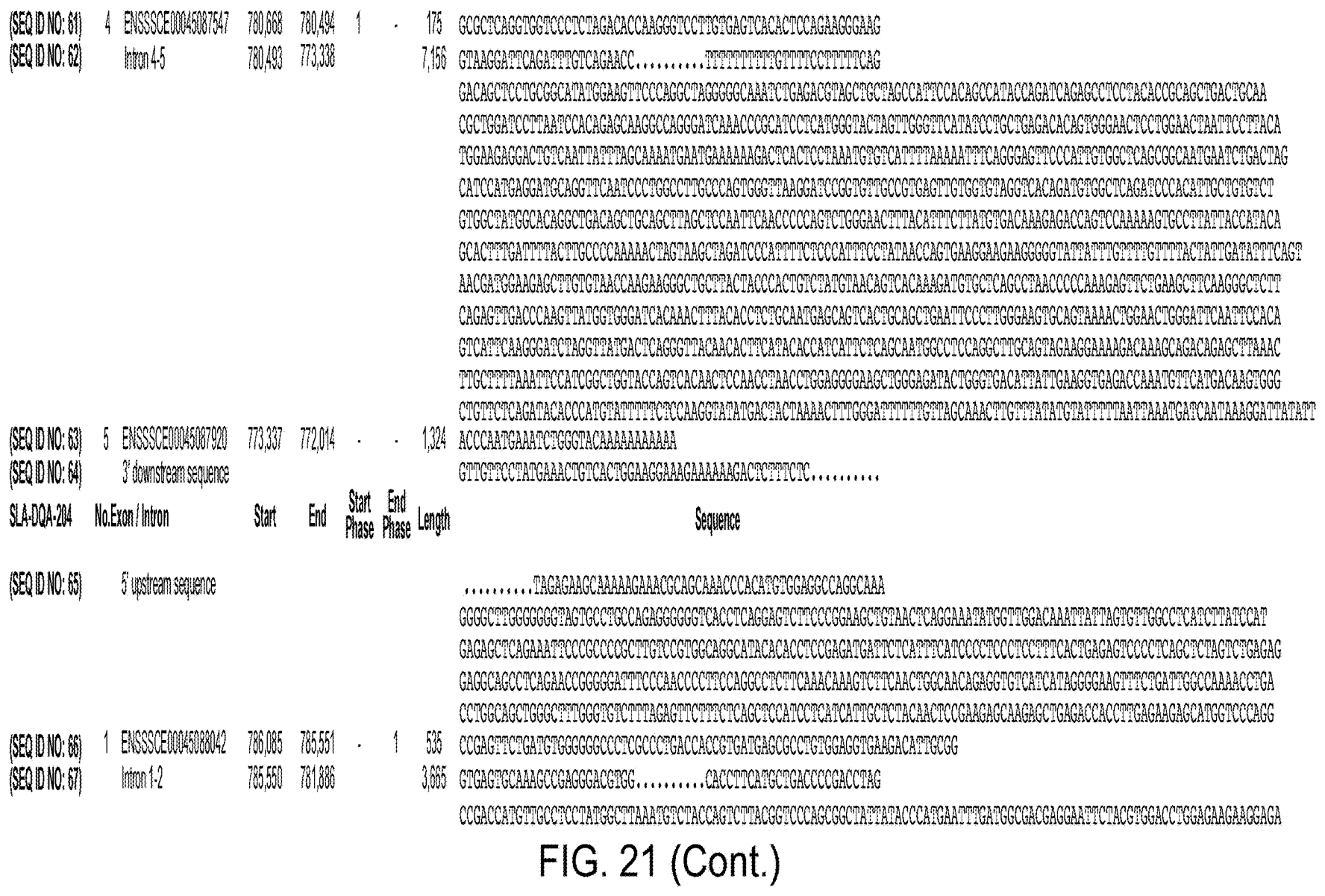
Figure 21:
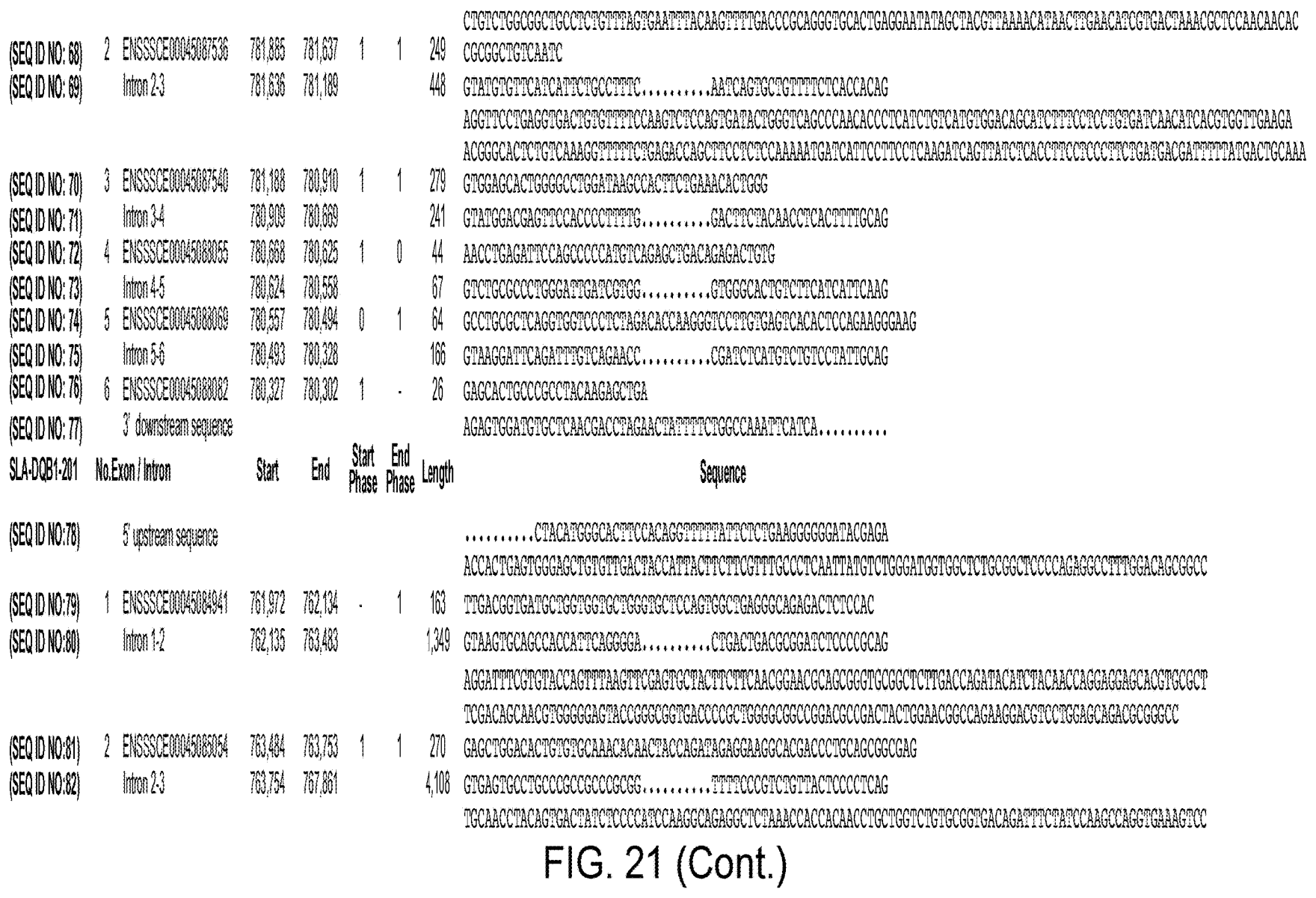
Figure 21:
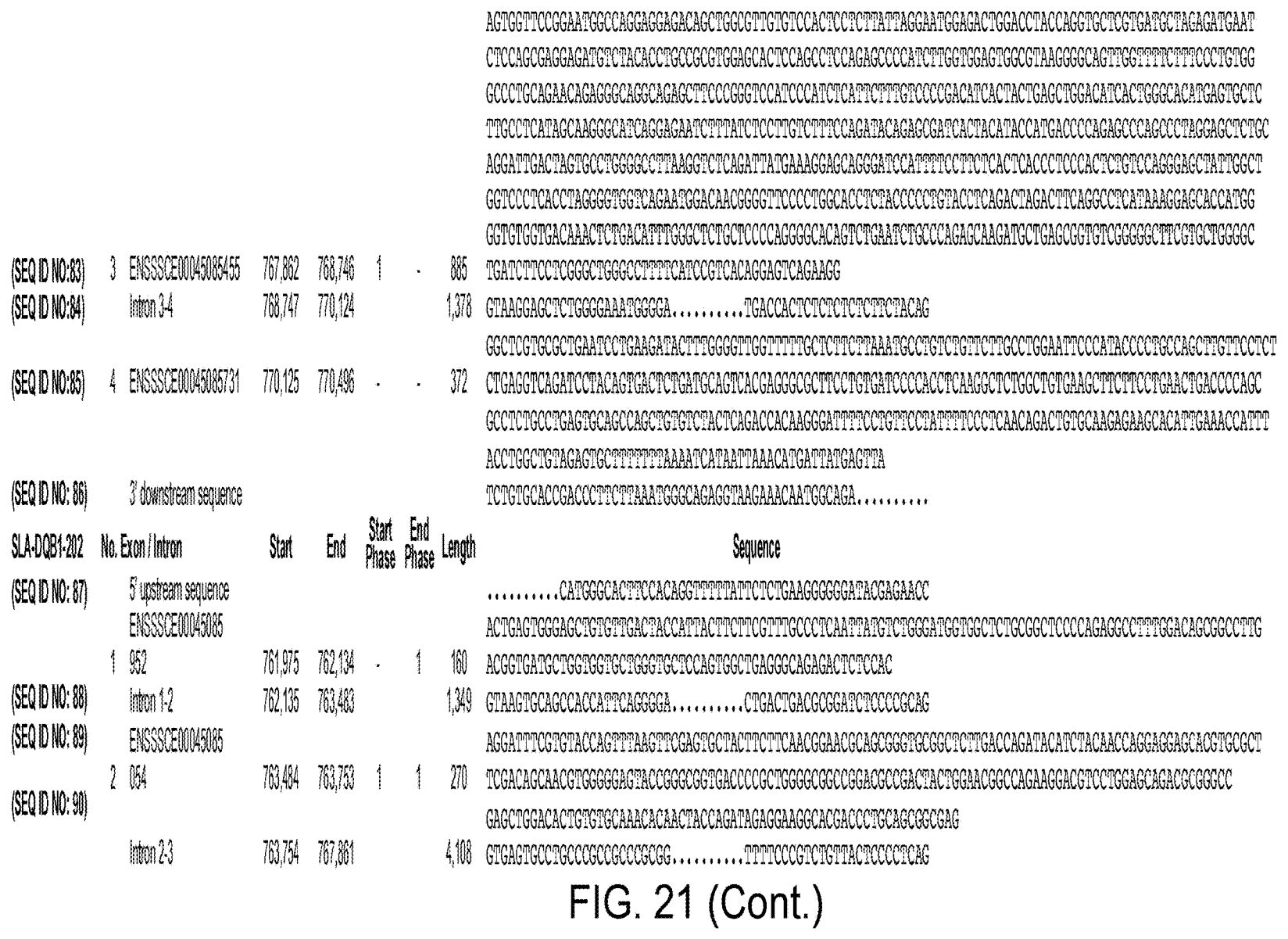
Figure 21:
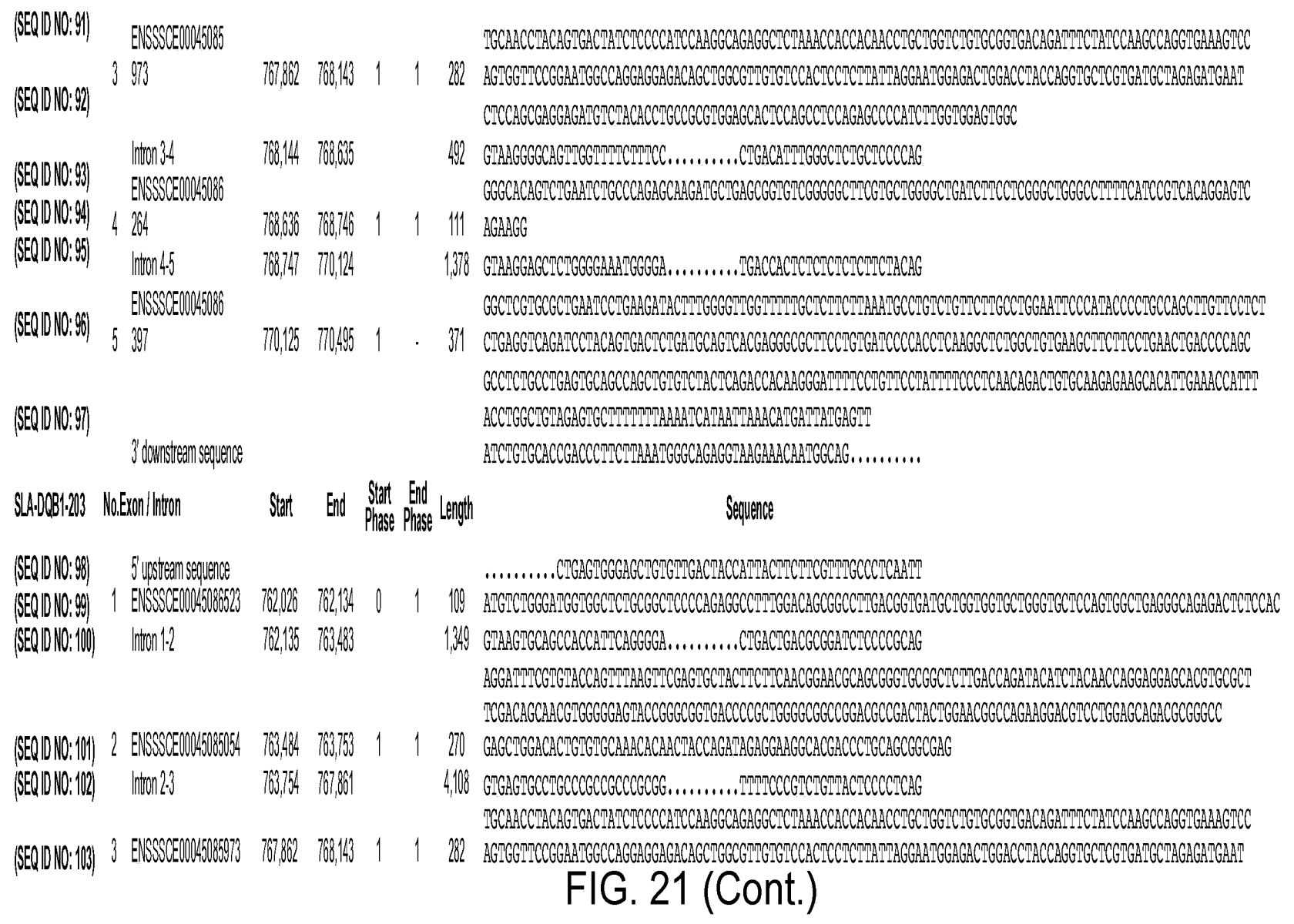
Figure 21:
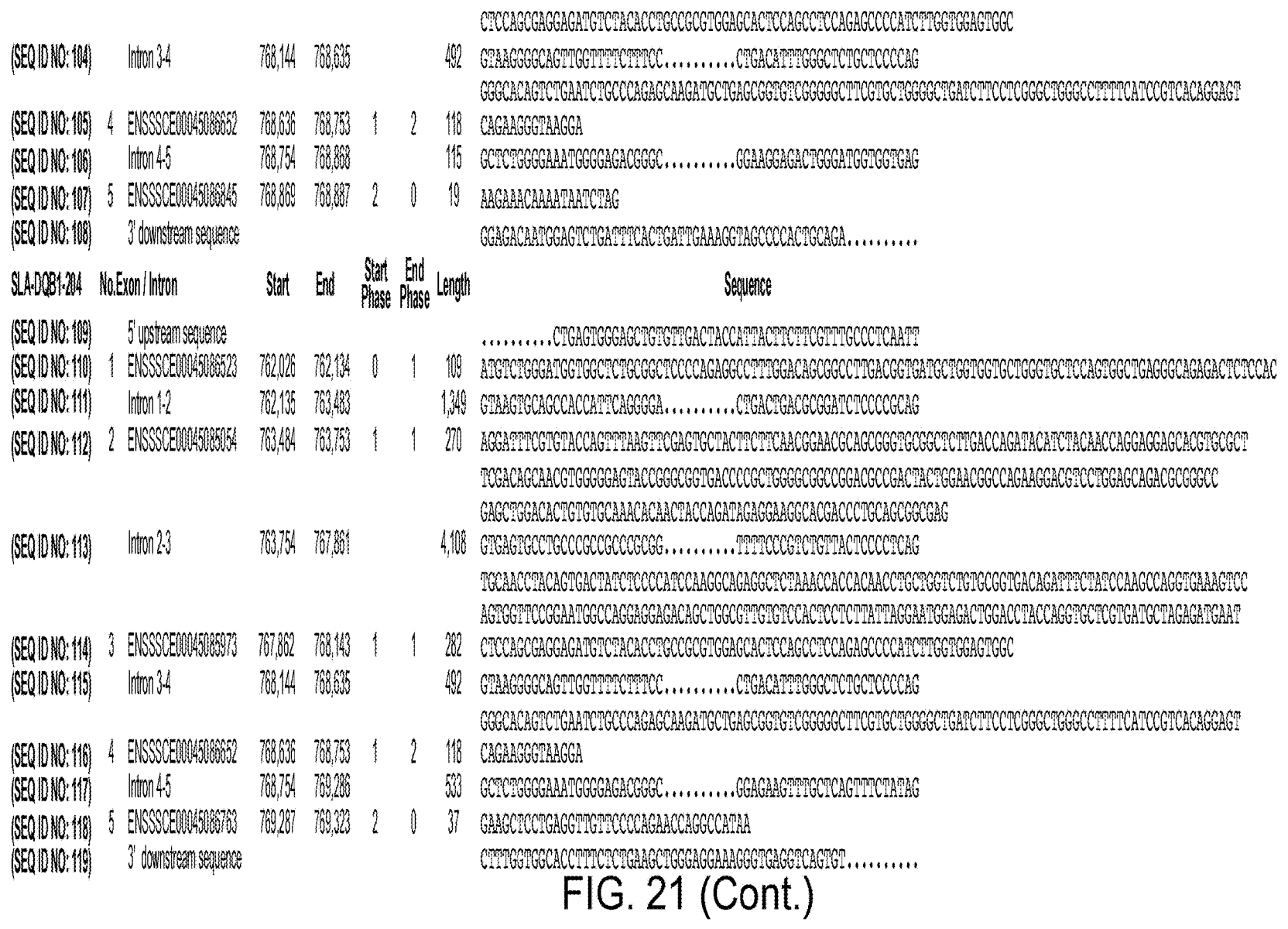

FIG. 21 shows a spreadsheet detailing nucleotide sequences of exons and introns of SLA-DQA and SLA-DQB1.

FIG. 22 shows SLA-DQ beta1 domain of *Sus scrofa* (wild boar).

FIG. 24 shows the length of exons and introns in HLA-DQA

FIG. 25A shows nucleotide sequence library between recipient specific HLA-DQA and HLA-DQA acquired from database, FIG. 25B shows Nucleotide Sequence Library identifying complete divergence between HLA vs SLA(DQ-A, Exon 2), FIG. 25C shows Human Capture Reference Sequence for DQ-A1 for Three Patients, FIG. 25D shows Human Capture Reference Sequence for DQ-B1 for Three Patients, FIG. 25E shows Human Capture Reference Sequence for DR-A for Three Patients, FIG. 25F shows Human Capture Reference Sequence for DQR-B1 for Three Patients.

FIG. 26A shows example of Human Capture Reference Sequence (DQ-A1) for Three Patients.

FIG. 28 shows comparison of amino acid sequences of exon 2 of human B2M vs exon 2 of swine B2M

FIG. 44A graphs systemic concentrations of soluble CD40L as measured by Luminex 23-plex at POD-0, POD-7, POD-14, POD-21, and POD-30. FIG. 44B graphs systemic concentrations of TGF-alpha as measured by Luminex 23-plex at POD-0, POD-7, POD-14, POD-21, and POD-30.

FIG. 45 illustrates a method for preparing a skin product in accordance with the present invention.

FIG. 46 shows a cryovial used to store a xenotransplantation product.

FIG. 50A graphs MTT reduction assays fresh vs. cryopreserved (7 years) in porcine tissue samples showing no statistical difference. FIG. 50B graphs MTT reduction assays heat deactivated vs. cryopreserved (7 years) in porcine tissue samples showing a statistically significant different in quantity of formazan produced.

DETAILED DESCRIPTION OF THE INVENTION

Figure 1:
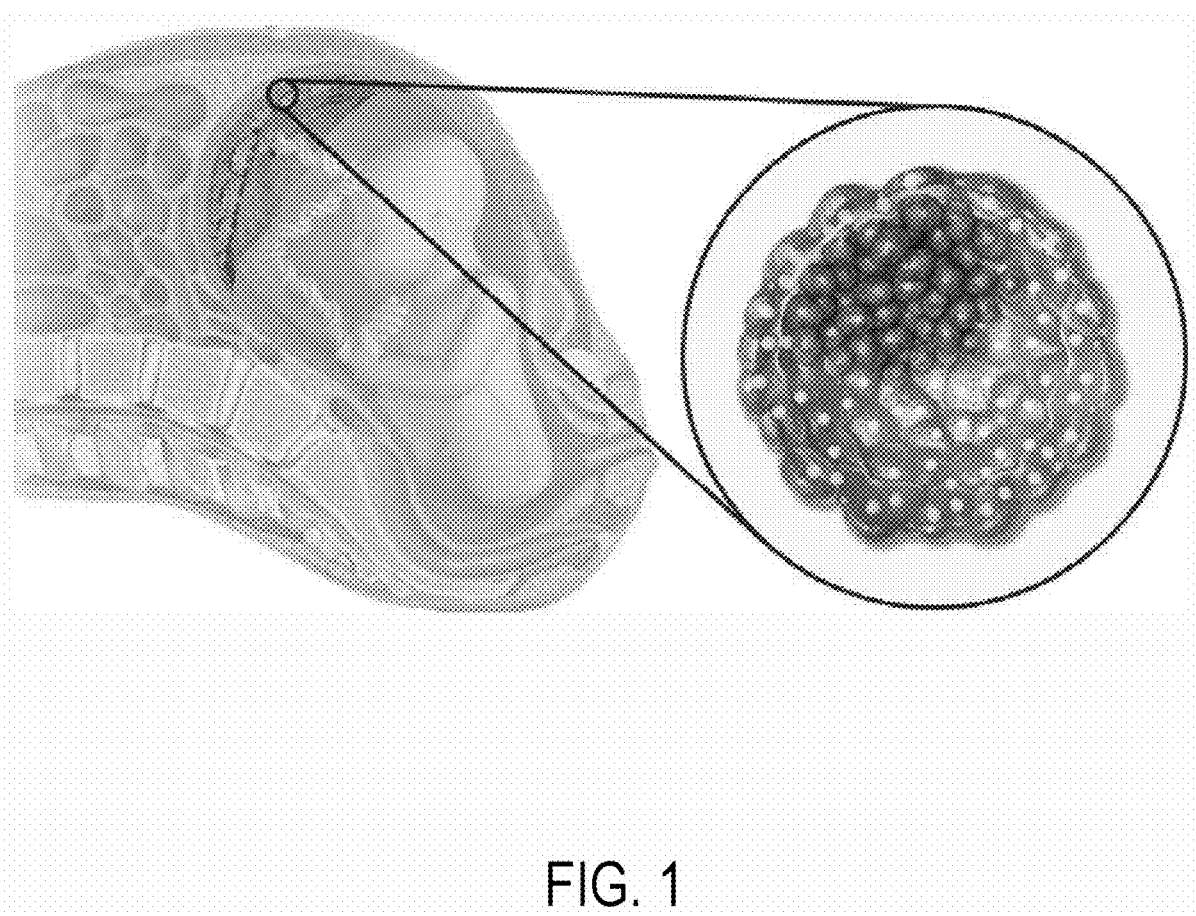
FIG. 1 illustrates an image of human trophoblast and trophoblast cells.

While aspects of the subject matter of the present disclosure may be embodied in a variety of forms, the following description is merely intended to disclose some of these forms as specific examples of the subject matter encompassed by the present disclosure. Accordingly, the subject matter of this disclosure is not intended to be limited to the forms or aspects so described.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. Other features and advantages of the invention will be apparent from the following detailed description and figures, and from the claims.

"Best alignment" or "optimum alignment" means the alignment for which the identity percentage determined as described below is the highest. Comparisons of sequences between two nucleic acid sequences are traditionally made by comparing these sequences after aligning them optimally, the said comparison being made by segment or by "comparison window" to identify and compare local regions for similar sequences. For the comparison, sequences may be optimally aligned manually, or by using alignment software, e.g., Smith and Waterman local homology algorithm (1981), the Neddleman and Wunsch local homology algorithm (1970), the Pearson and Lipman similarity search method (1988), and computer software using these algorithms (GAP, BESTFIT, BLAST P, BLAST N, FASTA and TFASTA in the Wisconsin Genetics Software Package, Genetics Computer Group, 575 Science Dr., Madison, Wis.). In some aspects, the optimum alignment is obtained using the BLAST program with the BLOSUM 62 matrix or software having similar functionality. The "identity percentage" between two sequences of nucleic acids or amino acids is determined by comparing these two optimally aligned sequences, the sequence of nucleic acids or amino acids to be compared possibly including additions or deletions from the reference sequence for optimal alignment between these two sequences. The identity percentage is calculated by determining the number of positions for which the nucleotide or the amino acid residue is identical between the two sequences, by dividing this number of identical positions by the total number of compared positions and multiplying the result obtained by 100 to obtain the identity percentage between these two sequences.

"Conservative," and its grammatical equivalents as used herein include a conservative amino acid substitution, including substitution of an amino acid residue by another amino acid residue having a side chain R group with similar chemical properties (e.g., charge or hydrophobicity). Conservative amino acid substitutions may be achieved by modifying a nucleotide sequence so as to introduce a nucleotide change that will encode the conservative substitution. In general, a conservative amino acid substitution will not substantially change the functional properties of interest of a protein, for example, the ability of MHC I to present a peptide of interest. Examples of groups of amino acids that have side chains with similar chemical properties include aliphatic side chains such as glycine, alanine, valine, leucine, and isoleucine; aliphatic-hydroxyl side chains such as serine and threonine; amide-containing side chains such as asparagine and glutamine; aromatic side chains such as phenylalanine, tyrosine, and tryptophan; basic side chains such as lysine, arginine, and histidine; acidic side chains such as aspartic acid and glutamic acid; and, sulfur-containing side chains such as cysteine and methionine. Conservative amino acids substitution groups include, for example, valine/leucine/isoleucine, phenylalanine/tyrosine, lysine/arginine, alanine/valine, glutamate/aspartate, and asparagine/glutamine. One skilled in the art would understand that in addition to the nucleic acid residues encoding a human or humanized MHC I polypeptide and/or β2 microglobulin described herein, due to the degeneracy of the genetic code, other nucleic acid sequences may encode the polypeptide(s) of the invention. Therefore, in addition to a genetically modified non-human animal that comprises in its genome a nucleotide sequence encoding MHC I and/or β2 microglobulin polypeptide(s) with conservative amino acid substitutions, a non-human animal whose genome comprises a nucleotide sequence(s) that differs from that described herein due to the degeneracy of the genetic code is also provided.

"Conserved" and its grammatical equivalents as used herein include nucleotides or amino acid residues of a polynucleotide sequence or amino acid sequence, respectively, that are those that occur unaltered in the same position of two or more related sequences being compared. Nucleotides or amino acids that are relatively conserved are those that are conserved amongst more related sequences than nucleotides or amino acids appearing elsewhere in the sequences. Herein, two or more sequences are said to be "completely conserved" if they are 100% identical to one another. In some embodiments, two or more sequences are said to be "highly conserved" if they are at least 70% identical, at least 80% identical, at least 90% identical, or at least 95% identical, but less than 100% identical, to one another. In some embodiments, two or more sequences are said to be "conserved" if they are at least 30% identical, at least 40% identical, at least 50% identical, at least 60% identical, at least 70% identical, at least 80% identical, at least 90% identical, or at least 95% identical, but less than 100% identical, to one another. In some embodiments, two or more sequences are said to be "conserved" if they are about 30% identical, about 40% identical, about 50% identical, about 60% identical, about 70% identical, about 80% identical, about 90% identical, about 95% identical, about 98% identical, or about 99% identical to one another.

"Designated pathogen free," and its grammatical equivalents as used herein include reference to animals, animal herds, animal products derived therefrom, and/or animal facilities that are free of one or more specified pathogens. Preferably, such "designated pathogen free" animals, animal herds, animal products derived therefrom, and/or animal facilities are maintained using well-defined routines of testing for such designated pathogens, utilizing proper standard operating procedures (SOPs) and practices of herd husbandry and veterinary care to assure the absence and/or destruction of such designated pathogens, including routines, testing, procedures, husbandry, and veterinary care disclosed and described herein. It will be further understood that as used herein the term "free," and like terms when used in connection with "pathogen free" are meant to indicate that the subject pathogens are not present, not alive, not active, or otherwise not detectable by standard or other testing methods for the subject pathogens.

"Alter," "altering," "altered" and grammatical equivalents as used herein include any and/or all modifications to a gene including, but not limited to, deleting, inserting, silencing, modifying, reprogramming, disrupting, mutating, rearranging, increasing expression, knocking-in, knocking out, and/or any or all other such modifications or any combination thereof.

"Endogenous loci" and its grammatical equivalents as used herein include the natural genetic loci found in the animal to be transformed into the donor animal.

"Functional," e.g., in reference to a functional polypeptide, and its grammatical equivalents as used herein include a polypeptide that retains at least one biological activity normally associated with the native protein. For example, in some embodiments of the invention, a replacement at an endogenous locus (e.g., replacement at an endogenous non-human MHC I, MHC II, and/or β2 microglobulin locus) results in a locus that fails to express a functional endogenous polypeptide. Likewise, the term "functional" as used herein in reference to functional extracellular domain of a protein, can refer to an extracellular domain that retains its functionality, e.g., in the case of MHC I, ability to bind an antigen, ability to bind a T cell co-receptor, etc. In some embodiments of the invention, a replacement at the endogenous MHC locus results in a locus that fails to express an extracellular domain (e.g., a functional extracellular domain) of an endogenous MHC while expressing an extracellular domain (e.g., a functional extracellular domain) of a human MHC.

"Genetic or molecular marker," and their grammatical equivalents as used herein include polymorphic locus, i.e. a polymorphic nucleotide (a so-called single nucleotide polymorphism or SNP) or a polymorphic DNA sequence at a specific locus. A marker refers to a measurable, genetic characteristic with a fixed position in the genome, which is normally inherited in a Mendelian fashion, and which can be used for mapping of a trait of interest. Thus, a genetic marker may be a short DNA sequence, such as a sequence surrounding a single base-pair change, i.e. a single nucleotide polymorphism or SNP, or a long DNA sequence, such as microsatellites or Simple Sequence Repeats (SSRs). The nature of the marker is dependent on the molecular analysis used and can be detected at the DNA, RNA or protein level. Genetic mapping can be performed using molecular markers such as, but not limited to, RFLP (restriction fragment length polymorphisms; Botstein et al. (1980), Am J Hum Genet. 32:314-331; Tanksley et al. (1989), Bio/Technology 7:257-263), RAPD [random amplified polymorphic DNA; Williams et al. (1990), NAR 18:6531-6535], AFLP [Amplified Fragment Length Polymorphism; Vos et al. (1995) NAR 23:4407-4414], SSRs or microsatellites [Tautz et al. (1989), NAR 17:6463-6471]. Appropriate primers or probes are dictated by the mapping method used.

"Improving" and its grammatical equivalents as used herein include any improvement recognized by one of skill in the art. For example, improving transplantation can mean lessening hyperacute rejection, which can encompass a decrease, lessening, or diminishing of an undesirable effect or symptom. In some aspects, a clinically relevant improvement is achieved.

"Locus" (loci plural) or "site" and their grammatical equivalents as used herein include a specific place or places on a chromosome where, for example, a gene, a genetic marker or a QTL is found.

"Minimally altered" and its grammatical equivalents as used herein include alteration of a donor animal genome including removing and replacing certain distinct sequences of native base pairs appearing on the donor animal's genome and replacing each such sequence with a synthetic sequence comprising the same number of base pairs, with no net change to the number of base pairs in the donor animal's genome, while not disturbing other aspects of the donor animal's native genome including, for example, introns and other codons naturally existing in the donor animal genome. For example, in the case of a swine as donor animal, a minimally altered swine can include specific alterations removing or deactivating certain SLA exons to regulate the donor swine cell's extracellular expression or non-expression of MHC Class II, Ia, and/or Ib; reprogramming certain native, naturally occurring swine cell SLA exons to regulate the swine cell's extracellular expression or non-expression of MHC Class II; conserving or otherwise not removing swine introns existing in or in the vicinity of the otherwise engineered sequences; increasing the expression of swine CTLA4 and PD-1; and removing or deactivating alpha-1,3 galactosyltransferase, cytidine monophosphate-N-acetyl-neuraminic acid hydroxylase, and β1,4-N-acetylgalac-tosaminyltransferase.

"Minimally manipulated" and its grammatical equivalents as used herein include treatment of source animals, biological products derived from those source animals, and other biological products with minimal physical alteration of the related cells, organs or tissues such that such animals and products are substantially in their natural state.

"Ortholog," "orthologous," and their grammatical equivalents as used herein include a polynucleotide from one species that corresponds to a polynucleotide in another species, which has the same function as the gene or protein or QTL, but is (usually) diverged in sequence from the time point on when the species harboring the genes or quantitative trait loci diverged (i.e. the genes or quantitative trait loci evolved from a common ancestor by speciation).

"Quantitative trait locus (QTL)" and its grammatical equivalents as used herein include a stretch of DNA (such as a chromosome arm, a chromosome region, a nucleotide sequence, a gene, and the like) that is closely linked to a gene that underlies the trait in question. "QTL mapping" involves the creation of a map of the genome using genetic or molecular markers, like AFLP, RAPD, RFLP, SNP, SSR, and the like, visible polymorphisms and allozymes, and determining the degree of association of a specific region on the genome to the inheritance of the trait of interest. As the markers do not necessarily involve genes, QTL mapping results involve the degree of association of a stretch of DNA with a trait rather than pointing directly at the gene responsible for that trait. Different statistical methods are used to ascertain whether the degree of association is significant or not. A molecular marker is said to be "linked" to a gene or locus, if the marker and the gene or locus have a greater association in inheritance than would be expected from independent assortment, i.e. the marker and the locus co-segregate in a segregating population and are located on the same chromosome. "Linkage" refers to the genetic distance of the marker to the locus or gene (or two loci or two markers to each other). The closer the linkage, the smaller the likelihood of a recombination event taking place, which separates the marker from the gene or locus. Genetic distance (map distance) is calculated from recombination frequencies and is expressed in centiMorgans (cM) [Kosambi (1944), *Ann. Eugenet.* 12:172-175].

"Capture sequence" or "reference sequence" and their grammatical equivalents as used herein include a nucleic acid or amino acid sequence that has been obtained, sequenced or otherwise become known from a sample, animal (including humans), or population. For example, a capture sequence from a human patient is a "human patient capture sequence." A capture sequence from a particular human population is a "human population-specific human capture sequence." And a capture sequence from a human allele group is an "allele-group-specific human capture sequence."

"Humanized" and its grammatical equivalents as used herein include embodiments wherein all or a portion of an endogenous non-human gene or allele is replaced by a corresponding portion of an orthologous human gene or allele. For example, in some embodiments, the term "humanized" refers to the complete replacement of the coding region (e.g., the exons) of the endogenous non-human MHC gene or allele or fragment thereof with the corresponding capture sequence of the human MHC gene or allele or fragment thereof, while the endogenous non-coding region(s) (such as, but not limited to, the promoter, the 5' and/or 3' untranslated region(s), enhancer elements, etc.) of the non-human animal is not replaced.

"Personalized" or "individualized," and their grammatical equivalents as used herein, include a gene, allele, genome, proteome, cell, cell surface, tissue, or organ from a non-human animal which is adapted to the needs or special circumstances of an individual human recipient or a specific human recipient subpopulation.

"Reprogram," "reprogrammed," including in reference to "immunogenomic reprogramming," and their grammatical equivalents as used herein, refer to the replacement or substitution of endogenous nucleotides in the donor animal with orthologous nucleotides based on a separate reference sequence, wherein frameshift mutations are not introduced by such reprogramming. In addition, reprogramming results in no net loss or net gain in the total number of nucleotides in the donor animal genome, or results in a net loss or net gain in the total number of nucleotides in the donor animal genome that is equal to no more than 1%, no more than 2%, no more than 3%, no more than 4%, no more than 5%, no more than 6%, no more than 7%, no more than 8%, no more than 9%, no more than 10%, no more than 12%, no more than 15%, or no more than 20% of the number of nucleotides in the separate reference sequence. In one example of "reprogramming," an endogenous non-human nucleotide, codon, gene or fragment thereof is replaced with a corresponding synthetic nucleotide, codon, gene or fragment thereof based on a human capture sequence, through which the total number of base pairs in the donor animal sequence is equal to the total number of base pairs of the human capture sequence.

"Tolerogenic" and its grammatical equivalents as used herein include characteristics of an organ, cell, tissue, or other biological product that are tolerated by the reduced response by the recipient's immune system upon transplantation.

"Transgenic" and its grammatical equivalents as used herein, include donor animal genomes that have been modified to introduce non-native genes from a different species into the donor animal's genome at a non-orthologous, non-endogenous location such that the homologous, endogenous version of the gene (if any) is retained in whole or in part. "Transgene," "transgenic," and grammatical equivalents as used herein do not include reprogrammed genomes, knockouts or other modifications as described and claimed herein. By way of example, "transgenic" swine include those having or expressing hCD46 ("human membrane cofactor protein," or "MCP"), hCD55 ("human decay-accelerating factor," "DAF"), human B2M (beta-2-microglobulin), and/or other human genes, achieved by insertion of human gene sequences at a non-orthologous, non-endogenous location in the swine genome without the replacement of the endogenous versions of those genes.

Immunogenomic Reprogrammed Swine

As disclosed herein, tolerogenic non-human animal cells, tissues and organs for several human Class I and/or Class II MHC molecules are provided.

The human immune response system is a highly complex and efficient defense system against invading organisms. T-cells are the primary effector cells involved in the cellular response. Just as antibodies have been developed as therapeutics, (TCRs), the receptors on the surface of the T-cells, which give them their specificity, have unique advantages as a platform for developing therapeutics. While antibodies are limited to recognition of pathogens in the blood and extracellular spaces or to protein targets on the cell surface, TCRs recognize antigens displayed by MHC molecules on the surfaces of cells (including antigens derived from intracellular proteins). Depending on the subtype of T-cells that recognize displayed antigen and become activated, TCRs and T-cells harboring TCRs participate in controlling various immune responses. For instance, helper T-cells are involved in regulation of the humoral immune response through induction of differentiation of B cells into antibody secreting cells. In addition, activated helper T-cells initiate cell-mediated immune responses by cytotoxic T-cells. Thus, TCRs specifically recognize targets that are not normally seen by antibodies and also trigger the T-cells that bear them to initiate wide variety of immune responses.

It will be understood, that T-cell recognizes an antigen presented on the surfaces of cells by means of the TCRs expressed on their cell surface. TCRs are disulfide-linked heterodimers, most consisting of $\alpha$ and $\beta$ chain glycoproteins. T-cells use recombination mechanisms to generate diversity in their receptor molecules similar to those mechanisms for generating antibody diversity operating in B cells (Janeway and Travers, Immunobiology 1997). Similar to the immunoglobulin genes, TCR genes are composed of segments that rearrange during development of T-cells. TCR polypeptides consist of variable, constant, transmembrane and cytoplasmic regions. While the transmembrane region anchors the protein and the intracellular region participates in signaling when the receptor is occupied, the variable region is responsible for specific recognition of an antigen and the constant region supports the variable region-binding surface. The TCR $\alpha$ chain contains variable regions encoded by variable (V) and joining (J) segments only, while the $\beta$ chain contains additional diversity (D) segments.

Figure 3:
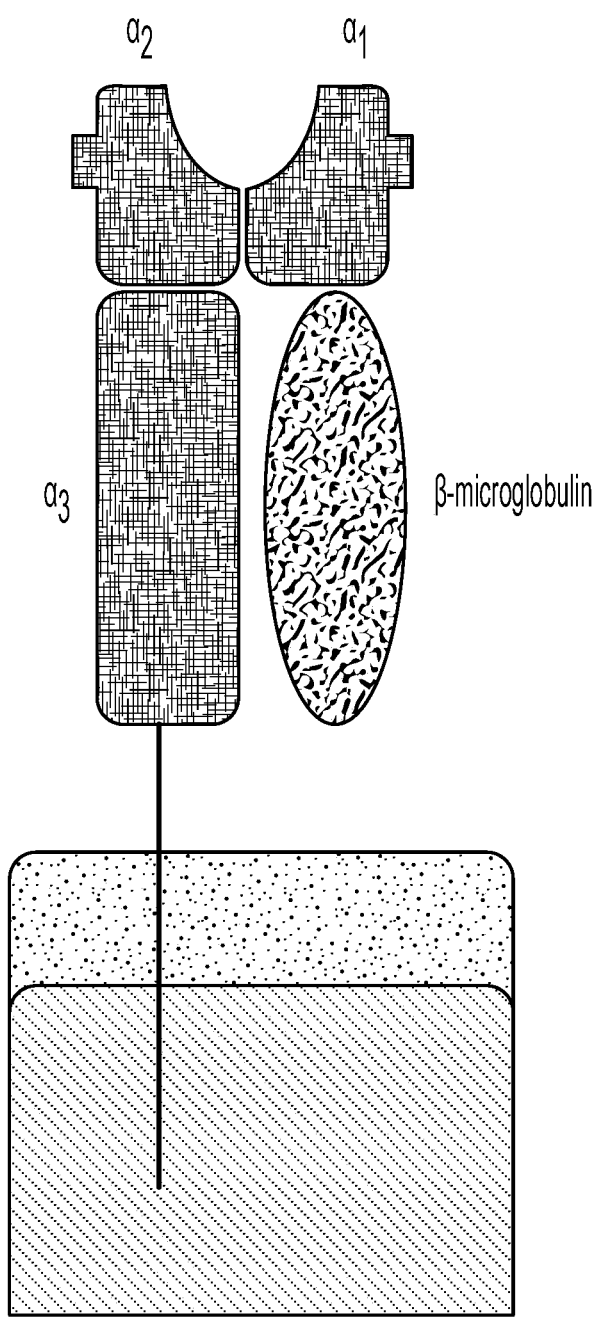
FIG. 3 schematically illustrates HLA Class I on the surface of a cell.
Figure 4:
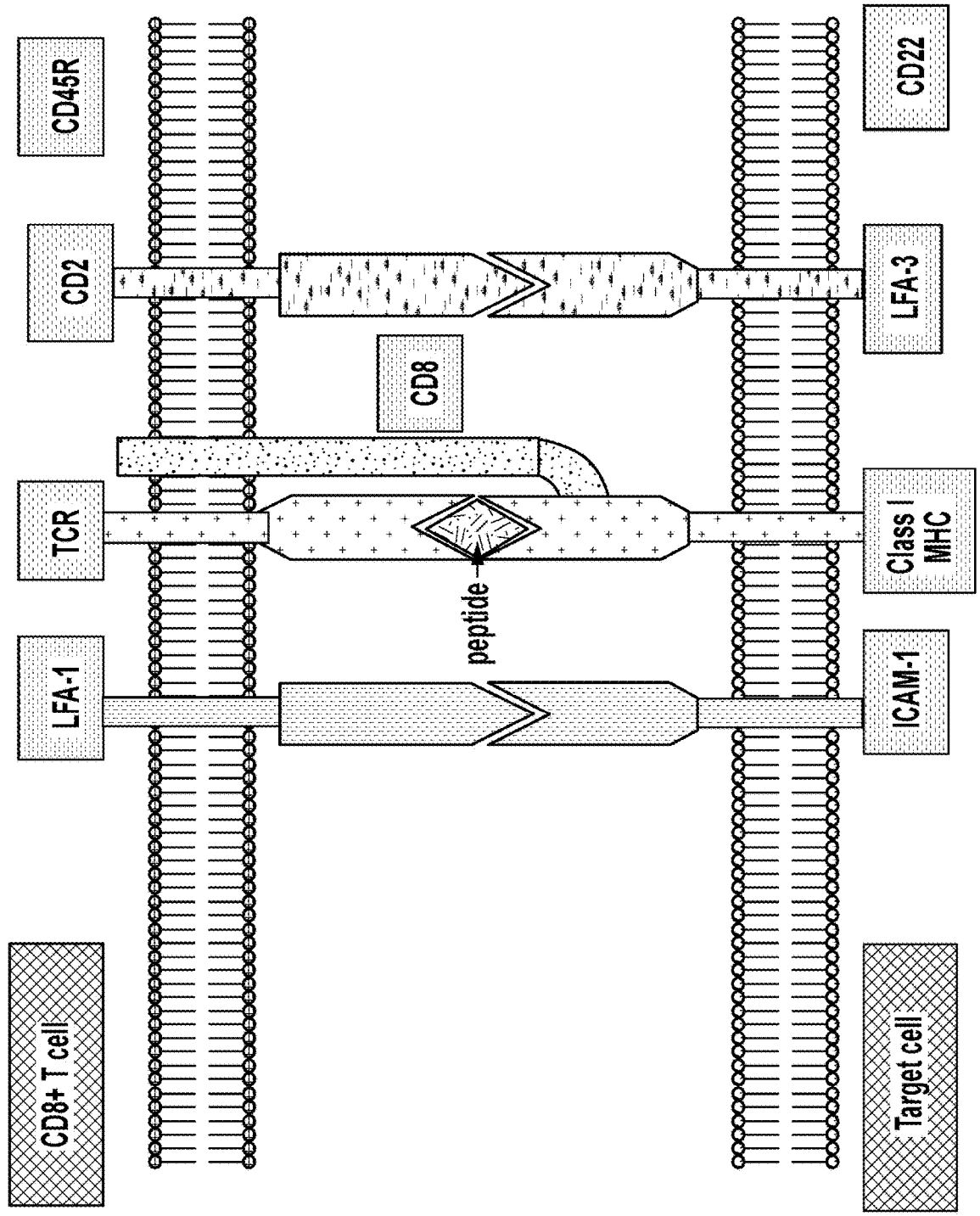
FIG. 4 schematically illustrates a Cytotoxic T Cell (CD8+)-Target Cell Interaction.
Figure 5:
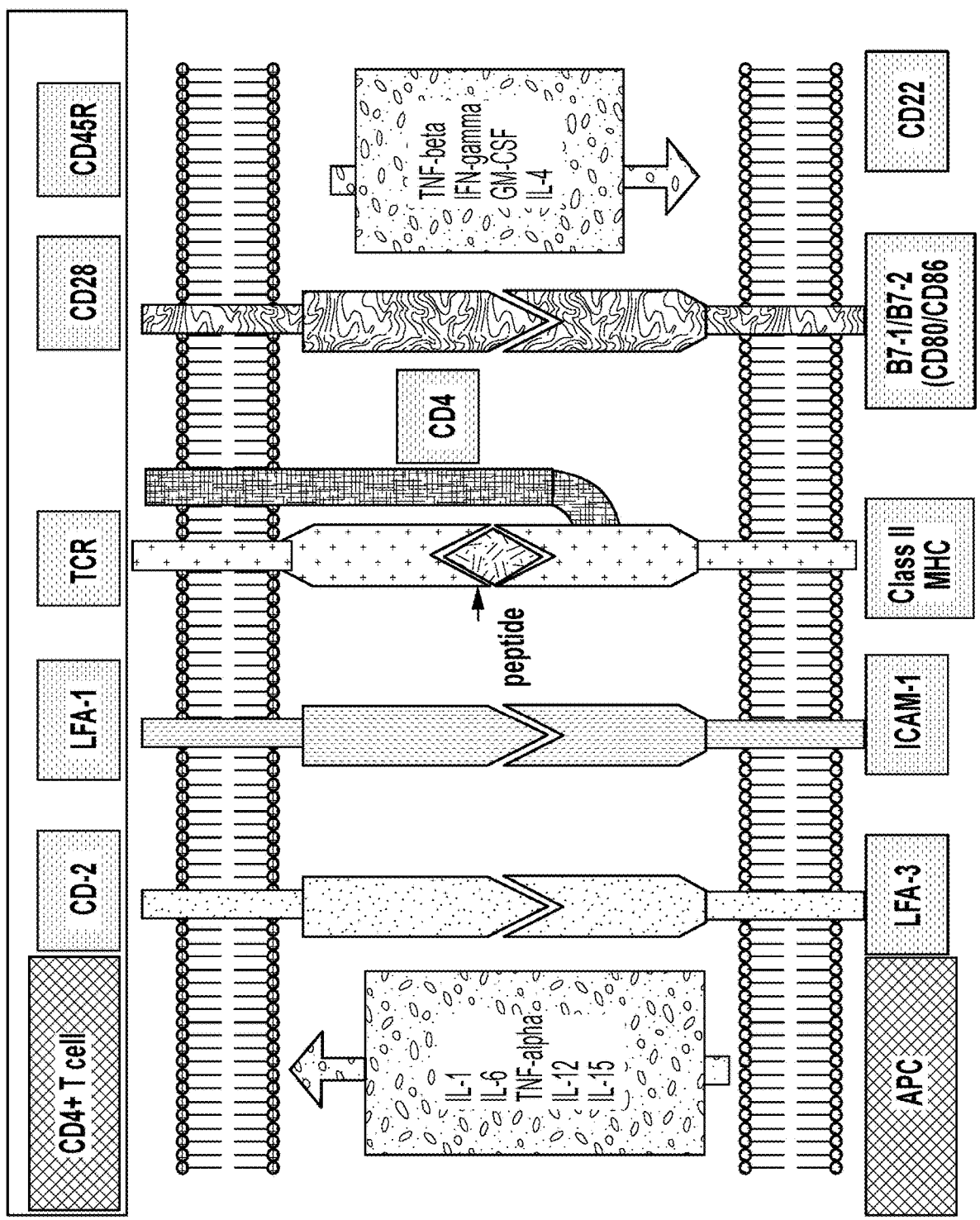
FIG. 5 schematically illustrates a Cytotoxic T Cell (CD4+)-Target Cell Interaction.

Major histocompatibility complex Class I (MHCI) and Class II (MHCII) molecules display peptides on antigen-presenting cell surfaces for subsequent T-cell recognition. See FIG. 2. Within the human population, allelic variation among the classical MHCI and II gene products is the basis for differential peptide binding, thymic repertoire bias and allograft rejection. MHC molecules are cell-surface glycoproteins that are central to the process of adaptive immunity, functioning to capture and display peptides on the surface of antigen-presenting cells (APCs). MHC Class I (MHCI) molecules are expressed on most cells, bind endogenously derived peptides with sizes ranging from eight to ten amino acid residues and are recognized by CD8 cytotoxic T-lymphocytes (CTL). See FIG. 3 and FIG. 4. On the other hand, MHC Class II (MHCII) are present only on specialized APCs, bind exogenously derived peptides with sizes varying from 9 to 22 residues, and are recognized by CD4 helper T-cells. See FIG. 5. These differences indicate that MHCI and MHCII molecules engage two distinct arms of the T-cell-mediated immune response, the former targeting invasive pathogens such as viruses for destruction by CD8 CTLs, and the latter inducing cytokine-based inflammatory mediators to stimulate CD4 helper T-cell activities including B-cell activation, maturation and antibody production. In some aspects, the biological product of the present disclosure is not recognized by CD8+ T cells, do not bind anti-HLA antibodies, and are resistant to NK-mediated lysis.

Figure 6:
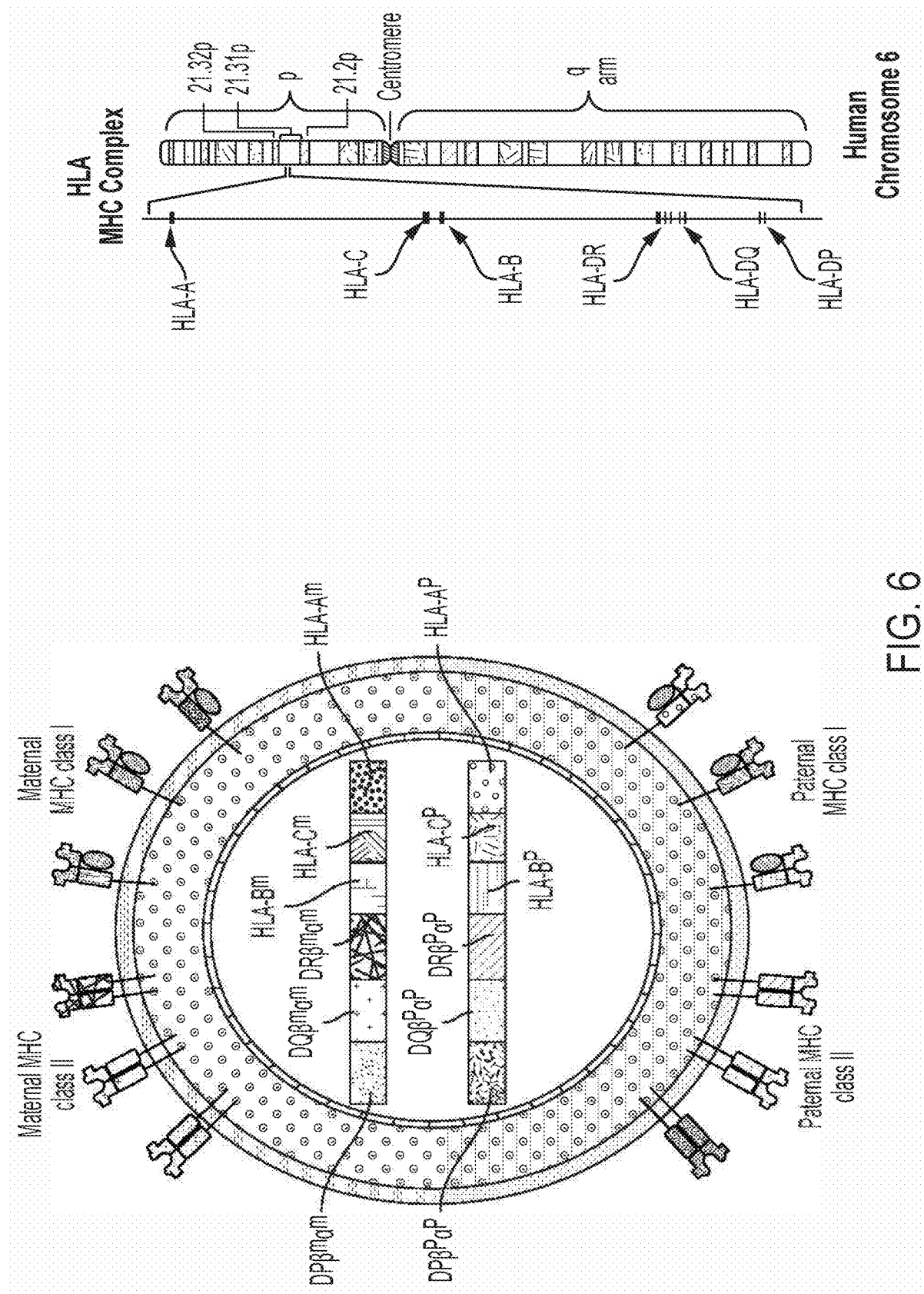
FIG. 6 schematically illustrates codominant expression of HLA genes and the position of HLA genes on human chromosome 6.
Figure 8:
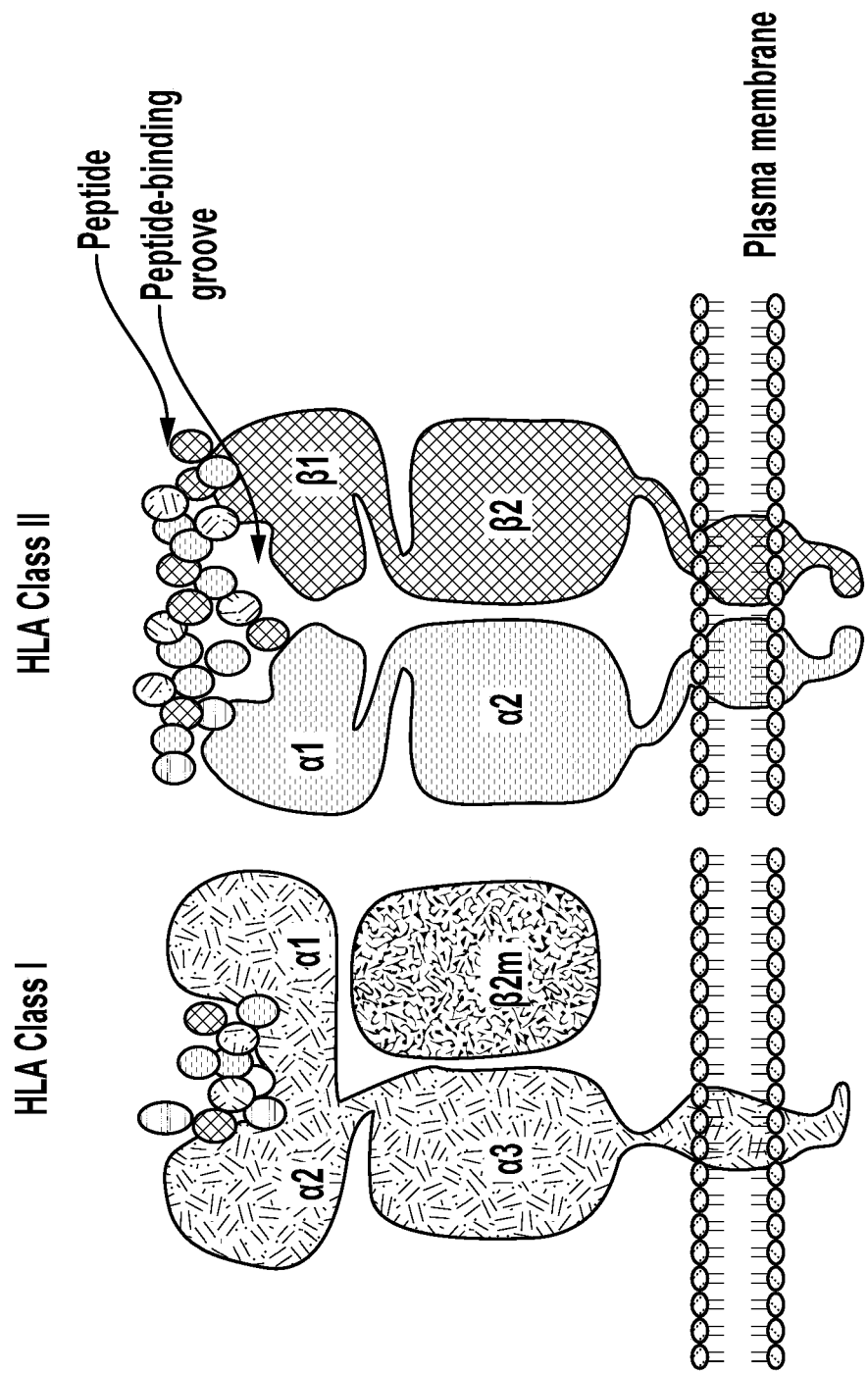
FIG. 8 schematically illustrates HLA Class I and Class II on the surface of a cell.
Figure 9:
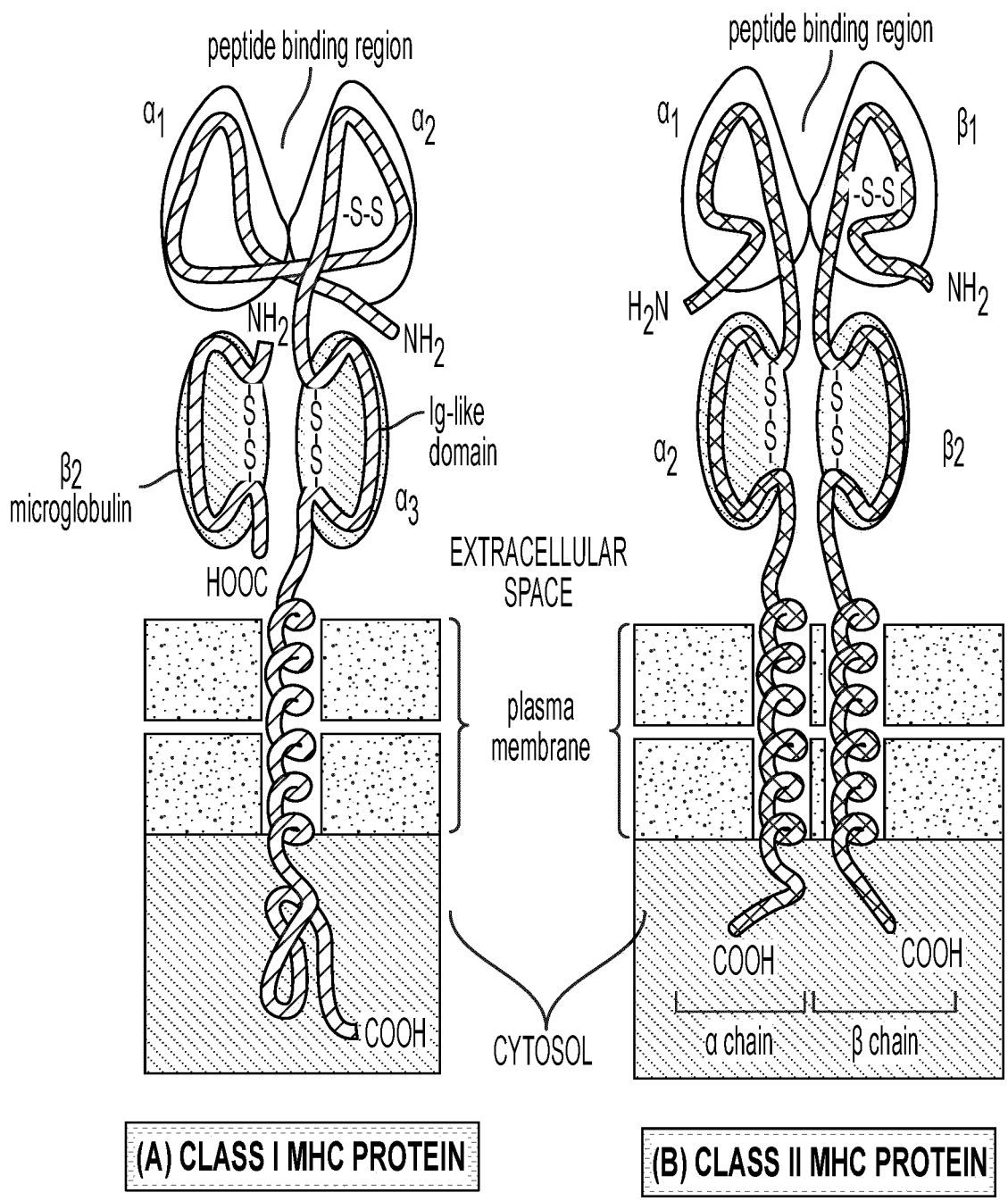
FIG. 9 shows the structure of MHC Class I (A) and Class II proteins (B). The two globular domains furthest from the plasma membrane that form the peptide binding region (PBR) are shaded in blue. The two Ig-like domains, including the β2-microglobulin, are shaded in grey.

The human leukocyte antigen (HLA) system or complex is a gene complex encoding the major histocompatibility complex (MHC) proteins in humans. These cell-surface proteins are responsible for the regulation of the immune system in humans. The HLA gene complex resides on a 3 Mbp stretch within chromosome 6p21. See FIG. 6. HLA genes are highly polymorphic, which means that they have many different alleles, allowing them to fine-tune the adaptive immune system. See FIG. 7. The proteins encoded by certain genes are also known as antigens, as a result of their historic discovery as factors in organ transplants. Different classes have different functions. See FIG. 8 and FIG. 9.

Figure 10:
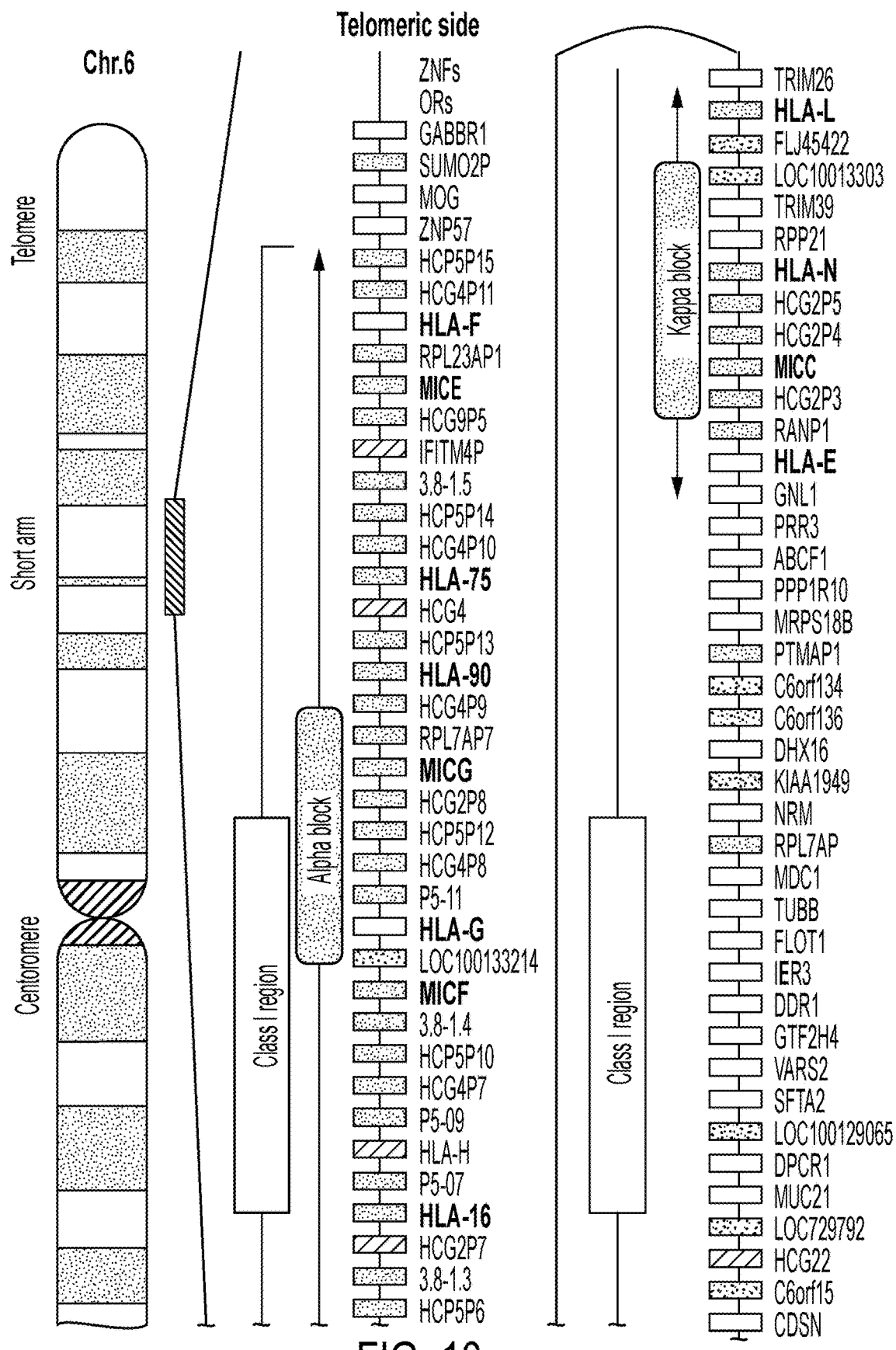
FIG. 10 shows the HLA genomic loci map.
Figure 10:
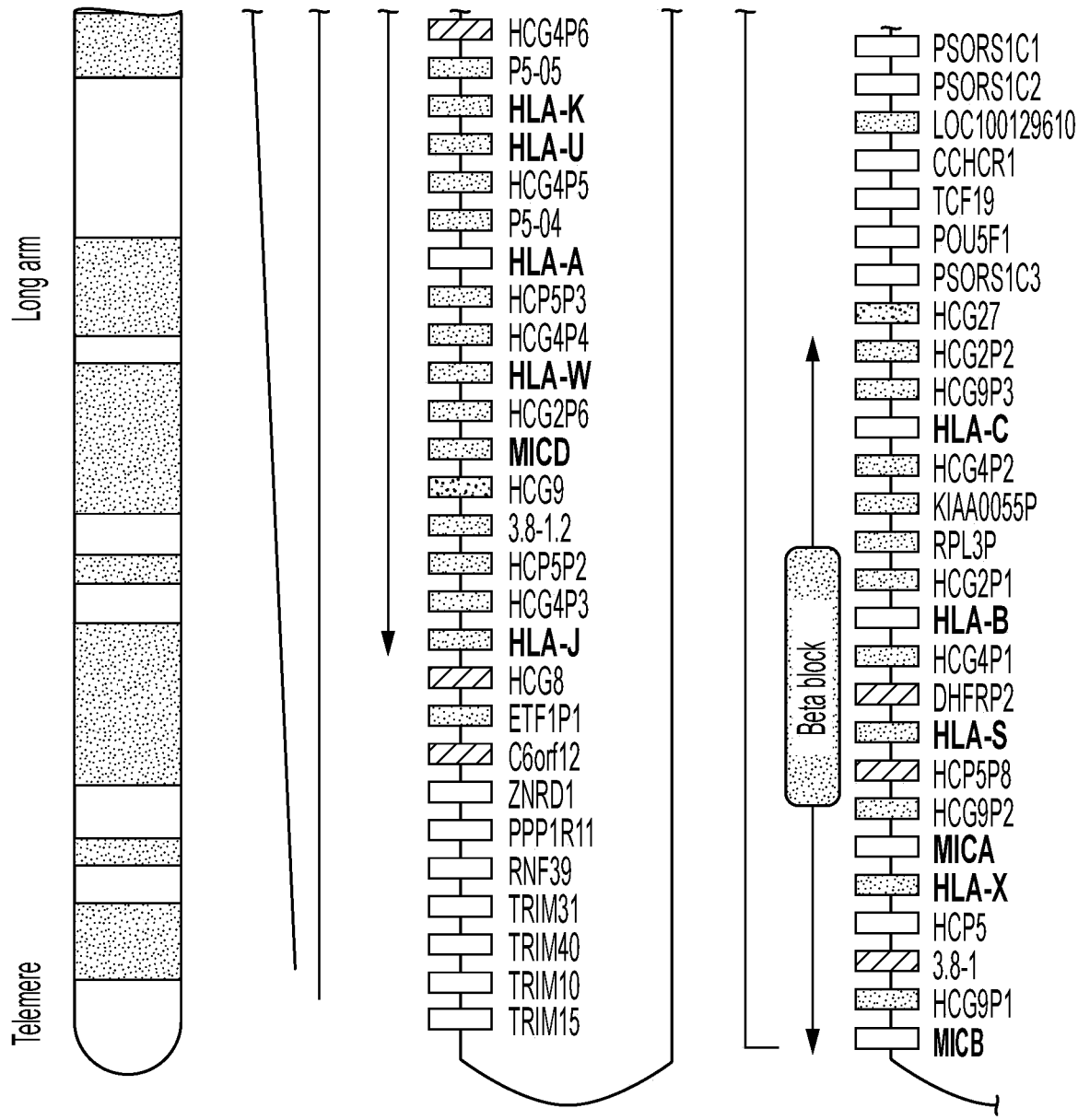
Figure 10:
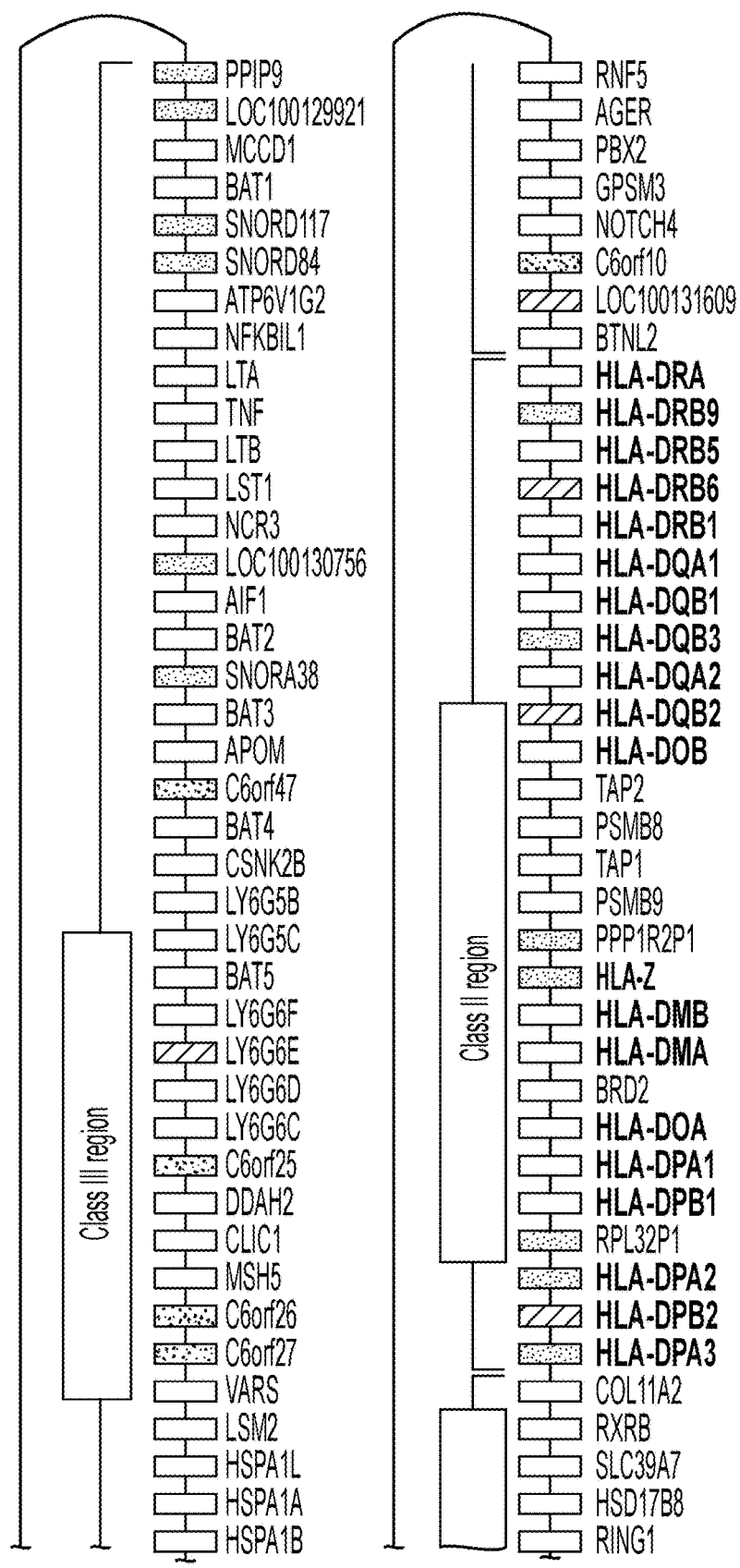
Figure 10:
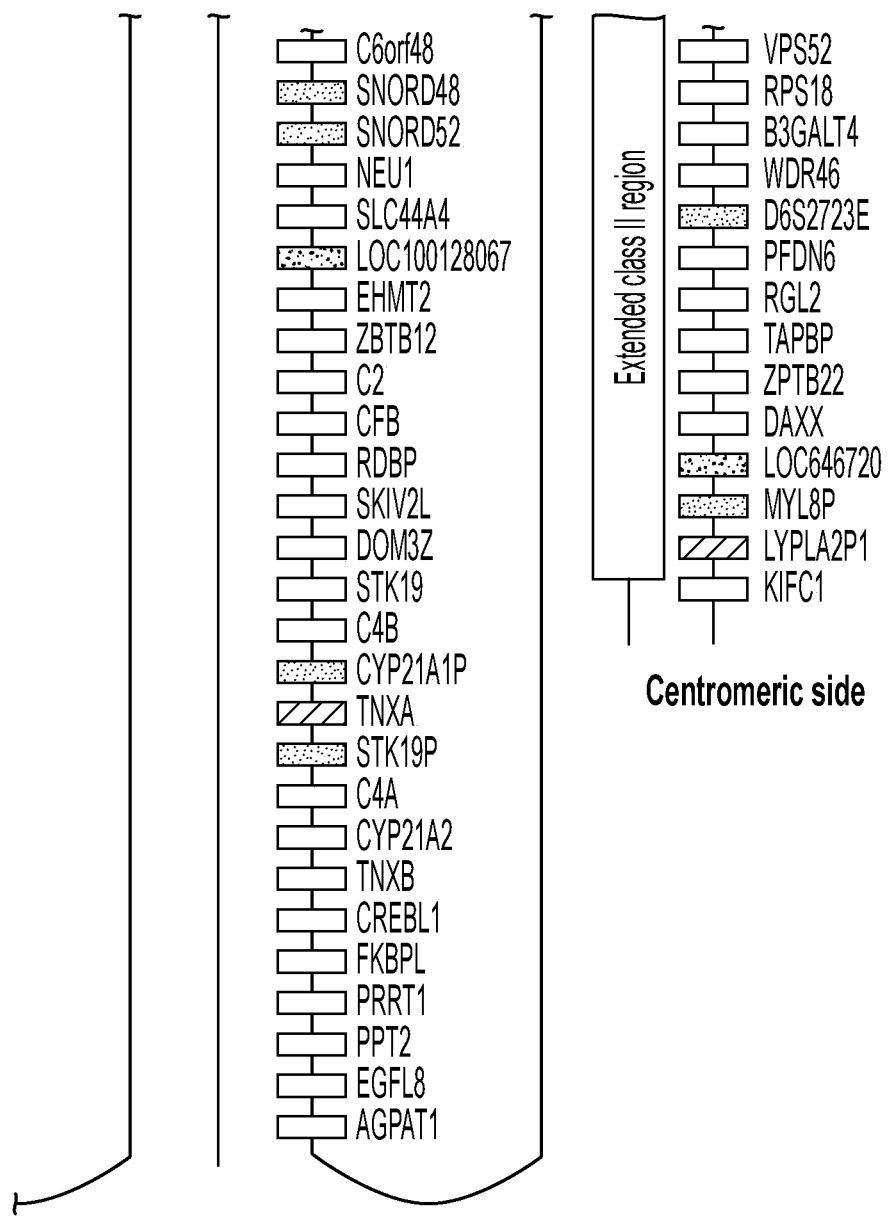
Figure 11:
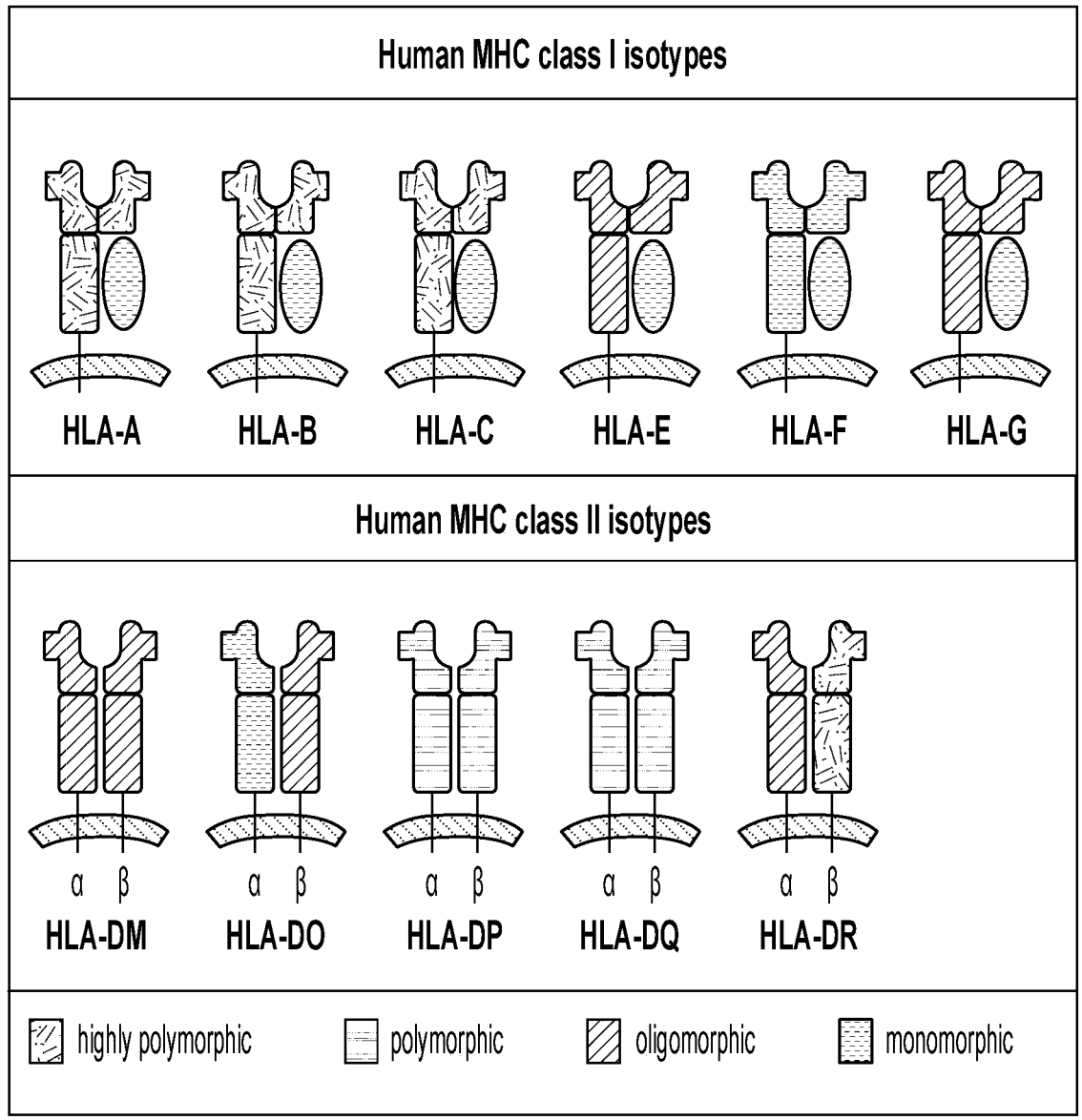
FIG. 11 schematically illustrates Human MHC Class I and Class II isotypes.

The HLA segment is divided into three regions (from centromere to telomere), Class II, Class III and Class I. See FIG. 10. Classical Class I and Class II HLA genes are contained in the Class I and Class II regions, respectively, whereas the Class III locus bears genes encoding proteins involved in the immune system but not structurally related to MHC molecules. The classical HLA Class I molecules are of three types, HLA-A, HLA-B and HLA-C. Only the $\alpha$ chains of these mature HLA Class I molecules are encoded within the Class I HLA locus by the respective HLA-A, HLA-B and HLA-C genes. See FIG. 11. In contrast, the beta-2 microglobulin $\beta 2m$ chain encoded by the $\beta 2m$ gene is located on chromosome 15. The classical HLA Class II molecules are also of three types (HLA-DP, HLA-DQ and HLA-DR), with both the $\alpha$ and $\beta$ chains of each encoded by a pair of adjacent loci. In addition to these classical HLA Class I and HLA Class II genes, the human MHC locus includes a long array of HLA pseudogenes as well as genes encoding non-classical MHCI and MHCII molecules. HLA-pseudogenes are an indication that gene duplication is the main driving force for HLA evolution, whereas non-classical MHCI and MHCII molecules often serve a restricted function within the immune system quite distinct from that of antigen presentation to $\alpha\beta$ TCRs.

Aside from the genes encoding the antigen-presenting proteins, there are a large number of other genes, many involved in immune function, located on the HLA complex. Diversity of HLAs in the human population is one aspect of disease defense, and, as a result, the chance of two unrelated individuals with identical HLA molecules on all loci is extremely low. HLA genes have historically been identified as a result of the ability to successfully transplant organs between HLA-similar individuals.

Class I MHC molecules are expressed on all nucleated cells, including tumor cells. They are expressed specifically on T and B lymphocytes, macrophages, dendritic cells and neutrophils, among other cells, and function to display peptide fragments (typically 8-10 amino acids in length) on the surface to CD8+ cytotoxic T lymphocytes (CTLs). CTLs are specialized to kill any cell that bears an MHC I-bound peptide recognized by its own membrane-bound TCR. When a cell displays peptides derived from cellular proteins not normally present (e.g., of viral, tumor, or other non-self origin), such peptides are recognized by CTLs, which become activated and kill the cell displaying the peptide.

Figure 12:
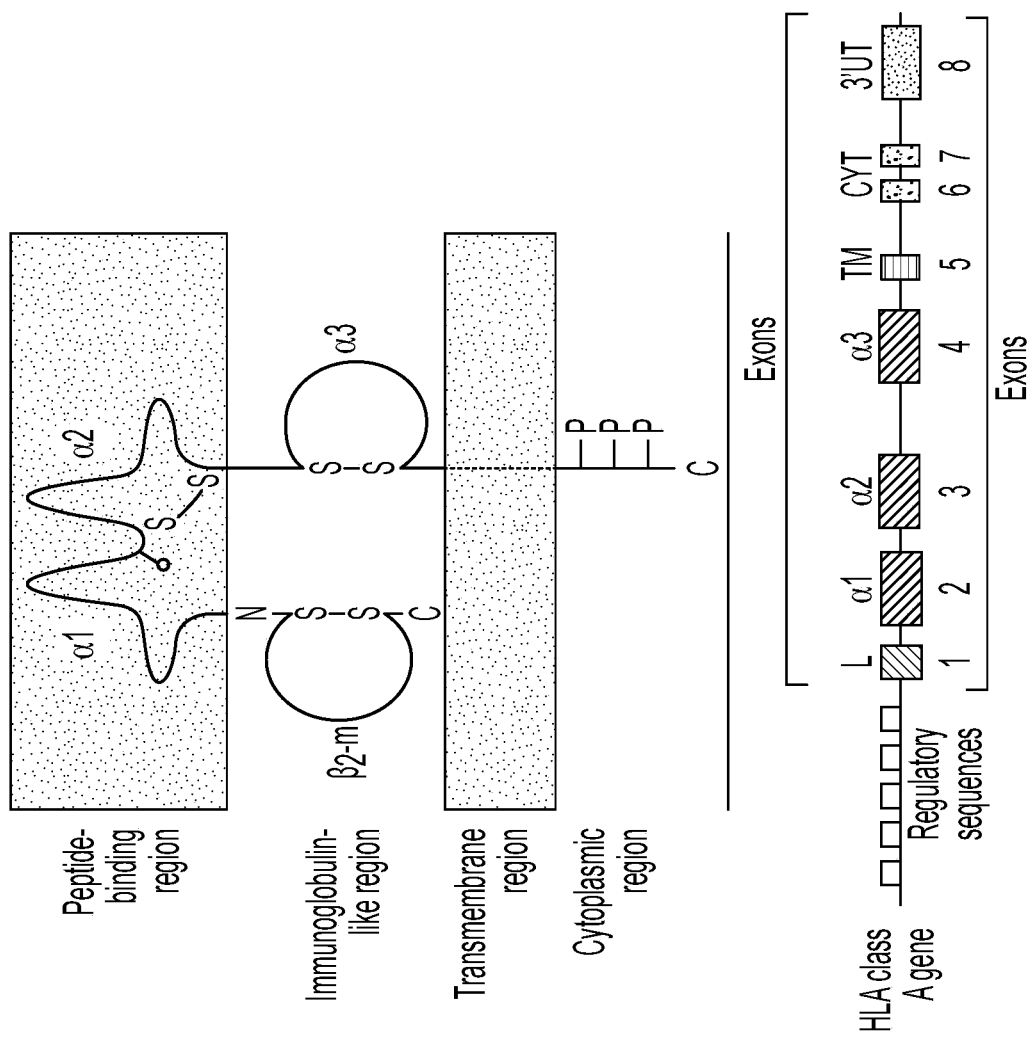
FIG. 12 shows the schematic molecular organization of the HLA Class I genes. Exons are represented by the rectangles and introns by lines.
Figure 12:
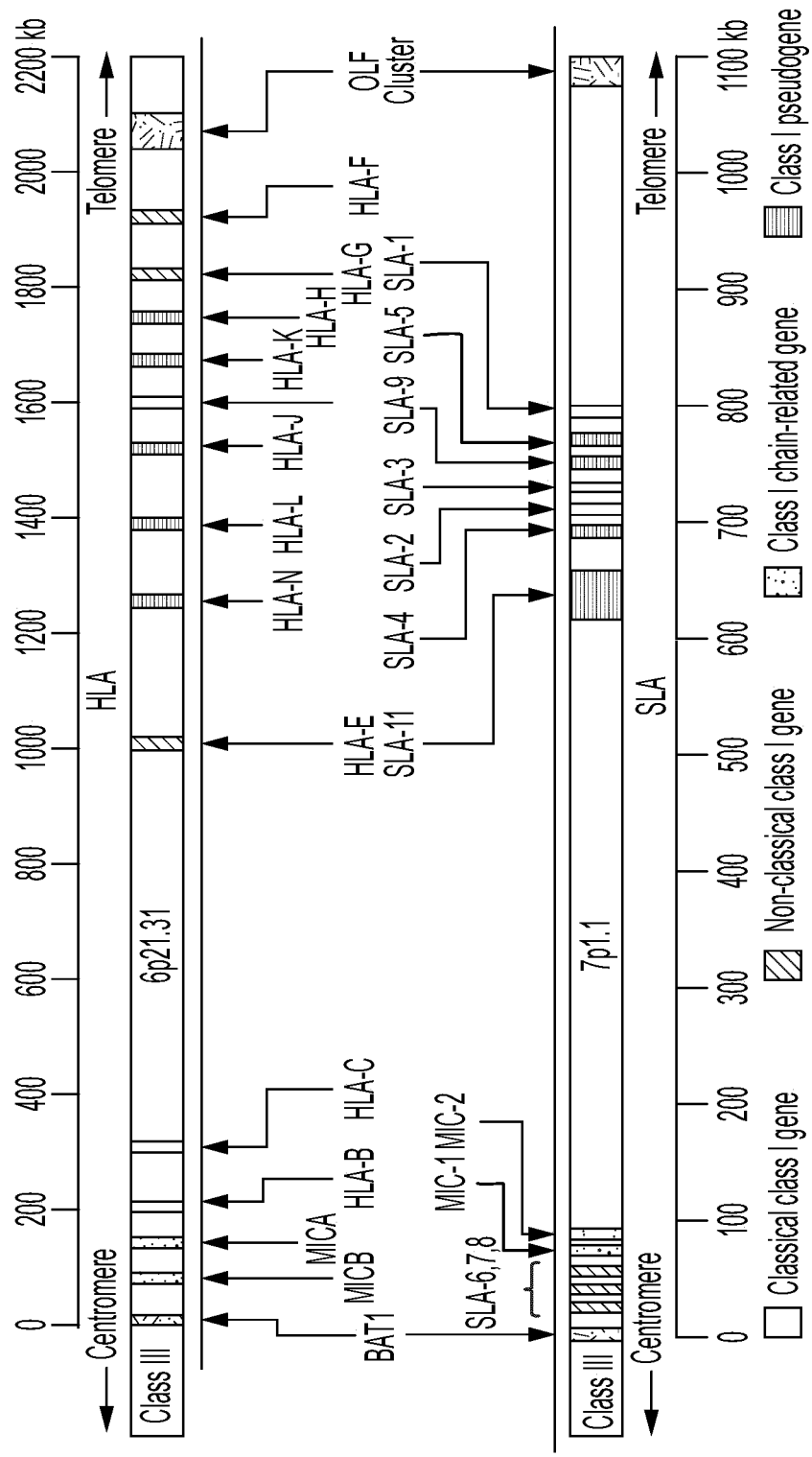

As shown in FIG. 12, MHC Class I protein comprises an extracellular domain (which comprises three domains: $\alpha_1$, $\alpha_2$ and $\alpha_3$), a transmembrane domain, and a cytoplasmic tail. The $\alpha_1$ and $\alpha_2$ domains form the peptide-binding cleft, while the α$_3$ interacts with β2-microglobulin. Class I molecules consist of two chains: a polymorphic α-chain (sometimes referred to as heavy chain) and a smaller chain called β2-microglobulin (also known as light chain), which is generally not polymorphic. These two chains form a non-covalent heterodimer on the cell surface. The α-chain contains three domains (α1, α2 and α3). As illustrated in FIG. 12, Exon 1 of the α-chain gene encodes the leader sequence, exons 2 and 3 encode the α1 and α2 domains, exon 4 encodes the α3 domain, exon 5 encodes the transmembrane domain, and exons 6 and 7 encode the cytoplasmic tail. The α-chain forms a peptide-binding cleft involving the α1 and α2 domains (which resemble Ig-like domains) followed by the α3 domain, which is similar to β2-microglobulin.

β2 microglobulin is a non-glycosylated 12 kDa protein; one of its functions is to stabilize the MHC Class I α-chain. Unlike the α-chain, the β2 microglobulin does not span the membrane. The human β2 microglobulin locus is on chromosome 15 and consists of 4 exons and 3 introns. Circulating forms of β2 microglobulin are present in serum, urine, and other body fluids; non-covalently MHC I-associated β2 microglobulin can be exchanged with circulating (32 microglobulin under physiological conditions.

Figure 13:
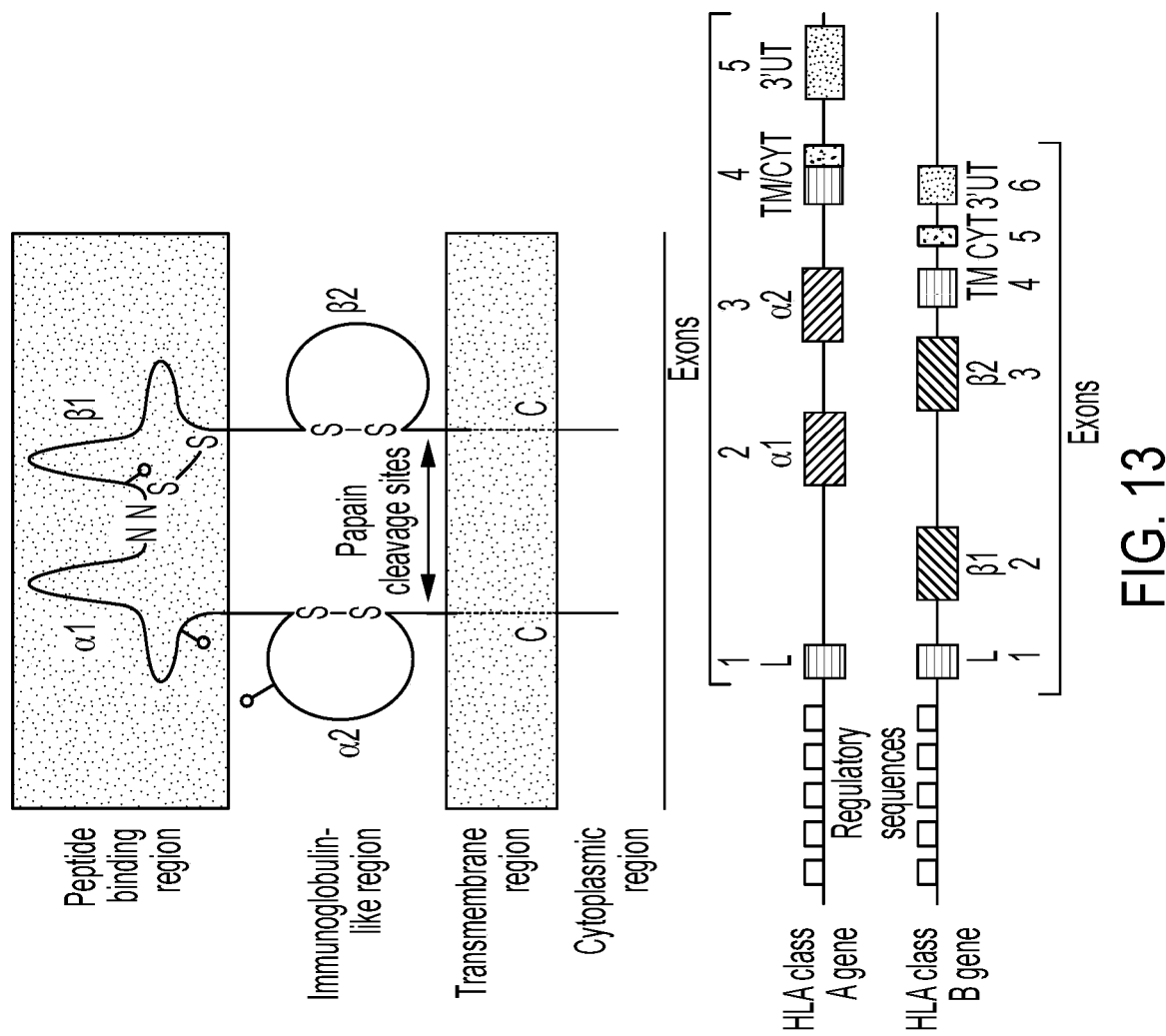
FIG. 13 shows the schematic molecular organization of the HLA Class II genes. Exons are represented by the rectangles and introns by lines.
Figure 13:
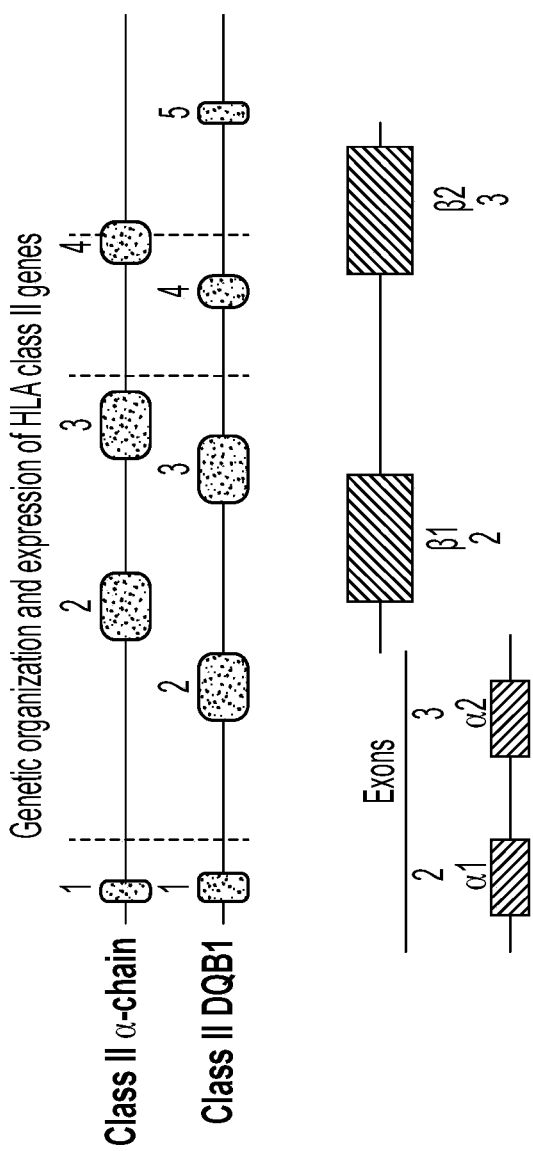

As shown in FIG. 13, MHC Class II protein comprises an extracellular domain (which comprises three domains: α$_1$, α$_2$, β1, and β1), a transmembrane domain, and a cytoplasmic tail. The α$_1$ and β1 domains form the peptide-binding cleft, while the α$_1$ and β1 interacts with the transmembrane domain.

In addition to the aforementioned antigens, the Class I antigens include other antigens, termed non-classical Class I antigens, in particular the antigens HLA-E, HLA-F and HLA-G; this latter, in particular, is expressed by the extravillous trophoblasts of the normal human placenta in addition to HLA-C.

Cell Phenotype

Referring generally to FIG. 1, Dr. Peter Medawar profoundly said "the success of human pregnancy, where the fetus resides comfortably within the maternal uterus for 9 months, defies the precepts of immunology." Paraphrasing, he observed that the most common, successful transplant on earth is pregnancy.

The trophoblast expression of cell surface markers is well characterized, and by replicating such phenotype in the porcine cell where appropriate and necessary to retain, critical and desired cellular function can be obtained. According to literature, extravillous trophoblast cells express HLA Class Ia molecule (HLA-C) and all of HLA Class Ib molecules. Compared to HLA-E and HLA-G, both of which are highly expressed on extravillous trophoblast cells, HLA-C and HLA-F are weakly expressed. See, e.g., Djurisic et al., "HLA Class Ib Molecules and Immune Cells in Pregnancy and Preeclampsia," *Frontiers in Immunology*, Vol 5, Art. 652 (2014). In addition to MHC molecules, PD-L1 is upregulated in trophoblastic cells in normal pregnancy, particularly in syncytiotrophoblast cells. HLA Class II molecules are not present on trophoblasts, which may facilitate survival and detection of the embryo in the presence of maternal lymphocytes. See, e.g., Veras et al., "PD-L1 Expression in Human Placentas and gestational Trophoblastic Diseases," *Int. J. Gynecol. Pathol.* 36(2): 146-153 (2017).

The present invention provides a method of creating a tolerogenic xenotransplantation swine cell that mimics the extracellular configuration of a human trophoblast. This method includes, but is not limited to, removing or deactivating certain SLA exons to regulate the swine cell's extracellular expression or non-expression of MHC Class II, Ia, and/or Ib; reprogramming certain native, naturally occurring swine cell SLA exons to regulate the swine cell's extracellular expression or non-expression of MHC Class II; conserving or otherwise not removing swine introns existing in or in the vicinity of the otherwise engineered sequences; increasing the expression of swine CTLA4 and PD-1; and removing or deactivating alpha-1,3 galactosyltransferase, cytidine monophosphate-N-acetylneuraminic acid hydroxylase, and β1,4-N-acetylgalactosaminyltransferase. Such removal, reprogramming, and modification to cause such increase of expression, and other engineered aspects of a swine genome, to create a tolerogenic xenotransplantation swine cell that mimics the extracellular configuration of a human trophoblast, is described as follows.

The former and current attempts to this unmet clinical need has precisely followed the classic medical dogma of "one-size fits all". We refer to this as the "downstream" approach—which must contend with addressing all of the natural immune processes in sequence. Instead of adopting this limited view, the present invention takes a "patient-specific" solution to dramatically improve clinical outcome measures. The latter, our approach, we term the "upstream" approach—one which represents the culmination of unfilled scientific effort into a coordinated translational effort. The central theorem of our approach is countervailing to the existing and previous dogmatic approaches. The "downstream" approach accepts the innate and immovable disparity between donor and recipient, and focuses on interventions, gene alterations, and/or concomitant exogenous immunosuppressive medications used as a method of reducing/eliminating/negatively-altering the recipients' naturally resulting immunologic response. In contrast, we intentionally choose to reverse the focus of the otherwise area of fundamental scientific dogma. Rather than accept the immunological incompatibilities between the donor and recipient, specifically (but not limited to) those mismatches of the Major Histocompatibility Complex(es), we alter these catalytic antigens at the source, thereby eliminating all of the precipitating mechanisms that are the causative effectors of cell, tissue, and organ rejection between donor and recipient. This approach applies beyond the field of xenotransplantation including, but not limited to, the fields of genetics, obstetrics, infectious disease, oncology, agriculture, animal husbandry, food industry and other areas.

The present disclosure embodies the above modification in creating a non-transgenic genetically reprogrammed swine for xenotransplantation, wherein the MHC surface characterization of the swine mimic that of the recipient's trophoblast, wherein the immune response from the xenotransplantation is significantly reduced. The human extravillous trophoblast cells express HLA-C, HLA-E, HLA-F, and HLA-G, but not HLA-A, HLA-B, HLA-DQ and HLA-DR. As such, the current embodiment combines the unique MHC surface characterization of human trophoblast with site-directed mutagenic substitutions to minimize or remove the immune response associated with xenotransplantation while minimizing off target effects on the native donor swine's SLA/MHC gene.

The human immune response system is a highly complex and efficient defense system against invading organisms. T-cells are the primary effector cells involved in the cellular response. Just as antibodies have been developed as therapeutics, (TCRs), the receptors on the surface of the T-cells, which give them their specificity, have unique advantages as a platform for developing therapeutics. While antibodies are limited to recognition of pathogens in the blood and extracellular spaces or to protein targets on the cell surface, TCRs recognize antigens displayed by MHC molecules on the surfaces of cells (including antigens derived from intracellular proteins). Depending on the subtype of T-cells that recognize displayed antigen and become activated, TCRs and T-cells harboring TCRs participate in controlling various immune responses. For instance, helper T-cells are involved in regulation of the humoral immune response through induction of differentiation of B cells into antibody secreting cells. In addition, activated helper T-cells initiate cell-mediated immune responses by cytotoxic T-cells. Thus, TCRs specifically recognize targets that are not normally seen by antibodies and also trigger the T-cells that bear them to initiate wide variety of immune responses.

Figure 2:
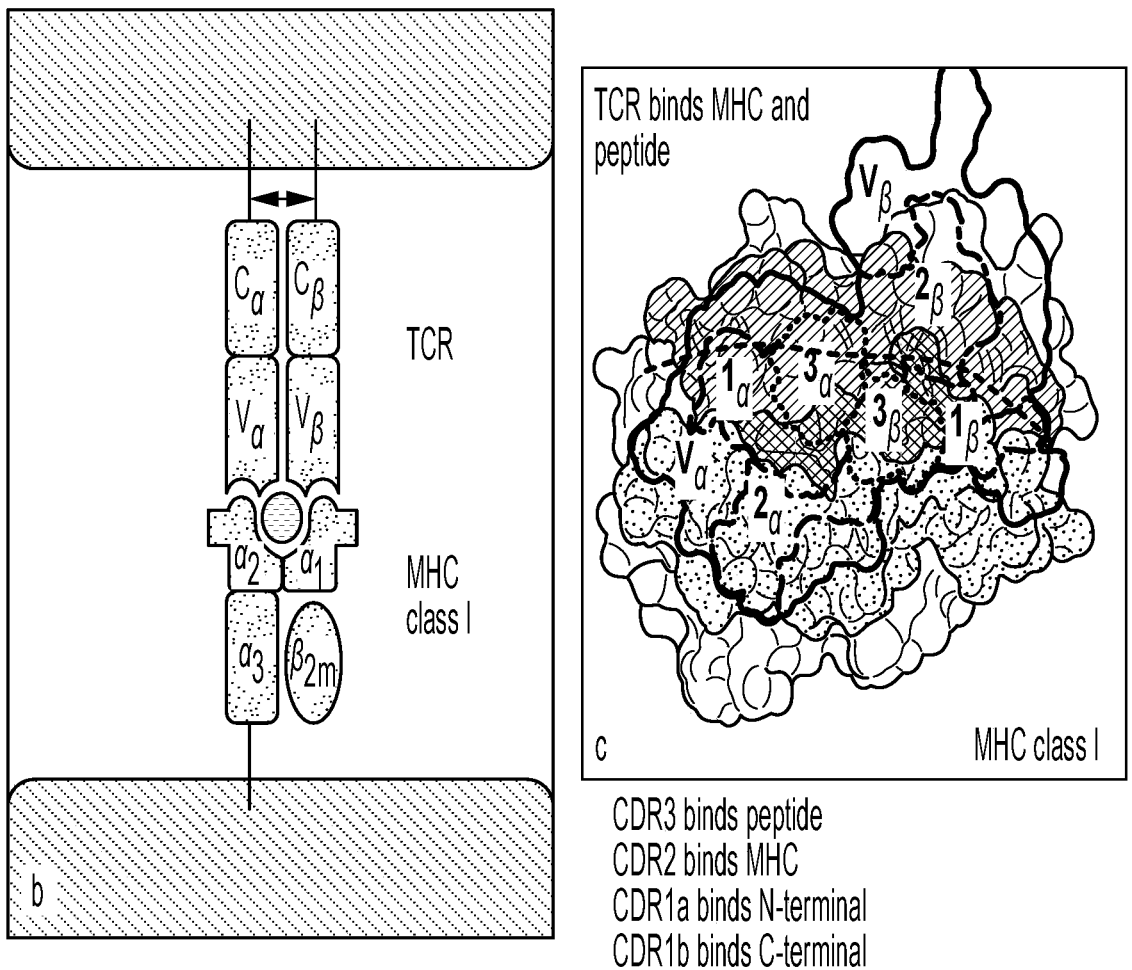
FIG. 2 schematically illustrates a T Cell Receptor (TCR) binding MHC Class I and a peptide.

As shown in FIG. 2, a T-cell recognizes an antigen presented on the surfaces of cells by means of the TCRs expressed on their cell surface. TCRs are disulfide-linked heterodimers, most consisting of α and β chain glycoproteins. T-cells use recombination mechanisms to generate diversity in their receptor molecules similar to those mechanisms for generating antibody diversity operating in B cells (Janeway and Travers, Immunobiology 1997). Similar to the immunoglobulin genes, TCR genes are composed of segments that rearrange during development of T-cells. TCR polypeptides consist of variable, constant, transmembrane and cytoplasmic regions. While the transmembrane region anchors the protein and the intracellular region participates in signaling when the receptor is occupied, the variable region is responsible for specific recognition of an antigen and the constant region supports the variable region-binding surface. The TCR α chain contains variable regions encoded by variable (V) and joining (J) segments only, while the β chain contains additional diversity (D) segments.

A TCR recognizes a peptide antigen presented on the surfaces of antigen presenting cells in the context of self-Major Histocompatibility Complex (MHC) molecules. Two different types of MHC molecules recognized by TCRs are involved in antigen presentation, the Class I MHC and class II MHC molecules. Mature T-cell subsets are defined by the co-receptor molecules they express. These co-receptors act in conjunction with TCRs in the recognition of the MHC-antigen complex and activation of the T-cell. Mature helper T-cells recognize antigen in the context of MHC Class II molecules and are distinguished by having the co-receptor CD4. Cytotoxic T-cells recognize antigen in the context of MHC Class I determinants and are distinguished by having the CD8 co-receptor.

In the human, MHC molecules are referred to as HLA, an acronym for human leukocyte antigens, and are encoded by the chromosome 6p21.3-located HLA region.8,9 The HLA segment is divided into three regions (from centromere to telomere), Class II, Class III and Class I. See FIG. 10. Classical Class I and Class II HLA genes are contained in the Class I and Class II regions, respectively, whereas the Class III locus bears genes encoding proteins involved in the immune system but not structurally related to MHC molecules. The classical HLA Class I molecules are of three types, HLA-A, HLA-B and HLA-C. Only the α chains of these mature HLA Class I molecules are encoded within the Class I HLA locus by the respective HLA-A, HLA-B and HLA-C genes. See FIG. 11. In contrast, the beta-2 microglobulin β2m chain encoded by the β2m gene is located on chromosome 15. The classical HLA Class II molecules are also of three types (HLA-DP, HLA-DQ and HLA-DR), with both the α and β chains of each encoded by a pair of adjacent loci. In addition to these classical HLA Class I and HLA Class II genes, the human MHC locus includes a long array of HLA pseudogenes as well as genes encoding non-classical MHCI and MHCII molecules. HLA-pseudogenes are an indication that gene duplication is the main driving force for HLA evolution, whereas non-classical MHCI and MHCII molecules often serve a restricted function within the immune system quite distinct from that of antigen presentation to αβ TCRs.

Human leukocyte antigen (HLA) genes show incredible sequence diversity in the human population. For example, there are >4,000 known alleles for the HLA-B gene alone. The genetic diversity in HLA genes in which different alleles have different efficiencies for presenting different antigens is believed to be a result of evolution conferring better population-level resistance against the wide range of different pathogens to which humans are exposed. This genetic diversity also presents problems during xenotransplantation where the recipient's immune response is the most important factor dictating the outcome of engraftment and survival after transplantation.

In humans, the classical Class I genes, termed HLA-A, HLA-B and HLA-C, consist of two chains: a polymorphic α-chain (sometimes referred to as heavy chain) and a smaller chain called β2-microglobulin (also known as light chain), which is generally not polymorphic. These two chains form a non-covalent heterodimer on the cell surface. As shown in FIG. 12, the α-chain contains three domains (α1, α2 and α3). Exon 1 of the α-chain gene encodes the leader sequence, exons 2 and 3 encode the α1 and α2 domains, exon 4 encodes the α3 domain, exon 5 encodes the transmembrane domain, and exons 6 and 7 encode the cytoplasmic tail. The α-chain forms a peptide-binding cleft involving the α1 and α2 domains (which resemble Ig-like domains) followed by the α3 domain, which is similar to β2-microglobulin.

β2 microglobulin is a non-glycosylated 12 kDa protein; one of its functions is to stabilize the MHC Class I α-chain. Unlike the α-chain, the β2 microglobulin does not span the membrane. The human β2 microglobulin locus is on chromosome 15 and consists of 4 exons and 3 introns. β2-microglobulin-bound protein complexes undertake key roles in various immune system pathways, including the neonatal Fc receptor (FcRn), cluster of differentiation 1 (CD1) protein, non-classical major histocompatibility complex (MHC), and well-known MHC Class I molecules.

Class I MHC molecules are expressed on all nucleated cells, including tumor cells. They are expressed specifically on T and B lymphocytes, macrophages, dendritic cells and neutrophils, among other cells, and function to display peptide fragments (typically 8-10 amino acids in length) on the surface to CD8+ cytotoxic T lymphocytes (CTLs). CTLs are specialized to kill any cell that bears an MHC I-bound peptide recognized by its own membrane-bound TCR. When a cell displays peptides derived from cellular proteins not normally present (e.g., of viral, tumor, or other non-self origin), such peptides are recognized by CTLs, which become activated and kill the cell displaying the peptide.

MHC loci exhibit the highest polymorphism in the genome. All Class I and II MHC genes can present peptide fragments, but each gene expresses a protein with different binding characteristics, reflecting polymorphisms and allelic variants. Any given individual has a unique range of peptide fragments that can be presented on the cell surface to B and T cells in the course of an immune response.

In addition to the aforementioned antigens, the Class I antigens include other antigens, termed non-classical Class I antigens, in particular the antigens HLA-E, HLA-F and HLA-G; this latter, in particular, is expressed by the extravillous trophoblasts of the normal human placenta in addition to HLA-C.

MHC Class II protein comprises an extracellular domain (which comprises three domains: α1, α2, β1, and β1), a transmembrane domain, and a cytoplasmic tail as shown in FIG. 13. The α2 and β2 domains form the peptide-binding cleft, while the α1 and β1 interacts with the transmembrane domain.

With respect to the MHC-I proteins, the current disclosure either inactivate, or where necessary to retain the function of the "find and replace" orthologous SLA proteins with HLA analogs that would result in minimal immune recognition. In some aspects, silencing the genes which encode and are responsible for the expression of SLA-1 removes the highly-problematic and polymorphic HLA-A analog. Similarly, inactivation or complete removal of genes associated with SLA-2 would reduce the burden imposed by mismatched HLA-B proteins. This would, at the cell surface interface, appear to the human recipient's T cells as a HLA-A and HLA-B negative cell. With respect to the last of the classical MHC Class I proteins, HLA-C, site-directed mutagenesis of genes that encode for SLA-3 using a reference HLA-C sequence would mimic an allo-transplant with such a disparity. Given the "less-polymorphic" nature of HLA-C, as compared to HLA-A and HLA-B, this would be further improved by the replacement of SLA-3 with a reference replacement sequence based on the subclass of HLA-C that is naturally prevalent in nature, and also invoking mechanisms that would allow for the minimal but requisite level of expression that would afford functionality and non-interruption of the numerous known and also those unknown MHC-I dependent processes.

With respect to the MHC-I proteins, the current disclosure either inactivate, or where necessary to retain the function of the "find and replace" orthologous SLA proteins with HLA analogs that would result in minimal immune recognition. In some aspects, silencing the genes which encode and are responsible for the expression of SLA-1 removes the highly-problematic and polymorphic HLA-A analog. Similarly, inactivation or complete removal of genes associated with SLA-2 would reduce the burden imposed by mismatched HLA-B proteins. This would, at the cell surface interface, appear to the human recipient's T cells as a HLA-A and HLA-B negative cell. With respect to the last of the classical MHC Class I proteins, HLA-C, site-directed mutagenesis of genes that encode for SLA-3 using a reference HLA-C sequence would mimic an allo-transplant with such a disparity. Given the "less-polymorphic" nature of HLA-C, as compared to HLA-A and HLA-B, this would be further improved by the replacement of SLA-3 with a reference replacement sequence based on the subclass of HLA-C that is naturally prevalent in nature, and also invoking mechanisms that would allow for the minimal but requisite level of expression that would afford functionality and non-interruption of the numerous known and also those unknown MHC-I dependent processes.

Furthermore, the expression of non-classical MHC proteins—those included in the I-b category, which include HLA-E, F, and G are vitally important to both the survival of the fetus and synergistic existence of the trophoblast(s). Fortunately, these are significantly less polymorphic than the "classical" MHC-Ia variety. Without expression of these, heightened upregulation of cell lysis is a direct result of NK cell recognition and activation is observed. In an identical manner as described to the MHC-Ia components, the orthologous SLA proteins with HLA analogs are either inactivated, or where necessary, to "find and replace(d)" FIG. 14 shows specific alterations that are included in the present disclosure.

HLA-G can be a potent immuno-inhibitory and tolerogenic molecule. HLA-G expression in a human fetus can enable the human fetus to elude the maternal immune response. Neither stimulatory functions nor responses to allogeneic HLA-G have been reported to date. HLA-G can be a non-classical HLA Class I molecule. It can differ from classical MHC Class I molecules by its genetic diversity, expression, structure, and function. HLA-G can be characterized by a low allelic polymorphism. Expression of HLA-G can be restricted to trophoblast cells, adult thymic medulla, and stem cells. The sequence of the HLA-G gene (HLA-6.0 gene) has been described by GERAGHTY et al., (Proc. Natl. Acad. Sci. USA, 1987, 84, 9145-9149): it comprises 4,396 base pairs and exhibits an intron/exon organization which is homologous to that of the HLA-A, HLA-B and HLA-C genes. More precisely, this gene comprises 8 exons and an untranslated, 3'UT, end, with the following respective correspondence: exon 1: signal sequence, exon 2: α1 domain, exon 3: α2 domain, exon 4: α3 domain, exon 5: transmembrane region, exon 6: cytoplasmic domain I, exon 7: cytoplasmic domain II, exon 8: cytoplasmic domain III and 3' untranslated region (GERAGHTY et al., mentioned above, ELLIS et al., J. Immunol., 1990, 144, 731-735). However, the HLA-G gene differs from the other Class I genes in that the in-frame translation termination codon is located at the second codon of exon 6; as a result, the cytoplasmic region of the protein encoded by this gene HLA-6.0 is considerably shorter than that of the cytoplasmic regions of the HLA-A, HLA-B and HLA-C proteins.

Natural killer (NK) cell-mediated immunity, comprising cytotoxicity and cytokine secretion, plays a major role in biological resistance to a number of autologous and allogeneic cells. The common mechanism of target cell recognition appears to be the lack or modification of self MHC Class I-peptide complexes on the cell surface, which can lead to the elimination of virally infected cells, tumor cells and major histocompatibility MHC-incompatible grafted cells. KIR's, members of the Ig superfamily which are expressed on NK cells, have recently been discovered and cloned. KIR's are specific for polymorphic MHC Class I molecules and generate a negative signal upon ligand binding which leads to target cell protection from NK cell-mediated cytotoxicity in most systems. In order to prevent NK cell autoimmunity, i.e., the lysis of normal autologous cells, it is believed that every given NK cell of an individual expresses at least on KIR recognizing at least one of the autologous HLA-A, B, C, or G alleles.

According to the present disclosure, in the context of swine-to-human xenotransplantation, each human recipient will have a major histocompatibility complex (MHC) (Class I, Class II and/or Class III) that is unique to that individual and will not match the MHC of the donor swine. Accordingly, when a donor swine graft is introduced to the recipient, the swine MHC molecules themselves act as antigens, provoking an immune response from the recipient, leading to transplant rejection.

According to this aspect of the present disclosure (i.e., reprogramming the SLA/MHC to express specifically selected human MHC alleles), when applied to swine cells, tissues, and organs for purposes of xenotransplantation will decrease rejection as compared to cells, tissues, and organs derived from a wild-type swine or otherwise genetically modified swine that lacks this reprogramming, e.g., transgenic swine or swine with non-specific or different genetic modifications.

With the previous modifications incorporated, insertion or activation of additional extracellular ligands that would create a protective, localized immune response as seen with the maternal-fetal symbiosis, would be an additional step to minimize deleterious cellular-mediated immunological functions that may remain as a result of minor-antigen disparities. Therefore, porcine ligands for SLA-MIC2 is orthologously reprogrammed with human counterparts, MICA. Human Major Histocompatibility Complex Class I Chain-Related gene A (MICA) is a cell surface glycoprotein expressed on endothelial cells, dendritic cells, fibroblasts, epithelial cells, and many tumours. It is located on the short arm of human chromosome 6 and consists of 7 exons, 5 of which encodes the transmembrane region of the MICA molecule. MICA protein at normal states has a low level of expression in epithelial tissues but is upregulated in response to various stimuli of cellular stress. MICA is classified as a non-classical MHC Class I gene, and functions as a ligand recognized by the activating receptor NKG2D that is expressed on the surface of NK cells and CD8+ T cells (atlasgeneticsoncology.org/Genes/MICAID41364ch6p21.html).

In addition, porcine ligands for PD-L1, CTLA-4, and others are overexpressed and/or otherwise orthologously reprogrammed with human counterparts. PD-L1 is a transmembrane protein that has major role in suppressing the adaptive immune system in pregnancy, allografts, and autoimmune diseases. It is encoded by the CD274 gene in human and is located in chromosome 9. PD-L1 binds to PD-1, a receptor found on activated T cells, B cells, and myeloid cells, to modulate activation or inhibition. Particularly, the binding of PD-L1 to receptor PD-1 on T cells inhibits activation of IL-2 production and T cell proliferation. CTLA4 is a protein receptor that also functions as an immune checkpoint that downregulates immune responses. It is encoded by the CTLA4 gene and is located in chromosome 2 in human. It is constitutively expressed on regulatory T cells but are upregulated in activated T cells. Gene expression for CTLA-4 and PD-L1 is increased, for example, based on reprogramming promoters thereof. There is a relationship between genotype and CTLA-4 or PD-L1 expression. For example, individuals carrying thymine at position −318 of the CTLA4 promoter (T(−318)) and homozygous for adenine at position 49 in exon 1 showed significantly increased expression both of cell-surface CTLA-4 after cellular stimulation and of CTLA-4 mRNA in non-stimulated cells in Ligers A, et al. CTLA-4 gene expression is influenced by promoter and exon 1 polymorphisms, Genes Immun. 2001 May; 2(3):145-52, which is incorporated herein by reference in its entirety for all purposes. A similar upregulation can be achieved to overexpress PD-L1 using a PD-L1 promoter reprogramming.

Further, anti-coagulant porcine ligands for Endothelial protein C receptor (EPCR), Thrombomodulin (TBM), Tissue Factor Pathway Inhibitor (TFPI), and others are orthologously reprogrammed with human counterparts, as shown in FIG. 14. Endothelial protein C receptor is endothelial cell-specific transmembrane glycoprotein encoded by PROCR gene that is located in chromosome 20 in human. It enhances activation of Protein C, an anti-coagulant serine protease, and has crucial role in activated protein C mediated cytoprotive signaling. Thrombomodulin is an integral membrane glycoprotein present on surface of endothelial cells. It is encoded by THBD gene that is located in chromosome 20 in human. In addition to functioning as cofactor in the thrombin-induced activation of protein C in the anticoagulant pathway, it also functions in regulating C3b inactivation. Tissue Factor Pathway Inhibitor (TFPI) is a glycoprotein that functions as natural anticoagulant by inhibiting Factor Xa. It encoded by TFPI gene located in chromosome 2 in human and the protein structure consists of three tandemly linked Kunitz domains. In human, two major isoforms of TFPi exists, TFPIα and TFPIβ. TFPIα consists of three inhibitory domains (K1, K2, and K3) and a positively charged C terminus while TFPIβ consists of two inhibitory domains (K1 and K2) and C terminus. While K1 and K2 domains are known to bind and inhibit Factor VII and Factor Xa, respectively, the inhibitory function of K3 is unknown. In certain aspects, the present disclosure centralizes (predicates) the creation of hypoimmunogenic and/or tolerogenic cells, tissues, and organs that does not necessitate the transplant recipients' prevalent and deleterious use of exogenous immunosuppressive drugs (or prolonged immunosuppressive regimens) following the transplant procedure to prolong the life-saving organ.

The table provided in FIG. 14 shows conceptual design that exhibit summation of various edits to create tolerogenic xenotransplantation swine cell that mimics the extracellular configuration of a human trophoblast. As exhibited in the FIG. 14, SLA-1, a swine gene orthologous to HLA-A, is silenced to mimic trophoblast, as HLA-A is not expressed on trophoblast. As further exhibited in the FIG. 14, SLA-8, a swine gene orthologous to HLA-G, is humanized through replacement with "human-capture" reference sequence, as HLA-G is expressed in trophoblast and has crucial role in maternal fetal tolerance, given its interaction with NK cells.

It is therefore understood that multiple source animals, with an array of biological properties including, but not limited to, genome modification and/or other genetically engineered properties, can be utilized to reduce immunogenicity and/or immunological rejection (e.g., acute, hyperacute, and chronic rejections) in humans resulting from xenotransplantation. In certain aspects, the present disclosure can be used to reduce or avoid thrombotic microangiopathy by transplanting the biological product of the present disclosure into a human patient. In certain aspects, the present disclosure can be used to reduce or avoid glomerulopathy by transplanting the biological product of the present disclosure into a human patient. It will be further understood that the listing of source animals set forth herein is not limiting, and the present invention encompasses any other type of source animal with one or more modifications (genetic or otherwise) that serve(s) to reduce immunogenicity and/or immunological rejection, singularly or in combination.

Bioinformatic Sequence Analysis Comparing Identities of Conserved and Non-Conserved Nucleotides Between Human Versus Swine Genomes at Various Immunologically Critical Loci To reprogram the MHC disparities between the Swine Leukocyte Antigen (SLA) and the Human Leukocyte Antigen (HLA), the present disclosure includes using highly conserved MHC-loci between these two species, e.g., numerous genes that correspond in function. The MHC Class Ia, HLA-A, HLA-B, and HLA-C have an analogous partner in the swine (the SLA 1, 2 and 3 respectively). In MHC Class II there are also numerous matches to be utilized during immunogenomic reprogramming according to the present disclosure.

Figure 15:
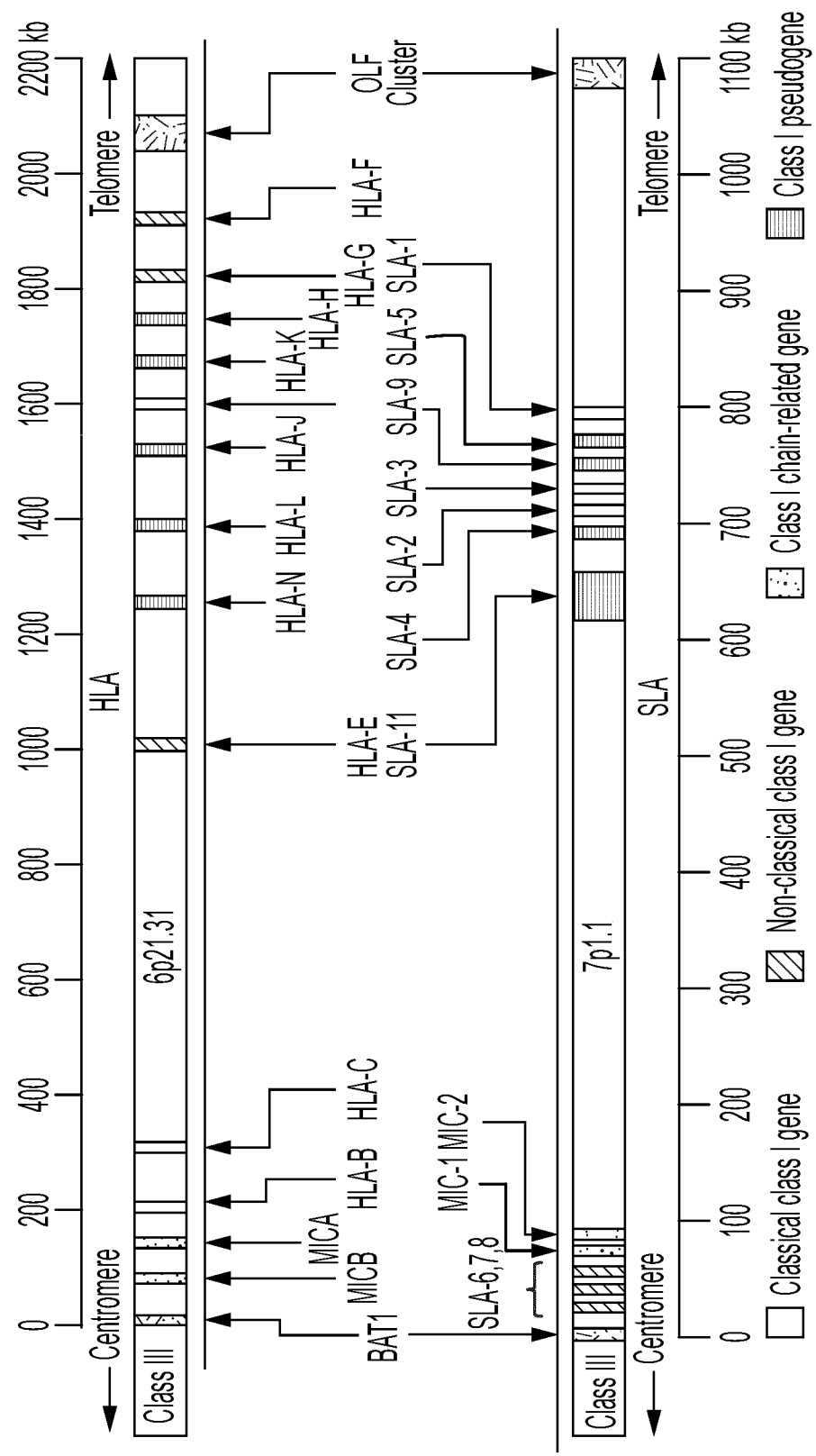
FIG. 15 shows comparative genomic organization of the human and swine major histocompatibility complex (MHC) Class I region. The human leukocyte antigen (HLA) Class I map is adapted from Ref. [17] and the swine leukocyte antigen (SLA) Class I map is based only on one fully sequenced haplotype (Hp-1.1, H01) [4]. Note that not all the genes are shown here and the scale is approximate. The number and location of expressed SLA Class I genes may vary between haplotypes.

As illustrated in FIG. 15, MHC genes are categorized into three classes; Class I, Class II, and Class III, all of which are encoded on human chromosome 6. The MHC genes are among the most polymorphic genes of the swine and human genomes, MHC polymorphisms are presumed to be important in providing evolutionary advantage; changes in sequence can result in differences in peptide binding that allow for better presentation of pathogens to cytotoxic T cells.

The known human HLA/MHC or an individual recipient's sequenced HLA/MHC sequence(s) may be utilized as a template to reprogram with precise substitution the swine leukocyte antigen (SLA)/MHC sequence to match, e.g., to have 80%, 85%, 90%, 95%, 98%, 99%, or 100% sequence homology to a known human HLA/MHC sequence or the human recipient's HLA/MHC sequence. Upon identifying a known human recipient HLA/MHC sequence to be used or performing genetic sequencing of a human recipient to obtain HLA/MHC sequences, 3 reprogramming may be performed to SLA/MHC sequences in cells of the swine based on desired HLA/MHC sequences. For example, several targeting guide RNA (gRNA) sequences are administered to the swine of the present disclosure to reprogram SLA/MHC sequences in cells of the swine with the template HLA/MHC sequences of the human recipient.

The term "MHC I complex" or the like, as used herein, includes the complex between the MHC I α chain polypeptide and the β2-microglobulin polypeptide. The term "MHC I polypeptide" or the like, as used herein, includes the MHC I α chain polypeptide alone. Typically, the terms "human MHC" and "HLA" can be used interchangeably.

Figure 16:
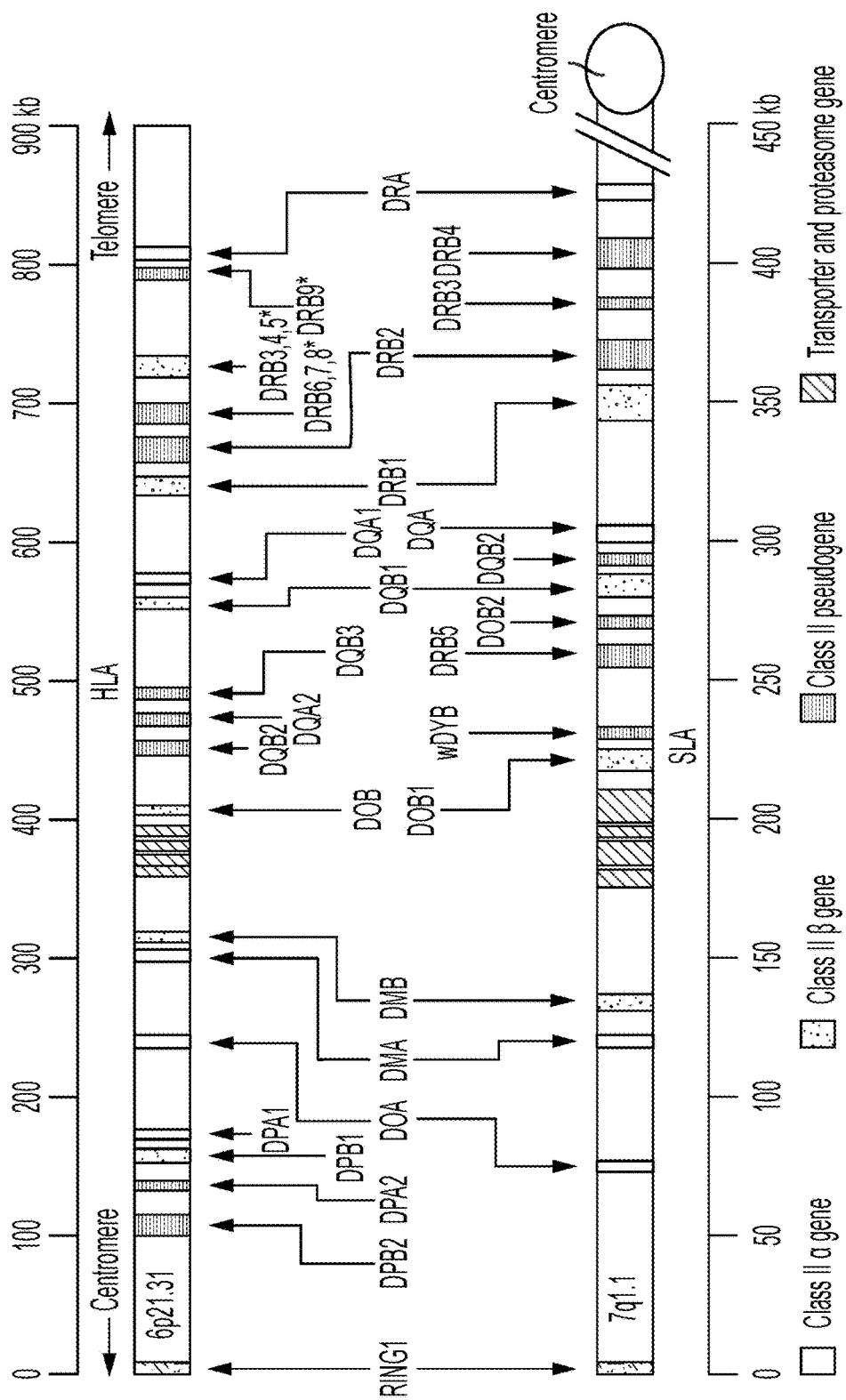
FIG. 16 shows comparative genomic organization of the human and swine major histocompatibility complex (MHC) Class II region. The human leukocyte antigen (HLA) Class II map is adapted from Ref. [17] and the swine leukocyte antigen (SLA) Class II map is based only on one fully sequenced haplotype (H01) [4]. Note that not all the genes are shown here and the scale is approximate. *The number and location of expressed HLA-DRB genes and pseudogenes may vary between haplotypes.
Figure 17:
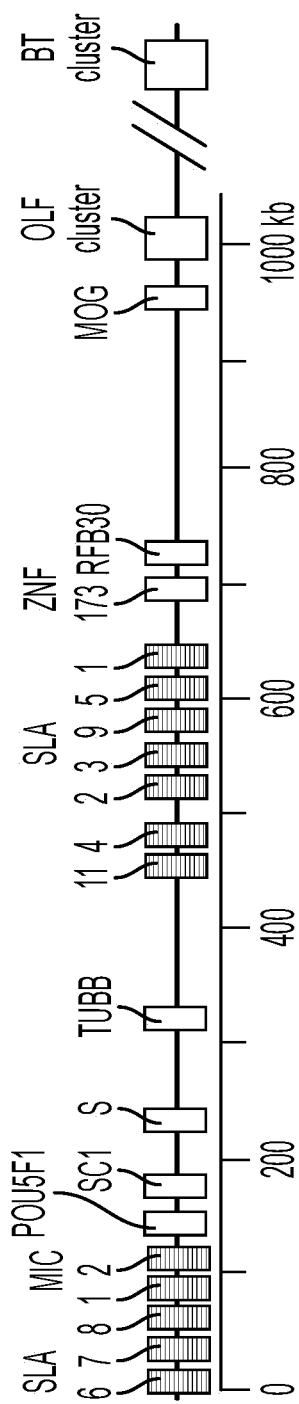
FIG. 17 shows a physical map of the SLA complex. Black boxes: loci containing MHC-related sequences. White boxes: loci without MHC-related sequences. From the long arm to the short arm of the chromosome, the order of the regions is Class II (II), Class III (III) and Class I (I).
Figure 17:
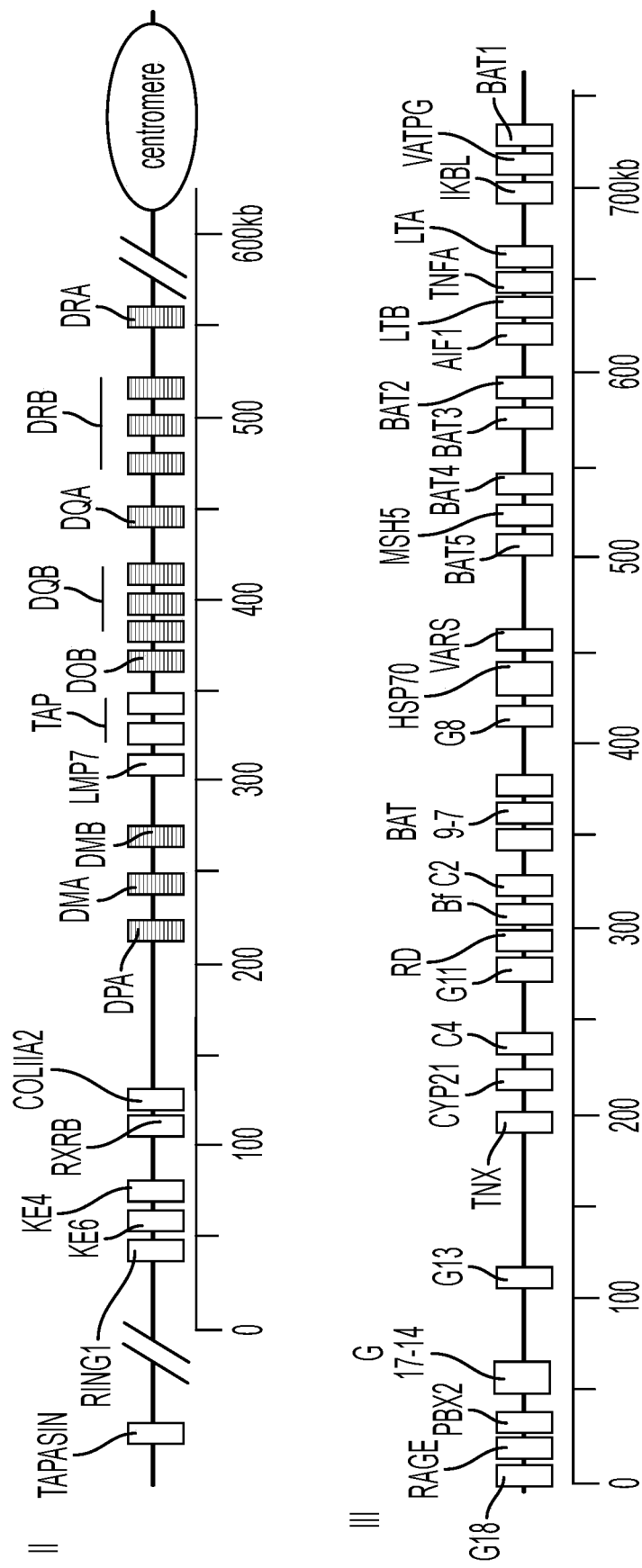
Figure 18:
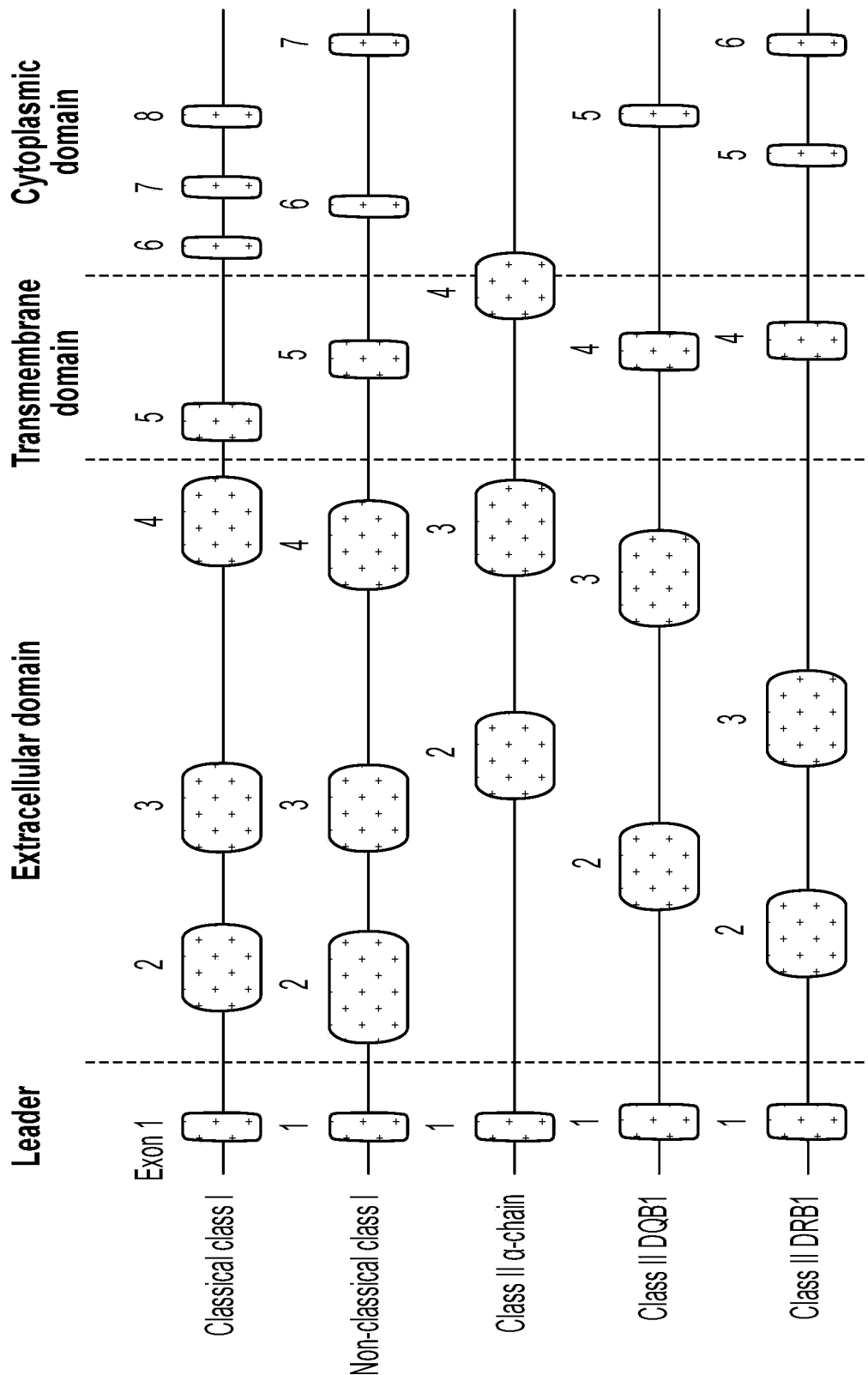
FIG. 18 shows the schematic molecular organization of the SLA genes. Exons are represented by the gray ovals and introns by lines. Gene length is approximate to that found for the Hp-1.1 genome sequence.
Figure 19:
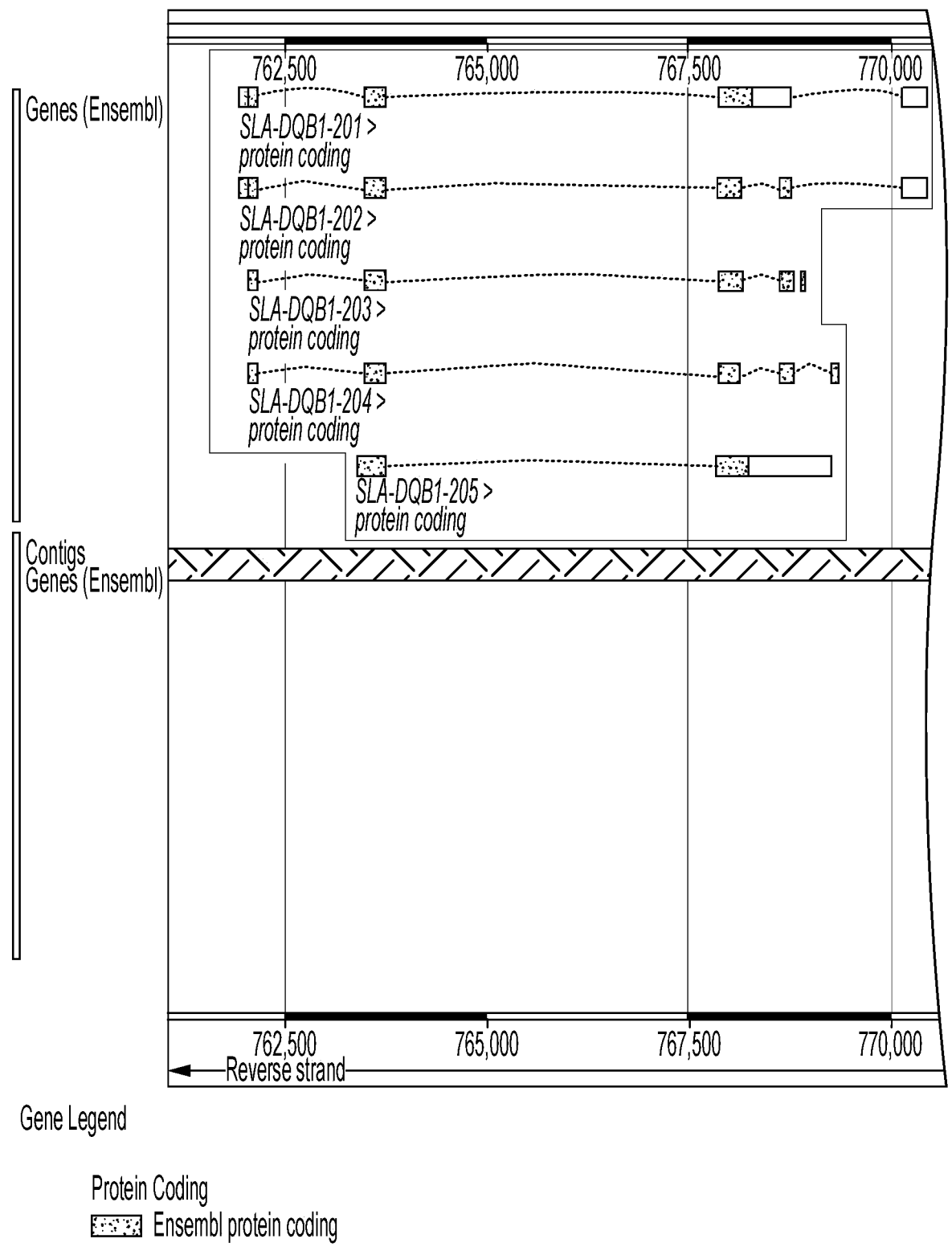
FIG. 19 shows a side-by-side genomic analysis of the peptide sequences.
Figure 19:
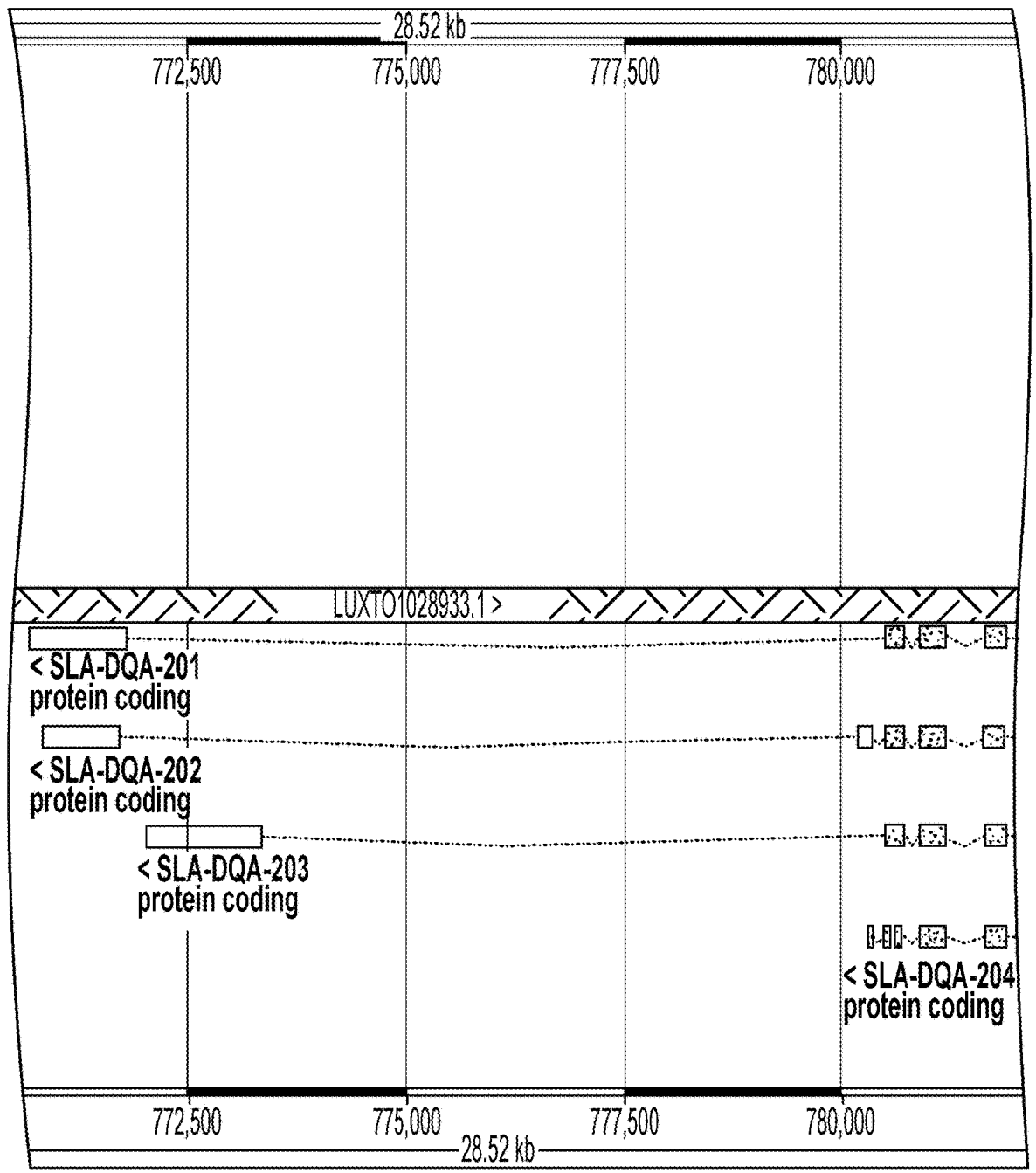
Figure 19:
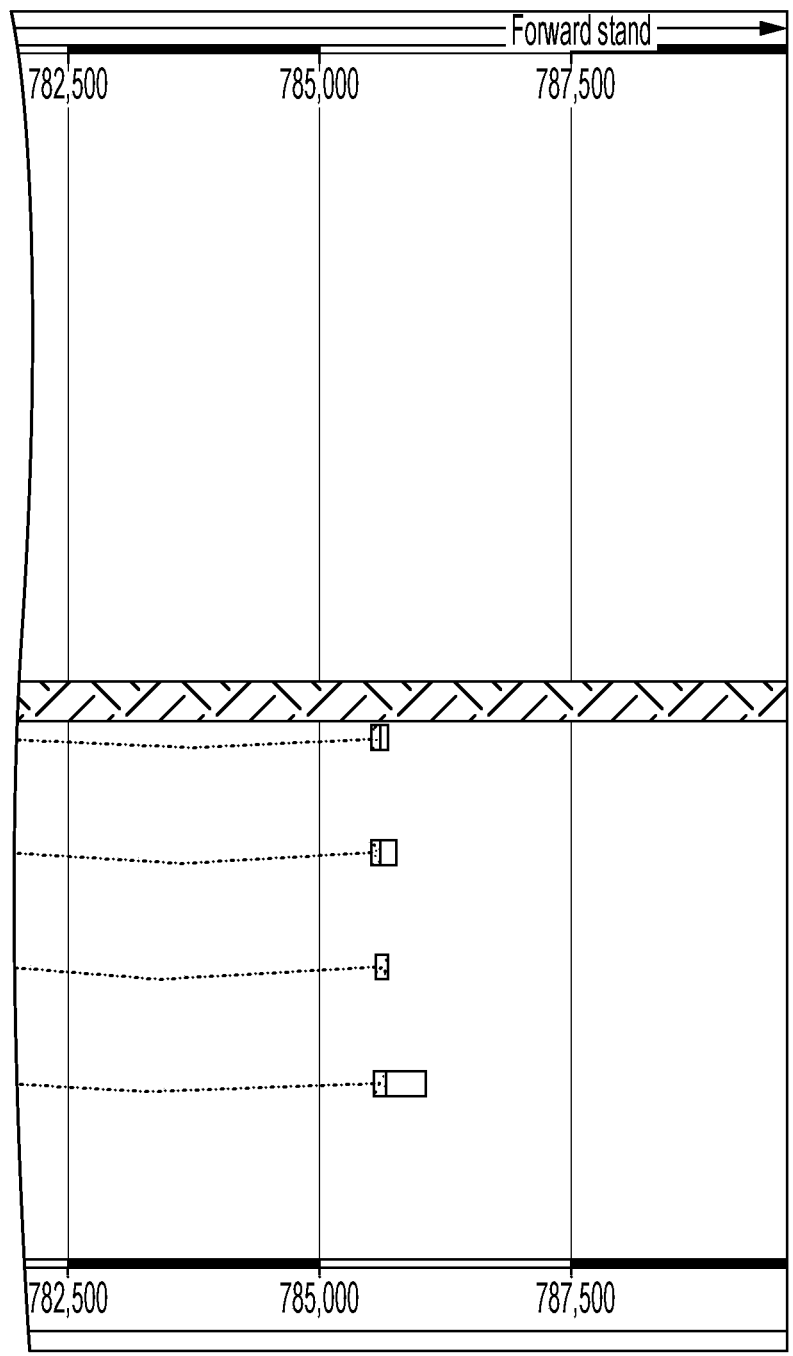
Figure 20:
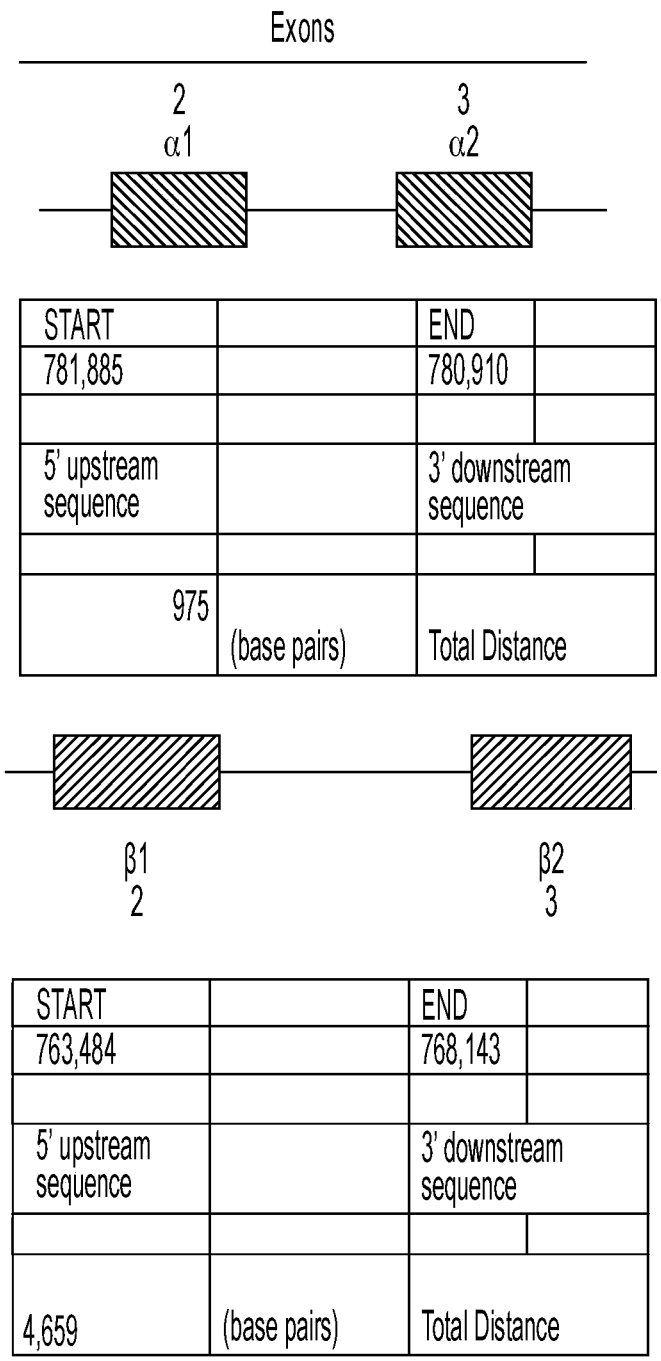
FIG. 20 shows the location and the length α1(exon 2) of SLA-DQA and β1(exon 2) of SLA-DQB1.

For purposes of modifying donor SLA/MHC to match recipient HLA/MHC, comparative genomic organization of the human and swine histocompatibility complex has been mapped as illustrated in FIG. 16 and FIG. 17. For example, such SLA to HLA mapping can be found in: Lunney, J., "Molecular genetics of the swine major histocompatibility complex, the SLA complex," Developmental and Comparative Immunology 33: 362-374 (2009) ("Lunney"), the entire disclosure of which is incorporated herein by reference. Further, by comparing the loci of HLA and schematic molecular organization of various HLA genes, as illustrated in FIG. 12 and FIG. 13, with the loci of SLA and schematic molecular organization of various SLA genes, as show in FIG. 17 and FIG. 18, it is readily discernible that the placement and number of exons in extracellular and transmembrane domain is common between HLA MHC and SLA MHC. Accordingly, a person of ordinary skill in the art effectively and efficiently genetically reprogram swine cells in view of the present disclosure and using the mapping of Lunney et al. as a reference tool.

The donor swine's SLA/MHC gene is used as a reference template in creating the replacement template. In implementing the present disclosure, the swine's SLA/MHC gene may be obtained through online archives or database such as Ensembl (http://vega.archive.ensembl.org/index.html). As illustrated in FIG. 19, FIG. 20, FIG. 21, and FIG. 22, the exact location of the SLA-DQA and SLA-DQB1 gene, the length of the respective gene (exon and intron), and the exact nucleotide sequences of SLA-DQA and SLA-DQB1 are mapped. In an alternative aspect of the present disclosure, the donor swine's SLA/MHC gene may be sequenced. In an alternative aspect of the present disclosure, the swine's whole genome may be sequenced. In one aspect, the sequenced SLA/MHC gene of the donor swine that can be used as a reference template include but are not limited to SLA-3, SLA-6, SLA-7, SLA-8, SLA-DQa, SLA-DQb, and beta-2 microglobulin. In another aspect, the sequenced SLA/MHC gene of the donor swine that can be used as a base template include but are not limited exon regions of SLA-3, SLA-6, SLA-7, SLA-8, SLA-DQa, SLA-DQb, and beta-2 microglobulin. In some aspects, other SLAs are unaltered and intron regions of the reprogrammed SLA regions are unaltered, thereby producing a minimally altered reprogrammed swine genome that provides cells, tissues and organs that are tolerogenic when transplanted into a human.

Figure 23:
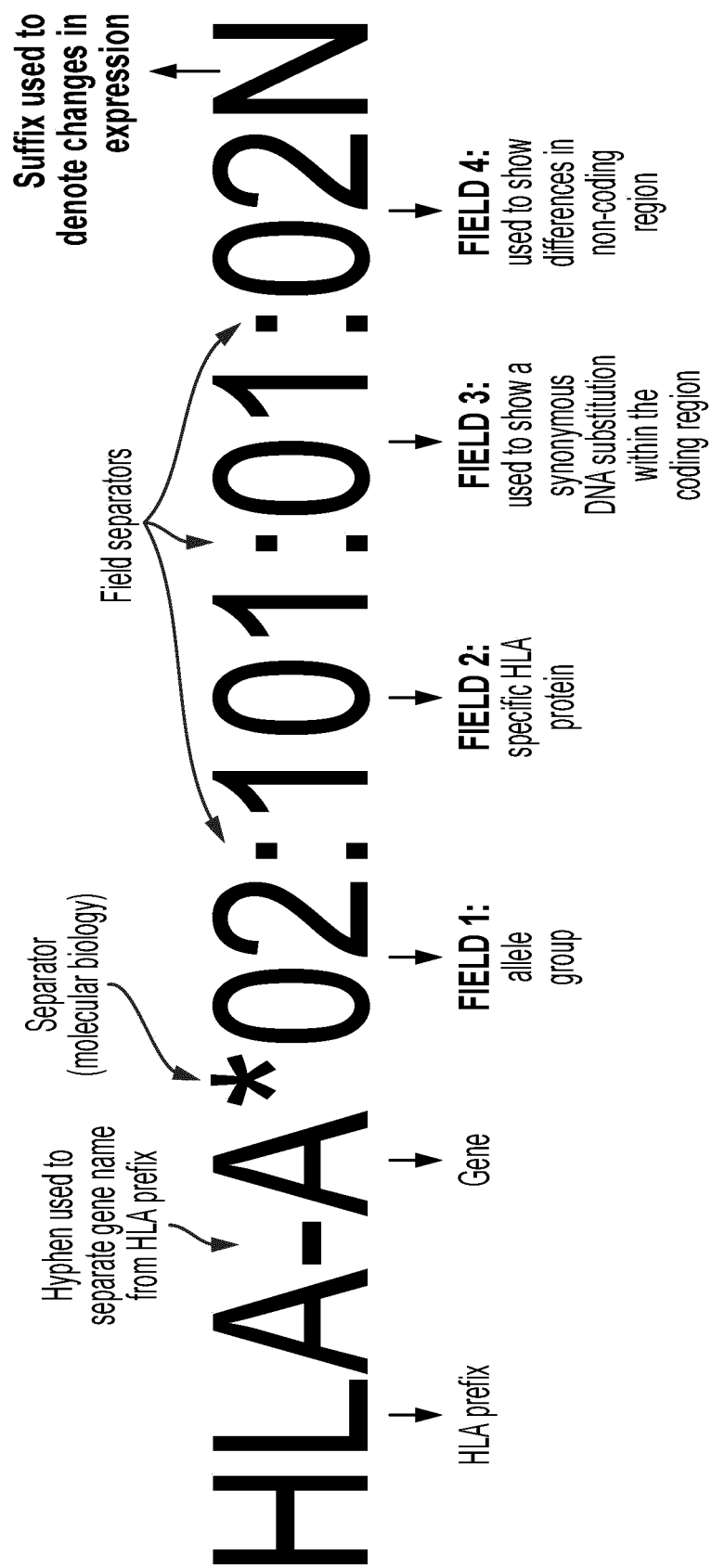
FIG. 23 illustrates nomenclature of HLA alleles. Each HLA allele name has a unique number corresponding to up to four sets of digits separated by colons. The length of the allele designation is dependent on the sequence of the allele and that of its nearest relative. All alleles receive at least a four digit name, which corresponds to the first two sets of digits, longer names are only assigned when necessary. The digits before the first colon describe the type, which often corresponds to the serological antigen carried by an allotype. The next set of digits are used to list the subtypes, numbers being assigned in the order in which DNA sequences have been determined. Alleles whose numbers differ in the two sets of digits must differ in one or more nucleotide substitutions that change the amino acid sequence of the encoded protein. Alleles that differ only by synonymous nucleotide substitutions (also called silent or non-coding substitutions) within the coding sequence are distinguished by the use of the third set of digits. Alleles that only differ by sequence polymorphisms in the introns, or in the 5' or 3' untranslated regions that flank the exons and introns, are distinguished by the use of the fourth set of digits.

In accordance with one aspect the present invention, a donor swine is provided with a genome that is biologically engineered to express a specific set of known human HLA molecules. Such HLA sequences can be obtained, e.g., from the IPD-IMGT/HLA database (available at ebi.ac.uk/ipd/imgt/hla/) and the international ImMunoGeneTics Information System® (available at imgt.org). Nomenclature for such genes is illustrated in FIG. 23. For example, HLA-A1, B8, DR17 is the most common HLA haplotype among Caucasians, with a frequency of 5%. Thus, the disclosed method can be performed using the known MHC/HLA sequence information in combination with the disclosures provided herein. The HLA sequences are obtainable through online archives or database such as Ensembl (vega.archive.ensembl.org/index.html). As illustrated in FIG. 24, the exact location of the HLA-DQA1 gene, the length of the respective gene (exon and intron), and the exact nucleotide sequences of HLA-DQA1 could be obtained.

In some aspects, the recipient's human leukocyte antigen (HLA) genes and MHC (Class I, II and/or III), are identified and mapped. It will be understood that ascertaining the human recipient's HLA/MHC sequence can be done in any number of ways known in the art. For example, HLA/MHC genes are usually typed with targeted sequencing methods: either long-read sequencing or long-insert short-read sequencing. Conventionally, HLA types have been determined at 2-digit resolution (e.g., A*01), which approximates the serological antigen groupings. More recently, sequence specific oligonucleotide probes (SSOP) method has been used for HLA typing at 4-digit resolution (e.g., A*01:01), which can distinguish amino acid differences. Currently, targeted DNA sequencing for HLA typing is the most popular approach for HLA typing over other conventional methods. Since the sequence-based approach directly determines both coding and non-coding regions, it can achieve HLA typing at 6-digit (e.g., A*01:01:01) and 8-digit (e.g., A*01:01:01:01) resolution, respectively. HLA typing at the highest resolution is desirable to distinguish existing HLA alleles from new alleles or null alleles from clinical perspective. Such sequencing techniques are described in, for example, Elsner H A, Blasczyk R: (2004) Immunogenetics of HLA null alleles: implications for blood stem cell transplantation. Tissue antigens. 64 (6): 687-695; Erlich R L, et al (2011) Next-generation sequencing for HLA typing of Class I loci. BMC genomics. 12: 42-10.1186/1471-2164-12-42; Szolek A, et al. (2014) OptiType: Precision HLA typing from next-generation sequencing data. Bioinformatics 30:3310-3316; Nariai N, et al. (2015) HLA-VBSeq: Accurate HLA typing at full resolution from whole-genome sequencing data. BMC Genomics 16:S7; Dilthey A T, et al. (2016) High-accuracy HLA type inference from whole-genome sequencing data using population reference graphs. PLoS Comput Biol 12:e1005151; Xie C., et al. (2017) Fast and accurate HLA typing from short-read next-generation sequence data with xHLA 114 (30) 8059-8064, each of which is incorporated herein in its entirety by reference.

A complete disruption of MHC Class I expression on xenograft has shown to have detrimental effects on the viability of the animal. In a study, SLA Class I expression on porcine cells were abrogated by targeting exon 2 of the porcine beta-2-microglobulin gene. The genomic sequencing of the produced piglets showed modification at the B2M locus leading to a frameshift, a premature stop codon, and ultimately a functional knockout. However, the piglets of the study did not survive for more than 4 weeks due to unexpected disease processes, revealing that such disruptive genetic modification may have a negative impact on the viability of the animals. Sake H J, Frenszel A, Lucas-Hahn A, et al. Possible detrimental effects of beta-2-microglobulin knockout in pigs. *Xenotransplantation.* 2019; 26:e12525.

In one aspect, a replacement template is created for site-directed mutagenic substitutions of nucleotides of the donor swine's SLA/MHC wherein the reprogramming introduces non-transgenic, minimally-required alteration that does not result in any frameshifts or frame disruptions in specific exon regions of the native donor swine's SLA/MHC. The nucleotide sequence(s) of the replacement template is identified by: a) obtaining a biological sample containing DNA from a transplant recipient, b) sequencing MHC Class I and II genes in the transplant recipient's sample, c) comparing the nucleotide sequence of the recipient with that of the donor swine at various loci, and d) creating a replacement template for one or more of said loci, wherein said nucleotide sequence of the replacement template are at least 95% identical to the transplant recipient's nucleotide sequences, as further described below.

Figure 26B:
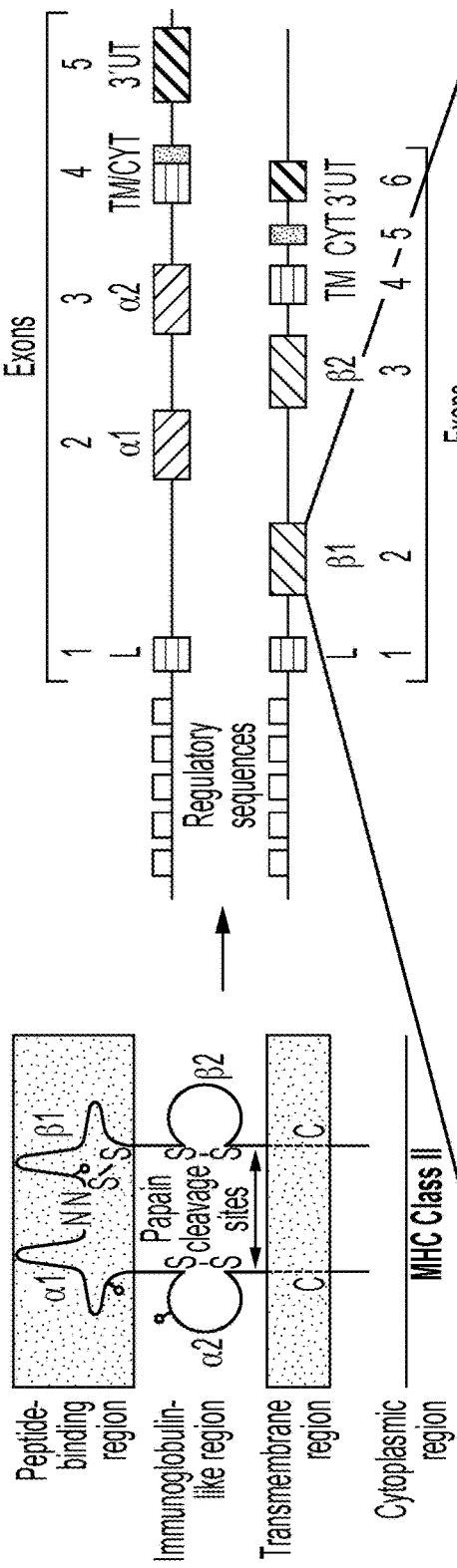
FIG. 26B shows example of Human Capture Reference Sequence (DQ-B1) for Three Patients.
Figure 26C:
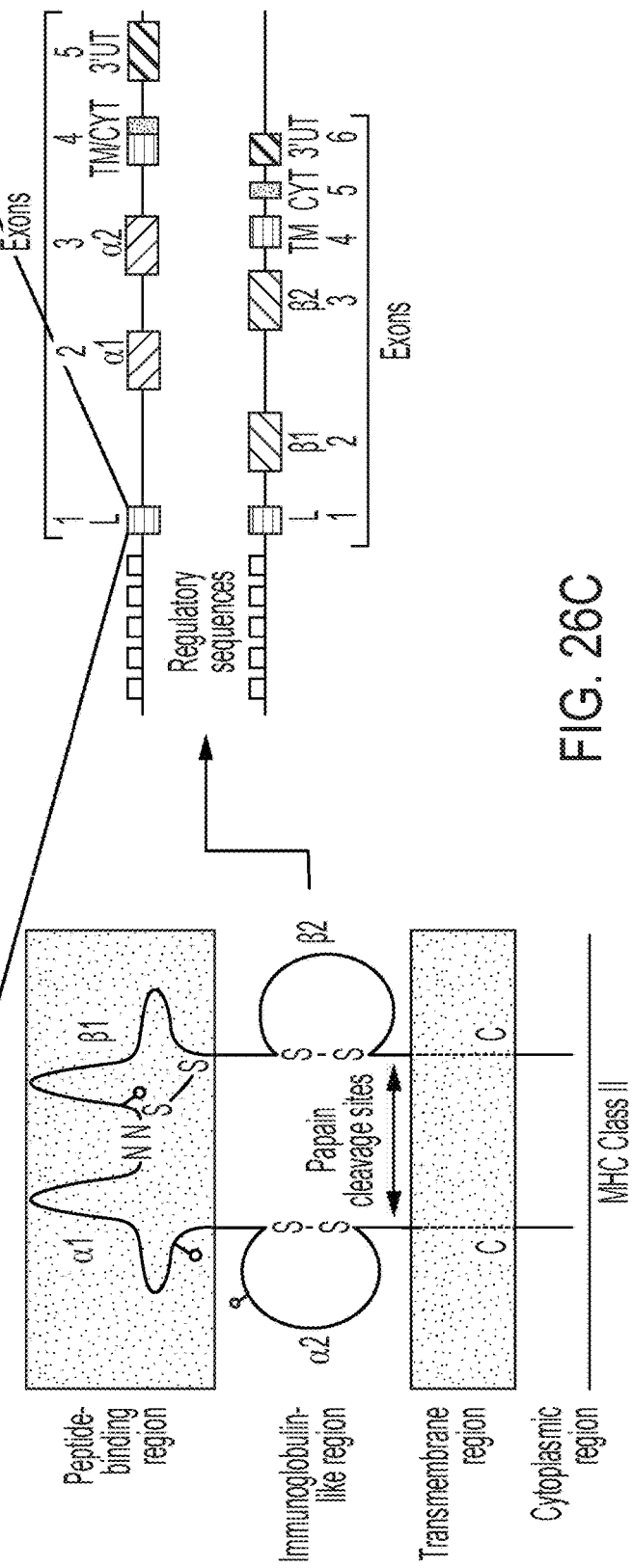
FIG. 26C shows example of Human Capture Reference Sequence (DR-A) for Three Patients.
Figure 26D:
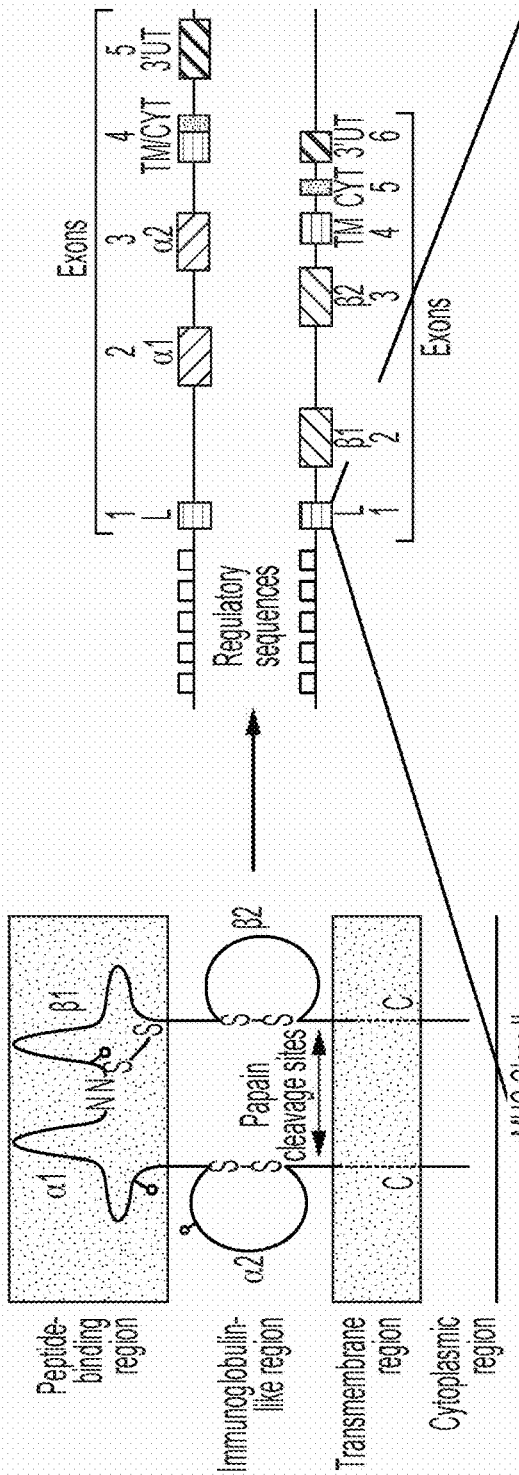
FIG. 26D shows example of Human Capture Reference Sequence (DR-B1) for Three Patients.

The spreadsheet in FIG. 25A and FIG. 25B, shows human capture reference sequence of exons of $DQ-A_1$ and $DQ-B_1$, respectively, of three individual recipients. As mentioned above, known human HLA/MHC or an individual recipient's sequenced HLA/MHC sequence(s) may be utilized as a template to reprogram with precise substitution the swine leukocyte antigen (SLA)/MHC sequence to match, e.g., to have 90%, 95%, 98%, 99%, or 100% sequence homology to a known human HLA/MHC sequence or the human recipient's HLA/MHC sequence. As shown in FIG. 25C, the known human HLA-DQA acquired through online database and individual recipients' sequenced HLA-DQA, can be compared in a nucleotide Sequence Library. FIG. 26D shows comparison of exon 2 region of the swine's SLA-DQA acquired through online database and the known and sequenced recipient's HLA-DQA1. Both exon 2 region of SLA-DQA and HLA-DQA1 contain 249 nucleotides. As illustrated in FIG. 25D, it can be observed that 11% of the aligned 249 nucleotides between exon 2 regions of SLA-DQA1 and HLA-DQA1 are completely divergent. Therefore, this disclosure disclose method of identifying the non-conserved nucleotide sequences at a specific exons of human and swine MHC complex. Furthermore, by using a human capture reference template, known or sequenced, a site-directed mutagenesis can be performed wherein the specific non-conserved nucleotide sequence between the specific exon regions of the SLA gene and the known or recipient's HLA gene are replaced without causing any frameshift. The site-directed mutagenesis of the SLA-DQA1 and SLA-DQB1 gene is shown in FIG. 26A and FIG. 26B, wherein the nucleotide sequences of the exon 2 region of the recipient specific HLA-DQA1 and HLA-DQB1 are used to create a human capture replacement sequence. Therefore, the use of synthetic replacement template specific to the exon regions of the MHC gene, leads to a non-transgenic, minimally altered genome that does not result in any frameshifts or frame disruptions in the native donor swine's SLA/MHC gene.

As mentioned above, disruptive genetic modification that causes frameshifts may have a negative impact on the viability of the animals. Therefore, the present invention discloses method of inhibiting expression of MHC proteins without causing frameshift in the MHC gene. The spreadsheet in FIG. 25E and FIG. 25F shows human capture reference sequence of exons of DR-A and $DR-B_1$, respectively, of three individual recipients. As shown in FIG. 26C and FIG. 26D, by replacing the initial three nucleotide sequences of the leader exon 1 to a STOP codon, the expression of DR molecule can be inhibited without causing frameshift. Specifically, for HLA-DRA and $DRB_1$, the initial three sequences of exon 1, ATG, is replaced with stop codon, TAA. Therefore, by using synthetic replacement template, wherein stop codon is placed in the beginning of exon 1, the invention provides method of inhibiting expression of desired MHC molecule, wherein the non-transgenic, minimally alteration of genome does not result in any frameshifts or frame disruptions in the native donor swine's SLA/MHC gene.

Figure 27:
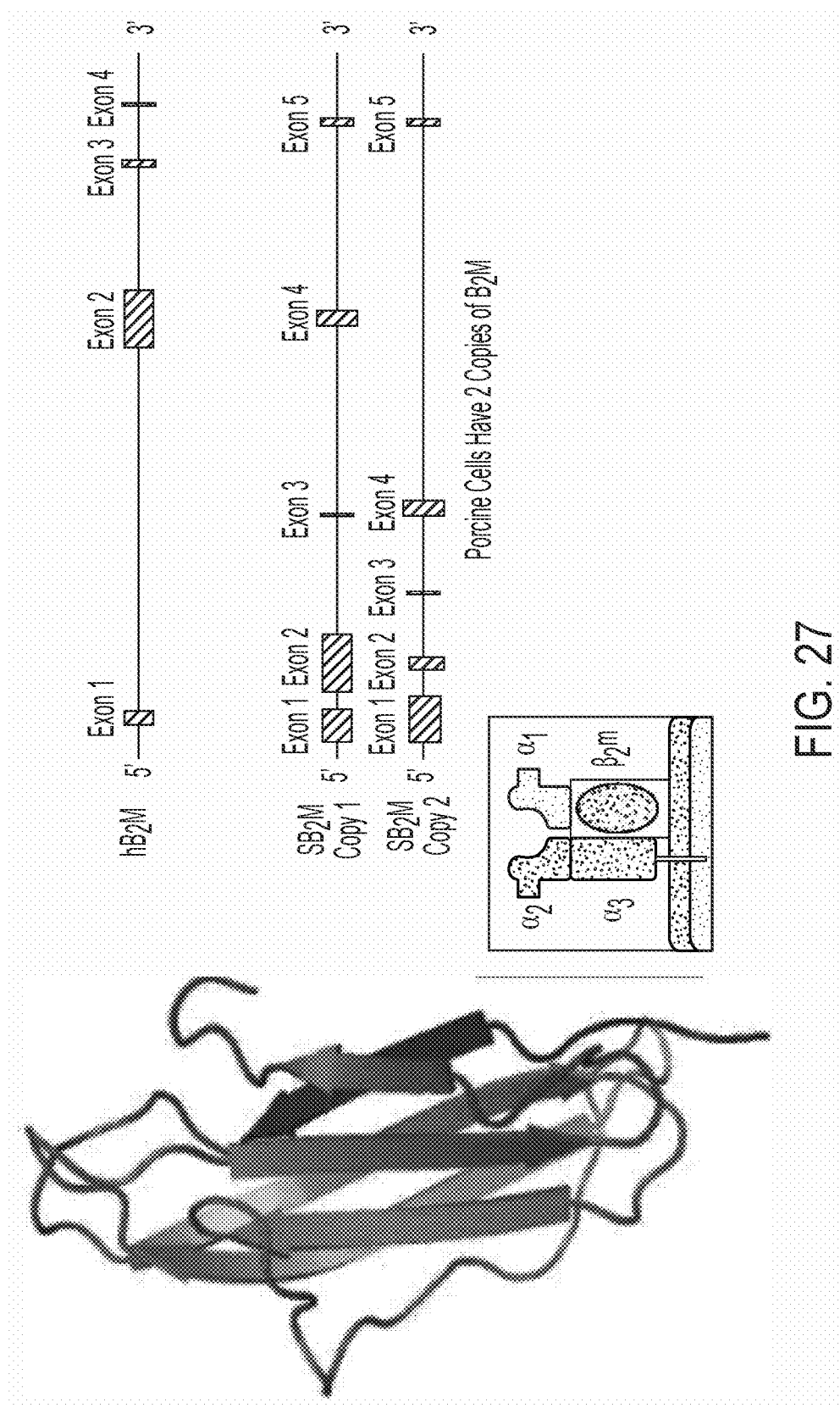
FIG. 27 shows the wild-type human beta-2 microglobulin protein and schematic molecular organization of the human B2M gene and swine B2M gene.

Further, the beta-2-microglobulin protein which comprises the heterodimer structure of each of the MHC-I proteins is species-specific. Based on the pig genome assembly SSC10.2, a segmental duplication of ~45.5 kb, encoding the entire B2M protein, was identified in pig chromosome 1, wherein functional duplication of the B2M gene identified with a completely identical coding sequence between two copies in pigs. The phylogenetic analysis of B2M duplication in ten mammalian species, confirming the presence of B2M duplication in cetartioldactyls, like cattle, sheep, goats, pigs and whales, but non-cetartiodactyl species, like mice, cats, dogs, horses, and humans. The density of long interspersed nuclear element (LINE) at the edges of duplicated blocks (39 to 66%) was found to be 2 to 3-fold higher than the average (20.12%) of the pig genome, suggesting its role in the duplication event. The B2M mRNA expression level in pigs was 12.71 and 7.57 times ($2-\Delta\Delta Ct$ values) higher than humans and mice, respectively. The identification of partially remaining duplicated B2M sequences in the genomes of only cetartiodactyls indicates that the event was lineage specific. B2M duplication could be beneficial to the immune system of pigs by increasing the availability of MHC class I light chain protein, B2M, to complex with the proteins encoded by the relatively large number of MHC class I heavy chain genes in pigs. As shown in FIG. 27, B2M molecule with respect to MHC Class I molecule can be observed. Further as stated above and shown in FIG. 27, swine has duplication of B2M gene while human has one. Thus, in one embodiment of the present disclosure, the first copy of the swine B2M gene is reprogrammed through site-directed mutagenesis, as previously disclosed. As shown in FIG. 28, the amino acid sequences of exon 2 of the swine B2M is compared with that of the human, wherein the non-conserved regions are identified. In addition, the expression of the second copy of the swine B2M gene is inhibited by use of STOP codon, as previously disclosed. Thus, in one embodiment of the present disclosure includes a genetic modification, wherein the first copy of the swine B2M gene is reprogrammed through site-directed mutagenesis and second duplicated B2M gene is not expressed, wherein the reprogramming does not result in frameshift of B2M gene.

Selection and Characterization of Pilot Cell Porcine Line for Humanization by Genetic Modification Primary macrophages and other antigen presenting cells (APC) are useful for studying immune response, however, the long term use of primary cells is limited by the cells' short life span. In addition, primary cells can only be genetically engineered and evaluated one time before the cells reach senescence. In the pig model, investigators frequently have used porcine aortic endothelial cells (PAECs) for these type of studies. An immortalized cell line that has the desired characteristics (expression of MHC Class I and II molecules and CD80/86) of a macrophage or representative APC would be ideal to conduct multiple modifications of the genome and address impact on immunological reactivity using the same genetic background. The ability to generate a viable immortalized pig cell line has been limited to fibroblasts and epithelial cell lines which are not relevant for the study of the immune response in xenotransplantation.

An immortalized porcine alveolar macrophage (PAM) line was developed from Landrace strain of pig [Weingartl 2002] and is commercially available through ATCC [3D4/21, ATCC CRL-2843]. The cell line showed some percentage of non-specific esterase and phagocytosis which was dependent upon conditions of the medium. Cells could be grown as anchorage dependent or in colonies under serum free conditions. Myeloid/monocyte markers (e.g. CD14) were detected. Desired characteristics of an immortalized cell line was MHC Class I and II. MHC Class I was shown to be broadly expressed on all cells, however, MHC Class II, DR and DQ, expression of 3D4/21 cells was initially reported as being low, 18% and 4%. PAEC have been shown to be activated and DR expression could be upregulated with exposure to IFN-gamma. 3D4/21 cells were exposed to IFN-gamma and Class II expression increased DR: 29.68% to 42.27% and DQ: 2.28% to 57.36% after 24 hours of exposure to IFN-gamma. In addition, CD80/86 are expressed on the cell surface, these glycoproteins are essential for the second signal of T cell activation and proliferation. PAM cells, 34D/21, have the desired characteristics of a porcine APC in which genetic changes in genes associated with the MHC can be documented using an immortalized cell line and the resulting changes in the phenotype can be assessed using flow cytometry to address expression or lack of expression of the glycoproteins of interest and cellular immune responses, Mixed Lymphocyte Response (MLR).

To test for cellular immune response, a one way MLR is set up in which one set of cells is identified as the stimulator cells, these are donor cells or unmodified or modified PAM cells, and the other set of cells is the responder cells, these are cells from the recipient (these could be from recipient's who share a similar expression of MHC molecules are the modified PAM cells. The stimulator cells are treated with an agent to prevent the cells from proliferating and this could be either radiation or incubation with mitomycin C which covalently crosslinks DNA, inhibiting DNA synthesis and cell proliferation. Hence, the stimulator cells do not proliferate in culture however, the responder cells proliferate in response to interaction at the MHC Class I and II and it is this proliferation that is measured in a MLR. A cell culture containing both stimulator and responder cells is prepared and incubated for 5-7 days and proliferation/activation is measured. Proliferation can be measured by the amount of radioactive thymidine [$^3$HTdr] or BrdU [analog of thymidine] that is incorporated into the DNA upon proliferation at the end of 5 or 7 days.

Combinations of the MLR. Responders cells can be either PBMC, CD4+ T cells, CD8+ T cells or other subpopulations of T cells. PBMC represent all the immune cells that are present in the recipient and the measured response reflects the ability of the responders to mount an immune response to the stimulator cells, [unmodified or modified PAM cells]. The measured proliferation consists of both CD4+ and CD8+ T cells which interact with MHC Class II and I, respectively. Using only CD4+ T cells against the unmodified or modified PAM cells is to measure the response to MHC Class II glycoproteins, DR and DQ. To observe a specific response to DQ, human antigen presenting cells (APCs) are absent from the culture such that the cellular response is not the result of pig antigens presented by the APCs. In parallel, responder CD8+ T cells will be used to assess an immune response to MHC Class I glycoproteins, SLA 1 AND 2. This type of analysis removes the contribution to the immune response from responder APCs as found in PBMC. Comparative data will demonstrate the contribution of these respective glycoproteins to the immune response of the genetically defined responder and reflects on the genetic modifications made to the PAM cells.

Flow cytometry, phenotypic analysis of the genetically modified PAM cells. The cell phenotype of genetically modified cells, e.g., cells from a genetically modified animal or cells made ex vivo, are analyzed to measure the changes in expression of the glycoproteins encoded by the genes that were modified. Cells are incubated with an antibody with a fluorescent label that binds to the glycoprotein of interest and labeled cells are analyzed using flow cytometry. The analysis has been performed on unmodified PAM cells to identify the expression of MHC Class I, Class II (DR and DQ) and CD80/86. Changes in modified PAM cells will be referenced to this database. Flow cytometry will also be used to characterize the expression of glycoproteins encoded by genes for SLA 3, 6, 7, and 8 as the genes in the PAM cells are modified with recipient specific sequences related to HLA C, E, F, and G.

In addition, this type of analysis is also used to ensure the glycoprotein encoded by a gene that is knock-out is not expressed. This technique can also be used to sort out genetically modified cells from a pool of cells with mixed phenotypes.

Complement Dependent Cytotoxicity (CDC) assays may be performed to determine if anti-HLA antibodies recognize the cells from the biological product of the present disclosure. Assay plates prepared by adding a specific human serum containing previously characterized anti-HLA antibodies (or control serum) can be used. IFN-γ treated donor cells are resuspended and added to the assay plates, incubated with a source of complement, e.g., rabbit serum. After at least 1 hour of incubation at room temperature, acridine orange/ethidium bromide solution is added. Percent cytotoxicity is determined by counting dead and live cells visualized on a fluorescent microscope, subtracting spontaneous lysis values obtained in the absence of anti-HLA antibodies, and scoring with a scale.

NK cell reactivity, modulation to decrease cytotoxicity. Potential mechanisms of activation, recognition, and elimination of target cells by NK cells, alone or in combination, induce the release of the content of their lytic granules (perforin, granzyme, and cytolysin). As an example, NK cells recognize the lack of self-major histocompatibility complex (MHC) Class I molecules on target cells by inhibitory NK cell receptors leading to direct NK cytotoxicity. This is the case for xenotransplantation. NK cells are regulated by HLA C that is recognized by inhibitory NK cell inhibitory killer cell immunoglobulin-like receptors (KIRs), KIR2DL2/2DL3, KIR2DL1, and KIR3DL1. NK cells inhibitory receptor, immunoglobulin-like transcript 2 (ILT2) interacts with MHC Class I and CD94-NKG2A recognizing HLA-E. HLA F and G have similar roles on the trophoblast.

The cytolytic activity of recipient NK cells to an unmodified PAM cell can be measured in vitro in which human NK cells are added to an adherent monolayer of unmodified PAM cells and cultured for 4 hours. Cell lysis is measured by release of radioactive $Cr^{51}$ or a chromophore measured by flow cytometry. PAM cells with modified SLA 3, 6, 7 or 8 to mirror HLA C, HLA E, HLA G or HLA F, respectively, can be assessed using this cytotoxicity assay.

For knock in cells, the desired sequences are knocked into the cell genome through insertion of genomic material using, e.g., homology-directed repair (HDR). To optimize expression of Class II molecules, the cells are incubated in porcine interferon gamma (IFN-γ) for 72 hours which stimulates expression. Expression is then measured by flow cytometry using target specific antibodies. Flow cytometry may include anti-HLA-C, HLA-E, HLA-G, or other HLA antibodies, or pan anti-HLA Class I or Class II antibodies. According to the present disclosure, cell surface HLA expression after knock-in is confirmed.

A study was conducted identify the impact of the stimulation by IFN-γ and IFN-γ+LPS on the phenotype of the porcine alveolar macrophages (PAM) purchased from ATCC® (3D4/21 cells cat #CRL-2843™) by flow cytometry.

PAM cells were thawed in RPMI-1640/10% FBS and cultured for two days in three different culture plates. On Day 3, for macrophage activation culture medium was replaced with RPMI-1640/20% FBS medium containing 100 ng/mL IFN-γ (Plate 1) and 100 ng/mL IFN-γ plus 10 ng/mL LPS (Plate 2). Untreated cells in RPMI-1640/20% FBS were used as control (Plate 3). Following 24 hours incubation, adherent cells were detached from the plate using TrypLE treatment. Cells were resuspended in FACS buffer (1×PBS pH=7.4, 2 mM EDTA, 0.5% BSA). Cell count and viability were determined by trypan blue exclusion method. A total of 1×105 cells were stained with mouse anti pig SLA Class I, SLA Class II DR, SLA Class II DQ antibodies for 30 min and APC-conjugated CD152(CTLA-4)-muIg fusion protein (binds to porcine CD80/CD86) for 45 min at 4° C. Cells were washed two times using FACS buffer and antibody stained cells resuspended in 100 μL FACS buffer containing anti mouse APC-conjugated polyclonal IgG secondary antibody. Followed by incubation for 30 min at 4° C. Cells were washed two times using FACS buffer. All cells were resuspended in 200 μL FACS buffer. Samples were acquired in Novacyte flow cytometry and data was analyzed using NovoExpress.

Analysis procedure is based on NovoExpress flow cytometry analysis software. Any equivalent software can be used for the data analysis. Depending on the software used analysis presentation maybe slightly different. Gates maybe named differently and % values might be slightly different.

Figure 29:
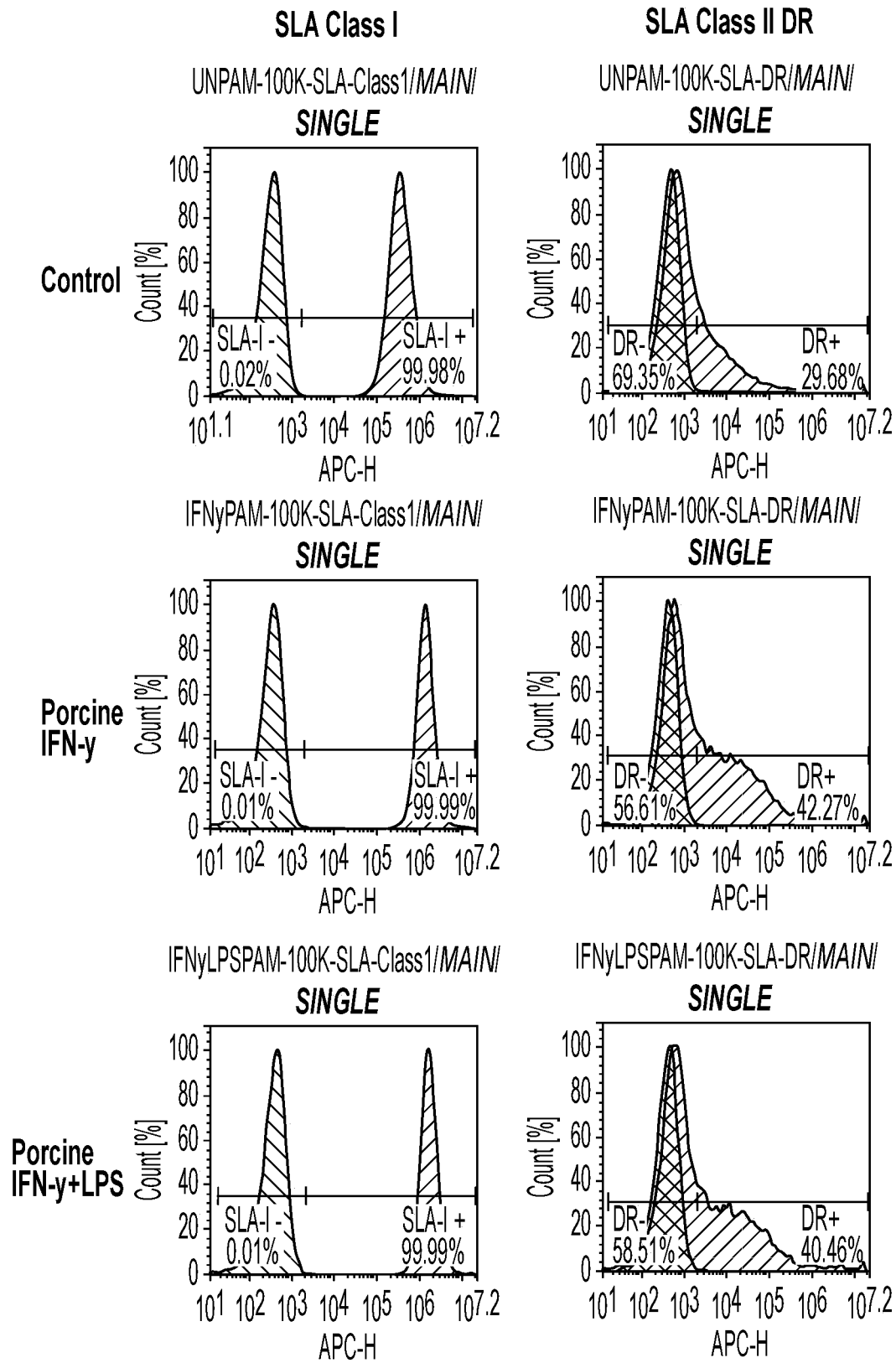
FIG. 29 shows Phenotyping analysis of porcine alveolar macrophages (PAM). Cells were cultured in medium alone (control), or were activated for 72 hours with 100 ng/mL IFN-γ or loaded 30 μg/mL KLH for 24 hours. The cells were stained for SLA-DQ and marker is detected using anti mouse APC-conjugated polyclonal IgG secondary antibody. Data is presented as histograms of count (y axis) versus fluorescence intensity in log scale (x axis). Percentage of positive and negative cells for SLA-DQ for activated cells are shown on histograms.
Figure 29:
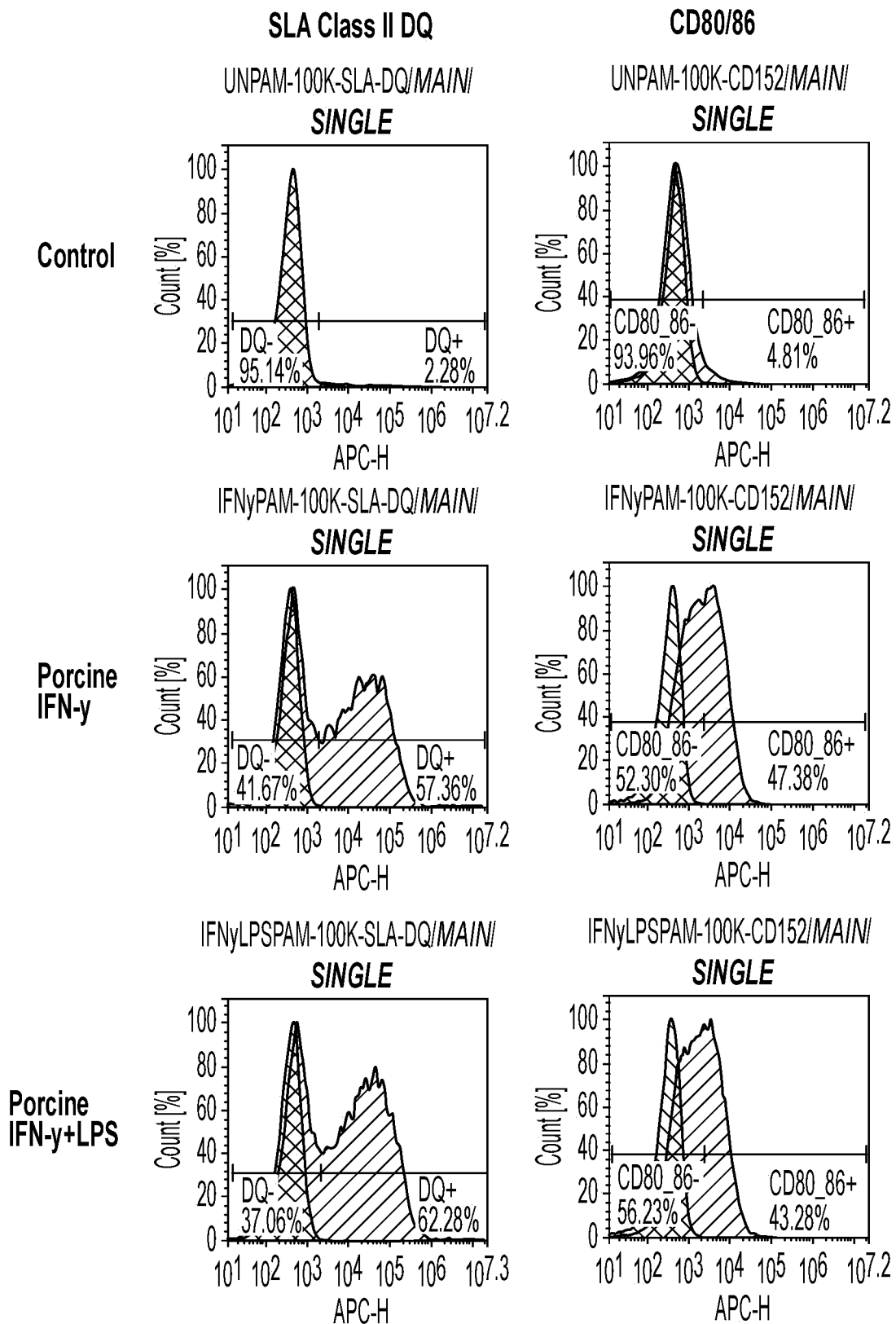

As shown in FIG. 29, untreated PAM cells result 99.98%, 29.68%, and 2.28% SLA Class I, SLA Class II DR and DQ molecules expression respectively. These cells were 4.81% CD80/86+. 24 hours of culturing cells in the presence of IFN-γ increased all SLA molecule expression (99.99% SLA Class I+ with increased median fluorescence intensity, 42.27% DR+, 57.36% DQ+) and CD80/86 levels (47.38%). IFN-γ containing cells with LPS resulted similar levels of SLA molecules and CD80/86 expression compared to cells only treated with IFN-γ.

PAM cells were treated with porcine IFN-γ for 24 hours and stained with primary MAbs and fluorescein conjugated secondary antibody and APC conjugated CD152 which has a high affinity for co-stimulatory molecules CD80 (B7-1) and CD86 (B7-2). Upon treatment with IFN-γ, the cells displayed increased SLA and CD80/86 costimulatory molecules expression compared to unstimulated PAM cells. While unstimulated cells were 99.98% SLA Class I+, 29.68% DR+2.28% DQ+ and 4.81% CD80/86+, IFN-γ stimulated cells were 99.99% SLA Class I+, 42.27% DR+, 57.36% DQ+, 47.38% CD80/86+. IFN-γ containing cells with LPS resulted similar levels of SLA molecules and CD80/86 expression compared to cells only treated with IFN-γ.

In basal conditions, macrophages express low levels of SLA Class II and CD80/86 costimulatory molecules. IFN-γ and IFN-γ-LPS treatment for 24 hours induces the expression of SLA Class II and CD80/86 costimulatory molecules as well as SLA Class I molecules. Extended incubations would perhaps increase the expression of these molecules further.

Figure 30A:
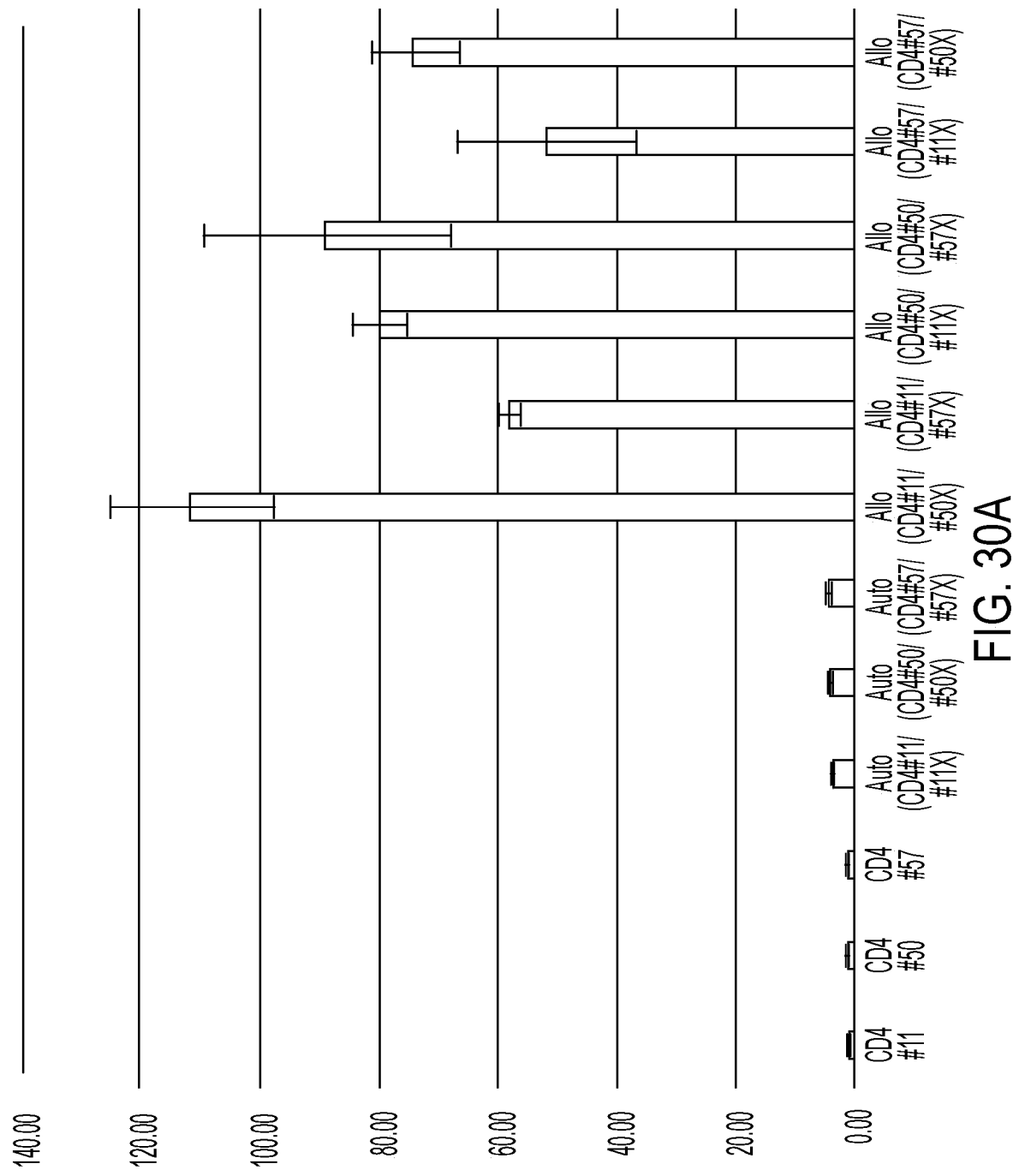
FIGS. 30A-30B show SI values for BrdU ELISA. Proliferation response of three human CD4+ T cells (A) and PBMCs (B) to untreated and IFN-γ activated PAM cells (15K) after seven days incubation.
Figure 30B:
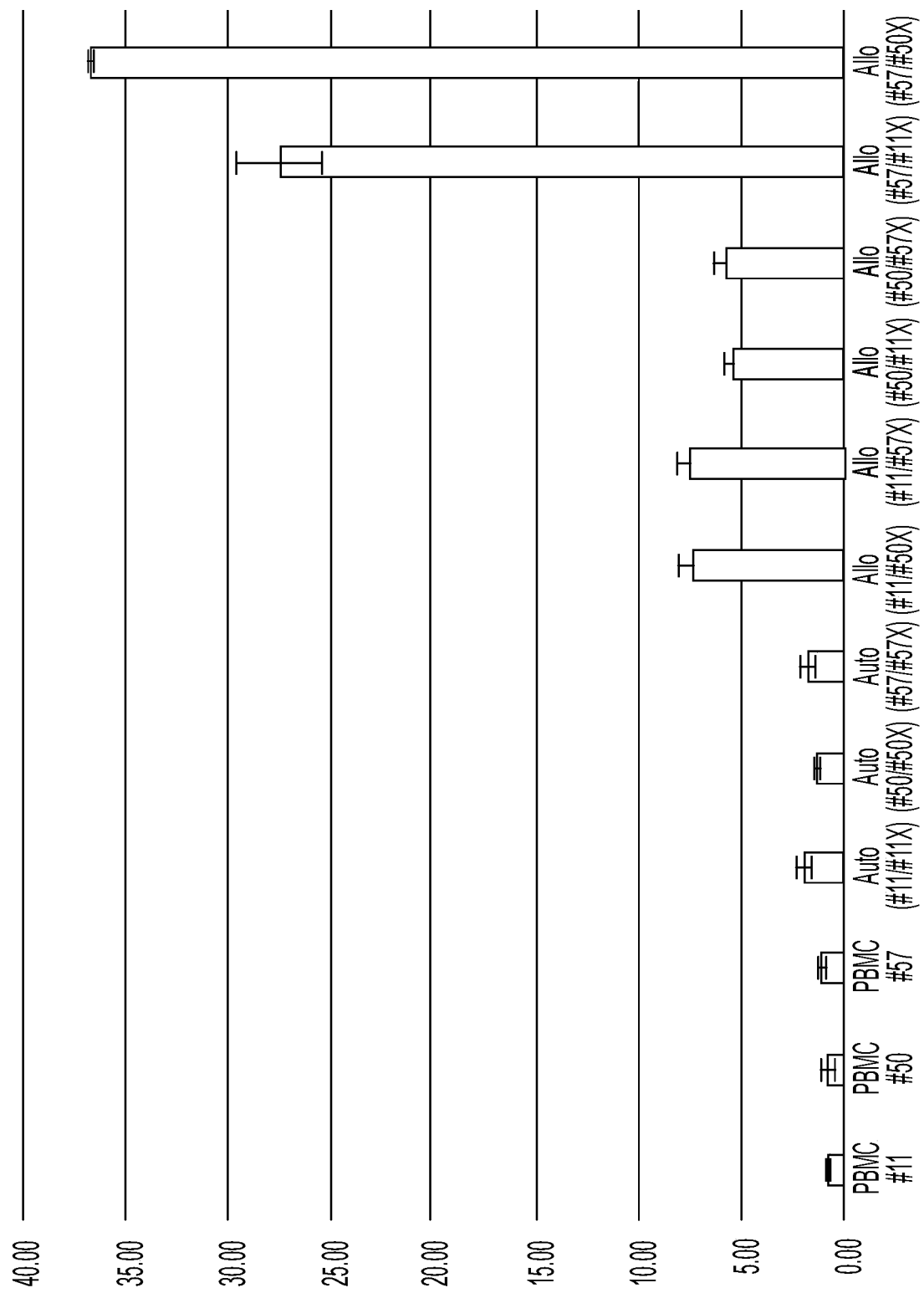

Further, a study was conducted to evaluate the immune proliferative responsiveness of human PBMCs (Peripheral Blood Mononuclear Cells), CD8 and CD4 positive T cells when they are co-cultured with porcine alveolar macrophages (PAM) cells. Human donor PBMCs or their CD4+ T cells were co-cultured with untreated, IFN-γ activated and KLH loaded PAM cells for seven days. As shown in FIG. 30A and FIG. 30B, one-way allogeneic and autologous MLR experiments were performed using the cells isolated from Donor #11, #50, and #57 as positive and negative controls respectively. Background controls were performed for Mitomycin C (X) treated and untreated PAM cells, and each human donor cells. Proliferative response is determined utilizing a bromo-deoxy uridine (BrdU) ELISA assay. On Day 6, BrdU addition was completed. On Day 7 media was collected for cytokine (IFN-γ and IL-2) analysis and proliferative responses were determined. Cells were observed under the Olympus CK40 microscopy at 200× magnification on Day 7 of co-culturing.

Figure 31:
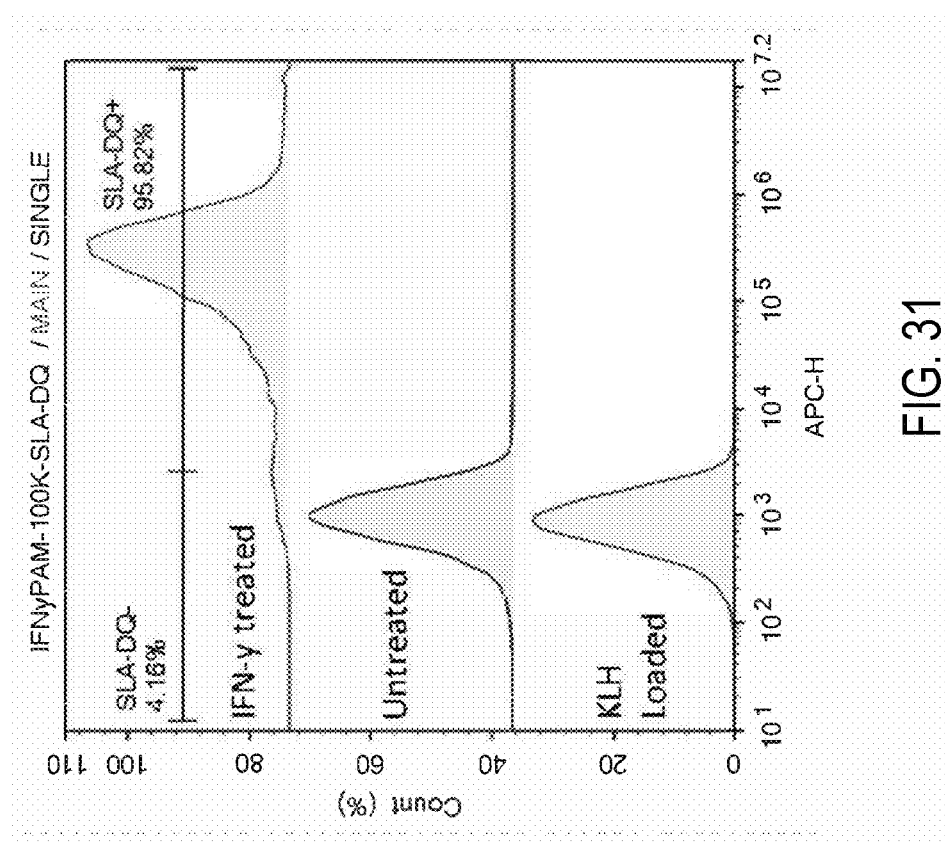
FIG. 31 shows a schematic depiction of a humanized porcine cell according to the present disclosure
Figure 32A:
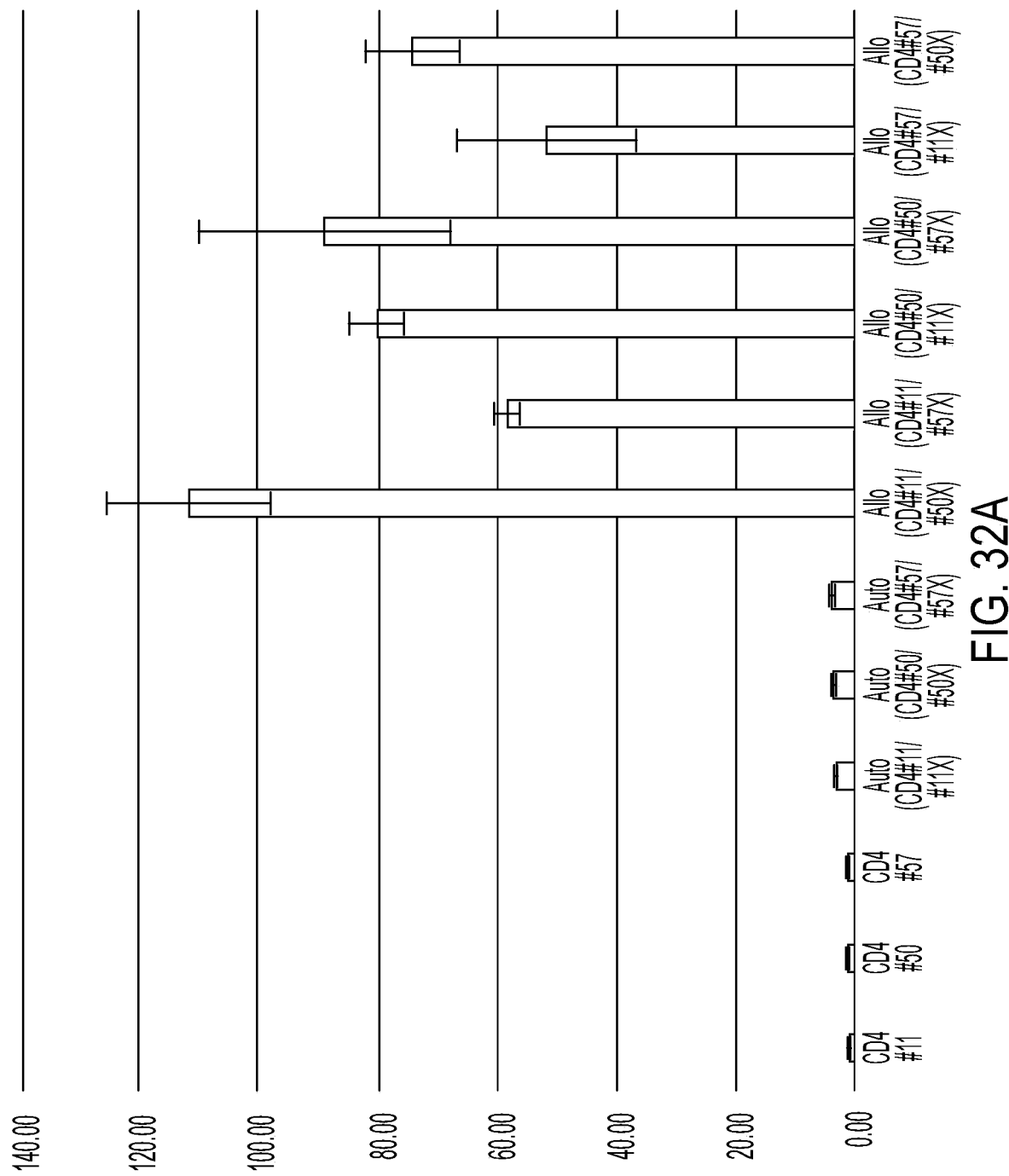
FIGS. 32A-32B show SI values for BrdU ELISA. Proliferation response of three human CD4+ T cells (A) and PBMCs (B) to untreated and IFN-γ activated PAM cells (15K) after seven days incubation.
Figure 32B:
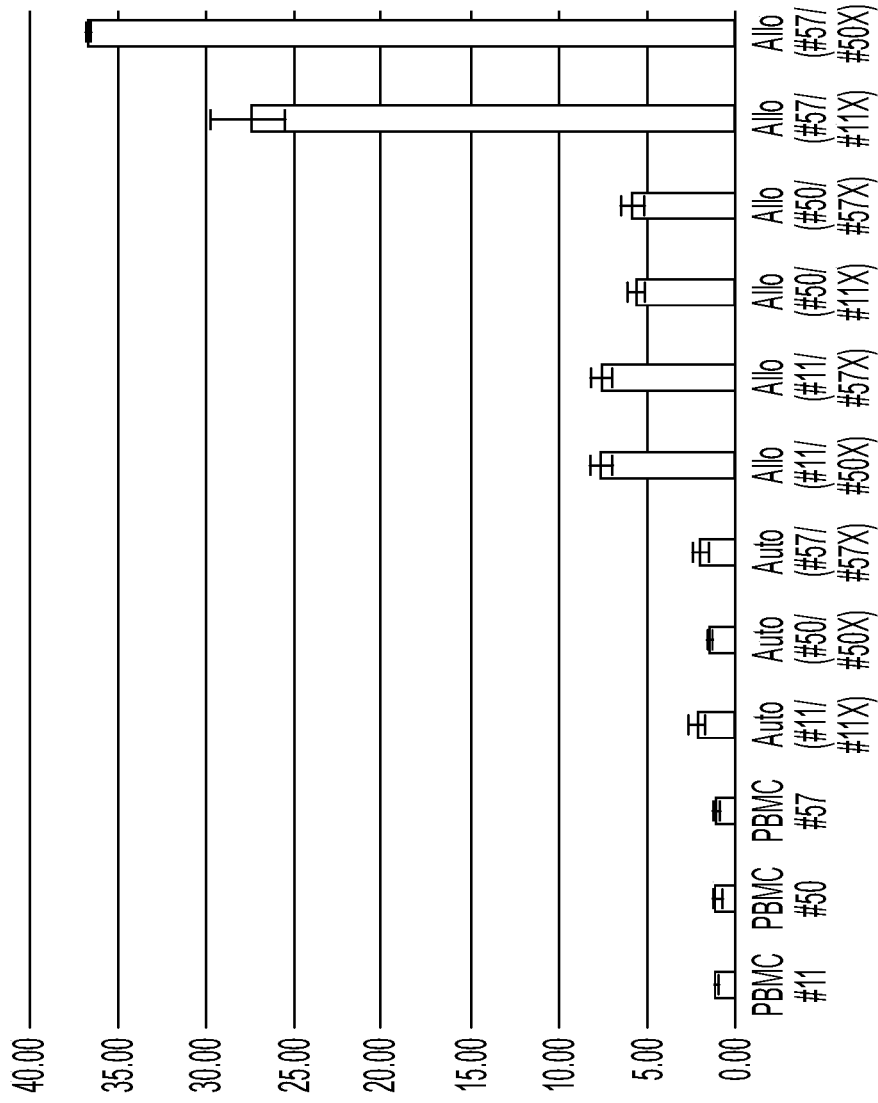

As shown in FIG. 31, 72 hours of culturing PAM cells in the presence of IFN-γ increased SLA Class II DQ molecule expression from 2.55% to 95.82%. KLH loaded PAM cells resulted expression of similar level of SLA Class II DQ molecules with untreated cells. All the allogeneic controls had a positive proliferative response over baseline values and mitomycin C treated PBMCs and PAM cells had a decreased proliferative response compared to baseline values. 1×105 purified human CD8+ T cells or human PBMC were stimulated with increasing numbers of irradiated (30 Gy) porcine PBMC from four-fold knockout pig 10261 or a wild-type pig. Proliferation was measured after 5 d+16 h by 3H-thymidine incorporation. Data representing mean cpm±SEM of triplicate cultures were obtained with cells from one human blood donor in a single experiment. Similar response patterns were observed using responder cells from a second blood donor and stimulator cells from four-fold knockout pig 10262. Proliferation of human CD8+ T cells decreased after stimulation with four-fold knockout porcine PBMC. (Fischer, et al., 2019). Human PBMCs and CD4+ proliferative responses resulted in allogeneic responses that were higher than the xenogeneic responses with PAM cells. The proliferative responses of three different human CD4+ T cells displayed similar xenogeneic responses with PAM cells SI (Stimulation Indexes) values being between 15 and 18.08. The proliferative responses were highest in xenogeneic cultures from PBMC Donor #57 ($SI_{w/PAMX,\ PAM-IFN\gamma X,\ KLHx}$=3.12, 2.75, and 3.79).

Gene Editing Schema to Create Multiple, Independent, Single-Variable Humanized Pilot Porcine Cell Lines by CRISPR-Cas9 Genetic Modification The genetic modification can be made utilizing known genome editing techniques, such as zinc-finger nucleases (ZFNs), transcription activator-like effector nucleases (TALENs), adeno-associated virus (AAV)-mediated gene editing, and clustered regular interspaced palindromic repeat Cas9 (CRISPR-Cas9). These programmable nucleases enable the targeted generation of DNA double-stranded breaks (DSB), which promote the upregulation of cellular repair mechanisms, resulting in either the error-prone process of non-homologous end joining (NHEJ) or homology-directed repair (HDR), the latter of which is used to integrate exogenous donor DNA templates. CRISPR-Cas9 may also be used to perform precise modifications of genetic material. For example, the genetic modification via CRISPR-Cas9 can be performed in a manner described in Kelton, W. et. al., "Reprogramming MHC specificity by CRISPR-Cas9-assisted cassette exchange," Nature, Scientific Reports, 7:45775 (2017) ("Kelton"), the entire disclosure of which is incorporated herein by reference. Accordingly, the present disclosure includes reprogramming using CRISPR-Cas9 to mediate rapid and scarless exchange of entire alleles, e.g., MHC, HLA, SLA, etc.

According to the present disclosure, CRISPR-Cas9 is used to mediate rapid and scarless exchange of entire MHC alleles at specific native locus in swine cells. Multiplex targeting of Cas9 with two gRNAs is used to introduce single or double-stranded breaks flanking the MHC allele, enabling replacement with the template HLA/MHC sequence (provided as a single or double-stranded DNA template).

In some aspects, the expression of polymorphic protein motifs of the donor animal's MHC can be further modified by knock-out methods known in the art. For example, knocking out one or more genes may include deleting one or more genes from a genome of a non-human animal. Knocking out may also include removing all or a part of a gene sequence from a non-human animal. It is also contemplated that knocking out can include replacing all or a part of a gene in a genome of a non-human animal with one or more nucleotides. Knocking out one or more genes can also include substituting a sequence in one or more genes thereby disrupting expression of the one or more genes. Knocking out one or more genes can also include replacing a sequence in one or more genes thereby disrupting expression of the one or more genes without frameshifts or frame disruptions in the native donor swine's SLA/MHC gene. For example, replacing a sequence can generate a stop codon in the beginning of one or more genes, which can result in a nonfunctional transcript or protein. For example, if a stop codon is created within one or more genes, the resulting transcription and/or protein can be disrupted, silenced and rendered nonfunctional.

In another aspect, the present invention utilizes alteration by nucleotide replacement of STOP codon at exon regions of the wild-type swine's SLA-DR to avoid provocation of natural cellular mediated immune response (CD8+ T Cell) by the recipient, including making cells that lack functional expression of SLA-DR, SLA-1, SLA-2. For example, the present invention utilizes TAA. In other embodiments, the invention utilizes TAG. In other embodiments, the invention utilizes TGA.

In one aspect, the present invention utilizes insertion or creation (by nucleotide replacement) of STOP codon at exons regions of the wild-type swine's second, identical duplication B2-microglobulin gene to reduce the B2-microglobulin mRNA expression level in pigs. It will be understood that B2-microglobulin is a predominant immunogen, specifically a non-gal xeno-antigen.

In one aspect, the recipient's HLA/MHC gene is sequenced and template HLA/MHC sequences are prepared based on the recipient's HLA/MHC genes. In another aspect, a known human HLA/MHC genotype from a World Health Organization (WHO) database may be used for genetic reprogramming of swine of the present disclosure.

CRISPR-Cas9 plasmids are prepared, e.g., using polymerase chain reaction and the recipient's HLA/MHC sequences are cloned into the plasmids as templates. CRISPR cleavage sites at the SLA/MHC locus in the swine cells are identified and gRNA sequences targeting the cleavage sites and are cloned into one or more CRISPR-Cas9 plasmids. CRISPR-Cas9 plasmids are then administered into the swine cells and CRIPSR/Cas9 cleavage is performed at the MHC locus of the swine cells.

The SLA/MHC locus in the swine cells are precisely replaced with one or more template HLA/MHC sequences matching the known human HLA/MHC sequences or the recipient's sequenced HLA/MHC genes. Cells of the swine are sequenced after performing the SLA/MHC reprogramming steps in order to determine if the SLA/MHC sequences in the swine cells have been successfully reprogrammed. One or more cells, tissues, and/or organs from the HLA/MHC sequence-reprogrammed swine are transplanted into a human recipient.

The modification to the donor SLA/MHC to match recipient HLA/MHC causes expression of specific MHC molecules in the new swine cells that are identical, or virtually identical, to the MHC molecules of a known human genotype or the specific human recipient. In one aspect, the present disclosure involves making modifications limited to only specific portions of specific SLA regions of the swine's genome to retain an effective immune profile in the swine while biological products are tolerogenic when transplanted into human recipients such that use of immunosuppressants can be reduced or avoided. In contrast to aspects of the present disclosure, xenotransplantation studies of the prior art required immunosuppressant use to resist rejection. In one aspect, the swine genome is reprogrammed to disrupt, silence, cause nonfunctional expression of swine genes corresponding to HLA-A, HLA-B, and DR, and to reprogram via substitution of HLA-C, HLA-E, HLA-F, and/or HLA-G. In some aspects, the swine genome is reprogrammed to knock-out swine genes corresponding to HLA-A, HLA-B, HLA-C, HLA-F, DQ, and DR, and to knock-in HLA-C, HLA-E, HLA-G. In some aspects, the swine genome is reprogrammed to knock-out swine genes corresponding to HLA-A, HLA-B, HLA-C, HLA-F, DQ, and DR, and to knock-in HLA-C, HLA-E, HLA-G, HLA-F, and DQ. In one aspect, the swine genome is reprogrammed to knock-out SLA-1; SLA-6,7,8; SLA-MIC2; and SLA-DQA; SLA-DQB1; SLA-DQB2, and to knock-in HLA-C; HLA-E; HLA-G; and HLA-DQ. In certain aspects, HLA-C expression is reduced in the reprogrammed swine genome. By reprogramming the swine cells to be invisible to a human's immune system, this reprogramming thereby minimizes or even eliminates an immune response that would have otherwise occurred based on swine MHC molecules otherwise expressed from the donor swine cells.

Various cellular marker combinations in swine cells are made and tested to prepare biologically reprogrammed swine cells for acceptance by a human patient's body for various uses. For these tests, Porcine Aorta Endothelial Cells, fibroblast, or a transformed porcine macrophage cell line available from ATCC® (3D4/21) are used.

The knockout only and knockout plus knock in cell pools are generated by designing and synthesizing a guide RNA for the target gene. Each guide RNA is composed of two components, a CRISPR RNA (crRNA) and a trans-activating RNA (tracrRNA). These components may be linked to form a continuous molecule called a single guide RNA (sgRNA) or annealed to form a two-piece guide (cr:tracrRNA).

CRISPR components (gRNA and Cas9) can be delivered to cells in DNA, RNA, or ribonucleoprotein (RNP) complex formats. The DNA format involves cloning gRNA and Cas9 sequences into a plasmid, which is then introduced into cells. If permanent expression of gRNA and/or Cas9 is desired, then the DNA can be inserted into the host cell's genome using a lentivirus. Guide RNAs can be produced either enzymatically (via in vitro transcription) or synthetically. Synthetic RNAs are typically more pure than IVT-derived RNAs and can be chemically modified to resist degradation. Cas9 can also be delivered as RNA. The ribonucleoproteins (RNP) format consists of gRNA and Cas9 protein. The RNPs are pre-complexed together and then introduced into cells. This format is easy to use and has been shown to be highly effective in many cell types.

After designing and generating the guide RNA, the CRISPR components are introduced into cells via one of several possible transfection methods, such as lipofection, electroporation, nucleofection, or microinjection. After a guide RNA and Cas9 are introduced into a cell culture, they produce a DSB at the target site within some of the cells. The NHEJ pathway then repairs the break, potentially inserting or deleting nucleotides (indels) in the process. Because NHEJ may repair the target site on each chromosome differently, each cell may have a different set of indels or a combination of indels and unedited sequences.

For knock in cells, the desired sequences are knocked into the cell genome through insertion of genomic material using, e.g., homology-directed repair (HDR).

It will be further understood that disruptions and modifications to the genomes of source animals provided herein can be performed by several methods including, but not limited to, through the use of clustered regularly interspaced short palindromic repeats ("CRISPR"), which can be utilized to create animals having specifically tailored genomes. See, e.g., Niu et al., "Inactivation of porcine endogenous retrovirus in pigs using CRISPR-Cas-9," Science 357:1303-1307 (22 Sep. 2017). Such genome modification can include, but not be limited to, any of the genetic modifications disclosed herein, and/or any other tailored genome modifications designed to reduce the bioburden and immunogenicity of products derived from such source animals to minimize immunological rejection.

CRISPR/CRISPR-associated protein (Cas), originally known as a microbial adaptive immune system, has been adapted for mammalian gene editing recently. The CRISPR/Cas system is based on an adaptive immune mechanism in bacteria and archaea to defend the invasion of foreign genetic elements through DNA or RNA interference. Through mammalian codon optimization, CRISPR/Cas has been adapted for precise DNA/RNA targeting and is highly efficient in mammalian cells and embryos. The most commonly used and intensively characterized CRISPR/Cas system for genome editing is the type II CRISPR system from Streptococcus pyogenes; this system uses a combination of Cas9 nuclease and a short guide RNA (gRNA) to target specific DNA sequences for cleavage. A 20-nucleotide gRNA complementary to the target DNA that lies immediately 5' of a PAM sequence (e.g., NGG) directs Cas9 to the target DNA and mediates cleavage of double-stranded DNA to form a DSB. Thus, CRISPR/Cas9 can achieve gene targeting in any N20-NGG site.

Thus, also encompassed by the invention is a genetically modified non-human animal whose genome comprises a nucleotide sequence encoding a human or humanized MHC I polypeptide and/or β2 microglobulin polypeptide, wherein the polypeptide(s) comprises conservative amino acid substitutions of the amino acid sequence(s) described herein.

One skilled in the art would understand that in addition to the nucleic acid residues encoding a human or humanized MHC I polypeptide and/or β2 microglobulin described herein, due to the degeneracy of the genetic code, other nucleic acids may encode the polypeptide(s) of the invention. Therefore, in addition to a genetically modified non-human animal that comprises in its genome a nucleotide sequence encoding MHC I and/or β2 microglobulin polypeptide(s) with conservative amino acid substitutions, a non-human animal whose genome comprises a nucleotide sequence(s) that differs from that described herein due to the degeneracy of the genetic code is also provided.

In an additional or alternative approach, the present disclosure includes reprogramming, or leveraging the inhibitory and co-stimulatory effects of the MHC-I (Class B) molecules. Specifically, the present disclosure includes a process that "finds and replaces" portions of the donor animal genome corresponding to portions of the HLA gene, e.g., to overexpress HLA-G where possible, retaining and overexpressing portions corresponding to HLA-E, and/or "finding and replacing" portions corresponding to HLA-F. As used herein, the term "find and replace" includes identification of the homologous/analogous/orthologous conserved genetic region and replacement of the section or sections with the corresponding human components through gene editing techniques.

Another aspect includes finding and replacing the beta-2 microglobulin protein which is expressed in HLA-A, -B, -C, -E, -F, and -G. Homologous/analogous/orthologous conserved cytokine mediating complement inhibiting or otherwise immunomodulatory cell markers, or surface proteins, that would enhance the overall immune tolerance at donor-recipient cellular interface.

In an additional or alternative approach, the present invention utilizes immunogenomic reprogramming to reduce or eliminate MHC-I (Class A) components to avoid provocation of natural cellular mediated immune response by the recipient. In another aspect, exon regions in the donor animal (e.g., swine) genome corresponding to exon regions of HLA-A and HLA-B are disrupted, silenced or otherwise nonfunctionally expressed on the donor animal. In another aspect, exon regions in the donor animal (e.g., swine) genome corresponding to exon regions of HLA-A and HLA-B are disrupted, silenced or otherwise nonfunctionally expressed in the genome of the donor animal and exon regions in the donor animal (e.g., swine) genome corresponding to exon regions of HLA-C may be modulated, e.g., reduced. In one aspect, the present disclosure includes silencing, knocking out, or causing the minimal expression of source animal's orthologous HLA-C (as compared to how such would be expressed without such immunogenomic reprogramming).

Further, the beta-2-microglobulin protein which comprises the heterodimer structure of each of the MHC-I proteins is species-specific. Thus, in one embodiment of the present disclosure, it is reprogrammed. In contrast to its counterparts, the genetic instructions encoding for this prevalent, building-block protein is not located in the MHC-gene loci. Thus, in one embodiment of the present disclosure includes a genetic modification in addition to those specific for the respective targets as described herein.

Figure 33:
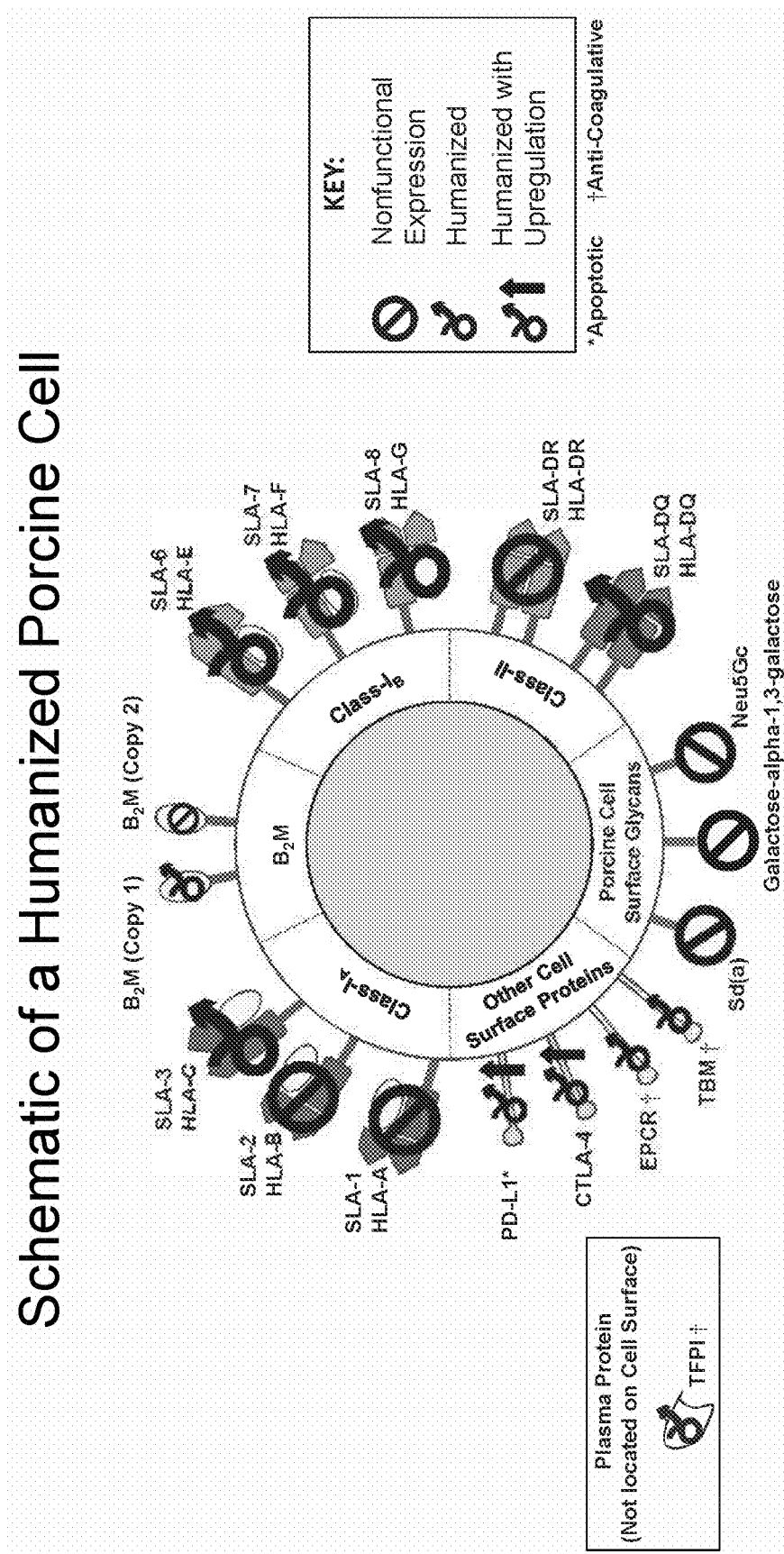
FIG. 33 shows schematic depiction of a humanized porcine cell according to the present disclosure.

FIG. 33 is a schematic depiction of a humanized porcine cell according to the present disclosure. As shown therein, the present disclosure involves reprogramming exons encoding specific polypeptides or glycoproteins, reprogramming and upregulating specific polypeptides or glycoproteins, and reprogramming the nuclear genome to have non-functional expression of specific polypeptides or glycoproteins, all of which are described in detail herein.

Characterization of Humanized Pilot Porcine Cell Lines and In Vitro Evaluation of Resultant Impact to Immunological Genetically modified cells, e.g., cells from a genetically modified animal or cells made ex vivo, can be analyzed and sorted. In some cases, genetically modified cells can be analyzed and sorted by flow cytometry, e.g., fluorescence-activated cell sorting. For example, genetically modified cells expressing a gene of interest can be detected and purified from other cells using flow cytometry based on a label (e.g., a fluorescent label) recognizing the polypeptide encoded by the gene. In this application, the surface expression of SLA-1, SLA-2, SLA-3, SLA-6, SLA-7, SLA-8, SLA-DR and SLA-DQ on unmodified PAM cells is established using labeled antibodies directed to epitopes on those glycoproteins. In the case of specific gene knock outs (e.g. SLA-1, SLA-2 and SLA-DR), analysis by flow cytometry is used to demonstrate the lack of expression of these glycoproteins even after incubation of the cells with interferon gamma. Genes for SLA-3, SLA-6, SLA-7, SLA-8, and SLA-DQ will be modified such that glycoproteins expressed on the cell surface will reflect HLA-C, HLA-E, HLA-F, HLA-G and HLA-DQ glycoproteins, respectively. Hence a different set of antibodies specific for the HLA epitopes will be used to detect expression of the glycoproteins encoded by the modified genes and antibodies directed to the SLA related glycoproteins will not bind to the cell surface of the modified PAM cells.

When knocking out surface sugar glycan epitopes, a cell line that does not express the sugar moieties is obtained, so there is no binding of natural preformed antibodies found in human serum. This is detected using flow cytometry and human serum and a labeled goat anti human IgG or IgM antibody; or specific antibodies directed against sugars; or labeled sugar specific isolectins. The result is no binding of the antibodies (isolectins) to the final cell line. Positive control is the original cell line (WT) without genetic modifications. In addition, a molecular analysis demonstrates changes in those genes.

For knock in cells, the desired sequences are knocked into the cell genome through insertion of genomic material using, e.g., homology-directed repair (HDR). To optimize expression of Class II molecules, the cells are incubated in porcine interferon gamma (IFN-γ) for up to 72 hours which stimulates expression. Expression is then measured by flow cytometry using target specific antibodies. Flow cytometry may include anti-HLA-C, HLA-E, HLA-G, or other HLA antibodies, or pan anti-HLA Class I or Class II antibodies. According to the present disclosure, cell surface HLA expression after knock-in is confirmed.

The immune response of the modified swine cells are evaluated through Mixed Lymphocyte Reaction (MLR) study. Responders cells can be either PBMC, CD4+ T cells, CD8+ T cells or other subpopulations of T cells. PBMC represent all the immune cells that are present in the recipient and the measured response reflects the ability of the responders to mount an immune response to the stimulator cells, for example, a comparison of unmodified PAM cells and modified PAM cells. Alternatively, PAECs or fibroblasts may be used. The measured proliferation consists of both CD4+ and CD8+ T cells which interact with MHC Class II and I, respectively. Using only CD4+ T cells against the unmodified or modified PAM cells measures the response to MHC Class II glycoproteins, DR and DQ. For example, in an MLR where SLA DR is knocked out in the PAM cells, the CD4+ T cell proliferative response will be decreased; or when SLA-DQ gene is modified by using a sequence from a "recipient" [the responder] the proliferative response will be decreased since in this case the responder recognizes the DQ glycoprotein as self, whereas, in the DR knock-out, DR was absent and thus a signal could not be generated.

Responder CD8+ T cells were used to assess an immune response to MHC Class I glycoproteins, SLA-1 and SLA-2. $1 \times 10^5$ purified human CD8+ T cells (A) or human PBMC (B) were stimulated with increasing numbers of irradiated (30 Gy) porcine PBMC from four-fold knockout pig 10261 or a wild-type pig. Proliferation was measured after 5 d+16 h by 3H-thymidine incorporation. Data represent mean cpm±SEM of triplicate cultures obtained with cells from one human blood donor in a single experiment. Similar response patterns were observed using responder cells from a second blood donor and stimulator cells from four-fold knockout pig 10262. Proliferation of human CD8+ T cells decreased after stimulation with four-fold knockout porcine PBMC. (Fischer, et al., Viable pigs after simultaneous inactivation of porcine MHC Class I and three xenoreactive antigen genes GGTA1, CMAH and B4GALNT2, Xenotransplantation, 2019). Modified knock out PAM cells not expressing SLA-1 and SLA-2 will not generate a CD8+ T cell response. This is in contrast with a response using PBMC as the responders. See FIG. 34.

Complement Dependent Cytotoxicity (CDC) assays may be performed to determine if anti-HLA antibodies recognize the cells from the biological product of the present disclosure. Assay plates prepared by adding a specific human plasma containing previously characterized anti-HLA antibodies (or control plasma) can be used. Plasma is serially diluted starting at 1:50 to 1:36450 in HBSS media with calcium and magnesium, incubated with modified or unmodified PAM cells for 30 minutes at 4° C. followed by incubation with freshly reconstituted baby rabbit complement for 1 hour at 37° C. The cells were then stained with Fluorescein Diacetate (FDA) and Propidium Iodide (PI) for 15 minutes and analyzed by flow cytometry. Appropriate compensation controls were run for each assay. Cells were acquired and analyzed on an ACEA NovoCyte Flow Cytometer. PAM cells can also be treated with interferon gamma to increase surface expression of MHC molecules.

Cell populations were determined for the following conditions:
 a. Dead Cells: PI+, FDA−
 b. Damaged Cells: PI+, FDA+
 c. Live Cells: PI−, FDA+

Figure 36A:
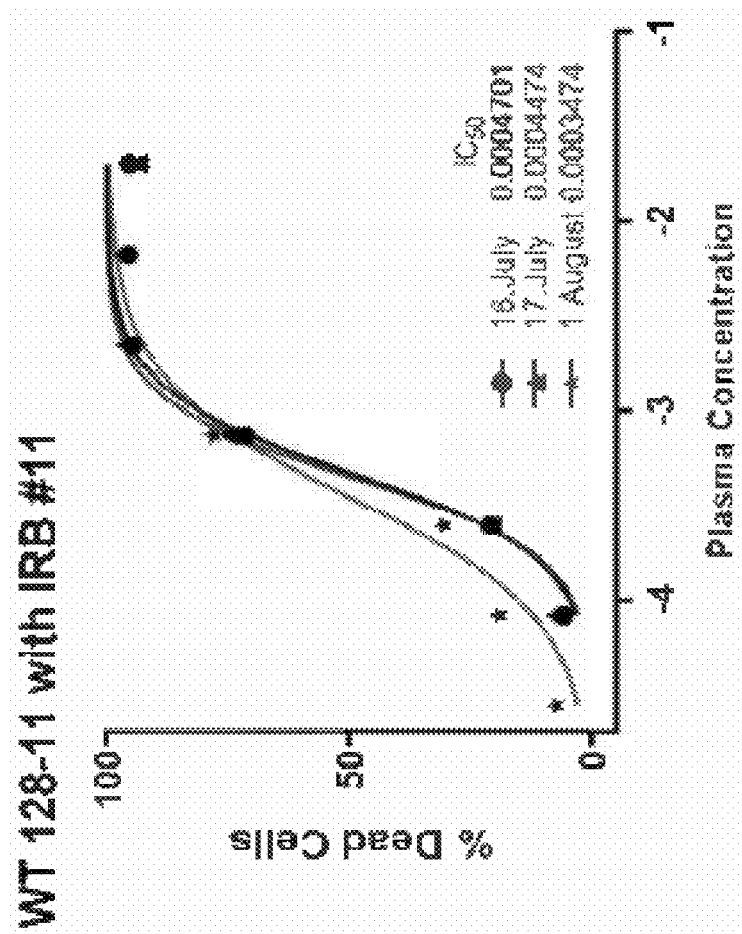
FIGS. 36A-36B show graphs of % cytotoxicity for each concentration (dilution) of plasma, and the results plotted in Prism. Based on the cytotoxicity curve, the required dilution for 50% kill (IC50) was determined.
Figure 36B:
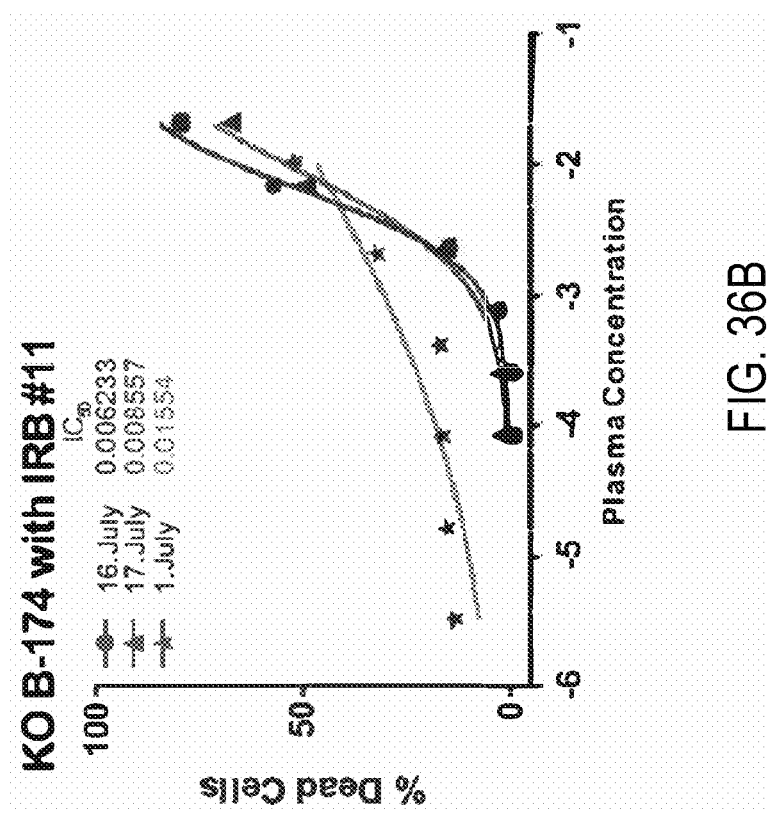

Appropriate calculations were performed to determine % cytotoxicity for each concentration (dilution) of plasma, and the results plotted in Prism. Based on the cytotoxicity curve, the required dilution for 50% kill (IC50) was determined. This is illustrated using human plasma against WT or GalTKO porcine PBMC in FIG. 36A and FIG. 36B, where reduced cytotoxicity was identified against cells lacking a 1,3-galactose on the glycoproteins.

Figure 34:
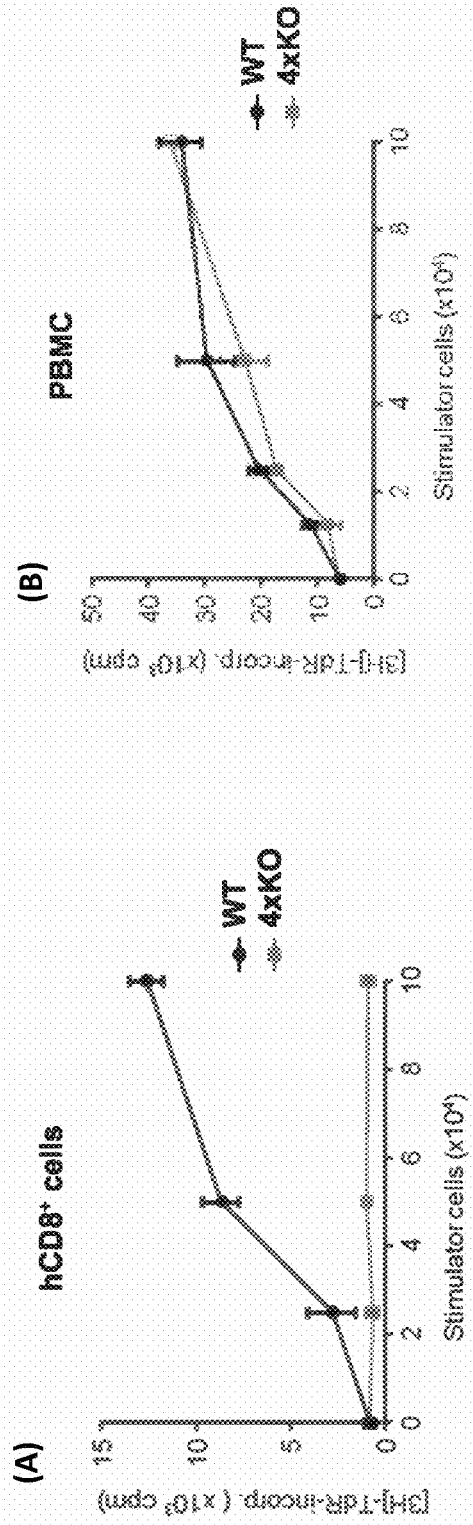
FIG. 34 shows graph of proliferation of human plasma donors run on 3 separate days with WT 128-11 and Gal T-KO B-174 PBMCs
Figure 35:
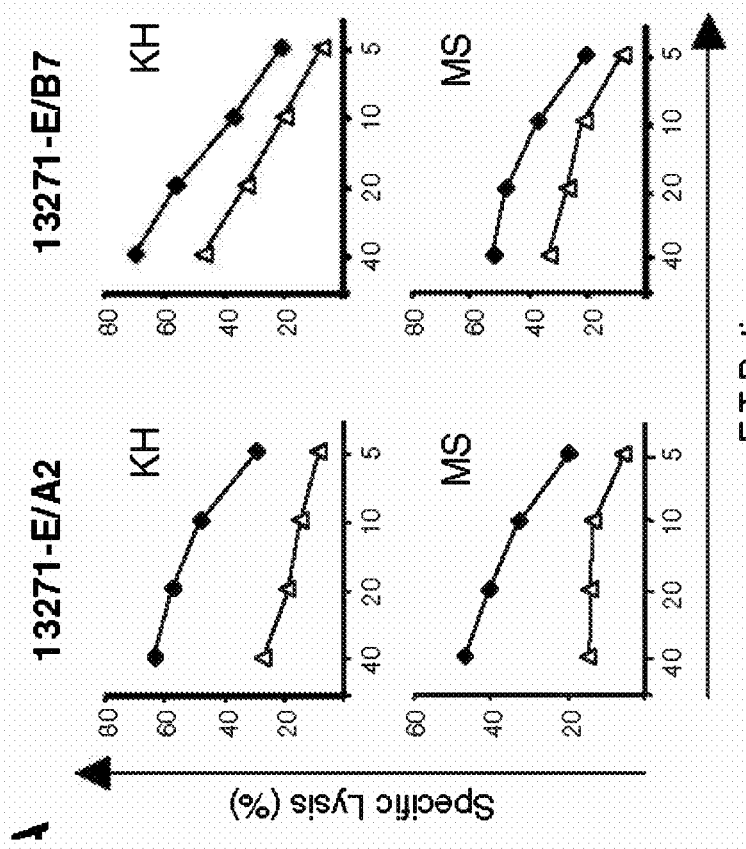
FIG. 35 shows NK cytotoxicity of two donors (upper panel: KH; lower panel: MS) against 13 271 cells transfected with HLA-E/A2 (left column) and HLA-E/B7 (right column) compared to the lysis of untransfected 13 271 cells. Results are depicted as percentage of specific lysis and were obtained at four different E:T ratios. Data are representative of three independent experiments. Open triangles represent HLA-E-transfected 13 271 cells, filled diamonds represent un-transfected 13 271 cells. (Forte, et al., 2005)

NK cytotoxicity against unmodified and modified PAM cells where genes for SLA 3, SLA 6, SLA 7, and SLA 8 are modified such that glycoproteins expressed on the cell surface will reflect HLA C, HLA E, HLA F, and HLA G glycoproteins, respectively. The cytotoxic activity of freshly isolated and IL-2-activated human NK cells was tested in 4-hr 51Cr release assays in serum-free AIM-V medium. Labeled unmodified and modified PAM cells are cultured in triplicate with serial 2-fold dilutions of NK cells four E:T ratios ranging from 40:1 to 5:1. After incubation for 4 hr at 37° C., the assays are stopped, $^{51}$Cr release is analyzed on a gamma counter, and the percentage of specific lysis was calculated. NK cells from a specific genetically matched "recipient" will have reduced killing of modified PAM cells compared to unmodified PAM cells. The protection provided by HLA E in transfected PAEC cells against NK cells is illustrated in FIG. 34.

HLA E expression on porcine lymphoblastoid cells inhibits xenogeneic human NK cytotoxicity. NK cytotoxicity of 2 donors, KH and MS, against 13271-E/A2 or 13271-E/B7 (solid diamonds) transfected with HLA E/A2 or HLA E/B7, respectively or untransfected 13271 cells (open triangle). To optimize expression of Class II molecules, the cells are incubated in porcine interferon gamma (IFN-γ) for 72 hours which stimulates expression. Expression is then measured by flow cytometry using target specific antibodies. Flow cytometry may include anti-HLA-C, HLA-E, HLA-G, or other HLA antibodies, or pan anti-HLA Class I or Class II antibodies. According to the present disclosure, cell surface HLA expression after knock-in is confirmed.

Multiple, Simultaneous Genetic Modifications in a Single Pilot Porcine Cell Line to Achieve Relative Humanized Phenotype and Consequential Reduction of CD8+, CD4+, and Natural Killer Cell Immune Reactivity as a Direct Result of Multiple CRISPRCas9 Genetic Modification Schema In some aspects, genetic modifications in a porcine cell line to insert the modifications listed in table listed in FIG. 33. In some aspects, in addition to the genetic modifications listed in FIG. 33, the three predominant swine cell surface glycans (alpha-Gal, Neu5Gc, and Sda) are not expressed in order to reduce the hyperacute rejection phenomenon and the deleterious activation of antibody-mediated immune pathways, namely activation of the complement cascade. With this step, creation of an allogeneic-"like" cell with respect to non-MHC cell markers is grossly achieved.

Genetically modified cells, e.g., cells from a genetically modified animal or cells made ex vivo, are analyzed and sorted. In some cases, genetically modified cells can be analyzed and sorted by flow cytometry, e.g., fluorescence-activated cell sorting. For example, genetically modified cells expressing a gene of interest can be detected and purified from other cells using flow cytometry based on a label (e.g., a fluorescent label) recognizing the polypeptide encoded by the gene. The gene of interest may be as small as a few hundred pairs of cDNA bases, or as large as about a hundred thousand pairs of bases of a genic locus comprising the exonic-intron encoding sequence and regulation sequences necessary to obtain an expression controlled in space and time. Preferably, the size of the recombined DNA segment is between 25 kb and longer than 500 kb. In any case, recombined DNA segments can be smaller than 25 kb and longer than 500 kb.

It will be further understood that causing the donor swine cells, tissues, and organs to express a known human MHC genotype or the recipient's MHC specifically as described herein, combined with the elimination in the donor swine cells of alpha-1,3-galactosytransferase, Neu5Gc, and β1,4-N-acetylgalactosaminyltransferase (B4GALNT2) (e.g., "single knockout," "double knockout," or "triple knockout"), presents a swine whose cells will have a decreased immunological rejection as compared to a triple knockout swine that lacks the specific SLA/MHC reprogramming of the present disclosure.

The immune response of the modified swine cells are evaluated through Mixed Lymphocyte Reaction (MLR) study. The impact of the modification or non-expression of MHC Ia polypeptides on the immune response are measured through the immune response of CD8+ T Cells. The impact of the modification of MHC Ib polypeptides on the immune response are measured through the immune response of NK Cells. The impact of the modification or non-expression of MHC II polypeptides on the immune response are measured through the immune response of CD4+ T Cells. The MLR study, herein, not only measures the efficacy of the site-directed mutagenic substitution, but also evaluates and identifies the impact of individual modifications, individually and as a whole, as measurements are taken iteratively as additional site-directed mutagenic substitutions are made.

For knock in cells, the desired sequences are knocked into the cell genome through insertion of genomic material using, e.g., homology-directed repair (HDR). To optimize expression of Class II molecules, the cells are incubated in porcine interferon gamma (IFN-γ) for 72 hours which stimulates expression. Expression is then measured by flow cytometry using target specific antibodies. Flow cytometry may include anti-HLA-C, HLA-E, HLA-G, or other HLA antibodies, or pan anti-HLA Class I or Class II antibodies. According to the present disclosure, cell surface HLA expression after knock-in is confirmed.

Complement Dependent Cytotoxicity (CDC) assays may be performed to determine if anti-HLA antibodies recognize the cells from the biological product of the present disclosure. Assay plates prepared by adding a specific human serum containing previously characterized anti-HLA antibodies (or control serum) can be used. IFN-γ treated donor cells are resuspended and added to the assay plates, incubated with a source of complement, e.g., rabbit serum. After at least 1 hour of incubation at room temperature, acridine orange/ethidium bromide solution is added. Percent cytotoxicity is determined by counting dead and live cells visualized on a fluorescent microscope, subtracting spontaneous lysis values obtained in the absence of anti-HLA antibodies, and scoring with a scale.

When knocking out or otherwise silencing surface sugar glycans, a cell line that does not express the sugar moieties is obtained, so there is no binding of natural preformed antibodies found in human serum. This is detected using flow cytometry and human serum and a labeled goat anti human IgG or IgM antibody; or specific antibodies directed against sugars. The result is no binding of the antibodies to the final cell line. Positive control is the original cell line (WT) without genetic modifications. In addition, a molecular analysis demonstrates changes in those genes.

In knocking out or otherwise silencing expression of SLA Class I molecules using CRISPR technologies, the resulting cell line lacks the above sugar moieties as well as SLA Class I expression. Analysis by flow cytometry and molecular gene are performed to demonstrate no surface expression and changes made at the gene level. Cellular reactivity is assessed using a mixed lymphocyte reaction (MLR) with human PBMCs and the irradiated cell line. In comparison to the WT line, there is a reduction in the T cell proliferation, predominantly in the CD8+ T cells.

Reactivity against expression of SLA Class II molecules, DR and DQ is also minimized or eliminated (there is no porcine DP). Analysis is performed at the molecular level, cell surface expression, and in vitro reactivity with human PBMC. There is a significant downward modulation of reactivity against the resulting cell line.

To test for cellular reactivity, all cells are incubated with porcine IFN-γ for 72 hours then human CD4+ T cells are added to porcine cell lines and cultured for 7 days. The readout is a form of activation/proliferation depending on the resources available.

To observe a specific response to DQ, human antigen presenting cells (APCs) are absent from the culture such that the cellular response is not the result of pig antigens presented by the APCs.

Creation of a Humanized, "Bespoke", Designated-Pathogen Free, (Non-Human) Donor of Cells, Tissues, and Organs for Transplantation Others have attempted to develop homozygous transgenic pigs, which is a slow process, requiring as long as three years using traditional methods of homologous recombination in fetal fibroblasts followed by somatic cell nuclear transfer (SCNT), and then breeding of heterozygous transgenic animals to yield a homozygous transgenic pig. The attempts at developing those transgenic pigs for xenotransplantation has been hampered by the lack of pluripotent stem cells, relying instead on the fetal fibroblast as the cell upon which genetic engineering was carried out. For instance, the production of the first live pigs lacking any functional expression of α(1,3) galactosyltransferase (GTKO) was first reported in 2000. In contrast to such prior attempts, the present disclosure provides a faster and fundamentally different process for making non-transgenic reprogrammed swine as disclosed herein. In some aspects, porcine fetal fibroblast cells are reprogrammed using gene editing, e.g., by using CRISPR/Cas for precise reprogramming and transferring a nucleus of the genetically modified porcine fetal fibroblast cell to a porcine enucleated oocyte to generate an embryo; and d) transferring the embryo into a surrogate pig and growing the transferred embryo to the genetically modified pig in the surrogate pig.

Upon confirmation of study results, genetically reprogrammed pigs are bred so that several populations of pigs are bred, each population having one of the desirable human cellular modifications determined from the above assays. The pigs' cellular activity after full growth is studied to determine if the pig expresses the desired traits to avoid rejection of the pigs' cells and tissues after xenotransplantation. Thereafter, further genetically reprogrammed pigs are bred having more than one of the desirable human cellular modifications to obtain pigs expressing cells and tissues that will not be rejected by the human patient's body after xenotransplantation.

The generation of an induced pluripotent stem cell (iPSC) from pigs offers an opportunity beyond the use of primary cells from fetal fibroblasts. The ability of iPSC to proliferate almost indefinitely, which contrasts with the limited number of cell divisions that primary somatic cells can undergo before they senesce, likely means that the iPSC will tolerate the multiple selection steps needed to accommodate directed changes in several genes, especially for gene knock-outs and knock-ins, before nuclear transfer. Another advantage of iPSC over somatic cells is that it has been predicted that cloning efficiency should be inversely correlated with differentiation state and associated epigenetic state. The PAM cells presented in this disclosure are a transformed cell line but the genetic engineering schema can be transferred to porcine iPSC. The specific genetically modified iPSC line would then be used for somatic cell nuclear transfer (SCNT), transferring a nucleus of the genetically modified porcine fetal fibroblast cell to a porcine enucleated oocyte to generate an embryo; and transferring the embryo into a surrogate pig and growing the transferred embryo to the genetically modified pig in the surrogate pig. This has the advantage in that the transferred nucleus contains the specific genome, hence the piglets do not need to go through breeding to obtain a homozygous offspring. The genotype and phenotype of the piglets are identical to the iPSC.

Specific populations of gene modified iPSC can be cryopreserved as a specific cell line and used as required for development of pigs needed for that genetic background. Thawed iPSCs are cultured and nucleus is transferred into enucleated oocytes to generate blastocysts/embryos for implantation into surrogate pig. This creates a viable bank of genetically modified iPSC for generation of pigs required for patient specific tissue, organ, or cell transplantation.

Restated, the former/previous approach to this unmet clinical need has precisely followed the classic medical dogma of "one-size fits all". Instead of following this limited approach, we pragmatically demonstrate the ability to harness present technological advances and fundamental principles to achieve a "patient-specific" solution which dramatically improves clinical outcome measures. The former, we refer as the "downstream" approach—which must contend with addressing all of the natural immune processes in sequence. The latter, our approach, we optimistically term the "upstream" approach—one which represents the culmination of unfilled scientific effort into a coordinated translational effort.

In another aspect, disclosed herein is a method for making a genetically modified animal described in the application, comprising: a) obtaining a cell with reduced expression of one or more of a component of a MHC I-specific enhanceosome, a transporter of a MHC I-binding peptide, and/or C3; b) generating an embryo from the cell; and c) growing the embryo into the genetically modified animal. In some cases, the cell is a zygote.

In certain aspects, HLA/MHC sequence-reprogrammed swine are bred for at least one generation, or at least two generations, before their use as a source for live tissues, organs and/or cells used in xenotransplantation. In certain aspects, the CRISPR/Cas9 components can also be utilized to inactivate genes responsible for PERV activity, e.g., the pol gene, thereby simultaneously completely eliminating PERV from the swine donors.

In certain aspects, the present disclosure includes embryogenesis and live birth of SLA-free and HLA-expressing biologically reprogrammed swine. In certain aspects, the present disclosure includes breeding SLA-free and HLA-expressing biologically reprogrammed swine to create SLA-free and HLA-expressing progeny. In certain aspects, the CRISPR/Cas9 components are injected into swine zygotes by intracytoplasmic microinjection of porcine zygotes. In certain aspects, the CRISPR/Cas9 components are injected into swine prior to selective breeding of the CRISPR/Cas9 genetically modified swine. In certain aspects, the CRISPR/Cas9 components are injected into donor swine prior to harvesting cells, tissues, zygotes, and/or organs from the swine. In certain aspects, the CRISPR/Cas9 components include all necessary components for controlled gene editing including self-inactivation utilizing governing gRNA molecules as described in U.S. Pat. No. 9,834,791 (Zhang), which is incorporated herein by reference in its entirety.

Upon confirmation of study results, genetically reprogrammed pigs are bred so that several populations of pigs are bred, each population having one of the desirable human cellular modifications determined from the above assays. The pigs' cellular activity after full growth is studied to determine if the pig expresses the desired traits to avoid rejection of the pigs' cells and tissues after xenotransplantation. Thereafter, further genetically reprogrammed pigs are bred having more than one of the desirable human cellular modifications to obtain pigs expressing cells and tissues that will not be rejected by the human patient's body after xenotransplantation.

Any of the above protocols or similar variants thereof can be described in various documentation associated with a medical product. This documentation can include, without limitation, protocols, statistical analysis plans, investigator brochures, clinical guidelines, medication guides, risk evaluation and mediation programs, prescribing information and other documentation that may be associated with a pharmaceutical product. It is specifically contemplated that such documentation may be physically packaged with cells, tissues, reagents, devices, and/or genetic material as a kit, as may be beneficial or as set forth by regulatory authorities.

In another aspect, disclosed herein is a method for making a genetically modified animal described in the application, comprising: a) obtaining a cell with reduced expression of one or more of a component of a MHC I-specific enhanceosome, a transporter of a MHC I-binding peptide, and/or C3; b) generating an embryo from the cell; and c) growing the embryo into the genetically modified animal. In some cases, the cell is a zygote.

Muscle and skin tissue samples taken from each of these pigs were dissected and cultured to grow out the fibroblast cells. The cells were then harvested and used for somatic cell nuclear transfer (SCNT) to produce clones. Multiple fetuses (up to 8) were harvested on day 30. Fetuses were separately dissected and plated on 150 mm dishes to grow out the fetal fibroblast cells. Throughout culture, fetus cell lines were kept separate and labeled with the fetus number on each tube or culture vessel. When confluent, cells were harvested and frozen at about 1 million cells/mL in FBS with 10% DMSO for liquid nitrogen cryo-storage.

Added from different example: In certain aspects, the CRISPR/Cas9 components are injected into swine oocytes, ova, zygotes, or blastocytes prior to transfer into foster mothers.

Creation of, Procurement of Personalized, Tolerogenic Cells, Tissues, and Organs Donor of Cells, Tissues, and Organs for Transplantation from Humanized, "Bespoke", Designated-Pathogen Free, (Non-Human) Donor Source Animal Facility ("SAF")

Figure 37:
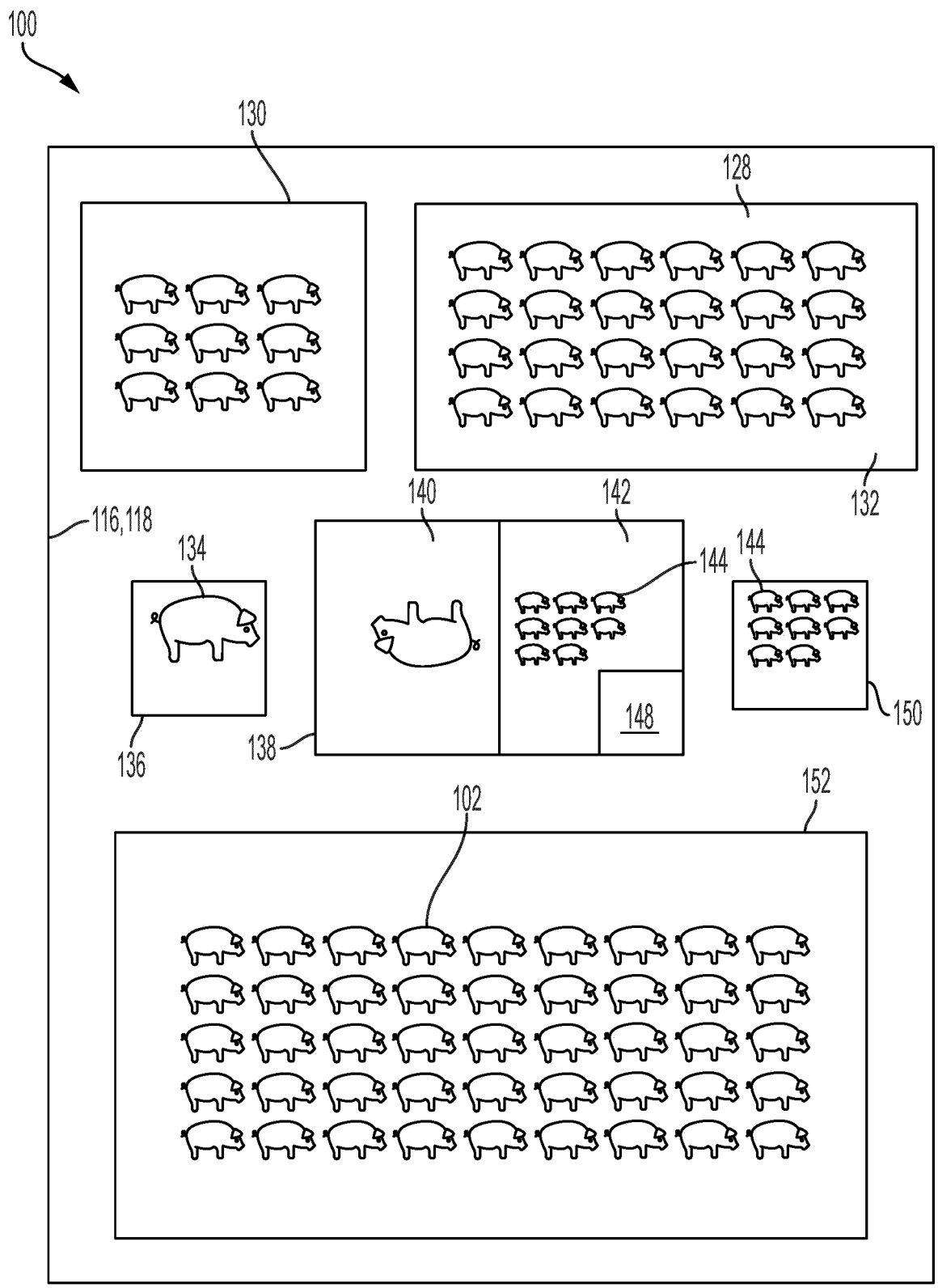
FIG. 37 illustrates a source animal facility and corresponding designated pathogen free facilities, animals, and herds in accordance with the present invention.

Referring to FIG. 37, a barrier source animal location, including, but not limited to, a Source Animal Facility ("SAF") 100, that can be used for the housing, propagation, maintenance, care and utilization of a closed colony swine, including a closed colony that is designated pathogen free ("DPF") ("DPF Closed Colony") 102, is shown. As contained herein, the SAF has positive pressure, biocontainment characteristics is operated under specific isolation-barrier conditions.

As described herein, the DPF Closed Colony 102 is comprised of source animals maintained and propagated for harvesting various biological products for use in human xenotransplantation and other therapies, wherein such products have reduced bioburden and demonstrate reduced immunogenicity resulting from xenotransplantation and other therapeutic procedures. In some aspects, xenotransplantation products of the present disclosure are less immunogenic than a xenotransplantation product made from conventional Gal-T knockout swine, from conventional triple knockout swine, from transgenic swine, from wild-type animals, and/or allograft. For example, as shown in Examples 1 and 2, biological products made according to the present disclosure provided unexpectedly high clinical benefit when using a single knockout pig as the donor animal in that, despite the presence of Neu5Gc and porcine B4GALNT2, the biological product made according to the present disclosure had less immunogenicity than allograft, vascularized, and was resistant to rejection for the entire duration of the study period.

As further described herein, the SAF 100 and each of its accompanying areas (e.g., rooms, suites or other areas) can be utilized to house and maintain source animals from which biological products are harvested and/or processed. The SAF 100 and its areas are designed to minimize and eliminate the potential for contamination of the harvested and/or processed biological products and cross-contamination between such products.

Within the SAF 100, in some aspects, utilized animal areas are ventilated. For example, animal areas are ventilated with high efficiency particulate air (HEPA)-filtered fresh air from the roof of the building, for example, having at least 10-15 air changes per hour. Additionally, one or more laminar flow hoods (e.g., Class II Type A2 Laminar Airflow Biosafety Cabinets) are utilized in the SAF rooms, including in a xenotransplantation drug processing suite to providing additional ventilation to minimize or eliminate cross contamination.

In some aspects, utilized areas are also temperature controlled and monitored. For example, the areas are heated and cooled to maintain temperature within the range specified by, for example, the Guide for the Care and Use of Laboratory Animals. Utilized animal holding rooms are also alarmed and centrally monitored for high or low temperatures, and staff are notified immediately if temperatures are beyond required temperature.

In some aspects, the SAF 100 has multiple levels of containment for the source animals. For example, source animals are contained in a primary level of containment consisting of pens and cages which are secured by stainless steel latches. With respect to secondary level of containment, functionally designated areas (e.g., rooms, suites or other areas) can have latched inner doors, and an ante-room with card-controlled access to a hallway. A tertiary level of containment can include outside perimeter fencing.

The entire SAF is located within a single building. Primary entrance is through a single door via programmable identification (ID) card. All other external doors are alarmed, remain locked, and are for emergency use only.

Security is also a consideration to ensure security of the SAF 100 in general, and to control individuals entering the SAF 100 to minimize the risk of outside contaminants entering the SAF 100 and reaching the source animals. Therefore, in one aspect, the primary entrance to the SAF 100 is through a single door 116 via programmable identification (ID) card 118. All other external doors 120 are alarmed, remain locked, and are for emergency use only.

It will be understood that the SAF 100 and its features as disclosed herein are set out as examples, and it will be further understood that other facilities with various features can also be utilized to perform the methods and produce the products disclosed herein.

In some aspects, the SAF 100 animal program is licensed and/or accredited and overseen, evaluated and operated by a team of highly experienced, professional staff. For example, the program is registered and/or accredited with the USDA Animal and Plant Health Inspection Service (as a licensed animal research facility), National Institute of Health (NIH) Office of Laboratory Animal Welfare (OLAW) (confirming compliance with Public Health and Safety (PHS) regulations, Association for Assessment and Accreditation of Laboratory Animal Care (AAALAC) (with veterinary care of the source animals housed at the SAF under the direction of an attending veterinarian), and other federal, state and local regulatory authorities.

In some aspects, to ensure the welfare of the source animals, SAF personnel, and caretakers of source animals adhere to procedures for animal husbandry, tissue harvesting, and termination of animals that are approved by an appropriate Institutional Animal Care and Use Committee, in accordance with the Animal Welfare Act (7 U.S.C. 2131, et seq.), accredited by the AAALAC, and in compliance of the standards as set forth in the Guide for the Care and Use of Laboratory Animals.

In some aspects, caretakers have extensive training and experience in handling and caring for the source animals being managed in accordance with the present invention. For example, each caretaker undergoes a documented training program covering the standard operating procedures governing handling and care of these source animals, and be skilled in making daily health assessments and insuring prompt care is directed to any animal in need. In addition, the caretakers can be trained in scrubbing and gowning procedures prior to entry into the isolation areas (e.g., rooms, suites or other areas) as described herein, and under a medical surveillance program to ensure staff health and the health of the source animals.

To minimize and eliminate contamination risk to the SAF, any personnel or visitors entering the SAF wear personnel protective equipment or change into facility dedicated clothing and footwear before entry into any containment areas. Visitors who wish to enter animal areas must not have had any contact with live swine for at least 24 hours preceding the visit or must shower at the facility prior to entry.

It will be understood that the approaches and procedures set forth herein are examples as to how to ensure contamination does not reach the source animals within SAF 100. It will be further understood that a multitude of approaches can also be utilized to achieve a designated pathogen free environment for source animals.

Source Animals

In some aspects, as described herein, swine can be utilized as source animals. As used herein, unless otherwise specified, the terms "swine," "pig" and "porcine" are generic terms referring to the same type of animal without regard to gender, size, or breed. It will be understood that any number of source animals could be utilized in accordance with the present invention, including, but not limited to, pigs, non-human primates, monkeys, sheep, goats, mice, cattle, deer, horses, dogs, cats, rats, mules, and any other mammals. Source animals could also include any other animals including, but not limited to, birds, fish, reptiles, and amphibians.

It will be further understood that any animal serving as a source animal hereunder, including swine, regardless of how such swine may be configured, engineered, or otherwise altered and/or maintained, may be created, bred, propagated and/or maintained in accordance with the present disclosure to create and maintain animals and resulting biological products to be used in or in preparation or pursuit of clinical xenotransplantation.

For example, the present disclosure includes non-human animals, e.g., swine, having certain combinations of specific genetic characteristics, breeding characteristics and pathogen-free profile. Such animals may include, as described above and herein, immunogenomic reprogrammed swine having a biologically reprogrammed genome such that it does not express one or more extracellular surface glycan epitopes, e.g., genes encoding alpha-1,3 galactosyltransferase, cytidine monophosphate-N-acetylneuraminic acid hydroxylase (CMAH), and β1,4-N-acetylgalactosaminyltransferase are disrupted such that surface glycan epitopes encoded by said genes are not expressed, as well as other modifications to the swine's SLA to express MHC-I or MHC-II, and regulation of PD-1 and CTLA4, as described above and herein. Resulting from the process described herein, the swine is free of at least the following zoonotic pathogens:

(i) *Ascaris* species, *Cryptosporidium* species, *Echinococcus, Strongyloids sterocolis*, and *Toxoplasma gondii* in fecal matter;

(ii) *Leptospira* species, *Mycoplasma hyopneumoniae*, porcine reproductive and respiratory syndrome virus (PRRSV), pseudorabies, transmissible gastroenteritis virus (TGE)/Procine Respiratory Coronavirus, *Toxoplasma Gondii* in antibody titers;

(iii) Porcine Influenza;

(iv) the following bacterial pathogens as determined by bacterial culture: *Bordetella bronchisceptica*, Coagulase-positive staphylococci, Coagulase-negative staphylococci, Livestock-associated methicillin resistant *Staphylococcus aureus* (LA MRSA), *Microphyton* and *Trichophyton* spp.;

(v) Porcine cytomegalovirus; and (vi) *Brucella suis*;

is raised and maintained according to a bioburden-reducing procedure, the procedure comprising maintaining the swine in an isolated closed herd, wherein all other animals in the isolated closed herd are confirmed to be free of said zoonotic pathogens; wherein the swine is isolated from contact with any non-human animals and animal housing facilities outside of the isolated closed herd.

As indicated previously, in some aspects, the swine source animals may have a combination of one or more genetic modifications including "knockout" and/or "knock-in" swine having one or more characteristics of swine disclosed in U.S. Pat. No. 7,795,493 ("Phelps"), the entire disclosure of which is incorporated herein by reference. Such swine lack active (and/or have disrupted) α-(1,3) galactosyl epitopes responsible for hyperacute rejection in humans upon transplantation. Multiple methods of production of knockout/knock-in swine are disclosed in Phelps including: the inactivation of one or both alleles of the alpha-1,3-GT gene by one or more point mutations (for example by a T-to-G point mutation at the second base of exon 9) and/or genetic targeting events as disclosed at col. 9, line 6 to col. 10, line 13; col. 21, line 53 to col. 28, line 47; and col. 31, line 48 to col. 38, line 22 of Phelps, incorporated herein by reference. The creation of such swine through the described methods, and/or the utilization of such swine and progeny following creation, can be employed in the practice of the present invention, including, but not limited to, utilizing organs, tissue and/or cells derived from such swine.

Similarly, in other aspects, the swine source animals include "knockout" and "knock-in" swine having one or more characteristics of swine disclosed in U.S. Pat. No. 7,547,816 ("Day"), the entire disclosure of which is incorporated herein by reference. Such swine also lack active (and/or have disrupted) α-(1,3) galactosyl epitopes responsible for hyper-acute rejection in humans upon transplantation. Multiple methods of production of knockout/knock-in swine are disclosed in Day including: enucleating an oocyte, fusing the oocyte with a porcine cell having a non-functional alpha-1,3-GT gene, followed by implantation into a surrogate mother, as described more fully at col. 4, line 61 to col. 18, line 55 of Day, incorporated herein by reference. The creation of such swine through the described methods, and/or the utilization of such swine and progeny following creation, can be employed in the practice of the present invention, including, but not limited to, utilizing organs, tissue and/or cells derived from such swine.

Similarly, in other aspects, the swine source animals include GGTA Null ("knockouts" and "knock-ins") swine having one or more characteristics of swine disclosed in U.S. Pat. No. 7,547,522 ("Hawley"), the entire disclosure of which is incorporated herein by reference. Such swine also lack active (and/or have disrupted) α-(1,3) galactosyl epitopes responsible for hyper-acute rejection in humans upon transplantation. As disclosed in Hawley, production of knockout/knock-in swine includes utilizing homologous recombination techniques, and enucleating oocytes followed by fusion with a cell having a non-functional alpha-1,3-GT gene and implantation into a surrogate mother (as disclosed more fully at col. 6, line 1 to col. 14, line 31). The creation of such swine through the described methods, and/or the utilization of such swine and progeny following creation, can be employed in the practice of the present invention, including, but not limited to, utilizing organs, tissue and/or cells derived from such swine.

In yet other aspects, the swine source animals include swine and swine that lack active (and/or have disrupted) α-(1,3) galactosyl epitopes having one or more characteristics of swine as described in U.S. Pat. No. 9,883,939 ("Yamada"), the entire disclosure of which is incorporated by reference herein. In certain aspects, the swine source animals for use or modification in accordance with the present disclosure include the swine having one or more characteristics of swine described in U.S. 2018/0184630 (Tector, III), the disclosure of which is incorporated by reference herein in its entirety. The creation of such swine through the described methods, and/or the utilization of such swine and progeny following creation, can be employed in the practice of the present invention, including, but not limited to, utilizing organs, tissue and/or cells derived from such swine.

In yet other aspects, swine source animals include the swine having one or more characteristics of swine disclosed in U.S. Pat. No. 8,106,251 (Ayares), U.S. Pat. No. 6,469,229 (Sachs), U.S. Pat. No. 7,141,716 (Sachs), each of the disclosures of which are incorporated by reference herein. The creation of such swine through the described methods, and/or the utilization of such swine and progeny following creation, can be employed in the practice of the present invention, including, but not limited to, utilizing organs, tissue and/or cells derived from such swine.

In some aspects, the swine can originate from one or more highly inbred herds of pigs (whether genetically modified or not (i.e., wild-type)) with a co-efficient of inbreeding of 0.50 or greater. A higher coefficient of inbreeding indicates the products derived from the source animals may have more consistent biological properties for use in pig-to-human xenotransplantation (e.g., a coefficient of inbreeding of 0.80 or greater in one aspect). Coefficients of inbreeding for animals are disclosed in Mezrich et al., "Histocompatible Miniature Swine: An Inbred Large-Animal Model," *Transplantation,* 75(6):904-907 (2003). An example of a highly inbred herd of swine includes miniature swine descendant from the miniature swine disclosed in Sachs, et al., "Transplantation in Miniature Swine. I. Fixation of the Major Histocompatibility Complex," *Transplantation* 22:559 (1976), which is a highly inbred line possessing reasonable size matches particularly for organs eventually utilized for clinical transplantation. The creation of such swine through the described methods, and/or the utilization of such swine and progeny following creation, can be employed in the practice of the present invention, including, but not limited to, utilizing organs, tissue and/or cells derived from such swine.

Source animals can also include animals swine that lack active (and/or have disrupted) alpha-1,3-galactosyltransferase, Neu5Gc, and β1,4-N-acetylgalactosaminyltransferase as described in U.S. Patent Publication No. US2017/0311579 (Tector), the entire disclosure of which is incorporated herein by reference. The creation of such swine through the described methods, and/or the utilization of such swine and progeny following creation, can be employed in the practice of the present invention, including, but not limited to, utilizing organs, tissue and/or cells derived from such swine.

It is therefore understood that multiple source animals, with an array of biological properties including, but not limited to, genome modification and/or other genetically engineered properties, can be utilized to reduce immunogenicity and/or immunological rejection (e.g., acute, hyper-acute, and chronic rejections) in humans resulting from xenotransplantation. In certain aspects, the present disclosure can be used to reduce or avoid thrombotic microangiopathy by transplanting the biological product of the present disclosure into a human patient. In certain aspects, the present disclosure can be used to reduce or avoid glomerulopathy by transplanting the biological product of the present disclosure into a human patient. It will be further understood that the listing of source animals set forth herein is not limiting, and the present invention encompasses any other type of source animal with one or more modifications (genetic or otherwise) that serve(s) to reduce immunogenicity and/or immunological rejection, singularly or in combination.

In some embodiments, preterm swine fetuses and neonatal piglets are derived as offspring from DPF Closed Colony, α-1,3-galactosyltransferase [Gal-T] knockout pigs, as shown and described herein in accordance with the present invention.

Such preterm swine fetuses and neonatal piglets are utilized as a source for cells, tissues and organs for xenotransplantation therapies, including, but not limited to, in regenerative or direct transplantation therapies. It will be understood that such cells, tissues and organs can be utilized as fresh or following cryopreservation in accordance with the present invention (e.g., cryopreservation in the range of −80° C.).

In one aspect, mesenchymal cells, pluripotent cells, stem cells and/or other cells that have not differentiated are harvested from such preterm swine fetuses and utilized for regenerative therapies and other therapies as described herein, whereas such undifferentiated cells can be found in high proportion in swine fetuses as well as in neonatal piglets. Since these cells are derived from fetuses earlier along the gestation period, they are less differentiated and more pliable which offers greater potential for regenerative therapies. Furthermore, since these cells may be derived from DPF Closed Colony, α-1,3-galactosyltransferase [Gal-T] knockout pigs, as shown and described herein, they do not possess aggravating immunogenic, pathogenic and/or other aggravating factors causing rejection by the human immune system, and the cells will persist and differentiate inside a human recipient offering regain of function of growth of model tissue using these genetic and cellular building blocks.

By way of example, such cells may be utilized to generate an array of organs and/or tissues, through regenerative cell-therapy methods known in the art (e.g., through utilization of biological scaffolds), for xenotransplantation including, but not limited to, skin, kidneys, liver, brain, adrenal glands, anus, bladder, blood, blood vessels, bones, brain, brain, cartilage, ears, esophagus, eye, glands, gums, hair, heart, hypothalamus, intestines, large intestine, ligaments, lips, lungs, lymph, lymph nodes and lymph vessels, mammary glands, mouth, nails, nose, ovaries, oviducts, pancreas, penis, pharynx, pituitary, pylorus, rectum, salivary glands, seminal vesicles, skeletal muscles, skin, small intestine, smooth muscles, spinal cord, spleen, stomach, suprarenal capsule, teeth, tendons, testes, thymus gland, thyroid gland, tongue, tonsils, trachea, ureters, urethra, uterus, uterus, and vagina, areolar, blood, adenoid, bone, brown adipose, cancellous, cartaginous, cartilage, cavernous, chondroid, chromaffin, connective tissue, dartoic, elastic, epithelial, epithelium, fatty, fibrohyaline, fibrous, Gamgee, Gelatinous, Granulation, gut-associated lymphoid, Haller's vascular, hard hemopoietic, indifferent, interstitial, investing, islet, lymphatic, lymphoid, mesenchymal, mesonephric, mucous connective, multilocular adipose, muscle, myeloid, nasion soft, nephrogenic, nerve, nodal, osseous, osteogenic, osteoid, periapical, reticular, retiform, rubber, skeletal muscle, smooth muscle, and subcutaneous tissue.

Accordingly, preterm swine fetuses and neonatal piglets may be utilized as a source of tissue, cells and organs in accordance with the present invention based on their characteristics as compared to adult swine.

Closed Colonies

General Closed Colony

Referring now to FIG. 37, in one aspect, animals are secured from the outside to consider as candidates to add to the General Closed Colony 128 that is housed within the SAF 100 to help propagate the DPF Closed Colony 102 also housed within the SAF 100 in a separate isolation area 152. Transportation of the animals secured from the outside to the SAF is controlled to mitigate exposure to potential infectious agents. Such mitigation techniques include, but are not limited to, using a sterilized HEPA filtered cage during transport using a van cleaned with chlorhexidine and containing no other animals.

Candidate animals are initially quarantined to check health status and suitability for intake into the General Closed Colony 128. For example, in some aspects, animals coming from the outside are first housed in a quarantine intake area 130 within the SAF and accompanied by a complete health record (including, but not limited to, date of birth, vaccinations, infections, and antibiotic history), pedigree, and results of genetic tests. These animals reside in the quarantine intake area 130 for at least seven (7) days as the accompanying records are evaluated and other health screening measures are taken, including screening for some infectious agents.

In some aspects, animals with poor health, questionable medical status, or are not able to be treated for such medical issues, will not be accepted into the General Closed Colony 128 and/or will otherwise be culled from the quarantine area 130. Examples of acceptance criteria include, but are not limited to: (a) source animals are not born with any congenital defect that was unanticipated from the herd and that could have impacted the quality of health of the animal; (b) source animals have received all vaccinations according to age and the vaccinations were killed agents; (c) any infections that occurred in the source animal's lifetime have been reviewed as well as the clinical intervention, and it was determined that the infection and any treatment (if applicable) did not impact the quality of the health of the animal; (d) results of the surveillance testing has been reviewed and it has been verified that the source animal has been tested within the last 3 months (with all source animals tested at sacrifice and all tests must be negative); (e) if the animal was injured in any way which required medical attention, a review has been conducted and it has been confirmed that the impact of the injury and the medical intervention (if applicable) had no impact on the health of the animal; and/or (f) PERV tests have been performed and results recorded.

In some aspects, animals that pass this screening process and timetable are moved out of the quarantine intake area 130 and into a general holding area 132 within the SAF 100 to join or create an existing or newly formed General Closed Colony 128. It will be understood that the general holding area 132 is kept under closed colony conditions substantially similar to the conditions applied to the DPF Closed Colony 102 in the DPF Isolation Area 152.

It will be further understood that, excluding their offspring, candidate animals secured from the outside will never become members of the DPF Closed Colony. Piglets from the General Closed Colony 128 animals will be utilized to create and/or propagate the DPF Closed Colony as further described herein.

DPF Closed Colony

Pregnant Sows and DPF Piglets

In one aspect, pregnant sows 134 (or gilts) are obtained from the outside or from the General Closed Colony 128 to produce piglets to create and/or add to the DPF Closed Colony 102 herd. For example, in one aspect, sows 134 are placed in a sow quarantine area 136 within the SAF until the time to give birth, in this aspect via Cesarean section in order to avoid exposing the piglet to potential pathogens, including Porcine Cytomegalovirus (pCMV). Contraction of pCMV in piglets can occur when the piglets travel through the vagina of the sow during natural birth. The piglets, by virtue of their birthing through Cesarean section as described herein, prevents such contraction and the piglets produced through the methods described herein are pCMV-free.

Prior to the Cesarean section procedure, for example the morning of the procedure, an operating room 138 within the SAF 100 prepared according to standard operating room protocols in a sterile environment with 2 sides: Side A 140 for the Cesarean section of the sow, and Side B 142 to receive the piglets 144 that are candidates to either found or add to the DPF Closed Colony.

The sow 134 is brought into the operating room 138 for captive bolt euthanasia. Immediately following this, the sow 134 is placed in the left lateral decubitus position and the abdomen and torso are prepped widely with chlorhexidine and draped in a sterile fashion. A flank incision is expeditiously made and the abdominal muscles are split in order to gain access into the peritoneum. The uterus is exteriorized, incised and the piglets 144 are removed after doubly clamping and dividing the umbilical cord. Immediate execution of the surgical procedures following captive bolt euthanasia is critical to the survival of the piglets 144.

Infection controls for the piglets 144 are implemented at birth. The piglets 144 are placed in a warmed 1% chlorhexidine (or other sterilization agent, such as betadine) in sterile saline bath solution and then passed over to piglet handlers to a resuscitation area 148 for resuscitation, rewarming and gavage feeding of the first dose of colostrum. The sow's 134 carcass is closed by staff with suture and disposed of following appropriate procedures.

The piglets 144 are subsequently quarantined in a separate sterile piglet quarantine room 150 then transferred to a designated pathogen free isolation area ("DPF Isolation Area") 152 to either create or join the DPF Closed Colony 102. It will be understood that the DPF Isolation Area 152 can be of any size suitable to manage and maintain the DPF Closed Colony to the extent needed for breeding, rearing, birthing, harvesting, and overall management as described herein.

In one aspect, the DPF Isolation Area 152 that supports the DPF Closed Colony is a restricted access, positive-pressure barrier isolation suite, approximately 500 ft$^2$, with an animal husbandry capacity to support at least 9 animals (up to 20 kg each), inside the larger SAF 100. It will be understood that the DPF Isolation Area 152 can be significantly larger than this, and can include multiple areas (including, but not limited to, multiple rooms and suites), depending on the need of the number of source animals and demand for products, in accordance with the products and methods as described herein.

In some aspects, tracking of piglets is performed and piglets are handled under designated pathogen free conditions in the DPF Isolation Area 152. For example, handling of piglets is performed wearing personal protective equipment ("PPE") in the DPF Isolation Area 152, including face mask, gloves, shoe covers, and hair bonnet. The animals are handled by clean personnel, personnel who have not entered any animal room or facility where other swine are housed. For tracking, piglets are ear notched 3 days after birth and ear tagged with hand-labeled plastic ear tags at weaning (usually 3-5 weeks).

It will be understood that some piglets are raised in the DPF Closed Colony 102 in the DPF Isolation Area 152 as a source for xenotransplantation products, and some piglets in the DPF Closed Colony 102 are allowed to mature and be used to propagate the General Closed Colony 128. In the event of propagation of the General Closed Colony 128, the matured animal is removed from the DPF Isolation Area 152 and added to the General Closed Colony 128 for breeding. Since the DPF Isolation Area 152 is controlled to be DPF, once these or any other animals leave DPF Isolation Area 152, those animals never return to the DPF Isolation Area 152.

Precautions are taken to prevent the exposure of any animals within the DPF Closed Colony 102 to contamination (for example, blood, blood products or tissues obtained from animals outside the DPF Closed Colony 102). If any animals within the DPF Closed Colony 102 are inadvertently exposed to blood, blood products, or tissues obtained from animals outside the DPF Closed Colony 102, those animals are removed from the DPF Closed Colony 102 and will never return to the DPF Closed Colony 102. Aseptic techniques and sterile equipment for all parenteral interventions are used, and routine procedures such as vaccinations, treatment with drugs or biologics, phlebotomy, and biopsies are performed. The DPF Isolation Area 152 is restricted by card access only to specially authorized and trained staff.

In another aspect of the invention, in some aspects, newborn piglets are handled and hand-reared by trained and gowned staff in the DPF Isolation Area 152 to ensure their health and that they are maintained as designated pathogen free.

Propagation

The DPF Closed Colony 102 can be propagated in multiple ways. For example, as described herein, sows 134 may be taken from the outside or General Closed Colony 128, quarantined, and have their piglets 144 delivered via Cesarean section, with the piglets resuscitated, sterilized, quarantined, and placed into the DPF Isolation Area 152. Newborn piglets may be maintained at 26-30° C. or 80-85° F. In some aspects, heat lamps are used to keep animals warm. Newborn piglets are initially housed in sterilized medium crates in the SAF with sterile towels/drapes on the bottom.

The DPF Closed Colony 102 may also be propagated in other ways. For example, in one aspect, the DPF Closed Colony 102 is propagated through natural intercourse amongst the animals in the DPF Closed Colony 102 occurring entirely within the DPF Isolation Area 152. It will be understood that pregnancies may also occur in the DPF Closed Colony 102 within the DPF Isolation Area 152 as a result of artificial insemination or other breeding techniques that do not involve natural intercourse.

In such aspects, pregnant sows 154 (or gilts) in the DPF Closed Colony 102 within the DPF Isolation Area 152 carry the entire pregnancy and piglets are delivered through live vaginal birth and Caesarian section is not necessary. Importantly, the piglets resulting from natural intercourse and live vaginal birth within the DPF Isolation Area 152 are designated pathogen free, including no infection by pCMV.

Following the live vaginal birth, piglets are immediately taken away from the sow to prevent the sows from harming the piglets. The piglets are then hand-reared from birth by humans within the DPF Isolation Area 152 in the methods as described herein.

In the case of mating in the DPF Closed Colony 102 or General Closed Colony 128, the breeding of swine disclosed herein is typically homozygous to homozygous breeding. Females are given hormones two weeks before gestation then throughout pregnancy. Furthermore, as with the DPF Closed Colony 102, the General Closed Colony 128 may also be propagated through natural intercourse amongst the animals in the General Closed Colony 128, and may also occur as a result of artificial insemination or other assisted reproductive technologies (ARTs) that do not involve natural intercourse.

Various techniques have been developed and refined to obtain a large number of offspring from genetically superior animals or obtain offspring from infertile (or subfertile)

animals. These techniques include: artificial insemination, cryopreservation (freezing) of gametes or embryos, induction of multiple ovulations, embryo transfer, in vitro fertilization, sex determination of sperm or embryos, nuclear transfer, cloning, etc.

Artificial insemination (AI) has been used to obtain offspring from genetically superior males for more than 200 years. Improvements in methods to cryopreserve (freeze) and store semen have made AI accessible to more livestock producers. In the same manner as cryopreservation of semen, embryo freezing allowed for the global commercialization of animals with high genetic qualities.

Multiple ovulation and embryo transfer: Development of embryo transfer technology allows producers to obtain multiple progeny from genetically superior females. Depending on the species, fertilized embryos can be recovered from females (also called embryo donors) of superior genetic merit by surgical or nonsurgical techniques. The genetically superior embryos are then transferred to females (also called embryo recipients) of lesser genetic merit. In cattle and horses, efficient techniques recover fertilized embryos without surgery, but only one or sometimes two embryos are produced during each normal reproductive cycle. In swine and sheep, embryos must be recovered by surgical techniques. To increase the number of embryos that can be recovered from genetically superior females, the embryo donor is treated with a hormone regimen to induce multiple ovulations, or superovulation.

In vitro Fertilization: As an alternative to collecting embryos from donor animals, methods have been developed recently to produce embryos in vitro (in the laboratory). The methods are also called in vitro embryo production. Immature oocytes (female eggs) can be obtained from ovaries of infertile or aged females, or from regular embryo donors (described above). Ovum (egg) pick up is a nonsurgical technique that uses ultrasound and a guided needle to aspirate immature oocytes from the ovaries. Once the immature oocytes have been removed from the ovary, they are matured, fertilized, and cultured in vitro for up to seven days until they develop to a stage that is suitable for transfer or freezing.

Since the mid 1980s, technology has been developed to transfer the nucleus from either a blastomere (cells from early, and presumably undifferentiated cleavage stage embryos) or a somatic cell (fibroblast, skin, heart, nerve, or other body cell) to an enucleated oocyte (unfertilized female egg cell with the nucleus removed). This "nuclear transfer" produces multiple copies of animals that are themselves nearly identical copies of other animals (transgenic animals, genetically superior animals, or animals that produce high quantities of milk or have some other desirable trait, etc.). This process is also referred to as cloning. To date, somatic cell nuclear transfer has been used to clone cattle, sheep, pigs, goats, horses, mules, cats, rabbits, rats, and mice.

The technique involves culturing somatic cells from an appropriate tissue (fibroblasts) from the animal to be cloned. Nuclei from the cultured somatic cells are then microinjected into an enucleated oocyte obtained from another individual of the same or a closely related species. Through a process that is not yet understood, the nucleus from the somatic cell is reprogrammed to a pattern of gene expression suitable for directing normal development of the embryo. After further culture and development in vitro, the embryos are transferred to a recipient female and ultimately result in the birth of live offspring. The success rate for propagating animals by nuclear transfer is often less than 10 percent and depends on many factors, including the species, source of the recipient ova, cell type of the donor nuclei, treatment of donor cells prior to nuclear transfer, the techniques used for nuclear transfer, etc.

Most commonly used ARTs rely on fertilization as a first step. This joining of egg and sperm is accompanied by the recombination of the genetic material from the sire and dam, and is often referred to as "shuffling the genetic deck." It will be understood that these breeding techniques can be used either within the DPF Closed Colony, as a breeding step within the DPF Isolation Area 152, or could be used as a breeding step for females in the General Closed Colony and/or from the outside.

In the case of utilization of ART to impregnate females in the General Closed Colony, and/or a female from the outside, the birthing of piglets from such females can be as described herein, i.e., sows 134 may be taken from the outside or General Closed Colony 128, quarantined, and have their piglets 144 delivered via Cesarean section, with the piglets resuscitated, sterilized, quarantined, and placed into the DPF Isolation Area 152.

Maintenance of Closed Colonies

Designated pathogens may include any number of pathogens, including, but not limited to, viruses, bacteria, fungi, protozoa, parasites, and/or prions (and/or other pathogens associated with transmissible spongiform encephalopathies (TSEs)). Designated pathogens could include, but not be limited to, any and all zoonotic viruses and viruses from the following families: adenoviridae, anelloviridae, astroviridae, calicivirdae, circoviridae, coronaviridae, parvoviridae, picornaviridae, and reoviridae.

Designated pathogens could also include, but not be limited to, adenovirus, arbovirus, arterivirus, bovine viral diarrhea virus, calicivirus, cardiovirus, circovirus 2, circovirus 1, coronavirus, encephalomyocarditis virus, eperytherozoon, *Haemophilus suis*, herpes and herpes-related viruses, iridovirus, kobuvirus, leptospirillum, listeria, mycobacterium TB, *Mycoplasma*, orthomyxovirus, papovirus, parainfluenza virus 3, paramyxovirus, parvovirus, pasavirus-1, pestivirus, picobirnavirus (PBV), picornavirus, porcine circovirus-like (po-circo-like) virus, porcine astrovirus, porcine bacovirus, porcine bocavirus-2, porcine bocavirus-4, porcine enterovirus-9, porcine epidemic diarrhea virus (PEDV), porcine polio virus, porcine lymphotropic herpes virus (PLHV), porcine stool associated circular virus (PoSCV), posavirus-1, pox virus, rabies-related viruses, reovirus, rhabdovirus, rickettsia, sapelovirus, sapovirus, *Staphylococcus hyicus*, *Staphylococcus intermedius*, *Staphylococcus epidermidis*, coagulase-negative staphylococci, suipoxvirus, swine influenza, teschen, torovirus, torque teno sus virus-2 (TTSuV-2), transmissible gastroenteritus virus, vesicular stomatitis virus, and/or any and/or all other viruses, bacteria, fungi, protozoa, parasites, and/or prions (and/or other pathogens associated with TSEs). In some aspects, particularly in swine herds, testing for TSEs is not performed because TSEs are not reported in natural conditions in swine. In other aspects, testing for TSEs is performed as part of the methods of the present disclosure.

There are huge numbers of pathogens that could possibly be tested for in animal herds, and there is no regulatory guidance or standard, or understanding in the field as to what specific group of pathogens should be tested for in donor animals, and which specific group of pathogens should be removed from donor animal populations in order to ensure safe and effective xenotransplantation. In other words, before the present disclosure, there was no finite number of identified, predictable pathogens to be tested for and excluded.

Importantly, the present disclosure provides a specific group of pathogens identified by the present inventors that are critical to exclude for safe and effective xenotransplantation, as set forth in the following Table 1.

TABLE 1

| Test | Pathogen |
| --- | --- |
| Parasite Fecal Float | *Ascaris* species |
| | *Cryptosporidium* species |
| | Echinococcus |
| | Strongyloids sterocolis |
| | Toxoplasma gondii |
| *Brucella* BAPA (buffered acidified plate agglutination test) | *Brucella suis* |
| Lepto6 Screen | *Leptospira* species |
| M Hyo | Mycoplasma Hyopneumoniae |
| PRRS x3 ELISA | Porcine Reproductive and Respiratory Syndrome Virus (PRRSV) |
| PRVgb Test | Pseudorabies |
| TGE/PRCV Test | Porcine Respiratory Coronavirus |
| Toxoplasmosis ELISA | Toxoplasma Gondii |
| Porcine Cytomegalovirus PCR | Porcine CMV |
| Porcine Influenza PCR | Porcine Influenza A |
| Nasal swab | *Bordetella bronchiseptica* |
| Skin culture | Coagulase-positive *staphylococci* |
| Skin culture | Coagulase-negative *staphylococci* |
| Skin culture | Livestock-associated methicillin resistant *Staphylococcus aureus* (LA MRSA) |
| Skin culture | *Microphyton* and *Trichophyton* spp. |
| Porcine Endogenous Retrovirus RT-PCR Assay | Porcine Endogenous Retrovirus (PERV) C (PERV C) |

In certain aspects, a product of the present disclosure is sourced from animals having antibody titer levels below the level of detection for a plurality of or all of the pathogens discussed in the present disclosure. In certain aspects, subjects transplanted with a product of the present disclosure are tested and found to have antibody titer levels below the level of detection for a plurality of or all of the pathogens discussed in the present disclosure.

In some aspects, the present disclosure includes a method of testing for a specific group of pathogens consisting of no more than 18-35, e.g., 35, 34, 33, 32, 31, 30, 29, 28, 27, 26, 25, 24, 23, 22, 21, 20, 19, or 18 pathogens, the specific group of pathogens including each of the pathogens identified in Table 1. In some aspects, the present disclosure includes creating, maintaining and using donor animals that are free of the 18-35, e.g., 35, 34, 33, 32, 31, 30, 29, 28, 27, 26, 25, 24, 23, 22, 21, 20, 19, or 18 pathogens, the specific group of pathogens including each of the pathogens identified in Table 1.

As described herein, piglets born via live vaginal birth within the DPF Closed Colony 102 are not infected with pCMV, but are nonetheless tested for pCMV on a continuous basis. Testing for Porcine Cytomegalovirus (pCMV) and Porcine Endogenous Retrovirus (PERV), should be routine and continuous for screening and maintenance as described herein, and should occur routinely and continuously for the DPF Closed Colony. In some aspects of the present invention, the source animals described herein are positive for PERV A and B only, and some are positive for PERV A, B, and C. In other aspects, the source animals are free of PERV A, B and/or C (through utilization of CRISPR and other techniques).

With respect to PERV, it is understood that most, if not all, swine are known to be positive for PERV A and B. While PERV is recognized, the risk of transmission of PERV from treatment with swine derived tissue is expected to be rare. To date eight PERV mRNAs are expressed in all porcine tissues and in all breeds of swine and preclinical and clinical xenotransplantation studies of humans exposed to pig cells, tissues, and organs including pancreatic islets have failed to demonstrate transmission of PERV. See, e.g., Morozov V A, Wynyard S, Matsumoto S, Abalovich A, Denner J, Elliott R, "No PERV transmission during a clinical trial of pig islet cell transplantation," *Virus Res* 2017; 227:34-40. In the unlikely event that a human infection should occur, PERV is susceptible in vitro to nucleoside and non-nucleoside reverse transcriptase inhibitors in common clinical use. See, e.g., Wilhelm M, Fishman J A, Pontikis R, Aubertin A M, Wilhelm F X, "Susceptibility of recombinant porcine endogenous retrovirus reverse transcriptase to nucleoside and non-nucleoside inhibitors," *Cellular & Molecular Life Sciences* 2002; 59:2184-90; Schuurman, H., "Regulatory aspects of clinical xenotransplantation," Int. J. Surg., 23, (2015), pp. 312-321. Experimental data using the xenotransplantation product of the present disclosure indicated that PERV genetic material was not detected in the recipient's organs and that porcine DNA and cells did not migrate into the circulation of the recipient from the xenotransplanted organ.

The DPF Closed Colony 102 is maintained to ensure that the animals remain designated pathogen free and that appropriate standards of animal care and well-being are applied at all levels of the SAF 100 (i.e., breeding, maintenance, propagation). No animal is permitted into the DPF Closed Colony if it or a parent has tested positive for any of the pathogens in Table 1. For example, continuous testing for pathogens and other biological markers occurs including the numerous pathogens identified herein (including, but not limited to, pCMV and other pathogens). Environmental and blood samples are collected as necessary for genotyping and testing for pathogens. Test result(s) obtained for pathogens or other health concerns are evaluated by the facility veterinarian who may recommend follow-up testing and observations, and quarantine of the facility or areas (e.g., rooms, suites or other areas) within a facility as needed. Careful documentation of any antimicrobial agents used during routine care of the source animals should be maintained, and exclusive use of killed vaccines used. Examples of antimicrobial agents include cefazolin, bacitracin, neomycin, and polymyxin.

In some aspects, routine health surveillance and screening for pathogens (e.g., adventitious agents) of source animals is performed every 3 months. Samples of serum, nasal swabs, and stool for each animal in the General and DPF Closed Colonies are obtained and provided for analytical tests for detection of such pathogens every 3 months. Source animal samples of serum, nasal swabs, and stool for testing are obtained immediately after euthanasia via captive bolt and evaluated as disclosed herein including one or more of: conducting a sterility assay and confirming that aerobic and anaerobic bacteria do not grow in the sterility assay; conducting a *Mycoplasma* assay and confirming that *Mycoplasma* colonies do not grow in the *Mycoplasma* assay; conducting an endotoxin assay and confirming that the biological product is free of endotoxins in the endotoxin assay, conducting the MTT-reduction assay and confirming that the product has at least 50% cell viability in the MTT-reduction assay; conducting flow cytometry and confirming that the product does not have galactosyl-a-1,3- galactose epitopes as determined by the flow cytometry; conducting pathogen-detection assays specific for 18 to 35 pathogens and confirming that the product is free of *Ascaris* species, *Cryptosporidium* species, *Echinococcus, Strongyloids sterocolis, Toxoplasma gondii, Brucella suis, Leptospira* species, *Mycoplasma hyopneumoniae*, porcine reproductive and respiratory syndrome, pseudorabies, *Staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*.

In some aspects, all swine undergo routine health monitoring, which includes documentation of all illnesses, medical care, procedures, drugs administered, vaccinations, physical examinations, any treatments received, and general health assessments and observations each day at time of feeding with a visual health inspection indicating the animal is able to stand, move freely and appears clinically normal, as well as observations relating to the animal's appearance, activity and appetite, recording on the Animal Husbandry Log any deficiencies. In some aspects, animals are vaccinated against *Mycoplasma hyopneumoniae, Hemophilus Parasuis, Streptococcus Suis, Pasteurella Multocida, Bordatella bronchiseptica* and *Erysipelothrix rhusiopathiae*. All swine six months or older may be vaccinated against *Erysipelothrix rhusiopathiae, Leptospira* (Canicola-Grippotyphosa-Hardjo-Icterohaemorrhagiae-Pomona), Influenza and Parvovirus. Repeat vaccination may be performed, e.g., every six months.

In some aspects, health monitoring will normally be performed as part of daily husbandry procedures for cleaning and feeding to minimize entry into swine holding areas (e.g., rooms, suites or other areas). Prior to entering, personnel must wear personal protective equipment (PPE) and ensure that their footwear is free from gross contamination (e.g. visible dirt or mud). They will then don disposable shoe/boot covers prior to entry. Personnel in contact with any animals not housed in the designated pathogen free facility will change PPE if contaminated. All implements (shovel, other necessary tools) will undergo chlorhexidine immersion of no less than 2 minutes if exogenous to vivarium and judged necessary. Solid waste and soiled bedding is removed. Animal holding areas are sanitized with diluted Quat-PV or bleach a minimum of once every two weeks.

In some aspects, bedding is replaced daily using irradiated bedding wood shavings. The replacement amount is an approximate equal amount to that which was removed. All bedding is completely replaced on a weekly basis at a minimum. Daily activities including health status checks, cleaning and water levels are documented in the Animal Husbandry log. Appropriately labeled trash and biological waste is picked up by staff daily and incinerated.

With regard to piglet, newborns are handled and cared for by trained and gowned staff in an isolation suite. All supplies, room and crates are sanitized prior to housing of the piglets. Sterile drapes and towels are used to line the bottom of the crates. Room temperature is controlled to 80-85° F. Animals crates are maintained at 85-95° F. through the use of heat lamps. Piglets are maintained in the crates through the first 2 weeks after which time piglets are housed on the floor with irradiated wood shavings. Crates are cleaned daily and shavings are removed and replenished daily. Piglets are initially fed fresh-made, sterile colostrum (Bovine Colostrum IgG formulated for swine, Sterling Nursemate ASAP or equivalent) using a feeding tube every 1 to 2 hours until piglet is self-feeding from feeder. During the early days, the piglet is weighed twice a day and well-being is checked and recorded twice a day. Starting at day 14, piglets are fed 3 times per day with a Milk Replacer (Ralco Birthright or equivalent) that is further supplemented with irradiated piglet grain (antibiotic free creep feed, Blue Seal 813 or equivalent). The amount each piglet eats at each feeding is recorded. Vaccinations, genotyping, ear notching, and needle teeth trimming are performed within the first 7 days after birth of the piglet. In some aspects, vaccines use killed agents. Piglets are vaccinated against *Mycoplasma hyopneumoniae, Hemophilus parasuis, Streptococcus suis, Pasteurella multocida, Bordatella bronchiseptica* and *Erysipelothrix rhusiopathiae* at day 7 after birth, with a booster vaccination at 28 days of age. In one aspect, vaccines are killed agents. All swine six months or older are vaccinated against *Erysipelothrix rhusiopathiae, Leptospira* (Canicola-Grippotyphosa-Hardjo-Icterohaemorrhagiae-Pomona), Influenza and Parvovirus. Repeat vaccination is performed every six months.

The source animals for the xenotransplantation product are maintained in a positive pressure, biocontainment establishment, under specific isolation-barrier conditions governed by standard operation procedures adopted by the managers of the given program, and receive specialized care, under controlled conditions in order to mitigate adventitious agents. To ensure the welfare of the closed colony of source animals intended for xenotransplantation use, the SAF, personnel, and the caretakers of source animals adhere to procedures for animal husbandry, tissue harvesting, and sacrifice of animals. The source animals are housed in a positive pressure, biocontainment establishment, under specific isolation-barrier conditions.

In some aspects, food and bedding are delivered to a loading dock, transported, and stored in a specific feed room off of the clean cage wash area accessible only to staff in the inner hallway. All bedding and feed are sterilized by irradiation and double bagged to insure sterility. Feed used for the piglets and more mature animals is defined grain feed by a specific manufacturer. It does not contain any cattle protein. Water supply is provided either by use of the facility sterile system or purchased sterile water which is dispensed into sterile pans. Records for storage and delivery of feed, water, and other consumables are maintained, and include manufacturer, batch numbers, and other pertinent information, per protocol.

In some aspects, animal records are maintained to describe the feed provided to source animals for at least two generations before their use as a source for live tissues, organs and/or cells used in xenotransplantation. This includes source, vendor, and the type of feed used (including its contents). Use of feed that has been derived from animals is prohibited. Source animals are not provided feeds containing animal proteins or other cattle materials that are prohibited by the FDA feed ban as expanded in 2008 as source animals (21 CFR 589.2000) or feeds containing significant drug contamination or pesticide or herbicide residues for source animals (21 CFR 589.2001).

In some aspect, purified water is provided in sufficient quality to prevent unnecessary exposure of animals to infectious pathogens, drugs, pesticides, herbicides, and fertilizers. Newborn animals are provided colostrum specifically qualified for herd qualification. In some aspects, Bovine Colostrum IgG formulated for swine, Sterling Nursemate ASAP or equivalent is used to feed newborn animals.

Biological Products Derived from DPF Closed Colony

Biological Products

As described herein, biological products for xenotransplantation are derived from source animals produced and maintained in accordance with the present invention, including from the DPF Closed Colony 102 as described herein. Such biological products include, but are not limited to, liver, kidney, skin, lung, heart, pancreas, intestine, nerve and other organs, cells and/or tissues.

The present disclosure provides a continuous manufacturing process for a xenotransplantation product that has reduced immunogenicity, reduced antigenicity, increased viability, increased mitochondrial activity, a specifically required pathogen profile, and unexpectedly long shelf-life in xenotransplantation tissues subject to cryopreservation. The continuous manufacturing process is surprisingly and unexpectedly effective in avoiding hyperacute rejection, delayed xenograft rejection, acute cellular rejection, chronic rejection, cross-species transmission of diseases, cross-species transmission of parasites, cross-species transmission of bacteria, cross-species transmission of fungi, and cross-species transmission of viruses. The continuous manufacturing process is surprisingly and unexpectedly effective in creating a closed herd in which the donor animals survive normally without detectable pathological changes.

Harvesting of such biological products occurs in a single, continuous, and self-contained, segregated manufacturing event that begins with the sacrifice of the source animal through completion of the production of the final product. The animal is euthanized via captive bolt euthanasia, may be moved, if necessary, in a sterile, non-porous bag, to an operating room where the procedure to harvest biological product from the source animal will occur. All members of the operating team should be in full sterile surgical gear, e.g., dressed in sterile dress to maintain designated pathogen free conditions prior to receiving the source animal and in some instanced be double-gloved to minimize contamination, and surgical areas and tools are sterilized. The source animal is removed from the bag and container in an aseptic fashion. The source animal is scrubbed by operating staff, e.g., for at least 1-10 minutes with antiseptic, e.g., Chlorhexidine, brushes over the entire area of the animal where the operation will occur, periodically pouring Chlorhexidine over the area to ensure coverage. Surgical area(s) of the animal are scrubbed with opened Betadine brushes and sterile water rinse over the entire area of the animal where the operation will occur for, e.g., 1-10 minutes. For surgery, operators will be dressed in sterile dress in accordance with program and other standards to maintain designated pathogen free conditions. All organs, cells or tissue from the source animal that will be used for xenotransplantation is harvested within 15 hours of the animal being sacrificed.

Biological products can also include, but are not limited to, those disclosed herein (e.g., in the specific examples), as well as any and all other tissues, organs, and/or purified or substantially pure cells and cell lines harvested from the source animals. In some aspects, tissues that are utilized for xenotransplantation as described herein include, but are not limited to, areolar, blood, adenoid, bone, brown adipose, cancellous, cartaginous, cartilage, cavernous, chondroid, chromaffin, connective tissue, dartoic, elastic, epithelial, Epithelium, fatty, fibrohyaline, fibrous, Gamgee, Gelatinous, Granulation, gut-associated lymphoid, Haller's vascular, hard hemopoietic, indifferent, interstitial, investing, islet, lymphatic, lymphoid, mesenchymal, mesonephric, mucous connective, multilocular adipose, muscle, myeloid, nasion soft, nephrogenic, nerve, nodal, osseous, osteogenic, osteoid, periapical, reticular, retiform, rubber, skeletal muscle, smooth muscle, and subcutaneous tissue. In some aspects, organs that are utilized for xenotransplantation as described herein include, but are not limited to, skin, kidneys, liver, brain, adrenal glands, anus, bladder, blood, blood vessels, bones, cartilage, cornea, ears, esophagus, eye, glands, gums, hair, heart, hypothalamus, intestines, large intestine, ligaments, lips, lungs, lymph, lymph nodes and lymph vessels, mammary glands, mouth, nails, nose, ovaries, oviducts, pancreas, penis, pharynx, pituitary, pylorus, rectum, salivary glands, seminal vesicles, skeletal muscles, skin, small intestine, smooth muscles, spinal cord, spleen, stomach, suprarenal capsule, teeth, tendons, testes, thymus gland, thyroid gland, tongue, tonsils, trachea, ureters, urethra, uterus, and vagina.

In some aspects, purified or substantially pure cells and cell lines that are utilized for xenotransplantation as describe herein include, but are not limited to, blood cells, blood precursor cells, cardiac muscle cells, chondrocytes, cumulus cells, endothelial cells, epidermal cells, epithelial cells, fibroblast cells, granulosa cells, hematopoietic cells, Islets of Langerhans cells, keratinocytes, lymphocytes (B and T), macrophages, melanocytes, monocytes, mononuclear cells, neural cells, other muscle cells, pancreatic alpha-1 cells, pancreatic alpha-2 cells, pancreatic beta cells, pancreatic insulin secreting cells, adipocytes, epithelial cells, aortic endothelial cells, aortic smooth muscle cells, astrocytes, basophils, bone cells, bone precursor cells, cardiac myocytes, chondrocytes, eosinophils, erythrocytes, fibroblasts, glial cells, hepatocytes, keratinocytes, Kupffer cells, liver stellate cells, lymphocytes, microvascular endothelial cells, monocytes, neuronal stem cells, neurons, neutrophils, pancreatic islet cells, parathyroid cells, parotid cells, platelets, primordial stem cells., Schwann cells, smooth muscle cells, thyroid cells, tumor cells, umbilical vein endothelial cells, adrenal cells, antigen presenting cells, B cells, bladder cells, cervical cells, cone cells, egg cells, epithelial cells, germ cells, hair cells, heart cells, kidney cells, leydig cells, lutein cells, macrophages, memory cells, muscle cells, ovarian cells, pacemaker cells, peritubular cells, pituitary cells, plasma cells, prostate cells, red blood cells, retinal cells, rod cells, Sertoli cells, somatic cells, sperm cells, spleen cells, T cells, testicular cells, uterine cells, vaginal epithelial cells, white blood cells, ciliated cells, columnar epithelial cells, dopaminergic cells, dopaminergic cells, embryonic stem cells, endometrial cells, fibroblasts fetal fibroblasts, follicle cells, goblet cells, keratinized epithelial cells, lung cells, mammary cells, mucous cells, non-keratinized epithelial cells, osteoblasts, osteoclasts, osteocytes, and squamous epithelial cells.

An organ is a group of related cells that combine together to perform one or more specific functions within the body. Biologically, skin is the body's largest and fastest-growing organ, and is classified as the primary component of the integumentary system, one of the ten macro-organ systems found in "advanced" animals. Skin fulfills several critical roles including regulating temperature, providing a dynamic barrier to the external world, and serving as a conduit to support an immense network of sensory receptors. The skin performs several functions that are vital to the survival and health of the body. The skin heals to prevent the loss of blood after wounds, regulates body temperature by dissipating heat and as a layer against cold, absorption, secretion, thermal-regulation, sensory detection and orientation, and barrier protection. In fact, not only has success in transplantation of skin been recognized to correlate to transplantation of other organs, but skin transplants appear to be more sensitive to rejection than other organs, e.g., immune privileged organs such as liver, and skin transplants have even been suggested for use as "sentinel transplants," i.e., use of skin grafts in a human recipient as early predictors of rejection of transplanted solid organs in the same recipient. For example, as reported in Ali et al. *Transplant Proc.* 2016 October; 48(8): 2565-2570, evidence provided by experience with abdominal wall transplantation in some intestinal and multivisceral transplant recipients suggest that rejection may manifest in the skin component before emergence in the intestinal allograft, providing a "lead time" during which treatment of rejection of the abdominal wall could prevent the emergence of intestinal rejection.

Further, United States Code Title 42, Section 274 and Section 301, explicitly list skin in its formal definition of human organs, i.e., "'Human organ,' as covered by section 301 of the National Organ Transplant Act, as amended, means the human (including fetal) kidney, liver, heart, lung, pancreas, bone marrow and other hematopoietic stem/progenitor cells without regard to the method of their collection, cornea, eye, bone skin, and intestine, including the esophagus, stomach, small and/or large intestine, or any portion of the gastrointestinal tract." Similarly, the Human Organ Transplant Ordinance (HOTO), an internationally ratified ordinance to prevent organ trading and protect donor and recipient rights to self-determination. This global legislation lists skin—and whole segments of the integumentary system—formally as an organ, and more broadly defines an organ as "any part of the human body consisting of a structured arrangement of tissues which, if wholly removed, cannot be regenerated by the body . . . ." Following, the formal medical definition of a transplant is: "the removal of tissue from one part of the body or from one individual and its implantation or insertion in another especially by surgery." The HOTO defines a transplant as "the transfer of an organ from one person to another during a transplant operation, regardless of permanence."

With regard to skin, grafts typically consist of decellularized and/or reconstituted sheets of homogenized dermis that are used to achieve temporary, superficial wound coverage. Such grafts do not retain the original tissue structure nor the metabolically active, otherwise naturally present cells, and thus do not become vascularized; no capillary ingrowth or vessel-to-vessel connections are made. Consequently, immune rejection is not a concern—the skin graft becomes "ejected" rather than rejected by the growth of a complete host epithelium underneath the graft. Thus, while the term graft can be correctly applied to such solutions, the primary qualities that differentiate a transplant from a graft are that of heightened complexity, organization, and inclusion of one or more types of tissue. In the present case, a skin transplant is fundamentally differentiated from grafts known in the prior art. For example, a skin xenotransplant is comprised of live cells that perform the same function as the patient's original skin before eventually experiencing immune-mediated rejected. Thus, in this context, a skin xenotransplant according to the present disclosure is an organ transplant rather than a graft.

In terms of harvesting a biological product from the swine, wherein the harvesting comprises euthanizing the swine and aseptically removing the biological product from the swine; processing said biological product comprising sterilization after harvesting using a sterilization process that does not reduce cell viability to less than 50% cell viability in a 3-(4,5-dimethylthiazol-2-yl)-2,5-diphenyltetrazolium bromide (MTT)-reduction assay and does not reduce mitochondrial activity to less than 50% mitochondrial activity; and storing the biological product in a sterile container; and the non-human animal is a non-transgenic genetically reprogrammed swine for xenotransplantation of cells, tissue, and/or an organ isolated from the non-transgenic genetically reprogrammed swine, the non-transgenic genetically reprogrammed swine comprising a nuclear genome that has been reprogrammed to replace a plurality of nucleotides in a plurality of exon regions of a major histocompatibility complex of a wild-type swine with nucleotides from orthologous exon regions of a known human major histocompatibility complex sequence from a human capture sequence, wherein said reprogramming does not introduce any frameshifts or frame disruptions. Further specific aspects, details and examples are provided in the following disclosures and claims and any and all combinations of those aspects, details and examples constitute aspects of the present disclosure.

In other aspect, Xenogeneic kidneys are derived from a genetically engineered, reprogrammed and designated pathogen free swine is produced in accordance with the present invention and transplanted into a non-human primate and a human. It is expected that survival of at least fourteen months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

In another aspect, Xenogeneic lungs are derived from a genetically engineered, reprogrammed and designated pathogen free swine produced in accordance with the present invention and transplanted into a non-human primate and a human. It is expected that survival of at least 30 days is observed in each of the non-human primate and the human. In some aspects, it is expected that survival of at least 3 months is observed in each of the non-human primate and the human. In some aspects, it is expected that survival of at least 6 months is observed in each of the non-human primate and the human. In some aspects, it is expected that survival of at least 12 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

In another aspect, Xenogeneic hearts are derived from a genetically engineered, reprogrammed and designated pathogen free swine produced in accordance with the present invention and transplanted into a non-human primate and a human. It is expected that survival of at least 20 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

In another aspect, Xenogeneic nerve tissues are derived from a genetically engineered, reprogrammed and designated pathogen free swine produced in accordance with the present invention and transplanted into a non-human primate and a human. It is expected that survival of at least 75 days is observed in each of the non-human primate and the human. In some aspects, it is expected that survival of at least 3 months is observed in each of the non-human primate and the human. In some aspects, it is expected that survival of at least 6 months is observed in each of the non-human primate and the human. In some aspects, it is expected that survival of at least 12 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

In another aspect, Xenogeneic livers are derived from a genetically engineered, reprogrammed and designated pathogen free swine produced in accordance with the present invention and transplanted into a non-human primate and a human. It is expected that survival of at least 60 days is observed in each of the non-human primate and the human. In some aspects, it is expected that survival of at least 3 months is observed in each of the non-human primate and the human. In some aspects, it is expected that survival of at least 6 months is observed in each of the non-human primate and the human. In some aspects, it is expected that survival of at least 12 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

In some embodiments, use of pig livers produced in accordance with the present invention to serve as extracorporeal filters for humans are disclosed. In a study by Levy, et al., "Liver allotransplantation after extracorporeal hepatic support with transgenic (hCD55/hCD59) porcine livers: Clinical results and lack of pig-to-human transmission of the porcine endogenous retrovirus," *Transplantation,* 69(2): 272-280 (2000) ("Levy"), the entire contents of which are incorporated herein by reference, whole organ extracorporeal perfusion of a genetically modified transgenic porcine liver was proposed to sustain patients awaiting human liver transplantation for fulminant hepatic failure. The pig livers used were reported to be transgenic for human CD55 (decay-accelerating factor) and human CD59, however, the livers failed to suppress marked increase of [alpha]-gal antibodies.

In accordance with the present invention, in one aspect, a liver derived from a genetically reprogrammed source animal in accordance with the present invention is utilized for extracorporeal perfusion as a temporary filter for a human patient until a patient receives a human transplant. It will be understood that pigs with additional genetic modifications may also be utilized, including pigs genetically reprogrammed for any number of traits disclosed elsewhere herein.

Figure 38:
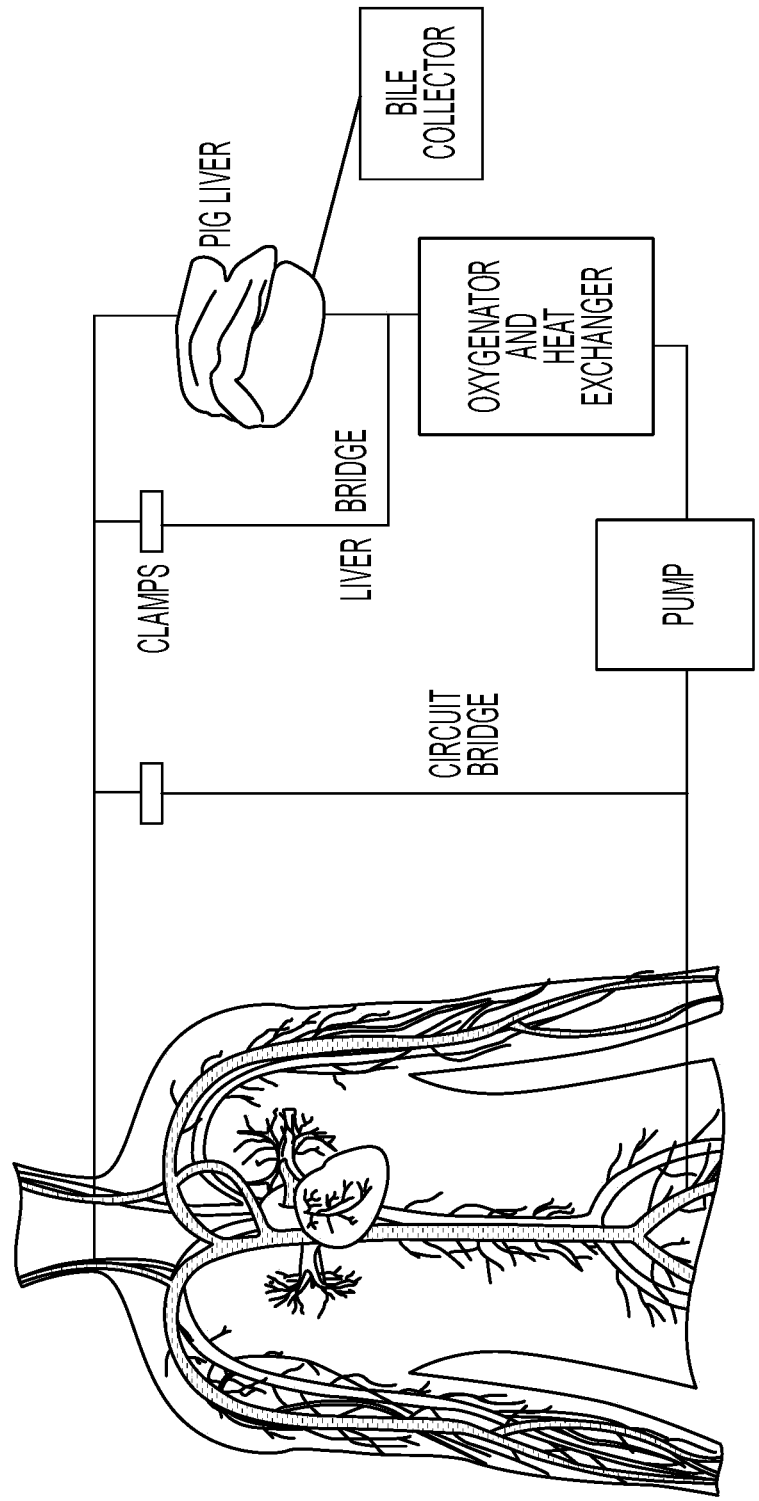
FIG. 38 illustrates an extracorporeal liver filter and circuit in accordance with the present invention.

In one aspect, as shown in FIG. 38, an extracorporeal circuit utilizes an oxygenator (e.g., Minimax Plus® hollow fiber oxygenator), a pump (e.g., Bio-Medicus model 540 Bio-Console® with a BP50 Pediatric Bio Pump® centrifugal pump), and a warmer (Bio-Medicus model 370 BioCal™ Temperature Controller). The circuit also utilizes a roller pump (e.g., Sarns model 7000; Sarns, Ann Arbor, Mich.) to supplement for lack of gravity return to the patient. Bridges and clamps are utilized to isolate both the perfused liver and the patient.

In an operating area within the DPF Isolation Area, a source animal is placed under a general anesthetic (ketamine, xylazine, enflurane) or euthanized by captive bolt. A hepatectomy is then performed on the source animal in designated pathogen free conditions.

The livers can be preserved in any number of ways known in the art prior to use as an extracorporeal filter, including, but not limited to, as disclosed in Levy (e.g., "a 4° C. lactated Ringer's/albumin solution and cannulated in the portal vein (28F Research Medical, model SPC-641-28) and the inferior vena cava (36F Research Medical, model SPC-641-36)").

The common bile duct can be intubated in any number of ways, including, but not limited to, as set forth in Levy (e.g., "with an intravenous extension tube (Extension Set 30, Abbott Hospitals, Inc., Chicago, Ill.) to allow subsequent quantification of bile production.")

The liver product derived from the source animal can be packaged and transported to the location of the procedure in accordance with current practice with human donor livers.

The procedure to utilize the liver filtration product can be performed, for example, by percutaneously cannulating a patient's internal jugular vein for venous return with a 12F pediatric arterial cannula (e.g., Medtronic DLP, Grand Rapids, Mich.) and percutaneously cannulating a patient's femoral vein for venous outflow with a 19F femoral artery cannula (e.g., Medtronic Bio-Medicus, Eden Prairie, Minn.). These cannulas are connected to a bypass circuit, having a centrifugal pump (e.g., Bio-Medicus), a heat exchanger (Medtronic Bio-Medicus), an oxygenator (e.g., Medtronic Cardiopulmonary, Anaheim, Calif.), and a roller pump (e.g., Sams) incorporated therein.

This circuit is primed with crystalloids and run for a period of time (e.g., 20 minutes) before the liver obtained from the genetically reprogrammed source animal is incorporated at a stabilized flow rate of 800 ml/min, maintained in a crystalloid bath occasionally supplemented with warm solution.

In other aspect, Xenogeneic pancreases are derived from a genetically engineered, reprogrammed and designated pathogen free swine is produced in accordance with the present invention Xenogeneic pancreas derived from a genetically reprogrammed swine produced in accordance with the present invention is transplanted into a non-human primate and a human. It is expected that survival of at least 20 months is observed in each of the non-human primate and the human. In some aspects, it is expected that survival of at least 24 months is observed in each of the non-human primate and the human. In some aspects, it is expected that survival of at least 36 months is observed in each of the non-human primate and the human. In some aspects, it is expected that survival of at least 48 months is observed in each of the non-human primate and the human. In some aspects, it is expected that survival of at least 60 months is observed in each of the non-human primate and the human.

While the subject matter of this disclosure has been described and shown in considerable detail with reference to certain illustrative aspects, including various combinations and sub-combinations of features, those skilled in the art will readily appreciate other aspects and variations and modifications thereof as encompassed within the scope of the present disclosure. Moreover, the descriptions of such aspects, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

In other aspect, Xenogeneic dermal combination product derived from a genetically engineered, reprogrammed and designated pathogen free swine is produced in accordance with the present invention.

Some skin transplantation products for the treatment of burns and other ailments utilize cultured epidermal autografts (see, e.g., products produced by Vericel Corporation under the Epicel® brand name). Such epidermal autografts can be utilized for patients with burns (including severe burns) and result in reduced or no rejection in the transplanted epidermal material since the material is derived from the patient's own skin.

Figure 39:
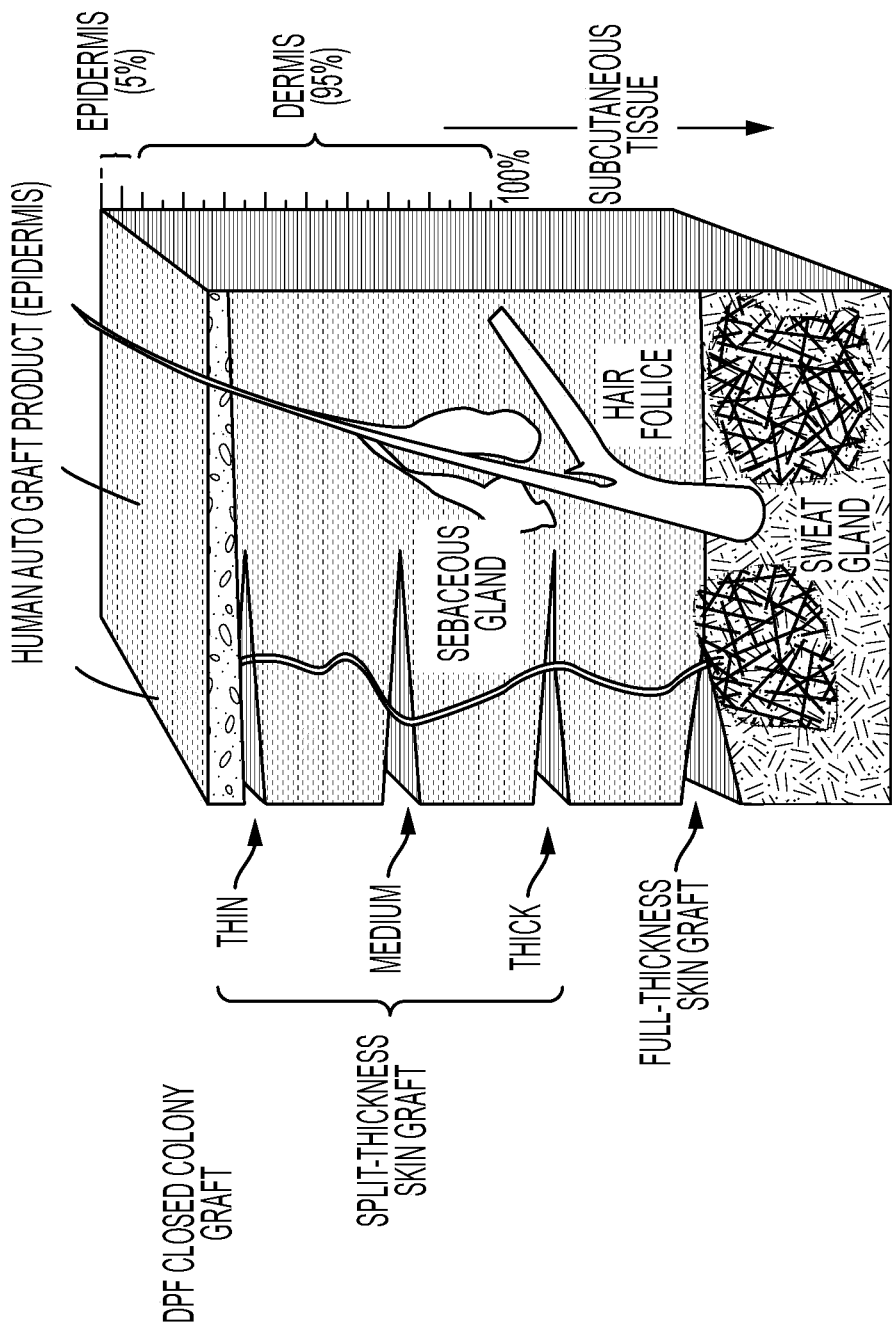
FIG. 39 illustrates a combination skin product in accordance with the present invention.

However, such products are limited to the epidermis only, and do not include the dermis portion of the skin. Referring to FIG. 39, it will be understood that the dermis (which typically accounts for 95% of the thickness of the skin) performs significantly different functions than the epidermis (which is the outer portion of the skin that typically accounts for 5% of the thickness of the skin).

Since epidermal autografts alone lack the ability to perform the critical functions of the dermis, such products are used in combination with a viable dermis. In some injuries, the wound bed includes remaining portions of the patient's own dermis, which is the ideal dermis to utilize in a procedure grafting cultured epidermal autografts onto a patient. However, in some cases the burn is more severe, and the patient's own dermis no longer exists or is no longer viable. In those instances, a different dermis is required since an epidermal autograft alone will not suffice.

In one aspect, a full thickness skin graft wound dressing consisting of dermal tissue derived from designated pathogen free α-1,3-galactosyltransferase [Gal-T] knockout swine in accordance with the present invention is used in conjunction or combination with cultured epidermal autografts. One treatment process utilizing this combination is as follows.

A patient with severe burn wounds is taken to an operating room within 48-72 hours of injury. A biopsy is taken as soon as possible after the patient undergoes care, and the epidermis skin cells are isolated and grown separately according to the known procedures for creating cultured epidermal autografts (see, e.g., products produced by Vericel Corporation under the Epicel® brand name).

Depending on how much of the patient's body is damaged, epidermal autografts are taken from healthy areas to treat burned areas and/or to later create an epidermal autograft mesh used in the grafting process.

Areas of severe burns are treated with the skin products described herein, e.g., skin products derived from a designated pathogen free α-1,3-galactosyltransferase [Gal-T] knockout swine produced in accordance with the present invention. Such treatments comprise temporary wound coverage until sufficient autografts are utilized to treat the patient long-term.

Prior to application of the epidermal autografts, significant debridement of wound bed is required to ensure an adequate substrate. To confirm a wound bed is ready for an epidermal autograft, apply the skin products described herein, e.g., skin products derived from a designated pathogen free α-1,3-galactosyltransferase [Gal-T] knockout swine produced in accordance with the present invention to confirm adherence. Once adherence is confirmed, the temporary wound coverage product is removed, and in some aspects, the wound bed is covered with a meshed autograft, and one or more cultured epidermal autograft products are placed on top to close the gaps in the autograft mesh.

The debridement may include mechanical debridement, chemical debridement, enzymatic debridement, or a combination thereof. Mechanical debridement may include surgical excision, e.g., tangential excision to remove thin layers of dermis until healthy tissue is visualized, or fascial excision to remove the full thickness of dermis down to the underlying fascia. Tangential excision allows less viable tissue to be removed with the necrotic tissue, but typically results in higher blood loss, is a larger physiologic stressor than fascial excision, and is more likely to result in "incomplete" debridement, with some devitalized tissue remaining in place. In fascial excision, blood loss and operative time are minimized, but often a large amount of healthy tissue is removed with the burned tissue. Debriding agents may include agents capable of cleaning a burn wound by removing foreign material and dead tissue. Many such agents are known. In enzymatic debridement, collagenases or other proteolytic enzymes are employed that break down proteins of the extracellular matrix, allowing devitalized tissue to be wiped away without the need for surgery while preferably leaving healthy tissue substantially intact. Enzymatic debridement involves the application of proteolytic and optionally other exogenous enzymes to a wound surface to break down necrotic tissue. Enzymatic debridement may be a relatively slow process, carried out over a period of a number of weeks in combination with other topical preparations, soakings and repeated dressings. Alternately, rapid enzymatic debridement can be accomplished using multi-enzyme products, for example, those extracted from the stem of the pineapple plant, as disclosed for example in WO 98/053850 and WO 2006/0006167, and as provided in the product marketed under the trade name Debrase®. A procedure for enzymatic debridement generally utilizes an enzyme such as bromelain derivatives, debridase, collagenase, papain derivatives, streptokinase, sutilains, fibrinolysin, deoxyribonuclease, krill derivatives, trypsin or combinations thereof. Autolytic debridement relies on enhancing the natural process of selective liquefaction, separation and digestion of necrotic tissue and eschar from healthy tissue that occurs in wounds due to macrophage and endogenous proteolytic activity. This is achieved by the use of occlusive, semi-occlusive or moist interactive dressings. Enzymatic debridement agents include a bromelain enriched enzyme product, other collagenases, or other enzyme products capable of clearing devitalized tissue or wound debris. NexoBrid™ (MediWound Ltd.) is one such bromelain enriched product that specifically targets heat-denatured collagen for degradation, resulting in partial-thickness and full-thickness wounds requiring a wound coverage or dressing product. Such products and methods are described in U.S. Pat. Nos. 8,540,983; 8,119,124; 7,128,719; 7,794,709; 8,624,077; and US2009/0010910A1, each of which is incorporated by reference herein.

In some aspects, the wound bed may include or be a chronic wound or an acute wound. Chronic wounds include but are not limited to venous leg ulcers, pressure ulcers, and diabetic foot ulcers. Acute wounds include but are not limited to burns, traumatic injuries, amputation wounds, skin graft donor sites, bite wounds, frostbite wounds, dermabrasions, and surgical wounds.

In the cases where there is no dermis, skin products derived from a designated pathogen free α-1,3-galactosyltransferase [Gal-T] knockout swine produced in accordance with the present invention are utilized. The epidermis is removed from such products (e.g., before dermis harvesting on the pig with a VERSAJET™ Hydrosurgery system), so that just the dermis remains. Then, the subject swine dermis is placed on the patient's subcutaneous tissue, serving as a substrate for the cultured epidermal autograft process described above.

Product Characteristics, Testing and Therapeutic Uses

In some aspects, the xenotransplantation products described and disclosed herein are temporary, i.e., their use in patients for xenotransplantation is non-permanent, utilized primarily for the treatment of acute ailments and injuries, able to be utilized for longer periods of time as compared to products that are not produced in accordance with the present invention. It will be understood that some of the aspects of the products described and disclosed herein may also be permanent or more permanent, with transplanted organs, tissues and/or cells being accepted by human recipients over much longer periods of time without adverse rejection.

In other aspects, the xenotransplantation products described and disclosed herein are viable, live cell (e.g., vital, biologically active) products; distinct from synthetic or other tissue-based products comprised of terminally sterilized, non-viable cells which are incapable of completing the vascularization process. Further, in some aspects, the product of the present disclosure is not devitalized, or "fixed" with glutaraldehydes or radiation treatment.

In yet other aspects, the xenotransplantation products described and disclosed herein are minimally manipulated (e.g., without physical alteration of the related cells, organs or tissues) such that such products are substantially in their natural state.

In certain aspects, the xenotransplantation products described and disclosed herein are obtained from a non-human animal, e.g., a non-transgenic genetically reprogrammed swine, including cells, tissue, and/or an organ isolated from the non-transgenic genetically reprogrammed swine, the non-transgenic genetically reprogrammed swine comprising a nuclear genome that has been reprogrammed to replace a plurality of nucleotides in a plurality of exon regions of a major histocompatibility complex of a wild-type swine with nucleotides from orthologous exon regions of a known human major histocompatibility complex sequence from a human capture sequence, and wherein cells of said genetically reprogrammed swine do not present one or more surface glycan epitopes, wherein said reprogramming does not introduce any frameshifts or frame disruptions. For example, genes encoding alpha-1,3 galactosyltransferase, cytidine monophosphate-N-acetylneuraminic acid hydroxylase (CMAH), and β1,4-N-acetylgalactosaminyltransferase are disrupted such that surface glycan epitopes encoded by said genes are not expressed. Further specific aspects, details and examples are provided in the following disclosures and claims and any and all combinations of those aspects, details and examples constitute aspects of the present disclosure.

In yet other aspects, the xenotransplantation products described and disclosed herein are capable of making an organic union with the human recipient, including, but not limited to, being compatible with vascularization, collagen growth (e.g., in regard to skin), and/or other interactions from the transplant recipient inducing graft adherence, organic union, or other temporary or permanent acceptance by the recipient.

In yet other aspects, the xenotransplantation products described and disclosed herein are utilized in xenotransplantation without the need to use, or at least reduction of use, of immunosuppressant drugs or other immunosuppressant therapies to achieve desired therapeutic results.

In other aspects, some of the xenotransplantation products described and disclosed herein (e.g., skin) are stored by cryopreservation, stored fresh (without freezing), or stored via other methods to preserve such products consistent with this invention. Storage involves using conditions and processes that preserve cell and tissue viability.

In some aspects, storage may involve storing organs, tissues, or cells, in any combination of a sterile isotonic solution (e.g., sterile saline with or without antibiotics), on ice, in a cryopreservation fluid, cryopreserved at a temperature of around −40° C. or around −80° C., and other methods known in the field. Such storage can occur in a primary containment system and secondary containment system.

In yet other aspects, the xenotransplantation products described and disclosed herein are for homologous use, i.e., the repair, reconstruction, replacement or supplementation of a recipient's organ, cell and/or tissue with a corresponding organ, cell and/or tissue that performs the same basic function or functions as the donor (e.g., swine kidney is used as a transplant for human kidney, swine liver is used as a transplant for human liver, swine skin is used as a transplant for human skin, swine nerve is used as a transplant for human nerve and so forth).

In yet other aspects, the xenotransplantation products described and disclosed herein have a low bioburden, minimizing pathogens, antibodies, genetic markers, and other characteristics that may serve to increase the product's bioburden and the human body's immunological rejection of the product upon xenotransplantation. This may include the innate immune system, through PRRs TLRs, detecting PAMPs and rejecting the subject xenotransplantation product.

It will be understood that the aspects disclosed and described herein can be applied in any number of combinations to create an array or different aspects comprising one or more of the features and/or aspects of the aspects encompassed by the present invention.

It will be understood that there are numerous therapeutic applications for products derived from DPF Closed Colony in accordance with the present invention. For example, such products may be utilized to treat acute and/or chronic disease, disorders, or injuries to organ, cells or tissue, and any and all other ailments that can utilize the products disclosed herein. Such treatments and/or therapies can include utilizing such products to repair, reconstruct, replace or supplement (in some aspects on a temporary basis and in other aspects a permanent basis), a human recipient's corresponding organ, cell and/or tissue that performs the same basic function or functions as the donor.

Specific treatment applications include, but are not limited to, lung transplants, liver transplants, kidney transplants, pancreas transplants, heart transplants, nerve transplants and other full or partial transplants. With regard to skin, treatment applications also include, but are not limited to, treatment of burn wounds, diabetic ulcerations, venous ulcerations, chronic skin conditions, and other skin ailments, injuries and/or conditions (including, but not limited to, severe and extensive, deep partial and full thickness injuries, ailments and/or conditions) (see, e.g., Example 2 herein); use in adult and pediatric patients who have deep dermal or full thickness burns comprising a total body surface area greater than or equal to 30%, optionally in conjunction with split-thickness autografts, or alone in patients for whom split-thickness autografts may not be an option due to the severity and extent of their wounds/burns; treatment of liver failure, wounds, ailments, injuries and/or conditions with liver products derived in accordance with the present invention; treatment of peripheral nerve damage, and other nerve ailments, injuries and/or conditions; and cell and other therapies utilizing materials harvested from the DPF Closed Colony, including the therapeutic uses disclosed in U.S. Pat. No. 7,795,493 ("Phelps"), including cell therapies and/or infusion for certain disorders (as disclosed in col. 30, line 1 to col. 31, line 9) and treatment or certain disorders or pathologies (as disclosed in col. 31, lines 10 to 42), the disclosure of which is incorporated by reference herein.

It will be understood that the specific recitation of therapies herein in no way limits the types of therapeutic applications for the products disclosed and described herein, which encompass acute and/or chronic disease, disorders, injuries to the following organs, tissues and/or cells: skin, kidneys, liver, brain, adrenal glands, anus, bladder, blood, blood vessels, bones, brain, brain, cartilage, ears, esophagus, eye, glands, gums, hair, heart, hypothalamus, intestines, large intestine, ligaments, lips, lungs, lymph, lymph nodes and lymph vessels, mammary glands, mouth, nails, nose, ovaries, oviducts, pancreas, penis, pharynx, pituitary, pylorus, rectum, salivary glands, seminal vesicles, skeletal muscles, skin, small intestine, smooth muscles, spinal cord, spleen, stomach, suprarenal capsule, teeth, tendons, testes, thymus gland, thyroid gland, tongue, tonsils, trachea, ureters, urethra, uterus, uterus, vagina, areolar, blood, adenoid, bone, brown adipose, cancellous, cartaginous, cartilage, cavernous, chondroid, chromaffin, connective tissue, dartoic, elastic, epithelial, Epithelium, fatty, fibrohyaline, fibrous, Gamgee, Gelatinous, Granulation, gut-associated lymphoid, Haller's vascular, hard hemopoietic, indifferent, interstitial, investing, islet, lymphatic, lymphoid, mesenchymal, mesonephric, mucous connective, multilocular adipose, muscle, myeloid, nasion soft, nephrogenic, nerve, nodal, osseous, osteogenic, osteoid, periapical, reticular, retiform, rubber, skeletal muscle, smooth muscle, and subcutaneous tissue; blood cells, blood precursor cells, cardiac muscle cells, chondrocytes, cumulus cells, endothelial cells, epidermal cells, epithelial cells, fibroblast cells, granulosa cells, hematopoietic cells, Islets of Langerhans cells, keratinocytes, lymphocytes (B and T), macrophages, melanocytes, monocytes, mononuclear cells, neural cells, other muscle cells, pancreatic alpha-1 cells, pancreatic alpha-2 cells, pancreatic beta cells, pancreatic insulin secreting cells, adipocytes, epithelial cells, aortic endothelial cells, aortic smooth muscle cells, astrocytes, basophils, bone cells, bone precursor cells, cardiac myocytes, chondrocytes, eosinophils, erythrocytes, fibroblasts, glial cells, hepatocytes, keratinocytes, Kupffer cells, liver stellate cells, lymphocytes, microvascular endothelial cells, monocytes, neuronal stem cells, neurons, neutrophils, pancreatic islet cells, parathyroid cells, parotid cells, platelets, primordial stem cells, Schwann cells, smooth muscle cells, thyroid cells, tumor cells, umbilical vein endothelial cells, adrenal cells, antigen presenting cells, B cells, bladder cells, cervical cells, cone cells, egg cells, epithelial cells, germ cells, hair cells, heart cells, kidney cells, leydig cells, lutein cells, macrophages, memory cells, muscle cells, ovarian cells, pacemaker cells, peritubular cells, pituitary cells, plasma cells, prostate cells, red blood cells, retinal cells, rod cells, Sertoli cells, somatic cells, sperm cells, spleen cells, T cells, testicular cells, uterine cells, vaginal epithelial cells, white blood cells, ciliated cells, columnar epithelial cells, dopaminergic cells, dopaminergic cells, embryonic stem cells, endometrial cells, fibroblasts fetal fibroblasts, follicle cells, goblet cells, keratinized epithelial cells, lung cells, mammary cells, mucous cells, non-keratinized epithelial cells, osteoblasts, osteoclasts, osteocytes, and squamous epithelial cells. This listing is in no way meant to limit the array of therapeutic uses to treat acute and/or chronic disease, disorders, injuries, organ or tissue failures, and any and all other ailments that can utilize the products disclosed herein.

With respect to the treatment of burns, including but not limited to e.g., second- and third-degree burns, in some aspects, skin products derived in accordance with the present invention are used to treat human patients with severe and extensive deep partial and/or full thickness burn wounds. Such products contain terminally-differentiated cell types that are not expanded ex vivo prior to use and do not migrate from the site of application during intended duration of treatment. Therefore, potential for tumorigenicity is negligible.

Such products adhere to the wound bed and provides a barrier function in the immediate post-burn period. Such products have non-terminally sterilized, viable cells, allowing for vascularization of the graft tissue with the recipient. In some aspects, the epidermis remains fully intact, and dermal components are maintained without change to structural morphology or organization of the various cells and tissues. This physiologic mechanism supports the prolonged survival of the graft material, and provides at least a temporary barrier function with significant clinical impact on par with, or better than, allograft. In some aspects, if clinical signs of infection, e.g., pain, edema, erythema, warmth, drainage, odor or unexplained fever, are present or developing, the product of the present disclosure is not applied until the clinical signs of the infection are reduced or eliminated for a predetermined period of time, e.g., 1, 2, 3, 4, 5, 6, or 7 days, 1, 2, 3, or 4 weeks, or if the subject has tested negative for the infection. In some aspects, the wound is cleaned, confirmed to be well-vascularized and nonexuding. If a dermal substitute such as cadaver allograft is also being used, the epidermal layer is removed from engrafted allograft prior to the application of the product without removing the engrafted dermis. The epidermal layer may be removed with a dermatome or other instrument according to standard operating procedures of the facility.

Grafts conventionally used in clinical practice consist of decellularized and/or reconstituted sheets of homogenized dermis that are used to achieve temporary, superficial wound coverage. Such conventional grafts do not retain the original tissue structure nor the metabolically active, otherwise naturally present cells, and thus do not become vascularized; no capillary ingrowth or vessel-to-vessel connections are made. In contrast, skin products described herein are fundamentally differentiated from such grafts because the product of the present disclosure includes live cells that perform the same function as the patient's original skin, i.e., the product acts as an organ transplant. Skin performs additional, critical roles related to homeostasis, temperature regulation, fluid exchange, and infection prevention. The absence of a sufficient amount of skin can compromise the ability to perform these functions leading to high incidences of mortality and morbidity from infections and fluid loss. Skin transplants have been reliably used with notable clinical benefit to prevent these outcomes in patients with significant wounds; regardless of whether the graft is temporary or permanent. Thus, unlike other proposed transplants, use of immunosuppressive drugs would be reduced or not be necessary. In fact, such regimens would be contraindicated in burn patients whose injuries already exhibit some level of comprised immune function. Thus, the xenotransplantation product of the present disclosure should not be confused with traditional "xenograft" products consisting of econstituted, homogenized wild-type porcine dermis fashioned into sheets or meshed, such as EZ-Derm™ or Medi-Skin™. Such porcine xenografts do not vascularize and are primarily only useful for temporary coverage of superficial burns. In stark contrast, the xenotransplantation product of the present disclosure contains metabolically active, minimally manipulated cells in identical conformations and unchanged morphologies as the source tissue.

In some aspects, the present disclosure includes using xenotransplanted donor skin as a test for prediction of rejection of other organs from the same animal donor. Techniques for performing such predictive tests using human donor skin have previously been described, e.g., in Moraes et al., Transplantation. 1989; 48(6):951-2; Starzl, et al., Clinical and Developmental Immunology, vol. 2013, Article ID 402980, 1-9; Roberto et al., Shackman et al., Lancet. 1975; 2(7934):521-4, the disclosures of which are incorporated herein by reference in their entireties for all purposes. Moraes reported that the crossmatch procedure was highly accurate in predicting early kidney transplant rejection. Shackman reported that the fate of skin grafts taken from live human prospective kidney donors correlates well with the outcome of kidney transplantation from the same donors. According to the present disclosure, in one aspect, the present disclosure includes a method of using a xenotransplanted skin sample in a human patient in order to determine whether there is a risk of rejection of other organs xenotransplanted from the same animal donor in the human patient.

The skin grafting methods described herein can be used to treat any injury for which skin grafts are useful, e.g., for coverage of partial thickness and full thickness wounds including but not limited to burns, e.g. partial thickness or excised full thickness burn wounds; avulsed skin e.g. on an extremity; diabetic wounds, e.g., non-healing diabetic foot wounds, venous stasis ulcers.

In some aspects, the xenotransplantation product of the present disclosure has pharmacokinetic and pharmacodynamics properties that meet regulatory requirements. Characterization of such properties requires a unique approach with respect to classical meanings of drug absorption, distribution, metabolism, and excretion. "Absorption" of the xenotransplantation product for the purposes of consideration of pharmacokinetics, may be described by the vascularization process the xenotransplantation product experiences. For example, shortly after surgery, skin xenotransplantation products may present as warm, soft, and pink, whereas wild-type or traditional xenografts appear as non-vascularized "white grafts." In some aspects, the distribution of the transplant is limited to the site of transplant as confirmed by DNA PCR testing to demonstrate the presence or absence of pig cells in peripheral blood beyond the transplantation site.

In other aspects, the cells of the biological products produced in accordance with the present invention do not migrate following xenotransplantation into the recipient, including into the circulation of the recipient. This includes that PERV or PERV-infected porcine cells do not migrate into the recipient. Confirmation that such cells do not migrate into the recipient can be performed in a number of ways, including via DNA-PCR analysis of peripheral blood mononuclear cells (PBMCs) and samples from the transplantation site and of highly perfused organs (e.g., liver, lung, kidney and spleen) to determine and otherwise demonstrate that migrations of porcine cells (DNA) or porcine retroviral (RNA) components in the peripheral blood did not occur in the recipient.

Moreover, bioavailability and mechanism of action of the xenotransplantation product is not affected by size. The distribution of the xenotransplantation product is limited to the site of the administration. For example, in the case of a skin transplant, the debrided wound bed initially created by the trauma or burn injury is the site of administration. The present disclosure includes testing to detect distribution of cells from the xenotransplantation product in the peripheral blood, wound beds, spleen and/or kidney beyond the site of administration. In certain aspects, such testing will demonstrate an absence of cells from the xenotransplantation product in the peripheral blood, wound beds, spleen and/or kidney beyond the site of administration. Such testing may include DNA PCR testing for various cellular markers present in the type of animal from which the product is obtained, e.g., PERV, swine MHC, and other swine DNA sequences. In certain aspects, cells and nucleic acids from the xenotransplantation product remain limited to the site of administration.

The metabolism of the xenotransplantation product, traditionally defined as the metabolic breakdown of the drug by living organisms, typically via specialized enzymes or enzymatic systems, may be congruent with the aforementioned natural host rejection phenomenon, which occurs in the absence of exogenous immunosuppressive drugs. Via the same formulation and identical route of administration as intended for future human use, such xenotransplantation products undergo a delayed, immune rejection course similar to allograft comparators for clinically useful durations.

In similar fashion, excretion of the xenotransplantation product could be modeled and experientially monitored by the clinical "sloughing" phenomenon as a result of necrotic ischemia of the transplant, due to antibody-mediated vascular injury, ultimately leading to the death of the tissue.

The demonstrated efficacy of the xenotransplantation product of the present disclosure, along with safety, availability, storage, shelf-life, and distribution, provide significant advantages over current standards of care.

In some aspects, the "dosage" of the xenotransplantation product of the present disclosure is expressed as percentage of viable cells in the product per unit area of transplantation. As such, in some aspects, the xenotransplantation product of the present disclosure can be considered as analogous to the active pharmaceutical ingredient in a pharmaceutical drug product.

Survival of the xenogeneic cells, tissues, or organs of the present disclosure is increased by avoiding: (a) infiltration of immune or inflammatory cells into the xenotransplantation product or alteration of such cells in other relevant compartments, such as the blood and cerebrospinal fluid; (b)

fibrotic encapsulation of the xenotransplantation product, e.g., resulting in impaired function or xenotransplantation product loss; (c) xenotransplantation product necrosis; (d) graft versus host disease (GVHD); and (e) in vivo function and durability of encapsulation or barriers intended to diminish rejection or inflammatory responses.

Blood samples from piglets are obtained and tested for phenotype, lack of expression of alpha galactose on the cell surface of blood cells using FITC-IB4 labeling and flow cytometry. At this stage of development, all progeny will be genotyped at birth. A PCR assay has been established to determine if a pig has a wild type galactose-α1,3galactose transferase gene (Gal-T) or if it is heterozygous or homozygous for the Gal-T knockout (Gal-T-KO) using DNA isolated from ear notches or PBMC. Genomic DNA is isolated from PBMC (or skin tissues) using DNeasy Kit following the Qiagen DNeasy kit directions. PCR is performed on genomic DNA and control template DNA, Wild type Gal-T (+/+) Heterozygote Gal-T-KO (+/−) and Homozygous Gal-T-KO (−/−).

Punch biopsies of skin grafts are co-cultured with sub-confluent target cells, human 293 (kidney epithelium) and porcine ST-IOWA cell lines maintained in culture medium (Dulbecco's modified Eagle's medium supplemented with 10% fetal bovine serum and glutamine, penicillin, and streptomycin) in a 75-cm2 flask. The biopsies are kept in contact with the target cells for 5 days, after which the culture medium and remaining tissue are removed and the target cell co-cultures are maintained by subculturing as necessary. PERV infection of target cells is determined by the presence of reverse transcriptase (RT) activity in the culture supernatants. Transmission assays are maintained for a minimum of 60 days before being considered negative.

Product characterization to measure safety, identity, purity and potency is performed. Safety tests include bacterial and fungal sterility, *Mycoplasma*, and viral agents. The present disclosure includes cryopreserving and archiving for further testing, as needed, samples of all final xenotransplantation products (i.e., cells or tissues or biopsies of organs), whether fresh or from culture ex vivo. In some cases, for example if the xenotransplantation product is a whole intact organ, a relevant surrogate sample (e.g., adjacent tissues or contralateral organ) is archived.

With regard to skin, storage and cryopreservation of porcine skin has not been fully characterized, especially with regards to viability, as most porcine xenografts are intentionally devitalized, or "fixed" with glutaraldehydes or radiation treatment. Such information is necessary to support the use of vital porcine skin grafts—or porcine skin transplants—as a temporary and clinically advantageous option.

In procedures in which the xenotransplantation product is transplanted immediately after removal from the source animal, such as xenotransplantation of whole organs, results of testing of the xenotransplantation product may not be available before its clinical use. In such cases, testing of the source animal, itself, may be all the testing that is possible before the procedure. Testing of samples taken from such xenotransplantation products or appropriate relevant biological surrogates, e.g., adjacent tissues or contra-lateral organs, may be performed according to the present disclosure. Microbiological examination methods may include aspects set forth in the following Table 2:

TABLE 2

| | TEST DETAILS | GROWTH PROMOTION | | SUITABILITY OF COUNTING METHOD IN THE PRESENCE OF PRODUCT | |
|---|---|---|---|---|---|
| | | Total | Total | | Total |
| Microorganism | Preparation of Test Strain | Total Aerobic Microbial Count | Yeasts and Molds Count | Total Aerobic Microbial Count | Yeasts and Molds Count |
| *Staphylococcus aureus* such as ATCC 6538, NCIMB 9518, CIP 4.83, or NBRC 13276 | Soybean-Casein Digest Agar or Soybean-Casein Digest Broth 30°-35° 18-24 hours | Soybean-Casein Digest Agar and Soybean-Casein Digest Broth ≤100 cfu 30°-35° ≤3 days | | Soybean-Casein Digest Agar/MPN Soybean-Casein Digest Broth ≤100 cfu 30°-35° ≤3 days | |
| *Pseudomonas aeruginosa* such as ATCC 9027, NCIMB 8626, CIP 82.118, or NBRC 1 3275 | Soybean-Casein Digest Agar or Soybean-Casein Digest Broth 30°-35° 18-24 hours | Soybean-Casein Digest Agar and Soybean-Casein Digest Broth ≤100 cfu 30°-35° ≤3 days | | Soybean-Casein Digest Agar/MPN Soybean-Casein Digest Broth ≤100 cfu 30°-35° ≤3 days | |
| *Bacillus subtilis* such as ATCC 6633, NCIMB 8054, CIP 52.62, or NBRC 3134 | Soybean-Casein Digest Agar or Soybean-Casein Digest Broth 30°-35° 18-24 hours | Soybean-Casein Digest Agar and Soybean-Casein Digest Broth ≤100 cfu 30°-35° ≤3 days | | Soybean-Casein Digest Agar/MPN Soybean-Casein Digest Broth ≤100 cfu 30°-35° ≤3 days | |

TABLE 2-continued

| | TEST DETAILS | | GROWTH PROMOTION | | SUITABILITY OF COUNTING METHOD IN THE PRESENCE OF PRODUCT | |
|---|---|---|---|---|---|---|
| | | | Total | Total | | Total |
| Microorganism | Preparation of Test Strain | | Aerobic Microbial Count | Yeasts and Molds Count | Total Aerobic Microbial Count | Yeasts and Molds Count |
| Candida albicans such as ATCC 10231, NCPF 3179, IP 48.72, or NBRC 1594 | Sabouraud Dextrose Agar or Sabouraud Dextrose Broth 20°-25° 2-3 days | | Soybean-Casein Digest Agar ≤100 cfu 30°-35° ≤5 days | Sabouraud Dextrose ≤100 cfu 20°-25° ≤5 days | Soybean-Casein Digest Agar ≤100 cfu 30°-35° ≤5 days MPN: not applicable | Sabouraud Dextrose Agar ≤100 cfu 20°-25° ≤5 days |
| Aspergillus brasiiiensis such as ATCC16404, IMI 149007, IP 1431.83, or NBRC 9455 | Sabouraud Dextrose Agar or Potato-Dextrose Agar 20°-25° 5-7 days, or until good sporulation is achieved | | Soybean-Casein Digest Agar ≤100 cfu 30°-35° ≤5 days | Sabouraud Dextrose ≤100 cfu 20°-25° ≤5 days | Soybean-Casein Digest Agar ≤100 cfu 30°-35° ≤5 days MPN: not applicable | Sabouraud Dextrose Agar ≤100 cfu 20°-25° ≤5 days |

The present disclosure includes using Buffered Sodium Chloride-Peptone Solution pH 7.0 or Phosphate Buffer Solution pH 7.2 to make test suspensions; to suspend *A. brasiliensis* spores, 0.05% of polysorbate 80 may be added to the buffer. The present disclosure includes using the suspensions within 2 hours, or within 24 hours if stored between 2° C. and 8° C. As an alternative to preparing and then diluting a fresh suspension of vegetative cells of *A. brasiliensis* or *B. subtilis*, a stable spore suspension is prepared and then an appropriate volume of the spore suspension is used for test inoculation. The stable spore suspension may be maintained at 2° to 8° for a validated period of time. To verify testing conditions, a negative control is performed using the chosen diluent in place of the test preparation. There must be no growth of microorganisms. A negative control is also performed when testing the products as described under Testing of Products. A failed negative control requires an investigation. Microbiological Examination may be performed according to USP 61, USP 63, USP 71, USP 85 EP section 2.6.13 Microbial Examination of Non-sterile Products (Test for Specified Microorganisms), each of which is incorporated herein by reference in its entirety.

With regard to testing for porcine cytomegalovirus (PCMV), source animals are screened for PCMV on a quarterly basis. However, caesarian derived piglets, which are then consistently raised in the closed colony are not infected with PCMV. Analysis for PCMV was conducted during the studies in Example 1 herein and no PCMV was detected in the punch biopsies using the following PCR method. These results were consistent to the PCR results from nasal swabs. Quantitative Real-Time PCR is utilized for PCMV testing. Target DNA sequences were quantified by real-time PCR using a Stratagene Mx3005P. Sequence-specific primers and TaqMan probe were generated for each gene target. Each 25 uL PCR reaction included target DNA, 800 nM primers 200 nM TaqMan probe, 20 nM Rox reference and 1× Brilliant III Ultra Fast Master Mix. The PCR cycling conditions were as follows: 1 cycle at 95° C. for 5 min followed by 50 cycles of denaturation at 95° C. for 10 seconds, and annealing-extension at 60° C. for 30 seconds with data collection following each extension. Serial dilutions of gel-extracted amplicon cloned into Invitrogen TOPO plasmid served as quantifying standards. Target DNA is detected with a linear dynamic range of 10 to 106 copies. For quantification of PCMV DNA, 300 ng of xenograft pig kidney DNA was run in a TaqMan PCR in triplicate. Primers and probes specific for PCMV DNA polymerase gene have been shown to have no cross-reactivity with PLHV-1. Utilization of cesarean-derived swine as source animals, combined with animal husbandry of the resulting closed colony and maintenance of the barrier-isolation conditions is attributed the animals being PCMV free. With regard to skin, the inventors noted that the safety and efficacy results achieved in Example 1 using single knockout swine (as opposed to triple knockout or even further genetically modified swine) were quite surprising given the comparable performance to allograft.

In some aspects, the analytical procedures used to test the xenotransplantation product can also include:

a. USP<71> Sterility.

Samples are transferred to Tryptic Soy Broth (TSB) or Fluid Thioglycollate Medium (FTM) as appropriate. For Bacteriostasis and fungistasis, TSB samples are spiked with an inoculum of <100 Colony Forming Units (CFUs) of 24-hour cultures of *Bactillus subtilis, Candida albicans*, and with <100 spores of *Aspergilius braseiliensis*. The FTM samples will be spiked with an inoculum of <100 CFU's of 24-hour cultures of *Staphyloccocus aureus, Pseudomonas aeruginosa*, and *Clostridium sporogenes*. If growth is not observed, the product is found to be bacteriostatic or fungistatic and fails the USP <71> Sterility Test.

b. Aerobic and Anaerobic Bacteriological Cultures.

Samples are transferred to Tryptic Soy Broth (TSB) or Fluid Thioglycollate Medium (FTM) as appropriate. Vessels will be incubated to allow for potential growth. If no evidence of microbial growth is found, the product will be judged to comply with the test for sterility as described by USP<71>.

c. *Mycoplasma* Assay USP <63>.

Fresh samples will be added to 100 mL of *Mycoplasma* Hayflick broth and incubated at 37° C. for up to 21 days. The sample is subcultured after 2-4 days, 7-10 days, 14 days, and 21 days. The plates are then incubated at 37° C. for up to 14 days and checked for the presence of *Mycoplasma* colonies. If none are detected, the product is found to be in compliance with USP<63> and is *Mycoplasma* free.

d. Endotoxin USP<85>.

Three samples from the same lot will be tested for the Inhibition/Enhancement of the Limulus amoebocyte lysate (LAL) test. Samples will be extracted with 40 mL of WFI per sample at 37° C. for 1 hour. Samples will then be tested in the LAL Kinetic Chromogenic Test with a standard curve ranging from 5-50 EU/mL at a validated dilution. Assays will be performed in compliance with USP<85>.

e. MTT Assay for Cell Viability.

The metabolic activity of the drug product is tested relative to control tissue samples using a biochemical assay for [3-4,5 dimethylthiazol-2-yl]-2,5 diphenyltetrazolium bromide (MTT) metabolism. Positive and negative control samples of fresh xenotransplantation product tissue (positive control) or heat inactivated discs of xenotransplantation product tissue (negative control) or the test article of Xenotransplantation product are placed in amber microcentrifuge tubes containing MTT solution (0.3 m g/mL in DMEM, 0.5 mL). The discs are treated with MTT formazan and incubated for 180±15 minutes at 37° C. and an atmosphere of 5% CO 2 in air. The reaction is terminated by removal of the discs and the formazan is extracted by incubation at either ambient temperature for ≤24 hours or refrigerated at 4° C. for ≤72 hours. Samples are protected from light during this time. Aliquots are taken after the extraction is complete and the absorbance at 550 nm (with a reference wavelength of 630 nm) is measured and compared to a standard curve.

f. IB4 Assay for Extracellular Glycan Epitope.

The absence of the galactosyl-α-1,3-galactose (Alpha-Gal) epitope on cells will be determined using fluorescence activated flow cytometry. White blood cells in whole blood are stained with a fluorochrome labeled isolectin-B4 (FITC-I-B4) and comparisons are made against blood obtained from wild type positive controls and the Gal-T-KO source animal twice. First, all source animals are tested at birth. Second, the same test will be performed from whole blood collected at sacrifice of the source animal and tested for stability of the gene knockout, and the negative phenotype for Alpha-Gal. The isolectin binds to the epitope on cells from the wild type pig but no binding occurs on the cells from the Gal-T-KO pigs. The assay serves to confirm alpha-gal epitope is not present in the genetically engineered source animal. Spontaneous re-activation of the gene, and re-expression of the Alpha-Gal moiety post sacrifice is highly improbable and unreasonable to expect; its inclusion would only deteriorate the efficacy of the xenotransplantation product causing it to resemble wild-type porcine tissue and hyperacutely reject as previously demonstrated.

g. PERV Viral Assay.

PERV pol quantitation 10 uL of a 1:625 dilution of the RT reaction was amplified in a 50 cycle PERV polymerase quantitative TaqMan PCR in triplicate using a Stratagene MX300P real-time thermocycler (Agilent Technologies). 10 uL of a 1:25 dilution of the "No RT enzyme" control RT reaction was similarly treated. PCR conditions included PERV pol forward and reverse primers at 800 nM final concentration and PERV pol probe at 200 nM final concentration. Brilliant III Ultra Fast master mix (600880 Agilent Technologies) was used supplemented to 20 nM with ROX reporter dye (600880 Agilent Technologies) and 0.04 Units/μL UNG nuclease (N8080096, Life Technologies). Cycling conditions included 1 cycle of 10 minutes at 50° C. followed by one cycle of 10 minutes at 95° C. and 50 cycles of 10 seconds at 95° C. followed by 30 seconds at 60° C. with data collected at the end of each cycle. Absolute copies of PERV pol, and of porcine MHC-I and porcine GAPDH nucleic acids were measured per nanogram of input cDNA. Punch biopsies of thawed as described herein and washed xenotransplantation product are tested for the presence of PERV DNA and RNA.

h. Histology and Morphology.

Samples of the xenotransplantation product, following the described manufacturing process, are sampled for examination for cell morphology and organization. Verification under microscope via visible examination to ensure correct cell morphology and organization of xenotransplantation product tissues and absent for abnormal cell infiltrate populations.

i. Release Assay Sampling Methodology.

Once all units of the final xenotransplantation product lot have been created, units are independently, randomly selected for use in manufacturing release assays for the required acceptance criteria. These units will be marked for lot release to the various laboratory contractors, and the various analytical tests will be performed per the required cGMP conditions.

Similarly, prior to validation for human clinical use, all final xenotransplantation product must meet acceptance criteria for selecting a donor pig for material including (i) reviewing the medical record for a defined pedigree, (ii) reviewing the medical record for the test results for alpha-1,3-galactose by Flowmetrics, (iii) reviewing the medical record for a history of full vaccinations; (iv) reviewing the medical record for the surveillance tests performed over the lifetime of the pig; (v) adventitious agent screening of source animal; (vi) reviewing the medical record for infections over the lifetime of the pig; and (vi) reviewing the medical record for any skin abnormalities noted in the animal's history.

The final xenotransplantation product control strategy and analytical testing is conducted at the conclusion of the manufacturing process prior to release for clinical use. Results of the required analytical tests will be documented via a xenotransplantation product drug product Certificate of Analysis (COA) that is maintained with a master batch record pertaining to each lot of xenotransplantation product drug product.

The following Table 3 is a list of the assays and results of the battery of tests performed on the xenotransplantation product materials.

TABLE 3

| Test | Test Method | Sample Material Tested | Result |
|---|---|---|---|
| Sterility Testing Aerobic Bacteria Anaerobic Bacteria | Tissue Culture | 3 mm Punch Biopsy of Xenotrans- | No growth detected |

TABLE 3-continued

| Test | Test Method | Sample Material Tested | Result |
|---|---|---|---|
| Fungi<br>Acid fast cultures<br>Specific bacterial screen<br>Mycological Screen | Mycoplasma Assay | plantation product (Post Thaw)<br>3 mm Punch Biopsy of Xenotransplantation product (Post Thaw) | No growth detected after 28 days |
| Bacteriostasis & Fungistasis | USP<71> Gibraltar Laboratory | Xenotransplantation product (Post Thaw) | Bacteriostatic, no growth of specific indicator organism |
| Endotoxin Test | USP<85> LAL, Kinetic Chromogenic Test | Xenotransplantation product (Post Thaw) | <0.2 EU/unit |
| Endogenous Viral Testing (PERV) | RT-qPCR Co-culture Assay MGH-Infectious Disease-Fishman Laboratory | 3 mm Punch Biopsy of Xenotransplantation product (Post Thaw) | Presence of PERV A, B, C confirmed |
| Viability Testing | MTT and Phenyl Acetate Assays | 3 mm Punch Biopsy of Xenotransplantation product (Post Thaw) | Greater than 70% Mitochondrial Activity remaining following freeze-thaw cycle, confirmed by both assays |
| Identity Cell Morphology | Histology, Hematoxylin and Eosin Staining | 3 mm Punch Biopsy of Xenotransplantation product (Post Thaw) | No abnormalities noted. Cell morphology and organization consistent with skin graft No presence of Alpha-GAL detected |
| Confirmation of absence of Alpha-GAL (Gal-T-Knockout confirmation) | Flow Cytometry, isolectin-B4 (FITC-I-B4) | Whole Blood, 2 ml, obtained from source animal, at sacrifice. | |

In another aspect it will be understood that there includes an adventitious agent control strategy developed based on the source animal, including the species, strain, geographic origin, type of tissue, and proposed indication. Analytical Tests are conducted for adventitious agents, to include bacteria, fungi, *Mycoplasma*, and viral microorganisms, including as follows:

j. Bacteriological Free Status—

The bacteriological screen is conducted to confirm the drug product is free of potential biological agents of concern Humans. Both Aerobic and Anaerobic screens are conducted to ensure sterility. Samples are thawed as described herein and transferred to Tryptic Soy Broth (TSB) or Fluid Thioglycollate Medium (FTM) as appropriate. Vessels will be incubated to allow for potential growth. If no evidence of microbial growth is found, the product will be judged to comply with the test for sterility.

k. Mycological (Fungal) Free Status—

The mycological screen is conducted to confirm the Drug Product is free of potential fungal agents of concern. Samples are thawed as described herein. After thawing, samples are transferred to a soybean-casein digest agar. Vessels will be incubated to allow for potential growth. If no evidence of fungal growth is found, the product will be judged to comply with the test for sterility per USP<71>.

l. *Mycoplasma* Free Status—

The *Mycoplasma* screen is conducted to confirm the drug product is free of *Mycoplasma*. Samples are thawed as described herein and added to 100 mL of *Mycoplasma* broth and incubated at 37° C. for up to 21 days. The sample is sub-cultured after 2-4 days, 7-10 days, 14 days, and 21 days. The plates are then incubated at 37° C. for up to 14 days and checked for the presence of *Mycoplasma* colonies. If none are detected, the product is found to be in compliance with USP<63> and is *Mycoplasma* free.

m. Endotoxin Free Status—

The endotoxin free status is conducted to confirm the drug product is free of endotoxins and related agents of concern. Three samples from the same lot will be tested for the Inhibition/Enhancement of the Limulus amoebocyte lysate (LAL) test. Samples will be thawed as described herein and extracted with 40 mL of WFI per sample at 37° C. for 1 hour. Samples will then be tested in the LAL Kinetic Chromogenic Test with a standard curve ranging from 5-50 EU/mL at a validated dilution. Assays will be performed in compliance with USP<85>.

n. Viral Assays Conducted—

The viral assays are conducted to confirm the source animal is free of potential viral agents of concern, confirmation of endogenous viruses (see below). This includes co-culturing and RT-PCR testing for specific latent endogenous viruses including PERV. In vivo assays are also conducted on the animal source to monitor animal health and freedom from viral infection as key aspects of the lot release criteria. Due to the endemic nature of PERV in porcine tissue, this qualifies as a positive result that does not preclude the use of such tissue. However, the virus is identified and characterized in lot release to provide information for monitoring the recipient of the xenotransplantation product.

o. Cell Viability Assay—

The MTT assay is conducted to confirm the biologically active status of cells in the xenotransplantation product. Evidence of viability is provided through surrogate markers of mitochondrial activity as compared to positive (fresh, not cryopreserved) and negative (heat-denatured) controls. The activity of the cells is required for the xenotransplantation product to afford the intended clinical function. This is required as a lot release criteria, and is currently established that tissue viability should not be less than 50% of the metabolic activity demonstrated by the fresh tissue control comparator.

p. Histology and Morphology—

Verification under microscope via visible examination of Hematoxylin and Eosin (H&E) section staining of the epidermal and dermal layers, to ensure correct cell morphology and organization of the xenotransplantation product tissues and cell infiltrate populations. This is conducted to confirm the appropriate physiologic appearance and identity of cells present in the xenotransplantation product. The xenotransplantation product is composed of minimally manipulated porcine dermal and epidermal tissue layers. This is required as a lot release criteria. Evidence of the following cell layers (from most superficial to deepest), in the epidermal layer are verified:
  i. Stratum Corneum
  ii. Stratum Granulosum
  iii. Stratum Spinosum
  iv. Stratum Basale
Evidence of the following cellular structures in the dermal layer are verified:
  v. Blood vessels, evidence of vasculature
  vi. Nerves
  vii. Various glands
  viii. Hair follicles
  ix. Collagen The genetically engineered source animals do not contain any foreign, introduced DNA into the genome; the gene modification employed is exclusively a knock-out of a single gene that was responsible for encoding for an enzyme that causes ubiquitous expression of a cell-surface antigen. It will be understood that the xenotransplantation product in one or more aspects do not incorporate transgene technologies, such as CD-46 or CD-55 transgenic constructs.

An endotoxin free status is conducted to confirm the drug product is free of endotoxins and related agents of concern. Protocols for the assurance of Endotoxin free status are as follows: Three samples from the same lot are tested for Inhibition/Enhancement of the Limulus amoebocyte lysate (LAL) test. Samples are thawed, extracted, and tested in the LAL Kinetic Chromogenic Test with a standard curve ranging from 5-50 EU/mL at a validated dilution in compliance with USP<85>.

The MTT assay is conducted to confirm the biologically active status of cells in the product. Evidence of viability is provided through surrogate markers of mitochondrial activity as compared to positive (fresh, not cryopreserved) and negative (heat-denatured) controls. The activity of the cells is required for the product to afford the intended clinical function and the viability parameters for one aspect ranging from 50% to 100% mitochondrial activity.

Verification under microscope via visible examination of Hematoxylin and Eosin (H&E) section staining of the epidermal and dermal layers, to ensure correct cell morphology and organization of the xenotransplantation product tissues and cell infiltrate populations. This is conducted to confirm the appropriate physiologic appearance and identity of cells present in the product.

For skin xenotransplantation products, evidence of the following cell layers (from most superficial to deepest), in the epidermal layer are verified: Stratum Corneum; Stratum Granulosum; Stratum Spinosum; Stratum Basale. Evidence of the following cellular structures in the dermal layer are verified: Blood vessels, evidence of vasculature; Nerves; Various glands; Hair follicles; Collagen.

The xenotransplantation product may be further processed to ensure that it remains free of aerobic and anaerobic bacteria, fungi, viruses, and *Mycoplasma*. Under sterile conditions in a laminar flow hood in a drug product processing suite using applicable aseptic techniques, immediately after, within 1, 2, 3, 4, 5, 6, 7, 8, 9, 10 seconds, within 10 seconds to 1 minute, within 1 minute to 1 hour, within 1 hour to 15 hours, or within 15 hours to 24 hours following harvest, the xenotransplantation product is sterilized, e.g., using one or more of UV irradiation or an anti-microbial/anti-fungal. In one aspect, the product may be placed into an anti-microbial/anti-fungal bath ("antipathogen bath"). The antipathogen bath may include: one or more anti-bacterial agents, e.g., ampicillin, ceftazidime, neomycin, streptomycin, chloramphenicol, cephalosporin, penicillin, tetracycline, vancomyocin, and the like; one or more anti-fungal agents, e.g., amphotericin-B, azoles, imidazoles, triazoles, thiazoles, candicidin, hamycin, natamycin, nystatin, rimocidin, allylamines, echinocandins, and the like; and/or one or more anti-viral agents. The anti-pathogen bath may include a carrier or medium as a diluent, e.g., RPMI-1640 medium. In some aspects, the anti-pathogen bath may include at least 2 anti-bacterial agents. In some aspects, the anti-pathogen bath may include at least 2 anti-bacterial agents and at least one anti-fungal agent. In some aspects, the anti-pathogen bath may include at least four agents. In some aspects, the anti-pathogen bath may include no more than 4, 5, 6, 7, 8, 9, or 10 agents. In some aspects, the anti-pathogen bath may include any combination of the foregoing.

The product may be sterilized using UV light sterilization. For example, the product is placed under the UV lamp for a desired period of time, e.g., 0.5, 1, 1.5, 2, 3, 4, 5, 6, minutes or more, then turned over to the other side, and put under the UV lamp for the same or a different period of time on opposite side. The time period for exposing a given sample to the UV may be varied based on the specific biological agents or the types of biological agents to be sterilized, e.g., as shown in the following Table 11 below. For example, the product may be sterilized using a UV lamp having a UV-C intensity of at least 100 uW/cm$^2$ for at least 2 minutes and up to 15, 12, 10, 8, 6, 5, 4, 3, or 2.5 minutes, and turned over such that its opposite surface is exposed to the UV lamp for at least 2 minutes and up to 15, 12, 10, 8, 6, 5, 4, 3, or 2.5 minutes to obtain a UV-treated product; a UV-C dosage of at least 100,000 uW sec/cm$^2$ and up to 800,000, 700,000, 600,000, 500,000, 400,000, 300,000 or 200,000 uW sec/cm$^2$; a UV-C dosage of at least 200,000 uW sec/cm$^2$ and up to 800,000, 700,000, 600,000, 500,000, 400,000, or 300,000 uW sec/cm$^2$; a UV lamp having a UV-C intensity of at least 100 uW/cm$^2$ for at least 2 minutes and up to 15, 12, 10, 8, 6, 5, 4, 3, or 2.5 minutes.

Product processing occurs in a single, continuous, and self-contained, segregated manufacturing event that begins with the sacrifice of the source animal through completion of the production of the final product. The animal is euthanized via captive bolt euthanasia, may be moved, if necessary, in a sterile, non-porous bag, to an operating room where the procedure to harvest biological product from the source animal will occur. All members of the operating team should be in full sterile surgical gear, e.g., dressed in sterile dress to maintain designated pathogen free conditions prior to receiving the source animal and in some instanced be double-gloved to minimize contamination, and surgical areas and tools are sterilized. The source animal is removed from the bag and container in an aseptic fashion. The source animal is scrubbed by operating staff, e.g., for at least 1-10 minutes with antiseptic, e.g., Chlorhexidine, brushes over the entire area of the animal where the operation will occur, periodically pouring Chlorhexidine over the area to ensure coverage. Surgical area(s) of the animal are scrubbed with opened Betadine brushes and sterile water rinse over the entire area of the animal where the operation will occur for, e.g., 1-10 minutes.

In one aspect, with regard to skin, a full thickness skin graft wound dressing consisting of dermal tissue derived from a swine in accordance with the present invention is used in conjunction or combination with cultured epidermal autografts to produce a product according to the present disclosure and that can be used in methods of the present disclosure. Prior to application of the epidermal autografts, significant debridement of wound bed is required to ensure an adequate substrate. To confirm a wound bed is ready for an epidermal autograft, apply the skin products described herein, e.g., biological skin products derived from animals of the present disclosure to confirm adherence. Once adherence is confirmed, the temporary wound coverage product is removed, and in some aspects, the wound bed is covered with a meshed autograft, and one or more cultured epidermal autograft products are placed on top to close the gaps in the autograft mesh.

The debridement may include mechanical debridement, chemical debridement, enzymatic debridement, or a combination thereof. Mechanical debridement may include surgical excision, e.g., tangential excision to remove thin layers of dermis until healthy tissue is visualized, or fascial excision to remove the full thickness of dermis down to the underlying fascia. Tangential excision allows less viable tissue to be removed with the necrotic tissue, but typically results in higher blood loss, is a larger physiologic stressor than fascial excision, and is more likely to result in "incomplete" debridement, with some devitalized tissue remaining in place. In fascial excision, blood loss and operative time are minimized, but often a large amount of healthy tissue is removed with the burned tissue. Debriding agents may include agents capable of cleaning a burn wound by removing foreign material and dead tissue. Many such agents are known. In enzymatic debridement, collagenases or other proteolytic enzymes are employed that break down proteins of the extracellular matrix, allowing devitalized tissue to be wiped away without the need for surgery while preferably leaving healthy tissue substantially intact. Enzymatic debridement involves the application of proteolytic and optionally other exogenous enzymes to a wound surface to break down necrotic tissue. Enzymatic debridement may be a relatively slow process, carried out over a period of a number of weeks in combination with other topical preparations, soakings and repeated dressings. Alternately, rapid enzymatic debridement can be accomplished using multi-enzyme products, for example, those extracted from the stem of the pineapple plant, as disclosed for example in WO 98/053850 and WO 2006/0006167, and as provided in the product marketed under the trade name Debrase®. A procedure for enzymatic debridement generally utilizes an enzyme such as bromelain derivatives, debridase, collagenase, papain derivatives, streptokinase, sutilains, fibrinolysin, deoxyribonuclease, krill derivatives, trypsin or combinations thereof. Autolytic debridement relies on enhancing the natural process of selective liquefaction, separation and digestion of necrotic tissue and eschar from healthy tissue that occurs in wounds due to macrophage and endogenous proteolytic activity. This is achieved by the use of occlusive, semi-occlusive or moist interactive dressings. Enzymatic debridement agents include a bromelain enriched enzyme product, other collagenases, or other enzyme products capable of clearing devitalized tissue or wound debris. NexoBrid™ (MediWound Ltd.) is one such bromelain enriched product that specifically targets heat-denatured collagen for degradation, resulting in partial-thickness and full-thickness wounds requiring a wound coverage or dressing product. Such products and methods are described in U.S. Pat. Nos. 8,540,983; 8,119,124; 7,128,719; 7,794,709; 8,624,077; and US2009/0010910A1, each of which is incorporated by reference herein.

In some aspects, the wound bed may include or be a chronic wound or an acute wound. Chronic wounds include but are not limited to venous leg ulcers, pressure ulcers, and diabetic foot ulcers. Acute wounds include but are not limited to burns, traumatic injuries, amputation wounds, skin graft donor sites, bite wounds, frostbite wounds, dermabrasions, and surgical wounds.

In the cases where there is no dermis, biological products produced in accordance with the present invention are utilized. The epidermis is removed from such products (e.g., before dermis harvesting on the pig with a VERSAJET™ Hydrosurgery system), so that just the dermis remains. Then, the subject biological product is placed on the patient's subcutaneous tissue, serving as a substrate for the cultured epidermal autograft process described herein.

In one aspect, a liver derived in accordance with the present disclosure is utilized for extracorporeal perfusion as a temporary filter for a human patient until a patient receives a human transplant. In an operating area within the DPF Isolation Area, a source animal is placed under a general anesthetic (ketamine, xylazine, enflurane) or euthanized by captive bolt. A hepatectomy is then performed on the source animal in designated pathogen free conditions. The liver product derived from the source animal can be packaged and transported to the location of the procedure in accordance with current practice with human donor livers. The procedure to utilize the liver filtration product can be performed, for example, by percutaneously cannulating a human patient's internal jugular vein for venous return with an arterial cannula and percutaneously cannulating a patient's femoral vein for venous outflow with an artery cannula. These cannulas are connected to a bypass circuit, having a centrifugal pump, a heat exchanger, an oxygenator, and a roller pump incorporated therein. This circuit is primed with crystalloids and run for a period of time (e.g., 10-30 minutes) before the liver from an animal according to the present disclosure is incorporated at a stabilized flow rate, e.g., 600-1000 ml/min, maintained in a crystalloid bath occasionally supplemented with warm solution, e.g., 30-40° C.

It will be understood that, in the context of swine-to-human xenotransplantation, each human recipient will have a major histocompatibility complex (MHC) (Class I, Class II and/or Class III) that is unique to that individual and will not match the MHC of the donor swine. Accordingly, it will be understood that when a donor swine graft is introduced to the recipient, the swine MHC molecules themselves act as non-gal xeno-antigens, provoking an immune response from the recipient, leading to transplant rejection.

Human leukocyte antigen (HLA) genes show incredible sequence diversity in the human population. For example, there are >4,000 known alleles for the HLA-B gene alone. The genetic diversity in HLA genes in which different alleles have different efficiencies for presenting different antigens is believed to be a result of evolution conferring better population-level resistance against the wide range of different pathogens to which humans are exposed. This genetic diversity also presents problems during xenotransplantation where the recipient's immune response is the most important factor dictating the outcome of engraftment and survival after transplantation.

In accordance with one aspect the present invention, a donor swine is provided with a genome that is biologically engineered to express a specific set of known human HLA molecules. Such HLA sequences are available, e.g., in the IPD-IMGT/HLA database (available at ebi.ac.uk/ipd/imgt/hla/) and the international ImMunoGeneTics Information System® (available at imgt.org). For example, HLA-A1, B8, DR17 is the most common HLA haplotype among Caucasians, with a frequency of 5%. Thus, the disclosed method can be performed using the known MHC/HLA sequence information in combination with the disclosures provided herein.

In some aspects, the recipient's human leukocyte antigen (HLA) genes and MHC (Class I, II and/or III), are identified and mapped. It will be understood that ascertaining the human recipient's HLA/MHC sequence can be done in any number of ways known in the art. For example, HLA/MHC genes are usually typed with targeted sequencing methods: either long-read sequencing or long-insert short-read sequencing. Conventionally, HLA types have been determined at 2-digit resolution (e.g., A*01), which approximates the serological antigen groupings. More recently, sequence specific oligonucleotide probes (SSOP) method has been used for HLA typing at 4-digit resolution (e.g., A*01:01), which can distinguish amino acid differences. Currently, targeted DNA sequencing for HLA typing is the most popular approach for HLA typing over other conventional methods. Since the sequence-based approach directly determines both coding and non-coding regions, it can achieve HLA typing at 6-digit (e.g., A*01:01:01) and 8-digit (e.g., A*01:01:01:01) resolution, respectively. HLA typing at the highest resolution is desirable to distinguish existing HLA alleles from new alleles or null alleles from clinical perspective. Such sequencing techniques are described in, for example, Elsner H A, Blasczyk R: (2004) Immunogenetics of HLA null alleles: implications for blood stem cell transplantation. Tissue antigens. 64 (6): 687-695; Erlich R L, et al (2011) Next-generation sequencing for HLA typing of Class I loci. BMC genomics. 12: 42-10.1186/1471-2164-12-42; Szolek A, et al. (2014) OptiType: Precision HLA typing from next-generation sequencing data. Bioinformatics 30:3310-3316; Nariai N, et al. (2015) HLA-VBSeq: Accurate HLA typing at full resolution from whole-genome sequencing data. BMC Genomics 16:S7; Dilthey A T, et al. (2016) High-accuracy HLA type inference from whole-genome sequencing data using population reference graphs. PLoS Comput Biol 12:e1005151; Xie C., et al. (2017) Fast and accurate HLA typing from short-read next-generation sequence data with xHLA 114 (30) 8059-8064, each of which is incorporated herein in its entirety by reference.

The known human HLA/MHC or an individual recipient's sequenced HLA/MHC sequence(s) may be utilized as a template to modify the swine leukocyte antigen (SLA)/MHC sequence to match, e.g., to have 80%, 85%, 90%, 95%, 98%, 99%, or 100% sequence homology to a known human HLA/MHC sequence or the human recipient's HLA/MHC sequence. Upon identifying a known human recipient HLA/MHC sequence to be used or performing genetic sequencing of a human recipient to obtain HLA/MHC sequences, biological reprogramming may be performed to SLA/MHC sequences in cells of the swine based on desired HLA/MHC sequences. For example, several targeting guide RNA (gRNA) sequences are administered to the swine of the present disclosure to reprogram SLA/MHC sequences in cells of the swine with the template HLA/MHC sequences of the human recipient.

CRISPR-Cas9 is used to mediate rapid and scarless exchange of entire MHC alleles at specific native locus in swine cells. Multiplex targeting of Cas9 with two gRNAs is used to introduce single or double-stranded breaks flanking the MHC allele, enabling replacement with the template HLA/MHC sequence (provided as a single or double-stranded DNA template). In certain aspects, the CRISPR/Cas9 components are injected into swine oocytes, ova, zygotes, or blastocytes prior to transfer into foster mothers.

In certain aspects, the present disclosure includes embryogenesis and live birth of SLA-free and HLA-expressing biologically reprogrammed swine. In certain aspects, the present disclosure includes breeding SLA-free and HLA-expressing biologically reprogrammed swine to create SLA-free and HLA-expressing progeny. In certain aspects, the CRISPR/Cas9 components are injected into swine zygotes by intracytoplasmic microinjection of porcine zygotes. In certain aspects, the CRISPR/Cas9 components are injected into swine prior to selective breeding of the CRISPR/Cas9 genetically modified swine. In certain aspects, the CRISPR/Cas9 components are injected into donor swine prior to harvesting cells, tissues, zygotes, and/or organs from the swine. In certain aspects, the CRISPR/Cas9 components include all necessary components for controlled gene editing including self-inactivation utilizing governing gRNA molecules as described in U.S. Pat. No. 9,834,791 (Zhang), which is incorporated herein by reference in its entirety.

The genetic modification can be made utilizing known genome editing techniques, such as zinc-finger nucleases (ZFNs), transcription activator-like effector nucleases (TALENs), adeno-associated virus (AAV)-mediated gene editing, and clustered regular interspaced palindromic repeat Cas9 (CRISPR-Cas9). These programmable nucleases enable the targeted generation of DNA double-stranded breaks (DSB), which promote the upregulation of cellular repair mechanisms, resulting in either the error-prone process of non-homologous end joining (NHEJ) or homology-directed repair (HDR), the latter of which can be used to integrate exogenous donor DNA templates. CRISPR-Cas9 may also be used to remove viral infections in cells. For example, the genetic modification via CRISPR-Cas9 can be performed in a manner described in Kelton, W. et. al., "Reprogramming MHC specificity by CRISPR-Cas9-assisted cassette exchange," Nature, Scientific Reports, 7:45775 (2017) ("Kelton"), the entire disclosure of which is incorporated herein by reference. Accordingly, the present disclosure includes reprogramming using CRISPR-Cas9 to mediate rapid and scarless exchange of entire alleles, e.g., MHC, HLA, SLA, etc.

In one aspect, the recipient's HLA/MHC gene is sequenced and template HLA/MHC sequences are prepared based on the recipient's HLA/MHC genes. In another aspect, a known human HLA/MHC genotype from a WHO database may be used for genetic reprogramming of swine of the present disclosure. CRISPR-Cas9 plasmids are prepared, e.g., using polymerase chain reaction and the recipient's HLA/MHC sequences are cloned into the plasmids as templates. CRISPR cleavage sites at the SLA/MHC locus in the swine cells are identified and gRNA sequences targeting the cleavage sites and are cloned into one or more CRISPR-Cas9 plasmids. CRISPR-Cas9 plasmids are then administered into the swine cells and CRIPSR/Cas9 cleavage is performed at the MHC locus of the swine cells.

The SLA/MHC locus in the swine cells are replaced with one or more template HLA/MHC sequences matching the known human HLA/MHC sequences or the recipient's sequenced HLA/MHC genes. Cells of the swine are sequenced after performing the SLA/MHC reprogramming steps in order to determine if the HLA/MHC sequences in the swine cells have been successfully reprogrammed. One or more cells, tissues, and/or organs from the HLA/MHC sequence-reprogrammed swine are transplanted into a human recipient.

In certain aspects, HLA/MHC sequence-reprogrammed swine are bred for at least one generation, or at least two generations, before their use as a source for live tissues, organs and/or cells used in xenotransplantation. In certain aspects, the CRISPR/Cas9 components can also be utilized to inactivate genes responsible for PERV activity, e.g., the pol gene, thereby simultaneously completely eliminating PERV from the swine donors.

For purposes of modifying donor SLA/MHC to match recipient HLA/MHC, comparative genomic organization of the human and swine histocompatibility complex has been mapped. For example, such SLA to HLA mapping can be found in: Lunney, J., "Molecular genetics of the swine major histocompatibility complex, the SLA complex," Developmental and Comparative Immunology 33: 362-374 (2009) ("Lunney"), the entire disclosure of which is incorporated herein by reference. Accordingly, a person of ordinary skill in the art effectively and efficiently genetically reprogram swine cells in view of the present disclosure and using the mapping of Lunney et al. as a reference tool.

The modification to the donor SLA/MHC to match recipient HLA/MHC causes expression of specific MHC molecules from the swine cells that are identical, or virtually identical, to the MHC molecules of a known human genotype or the specific human recipient. In one aspect, the present disclosure involves making modifications limited to only specific portions of specific SLA regions of the swine's genome to retain an effective immune profile in the swine while biological products are hypoimmunogenic when transplanted into human recipients such that use of immunosuppressants can be reduced or avoided. In contrast to aspects of the present disclosure, xenotransplantation studies of the prior art required immunosuppressant use to resist rejection. In one aspect, the swine genome is reprogrammed to knock-out swine genes corresponding to HLA-A, HLA-B, HLA-C, and DR, and to knock-in HLA-C, HLA-E, HLA-G. In some aspects, the swine genome is reprogrammed to knock-out swine genes corresponding to HLA-A, HLA-B, HLA-C, HLA-F, DQ, and DR, and to knock-in HLA-C, HLA-E, HLA-G. In some aspects, the swine genome is reprogrammed to knock-out swine genes corresponding to HLA-A, HLA-B, HLA-C, HLA-F, DQ, and DR, and to knock-in HLA-C, HLA-E, HLA-G, HLA-F, and DQ. In one aspect, the swine genome is reprogrammed to knock-out SLA-11; SLA-6,7,8; SLA-MIC2; and SLA-DQA; SLA-DQB1; SLA-DQB2, and to knock-in HLA-C; HLA-E; HLA-G; and HLA-DQ. In certain aspects, HLA-C expression is reduced in the reprogrammed swine genome. By reprogramming the swine cells to be invisible to a human's immune system, this reprogramming thereby minimizes or even eliminates an immune response that would have otherwise occurred based on swine MHC molecules otherwise expressed from the donor swine cells.

It will therefore be understood that this aspect (i.e., reprogramming the SLA/MHC to express specifically selected human MHC alleles), when applied to swine cells, tissues, and organs for purposes of xenotransplantation will decrease rejection as compared to cells, tissues, and organs derived from a wild-type swine or otherwise genetically modified swine that lacks this reprogramming, e.g., transgenic swine or swine with non-specific or different genetic modifications.

It will be further understood that causing the donor swine cells, tissues, and organs to express a known human MHC genotype or the recipient's MHC specifically as described herein, combined with the elimination in the donor swine cells of alpha-1,3-galactosytransferase, Neu5Gc, and β1,4-N-acetylgalactosaminyltransferase (B4GALNT2) (e.g., "single knockout," "double knockout," or "triple knockout"), presents a swine whose cells will have a decreased immunological rejection as compared to a triple knockout swine that lacks the specific SLA/MHC reprogramming of the present disclosure.

Cryopreservation and storage according to the present disclosure includes preparing biological product according to the present disclosures, placing in a container, adding freeze media to the container and sealing. For example. 15% dimethyl sulfoxide (DMSO) cryoprotective media is combined with fetal porcine serum (FPS) or donor serum (if FPS is unavailable) in a 1:1 ratio, filtered (0.45 micron), and chilled to 4° C. prior to use. The containers are subsequently frozen in a controlled rate, phase freezer at a rate of 1° C. per minute to −40° C., then rapidly cooled to a temperature −80° C. DMSO displaces intracellular fluid during the freezing process. Cryoprotective media, e.g., CryoStor is used in an amount of about 40-80%, or 50-70% based on maximum internal volume of the cryovial (10 ml) less the volume of the xenotransplantation product. In order to thaw the cryopreserved biological product for surgical use, sealed vials were placed in ~37° C. water baths for approximately 0.5 to 2 minutes, at which point the container is opened and the product was removed using sterile technique. Subsequently, products undergo three, 1-minute serial washes, e.g., in saline with gentle agitation, in order to dilute and systematically remove ambient, residual DMSO and prevent loss of cell viability. The product may then be used surgically.

It will be understood that the xenotransplantation product may be processed, stored, transported, and/or otherwise handled using materials, containers and processes to ensure preserved sterility and prevent damage thereto. In some aspects, a sterile non-adhesive material may be used to protect the xenotransplantation product, e.g., to support the xenotransplantation product and prevent adhesive of the product to surfaces and/or to prevent self-adhesion of the xenotransplantation product during manipulation, storage, or transport. Unintentional adhesion of the xenotransplantation product may disrupt the integrity of the xenotransplantation product and potentially reduce its therapeutic viability. Inclusion of the sterile non-adhesive material provides protection and/or physical support and prevents adhesion. In some aspects, the sterile non-adhesive material is not biologically or chemically active and does not directly impact the metabolic activity or efficacy of the xenotransplantation product itself.

Aspects of the present disclosure are further described by the following non-limiting list of items:

Item 1. A biological system for generating and preserving a repository of personalized, humanized transplantable cells, tissues, and organs for transplantation, wherein the biological system is biologically active and metabolically active, the biological system comprising genetically reprogrammed cells, tissues, and organs in a non-human animal for transplantation into a human recipient, wherein the non-human animal is a genetically reprogrammed swine for xenotransplantation of cells, tissue, and/or an organ isolated from the genetically reprogrammed swine, the genetically reprogrammed swine comprising a nuclear genome that has been reprogrammed to replace a plurality of nucleotides in a plurality of exon regions of a major histocompatibility complex of a wild-type swine with a plurality of synthesized nucleotides from a human captured reference sequence, and wherein cells of said genetically reprogrammed swine do not present one or more surface glycan epitopes selected from alpha-Gal, Neu5Gc, and SD$^a$, and wherein genes encoding alpha-1,3 galactosyltransferase, cytidine monophosphate-N-acetylneuraminic acid hydroxylase (CMAH), and β1,4-N-acetylgalactosaminyltransferase are altered such that the genetically reprogrammed swine lacks functional expression of surface glycan epitopes encoded by said genes, wherein the reprogrammed genome comprises site-directed mutagenic substitutions of nucleotides at exon regions of: i) at least one of the wild-type swine's SLA-1, SLA-2, and SLA-3 with nucleotides from an orthologous exon region of HLA-A, HLA-B, and HLA-C, respectively, of the human captured reference sequence; and ii) at least one the wild-type swine's SLA-6, SLA-7, and SLA-8 with nucleotides from an orthologous exon region of HLA-E, HLA-F, and HLA-G, respectively, of the human captured reference sequence; and iii) at least one of the wild-type swine's SLA-DR and SLA-DQ with nucleotides from an orthologous exon region of HLA-DR and HLA-DQ, respectively, of the human captured reference sequence, wherein the reprogrammed genome comprises at least one of A-C:
A) wherein the reprogrammed swine nuclear genome comprises site-directed mutagenic substitutions of nucleotides at exon regions of the wild-type swine's β2-microglobulin with nucleotides from orthologous exons of a known human β2-microglobulin from the human captured reference sequence;
B) wherein the reprogrammed swine nuclear genome comprises a polynucleotide that encodes a polypeptide that is a humanized beta 2 microglobulin (hB2M) polypeptide sequence that is at least 95% identical to the amino acid sequence of beta 2 microglobulin glycoprotein expressed by the human captured reference genome;
C) wherein the reprogrammed swine nuclear genome has been reprogrammed such that, at the swine's endogenous β2-microglobulin locus, the nuclear genome has been reprogrammed to comprise a nucleotide sequence encoding β2-microglobulin polypeptide of the human recipient, wherein the reprogrammed swine nuclear genome has been reprogrammed such that the genetically reprogrammed swine lacks functional expression of the wild-type swine's endogenous β2-microglobulin polypeptides, and wherein said reprogramming does not introduce any frameshifts or frame disruptions.

Item 2. The biological system of item 1, wherein the genetically reprogrammed swine is non-transgenic.

Item 3. The biological system of item 1 or item 2, wherein intron regions of the wild-type swine's genome are not reprogrammed.

Item 4. The biological system of any one of or combination of items 1-3, wherein said genetically reprogrammed swine is free of at least the following pathogens: *Ascaris* species, *Cryptosporidium* species, *Echinococcus*, *Strongyloids sterocolis*, *Toxoplasma gondii*, *Brucella suis*, *Leptospira* species, *Mycoplasma hyopneumoniae*, porcine reproductive and respiratory syndrome, pseudorabies, *Staphylococcus* species, *Microphyton* species, *Trichophyton* species, porcine influenza, porcine cytomegalovirus, arterivirus, coronavirus, *Bordetella bronchiseptica*, and Livestock-associated methicillin-resistant *Staphylococcus aureus*.

Item 5. The biological system of any one of or combination of items 1-4, wherein said genetically reprogrammed swine is maintained according to a bioburden-reducing procedure, said procedure comprising maintaining the swine in an isolated closed herd, wherein all other animals in the isolated closed herd are confirmed to be free of said pathogens, and wherein the swine is isolated from contact with any non-human animals and animal housing facilities outside of the isolated closed herd.

Item 6. The biological system of any one of or combination of items 1-4, wherein the wild-type swine genome comprises reprogrammed nucleotides at SLA-MIC-2 gene and at exon regions encoding SLA-3, SLA-6, SLA-7, SLA-8, SLA-DQ, CTLA-4, PD-L1, EPCR, TBM, TFPI, and beta-2-microglobulin using the human capture reference sequence, wherein the human cell, tissue, or organ lacks functional expression of swine beta-2-microglobulin, SLA-1, SLA-2, and SLA-DR.

Item 7. The biological system of any one of or combination of items 1-5, wherein the wild-type swine genome comprises reprogrammed nucleotides at one or more of a CTLA-4 promoter and a PD-L1 promoter, wherein the one or more of the CTLA-4 promoter and the PD-L1 promoter are reprogrammed to increase expression of one or both of reprogrammed CTLA-4 and reprogrammed PD-L1 compared to the wild-type swine's endogenous expression of CTLA-4 and PD-L1.

Item 8. The biological system of any one of or combination of items 1-6, wherein a total number of the synthesized nucleotides is equal to a total number of the replaced nucleotides, such that there is no net loss or net gain in number of nucleotides after reprogramming the genome of the wild-type swine with the synthesized nucleotides.

Item 9. The biological system of any one of or combination of items 1-7, wherein the reprogramming with the plurality of synthesized nucleotides do not include replacement of nucleotides in codon regions that encode amino acids that are conserved between the wild-type swine MHC sequence and the human captured reference sequence Item 10. The biological system of any one of or combination of items 1-8, wherein the reprogrammed genome comprises site-directed mutagenic substitutions of nucleotides at the major histocompatibility complex of the wild-type swine with orthologous nucleotides from the human captured reference sequence.

Item 11. The biological system of any one of or combination of items 1-9, wherein site-directed mutagenic substitutions are made in germ-line cells used to produce the non-human animal.

Item 12. The biological system of any one of or combination of items 1-10, wherein the human captured reference sequence is a human patient capture sequence, a human population-specific human capture sequence, or an allele-group-specific human capture sequence.

Item 13. The biological system of any one of or combination of items 1-11, wherein the reprogrammed genome comprises site-directed mutagenic substitutions of nucleotides at exon regions of the wild-type swine's SLA-1 with nucleotides from an orthologous exon region of a HLA-A captured reference sequence.

Item 14. The biological system of any one of or combination of items 1-12, wherein the reprogrammed genome comprises site-directed mutagenic substitutions of nucleotides at exon regions of the wild-type swine's SLA-2 with nucleotides from an orthologous exon region of a HLA-B captured reference sequence.

Item 14. The biological system of any one of or combination of items 1-13, wherein the reprogrammed genome comprises site-directed mutagenic substitutions of nucleotides at exon regions of the wild-type swine's SLA-3 with nucleotides from an orthologous exon region of a HLA-C captured reference sequence.

Item 15. The biological system of any one of or combination of items 1-14, wherein the reprogrammed genome comprises site-directed mutagenic substitutions of nucleotides at exon regions of the wild-type swine's SLA-6 with nucleotides from an orthologous exon region of a HLA-E captured reference sequence.

Item 16. The biological system of any one of or combination of items 1-15, wherein the reprogrammed genome comprises site-directed mutagenic substitutions of nucleotides at exon regions of the wild-type swine's SLA-7 with nucleotides from an orthologous exon region of a HLA-F captured reference sequence.

Item 17. The biological system of any one of or combination of items 1-16, wherein the reprogrammed genome comprises site-directed mutagenic substitutions of nucleotides at exon regions of the wild-type swine's SLA-8 with nucleotides from an orthologous exon region of a HLA-G captured reference sequence.

Item 18. The biological system of any one of or combination of items 1-17, wherein the reprogrammed genome comprises site-directed mutagenic substitutions of nucleotides at exon regions of the wild-type swine's MHC class I chain-related 2 (MIC-2).

Item 19. The biological system of any one of or combination of items 1-18, wherein the reprogrammed genome lacks functional expression of SLA-1, SLA-2, SLA-DR, or a combination thereof.

Item 20. The biological system of any one of or combination of items 1-19, wherein the reprogrammed genome comprises site-directed mutagenic substitutions of nucleotides at exon regions of the wild-type swine's SLA-DQA from an orthologous exon region of a HLA-DQA1 captured reference sequence.

Item 21. The biological system of any one of or combination of items 1-20, wherein the reprogrammed genome comprises site-directed mutagenic substitutions of nucleotides at exon regions of the wild-type swine's SLA-DQB from an orthologous exon region of a HLA-DQB1 captured reference sequence.

Item 22. The biological system of any one of or combination of items 1-21, wherein the reprogrammed genome comprises site-directed mutagenic substitutions of nucleotides at exon regions of the wild-type swine's SLA-DRA and SLA-DRB1 with nucleotides from orthologous exon regions of HLA-DRA1 and HLA-DRB1 of the human captured reference sequence, or wherein the reprogrammed genome lacks functional expression of SLA-DRA and SLA-DRB1.

Item 23. The biological system of any one of or combination of items 1-22, wherein the reprogrammed genome comprises site-directed mutagenic substitutions of nucleotides at exon regions of the wild-type swine's SLA-DQA and SLA-DQB1 with nucleotides from orthologous exon regions of HLA-DQA1 and HLA-DQB1 of the human captured reference sequence.

Item 24. The biological system of any one of or combination of items 1-23, wherein the site-directed mutagenic substitutions of nucleotides are at codons that are not conserved between the wild-type swine's nuclear genome and the known human sequence.

Item 25. The biological system of any one of or combination of items 1-24, wherein the reprogrammed genome comprises site-directed mutagenic substitutions of nucleotides at exon regions of the wild-type swine's B2-microglobulin with nucleotides from orthologous exons of a known human B2-microglobulin.

Item 26. The biological system of any one of or combination of items 1-25, wherein the reprogrammed swine nuclear genome comprises a polynucleotide that encodes a polypeptide that is a humanized beta 2 microglobulin (hB2M) polypeptide sequence that is at least 95% identical to the amino acid sequence of beta 2 microglobulin glycoprotein expressed by the human captured reference genome;

Item 27. The biological system of any one of or combination of items 1-26, wherein said nuclear genome has been reprogrammed such that the genetically reprogrammed swine lacks functional expression of the wild-type swine's endogenous β2-microglobulin polypeptides.

Item 28. The biological system of any one of or combination of items 1-27, wherein said nuclear genome has been reprogrammed such that, at the swine's endogenous β2-microglobulin locus, the nuclear genome has been reprogrammed to comprise a nucleotide sequence encoding β2-microglobulin polypeptide of the human captured reference sequence.

Item 29. The biological system of any one of or combination of items 1-28, wherein the reprogrammed genome comprises site-directed mutagenic substitutions of nucleotides at exon regions of SLA-3, SLA-6, SLA-7, SLA-8, and MIC-2.

Item 30. The biological system of any one of or combination of items 1-29, wherein the reprogrammed genome comprises site-directed mutagenic substitutions of nucleotides at exon regions of SLA-DQ and MIC-2.

Item 31. The biological system of any one of or combination of items 1-30, wherein the reprogrammed genome comprises site-directed mutagenic substitutions of nucleotides at SLA-3, SLA-6, SLA-7, SLA-8, SLA-DQ, and MIC-2.

Item 32. The biological system of any one of or combination of items 1-31, wherein the reprogrammed genome lacks functional expression of SLA-DR, SLA-1, and/or SLA-2.

Item 33. The biological system of any one of or combination of items 1-32, wherein the nuclear genome is reprogrammed using scarless exchange of the exon regions, wherein there are no frameshifts, insertion mutations, deletion mutations, missense mutations, and nonsense mutations.

Item 34. The biological system of any one of or combination of items 1-33, wherein the nuclear genome is reprogrammed without introduction of any net insertions, deletions, truncations, or other genetic alterations that would cause a disruption of protein expression via frame shift, nonsense, or missense mutations.

Item 35. The biological system of any one of or combination of items 1-34, wherein nucleotides in intron regions of the nuclear genome are not altered.

Item 36. The biological system of any one of or combination of items 1-35, wherein said nuclear genome is reprogrammed to be homozygous at the reprogrammed exon regions.

Item 37. The biological system of any one of or combination of items 1-36, wherein said nuclear genome is reprogrammed such that extracellular, phenotypic surface expression of polypeptide is tolerogenic in a human recipient.

Item 38. The biological system of any one of or combination of items 1-37, wherein said nuclear genome is reprogrammed such that expression of cytotoxic T-lymphocyte-associated protein 4 (CTLA-4) is increased by reprogramming a CTLA-4 promoter sequence.

Item 39. The biological system of any one of or combination of items 1-38, wherein the reprogrammed genome comprises site-directed mutagenic substitutions of nucleotides at exon regions of the wild-type CTLA-4 with nucleotides from orthologous exons of a human captured reference sequence CTLA-4.

Item 40. The biological system of any one of or combination of items 1-39, wherein the reprogrammed nuclear genome comprises a polynucleotide that encodes a protein that is a humanized CTLA-4 polypeptide sequence that is at least 95% identical to CTLA-4 expressed by the human captured reference genome.

Item 41. The biological system of any one of or combination of items 1-40, wherein said nuclear genome is reprogrammed such that expression of Programmed death-ligand 1 (PD-L1) is increased by reprogramming a PD-L1 promoter sequence.

Item 42. The biological system of any one of or combination of items 1-41, wherein the reprogrammed genome comprises site-directed mutagenic substitutions of nucleotides at exon regions of the wild-type PD-L1 with nucleotides from orthologous exons of a known human PD-L1.

Item 43. The biological system of any one of or combination of items 1-42, wherein the reprogrammed nuclear genome comprises a polynucleotide that encodes a protein that is a humanized PD-L1 polypeptide sequence that is at least 95% identical to PD-L1 expressed by the human captured reference genome.

Item 44. A genetically reprogrammed, biologically active and metabolically active non-human cell, tissue, or organ obtained from the biological system of any one of or combination of items 1-43.

Item 45. The genetically reprogrammed, biologically active and metabolically active non-human cell, tissue, or organ of item 44, wherein the genetically reprogrammed, biologically active and metabolically active non-human cell is a stem cell, an embryonic stem cell, a pluripotent stem cell, or a differentiated stem cell.

Item 46. The genetically reprogrammed, biologically active and metabolically active non-human cell, tissue, or organ of item 45, wherein the stem cell is a hematopoietic stem cell.

Item 47. The genetically reprogrammed, biologically active and metabolically active non-human cell, tissue, or organ of item 44, wherein the genetically reprogrammed, biologically active and metabolically active non-human tissue is a nerve, cartilage, or skin.

Item 48. The genetically reprogrammed, biologically active and metabolically active non-human cell, tissue, or organ of item 44, wherein the genetically reprogrammed, biologically active and metabolically active non-human organ is a solid organ.

Item 49. A method of preparing a genetically reprogrammed swine comprising a nuclear genome that lacks functional expression of surface glycan epitopes selected from alpha-Gal, Neu5Gc, and $SD^a$ and is genetically reprogrammed to express a humanized phenotype of a human captured reference sequence comprising:
  a. obtaining a porcine fetal fibroblast cell, a porcine zygote, a porcine Induced Pluripotent Stem Cells (IPSC), or a porcine germ-line cell;
  b. genetically altering said cell in a) to lack functional alpha-1,3 galactosyltransferase, cytidine monophosphate-N-acetylneuraminic acid hydroxylase (CMAH), and β1,4-N-acetylgalactosaminyltransferase;
  c. genetically reprogramming said cell in b) using clustered regularly interspaced short palindromic repeats (CRISPR)/Cas for site-directed mutagenic substitutions of nucleotides at exon regions of: i) at least one of the wild-type swine's SLA-1, SLA-2, and SLA-3 with nucleotides from an orthologous exon region of HLA-A, HLA-B, and HLA-C, respectively, of the human captured reference sequence; and ii) at least one the wild-type swine's SLA-6, SLA-7, and SLA-8 with nucleotides from an orthologous exon region of HLA-E, HLA-F, and HLA-G, respectively, of the human captured reference sequence; and iii) at least one of the wild-type swine's SLA-DR and SLA-DQ with nucleotides from an orthologous exon region of HLA-DR and HLA-DQ, respectively, of the human captured reference sequence,
wherein intron regions of the wild-type swine's genome are not reprogrammed, and
wherein the reprogrammed genome comprises at least one of A-C:
A) wherein the reprogrammed swine nuclear genome comprises site-directed mutagenic substitutions of nucleotides at exon regions of the wild-type swine's β2-microglobulin with nucleotides from orthologous exons of a known human β2-microglobulin from the human captured reference sequence;
B) wherein the reprogrammed swine nuclear genome comprises a polynucleotide that encodes a polypeptide that is a humanized beta 2 microglobulin (hB2M) polypeptide sequence that is at least 95% identical to beta 2 microglobulin expressed by the human captured reference genome;
C) wherein the reprogrammed swine nuclear genome has been reprogrammed such that the genetically reprogrammed swine lacks functional expression of the wild-type swine's endogenous β2-microglobulin polypeptides, wherein the reprogrammed swine nuclear genome has been reprogrammed such that, at the swine's endogenous β2-microglobulin locus, the nuclear genome has been reprogrammed to comprise a nucleotide sequence encoding β2-microglobulin polypeptide of the human recipient, wherein said reprogramming does not introduce any frameshifts or frame disruptions,
  d. generating an embryo from the genetically reprogrammed cell in c); and
  e. transferring the embryo into a surrogate pig and growing the transferred embryo in the surrogate pig.

Item 50. The method of item 49, wherein step (a) further comprises replacing a plurality of nucleotides in a plurality of exon regions of a major histocompatibility complex of a wild-type swine with nucleotides from orthologous exon regions of a major histocompatibility complex sequence from the human captured reference sequence, wherein said replacing does not introduce any frameshifts or frame disruptions.

Item 51. The method of any one of or combination of items 49-50, wherein said replacing comprises performing site-directed mutagenic substitutions of nucleotides at the major histocompatibility complex of the wild-type swine with orthologous nucleotides from the known human major histocompatibility complex sequence.

Item 52. The method of any one of or combination of items 49-51, wherein the human captured reference sequence is a human patient capture sequence, a human population-specific human capture sequence, or an allele-group-specific human capture sequence.

Item 53. The method of any one of or combination of items 49-52, wherein the orthologous exon regions are at one or more polymorphic glycoproteins of the wild-type swine's major histocompatibility complex.

Item 54. The method of any one of or combination of items 49-53, further comprising: impregnating the surrogate pig with the embryo, gestating the embryo, and delivering a piglet from the surrogate pig through Cesarean section, confirming that said piglet is free of at least the following zoonotic pathogens:
(i) *Ascaris* species, *Cryptosporidium* species, *Echinococcus*, *Strongyloids sterocolis*, and *Toxoplasma gondii* in fecal matter;
(ii) *Leptospira* species, *Mycoplasma hyopneumoniae*, porcine reproductive and respiratory syndrome virus (PRRSV), pseudorabies, transmissible gastroenteritis virus (TGE)/Porcine Respiratory Coronavirus, and *Toxoplasma Gondii* by determining antibody titers;
(iii) Porcine Influenza;
(iv) the following bacterial pathogens as determined by bacterial culture: *Bordetella bronchisceptica*, Coagulase-positive staphylococci, Coagulase-negative staphylococci, Livestock-associated methicillin resistant *Staphylococcus aureus* (LA MRSA), *Microphyton* and *Trichophyton* spp.;
(v) Porcine cytomegalovirus; and
(vi) *Brucella suis*; and
maintaining the piglet according to a bioburden-reducing procedure, said procedure comprising maintaining the piglet in an isolated closed herd, wherein all other animals in the isolated closed herd are confirmed to be free of said zoonotic pathogens, wherein the piglet is isolated from contact with any non-human animals and animal housing facilities outside of the isolated closed herd.

Item 55. The method of any one of or combination of items 49-54, wherein the wild-type swine genome comprises reprogrammed nucleotides at SLA-MIC-2 gene and at exon regions encoding SLA-3, SLA-6, SLA-7, SLA-8, SLA-DQ, CTLA-4, PD-L1, EPCR, TBM, TFPI, and beta-2-microglobulin using the human capture reference sequence, wherein the human cell, tissue, or organ lacks functional expression of swine beta-2-microglobulin, SLA-DR, SLA-1, and SLA-2.

Item 56. The method of any one of or combination of items 49-55, wherein the wild-type swine genome comprises reprogrammed nucleotides at one or more of a CTLA-4 promoter and a PD-L1 promoter, wherein the one or more of the CTLA-4 promoter and the PD-L1 promoter are reprogrammed to increase expression of one or both of reprogrammed CTLA-4 and reprogrammed PD-L1 compared to the wild-type swine's endogenous expression of CTLA-4 and PD-L1.

Item 57. The method of any one of or combination of items 49-56, wherein a total number of the synthesized nucleotides is equal to a total number of the replaced nucleotides, such that there is no net loss or net gain in number of nucleotides after reprogramming the genome of the wild-type swine with the synthesized nucleotides.

Item 58. The method of any one of or combination of items 49-57, wherein the reprogramming with the plurality of synthesized nucleotides do not include replacement of nucleotides in codon regions that encode amino acids that are conserved between the wild-type swine MHC sequence and the human captured reference sequence Item 59. The method of any one of or combination of items 49-58, wherein the reprogrammed genome comprises site-directed mutagenic substitutions of nucleotides at the major histocompatibility complex of the wild-type swine with orthologous nucleotides from the human captured reference sequence.

Item 60. The method of any one of or combination of items 49-59, wherein site-directed mutagenic substitutions are made in germ-line cells used to produce the non-human animal.

Item 61. The method of any one of or combination of items 49-60, wherein the human captured reference sequence is a human patient capture sequence, a human population-specific human capture sequence, or an allele-group-specific human capture sequence.

Item 62. The method of any one of or combination of items 49-61, wherein the reprogrammed genome comprises site-directed mutagenic substitutions of nucleotides at exon regions of the wild-type swine's SLA-1 with nucleotides from an orthologous exon region of a HLA-A captured reference sequence.

Item 63. The method of any one of or combination of items 49-62, wherein the reprogrammed genome comprises site-directed mutagenic substitutions of nucleotides at exon regions of the wild-type swine's SLA-2 with nucleotides from an orthologous exon region of a HLA-B captured reference sequence.

Item 64. The method of any one of or combination of items 49-63, wherein the reprogrammed genome comprises site-directed mutagenic substitutions of nucleotides at exon regions of the wild-type swine's SLA-3 with nucleotides from an orthologous exon region of a HLA-C captured reference sequence.

Item 65. The method of any one of or combination of items 49-64, wherein the reprogrammed genome comprises site-directed mutagenic substitutions of nucleotides at exon regions of the wild-type swine's SLA-6 with nucleotides from an orthologous exon region of a HLA-E captured reference sequence.

Item 66. The method of any one of or combination of items 49-65, wherein the reprogrammed genome comprises site-directed mutagenic substitutions of nucleotides at exon regions of the wild-type swine's SLA-7 with nucleotides from an orthologous exon region of a HLA-F captured reference sequence.

Item 67. The method of any one of or combination of items 49-66, wherein the reprogrammed genome comprises site-directed mutagenic substitutions of nucleotides at exon regions of the wild-type swine's SLA-8 with nucleotides from an orthologous exon region of a HLA-G captured reference sequence.

Item 68. The method of any one of or combination of items 49-67, wherein the reprogrammed genome comprises site-directed mutagenic substitutions of nucleotides at exon regions of the wild-type swine's MHC class I chain-related 2 (MIC-2).

Item 69. The method of any one of or combination of items 49-68, wherein the reprogrammed genome lacks functional expression of SLA-1, SLA-2, SLA-DR, or a combination thereof.

Item 70. The method of any one of or combination of items 49-69, wherein the reprogrammed genome comprises site-directed mutagenic substitutions of nucleotides at exon regions of the wild-type swine's SLA-DQA from an orthologous exon region of a HLA-DQA1 captured reference sequence.

Item 71. The method of any one of or combination of items 49-70, wherein the reprogrammed genome comprises site-directed mutagenic substitutions of nucleotides at exon regions of the wild-type swine's SLA-DQB from an orthologous exon region of a HLA-DQB1 captured reference sequence.

Item 72. The method of any one of or combination of items 49-71, wherein the reprogrammed genome comprises site-directed mutagenic substitutions of nucleotides at exon regions of the wild-type swine's SLA-DRA and SLA-DRB1 with nucleotides from orthologous exon regions of HLA-DRA1 and HLA-DRB1 of the human captured reference sequence.

Item 73. The method of any one of or combination of items 49-72, wherein the reprogrammed genome comprises site-directed mutagenic substitutions of nucleotides at exon regions of the wild-type swine's SLA-DQA and SLA-DQB1 with nucleotides from orthologous exon regions of HLA-DQA1 and HLA-DQB1 of the human captured reference sequence.

Item 74. The method of any one of or combination of items 49-73, wherein the site-directed mutagenic substitutions of nucleotides are at codons that are not conserved between the wild-type swine's nuclear genome and the known human sequence.

Item 75. The method of any one of or combination of items 49-74, wherein the reprogrammed genome comprises site-directed mutagenic substitutions of nucleotides at exon regions of the wild-type swine's B2-microglobulin with nucleotides from orthologous exons of a known human B2-microglobulin.

Item 76. The method of any one of or combination of items 49-75, wherein the reprogrammed swine nuclear genome comprises a polynucleotide that encodes a polypeptide that is a humanized beta 2 microglobulin (hB2M) polypeptide sequence that is at least 95% identical to the amino acid sequence of beta 2 microglobulin glycoprotein expressed by the human captured reference genome;

Item 77. The method of any one of or combination of items 49-76, wherein said nuclear genome has been reprogrammed such that the genetically reprogrammed swine lacks functional expression of the wild-type swine's endogenous β2-microglobulin polypeptides.

Item 78. The method of any one of or combination of items 49-77, wherein said nuclear genome has been reprogrammed such that, at the swine's endogenous β2-microglobulin locus, the nuclear genome has been reprogrammed to comprise a nucleotide sequence encoding β2-microglobulin polypeptide of the human captured reference sequence.

Item 79. The method of any one of or combination of items 49-78, wherein the reprogrammed genome comprises site-directed mutagenic substitutions of nucleotides at exon regions of SLA-3, SLA-6, SLA-7, SLA-8, and MIC-2.

Item 80. The method of any one of or combination of items 49-79, wherein the reprogrammed genome comprises site-directed mutagenic substitutions of nucleotides at exon regions of SLA-DQ, and MIC-2.

Item 81. The method of any one of or combination of items 49-80, wherein the reprogrammed genome comprises site-directed mutagenic substitutions of nucleotides at SLA-3, SLA-6, SLA-7, SLA-8, SLA-DQ, and MIC-2.

Item 82. The method of any one of or combination of items 49-81, wherein the reprogrammed genome lacks functional expression of SLA-DR, SLA-1, and/or SLA-2.

Item 83. The method of any one of or combination of items 49-82, wherein the nuclear genome is reprogrammed using scarless exchange of the exon regions, wherein there are no frameshifts, insertion mutations, deletion mutations, missense mutations, and nonsense mutations.

Item 84. The method of any one of or combination of items 49-83, wherein the nuclear genome is reprogrammed without introduction of any net insertions, deletions, truncations, or other genetic alterations that would cause a disruption of protein expression via frame shift, nonsense, or missense mutations.

Item 85. The method of any one of or combination of items 49-84, wherein nucleotides in intron regions of the nuclear genome are not altered.

Item 86. The method of any one of or combination of items 49-85, wherein said nuclear genome is reprogrammed to be homozygous at the reprogrammed exon regions.

Item 87. The method of any one of or combination of items 49-86, wherein said nuclear genome is reprogrammed such that extracellular, phenotypic surface expression of polypeptide is tolerogenic in a human recipient.

Item 88. The method of any one of or combination of items 49-87, wherein said nuclear genome is reprogrammed such that expression of cytotoxic T-lymphocyte-associated protein 4 (CTLA-4) is increased by reprogramming a CTLA-4 promoter sequence.

Item 89. The method of any one of or combination of items 49-88, wherein the reprogrammed genome comprises site-directed mutagenic substitutions of nucleotides at exon regions of the wild-type CTLA-4 with nucleotides from orthologous exons of a human captured reference sequence CTLA-4.

Item 90. The method of any one of or combination of items 49-89, wherein the reprogrammed nuclear genome comprises a polynucleotide that encodes a protein that is a humanized CTLA-4 polypeptide sequence that is at least 95% identical to CTLA-4 expressed by the human captured reference genome.

Item 91. The method of any one of or combination of items 49-90, wherein said nuclear genome is reprogrammed such that expression of Programmed death-ligand 1 (PD-L1) is increased by reprogramming a PD-L1 promoter sequence.

Item 92. The method of any one of or combination of items 49-91, wherein the reprogrammed genome comprises site-directed mutagenic substitutions of nucleotides at exon regions of the wild-type PD-L1 with nucleotides from orthologous exons of a known human PD-L1.

Item 93. The method of any one of or combination of items 49-92, wherein the reprogrammed nuclear genome comprises a polynucleotide that encodes a protein that is a humanized PD-L1 polypeptide sequence that is at least 95% identical to PD-L1 expressed by the human captured reference genome.

Item 94. A method of inducing at least partial immunological tolerance in a recipient human to a xenotransplanted cell, tissue, or organ, the method comprising:
producing or obtaining non-human cell, tissue, or organ obtained from the biological system of any one of or combination of items 1-48, wherein the wild-type swine genome comprises reprogrammed nucleotides at SLA-MIC-2 gene and at exon regions of one or more encoding the wild-type swine's MHC Class Ia, MHC class Ib, MHC Class II, and beta-2-microglobulin using the human capture reference sequence and wherein the human cell, tissue, or organ lacks functional expression of swine beta-2-microglobulin; and
implanting the non-human cell, tissue, or organ into the recipient human.

Item 95. A method of reducing Natural Killer cell-mediated rejection of a xenograft comprising: producing or obtaining non-human cell, tissue, or organ obtained from the biological system of any one of or combination of items 1-48, wherein the wild-type swine genome comprises reprogrammed nucleotides at SLA-MIC-2 gene and at exon regions encoding one or more of the wild-type swine's MHC Class Ia, MHC class Ib, MHC Class II, and beta-2-microglobulin using the human capture reference sequence and wherein the human cell, tissue, or organ lacks functional expression of swine beta-2-microglobulin, and wherein the wild-type swine genome comprises reprogrammed nucleotides at exon regions encoding one or more of the wild-type swine's CTLA-4 and PD-L1; and implanting the non-human cell, tissue, or organ into the recipient human.

Item 96. A method of reducing Cytotoxic T-cell Lymphocyte cell-mediated rejection of a xenograft comprising:
producing or obtaining non-human cell, tissue, or organ obtained from the biological system of any one of or combination of items 1-48, wherein the wild-type swine genome comprises reprogrammed nucleotides at SLA-MIC-2 gene and at exon regions encoding one or more of the wild-type swine's MHC Class Ia, MHC class Ib, MHC Class II, and beta-2-microglobulin using the human capture reference sequence and wherein the human cell, tissue, or organ lacks functional expression of swine beta-2-microglobulin, and wherein the wild-type swine genome comprises reprogrammed nucleotides at exon regions encoding one or more of the wild-type swine's CTLA-4 and PD-L1; and implanting the non-human cell, tissue, or organ into the recipient human.

Item 97. A method of preventing or reducing coagulation and/or thrombotic ischemia in a recipient human to a xenotransplanted cell, tissue, or organ, the method comprising:
producing or obtaining non-human cell, tissue, or organ obtained from the biological system of any one of or combination of items 1-48, wherein the wild-type swine genome comprises reprogrammed nucleotides at SLA-MIC-2 gene and at exon regions encoding one or more of the wild-type swine's MHC Class Ia, MHC class Ib, MHC Class II, and beta-2-microglobulin using the human capture reference sequence, wherein the human cell, tissue, or organ lacks functional expression of swine beta-2-microglobulin, and wherein the wild-type swine genome comprises reprogrammed nucleotides at exon regions encoding one or more of the wild-type swine's endothelial protein C receptor (EPCR), thrombomodulin (TBM), and tissue factor pathway inhibitor (TFPI); and
implanting the non-human cell, tissue, or organ into the recipient human.

Item 98. A method of reducing MHC Class Ia-mediated rejection of a xenograft comprising:
producing or obtaining non-human cell, tissue, or organ obtained from the biological system of any one of or combination of items 1-48, wherein the wild-type swine genome comprises reprogrammed nucleotides at SLA-MIC-2 gene and at exon regions encoding SLA-3 and one or more of the wild-type swine's MHC class Ib, MHC Class II, and beta-2-microglobulin using the human capture reference sequence, wherein the human cell, tissue, or organ lacks functional expression of swine beta-2-microglobulin, SLA-1, and SLA-2; and implanting the non-human cell, tissue, or organ into the recipient human.

Item 99. A method of reducing MHC Class Ib-mediated rejection of a xenograft comprising:
producing or obtaining non-human cell, tissue, or organ obtained from the biological system of any one of or combination of items 1-48, wherein the wild-type swine genome comprises reprogrammed nucleotides at SLA-MIC-2 gene and at exon regions encoding SLA-6, SLA-7, and SLA-8, and one or more of the wild-type swine's MHC class Ia, MHC Class II, and beta-2-microglobulin using the human capture reference sequence, wherein the human cell, tissue, or organ lacks functional expression of swine beta-2-microglobulin; and implanting the non-human cell, tissue, or organ into the recipient human.

Item 100. A method of reducing MHC Class II-mediated rejection of a xenograft comprising:
producing or obtaining non-human cell, tissue, or organ obtained from the biological system of any one of or combination of items 1-48, wherein the wild-type swine genome comprises reprogrammed nucleotides at SLA-MIC-2 gene and at exon regions encoding at least one of SLA-DR and SLA-DQ, and one or more of the wild-type swine's MHC class Ia, MHC Class Ib, and beta-2-microglobulin using the human capture reference sequence, wherein the human cell, tissue, or organ lacks functional expression of swine beta-2-microglobulin; and implanting the non-human cell, tissue, or organ into the recipient human.

Item 101. A method of inhibiting apoptotic cell-mediated rejection of a xenograft comprising:
producing or obtaining non-human cell, tissue, or organ obtained from the biological system of any one of or combination of items 1-48, wherein the wild-type swine genome comprises reprogrammed nucleotides at SLA-MIC-2 gene and at exon regions encoding one or more of the wild-type swine's MHC Class Ia, MHC class Ib, MHC Class II, and beta-2-microglobulin using the human capture reference sequence and wherein the human cell, tissue, or organ lacks functional expression of swine beta-2-microglobulin, and wherein the wild-type swine genome comprises reprogrammed nucleotides at exon regions encoding one or more of the wild-type swine's CTLA-4 and PD-L1; and
implanting the non-human cell, tissue, or organ into the recipient human.

Item 102. A method of producing a donor swine tissue or organ for xenotransplantation, wherein cells of said donor swine tissue or organ are genetically reprogrammed to be characterized by a recipient-specific surface phenotype comprising:

obtaining a biological sample containing DNA from a prospective human transplant recipient; performing whole genome sequencing of the biological sample to obtain a human capture reference sequence;
comparing the human capture reference sequence with the wild-type genome of the donor swine at loci (i)-(v):
(i) exon regions encoding at least one of SLA-1, SLA-2, and SLA-3;
(ii) exon regions encoding at least one of SLA-6, SLA-7, and SLA-8;
(iii) exon regions encoding at least one of SLA-DR and SLA-DQ;
(iv) one or more exons encoding beta 2 microglobulin (B2M);
(v) exon regions of SLA-MIC-2 gene and a gene encoding at least one of PD-L1, CTLA-4, EPCR, TBM, and TFPI, creating synthetic donor swine nucleotide sequences of 10 to 350 basepairs in length for one or more of said loci (i)-(v), wherein said synthetic donor swine nucleotide sequences are at least 95% identical to the human capture reference sequence at orthologous loci (vi)-(x) corresponding to swine loci (i)-(vi), respectively:
(vi) exon regions encoding at least one of HLA-A, HLA-B, and HLA-C;
(vii) exon regions encoding at least one of HLA-E, HLA-F, and HLA-G;
(viii) exon regions encoding at least one of HLA-DR and HLA-DQ;
(ix) one or more exons encoding human beta 2 microglobulin (hB2M);
(x) exon regions encoding at least one of MIC-A, MIC-B, PD-L1, CTLA-4, EPCR, TBM, and TFPI from the human capture reference sequence,
replacing nucleotide sequences in (i)-(v) with said synthetic donor swine nucleotide sequences; and
obtaining the swine tissue or organ for xenotransplantation from a genetically reprogrammed swine having said synthetic donor swine nucleotide sequences.

Item 103. The method of item 102, further comprising confirming that the genetically reprogrammed swine having said synthetic donor swine nucleotide sequences is free of at least the following zoonotic pathogens:
(i) *Ascaris* species, *Cryptosporidium* species, *Echinococcus*, *Strongyloids sterocolis*, and *Toxoplasma gondii* in fecal matter;
(ii) *Leptospira* species, *Mycoplasma hyopneumoniae*, porcine reproductive and respiratory syndrome virus (PRRSV), pseudorabies, transmissible gastroenteritis virus (TGE)/Porcine Respiratory Coronavirus, and *Toxoplasma gondii* by determining antibody titers;
(iii) Porcine Influenza;
(iv) the following bacterial pathogens as determined by bacterial culture: *Bordetella bronchisceptica*, Coagulase-positive staphylococci, Coagulase-negative staphylococci, Livestock-associated methicillin resistant *Staphylococcus aureus* (LA MRSA), *Microphyton* and *Trichophyton* spp.;
(v) Porcine cytomegalovirus; and
(vi) *Brucella suis*.

Item 104. The method of any one of or combination of items 102-103, further comprising maintaining the genetically reprogrammed swine according to a bioburden-reducing procedure, said procedure comprising maintaining the genetically reprogrammed swine in an isolated closed herd, wherein all other animals in the isolated closed herd are confirmed to be free of said zoonotic pathogens, wherein the genetically reprogrammed swine is isolated from contact with any non-human animals and animal housing facilities outside of the isolated closed herd.

Item 105. The method of any one of or combination of items 102-104, further comprising harvesting a biological product from said swine, wherein said harvesting comprises euthanizing the swine and aseptically removing the biological product from the swine.

Item 106. The method of any one of or combination of items 102-105, further comprising processing said biological product comprising sterilization after harvesting using a sterilization process that does not reduce cell viability to less than 50% cell viability as determined by a 3-(4,5-dimethylthiazol-2-yl)-2,5-diphenyltetrazolium bromide (MTT)-reduction assay.

Item 107. The method of any one of or combination of items 102-106, further comprising storing said biological product in a sterile container under storage conditions that preserve cell viability.

Item 108. A method of screening for off target edits or genome alterations in the genetically reprogrammed swine comprising a nuclear genome of any one of or combination of items 1-49, comprising:
performing whole genome sequencing on a biological sample containing DNA from a donor swine before performing genetic reprogramming of the donor swine nuclear genome, thereby obtaining a first whole genome sequence;
after reprogramming of the donor swine nuclear genome, performing whole genome sequencing to obtain a second whole genome sequence;
aligning the first whole genome sequence and the second whole genome sequence to obtain a sequence alignment;
analyzing the sequence alignment to identify any mismatches to the swine's genome at off-target sites.

Item 109. A synthetic nucleotide sequence having wild-type swine intron regions from a wild-type swine MHC Class Ia, and reprogrammed at exon regions encoding the wild-type swine's SLA-3 with codons of HLA-C from a human capture reference sequence that encode amino acids that are not conserved between the SLA-3 and the HLA-C from the human capture reference sequence.

Item 110. The synthetic nucleotide sequence of item 109, wherein the wild-type swine's SLA-1 and SLA-2 each comprise a stop codon.

Item 111. A synthetic nucleotide sequence having wild-type swine intron regions from a wild-type swine MHC Class Ib, and reprogrammed at exon regions encoding the wild-type swine's SLA-6, SLA-7, and SLA-8 with codons of HLA-E, HLA-F, and HLA-G, respectively, from a human capture reference sequence that encode amino acids that are not conserved between the SLA-6, SLA-7, and SLA-8 and the HLA-E, HLA-F, and HLA-G, respectively, from the human capture reference sequence.

Item 112. A synthetic nucleotide sequence having the synthetic nucleotide sequences of both items 109 and 111 or both items 110 and 111.

Item 113. A synthetic nucleotide sequence having wild-type swine intron regions from a wild-type swine MHC Class II, and reprogrammed at exon regions encoding the wild-type swine's SLA-DQ with codons of HLA-DQ, respectively, from a human capture reference sequence that encode amino acids that are not conserved between the SLA-DQ and the HLA-DQ, respectively, from the human capture reference sequence, and wherein the wild-type swine's SLA-DR comprises a stop codon.

Item 114. A synthetic nucleotide sequence having the synthetic nucleotide sequences of: both items 109 and 113; both items 110 and 113; or both items 112 and 113.

Item 115. A synthetic nucleotide sequence having wild-type swine intron regions from a wild-type swine beta-2-microglobulin and reprogrammed at exon regions encoding the wild-type swine's beta-2-microglobulin with codons of beta-2-microglobulin from a human capture reference sequence that encode amino acids that are not conserved between the wild-type swine's beta-2-microglobulin and the beta-2-microglobulin from the human capture reference sequence, wherein the synthetic nucleotide sequence comprises at least one stop codon in an exon region such that the synthetic nucleotide sequence lacks functional expression of the wild-type swine's β2-microglobulin polypeptides.

Item 116. A synthetic nucleotide sequence having wild-type swine intron regions from a wild-type swine MIC-2, and reprogrammed at exon regions of the wild-type swine's MIC-2 with codons of MIC-A or MIC-B from a human capture reference sequence that encode amino acids that are not conserved between the MIC-2 and the MIC-A or the MIC-B from the human capture reference sequence.

Item 117. A synthetic nucleotide sequence having wild-type swine intron regions from a wild-type swine CTLA-4, and reprogrammed at exon regions encoding the wild-type swine's CTLA-4 with codons of CTLA-4 from a human capture reference sequence that encode amino acids that are not conserved between the wild-type swine's CTLA-4 and the CTLA-4 from the human capture reference sequence.

Item 118. A synthetic nucleotide sequence having wild-type swine intron regions from a wild-type swine PD-L1 and reprogrammed at exon regions encoding the wild-type swine's PD-L1 with codons of PD-L1 from a human capture reference sequence that encode amino acids that are not conserved between the wild-type swine's PD-L1 and the PD-L1 from the human capture reference sequence.

Item 119. A synthetic nucleotide sequence having wild-type swine intron regions from a wild-type swine EPCR and reprogrammed at exon regions encoding the wild-type swine's EPCR with codons of EPCR from a human capture reference sequence that encode amino acids that are not conserved between the wild-type swine's EPCR and the EPCR from the human capture reference sequence.

Item 120. A synthetic nucleotide sequence having wild-type swine intron regions from a wild-type swine TBM and reprogrammed at exon regions encoding the wild-type swine's TBM with codons of TBM from a human capture reference sequence that encode amino acids that are not conserved between the wild-type swine's TBM and the TBM from the human capture reference sequence.

Item 121. A synthetic nucleotide sequence having wild-type swine intron regions from a wild-type swine TFPI and reprogrammed at exon regions encoding the wild-type swine's TFPI with codons of TFPI from a human capture reference sequence that encode amino acids that are not conserved between the wild-type swine's TFPI and the TFPI from the human capture reference sequence.

The present invention is described in further detail in the following examples which are provided to be illustrative only, and are not intended to limit the scope of the invention.

Example 1

DPF Closed Colony Skin Graft (Monkey Studies)

It has been discovered that skin grafts derived from a DPF Closed Colony, α-1,3-galactosyltransferase [Gal-T] knockout pigs produced in accordance with the present invention exhibit significantly longer rejection times than skin grafts derived from α-1,3-galactosyltransferase [Gal-T] knockout pigs but that were not derived from DPF Closed Colony pigs.

Numerous prior studies evaluating rejection time of α-1,3-galactosyltransferase [Gal-T] knockout pigs (not derived from a DPF Closed Colony) on monkeys show rejection times in the range of 11-13 days. See, e.g., Albritton et al., *Lack of Cross-Sensitization Between alpha-1,3-Galactosyltransferase Knockout Porcine and Allogeneic Skin Grafts Permits Serial Grafting*, Transplantation & Volume 97, Number 12, Jun. 27, 2014, (Gal-T-KO skin grafts on recipient baboons fully rejected by 12 or 13 days); Barone et al., "*Genetically modified porcine split-thickness skin grafts as an alternative to allograft for provision of temporary wound coverage: preliminary characterization*," Burns 41 (2015) 565-574 (Gal-T-KO skin grafts on recipient baboons fully rejected by 11 days); and Weiner et al., *Prolonged survival of Gal-T-KO swine skin on baboons*, Xenotransplantation, 2010, 17(2): 147-152 (Gal-T-KO xenogeneic split-thickness skin grafts on baboons fully rejected by 11 days).

The subject invention has been shown in nonclinical studies to perform on par and surprisingly better than its allograft comparators, without the inherent disadvantage of inconsistent quality and unreliable and limited availability. That is, surprisingly, at least Study No. 1 shows skin grafts derived from a DPF Closed Colony, α-1,3-galactosyltransferase [Gal-T] knockout pigs produced in accordance with the present invention performed better than allograft.

Two recent studies (Study No. 1 and Study No. 2 set out below) by applicant demonstrate that skin grafts derived from DPF Closed Colony, α-1,3-galactosyltransferase [Gal-T] knockout pigs produced in accordance with the present invention on monkeys show significantly higher rejection times, in Study 2 longer than 30 days. The genetically engineered source animals in this example did not contain any foreign, introduced DNA into the genome; the gene modification employed was exclusively a knock-out of a single gene that was responsible for encoding for an enzyme that causes ubiquitous expression of a cell-surface antigen. The xenotransplantation product in this example does not incorporate transgene technologies, such as CD-46 or CD-55 transgenic constructs.

Study No. 1

This study evaluated DPF Closed Colony, α-1,3-galactosyltransferase [Gal-T] knockout porcine xenotransplantation product material compared to allografts as temporary wound grafts prior to autograft placement in cynomolgus monkeys (*Macaca fascicularis*) in an experimental model of full thickness skin lesions.

Primary end points included screening for porcine endogenous retrovirus (PERV) in the grafts and the recipient as well as evaluation of the xenotransplantation product and allograft rejection and their potential effects on ultimate autograft take. Secondary end points included microbiologic and histopathologic analysis of kidney, spleen, liver, lung, grafts, and wound bed tissues collected at necropsy.

Four (4) cynomolgus monkeys were enrolled in this study. Four (4), full thickness wound beds measuring approximately 2-3 cm×2-3 cm were created on the dorsal region of each animal on Day 0.

Initially, wounds were treated with either Xenogeneic skin (xenotransplantation product), a split-thickness Gal-T-transgenic porcine xenotransplantation product material, or Allogenic skin (allograft), a split-thickness allograft material, on Day 0.

On Day 15 of the study, the xenotransplantation product and allografts were removed and replaced with split-thickness autologous skin grafts (autografts), after which the animals were survived to Day 22 of study (with the exception of moribund sacrifice Animals 1001 and 1004).

Figure 40A:
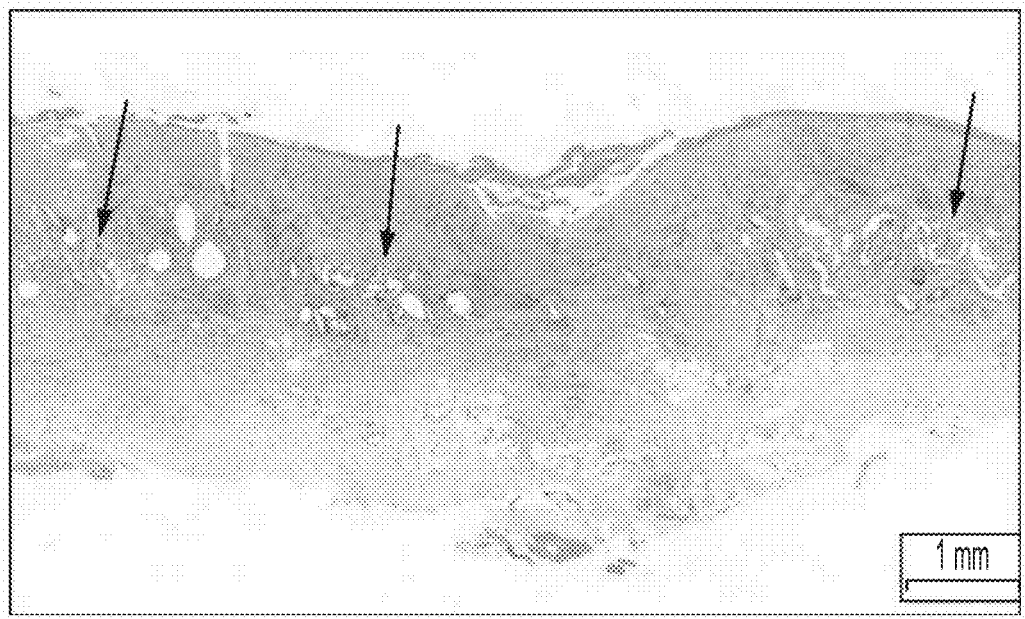
FIG. 40A depicts POD-15. H&E, H&E, high power image depicts tissue viability with surface and follicular epithelial necrosis.
Figure 40B:
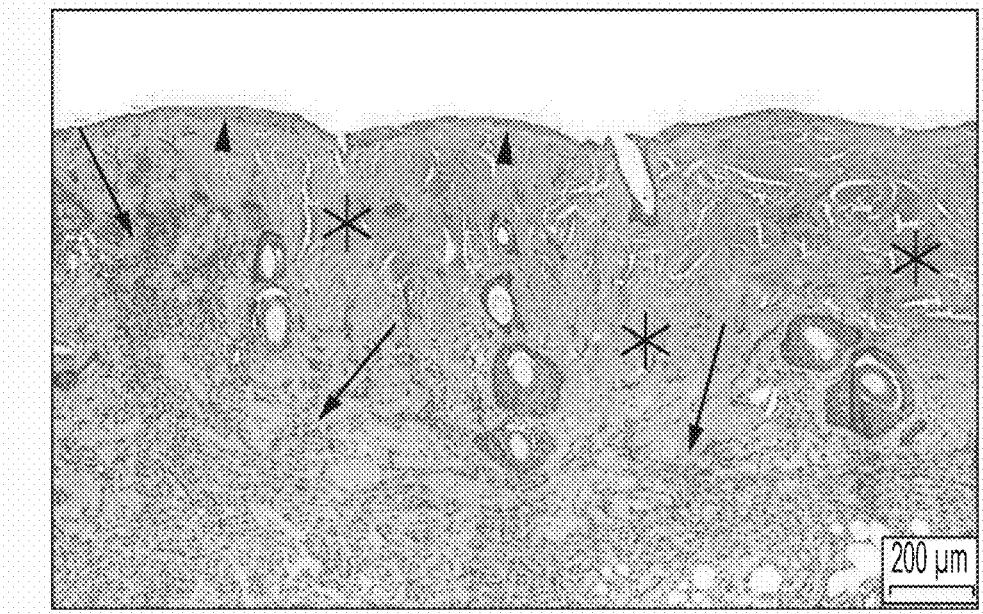
FIG. 40B depicts POD-22 H&E, high power image demonstrating residual autograft (asterisks) with good overall viability. No surface epithelium and some surface necrosis noted, along with extensive fibrosis with infiltration into the autograft (arrows).

Microscopic evaluation of full thickness wound beds in a cynomolgus monkey model treated with xenotransplantation product or allograft and removed on Day 12 or 15 (FIG. 40A) and survived up to Day 22 (FIG. 40B) demonstrated no evidence of acute tissue rejection with either the xenotransplantation product or allograft comparable to slightly better performance overall with the xenotransplantation product test article when compared to the allograft test article, and average to good autograft performance following pretreatment with either xenotransplantation product or allograft test articles. The significant survival times of the xenotransplantation product prompted a follow-on study (Study No. 2).

Study No. 2

The objective of this study was to evaluate the safety and immunogenicity of DPF Closed Colony, α-1,3-galactosyltransferase [Gal-T] knockout porcine xenotransplantation product material in cynomolgus monkeys (*Macaca fascicularis*).

Primary end points included screening for porcine endogenous retrovirus (PERV) pre- and post-graft placement and evaluation of the xenotransplantation product rejection.

Four (4) cynomolgus monkeys were enrolled in this study. Two (2) 9 cm² full thickness wound beds were created on the dorsal region of each animal created on Day 0.

Wounds were treated with split-thickness Gal-T-knockout porcine xenograft material consisting of dermal and epidermal tissue layers.

Figure 41:
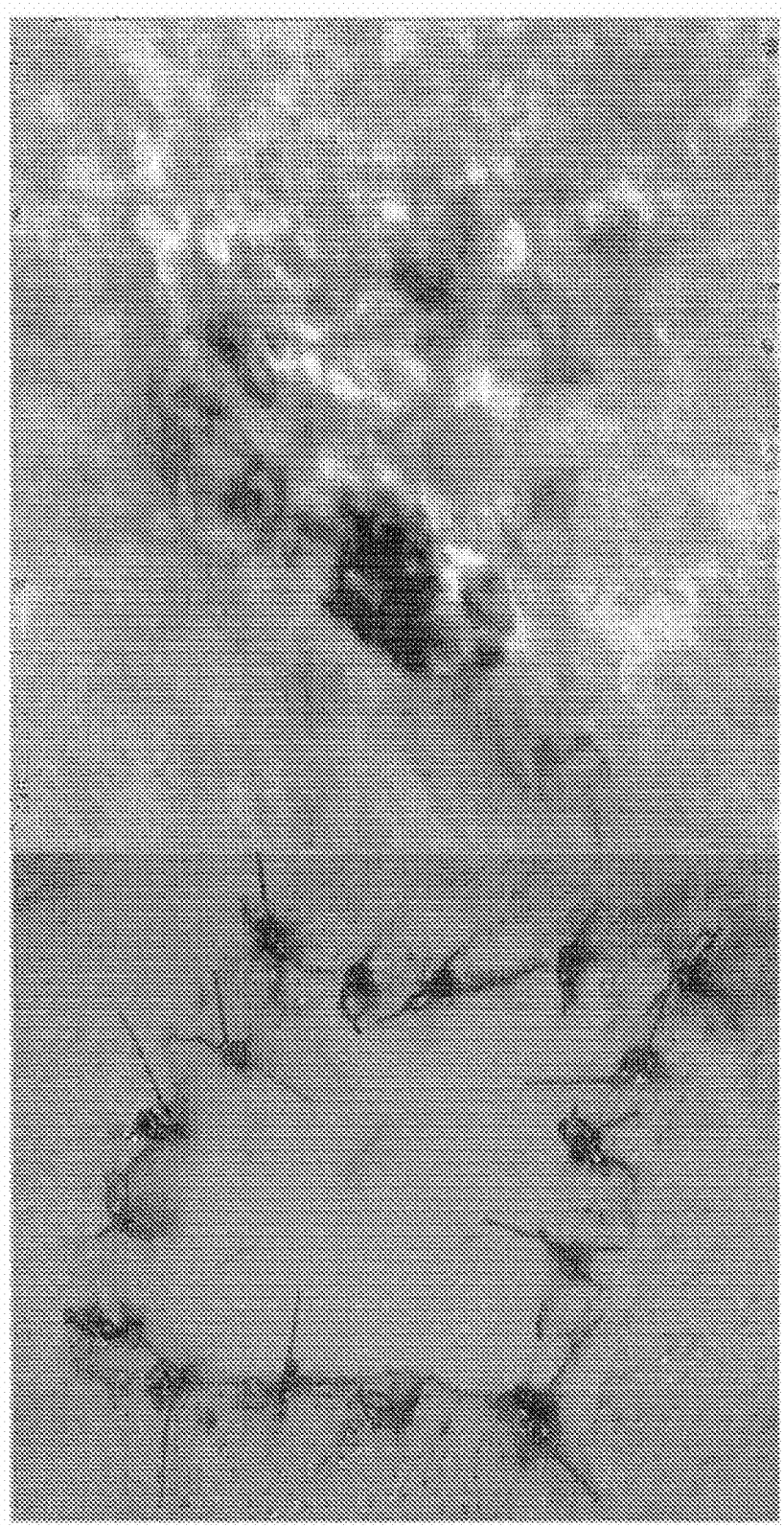
FIG. 41 depicts longitudinal progression of porcine split-thickness skin graft used as a temporary wound closure in treatment of full-thickness wound defects in a non-human primate recipient. Left: POD-0, xenotransplantation product at Wound Site 2. Right: POD-30, same xenotransplantation product at Wound Site 2.
Figure 42:
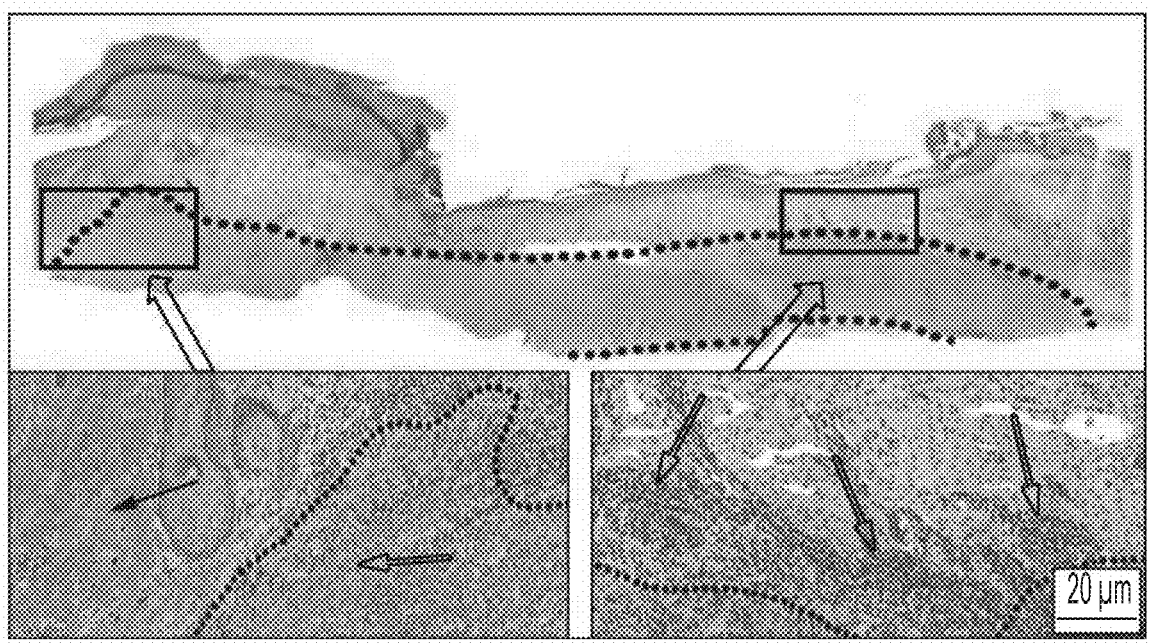
FIG. 42 shows POD-30 histological images for: Top, Center: H&E, Low power image of wound site depicts complete epithelial coverage. Dotted line surrounds the residual xenotransplantation product.

FIG. 41 shows the longitudinal progression of porcine split-thickness skin graft used as a temporary wound closure in treatment of full-thickness wound defects in a non-human primate recipient. Left: POD-0, xenograft at Wound Site 2. Right: POD-30, same xenograft at Wound Site 2. FIG. 42 shows POD-30 histological images for: Top, Center: H&E, Low power image of wound site depicts complete epithelial coverage. Dotted line surrounds the residual xenograft tissue. Bottom, Left: H&E, Higher power image of the large inset box. To the right and below the dotted line is the dermal component of the xenograft, with the xenograft dermal matrix indicated by an open arrow. To the left of the dotted line is the host dermis (black arrow) and the host dermal matrix. Mild inflammation is present and interpreted to be in response to the xenograft test article. Bottom, Right: H&E, higher power image of the small inset box. The dotted line roughly demonstrates the junction between the xenograft test article (below dotted line) and new collagen tissue (above dotted line), with intact epithelium at the top of the image. Mild inflammation in response to the xenograft (open arrows) is observed.

Figure 43A:
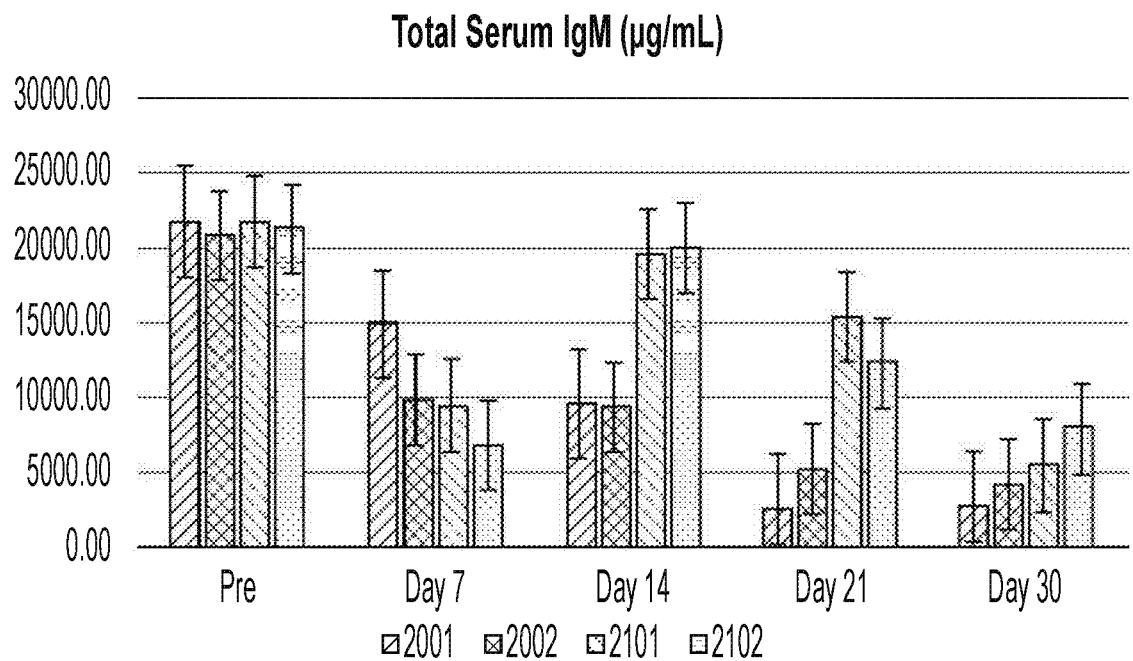
FIG. 43A graphs the total serum IgM ELISA (μg/mL) for all four subjects (2001, 2002, 2101, 2102) during the course of the study.
Figure 43B:
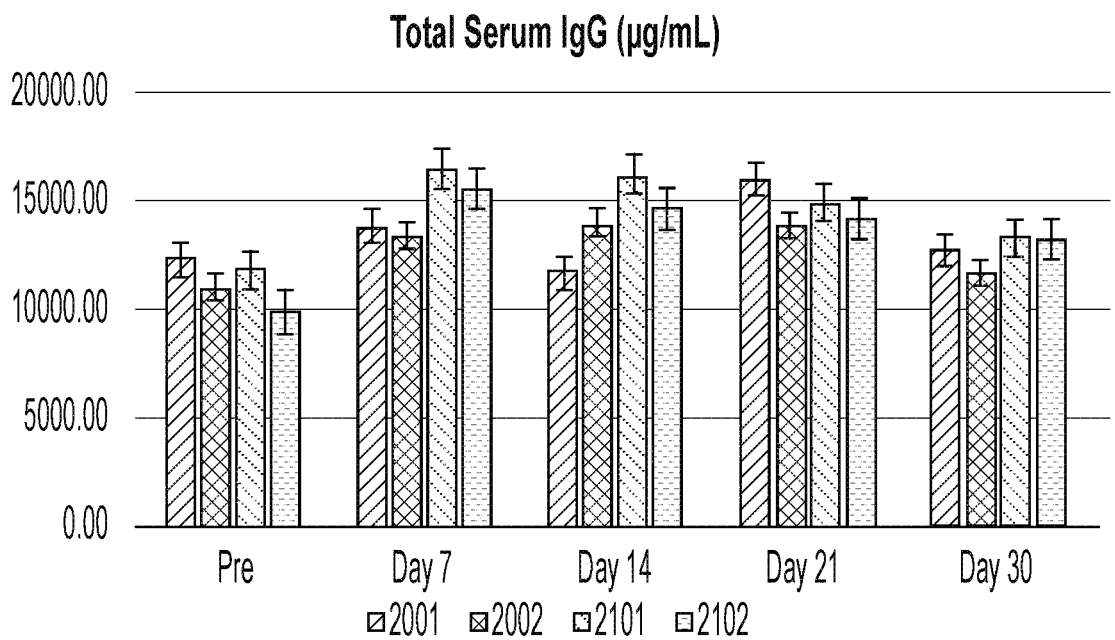
FIG. 43B graphs the total serum IgG ELISA (μg/mL) for all four subjects (2001, 2002, 2101, 2102) during the course of the study.

FIG. 43A graphs the total serum IgM ELISA (µg/mL) for all four subjects (2001, 2002, 2101, 2102) during the course of the study. FIG. 43B graphs the total serum IgG ELISA (µg/mL) for all four subjects (2001, 2002, 2101, 2102) during the course of the study. In some aspects, subjects transplanted with the product of the present disclosure will have serum IgM and IgG levels of less than 20,000 µg/ml each. In some aspects, subjects transplanted with the product of the present disclosure will have serum IgM and/or IgG levels below or less than 10%, 5%, 3%, or 1% higher than serum IgM and IgG levels measured prior to transplantation. In some aspects, the claimed method may demonstrate an immunoreactivity incidence rate of less than 5%, 3%, or 1% of subjects transplanted with the product of the present disclosure.

Figure 44C:
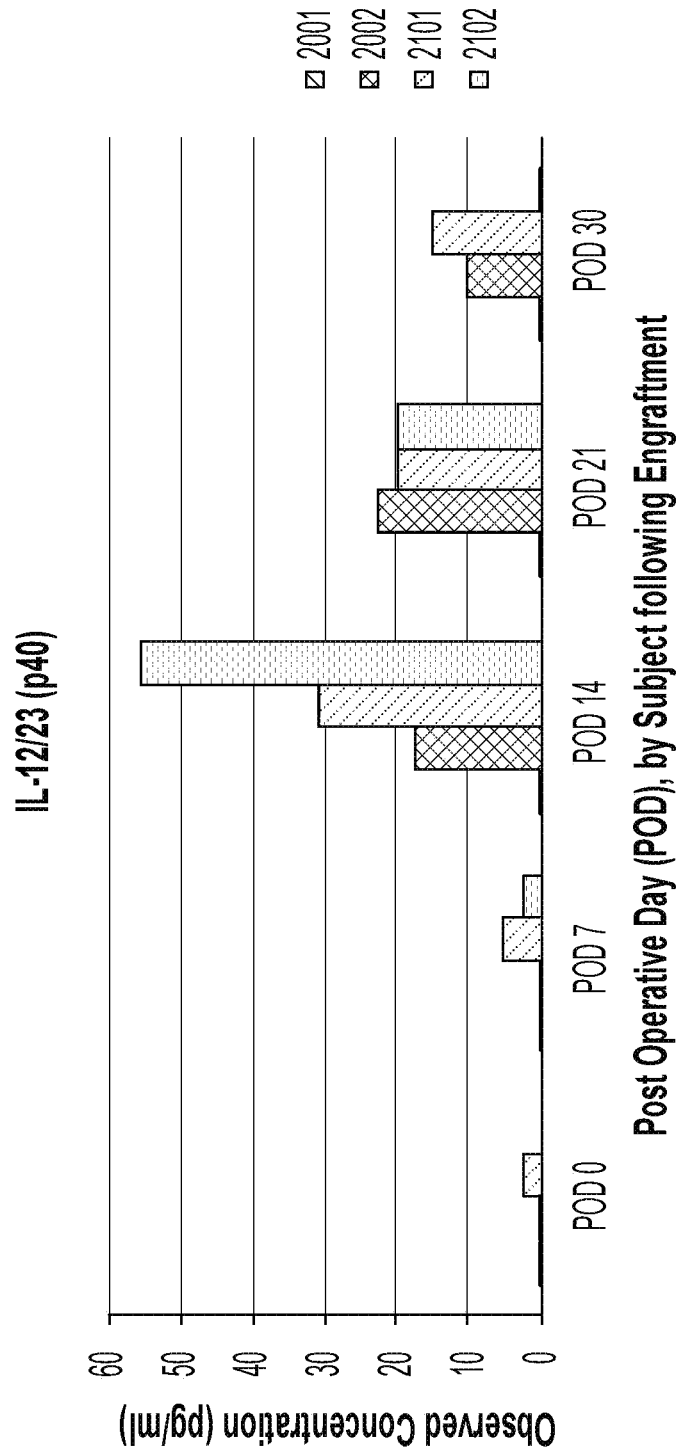
FIG. 44C graphs systemic concentrations of IL-12/23 (p40) as measured by Luminex 23-plex at POD-0, POD-7, POD-14, POD-21, and POD-30.

FIG. 44A graphs systemic concentrations of soluble CD40L as measured by Luminex 23-plex at POD-0, POD-7, POD-14, POD-21, and POD-30. FIG. 44B graphs systemic concentrations of TGF-alpha as measured by Luminex 23-plex at POD-0, POD-7, POD-14, POD-21, and POD-30. FIG. 44C graphs systemic concentrations of IL-12/23 (p40) as measured by Luminex 23-plex at POD-0, POD-7, POD-14, POD-21, and POD-30.

Animals were terminated at 30 or 31 Days, wound sites were collected and fixed in 10% neutral buffered formalin (NBF) or Modified Davidson's Solution for the testis and epididymis. It should be noted that while the animals were terminated at 30 or 31 days due to the study design and for comparison purposes, the xenotransplantation product of the present disclosure is capable of resisting rejection for longer than the study period used in this example.

Microscopic evaluation of full thickness wound beds in a cynomolgus monkey model treated with xenograft and terminated on Day 30 or 31 demonstrated good filling of the wound defect with host and xenograft tissue.

Screening for porcine endogenous retroviruses (PERV) and porcine cytomegalovirus (PCMV) was performed separately at specified post-operative intervals via specialized (porcine specific) polymerase chain reaction (PCR) and reverse transcriptase PCR (RT-PCR) testing of samples. The porcine xenografts, lysed PBMCS of the recipient, recipient wound bed, and highly perfused organs from the recipients at necropsy were evaluated for presence of porcine cell migration. All tests were performed in triplicate with internal controls for DNA and RNA, as well as assay performance. Microbiologic (bacterial, fungal, viral) assays and histopathologic analysis of kidney, spleen, liver, lung, xenografts, allografts, wound bed tissues collected at necropsy, and analysis of peripheral blood were performed to test for xenograft-related immunogenic biomarkers. DNA PCR was performed to test for porcine cell migration in PBMCs from the cynomolgus monkey model treated with the product of the present disclosure for the following samples: (A) (3) full-thickness (xenograft) wound beds, (B) (3) full-thickness (allograft) wound beds; (C) (2) spleen samples; and (D)(2) kidney samples. There was no evidence of cell migration or zoonotic transmission systemically to the host. The presence of PERV is attributed to the residual pig cells in the wound bed, as verified with porcine MHC controls. Our results suggest that porcine DNA and cells did not migrate into the circulation of the graft recipients from the grafts, and likewise PERV or PERV-infected porcine cells did not migrate past the wound bed.

The following Table 4 shows the analysis for porcine cell migration and transmission:

TABLE 4

| Item No. | PSKl7-01 Sample Analysis | PCMV | PERV | MHC (swine) | CCR5 (Control) |
|---|---|---|---|---|---|
| | PBMC @ End-of-Study Subject # (EoS Date) | | | | |
| 1 | NHP-1001 (POD-I S) | * | * | * | * |
| 2 | NHP-1002 (POD-22) | Neg (−) | Neg (−) | Neg (−) | Pos (+) |
| 3 | NHP-1003 (POD-22) | Neg (−) | Neg (−) | Neg (−) | Pos (+) |
| 4 | NHP-1004 (POD-12) | Neg (−) | Neg (−) | Neg (−) | Pos (+) |
| | Wound Bed @ End-of-Study Subject # (Test | | | | |

TABLE 4-continued

| Item No. | PSKl7-01 Sample Analysis (Article) (EoS Date) | PCMV | PERV | MHC (swine) | CCR5 (Control) |
|---|---|---|---|---|---|
| 5 | NHP-1001 (Xenograft) (POD-IS) | * | * | * | * |
| 6 | NHP-1001 (Allograft) (POD-IS) | * | * | * | * |
| 7 | NHP-1002 (Xenograft) (POD-22) | Neg (−) | Neg (−) | Neg (−) | Pos (+) |
| 8 | NHP-1002 (Allograft) (POD-22) | Neg (−) | Neg (−) | Neg (−) | Pos (+) |
| 9 | NHP-1003 (Xenograft) (POD-22) | Neg (−) | Neg (−) | Neg (−) | Pos (+) |
| 10 | NHP-1003 (Allograft) (POD-22) | Neg (−) | Neg (−) | Neg (−) | Pos (+) |
| 11 | NHP-1004 (Xenograft) (POD-12) | Neg (−) | Pos (+)[(4)] | Neg (−) | Pos (+) |
| 12 | NHP-1004 (Allograft) (POD-12) Spleen @ End-of-Study | Neg (−) | Neg (−) | Neg (−) | Pos (+) |
| 13 | NHP-1001 | Neg (−) | Neg (−) | Neg (−) | Pos (+) |
| 14 | NHP-1004 Kidney @ End-of-Study | Neg (−) | Neg (−) | Neg (−) | Pos (+) |
| 15 | NHP-1001 | Neg (−) | Neg (−) | Neg (−) | Pos (+) |
| 16 | NHP-1004 | Neg (−) | Neg (−) | Neg (−) | Pos (+) |

Key for Table 4:
Neg (−) = Negative
Pos (+) = Positive
*= Test Not Performed or Sample Not Acceptable, due to unrelated, study design-related logistical or preservation issue
Pos (+)[(4)] The wound bed for NHP 1004 (PERV positive) underwent co-culture studies to ascertain whether the detected virus present at the interface between graft and recipient (host) could infect permissive human cells.
Co-culture of the xenograft and recipient wound bed cells with permissive human cells for PERV infection and replication did not demonstrate productive infection in the target cells (HEK293), after a 23-day culture.

TABLE 5

Banff Grades and Pathologic Component Scores[1] of Skin Xenotransplants at POD-30

| Animal | Graft | Surgeon assessment | Banff Grade | pc[2] | pa[3] | ei[4] | e[5] | v[6] | c[7] | cav[8] |
|---|---|---|---|---|---|---|---|---|---|---|
| 2001 | 1 | 100% re-epithelialized | III | 3 | 3 | 3 | 1 | 0 | 1 | 0 |
| 2001 | 2 | 100% re-epithelialized | III-IV | 3 | 3 | 3 | 2 | 0 | 1 | 0 |
| 2002 | 1 | 30% re-epithelialized | III-IV | 3 | 3 | 3 | 3 | 0 | 0 | 0 |
| 2002 | 2 | 30% re-epithelialized | III-IV | 3 | 3 | 3 | 3 | 0 | 0 | 0 |
| 2101 | 1 | 40% re-epithelialized | II | 3 | 3 | 2 | 3 | 0 | 0 | 0 |
| 2101 | 2 | 40% re-epithelialized | III-IV | 3 | 3 | 3 | 2 | 0 | 0 | 0 |
| 2102 | 1 | 20% re-epithelialized | III-IV | 3 | 3 | 3 | 3 | 0 | 0 | 0 |
| 2102 | 2 | 20% re-epithelialized | II-III | 3 | 3 | 3 | 3 | 0 | 0 | 0 |

[1] Pathologic Component Scores developed by Rosales, et al.

[2] pc = perivascular cells - number of cells surrounding dermal vessels (venules, capillaries, and arterioles) in deep and superficial dermis; scored on the most involved vessels; pc3 >50 cells/vessel

[3] pa = perivascular dermal infiltrate area -percent area occupied by the most involved dermal vessels at 40× magnification; pa3 >75%

[4] ei = epidermal infiltrate - total number of mononuclear cells per four 20× fields; ei3 = transepidermal infiltrate, ei2 >20 cells

[5] e = epidermal injury and necrosis - presence of keratinocyte apoptosis and necrosis; e3 = sloughed, e2 = focal necrosis, e1 - apoptosis

[6] v = endarteritis - mononuclear cells underneath arterial endothelium; scored on the most involved artery; v0 = none

[7] c = capillaritis - maximum number of cells per capillary cross section; scored on most involved capillaries; c1 - 2-4/capillary. c0 = 0-1/capillary

[8] cav = chronic allograft vasculopathy - intimal thickening with luminal reduction; scored as percent luminal reduction; cav0 = none The general appearance for all xenotransplants for the course of the study was pink, warm to the touch and adherent to the wound bed. Epidermolysis (mild to moderate) was first noted by the surgeon on POD-14 but the dermis was adherent. Assessment at POD-21 revealed that the wound bed was re-granulating and there were signs of re-epithelialization, such that by POD-30, 20% to 100% of the wound had been re-epithelialized. (Table 5) During the clinical course of these skin xenotransplants, there was no sloughing of the xenotransplant tissue and exposure of the wound bed.

Hematoxylin and eosin (H&E)—prepared sections containing residual skin xenotransplants and the underlying wound beds, obtained at POD-30, were microscopically evaluated by a blinded pathologist. H&E staining showed minimal to moderate inflammatory response. There was ulceration of the epithelia in four out of eight treated sites. The response at the wound sites was characterized by filling of the wound defect with a mature dermal collagen network surrounded by a variable layer of new collagen. This mature collagen network was distinct in appearance from the host dermis bordering the wound site, and was interpreted to be the xenotransplant dermis. The skin xenotransplants were assessed using a systematic pathologic component scoring and Banff classification[47]. The Banff classification is useful in categorizing xenotransplant rejection, and it is complemented by the component score approach, providing a more comprehensive array of clinical thresholds for the diagnosis of rejection. The results of this assessment and Banff Grades for POD-30 are shown in Table 5. The Banff 2007 Working Classification for Composite Tissue Allografts is based on the level of epidermal apoptosis, epidermal infiltrates, and perivascular/dermal infiltrates[48]. The Banff Grades ranged from II (moderate) to IV (necrotizing acute rejection) with most showing Grade III (severe).

TABLE 6

Changes in Serum Cytokines and Chemokines after Xenograft Transplantation (pg/mL)

| Cytokine/Chemokine | POD-0 | POD-7 | POD-14 | POD-21 | POD-30 |
|---|---|---|---|---|---|
| sCD40L | 1900 ± 1000 | 7900†± 3100 | 7700†‡ ± 3100 | 8600†‡ ± 4000 | 8500†‡ ± 5200 |
| IL-1ra | 7.6 ± 2.8 | 50† ± 44 | 28† ± 11 | 66† ± 83 | 24† ± 13 |
| IL-2 | 29 ± 11 | 42† ± 18 | 37† ± 11 | 41† ± 9 | 30 ± 12 |
| IL-6 | 0.31 ± 0.6 | 7.3† ± 8.3 | 4.1† ± 2.6 | 8.5† ± 6.3 | 3.3† ± 2.7 |
| IL-8 | 2500 ± 1300 | 4200† ± 3200 | 3700† ± 2600 | 3900† ± 2300 | 2500 ± 2100 |
| IL-12/23 (p40) | 0.6 ± 1.0 | 1.8 ± 2.7 | 26† ± 22 | 16† ± 11 | 6.7† ± 7.7 |
| IL-15 | 3.1 ± 1.9 | 6.0† ± 2.0 | 7.1† ± 1.3 | 5.0† ± 1.3 | 6.0† ± 1.5 |
| MCP-1 | 360 ± 150 | 710† ± 540 | 420† ± 110 | 460† ± 110 | 310 ± 120 |
| TGF-α | 4.5 ± 4.6 | 22† ± 11 | 16† ± 11 | 5.2 ± 3.6 | 9.9 ± 8.9 |

POD = Postoperative day
Values are means (n = 4) ± SD
†Significant datapoints (p < 0.05) compared to POD 0, student t-test
‡Values include data at the upper level of detection (12,000 pg/mL)

As an evaluation of cell-mediated immune response, a total of 23 inflammatory and anti-inflammatory cytokines characteristic of initial wound healing processes or those anticipated in an immunological response to xenogeneic cells were measured. Twelve of the 23 cytokines/chemokines assayed were consistently below the level of detection throughout the entire study period: TNF-α, IFN-γ, TGF-β, G-CSF, GM-CSF, IL-1-β, IL-4, IL-5, IL-10, IL-13, IL-17, IL-18, and MIP-1-α. VEGF exceeded the level of detection at only three individual timepoints, and levels of MIP-1-beta were discernable only once (data not presented). Nine cytokines/chemokines detected over the period of the study are listed in Table 6. All cytokines/chemokines shown in the table were observed to increase above background at POD-7, the first day of sampling. IL-2, IL-8, MCP-1 and TGF-α peaked at POD-7 and decreased over time. IL-15 and IL-12/23 (p40) peaked at POD-14, while sCD40L, IL-1ra and IL-6 had an elevated peak at POD-21. In general, all of the factors showed a return to normal by POD-30 with the exception of sCD40L, which remained elevated at POD-30. Of interest, levels of IL-12/23 (p40) were nearly absent until conspicuously elevated on POD-14, gradually reducing in concentration over the remainder of the study.

TABLE 7

Post-Transplant Changes in Binding of Recipient Serum IgM and IgG to PBMC[1] Targets from GalT—KO[2] Swine Donors

| Recipient | Pre/Post Transplant[3] | IgM[5] rMFI[4] | Fold Change | IgG[6] rMFI[4] | Fold Change |
|---|---|---|---|---|---|
| 2001 | Pre | 8.51 | 0.0 | 16.28 | 0.0 |
|  | Post | 45.72 | 4.4 | 1089.85 | 65.9 |
| 2002 | Pre | 5.07 | 0.0 | 28.29 | 0.0 |
|  | Post | 30.01 | 4.9 | 840.64 | 28.7 |
| 2101 | Pre | 7.92 | 0.0 | 16.03 | 0.0 |
|  | Post | 22.48 | 1.8 | 730.83 | 44.6 |
| 2102 | Pre | 6.47 | 0.0 | 5.19 | 0.0 |
|  | Post | 15.49 | 1.4 | 372.88 | 70.8 |

[1]PBMC = peripheral blood mononuclear cell
[2]GalT—KO = alpha-1,3 galactosyltransferase knockout
[3]Pre-transplant = POD-0; Post-transplant = POD-30
[4]rMFI = relative Mean Fluorescent Intensity
[5]IgM = immunoglobulin M
[6]IgG = immunoglobulin G To assess the production of antibody to xenogeneic after skin transplant, binding of recipient serum IgM and IgG to peripheral blood mononuclear cell (PBMC) targets from GalT-KO donors was measured by flow cytometry. Serum IgM and IgG antibody levels were analyzed at pre-transplant and at POD-30. In Table 7, the relative mean fluorescent intensity (MFI) and fold increase in binding are summarized for each recipient. An increase in anti-xenogeneic IgM and IgG was detected in all animals. Between pre-transplant (POD-0) and post-transplant (POD-30), IgM anti-porcine antibodies increased between 1.4 to 4.9 fold and IgG anti-porcine antibodies increased between 28.7 to 70.8 fold. These results demonstrate a humoral response to non-Gal xenoantigens.

TABLE 8

Data for Postoperative Analysis of Wound Beds (Wound Site 1 and 2)

| Animal ID | Wound Site | PERV copies/500 ng (SD) | Micro-chimerism† | QC‡ |
|---|---|---|---|---|
| 2001 | W1 | <LOD† | − | + |
|  | W2 | 1495.6 (±521) | + | + |
| 2002 | W1 | 1518.8 (±21) | + | + |
|  | W2 | <LOD | − | + |
| 2101 | W1 | 527.1 (±134) | + | + |
|  | W2 | 137.8 (±16) | + | + |

TABLE 8-continued

Data for Postoperative Analysis of Wound Beds (Wound Site 1 and 2)

| Animal ID | Wound Site | PERV copies/500 ng (SD) | Micro-chimerism† | QC‡ |
|---|---|---|---|---|
| 2102 | W1 | <LOD | − | + |
|  | W2 | <LOD | − | + |

SD = Standard Deviation, LOD = Limit of Detection, QC = Quality Control
†Porcine microchimerism cannot be accurately quantified due to mixture of cells present in wound bed extraction
‡All QC gave a positive Ct, indicating no inhibition Naïve skin xenotransplants were analyzed for PERV copy number and as expected, each cell contained copies of PERV A (32±1), B (9±0.1) and C (16±0.1). Sera from the four recipients were evaluated for the presence of circulating PERV; all samples were found to be negative for PERV pol and below the limit of detection. PBMC samples from each of the four recipients were also tested for PERV and for microchimerism (i.e., the presence of circulating pig cells) and were also found negative, at all time points. Tissues taken at the end of the study (POD-30) were evaluated for PERV expression and again were found negative. Wound beds from animal 2102 were negative for the presence of PERV and for microchimerism. (Table 8) For the other animals, either one wound site or both were positive. This is not surprising due to the direct contact of the wound bed with the xenograft. It is expected that some porcine cells not associated with the graft may have sloughed off or been left behind in the process of removal at the end of the study. This is confirmed by the positive values achieved for the microchimerism assay attributing the PERV signal to porcine cell contamination. Altogether, these results provided no evidence of PERV transmission, consistent with previous studies.

Example 2

The following example provides a description of a process of harvesting and processing skin from a genetically reprogrammed swine produced in accordance with the present invention, with the skin to be used as a xenogeneic skin product for human transplantation. In some of these aspects, the xenotransplantation product consists of split thickness grafts consisting of dermal and epidermal tissue layers containing vital, non-terminally sterilized porcine cells derived from specialized, genetically reprogrammed, Designated Pathogen Free (DPF), source animals.

In one aspect, the genetically reprogrammed source animal is any genetically reprogrammed animal described in the present disclosure. In one non-limiting aspect, the genetically engineered source animals in this example do not contain any foreign, introduced DNA into the genome; the gene modification includes a knock-out of a single gene that was responsible for encoding for an enzyme that causes ubiquitous expression of a cell-surface antigen. The xenotransplantation product in this example does not incorporate transgene technologies, such as CD-46 or CD-55 transgenic constructs.

The process and techniques disclosed herein are but examples, and do not limit the scope of the invention. It will be fully understood that while this example is directed to xenotransplantation skin products, several of the steps in the following process and aspects of the overall approach can be applied to other organs or tissues, including, but not limited to, kidney, lung, liver, pancreas, nerve, heart, intestine, and other organs or tissue. It will be further understood that modifications to the processes and methods disclosed in this example (including additions or omissions of one or more process or method steps) can be made in relation to the harvesting and processing of other organs or tissue besides skin. This understanding is based in part on the fact that other organs and tissue will have different physical characteristics and so harvesting and processing steps for such other organs or tissue will be different from this example in certain practical ways (e.g., a kidney, heart, liver, lung, or other whole organ will not be cut to size and packaged in a cryovial supported by nylon mesh). Nonetheless, it will be further understood that additions or omissions of one or more process or method steps as applied to each such organ or tissue may be made to this example utilizing approaches known in the art (e.g., a harvested kidney, heart, liver, lung, or other whole organ will, in some aspects, be placed in an antipathogen bath or exposed to UV light as described herein for the removal of pathogens following harvest, and placed in one or more closure systems. For example, such one or more closure systems could include, but not be limited to, a first closure system (e.g., utilizing an inert material for initial closure to surround the organ to prevent the organ from coming into contact with or adhering to other materials proximate to the organ) and/or a second closure system (e.g., a sterile and secure outer container that contains the organ and first closure system (if a first closure system is utilized)). Such organs within such closure system(s) are configured to be transported to a clinical site as whole organs, stored, protected and transported in temperatures, sterility, and other conditions to maintain sterility and cell viability for transplantation as described herein at the clinical site.

Animal Preparation

Skin product processing occurs in a single, continuous, and self-contained, segregated manufacturing event that begins with the sacrifice of the source animal through completion of the production of the final product.

Xenogeneic skin grafts derived from the genetically reprogrammed source animal is received, with the swine being recently euthanized via captive bolt euthanasia in another section of the DPF Isolation Area. The source animal is contained in a sterile, non-porous bag that is contained within a plastic container which is delivered into the DPF Isolation Area and placed in an operating room where the procedure to harvest skin from the source animal will occur. All members of the operating team should be in full sterile surgical gear dressed in sterile dress to maintain designated pathogen free conditions prior to receiving the source animal and in some instanced be double-gloved to minimize contamination.

The operating area is prepared with materials required for harvesting skin from the source animal prior to decontamination (e.g., 24 hours prior with chlorine dioxide gas treatment) and prior to the procedure. Dermatome (electronic skin harvesting device, e.g., Amalgatome by Exsurco) power supply, and extension cord are sterilized and placed in the operating area prior to the operation. Any materials not in the room during the chlorine dioxide gas treatment (and therefore non-sterile) will be sprayed with 70% ethanol or isopropanol prior to entering the room.

The source animal is removed from the bag and container in an aseptic fashion, for example, a human lifting the source animal from the bag and container using sterilized gloves and/or sterilized device to aid lifting and minimize contamination. The source animal is scrubbed by operating staff for at least 2 minutes with Chlorhexidine brushes over the entire area of the animal where the operation will occur, periodically pouring Chlorhexidine over the area to ensure coverage.

The source animal is placed on its right lateral flank and dorsum towards the operating table leaving the left lateral flank and dorsum exposed. The exposed surface is scrubbed to the extreme visible surgical borders, and constrained by sterile drapes secured with towel clamps. The source animal is then scrubbed with opened Betadine brushes and sterile water rinse over the entire area of the animal where the operation will occur for approximately 2 minutes.

This Chlorhexidine and Betadine mixture will sit on the source animal for approximately 2 minutes, and staff (dressed in sterile dress to maintain designated pathogen free conditions) will then rinse and dry the source animal with sterile water and sterile gauze. The source animal's hair is removed so as to not impact the membrane or introduce another element that would degrade the cells. Hair removal is done using sterilized clippers and/or straight razor in the designated pathogen free environment immediately post-mortem with a clean blade utilizing a chlorhexidine lather. Staff will use the clippers and/or straight razor (lubricated in a sterile bath) to remove any remaining hair on the operating site, taking care to not puncture the skin. This procedure will be repeated (scrubbing to shaving) by turning the source animal onto the left lateral flank so as to expose the right side. The source animal will be rinsed with sterile water and dried with sterile towels and sprayed with 70% ethanol. The source animal will be inspected visually by the surgeon to ensure proper coverage of scrubbing. After the sterile scrub and final shaving, the source animal is ready for skin harvest.

Skin Harvesting

Operators will be dressed in sterile dress in accordance with program and other standards to maintain designated pathogen free conditions. All tissue from the source animal that will be used for xenotransplantation is harvested within 15 hours of the animal being sacrificed.

In one aspect, the source animal is laid on its side on an operating table. In this aspect, harvesting is done utilizing a dermatome circular blade, (for example and Amalgatome® SD). As the staff secures the animal in place, the surgeon determines the most appropriate width (e.g., 1, 2, 3, or 4 inches) and uses the circular dermatome to remove strips of split thickness skin grafts at a chosen thickness (e.g., 0.50 mm, 0.55 mm, 0.62 mm).

By way of further example, the thickness of the skin grafts could range from 0.01 mm to 4 mm, depending on the therapeutic needs at issue. It will also be understood that in some aspects a full thickness graft may also be utilized harvested with alternative harvesting and grafting procedures known in the art. Graft sizes can range from 1 $cm^2$ to 1000 $cm^2$ (or approximately 1 $ft^2$). It will be understood that larger graft sizes are also possible depending on the application and harvesting technique utilized and size of the source animal. It will be understood that for all aspects, other depths could be utilized as well, depending on the application and needs of the task at hand for therapeutic and/or other purposes.

In another aspect, skin harvesting involves surgically removing a skin flap from the animal first, then the skin flap is placed dermis-side down onto a harvest board (e.g., a solid board made of metal, plastic or other appropriate material) set upon on the operating table. In this aspect, sterile padding material is added beneath the skin flap and on top of the harvest board, to allow appropriate give for proper dermatome device function. The skin flap is then affixed to the harvest board firmly with steel clamps. Curved towel clamps are utilized on the side of the skin flap opposite the clamps until the skin is firm and taut. The surgeon will choose the most appropriate thickness on the dermatome and adjust per harvest conditions. The surgeon will use the dermatome on the secured skin flap, with an assistant maintaining tension along the dermatome progress. A second assistant may also provide assistance with skin flap tension, and may use rat tooth forceps to pull the graft product emerging from the dermatome.

Grafts are trimmed to desired sizes. By way of example, sizes can be: 5 cm×5 cm, with a total surface area of 25 $cm^2$ and uniform thickness of approximately 0.55 mm; 5 cm×15 cm, with a total surface area of 75 $cm^2$ and uniform thickness of approximately 0.55 mm; 8 cm×7.5 cm, with a total surface area of 60 $cm^2$ and uniform thickness of approximately 0.55 mm; 8 cm×15 cm with a total surface area of 120 $cm^2$ and uniform thickness of approximately 0.55 mm. It will be further understood that customizable sizes (i.e., width, thickness and length) can be created depending on patient needs, including larger sheets of skin can be harvested for use in xenotransplantation procedures.

The xenotransplantation product is further processed to be free of aerobic and anaerobic bacteria, fungus, and *Mycoplasma*. Under sterile conditions in a laminar flow hood in a drug product processing suite using applicable aseptic techniques, immediately after, within 1, 2, 3, 4, 5, 6, 7, 8, 9, 10 seconds, within 10 seconds to 1 minute, within 1 minute to 1 hour, within 1 hour to 15 hours, or within 15 hours to 24 hours following harvest, the xenotransplantation product is placed into an anti-microbial/anti-fungal bath ("antipathogen bath"). With regard to a skin product, this can occur after the skin product is trimmed to the proper dose size and shape (e.g., trimmed to squares, rectangles, or others shapes of desired size(s))

The antipathogen bath includes ampicillin, ceftazidime, vancomyocin, amphotericin-B placed in a sterile container and the xenotransplantation products are diluted as outlined in the following Table 5 and added to RPMI-1640 medium as outlined in the following Table 6. In one aspect, about 10 mL of medium is removed from the bottle before adding the above items.

TABLE 5

| Drug | Vial Mg | Diluent Vol | Diluent | Approx. Vol available | Approx. concentration |
|---|---|---|---|---|---|
| Ceftazidime | 1000 | 10.0 mL | Sterile water | 10.8 mL | 100 mg/mL |
| Ampicillin | 2000 | 10.0 mL | Sterile water | 11 mL | 180 mg/mL |
| Vancomycin | 500 | 10.0 mL | Sterile water | | 50 ug/mL |
| Amphotericin B | 50 | 5.0 mL | Sterile water | | 10 mg/mL |

TABLE 6

| Drug | Final Concentrations | mg/500 mL Media | Volume (mL) added to 500 mL RPMI 1640 |
|---|---|---|---|
| Ceftazidime | 500-2500 mg/L | 250-1250 mg | 2.5-10 |
| Ampicillin | 500-2500 mg/L | 250-1250 mg | 1-6 |
| Vancomycin | 25-125 mg/L | 10-75 mg | 0.25-2 |
| Amphotericin B | 40-200 mg/L | 20-100 mg | 2-10 |
| | | Total volume added | 5.75-28 |

It will be understood that while this example is directed to xenotransplantation skin products, other organs, including, but not limited to, kidney, lung, heart, liver, pancreas, and other organs can be bathed in the antipathogen bath in accordance with the present invention. The amounts of combination of drugs and other chemicals, and duration of exposure to such antipathogen bath, are performed to minimize the affect such exposure has on cell viability and mitochondrial activity to achieve both the desired antipathogen result and minimal manipulation of the xenotransplantation products in accordance with the present invention.

As an alternative, or in addition to, removing pathogens via the antipathogen bath, the products are made designated pathogen free by a process and system utilizing ultraviolet light. In this aspect, the operator is dressed in sterile dress in accordance with institutional standards to maintain designated pathogen free conditions. The operator wears eye protection safety glasses for ultraviolet light and lasers.

An ultraviolet laser lamp is set up in a laminar flow hood. Each of the four corners of the lamp is placed on two container lids that are stacked on top of each other, i.e., four pairs of lids are used to support the lamp, or other supporting items, able to position the lamp in a temporary or fixed position above the working surface of the hood. The distance from the lamp bulbs (2 bulb tubes total) to the floor of the hood is approximately 1.5 inches. The entire interior of the hood is sprayed with alcohol, e.g., ethanol or isopropanol. The lamp is turned on and the operator performs a calculation of time for desired exposure based on lamp specifications, number of bulbs, and distance between the bulbs and the xenotransplantation product.

The operator pours two baths (one chlorhexidine and one alcohol) into two separate bowls and places the two bowls under the hood.

A package of new sterilized cryovials is placed under the hood. Cryovial caps are unscrewed and placed into the chlorhexidine bath. Each cryovial (without cap) is then turned upside down and plunged open ended into the chlorhexidine bath, for one minute each and then set upright to air dry. Thereafter, the exterior of each cryovial is wiped with chlorhexidine and alcohol utilizing sterile gauze. The cryovial caps are removed from the chlorhexidine bath and placed on sterile gauze. The open ends of each vial were plunged into alcohol bath for 1 minute each and then set aside to air dry.

Xenotransplantation products recently obtained from the harvest/procurement phase in the surgical room are transferred into the product processing room, via a one-way entrance into the laminar flow hood. Anything entering the sterile field is wiped down with 70% ethanol prior to transfer to the operator. The operator will have access to all required materials in the laminar flow hood: xenotransplantation product (in sterile container), cryovials, 10 mL syringes and needles, phase freezer holding rack, and pre-cut nylon mesh. Only one size of the products is processed at a time to ensure proper control to final vials. The operator is seated at the laminar flow hood in compliance with sterile, aseptic techniques.

When using UV light sterilization, the product is placed under the UV lamp for a desired period of time, e.g., 2 minutes or more, then turned over to the other side, and put under the UV lamp for the same period of time, e.g., 2 minutes or more on opposite side. The time period for exposing a given sample to the UV is varied based on the specific biological agents or the types of biological agents to be sterilized, e.g., as shown in the following Table 7:

TABLE 7

| Biological Agent | Type of Biological Agent | UV-C Dosage (uW sec/cm$^2$) for 90% sterilization | Sterilization time (sec)* |
|---|---|---|---|
| *Penicillium* spp. | Fungus | 224,000 | 1800 |
| *Aspergillus flavus* | Fungus | 34,900 | 300 |
| *Aspergillus niger* | Fungus | 31,500 | 250 |
| Yeast | Fungus | 4000 | 30 |
| Influenza A | Virus | 1900 | 15 |
| HIV-1 | Virus | 28,000 | 220 |
| Vaccinia | Virus | 1500 | 10 |
| *Escherichia coli* | Bacteria | 2000 | 20 |
| *Staphylococcus aureus* | Bacteria | 6600 | 50 |
| *Bacillus subtilis* | Bacteria | 6800 | 50 |
| *Mycoplasma* spp. | Bacteria | 8400 | 70 |
| *Pseudomonas aeruginosa* | Bacteria | 2200 | 20 |

*Using a UV-C intensity of 125 uW/cm$^2$

With regard to other whole organs, product yield will typically depend on how many of each such whole organ a given source animal may have (e.g., one liver, two lungs, two kidneys, one heart, one pancreas and so forth).

It will also be understood that while this example is directed to xenotransplantation skin products, other organs, including, but not limited to, kidney, heart, lung, liver, pancreas, and other organs can be exposed to ultraviolet light and made designated pathogen free in accordance with the present invention. The UV exposure dosages, intensity, and duration of exposure to such ultraviolet light, are performed to minimize the affect such exposure has on cell viability and mitochondrial activity to achieve both the desired antipathogen result and minimal manipulation of the xenotransplantation products in accordance with the present invention.

Manufacturing Process

Generally

Through the continuous manufacturing event, source animals are processed into aseptic xenotransplantation products. Several items are involved in the manufacture of the product relating to the source animals, including, but not limited to:
  a) care and husbandry of the source animals (including, as described herein, providing certain vaccinations, carefully maintaining and analyzing pedigree records, performing proper animal husbandry, and maintaining the animals in isolation barrier conditions);
  b) product manufacturing (including, as described herein, processing the source animals into the subject product from euthanizing to harvest);
  c) analytical testing of the source animals (including, as described herein, screening for adventitious agents including parasitology, bacteriology, and virology assays);
  d) analytical testing of the source animals (including, as described herein, confirming the source animal is an alpha-1,3-galactotransferase knockout or has other characteristics that are desired for a given application); and
  e) analytical testing of the source animals (including, as described herein, viral assay for Endogenous Viruses (PERV)).

Several items are also involved in the manufacture and release testing of the resulting products, including, but not limited to:

a) product manufacturing (including, as described herein, processing the drug product, storing the drug product, and releasing the drug product);
b) analytical testing of the drug product (including, as described herein, viability testing (via, e.g., MTT assay)),
c) sterility testing (including, as described herein, aerobic bacteria culture, anaerobic bacteria culture, fungal culture, *Mycoplasma* assay, endotoxin test, USP <71>)),
d) adventitious agent testing (including, as described herein, PCR Assay for e.g., Endogenous Viruses (PERV)); and
e) analytical testing of the drug product (including, as described herein, histology).

For skin, the quantity of product yield from each animal can vary depending on the size of each animal. By way of example, some animals could yield between 3,000 and 6,000 cm$^2$ in product. In one aspect, a single batch of skin product is harvested from a single source animal in a continuous process. A batch description of the xenotransplantation product is provided in Table 8 and batch formula for the xenotransplantation product is provided in Table 9.

TABLE 8

Batch Size

| Product (strength) | Lot Size |
|---|---|
| Xenotransplantation product Drug Product, Dosage Strength 1 (7.5 grams, 25 cm$^2$) | 200 Units (180-220) (1.5 kgs per lot) (1.35 kg to 1.65 kg) |
| Xenotransplantation product Drug Product, Dosage Strength 2 (22.5 grams, 75 cm$^2$) | 67 units (60-75) (1.5 kgs per lot) (1.35 kg to 1.65 kg) |

TABLE 9

Batch Formula

| Component | Nominal Amount per Vial | Nominal Amount per Lot |
|---|---|---|
| Xenotransplantation product Drug Substance Dosage Strength 1 | 25 cm$^2$ | 200 Units |
| CryoStor | 7 ml | 1.4 L |
| Nylon Mesh | 60 cm$^2$ | 1200 cm$^2$ |
| Total Batch Size | 7.5 grams | 1.5 kgs |
| Xenotransplantation product Drug Substance Dosage Strength 1 | 75 cm$^2$ | 67 Units |
| CryoStor | 5 ml | 350 ml |
| Nylon Mesh | 180 cm$^2$ | 3600 cm$^2$ |
| Total Batch Size | 22.5 grams | 1.5 kgs |

Prior lot testing is performed under good laboratory practice ("GLP") conditions to ensure process sterility is maintained consistently. Assurance of sterility of the final product is determined prior to material release and clinical use. Prior to validation for human clinical use, all xenotransplantation products will meet certain acceptance criteria, including as described herein. The final drug product control strategy and analytical testing is conducted at the conclusion of the manufacturing process prior to release for clinical use. Results of the required analytical tests will be documented via a drug product certificate of analysis (COA) that is maintained with a master batch record pertaining to each lot of xenotransplantation products.

Source animal sample archives are generated and maintained through procurement of tissue samples of lung, liver, spleen, spinal cord, brain, kidney, and skin. These tissues are collected for source animal tissues for testing, archive, and stored for potential future testing. Archived samples of source animal tissue and bodily fluids should be stored at minus (−) 70 degrees Celsius or lower, as appropriate for preserving the sample. In other aspects, fixed samples can be maintained at room temperature. Appropriate tissue samples should be collected for formalin fixation and paraffin-embedding and for cryopreservation from source animals at the time the live cells, tissues, or organs are procured. Cryopreservation should be at least ten 0.5 cc aliquots of citrated- or EDTA-anticoagulated plasma; five aliquots of viable leukocytes (1×10$^7$/aliquot, for subsequent isolation of nucleic acids and proteins or for use as a source of viable cells for co-culture or other tissue culture assays.

Product Processing Following Harvesting

The previously harvested and minimally manipulated xenotransplantation skin product (here the skin integrity being minimally manipulated dermal and epidermal tissue layers with standard cellular morphology and organization) enters the separate, adjacent room with positive pressure above that of the surgical suite, designated as the Class 10,000 (ISO-7) product processing room.

The operating room will be setup per operating preparation procedures and the operating personnel will be dressed in Tyvex suits for fume hood work. If requested, an assistant will also be dressed in a Tyvex suit. Gowning and Dressing is done with aseptic techniques. Gloves and sleeves will be sprayed with alcohol if needed. The ABSL-2 laminar flow hood, having been prior sterilized via gaseous chlorine dioxide sterilization process, will be sprayed with alcohol, e.g. 70% ethanol, and the laminar flow exhaust will be initiated. Utilizing aseptic techniques, previously sterilized via autoclave, surgical instrument, cryovials, cryotray, flasks, syringes, needles, additional containers, and all processing equipment will be placed within the laminar flow hood. Exterior packaging is sprayed with alcohol prior to being transferred to the operator.

As described herein, prior to operation, nylon mesh graft backing should be cut into squares of appropriate size for the dosage levels, sealed in an autoclavable pouch, and sterilized via steam. Exterior of pouch will then be sterilized with 70% ethanol and placed in the fume hood. Exterior package of 10 mL Cryovials will be decontaminated with 70% ethanol and placed into the fume hood. Sterile, autoclaved surgical instrument package should be sprayed with 70% ethanol and transferred to the operator.

Sterile syringes and needles should be sprayed with 70% ethanol and transferred to the operator. Graft tissue recently harvest form the porcine donor will be transferred to the hood. Anything entering the sterile field is wiped down with 70% ethanol prior to transfer to the operator. Operator will have access to all required materials in the fume hood: Grafts (in sterile container), Cryovials, 10 mL syringes and needles, Phase Freezer holding rack, and cut Nylon mesh. Operator should be seated at the fume hood with in compliance with sterile, aseptic technique.

Referring to FIG. 45, each cryovial will be sterilized and labeled in advance to reduce processing time and unnecessary material exposure to DMSO prior to cryopreservation. Pans containing each xenotransplantation product and the RPMI 1640 Tissue Culture Media at room temperature with antibiotics (e.g., antipathogen bath) is placed under the laminar flow hood. The products had been bathing in the anti-pathogen bath for not less than 30 minutes to sterilize the xenotransplantation product.

In one aspect, when using UV light sterilization, the cryovials are sterilized using the UV lamp as described above. After the product is inserted into each vial, each new cap is placed on each new vial and screwed on securely. Each vial is placed under the lamp and periodically rolled for desired even exposure to light on the exterior of the vial. The vials are placed inside a glass jar that has an interior that has been previously sterilized and the exterior is sterilized by the operator with alcohol and chlorhexidine, including threads and caps. Vials are wiped down with alcohol and are placed into glass jars. The exteriors of the glass jars are drenched with alcohol outside of the hood. Under the hood, the operator bathes the glass jar lids and plunges the open ends of the jars into alcohol and wipes the exterior of the jars with alcohol (and optionally chlorhexidine) including threads of the jar. The vials are wiped with alcohol utilizing gauze and placed inside each glass jar with an instrument. The lids of the glass jars are then secured and the jars are handed to the assistant. Frequently and on a periodic basis throughout these processes, the assistant sprays the operator's gloves and arms with alcohol.

In this example, the xenotransplantation skin product, which was cut to form in the surgical suite with sterile scissors and was trimmed with 10-blade scalpel, will be re-measured with a sterile, stainless steel ruler to verify technical specifications and dimensions have been met. The xenotransplantation skin product is visually inspected to ensure no rips, tears, observable defects, or excessive or insufficient thickness are present.

Under the laminar flow hood the operator will use forceps to take a single xenotransplantation skin product from the antipathogen bath and place it upon a piece of nylon mesh that has been previously cut to fit the cryovial, centered on the nylon mesh, with the dermis side in contact with the mesh (e.g., dermis side down), taking 1 minute for each product (understanding the time could be less or more, and up to 5 minutes for each product). It will be understood that the sterile nylon mesh packaging component is utilized, among other things, to support the xenotransplantation product and prevent self-adhesion of the xenotransplantation product when rolled.

It will be further understood that the sterile nylon mesh packaging component can be of any dimension that would allow the xenotransplantation product to be placed onto the sterile nylon mesh packaging component and fit within the two dimensional surface area (i.e., the length and width not including the thickness) of the sterile nylon mesh packaging component (e.g., the two dimensional area dimension of the xenotransplantation product would be less than the two dimensional area dimension of the sterile nylon mesh packaging component).

It will be further understood that the dimensions of the sterile nylon mesh packaging component would be sized in accordance with the xenotransplantation product size and dosage. For example, the sterile nylon mesh packaging component is 8 cm×7.5 cm (60 cm$^2$) to fit a 5 cm×5 cm xenotransplantation skin product (25 cm$^2$) (7.5 grams) utilizing 7 ml of cryoprotective media when placed in the cryovial. It will be even further understood that the dimensions of the sterile nylon mesh packaging component is 8 cm×22.5 cm (180 cm$^2$) to fit a 5 cm×15 cm xenotransplantation skin product (75 cm$^2$) (22.5 grams) utilizing 5 ml of cryoprotective media when placed in the cryovial.

Unintentional adhesion of epidermal or dermal regions of the xenotransplantation skin product during packaging may disrupt the integrity of the xenotransplantation skin product and potentially reduce its therapeutic viability. Inclusion of the sterile nylon-mesh packaging component is intended to provide internal physical support to and prevent self-adhesion. The sterile nylon-mesh packaging component is not biologically or chemically active and does not directly impact the metabolic activity or efficacy of the xenotransplantation skin product itself.

During the course of numerous experiments, including the monkey studies described in Example 1 herein, use of this sterile nylon-mesh packaging component has never been observed to cause an adverse, undesired reaction with the xenotransplantation product, or degrade and contaminate the final xenotransplantation product causing adverse reactions or outcomes to the recipient. The sterile, nylon-mesh packaging component is not used in the grafting procedure. Following cryopreservation and thawing, and prior to use of the xenotransplantation product, it is discarded. Thus, selection of the specific material and associated specifications were carefully chosen for the given application. Medifab 100-Micron Nylon Mesh (Part #03-100/32-Medifab) is manufactured per cGMP standards, and was selected because of its physical characteristics and certified acceptability for human, clinical use.

Under the laminar flow hood, the operator will then tightly roll this combination of xenotransplantation product and nylon mesh packaging component and place the combination within a cryovial (e.g., 10 ml vial) taking 1 minute for each product (understanding the time could be less or more, and up to 5 minutes for each product). In this aspect, the mesh material is rolled to ensure that the vertical height of the cylinder is 8 cm and uniformly fits within the 10 ml cryovial (e.g., 10 cm length and 17 mm diameter) and once completed, can be secured with a threaded seal cap. The mesh material is oriented such that the protective mesh material is on the exterior of the xenotransplantation product, and that once the rolled is complete there is no exposed or visible xenotransplantation material and it is fully encased in the protective insert. The intrinsic tensile and material properties of the sterile nylon-mesh packaging component are homogenous, and the inelasticity or stiffness of the material causes it to expand to fill the volume of the cryovial. Thus, regardless of the initial "roll-density", the material will uniformly loosen and is therefore standardized.

Under the laminar flow hood the operator will then use a sterile syringe to draw up enough sterile cryoprotective media (e.g., 5-7 ml of the media with 5% dimethyl sulfoxide (DMSO) (Cryostor CS5, BioLife Solutions)) to fill the cryovial until the skin product roll is fully immersed, ensuring that the combination of xenotransplantation skin material, mesh backing, and cryoprotectant media is flush with the 10 ml fill line, taking 1 minute for each product (understanding the time could be less or more, and up to 5 minutes for each product).

Under the laminar flow hood, the operator will seal the cryovial with the threaded cap. The identity of the contents and label information are confirmed by the operator. Labels are prepopulated and applied to the exterior of the cryovials containing the product in advance of the product processing.

It will be understood that the preparation of the xenotransplantation products and packaging components described herein could be in the form of therapeutic dosages.

For example, the xenotransplantation drug product consists of:
q. Xenotransplantation split-thickness skin Drug Substance
r. Primary Container Closure System which includes
  i. Primary Packaging Component: a sterile, clear, polypropylene 10 ml cryovial with threaded seal-cap
  ii. Sterile nylon-mesh packaging component
  iii. Cryoprotective media packaging component The indicated dosage of Xenotransplantation product is 300 mg of vital, metabolically active, porcine xenotransplantation drug substance per $cm^2$, with a constant thickness of 0.55 mm. Example formulations include:
s. Dosage Strength 1: a 25 $cm^2$ split thickness skin graft, with uniform thickness of 0.55 mm, which weighs approximately 7.5 grams.
t. Dosage Strength 2: a 75 $cm^2$ split thickness skin graft, with uniform thickness of 0.55 mm, which weights approximately 22.5 grams.

An example xenotransplantation drug product primary packaging component is a sterile, clear, polypropylene 10 ml cryovial with threaded seal-cap. For example, the Simport Cryovial, T310 (10-ml) is manufactured by Simport Scientific. This product is composed of medical grade resin that is BPA free, Heavy Metal Free, and LATEX Free and meets USP Class VI limits.

A nylon-mesh packaging component is utilized during the xenotransplantation drug product manufacturing process. The prepared xenotransplantation drug product is placed on sterile nylon-mesh packaging component (e.g., Medifab 100-Micron Nylon Mesh) that has been previously trimmed to the following dimensions:
u. Dosage Strength 1: 7.5 cm in width by 8 cm in height; total area of 60 $cm^2$
v. Dosage Strength 2: 22.5 cm in width by 8 cm in height; total area of 180 $cm^2$ A cryoprotective media packaging component is also utilized during the drug manufacturing process. The xenotransplantation drug product is immersed in the following volumes of cryoprotective media packaging component prior to cryopreservation:
w. Dosage Strength 1: 7 ml of Cryostor CS5 (containing 5% DMSO).
x. Dosage Strength 2: 5 ml of Cryostor CS5 (containing 5% DMSO).

With regard to the assurance of saturation of cryoprotective media, the indicated amount of CryoStor CS5 media (per Dosage Strength) is applied via 10 ml syringe with the cryovial (such as a type of cryovial shown in FIG. 46) in the vertical position, under a laminar flow hood (ISO-5, FED STD 209E Class 100 conditions) Cryomedia fills the voided space(s), and gravity ensures that the fill-process begins from the base of the vertically oriented cryovial towards the fill line at the apex. Volume is added until it reaches the manufacturers demarcated 10 ml fill line. Filling the vial in this manner also facilitates the removal of air bubbles. Once complete, the threaded cap is sealed. Visual and physical verification of saturation and fill is accomplished, ensuring that contents the xenotransplantation product are unable to shift internally.

Cryopreservation

Product materials will be placed in the appropriate freezer rack containing cryovials with product as described above, and placed in a certified, Q-A control rate-phase freezer. Using a certified, Q-A control rate-phase freezer, the entire product is cryopreserved via one standardized control-rate freezing process:
y. Starting at 4° C., internal chamber and sample temperature probe will lower at a rate of 1° Celsius per minute until a temperature of −40° C. is achieved.
z. Once temperature of −40° C. has been reached in a controlled rate, control-rate freezer sample temperature probe should lower rapidly from −40° C. to −80° C.
aa. Material is then transferred to a GLP certified, −80° C. freezer until use.

Taking 40 minutes per batch time from room temperature to −80° C. (understanding the time could be less or more, and up to 2 hours). In some aspects, penetrative cryoprotectants such as DMSO, may be used to protect morphology and tissue structure, and retain metabolic activity levels comparable to that of fresh skin. In some aspects, cryopreservation may alternatively or additionally include one or more of glycerol, gentamicin, Nystatin, L-glutamine, and other processing solutions. In some aspects, β-lactam antibiotics are not used.

Inclusion of the cryoprotective-media packaging component is intended to support cell survival during the freeze-thaw cycle required for the xenotransplantation product. Failure to include the cryoprotective media packaging component of xenotransplantation product during packaging may disrupt the integrity of the xenotransplantation product or impede the cryopreservation process, and may potentially reduce the xenotransplantation product viability below acceptance criteria. Cryopreservation of the xenotransplantation product without inclusion a cryoprotective media results in destruction of biologically active cells contained in the xenotransplantation product. Rapid formation of ice crystals and disruption of cellular membranes and mitochondrial organelle barriers occurs during the freezing process, and the dimethyl-sulfoxide ingredient acts to displace intracellular fluid. Thus, the cryoprotective media reduces the formation of such ice crystals and rapid, disruptive increase in total cellular volume that would negatively impact the cellular viability and, thus, the efficacy of the Drug Product.

During the course of a number of experiments, including the monkey studies in Example 1 herein, use of this cryoprotective-media packaging component has never been observed to cause an adverse, undesired reaction with the xenotransplantation product, or degrade and contaminate the final xenotransplantation product causing adverse reactions or outcomes to the recipient. Thus, selection of the specific material and associated specifications were chosen to meet appropriate standards necessary of a xenotransplantation product intended for human, clinical use. This including identifying a cryoprotective media with minimal, subclinical levels of DMSO, one that would satisfactorily perform without the need for inclusion of an additional xenotransplantation material (porcine serum) in the formulation. The cryoprotective media-packaging component is not used in the grafting procedure. Upon thawing, and prior to use of the xenotransplantation for therapeutic uses including as a drug product, it is discarded. CryoStor CS5 is manufactured per cGMP standards and was selected because of its certified acceptability for human, clinical use.

Shipping to Clinical Site

Shipping the product to the clinical site should be done to maintain the xenotransplantation skin product material at −80° C. storage condition. One example shipping container is the EXP-6 Standard Dry Vapor Shipper having an extensive, having the following specifications:

Dynamic Holding Time 10 Days
Holding Temperature −150° C. or Colder
Core Technology Dry Vapor Liquid Nitrogen
Specimen Chamber 2.8" (71 mm) Diameter
11.5" (292 mm) Depth
Weight Dry 9.7 lbs/4.4 kg
Charged 18.3 lbs/8.3 kg
Domestic Dimensional 21.07 lbs/9.56 kg
International Dimensional 24.87 lbs/11.28 kg
Outer Box 12"×12"×22"
(305×305×559 mm)

Figure 47:
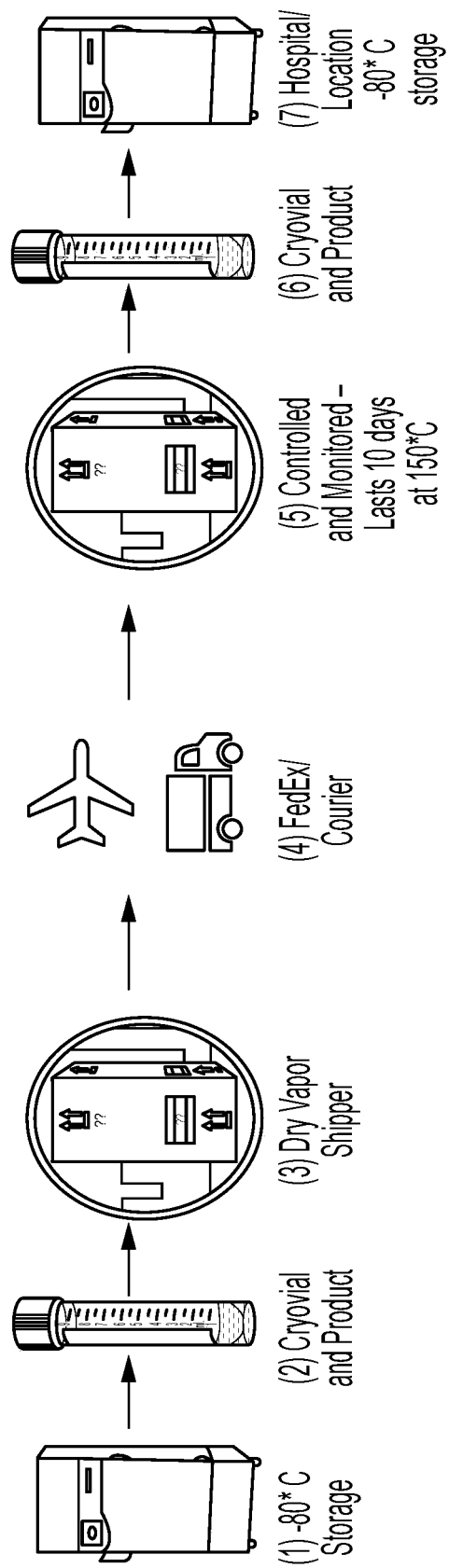
FIG. 47 shows a shipping process of a xenotransplantation product.

Aspects of the shipping process are also shown in FIG. 47 including, but not limited to, (1) cryopreservation storage; (2) xenotransplantation product in cryovial and media as described herein while in cryopreservation storage; (3) cryovial placed in dry vapor shipping container (or secondary closure system); (4) container and vial shipped via courier; (5) xenotransplantation product controlled and monitored at delivery location (can last at least 10 days at minus (−) 150 degrees Celsius or colder); (6) xenotransplantation product in cryovial and media as described herein removed from container/secondary closure system; (7) xenotransplantation product in cryovial and media as described herein placed in freezer at location being stored at −80° C.

Clinical Site Preparation

In one aspect, the drug product arrives at the clinical site as a cryopreserved xenotransplantation product. Prior to use, the xenotransplantation product must be thawed in a 37° C. water bath, removed from the vial and washed in a series of 3 sterile 0.9% saline baths at room temperature.

For the thawing process, sterile equipment and aseptic techniques are used:

a) Prepare 200 mL of normal saline into each of three 500 mL sterile, surgical bowls.
b) Place the unopened cryovial with the skin product in water bath having a temperature of about 25° C. In some embodiments, the temperature is about 37° C.
c) In the bath, swirl gently for approximately 5 minutes or until tissue is mobile within the cryovial, taking care to minimize unnecessary exposure time the xenotransplantation skin product tissue is suspended in the thawed DMSO as much as possible.
d) Open the cryovial and use sterile forceps to quickly remove tissue and mesh to transfer into a bowl of normal saline.
e) Using sterile forceps, ensure tissue is fully submerged in saline for 15 seconds, agitating by swirling gently to maximize coverage. The underlying, supportive mesh material should be separated from the skin xenotransplantation skin product material. Use a second pair of sterile forceps to separate if necessary. Mesh can be left in the bowl, or discarded.
f) Using sterile forceps, transfer the skin into a second bowl wash. Submerge fully and gently swirl for 15 seconds; this is a serial dilution or "rinse".
g) Repeat the previous step, using sterile forceps to transfer the skin into a third wash of normal saline. Submerge fully and gently swirl for about 15 seconds.
h) The entire duration of the rinse process should be completed within 60 seconds to minimize unnecessary exposure time the product is suspended in thawed DMSO in order to maximize product efficacy.
i) Tissue is now thawed, rinsed, and ready for application. Leave in normal saline until use, not to exceed 2 hours at about 25° C.

After the complete, thaw and rinse process is complete, the xenotransplantation product is ready for placement on the wound site. Serial washes in saline, once thawed provide ample dilutive solvent to remove the residual cryoprotectant (5% DMSO solution, CryoStor CS5) and replace the intracellular fluid levels to normal homeostatic conditions. Such dilution and use of a cryoprotective media containing a sub-clinical level of DMSO ensures that any minimal, residual DMSO remaining on the xenotransplantation skin product material post-thaw would be non-appreciable and would be highly unlikely to be clinically significant. This process also ensures retention of the maximum amount of metabolically active cells, and thereby maximizing the efficacy of the xenotransplantation product.

Example of Thawing. Following is one example of a thawing procedure for a xenotransplantation product. Thawing can occur in a BioSafety Cabinet with operator in sterile gloves as follows: (i) prepare 200 mL of Normal saline into each of three 500 mL surgical bowls; (ii) prepare the water bath by wiping it clean with chlorhexidine then spraying it down with 70% ethanol; (iii) after the ethanol has dried add sterile water solution into the water bath and heat to 37° C.+/−2° C.; (iv) the xenotransplantation drug product is in a double bag, leave it unopened and place it into the 37° C. water bath; (v) swirl gently for approximately 5 minutes or until the tissue is mobile within the cryovial; (vi) minimize the time the tissue spends in thawed DMSO as much as possible; (vii) spray the outside bags with ethanol and remove the vial from the outer bags and spray the xenotransplantation drug product cryovials with 70% ethanol before placing into Biosafety Cabinet; (viii) unscrew the cryovial and use forceps to quickly remove tissue and mesh to transfer into a bowl of normal saline; (ix) use forceps to ensure tissue is fully submerged in saline for 60 seconds, agitating by swirling gently to maximize coverage; (x) the mesh should be separated from the skin, using a second pair of forceps to separate if necessary; (xi) the mesh can be left in the bowl, or discarded; (xii) using forceps transfer the skin into the second bowl wash; (xiii) submerge fully and gently swirl for 60 seconds; (xiv) using forceps transfer the skin into the third bowl wash and submerge fully and gently swirl for 60 seconds. Tissue is now thawed and ready for application. Keep it moist with sterile saline in a sterile pan.

The process of rolling the inert, nylon mesh backing and the xenotransplantation skin product results in uniform "roll-density" of the xenotransplantation product. All mesh materials are cut to uniform dimensions, according to the prescribed dimensions for the given application, and are obtained from the same material lot, thus affording uniform material properties for all units of the skin product manufactured within a specific lot.

The intrinsic tensile and material properties of the nylon mesh insert are homogenous, and the inelasticity or stiffness of the material causes it to expand to fill the volume of the primary container closure system (cryovial). Thus, regardless of the initial "roll-density", the material will uniformly loosen and is therefore standardized.

The indicated amount of CryoStor CS5 media (per Dosage Strength) is applied via 10 ml-syringe with the cryovial in the vertical position, under Class 100, ISO5 conditions within an ABSL-2 laminar flow hood.

Cryomedia fills the voided space(s), and gravity ensures that the fill-process begins from the base of the vertically oriented cryovial towards the fill line at the apex. Volume is added until it reaches the manufacturers demarcated 10 ml fill line. Filling the vial in this manner also facilitates the removal of air bubbles.

Once complete, the threaded cap is sealed. Visual and physical assurance of saturation and fill is accomplished by the shaking the skin product ensuring that contents are unable to shift internally. Aspects of the cryovial are also shown in FIG. 46, with aspects that can include, among other things, 10 ml volume, size of 17 mm×84 mm, vertical ribs facilitating cap removal, silicone washer, cap and tube made of the same polypropylene material with the same coefficient of expansion ensuring seal at all temperatures, 1 and ¼ turn thread design, thick wall, large white marking area, and round bottom allowing for ease of emptying contents.

Figure 48:
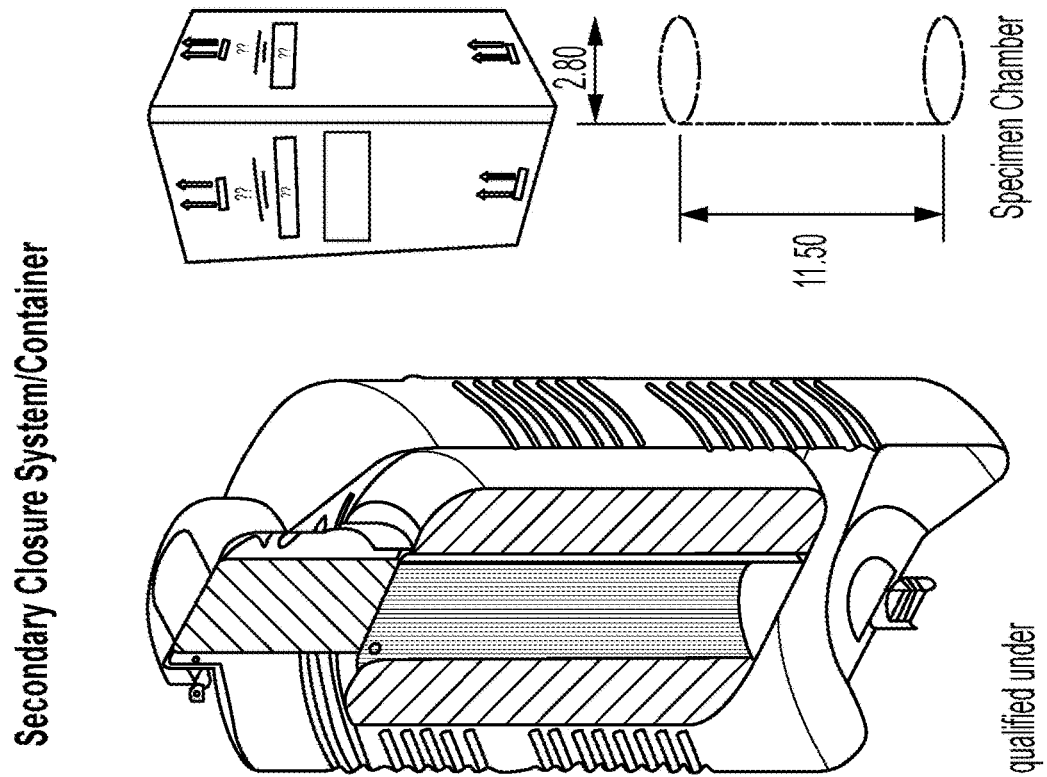
FIG. 48 shows a secondary closure or container system for storing a xenotransplantation product at temperatures below ambient temperature, including, but not limited to, −150 degrees Celsius and other temperatures.

Aspects of the secondary closure system is shown in FIG. 48, with aspects that can include, among other things, Tyvek-1073B medical grade construction, 5 inches wide× 12" high, storage ability of 15 canes or 2 cryovial boxes, holding temperature of −150 degrees Celsius or colder, utilization of dry vapor liquid nitrogen, IATA rated 10 days of dynamic holding time under normal shipping conditions, specimen chamber diameter of 2.8 inches (71 mm), specimen chamber depth of 11.5 inches (292 mm), dry weight of 9.7 lbs/4.4 kg, charged weight of 18.3 lbs./8.3 kg, domestic dimensional weight of 21.07 lbs./9.56 kg, international dimensional weight of 24.87 lbs./11.28 kg, outer box dimensions of 12"×12"×22."

No additional or external impurities in the product are anticipated to be present since processing involves only the minimal mechanical manipulation of the product, and no other chemical or biological agents are introduced during this closed process. Acceptance criteria testing required for use of the source animals for the product manufacturing process is conducted as described herein and documented via the Drug Product COA. The final product is evaluated for viral adventitious agents as described herein.

In terms of shelf life, continuous storage of the xenotransplantation product as described support a shelf life long-term stability (cell-viability) of up to at least 7 years (in one embodiment is a shelf life of 6 months) when stored continuously at −80° C. The shelf-life duration of continued cryopreservation of the xenotransplantation product with of at least 7 years. Table 10 shows stability time points that the xenotransplantation product will be tested.

TABLE 10

Stability Study Time Points

| Assay | Time points (Months) | | | | |
|---|---|---|---|---|---|
| | 0 | 12 | 24 | 36 | 60 |
| Histology | A | B | B | B | B |
| Sterility | A | B | B | B | B |
| Endotoxin | A | B | B | B | B |
| Viability | A | B | B | B | B |

A = initial product release testing
B = stability testing for Xenotransplantation product In accordance with one aspect, following in Table 11 are items that can be utilized in a certificate of analysis and release.

TABLE 11

Test Results

| Test | Method | Acceptance Criteria | Results |
|---|---|---|---|
| Appearance | Visual Inspection | Clear, colorless to slightly yellow liquid with no visible particulates | Conforms |
| pH | TM5110 USP <791> | 7.5 to 7.7 | 7.6 |
| Metabolic Activity Assay | TMS100 | Cell viability is 75% to 200% of cells preserved in the internal standard at Day 1 recovery following preservation. | 87 |
| Endotoxin | Kinetic Chromogenic USP <85> | ≤ 0.5 EU/ml | Conforms |
| Sterility | Membrane Filtration USP <71> | Sterile | Conforms |
| Identification | TMS111 FT-IR | Conforms to CryoStor CS5 Reference Standard | Conforms |
| Osmolality | TM 5112 USP <785> | 1360-1390 mOsm/kgH20 | 1388 |
| Specific Gravity | TM5114 | 1.055-1.063 | 1.059 |
| DMSO Content | Gas Chromatography (FID) | 4.0%-7.0% | 5.0 |

Example 3

Porcine skin shares fundamental properties with human skin and represents a potential alternative to human cadaver skin grafts for temporary coverage of severe burns. The impact of extended cryopreservation on porcine grafts on graft viability, graft take, and barrier function was examined in a study using a model of MHC matched and mismatched MHC Class II skin transplants.

Cellular viability was assessed using formazan-MTT and the biological properties of the grafts, were assessed by grafting on swine recipients. To complement the in vivo clinical assessments, histologic, and morphologic analyses, a series of MTT-reduction assays were performed to evaluate the residual viability of porcine grafts after cryopreservation and long-term storage. Mitochondria reduce MTT into a formazan metabolite, which can be observed as purple hue. Harnessing this phenomenon, an analysis of changes in optical density values measured by a spectrophotometer, or an interpolation of the quantities of formazan produced against standard curves, can provide differential assessments of cellular viability, between experimental samples and positive and negative controls. There were 2 cohorts of 2 animals each (total, N=4) based upon the MHC match and each swine received 4 grafts: one autograft and three allografts of identical MHC-profiles. Grafts were clinically assessed for graft-take, adherence, and time to graft rejection. Rejection was also assessed histologically via the Banff grading scale.

Direct comparisons between otherwise equivalent materials yield meaningful, differential times of survival, based solely on duration of storage, holding all other factors constant. Side-by-side, in vivo evaluations are performed between equivalent grafts, preserved in identical fashion, stored for periods of 15 minutes versus 7 years. Clinical gross assessments and photographs, paired with independent histological assessments, determine whether any appreciable differences in graft survival exist relative to the length of time in the frozen state. In tandem, separate in vitro assessments of graft viability, quantified by MTT-reduction assays, characterize the metabolic activity of cells post-cryopreservation and various storage terms. Further, independent histomorphological analysis, using standard histological (H&E) staining, provides evidence as to whether these processes cause observable changes to the graft material at a structural level. This study advantageously used materials that had been stored, uninterrupted, for such a time, along with the associated surgical records and standardized institutional protocols. Further, processing methods and protocols between the comparative groups were standardized, and identically applied, with respect to cryopreservation and thawing protocols, reagents, and methods employed. Combined, this allowed for isolated, side-by-side evaluation of duration of storage, and alleviated the need to model or extrapolate findings, or otherwise use normative predictive methods. Furthermore, the use of MHC-matched and Class II mismatched donor-recipient pairs in this model of allogeneic skin transplantation served as internal controls to both confirm the identity of the tissues obtained seven years earlier, and the veracity of the surgical notes and documentation. Further, equivalent behavior exhibited by the allografts also demonstrates that the antigenicity of the grafts was not altered as a result of the duration of storage.

Figure 49A:
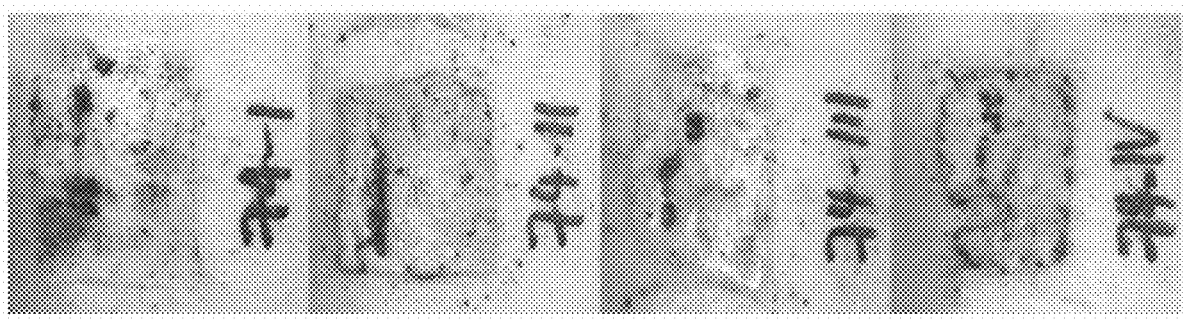
FIG. 49A depicts porcine split-thickness skin grafts at wound sites 1, 2, 3, and 4, respectively from left to right at POD-12.
Figure 49B:
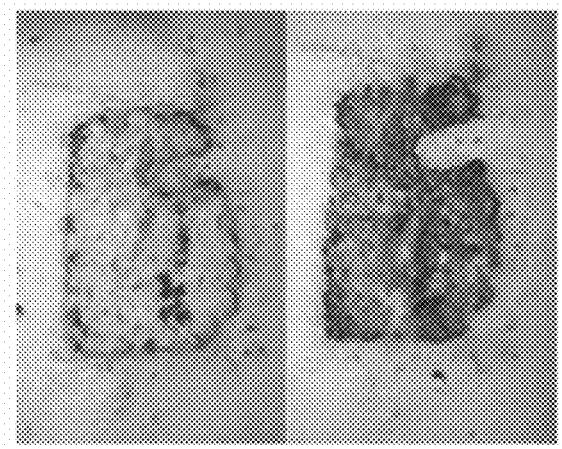
FIG. 49B depicts porcine split-thickness skin grafts at wound site 4 at POD-12 (left) and POD-14 (right).

There were no technical failures; all grafts adhered to their respective wound beds and re-vascularized. In cohort 1 (MHC-matched donor-recipient pair), all grafts remained adherent, and appeared uniformly healthy at postoperative day (POD) 12 (FIG. 49A), but at POD-14, signs of necrosis, progressive erythema and loss of adherence were observed (FIG. 49B). Clinical assessment of the 6 grafts in cohort 1 showed rejection at POD-14 to 18. In cohort 2, MHC Class II mismatched, allogeneic grafts appeared comparable to autografts through POD-4. However, by POD-8, all allogeneic grafts demonstrated mild erythema, consistent with rejection and were considered fully rejected by POD-10. No statistically significant difference in the duration, quality of adherence, or cellular viability among the fresh, recently preserved, and long term preserved skin grafts were observed. The cryopreserved materials were, statistically speaking, more alive than dead, and this finding was empirically witnessed in vivo, as all 7-year grafts demonstrated adherence to the wound bed and prolonged survivability. Such survivability would not have been exhibited by non-vital allografts. Without limiting the invention, it will be understood that the time period for cryopreservation for the present invention may, for example, include any length of time up to about 7 years.

Materials and Methods:

The study was conducted in accordance an IACUC approved protocol (2005N000279, Amendment 69) at the Center for Transplantation Sciences, and in compliance with the U.S. Department of Agriculture's (USDA) Animal Welfare Act (9 CFR Parts 1, 2 and 3), the Guide for the Care and Use of Laboratory Animals, and all state, local laws and regulations. Study protocols, surgical procedures, and animal care guidelines were independently reviewed and monitored by a standing IACUC committee.

A total of eight swine were enrolled in this experiment, and all were members of the Sachs-NIH, inbred miniature swine colony. At the time of surgery, all swine were between 10 and 20-kg in total body weight and between 2 and 4 months of age. Immunosuppression regimen(s) were not administered at any time during this experiment. Animals 24074 and 24075 were assigned to Cohort 1 and represented a MHC-matched donor-recipient pair. Animals 24043 and 24070 were assigned to Cohort 2 and represented a mismatch of MHC Class II donor-recipient pair. Separately, for the in vitro, MTT series of analyses, five, additional wild-type Göttingen miniature swine provided tissues for positive and negative controls.

Swine donors were anesthetized with I.M. 2 mg/kg telazol (tiletamine HCl and zolazepam HCl, Zoetis Inc., Kalamazoo, Mich.) and brought to the operating room for orotracheal intubation. Anesthesia was maintained using 2% isoflurane and oxygen. Skin surfaces were disinfected before surgery with chlorhexidine acetate (Nolvasan® Surgical Scrub, Fort Dodge Animal Health, Fort Dodge, Iowa) and povidone-iodine, 10% (Betadine Solution, Purdue Products, L.P., Stamford, Conn.). The animals were then draped, leaving the right side of the dorsum exposed. Split-thickness skin grafts, measuring approximately 25 $cm^2$ (surface area) were harvested between the scapula and inferior margin of the lowermost rib from each animal using an air-driven Zimmer dermatome (Medfix Solution, Inc., Tucson, Ariz.) with the depth set to 0.056-cm (0.022 inches).

Following skin graft harvest, grafts intended for cryopreservation and storage for limited duration grafts underwent a standardized institutional protocol and were maintained at −80° C. for 15 minutes prior to thawing. Long-term cryopreserved grafts had been continuously stored at −80° C. for a period of more than 7 years. All grafts, previously sized to approximately 25 $cm^2$, were placed on a sterile nylon mesh backing for structural support and rolled for placement into a threaded seal cryovial under a laminar flow hood. Once all grafts were prepared, approximately 5-mL of freeze media was added to the vial and sealed. The protocol required freeze media prepared by combining 15% dimethyl sulfoxide (DMSO) cryoprotective media (Lonza BioWhittaker) with fetal porcine serum (FPS) or donor serum (if FPS is unavailable) in a 1:1 ratio, filtering (0.45 micron), and chilling to 4° C. prior to use. The vials were subsequently frozen in a controlled rate, phase freezer at a rate of 1° C. per minute to −40° C., then rapidly cooled to a temperature −80° C., at which they remained for 15 minutes for those test articles in the control group subjected to limited storage duration, or for a period of more than 7 years in the case of the those experimental grafts in the test group exposed to extended duration of cryopreservation. DMSO displaces intracellular fluid during the freezing process. Cryoprotective media, e.g., CryoStor is used in an amount of about 40-80%, or 50-70% based on maximum internal volume of the cryovial (10 ml) less the volume of the xenotransplantation product.

In order to thaw the grafts for surgical use, sealed vials were placed in 37° C. water baths for approximately 1 minute, at which point the vial was opened and the frozen graft was removed using sterile technique. Subsequently, grafts underwent 3, 1-minute serial washes in normal saline with gentle agitation, in order to dilute and systematically remove ambient, residual DMSO and prevent loss of cell viability. Grafts were then taken to the surgical field in normal saline at 25° C. for engraftment.

Two separate, but identical, surgical events were performed in succession. The entire surgical plan included a total of four (n=4) donor-recipient swine, employing two animals per each of the two experimental cohorts (Cohort 1 and Cohort 2), paired intentionally based on SLA-configurations as described previously. In total, four technical controls and twelve (n=12) experimental grafts were engrafted and subsequently observed.

Each animal received four deep-partial defects along the animal's right dorsum, in a linear (caudal to cranial) orientation, ordered from 1 to 4, respectively. Deep-partial wound defects were surgically introduced via additional passes with the dermatome after the initial split thickness graft harvest. The resulting wound beds were uniform, free of visible debris, and demonstrated independent, punctate bleeding. These defects were interrupted, and not made in a single continuous pass with the dermatome. Instead, care was given to create four, isolated but equivalent wounds with regards to overall size, depth, and anatomical location.

Following thawing, but prior to engraftment, all split-thickness skin grafts were fenestrated using a 15 (size) blade to prevent seroma or hematoma formation. Graft test articles were independently placed on the prepared wound bed and uniformly sutured in place using simple interrupted, 3-0 nylon sutures, applied in a graft-to-wound bed manner. Approximately 16 points of fixation were introduced per graft, spaced evenly around the graft, with the resulting knot located on the wound border, not the graft article. This technique ensured that minimal, but adequate, residual tension was present and uniform, which is necessary for optimal graft-to-wound adherence, minimization of hematomas, and optimal graft survivability.

At Wound Site 1 (most caudal), a split-thickness autograft was placed, serving as a technical control. This autograft test article was harvested during the wound bed creation, subsequently underwent the same freeze-thaw process concomitantly with all experimental grafts, and was held in an identical, cryopreserved state for the same duration as the control grafts identified for a limited duration (15 minutes at −80° C.). At Wound Site 2, a split-thickness allograft from its respective cohort pair-mate was sutured into place. This graft represented test articles exposed to cryopreservation for a limited duration (15 minutes at −80° C.). At Wound Site 3, a split-thickness allograft from the wild-type donor, which represented a split-thickness graft, with identical SLA matching as those at Wound Site 2 that had experienced "extended" storage in the cryopreserved state (more than 7 years at −80° C.). At Wound Site 4 (most cranial), a split-thickness allograft from a genetically engineered knockout donor, which represented a split-thickness graft, with identical SLA matching as those grafts at Wound Site 2, sourced from the genetically engineered donor animal, that had also experienced "extended" exposure in the cryopreserved state (−80° C.) for more than 7 years.

Overlying pressure dressings, consisting of Xeroform petrolatum gauze (Medtronic), Telfa™ non-adhesive dressing (Covidien, Minneapolis, Minn.), and sterile gauze were maintained in place and dry with multiple, overlapping sheets of Tegaderm™ (3M, St. Paul, Minn.). Recipients were then dressed with cotton jackets to reduce interference with the grafts. Graft dressings were removed on POD-2 and changed daily thereafter. Total postoperative follow up was 20 days. Animals were monitored for signs of pain including vocalization, tachypnea, loss of appetite, and changes in attitude, behavior, and mobility. Transdermal fentanyl patches were applied for post-operative analgesia. All sutures were removed by POD-7.

To validate the assay method and establish boundary conditions specific to test articles of split thickness skin porcine skin, two independent assay series were performed on fresh (n=5, 5) and heat denatured samples (n=5, 5). The (geometric) average formazan produced on fresh samples was 0.221±0.022-mg/mL and 0.300±0.035-mg/mL, respectively. In contrast, the (geometric) average formazan produced by heat-denatured samples was 0.094±0.020-mg/mL and 0.105±0.009-mg/mL, respectively. These differences were statistically significant in both cases ($p<0.05$).

All four porcine recipients tolerated the surgical procedure and recovered fully without incident. All sixteen (n=16) grafts re-vascularized without evidence of technical complication, and uniformly exhibited adherence to the underlying wound bed (i.e. "good take"). Over the course of the post-operative observational period, no grafts were lost due to mechanical disturbance or exhibited any clinical signs of wound infection. All four (n=4) autografts at Wound Site 1 healed permanently and were indistinguishable from surrounding tissues at the study end-point, acting as a technical control for the skin grafting, cryopreservation and thawing technique.

In Cohort 1, all six (n=6) allogeneic grafts demonstrated equivalent adherence to the underlying wound bed and uniformly exhibited clinical signs consistent with vascularization and perfusion on postoperative days (POD) 2 and 4. Notable, however, was the contrast (loss) of color exhibited by the allografts that had been cryopreserved for an extended duration. All four of these grafts appeared paler as compared to the autograft and allografts at Wound Site 2. This appearance fully resolved in all grafts, in both Animals, by POD-6. All six (n=6) allografts exhibited mild sloughing of the superficial epidermis by POD-8, but grafts remained viable, adherent, and appeared otherwise healthy at inspection on POD-12. In Animal 24074, grafts at Wound Sites 2 and 3 showed initial signs of necrosis, progressive erythema, and loss of adherence by POD-14, and presented increasing signs of immune-mediated rejection, until final rejection at POD-18. However, the allograft at Wound Site 4 (most-cranial) did not similarly persist; instead, on POD-14 this graft was significantly darker and exhibited signs of complete necrosis and was clinically assessed to be fully rejected at this time. The rapid loss of the graft 4, from viability at POD-12 to complete avulsion by POD-14, dissimilar and distinct from Wound Site 2 and Wound Site 3, was notable. For grafts on Animal 24075, all grafts were rejected on POD-14.

In Cohort 2, animals presented similarly to those in Cohort 1 through POD-4, and equivalently to each other. Overall, clinical signs were comparable in progression to the minor-mismatched grafts in Cohort 1, but at an accelerated pace. The grafts that had experienced extended cryopreservation appeared paler at POD-2 and POD-4 than the grafts that had not experienced cryopreservation, and all grafts showed increased evidence of perfusion and vascularization by POD-6. By POD-8, all three allogeneic grafts in Animal 24043, showed clear signs of rejection and were considered fully rejected. In Animal 24070, all three allogeneic grafts showed clear signs of rejection and were considered fully rejected by POD-10. However, all allogeneic grafts survived at the same rate, irrespective of the genetics or length of storage.

With respect to grafts subjected to limited or extended durations of cryopreservation, 100% of allograft comparators at Wound Sites 2 and 3 (n=4 of 4) were identical with respect to clinical assessment of duration of graft survival. Comparison of Wound Sites 2 and 4 were coincident (n=3), with the exception of the allograft at Wound Site 4, Animal 24074, which survived until POD-14 (n=1), determined to be clinically and rejected four days prior to its counterparts.

Overall, histological assessments closely mirrored the clinical assessments. Following surgery, all grafts, including autografts, exhibited early signs of acute inflammation during initial observations on POD-2 and 4, that later resolved with time. All allografts in Cohort 2, as compared to those in Cohort 1, uniformly exhibited accelerated progression towards immune-mediated rejection.

Ultimately, all six (n=6) allogeneic grafts in Cohort 1, and three allogeneic grafts (n=3) from Animal 24043 in Cohort 2, independently demonstrated histological and microscopic signs of rejection coterminous with the independent gross clinical assessments. The single exception were the three allografts engrafted on Animal 24070, where each graft received Banff scores of 4 (of 4) on POD-10, but were not deemed officially rejected until POD-12, one assessment period (2 days) later than the corresponding clinical designation assigned at POD-10.

With respect to grafts subjected to limited or extended durations of cryopreservation, 100% of allograft comparators at Wound Sites 2 and 3 (n=4 of 4) were identical with respect to histological assessment of duration of graft survival. Comparison of Wound Sites 2 and 4 were coincident (n=3), with the exception of the allograft at Wound Site 4, Animal 24074, which survived 14 days post-operatively (n=1), determined to be histologically rejected four days prior to its counterparts.

Neither the MTT nor the neutral red staining technique, as applied on either testing occasion, were deemed effective for histological and microscopic evaluation, however the standard hemotoxylin and eosin staining demonstrated observable tissue destruction of the heat denatured specimens.

Overall, using a linear, mixed effect model with random intercept, the mean survival of grafts at Wound Site 3 was 0.00 (95% CI: −1.10, 1.10 days) less than allografts at Wound Site 2. The mean survival of grafts at Wound Site 4 was 2.00 (95% CI: 1.10, 3.10 days) less than allografts at Wound Site 2. Histological assessment finds on average 0.5 days more survival than grafts assessed grossly, but this is not statistically distinguishable (p=0.28). Seven of the eight experimental grafts fared equivalently to their comparators. The in vivo experiments showed no statistical difference between grafts subjected to short versus long-term storage. With the exception of the graft at Wound Site 4 on Animal 24074, which was assessed as fully rejected four days earlier than its comparators, graft performance and survivability were indistinguishable between the two groups.

As noted in previous publications, cryopreserved grafts appeared notably paler during the early imbibition and vascularization periods. This contrast was starkly evident for grafts at Wound Sites 3 and 4 in all animals. Ultimately, grafts fully resolved and adhered to the underlying wound bed to an equivalent degree.

Demonstrated viability was evidenced uniformly across the three, independent evaluation methods. The statistical analysis of the MTT-assay shows there was no significant difference between cryopreserved and fresh specimens (FIG. 50A), but significant differences were observed between fresh and cryopreserved specimens versus heat-denatured ones (FIG. 50B). This suggests broadly that the cryopreserved materials were, statistically speaking, more alive than dead. This outcome is substantiated in the in vivo outcomes in which all 7-year grafts demonstrated adherence to the wound bed and prolonged survivability, which would not be exhibited by non-vital grafts.

Regarding the MTT-reduction assays, substantial variability existed between absolute values resulting from such assays, from specimen to specimen and from cohort-to-cohort. Indeed, absolute values of formazan production were actually higher than those obtained from non-cryopreserved samples; it is unlikely that freezing enhanced cellular activity.

Pig skin can be cryopreserved for years, e.g., 1, 3, 5, 7 or more years and retain cell viability and that the genetic modification, Gal-T-KO, did not impact metabolic stability when compared to wild type pig skin processed and stored using the same procedures.

Furthermore, the use of MHC-matched and Class II mismatched donor-recipient pairs in this model of allogeneic skin transplantation served as internal controls to compare the effect of long term cryopreservation (7 years) on the survival of allogeneic skin grafts. The cell viability data after long term cryopreservation is supported by the survival of the skin in vivo. This also demonstrated that the genetic differences (wild type versus Gal-T-KO) of the grafts did not impact the survival of the grafts.

The hypothesis was that graft take, and overall survival, would be inversely proportional to the length of storage duration. In other words, it was expected that the longer the graft had been frozen, the less likely it would survive and mimic the comparator grafts preserved for shorter durations. Surprisingly, these studies revealed that the porcine tissue can be cryopreserved for significant durations, 7 years in the case of the present disclosure, and retain adequate cell viability. Moreover, the genetic modification (Gal-T-KO) did not impact metabolic activity, when compared to wild type skin processed identically. Lastly, the results confirm that the MTT-reduction assay can reliably provide an accurate, useful diagnostic method, and applicable to the assessment of porcine skin graft viability.

The promising results of this study indicate that it may be feasible to cryopreserve and store porcine skin for logistically relevant durations, and our findings are consistent with current industry practices and the multi-year "shelf life" guidance that the American Association for Tissue Banks has established for human cadaveric tissues.

Further, these data indicate that scalable, clinically useful methods of preserving and storing porcine xenotransplantation products with adequate viability are disclosed, and that vital porcine xenotransplantation products that can be effectively stored and distributed.

Example 4

Product Processing

Generally

A xenotransplantation product of the present disclosure was processed according to the following procedures.

Personnel

The operator was dressed in sterile dress in accordance with institutional standards to maintain designated pathogen free conditions. The operator wore eye protection safety glasses for ultraviolet light and lasers.

Preparation of Laminar Flow Hood and Product Processing

An ultraviolet laser lamp (Model #) was set up in a laminar flow hood. Each of the four corners of the lamp was placed on two container lids that were stacked on top of each other, i.e., four pairs of lids were used to support the lamp. The distance from the lamp bulbs (2 bulb tubes total) to the floor of the hood was approximately 1.5 inches. The entire interior of the hood was sprayed with alcohol, e.g., ethanol or isopropanol. The lamp was turned on and the operator performed a calculation of time for desired exposure based on lamp specifications, number of bulbs, and distance between the bulbs and the xenotransplantation product.

The operator poured two baths (one chlorhexidine and one alcohol) into two separate bowls and placed the two bowls under the hood.

A package of new sterilized vials was placed under the hood. Vial caps were unscrewed and placed into the chlorhexidine bath. Each vial (without cap) was then turned upside down and plunged open ended into the chlorhexidine bath, for one minute each and then set upright to air dry. Thereafter, the exterior of each vial was wiped with chlorhexidine and alcohol utilizing sterile gauze. The vial caps were removed from the chlorhexidine bath and placed on sterile gauze. The open ends of each vial were plunged into alcohol bath for 1 minute each and then set aside to air dry.

A xenotransplantation product "#46 product" (5×15 cm) having a mesh backing prepared according to Example 2 was removed from its original vial and the operator placed original vial into an empty bowl. Operator placed the #46 product on the paper side of an opened sterilized instrument package. The operator unrolled the #46 product and placed it under the lamp for 2 minutes, then turned it over to the other side, removed the mesh backing, and put it under the lamp for 2 minutes on opposite side, while still on the same paper. The time period for exposing a given sample to the UV light can be varied based on the specific biological agents or the types of biological agents to be sterilized, e.g., as shown in the following Table 12:

TABLE 12

| Biological Agent | Type of Biological Agent | UV-C Dosage (uW sec/cm$^2$) for 90% sterilization | Sterilization time (sec)* |
|---|---|---|---|
| Penicillium spp. | Fungus | 224,000 | 1800 |
| Aspergillus flavus | Fungus | 34,900 | 300 |
| Aspergillus niger | Fungus | 31,500 | 250 |
| Yeast | Fungus | 4000 | 30 |
| Influenza A | Virus | 1900 | 15 |
| HIV-1 | Virus | 28,000 | 220 |
| Vaccinia | Virus | 1500 | 10 |
| Escherichia coli | Bacteria | 2000 | 20 |
| Staphylococcus aureus | Bacteria | 6600 | 50 |
| Bacillus subtilis | Bacteria | 6800 | 50 |
| Mycoplasma spp. | Bacteria | 8400 | 70 |
| Pseudomonas aeruginosa | Bacteria | 2200 | 20 |

*Using a UV-C intensity of 125 uW/cm$^2$

Then the "#46 product was removed and cut in half. Each half was rolled by hand and placed into a new vial sterilized as explained above. Each new cap was placed on each new vial and screwed on securely. Each vial was placed under the lamp and periodically rolled for desired even exposure to light on the exterior of the vial. The vials were placed inside a glass jar that had an interior that had been previously sterilized and the exterior was sterilized by the operator with alcohol and chlorhexidine, including threads and caps.

A similar process was performed for the following xenotransplantation products, except instead of being placed on sterile paper prior to entry under the lamp, the mesh was not removed from the products and the products were placed under the lamp skin side up for 2 minutes, then the products were folded over so a first half of the bottom portion of each product faced the lamp for 2 minutes, then the second half of each product was folded over so that the other half of the bottom of each product faced the lamp for 2 minutes. Some of the products were cut into smaller sections and exposed to light, some for periods for longer than 2 minutes, but never less than 2 minutes.

Products #40 (5×15 cm), #63 (10×15 cm), #69 (10×15 cm), and #25, underwent the above processes and products #69 and #25 were rolled exclusively using instruments and the operator did not directly handle those products. As with #46, after operator securely screwed the cap on each vial, each vial was placed under the lamp and rolled for even exposure to light emitted from lamp. Vials were later removed from under the lamp and wiped down with alcohol prior to being placed into glass jars.

Four glass jars were utilized to store each of the sets of vials. Prior to being handed to the operator, the assistant drenched the exteriors of the glass jars with alcohol via a spray bottle. The assistant handed the glass jars to the operator by holding the bottom of each jar and handing to operator outside of hood. After receiving the glass jars from assistant, under the hood, the operator bathed the glass jar lids and plunged the open ends of the jars into alcohol and wiped the exterior of the jars with alcohol including threads of the jar.

The vials were wiped with alcohol utilizing gauze and placed inside each glass jar with an instrument. The lids of the glass jars were then secured and the jars were handed to the assistant. Frequently and on a periodic basis throughout these processes the assistant sprayed the operator's gloves and arms with alcohol.

Thereafter, the products were placed into the phase freezer at the conclusion of the procedures.

Example 5

Figure 51A:
FIGS. 51A-51G show images of a xenotransplantation product of the present disclosure for treatment of severe and extensive partial and full thickness burns in a human patient.

In a human evaluation of a xenotransplantation product of the present disclosure for treatment of severe and extensive partial and full thickness burns in a human patient, the following results were obtained:

The patient presented with a mixed depth, flame-induced burn injury, resulting in a 14% Total Body Surface Area (TBSA) defect to the (anatomic) right, upper torso—specifically, bordered: from the right lateral axilla (superior border) to the sixth right lateral rib (inferior border) as shown in FIG. 51A.

Figure 51B:
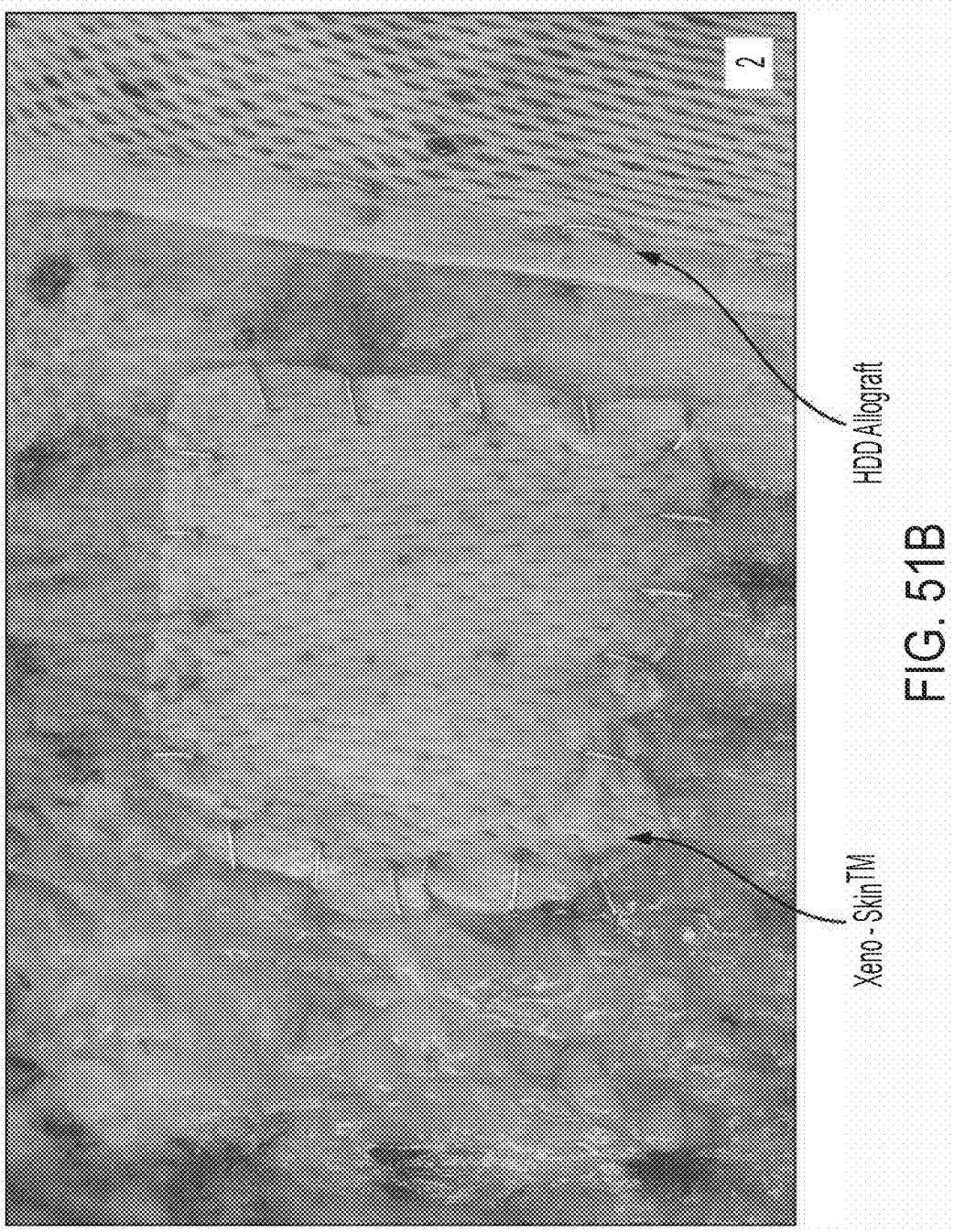

The surgeon temporarily grafted part of the affected wound area with Human Deceased Donor (HDD) allograft and the xenotransplant product of the present disclosure. The remaining regions of the wound area were covered with a negative pressure wound therapy (NPWT). The patient received approximately 150 cm$^2$ of HDD allograft, meshed to a 1:1.5 ratio, and 25 cm$^2$ of xenotransplant product of the present disclosure meshed to a 1:1 ratio during surgery, which is specifically shown in FIG. 51B

Both temporary wound closure dressings were placed adjacently, but not in direct contact, and were secured with staples on the perimeter of the tissue(s), overlaid with NPWT.

Figure 51C:
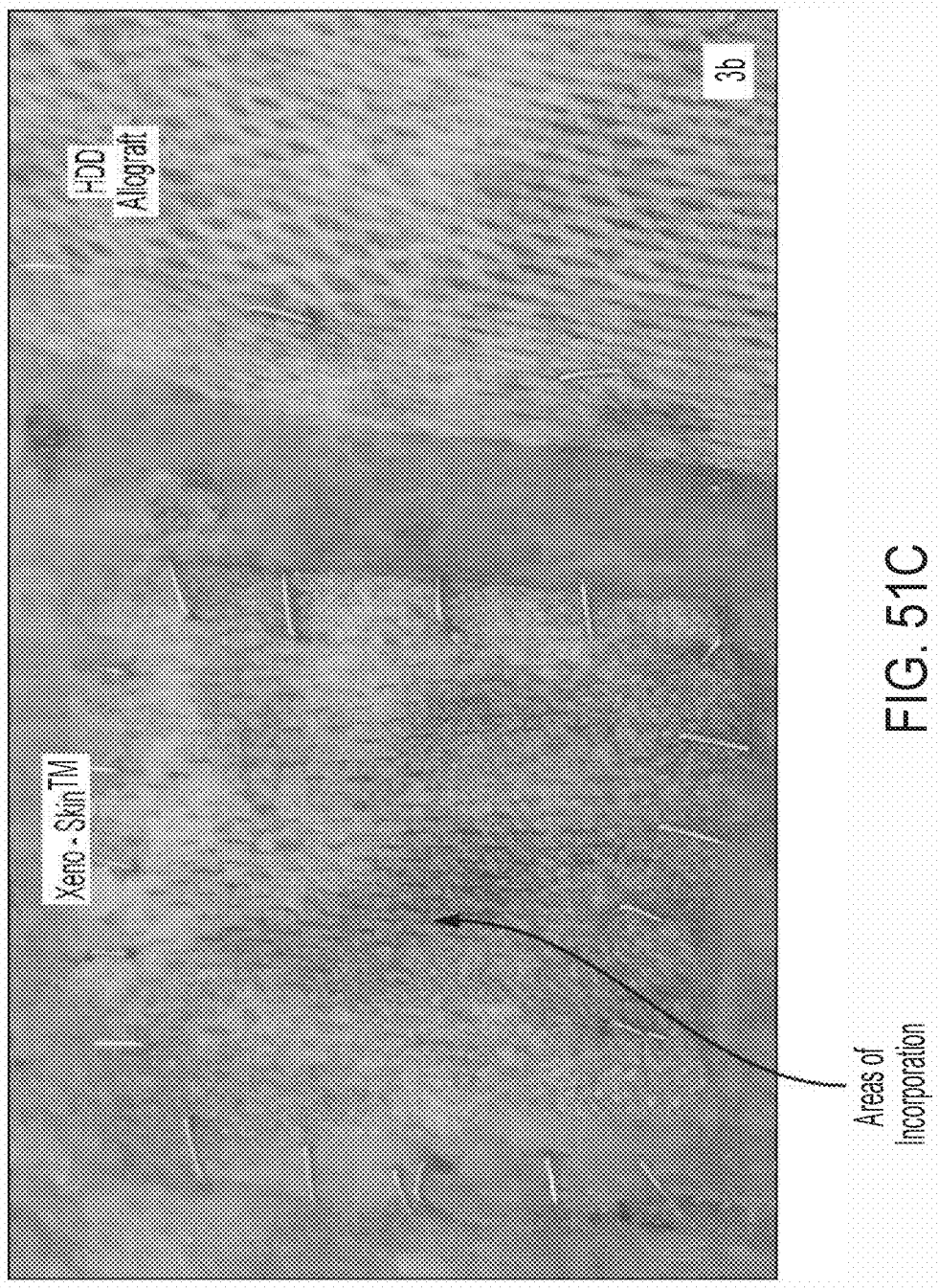

Upon clinical visual inspection of the first wound dressing change on POD-5, the HDD allograft and xenotransplant product of the present disclosure were both observed to be fully adherent to the underlying wound bed and were indistinguishable as shown in FIG. 51C.

The patient experienced no adverse events and no serious adverse events were observed or reported.

Figure 51D:
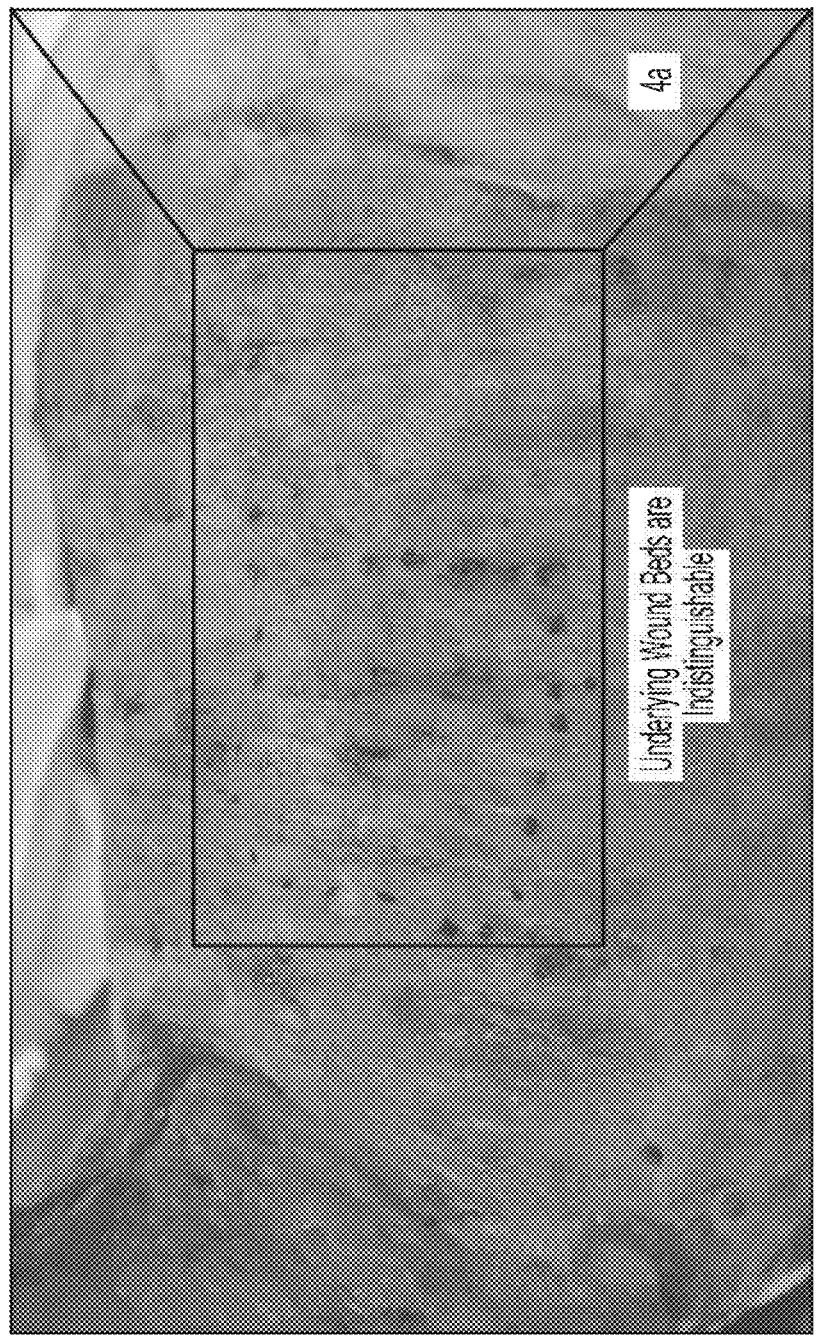

In accordance with the regular clinical standard of care, both HDD allograft and the xenotransplant product of the present disclosure were removed at the first wound dressing change. Following mechanical removal, the underlying wound beds were equally perfused (with visible punctate bleeding) and otherwise appeared equivalent as shown in FIG. 51D.

Figure 51E:
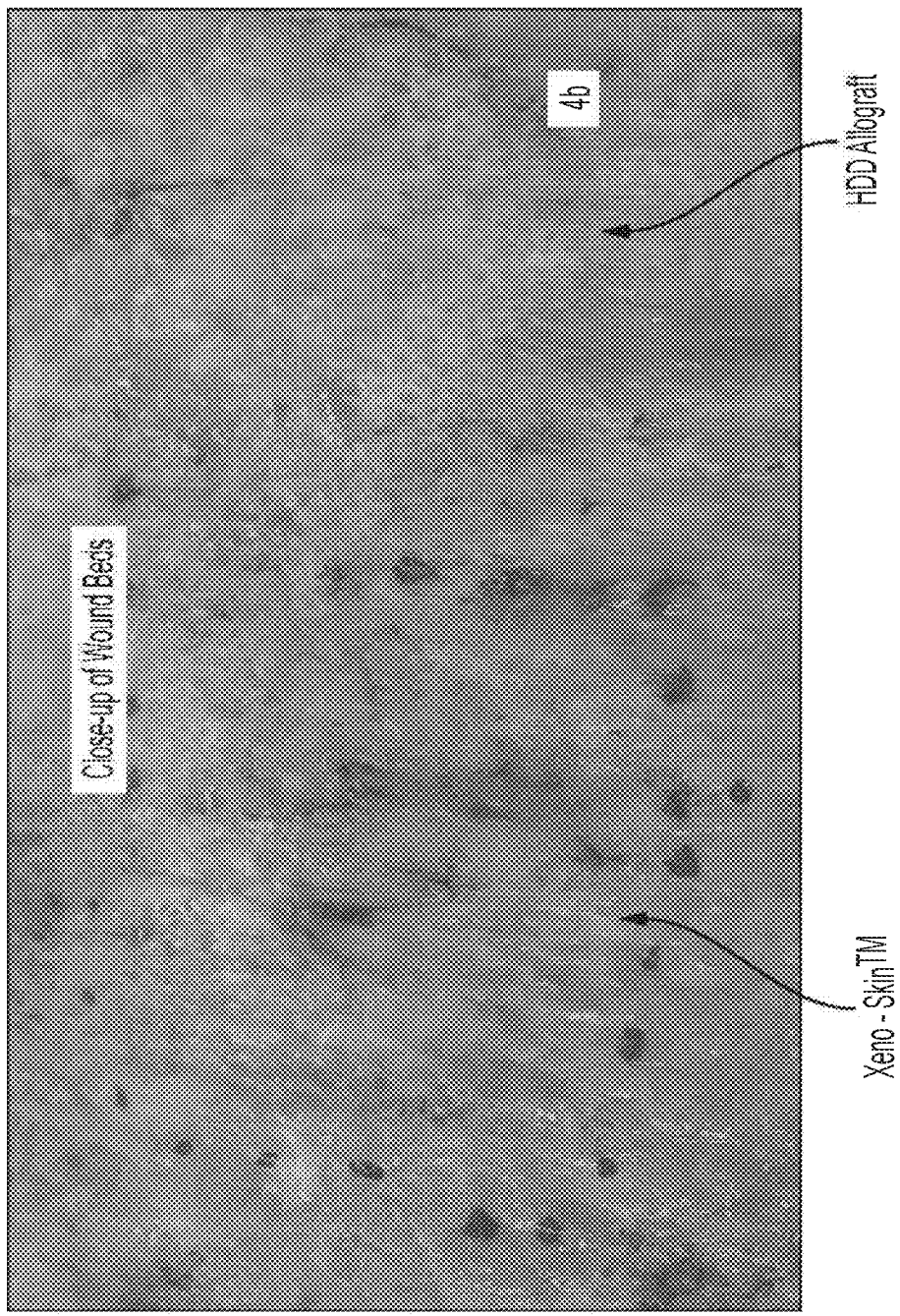

A POD-5 close-up image of the wound bed for the xenotransplant product of the present disclosure adjacent to wound bed for HDD allograft is shown in FIG. 51E.

Figure 51F:
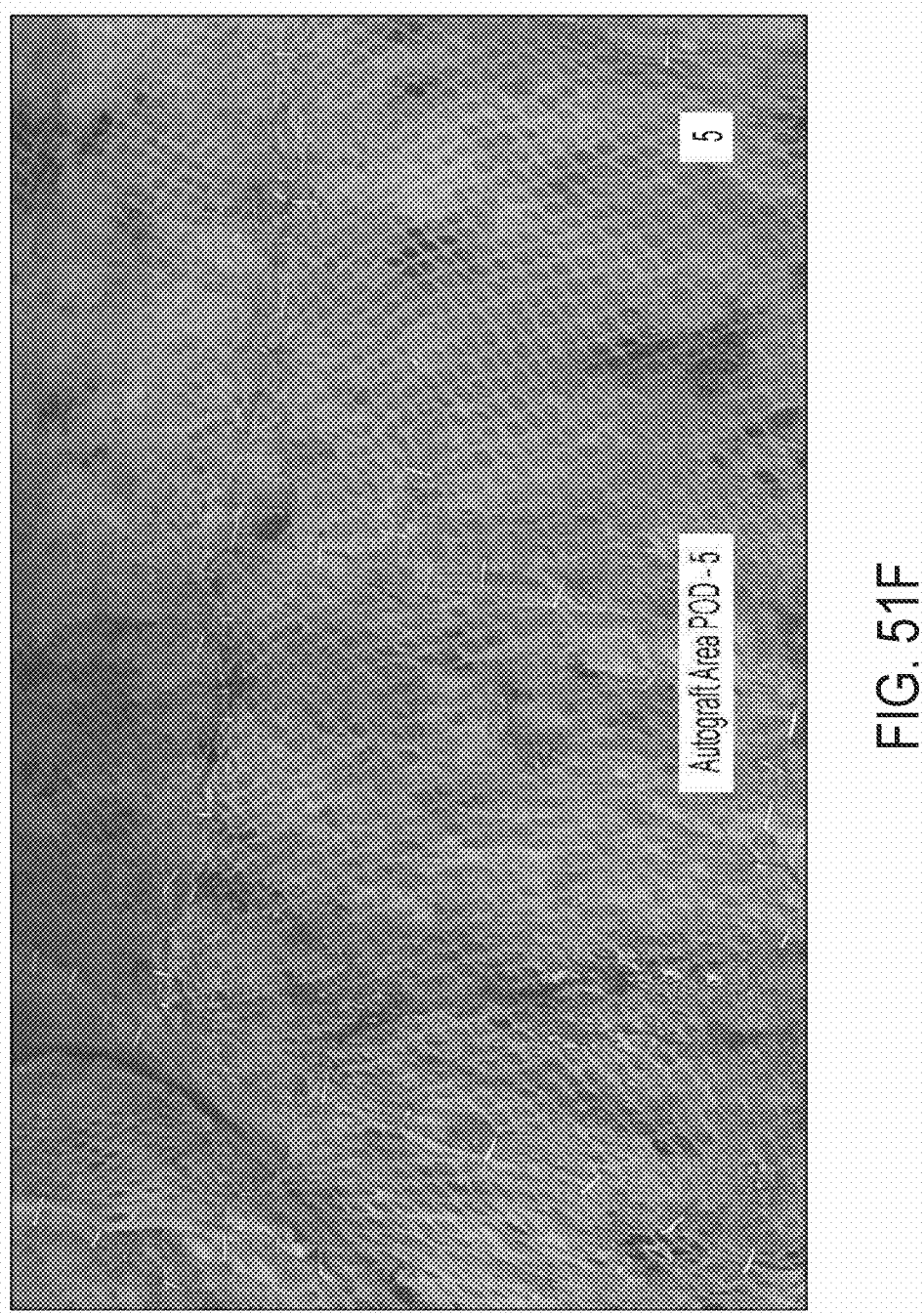

On POD-5 following removal, per clinical standard of care, the entire affected area received definitive wound closure via engraftment with a self (auto)graft (autologous split-thickness skin graft), obtained from the patient as shown in FIG. 51F.

Per protocol, blood samples for infectious disease, immunological response, and long-term evaluation were obtained, as well as pre-operative, peri-operative, and post-operative photographs.

Figure 51G:
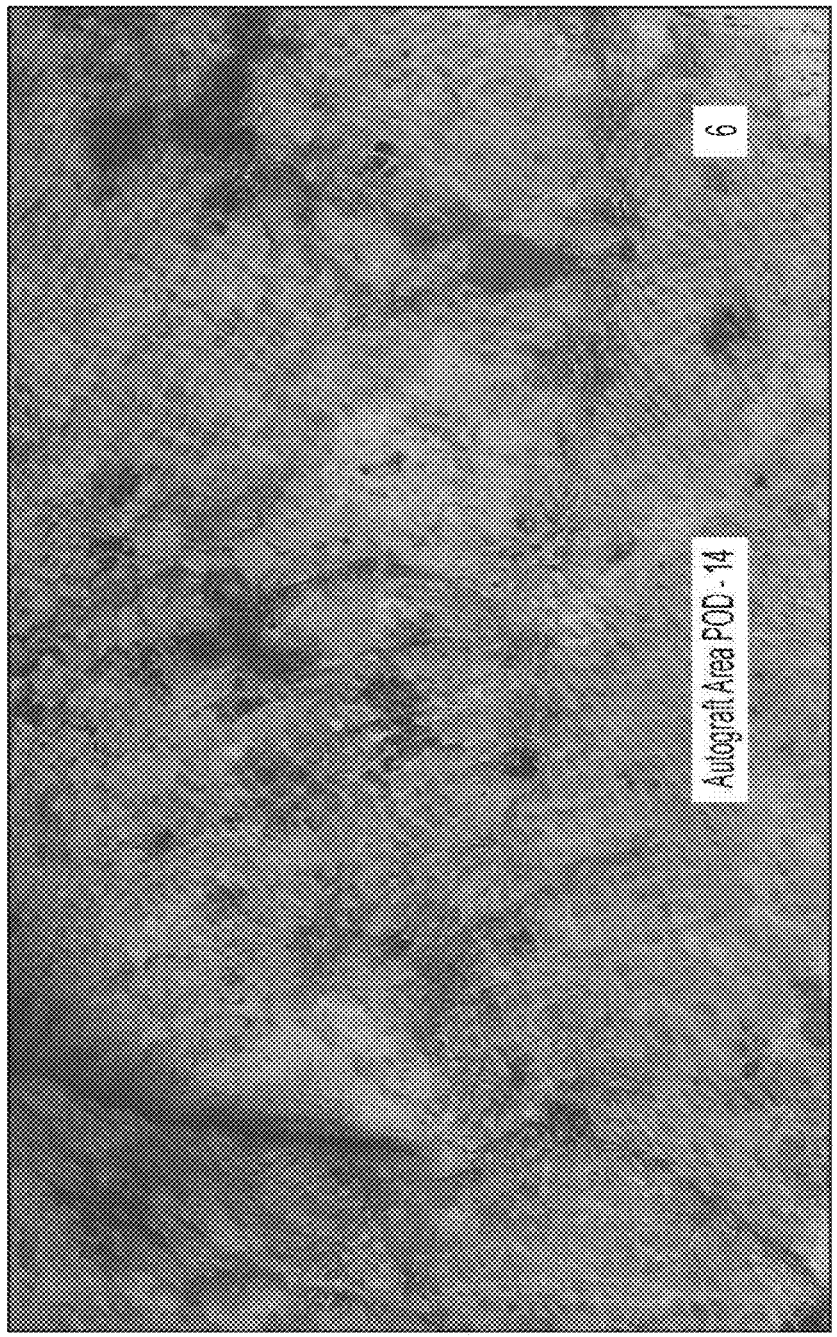

On POD-14 (from the first operation), clinical observations at the wound dressing change demonstrated no discernible differences in the wound healing rate or quality at any location as shown in FIG. 51G.

Per protocol, blood samples for infectious disease, immunological response, and long-term evaluation were obtained, as well as pre-operative, peri-operative, and post-operative photographs.

Testing for detection of PERV by quantitative RT-PCR was performed on baseline blood samples (25 mL), first dressing change (21 mL), and two week blood samples (23 mL). The results were as follows:

PERV was not detected by qPCR in either RNA or DNA isolated from PBMC and RNA isolated from plasma. Evidence of porcine cells as determined by qPCR directed to the porcine mtCOII gene was not found in RNA isolated from the PBMC.

| Source | Cq PERV pol | Cq porcine mtCOII | PERV | Porcine cells |
|---|---|---|---|---|
| DNA-PBMC | <LOD | <LOD | Negative | Negative |
| RNA-PBMC | <LOD | <LOD | Negative | Negative |
| RNA-plasma | <LOD | <LOD | Negative | Negative |

Further, a study is conducted to assess the proliferative response of human lymphocytes responder peripheral blood mononuclear cells (PBMC) in the presence of mitomycin C treated porcine stimulator cells (alpha-galactosyltransferase knock out (KO) pig B173) over time. PBMC samples were obtained from patients enrolled in Sponsor Study XT-001, both before and after the transplantation of porcine skin grafts. The porcine skin grafts were obtained from genetically modified alpha-galactosyltransferase knock out (KO) pigs.

Patient PBMC samples were previously prepared by Ficoll gradient centrifugation and cryopreserved. Whole blood from the skin donor pig (B173) was previously shipped to Xeno Diagnostics (XD) and PBMCs isolated by Ficoll gradient centrifugation and cryopreserved. The day prior to setting up the MLR, samples were thawed at 37° C., washed, and rested overnight in 10% FBS/RPMI. Porcine PBMCs were mitomycin C treated (stimulators) and mixed with an equal number of test human PBMCs (responders). The MLR was incubated for seven days with BrdU added on day six. On day seven, a BrdU ELISA was performed and proliferation measured.

Figure 52:
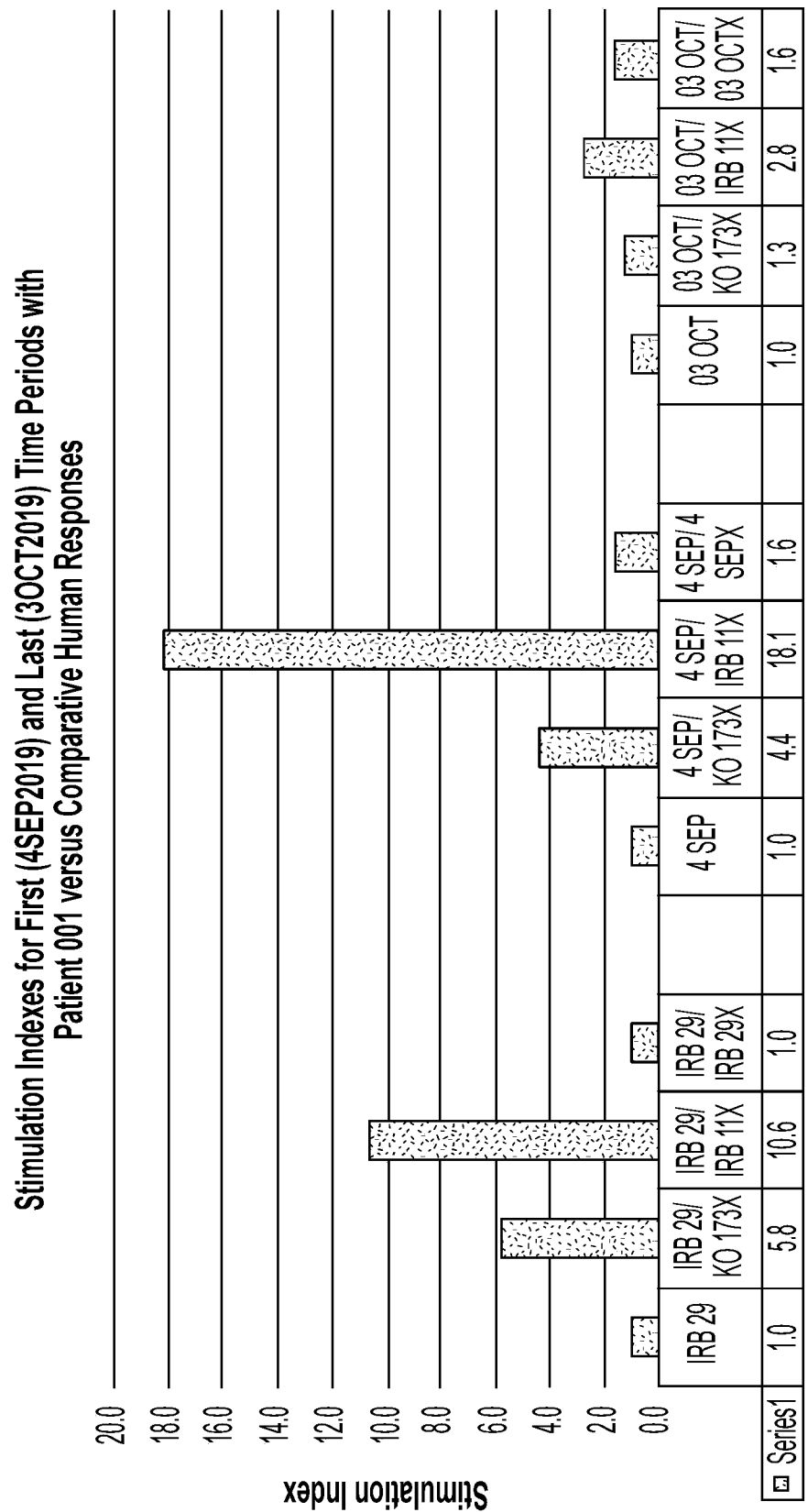
FIG. 52 shows a graph of proliferative response of human lymphocytes responder peripheral blood mononuclear cells (PBMC) in the presence of mitomycin C treated porcine stimulator cells.

As shown in FIG. 52, PBMC obtained from skin graft Patient XT-001 generated positive xenogeneic MLR PBMC mixed lymphocyte responses (MLR) when cocultured with alpha-Gal KO pig 173 PBMC (same source as skin graft). The xenogeneic proliferative responses were highest in cultures from sampling Days September 4 and September 19. In contrast, the xenogeneic proliferative response from sampling Day October 3 was reduced and near autologous MLR response levels. Overall, the xenogeneic response with KO pig 173 in all time periods tested was less than the human IRB 11 allogeneic comparator.

Furthermore, a study is conducted to measure the levels of human plasma anti-porcine IgM and IgG binding to porcine peripheral blood mononuclear cells (PBMCs) obtained from alpha-galactosyltransferase knock out (KO) pigs over time. Plasma samples are obtained from patients enrolled in Sponsor Study XT-001, both before and after the transplantation of porcine skin grafts. The porcine skin grafts were obtained from genetically modified alpha-galactosyltransferase knock out (KO) pigs.

In the study, the plasma samples were decomplemented in a 56° C. dry heat bath for 30 minutes. The samples were cooled and serially diluted in FACS binding/washing media. The diluted plasma samples were then incubated with KO porcine PBMCs followed by incubation with secondary antibody (PE-Goat anti human IgG and FITC-Goat anti human IgM). Appropriate compensation, Fluorescence Minus One (FMO), and Limit of Blank (LOB) controls were run in the same assay. Cells were acquired and analyzed on an ACEA NovoCyte Flow Cytometer. Binding of anti-porcine IgM and IgG was assessed using Median Fluorescence Intensity (MFI) and relative MFI obtained as follows: Relative MFI=Actual MFI value/LOB (MFI obtained using secondary antibody only in the absence of plasma).

Figure 53:
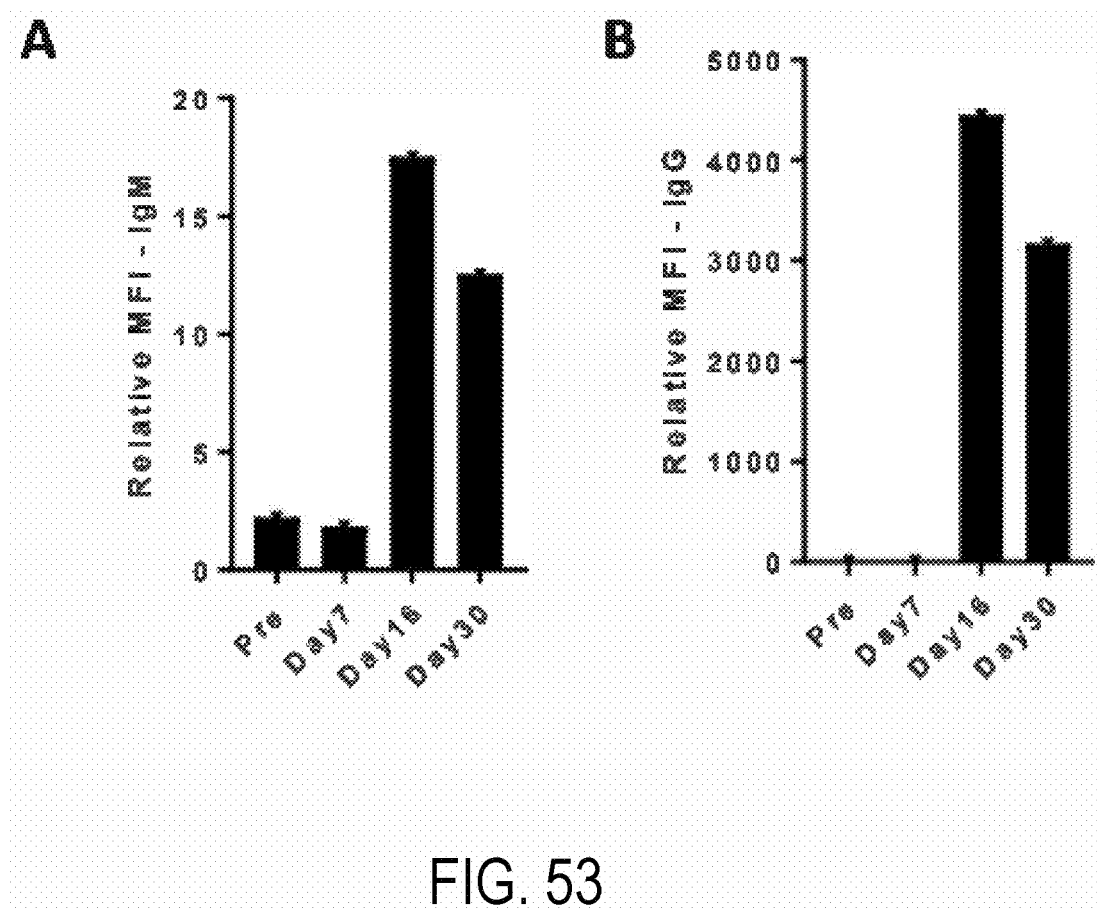
FIG. 53 shows anti-xenogeneic IgM (A) and IgG (B) antibody binding data relative to Median Fluorescence Intensities (MFI) for Xeno-001-00-1 patient sample at multiple time points, Pre, Day 7, Day 16, and Day 30. The data is shown for the plasma samples tested at 1:2 dilutions.

The human plasma IgM and IgG binding was measured at four time points including pre-grafting and post grafting (Day 7, Day 16, Day 30). All actual test samples at 1:2, and 1:10 dilutions showed MFI values higher than LOB values. As shown in FIG. 53, an increase in anti-xenogeneic IgM and IgG levels was obtained above pre-existing levels on Day 16 and Day 30 as shown by an increase in relative median fluorescence intensities. The average post-assay cell viability value determined by 7AAD was 92.82%. Cells were only gated on ALIVE cells to determine IgM and IgG binding to porcine PBMCs.

The invention claimed is:

1. A biological system for generating and preserving a repository of personalized, humanized transplantable cells, tissues, and organs for transplantation, wherein the biological system is biologically active and metabolically active, the biological system comprising genetically reprogrammed cells, tissues, and organs in a non-human animal for transplantation into a human recipient, wherein the non-human animal is a genetically reprogrammed swine for xenotransplantation of biologically active and metabolically active cells, tissue, and/or an organ isolated from the genetically reprogrammed swine, the genetically reprogrammed swine comprising a nuclear genome that has been reprogrammed to replace a plurality of nucleotides in a plurality of exon regions of a major histocompatibility complex of a wild-type swine with a plurality of synthesized nucleotides from a human captured reference sequence, and wherein cells of said genetically reprogrammed swine do not present one or more surface glycan epitopes selected from alpha-Gal, Neu5Gc, and SD$^a$, and wherein genes encoding alpha-1,3 galactosyltransferase, cytidine monophosphate-N-acetylneuraminic acid hydroxylase (CMAH), and β1,4-N-acetylgalactosaminyltransferase are altered such that the genetically reprogrammed swine lacks functional expression of surface glycan epitopes encoded by said genes, wherein the reprogrammed genome comprises site-directed mutagenic substitutions of nucleotides at exon regions of: i) at least one of the wild-type swine's SLA-1, SLA-2, and SLA-3 with nucleotides from an orthologous exon region of HLA-A, HLA-B, and HLA-C, respectively, of the human captured reference sequence; and ii) at least one the wild-type swine's SLA-6, SLA-7, and SLA-8 with nucleotides from an orthologous exon region of HLA-E, HLA-F, and HLA-G, respectively, of the human captured reference sequence; and iii) at least one of the wild-type swine's SLA-DR and SLA-DQ with nucleotides from an orthologous exon region of HLA-DR and HLA-DQ, respectively, of the human captured reference sequence, wherein intron regions of the wild-type swine's genome are not reprogrammed, and wherein the reprogrammed genome comprises at least one of A-C:

A) wherein the reprogrammed swine nuclear genome comprises site-directed mutagenic substitutions of nucleotides at exon regions of the wild-type swine's β2-microglobulin with nucleotides from orthologous exons of a known human β2-microglobulin from the human captured reference sequence;

B) wherein the reprogrammed swine nuclear genome comprises a polynucleotide that encodes a polypeptide that is a humanized beta 2 microglobulin (hB2M) polypeptide sequence that is at least 95% identical to the amino acid sequence of beta 2 microglobulin glycoprotein expressed by the human captured reference genome;

C) wherein the reprogrammed swine nuclear genome has been reprogrammed such that, at the swine's endogenous β2-microglobulin locus, the nuclear genome has been reprogrammed to comprise a nucleotide sequence encoding β2-microglobulin polypeptide of the human recipient,
wherein the reprogrammed swine nuclear genome has been reprogrammed such that the genetically reprogrammed swine lacks functional expression of the wild-type swine's endogenous β2-microglobulin polypeptides,
wherein said reprogramming does not introduce any frameshifts or frame disruptions,
wherein said genetically reprogrammed swine is free of at least the following pathogens:
(i) *Ascaris* species, *cryptosporidium* species, *Echinococcus*, *Strongyloids sterocolis*, and *Toxoplasma gondii* in fecal matter;
(ii) *Leptospira* species, *Mycoplasma hyopneumoniae*, porcine reproductive and respiratory syndrome virus (PRRSV), pseudorabies, transmissible gastroenteritis virus (TGE)/Porcine Respiratory Coronavirus, and *Toxoplasma Gondii* by determining antibody titers;
(iii) Porcine Influenza;
(iv) the following bacterial pathogens as determined by bacterial culture: *Bordetella bronchisceptica*, Coagulase-positive staphylococci, Coagulase-negative staphylococci, Livestock-associated methicillin resistant *Staphylococcus aureus* (LA MRSA), Microphyton and *Trichophyton* spp.;
(v) Porcine cytomegalovirus; and
(vi) *Brucella suis*,
wherein said genetically reprogrammed swine is maintained according to a bioburden-reducing procedure, said procedure comprising maintaining the swine in an isolated closed herd, wherein all other animals in the isolated closed herd are confirmed to be free of said pathogens, and wherein the swine is isolated from contact with any non-human animals and animal housing facilities outside of the isolated closed herd.

2. The biological system of claim 1, wherein the genetically reprogrammed swine is non-transgenic.

3. The biological system of claim 1, wherein the wild-type swine genome comprises reprogrammed nucleotides at SLA-MIC-2 gene and at exon regions encoding SLA-3, SLA-6, SLA-7, SLA-8, SLA-DQ, CTLA-4, PD-L1, EPCR, TBM, TFPI, and beta-2-microglobulin using the human capture reference sequence, wherein the human cell, tissue, or organ lacks functional expression of swine beta-2-microglobulin, SLA-1, SLA-2, and SLA-DR.

4. The biological system of claim 3, wherein the wild-type swine genome comprises reprogrammed nucleotides at one or more of a CTLA-4 promoter and a PD-L1 promoter, wherein the one or more of the CTLA-4 promoter and the PD-L1 promoter are reprogrammed to increase expression of one or both of reprogrammed CTLA-4 and reprogrammed PD-L1 compared to the wild-type swine's endogenous expression of CTLA-4 and PD-L1.

5. The biological system of claim 1, wherein a total number of the synthesized nucleotides is equal to a total number of the replaced nucleotides, such that there is no net loss or net gain in number of nucleotides after reprogramming the genome of the wild-type swine with the synthesized nucleotides.

6. The biological system of claim 1, wherein the nuclear genome is reprogrammed using scarless exchange of the exon regions, wherein the nuclear genome is reprogrammed without introduction of any net insertions, deletions, truncations, or other genetic alterations that would cause a disruption of protein expression via frame shift, nonsense, and missense mutations.

7. The biological system of claim 1, wherein site-directed mutagenic substitutions are made in porcine fetal fibroblast cell, a porcine zygote, a porcine Induced Pluripotent Stem Cells (IPSC), or a porcine germ-line cells.

8. The biological system of claim 1, wherein site-directed mutagenic substitutions are made in germ-line cells used to produce the non-human animal.

9. The biological system of claim 1, wherein the human captured reference sequence is a human patient capture sequence, a human population-specific human capture sequence, or an allele-group-specific human capture sequence.

10. The biological system of claim 1, wherein the reprogrammed genome comprises site-directed mutagenic substitutions of nucleotides at exon regions of the wild-type swine's MHC class I chain-related 2 (MIC-2).

11. The biological system of claim 1, wherein the reprogrammed genome lacks functional expression of SLA-1, SLA-2, SLA-DR, or a combination thereof.

12. The biological system of claim 1, wherein the reprogrammed genome comprises site-directed mutagenic substitutions of nucleotides at exon regions of the wild-type swine's SLA-DQA from an orthologous exon region of a HLA-DQA1 captured reference sequence.

13. The biological system of claim 1, wherein the reprogrammed genome comprises site-directed mutagenic substitutions of nucleotides at exon regions of the wild-type swine's SLA-DQB from an orthologous exon region of a HLA-DQB1 captured reference sequence.

14. The biological system of claim 1, wherein the reprogrammed genome comprises site-directed mutagenic substitutions of nucleotides at exon regions of the wild-type swine's SLA-DRA and SLA-DRB1 with nucleotides from orthologous exon regions of HLA-DRA1 and HLA-DRB1 of the human captured reference sequence, or wherein the reprogrammed genome lacks functional expression of SLA-DRA and SLA-DRB1.

15. The biological system of claim 14, wherein the site-directed mutagenic substitutions of nucleotides are at codons that are not conserved between the wild-type swine's nuclear genome and the known human sequence.

16. The biological system of claim 1, wherein the reprogrammed genome comprises site-directed mutagenic substitutions of nucleotides at exon regions of the wild-type swine's SLA-DQA and SLA-DQB1 with nucleotides from orthologous exon regions of HLA-DQA1 and HLA-DQB1 of the human captured reference sequence.

17. The biological system of claim 1, wherein the reprogrammed genome comprises site-directed mutagenic substitutions of nucleotides at exon regions of SLA-3, SLA-6, SLA-7, SLA-8, and MIC-2.

18. The biological system of claim 1, wherein the reprogrammed genome comprises site-directed mutagenic substitutions of nucleotides at exon regions of SLA-DQ and MIC-2.

19. The biological system of claim 1, wherein the reprogrammed genome comprises site-directed mutagenic substitutions of nucleotides at SLA-3, SLA-6, SLA-7, SLA-8, SLA-DQ, and MIC-2.

20. The biological system of claim 1, wherein said nuclear genome is reprogrammed to be homozygous at the reprogrammed exon regions, and wherein cells of said genetically reprogrammed swine have extracellular, phenotypic surface expression of polypeptides that are tolerogenic when the cells are transplanted into the human recipient.

* * * * *

SEQUENCE LISTING

<160> NUMBER OF SEQ ID NOS: 211

<210> SEQ ID NO 1
<211> LENGTH: 249
<212> TYPE: DNA
<213> ORGANISM: Artificial Sequence
<220> FEATURE:
<223> OTHER INFORMATION: SLA-DQA-201, ENSSSCE00045087536

<400> SEQUENCE: 1

```
ccgaccatgt tgcctcctat ggcttaaatg tctaccagtc ttacggtccc agcggctatt    60
atacccatga atttgatggc gacgaggaat tctacgtgga cctggagaag aaggagactg   120
tctggcggct gcctctgttt agtgaattta caagttttga cccgcagggt gcactgagga   180
atatagctac gttaaaacat aacttgaaca tcgtgactaa acgctccaac aacaccgcgg   240
ctgtcaatc                                                           249
```

```
<210> SEQ ID NO 2
<211> LENGTH: 50
<212> TYPE: DNA
<213> ORGANISM: Artificial Sequence
<220> FEATURE:
<223> OTHER INFORMATION: SLA-DQA-201 ENSSSCE00045087536 introns 2-3

<400> SEQUENCE: 2
```

```
gtatgtgttc atcattctgc ctttcaatca gtgctgtttt ctcaccacag               50
```

```
<210> SEQ ID NO 3
<211> LENGTH: 279
<212> TYPE: DNA
<213> ORGANISM: Artificial Sequence
<220> FEATURE:
<223> OTHER INFORMATION: SLA-DQA-201 ENSSSCE00045087540

<400> SEQUENCE: 3
```

```
aggttcctga ggtgactgtg ttttccaagt ctccagtgat actgggtcag cccaacaccc    60
tcatctgtca tgtggacagc atctttcctc ctgtgatcaa catcacgtgg ttgaagaacg   120
ggcactctgt caaggttttt tctgagacca gcttcctctc caaaaatgat cattccttcc   180
tcaagatcag ttatctcacc ttcctcccTT ctgatgacga tttttatgac tgcaaagtgg   240
agcactgggg cctggataag ccacttctga aacactggg                          279
```

```
<210> SEQ ID NO 4
<211> LENGTH: 249
<212> TYPE: DNA
<213> ORGANISM: Artificial Sequence
<220> FEATURE:
<223> OTHER INFORMATION: SLA-DQA-202 ENSSSCE00045087536

<400> SEQUENCE: 4
```

```
ccgaccatgt tgcctcctat ggcttaaatg tctaccagtc ttacggtccc agcggctatt    60
atacccatga atttgatggc gacgaggaat tctacgtgga cctggagaag aaggagactg   120
tctggcggct gcctctgttt agtgaattta caagttttga cccgcagggt gcactgagga   180
atatagctac gttaaaacat aacttgaaca tcgtgactaa acgctccaac aacaccgcgg   240
ctgtcaatc                                                           249
```

```
<210> SEQ ID NO 5
<211> LENGTH: 50
<212> TYPE: DNA
<213> ORGANISM: Artificial Sequence
<220> FEATURE:
<223> OTHER INFORMATION: SLA-DQA-202 ENSSSCE00045087536 introns 2-3

<400> SEQUENCE: 5
```

```
gtatgtgttc atcattctgc ctttcaatca gtgctgtttt ctcaccacag               50
```

```
<210> SEQ ID NO 6
<211> LENGTH: 279
<212> TYPE: DNA
```

<213> ORGANISM: Artificial Sequence
<220> FEATURE:
<223> OTHER INFORMATION: SLA-DQA-202 ENSSSCE00045087540

<400> SEQUENCE: 6

```
aggttcctga ggtgactgtg ttttccaagt ctccagtgat actgggtcag cccaacaccc      60
tcatctgtca tgtggacagc atctttcctc ctgtgatcaa catcacgtgg ttgaagaacg     120
ggcactctgt caaaggtttt tctgagacca gcttcctctc caaaaatgat cattccttcc     180
tcaagatcag ttatctcacc ttcctcccct ctgatgacga ttttttatgac tgcaaagtgg     240
agcactgggg cctggataag ccacttctga aacactggg                            279
```

<210> SEQ ID NO 7
<211> LENGTH: 249
<212> TYPE: DNA
<213> ORGANISM: Artificial Sequence
<220> FEATURE:
<223> OTHER INFORMATION: SLA-DQA-203 ENSSSCE00045087536

<400> SEQUENCE: 7

```
ccgaccatgt tgcctcctat ggcttaaatg tctaccagtc ttacggtccc agcggctatt      60
atacccatga atttgatggc gacgaggaat tctacgtgga cctggagaag aaggagactg     120
tctggcggct gcctctgttt agtgaattta caagttttga cccgcagggt gcactgagga     180
atatagctac gttaaaacat aacttgaaca tcgtgactaa cgctccaac aacaccgcgg     240
ctgtcaatc                                                            249
```

<210> SEQ ID NO 8
<211> LENGTH: 50
<212> TYPE: DNA
<213> ORGANISM: Artificial Sequence
<220> FEATURE:
<223> OTHER INFORMATION: SLA-DQA-203 ENSSSCE00045087536 INTRONS 2-3

<400> SEQUENCE: 8

```
gtatgtgttc atcattctgc cttcaatca gtgctgtttt ctcaccacag                 50
```

<210> SEQ ID NO 9
<211> LENGTH: 279
<212> TYPE: DNA
<213> ORGANISM: Artificial Sequence
<220> FEATURE:
<223> OTHER INFORMATION: SLA-DQA-203 ENSSSCE00045087540

<400> SEQUENCE: 9

```
aggttcctga ggtgactgtg ttttccaagt ctccagtgat actgggtcag cccaacaccc      60
tcatctgtca tgtggacagc atctttcctc ctgtgatcaa catcacgtgg ttgaagaacg     120
ggcactctgt caaaggtttt tctgagacca gcttcctctc caaaaatgat cattccttcc     180
tcaagatcag ttatctcacc ttcctcccct ctgatgacga ttttttatgac tgcaaagtgg     240
agcactgggg cctggataag ccacttctga aacactggg                            279
```

<210> SEQ ID NO 10
<211> LENGTH: 249
<212> TYPE: DNA
<213> ORGANISM: Artificial Sequence
<220> FEATURE:
<223> OTHER INFORMATION: SLA-DQA-204 ENSSSCE00045087536

<400> SEQUENCE: 10

```
ccgaccatgt tgcctcctat ggcttaaatg tctaccagtc ttacggtccc agcggctatt      60
```

```
atacccatga atttgatggc gacgaggaat tctacgtgga cctggagaag aaggagactg    120
tctggcggct gcctctgttt agtgaattta caagttttga cccgcagggt gcactgagga    180
atatagctac gttaaaacat aacttgaaca tcgtgactaa acgctccaac aacaccgcgg    240
ctgtcaatc                                                            249
```

<210> SEQ ID NO 11
<211> LENGTH: 50
<212> TYPE: DNA
<213> ORGANISM: Artificial Sequence
<220> FEATURE:
<223> OTHER INFORMATION: SLA-DQA-204 introns 2-3

<400> SEQUENCE: 11

```
gtatgtgttc atcattctgc ctttcaatca gtgctgtttt ctcaccacag               50
```

<210> SEQ ID NO 12
<211> LENGTH: 279
<212> TYPE: DNA
<213> ORGANISM: Artificial Sequence
<220> FEATURE:
<223> OTHER INFORMATION: SLA-DQA-204 ENSSSCE00045087540

<400> SEQUENCE: 12

```
aggttcctga ggtgactgtg ttttccaagt ctccagtgat actgggtcag cccaacaccc    60
tcatctgtca tgtggacagc atctttcctc ctgtgatcaa catcacgtgg ttgaagaacg    120
ggcactctgt caaaggtttt tctgagacca gcttcctctc caaaaatgat cattccttcc    180
tcaagatcag ttatctcacc ttcctcccct tctgatgacga ttttatgac tgcaaagtgg    240 agcactgggg cctggataag ccacttctga aacactggg                           279
```

<210> SEQ ID NO 13
<211> LENGTH: 270
<212> TYPE: DNA
<213> ORGANISM: Artificial Sequence
<220> FEATURE:
<223> OTHER INFORMATION: SLA-DQB1-201 ENSSSCE00045085054

<400> SEQUENCE: 13

```
aggatttcgt gtaccagttt aagttcgagt gctacttctt caacggaacg cagcgggtgc    60
ggctcttgac cagatacatc tacaaccagg aggagcacgt gcgcttcgac agcaacgtgg    120
gggagtaccg ggcggtgacc ccgctggggc ggccggacgc cgactactgg aacggccaga    180
aggacgtcct ggagcagacg cgggccgagc tggacactgt gtgcaaacac aactaccaga    240
tagaggaagg cacgaccctg cagcggcgag                                     270
```

<210> SEQ ID NO 14
<211> LENGTH: 50
<212> TYPE: DNA
<213> ORGANISM: Artificial Sequence
<220> FEATURE:
<223> OTHER INFORMATION: SLA-DQB1-201 introns 2-3

<400> SEQUENCE: 14

```
gtgagtgcct gcccgccgcc cgcggttttc ccgtctgtta ctcccctcag               50
```

<210> SEQ ID NO 15
<211> LENGTH: 885
<212> TYPE: DNA
<213> ORGANISM: Artificial Sequence
<220> FEATURE:

<223> OTHER INFORMATION: SLA-DQB1-201 ENSSSCE00045085455

<400> SEQUENCE: 15

| tgcaacctac agtgactatc tccccatcca aggcagaggc tctaaaccac cacaacctgc | 60 |
| tggtctgtgc ggtgacagat ttctatccaa gccaggtgaa agtccagtgg ttccggaatg | 120 |
| gccaggagga gacagctggc gttgtgtcca ctcctcttat taggaatgga gactggacct | 180 |
| accaggtgct cgtgatgcta gagatgaatc tccagcgagg agatgtctac acctgccgcg | 240 |
| tggagcactc cagcctccag agccccatct tggtggagtg gcgtaagggg cagttggttt | 300 |
| tctttccctg tgggccctgc agaacagagg gcaggcagag cttcccgggt ccatcccatc | 360 |
| tcattctttg tccccgacat cactactgag ctggacatca ctgggcacat gagtgctctt | 420 |
| gcctcatagc aagggcatca ggagaatctt tatctccttg tctttccaga tacagagcga | 480 |
| tcactacata ccatgacccc agagcccagc cctaggagct ctgcaggatt gactagtgcc | 540 |
| tggggcctta aggtctcaga ttatgaaagg agcagggatc catttccctt ctcactcacc | 600 |
| ctcccactct gtccagggag ctattggctg gtccctcacc taggggtggt cagaatggac | 660 |
| aacggggttc ccctggcacc tctacccccct gtacctcaga ctagacttca ggcctcataa | 720 |
| aggagcacca tggggtgtgg tgacaaaactc tgacatttgg gctctgctcc ccaggggcac | 780 |
| agtctgaatc tgcccagagc aagatgctga gcggtgtcgg gggcttcgtg ctggggctga | 840 |
| tcttcctcgg gctgggcctt ttcatccgtc acaggagtca gaagg | 885 |

<210> SEQ ID NO 16
<211> LENGTH: 270
<212> TYPE: DNA
<213> ORGANISM: Artificial Sequence
<220> FEATURE:
<223> OTHER INFORMATION: SLA-DQB1-202 ENSSSCE00045085054

<400> SEQUENCE: 16

| aggatttcgt gtaccagttt aagttcgagt gctacttctt caacggaacg cagcgggtgc | 60 |
| ggctcttgac cagatacatc tacaaccagg aggagcacgt gcgcttcgac agcaacgtgg | 120 |
| gggagtaccg ggcggtgacc ccgctggggc ggccggacgc cgactactgg aacggccaga | 180 |
| aggacgtcct ggagcagacg cgggccgagc tggacactgt gtgcaaacac aactaccaga | 240 |
| tagaggaagg cacgaccctg cagcggcgag | 270 |

<210> SEQ ID NO 17
<211> LENGTH: 50
<212> TYPE: DNA
<213> ORGANISM: Artificial Sequence
<220> FEATURE:
<223> OTHER INFORMATION: SLA-DQB1-202 introns 2-3

<400> SEQUENCE: 17

| gtgagtgcct gcccgccgcc cgcggttttc ccgtctgtta ctccccctcag | 50 |

<210> SEQ ID NO 18
<211> LENGTH: 282
<212> TYPE: DNA
<213> ORGANISM: Artificial Sequence
<220> FEATURE:
<223> OTHER INFORMATION: SLA-DQB1-202 ENSSSCE00045085973

<400> SEQUENCE: 18

| tgcaacctac agtgactatc tccccatcca aggcagaggc tctaaaccac cacaacctgc | 60 |
| tggtctgtgc ggtgacagat ttctatccaa gccaggtgaa agtccagtgg ttccggaatg | 120 |

```
gccaggagga cagcctggc gttgtgtcca ctcctcttat taggaatgga gactggacct    180
accaggtgct cgtgatgcta gagatgaatc tccagcgagg agatgtctac acctgccgcg    240
tggagcactc cagcctccag agccccatct tggtggagtg gc                      282
```

```
<210> SEQ ID NO 19
<211> LENGTH: 270
<212> TYPE: DNA
<213> ORGANISM: Artificial Sequence
<220> FEATURE:
<223> OTHER INFORMATION: SLA-DQB1-203 ENSSSCE00045085054

<400> SEQUENCE: 19
aggatttcgt gtaccagttt aagttcgagt gctacttctt caacggaacg cagcgggtgc    60
ggctcttgac cagatacatc tacaaccagg aggagcacgt gcgcttcgac agcaacgtgg   120
gggagtaccg ggcggtgacc ccgctggggc ggccggacgc cgactactgg aacggccaga   180
aggacgtcct ggagcagacg cggggccgagc tggacactgt gtgcaaacac aactaccaga   240
tagaggaagg cacgaccctg cagcggcgag                                    270
```

```
<210> SEQ ID NO 20
<211> LENGTH: 50
<212> TYPE: DNA
<213> ORGANISM: Artificial Sequence
<220> FEATURE:
<223> OTHER INFORMATION: SLA-DQB1-203 introns 2-3

<400> SEQUENCE: 20
gtgagtgcct gcccgccgcc cgcggttttc ccgtctgtta ctcccctcag               50
```

```
<210> SEQ ID NO 21
<211> LENGTH: 282
<212> TYPE: DNA
<213> ORGANISM: Artificial Sequence
<220> FEATURE:
<223> OTHER INFORMATION: SLA-DQB1-203 ENSSSCE00045085973

<400> SEQUENCE: 21
tgcaacctac agtgactatc tccccatcca aggcagaggc tctaaaccac cacaacctgc    60
tggtctgtgc ggtgacagat ttctatccaa gccaggtgaa agtccagtgg ttccggaatg   120
gccaggagga cagcctggc gttgtgtcca ctcctcttat taggaatgga gactggacct   180
accaggtgct cgtgatgcta gagatgaatc tccagcgagg agatgtctac acctgccgcg   240
tggagcactc cagcctccag agccccatct tggtggagtg gc                      282
```

```
<210> SEQ ID NO 22
<211> LENGTH: 270
<212> TYPE: DNA
<213> ORGANISM: Artificial Sequence
<220> FEATURE:
<223> OTHER INFORMATION: SLA-DQB1-204 ENSSSCE00045085054

<400> SEQUENCE: 22
aggatttcgt gtaccagttt aagttcgagt gctacttctt caacggaacg cagcgggtgc    60
ggctcttgac cagatacatc tacaaccagg aggagcacgt gcgcttcgac agcaacgtgg   120
gggagtaccg ggcggtgacc ccgctggggc ggccggacgc cgactactgg aacggccaga   180
aggacgtcct ggagcagacg cggggccgagc tggacactgt gtgcaaacac aactaccaga   240
tagaggaagg cacgaccctg cagcggcgag                                    270
```

```
<210> SEQ ID NO 23
<211> LENGTH: 50
<212> TYPE: DNA
<213> ORGANISM: Artificial Sequence
<220> FEATURE:
<223> OTHER INFORMATION: SLA-DQB1-204 introns 2-3

<400> SEQUENCE: 23
gtgagtgcct gcccgccgcc cgcggttttc ccgtctgtta ctcccctcag        50

<210> SEQ ID NO 24
<211> LENGTH: 282
<212> TYPE: DNA
<213> ORGANISM: Artificial Sequence
<220> FEATURE:
<223> OTHER INFORMATION: SLA-DQB1-204 ENSSSCE00045085973

<400> SEQUENCE: 24
tgcaacctac agtgactatc tccccatcca aggcagaggc tctaaaccac cacaacctgc        60
tggtctgtgc ggtgacagat ttctatccaa gccaggtgaa agtccagtgg ttccggaatg       120
gccaggagga gacagctggc gttgtgtcca ctcctcttat taggaatgga gactggacct       180
accaggtgct cgtgatgcta gagatgaatc tccagcgagg agatgtctac acctgccgcg       240
tggagcactc cagcctccag agccccatct tggtggagtg gc                         282

<210> SEQ ID NO 25
<211> LENGTH: 50
<212> TYPE: DNA
<213> ORGANISM: Artificial Sequence
<220> FEATURE:
<223> OTHER INFORMATION: SLA-DQB1-205 5' Upstream sequence

<400> SEQUENCE: 25
cggggccggg cacggccggg cacccggctt gggcggcggg tttcaggtgg        50

<210> SEQ ID NO 26
<211> LENGTH: 370
<212> TYPE: DNA
<213> ORGANISM: Artificial Sequence
<220> FEATURE:
<223> OTHER INFORMATION: SLA-DQB1-205 ENSSSCE00045086917

<400> SEQUENCE: 26
atgggcccag ctggcggcgg cggacgtctc cccgcctggc cgagcggtgg cggcgtcggg        60
ctggcgggcg gaggcctgac tgacgcggat ctccccgcag aggatttcgt gtaccagttt       120
aagttcgagt gctacttctt caacggaacg cagcgggtgc ggctcttgac cagatacatc       180
tacaaccagg aggagcacgt gcgcttcgac agcaacgtgg gggagtaccg ggcggtgacc       240
ccgctggggc ggccggacgc cgactactgg aacggccaga aggacgtcct ggagcagacg       300
cgggccgagc tggacactgt gtgcaaacac aactaccaga tagaggaagg cacgaccctg       360
cagcggcgag                                                              370

<210> SEQ ID NO 27
<211> LENGTH: 50
<212> TYPE: DNA
<213> ORGANISM: Artificial Sequence
<220> FEATURE:
<223> OTHER INFORMATION: SLA-DQB1-205 introns 1-2

<400> SEQUENCE: 27
gtgagtgcct gcccgccgcc cgcggttttc ccgtctgtta ctcccctcag        50
```

<210> SEQ ID NO 28
<211> LENGTH: 1441
<212> TYPE: DNA
<213> ORGANISM: Artificial Sequence
<220> FEATURE:
<223> OTHER INFORMATION: SLA-DQB1-205 ENSSSCE00045087028

<400> SEQUENCE: 28

| | | | | | |
|---|---|---|---|---|---|
| tgcaacctac | agtgactatc | tccccatcca | aggcagaggc | tctaaaccac | cacaacctgc | 60 |
| tggtctgtgc | ggtgacagat | ttctatccaa | gccaggtgaa | agtccagtgg | ttccggaatg | 120 |
| gccaggagga | gacagctggc | gttgtgtcca | ctcctcttat | taggaatgga | gactggacct | 180 |
| accaggtgct | cgtgatgcta | gagatgaatc | tccagcgagg | agatgtctac | acctgccgcg | 240 |
| tggagcactc | cagcctccag | agccccatct | tggtggagtg | gcgtaagggg | cagttggttt | 300 |
| tctttccctg | tgggccctgc | agaacagagg | gcaggcagag | cttcccgggt | ccatcccatc | 360 |
| tcattctttg | tccccgacat | cactactgag | ctggacatca | ctgggcacat | gagtgctctt | 420 |
| gcctcatagc | aagggcatca | ggagaatctt | tatctccttg | tctttccaga | tacagagcga | 480 |
| tcactacata | ccatgacccc | agagcccagc | cctaggagct | ctgcaggatt | gactagtgcc | 540 |
| tggggcctta | aggtctcaga | ttatgaaagg | agcagggatc | cattttcctt | ctcactcacc | 600 |
| ctcccactct | gtccaggag | ctattggctg | gtccctcacc | tagggtggt | cagaatggac | 660 |
| aacgggttc | ccctggcacc | tctaccccct | gtacctcaga | ctagacttca | ggcctcataa | 720 |
| aggagcacca | tggggtgtgg | tgacaaactc | tgacatttgg | gctctgctcc | caggggcac | 780 |
| agtctgaatc | tgcccagagc | aagatgctga | gcggtgtcgg | gggcttcgtg | ctggggctga | 840 |
| tcttcctcgg | gctgggcctt | ttcatccgtc | acaggagtca | gaagggtaag | gagctctggg | 900 |
| gaaatgggga | gacgggctgt | ggttgggacc | gtctgcaggg | aggccttgtc | tctagatgag | 960 |
| ctctttcctc | ctgaccgtga | aggaaggag | actgggatgg | tggtgagaag | aaacaaaata | 1020 |
| atctagggag | acaatggagt | ctgatttcac | tgattgaaag | gtagcccac | tgcagaggtg | 1080 |
| acaggtggaa | tttattctag | ggcttttttc | tagtgacaac | tctattcatt | gggaggatt | 1140 |
| ttatttaga | tcacttaagg | ccttgtgggt | agggaggaa | tatatttcca | gttaagttgc | 1200 |
| ttatctcatt | tcccttgggg | gtgagtgaga | cactgtgcca | tgagacattt | tgtgggacct | 1260 |
| cctgggcagg | taatgtttct | gctctgattc | accaggggtt | gtggggacag | ggaaaggagg | 1320 |
| gaggaagggg | tgaggtcagt | gtacctgggc | gcagtggtct | cattcacagc | ctatttactt | 1380 |
| ctgtgggatc | cagagttagg | ggagaagttt | gctcagtttc | tataggaagc | tcctgaggtt | 1440 |
| g | | | | | | 1441 |

<210> SEQ ID NO 29
<211> LENGTH: 50
<212> TYPE: DNA
<213> ORGANISM: Artificial Sequence
<220> FEATURE:
<223> OTHER INFORMATION: SLA-DQB1-205 3' downstream

<400> SEQUENCE: 29
ttccccagaa ccaggccata actttggtgg cacctttctc tgaagctggg          50

<210> SEQ ID NO 30
<211> LENGTH: 50
<212> TYPE: DNA
<213> ORGANISM: Artificial Sequence
<220> FEATURE:

<223> OTHER INFORMATION: SLA-DQA-201 5' upstream sequence

<400> SEQUENCE: 30
ccaaaacctg acctggcagc tgggctttgg gtgtctttag agttctttct         50

<210> SEQ ID NO 31
<211> LENGTH: 148
<212> TYPE: DNA
<213> ORGANISM: Artificial Sequence
<220> FEATURE:
<223> OTHER INFORMATION: SLA-DQA-201 ENSSSCE00045087534

<400> SEQUENCE: 31
cagctccatc ctcatcattg ctctacaact ccgaagagca agagctgaga ccaccttgag    60
aagagcatgg tcccaggccg agttctgatg tgggggccc tcgccctgac caccgtgatg   120
agcgcctgtg gaggtgaaga cattgcgg                                      148

<210> SEQ ID NO 32
<211> LENGTH: 50
<212> TYPE: DNA
<213> ORGANISM: Artificial Sequence
<220> FEATURE:
<223> OTHER INFORMATION: SLA-DQA-201 introns 1-2

<400> SEQUENCE: 32
gtgagtgcaa agccgaggga cgtggcacct tcatgctgac cccgacctag         50

<210> SEQ ID NO 33
<211> LENGTH: 249
<212> TYPE: DNA
<213> ORGANISM: Artificial Sequence
<220> FEATURE:
<223> OTHER INFORMATION: SLA-DQA-201 ENSSSCE00045087536

<400> SEQUENCE: 33
ccgaccatgt tgcctcctat ggcttaaatg tctaccagtc ttacggtccc agcggctatt    60
atacccatga atttgatggc gacgaggaat tctacgtgga cctggagaag aaggagactg   120
tctggcggct gcctctgttt agtgaattta caagttttga cccgcagggt gcactgagga   180
atatagctac gttaaaacat aacttgaaca tcgtgactaa acgctccaac aacaccgcgg   240
ctgtcaatc                                                            249

<210> SEQ ID NO 34
<211> LENGTH: 50
<212> TYPE: DNA
<213> ORGANISM: Artificial Sequence
<220> FEATURE:
<223> OTHER INFORMATION: SLA-DQA-201 introns 2-3

<400> SEQUENCE: 34
gtatgtgttc atcattctgc ctttcaatca gtgctgtttt ctcaccacag         50

<210> SEQ ID NO 35
<211> LENGTH: 279
<212> TYPE: DNA
<213> ORGANISM: Artificial Sequence
<220> FEATURE:
<223> OTHER INFORMATION: SLA-DQA-201 ENSSSCE00045087540

<400> SEQUENCE: 35
aggttcctga ggtgactgtg ttttccaagt ctccagtgat actgggtcag cccaacaccc    60
tcatctgtca tgtggacagc atctttcctc ctgtgatcaa catcacgtgg ttgaagaacg   120

```
ggcactctgt caaaggtttt tctgagacca gcttcctctc caaaaatgat cattccttcc    180
tcaagatcag ttatctcacc ttcctcccatt ctgatgacga tttttatgac tgcaaagtgg   240
agcactgggg cctggataag ccacttctga aacactggg                          279
```

```
<210> SEQ ID NO 36
<211> LENGTH: 50
<212> TYPE: DNA
<213> ORGANISM: Artificial Sequence
<220> FEATURE:
<223> OTHER INFORMATION: SLA-DQA-201 introns 3-4

<400> SEQUENCE: 36
gtatggacga gttccacccc ttttggactt ctacaacctc acttttgcag              50
```

```
<210> SEQ ID NO 37
<211> LENGTH: 175
<212> TYPE: DNA
<213> ORGANISM: Artificial Sequence
<220> FEATURE:
<223> OTHER INFORMATION: SLA-DQA-201 ENSSSCE00045087547

<400> SEQUENCE: 37
aacctgagat ccagccccc atgtcagagc tgacagagac tgtggtctgc gccctgggat    60
tgatcgtggg ccttgtgggc atcgtggtgg gcactgtctt catcattcaa ggcctgcgct   120
caggtggtcc ctctagacac caagggtcct tgtgagtcac actccagaag ggaag        175
```

```
<210> SEQ ID NO 38
<211> LENGTH: 50
<212> TYPE: DNA
<213> ORGANISM: Artificial Sequence
<220> FEATURE:
<223> OTHER INFORMATION: SLA-DQA-201 introns 4-5

<400> SEQUENCE: 38
gtaaggattc agatttgtca gaaccccagt cctgcctctt gtctttgcag              50
```

```
<210> SEQ ID NO 39
<211> LENGTH: 1115
<212> TYPE: DNA
<213> ORGANISM: Artificial Sequence
<220> FEATURE:
<223> OTHER INFORMATION: SLA-DQA-201 ENSSSCE00045087550

<400> SEQUENCE: 39
ggtcaaaagc aaagagctac ctatagagac ctgagggctc cctggacacc cagcacaagt    60
cctcttgatt tctccacggt gtcactctct ctttactcct attgtgaatg caatgtcca    120 ccctaaggaa gatgacagtg tcaacacaaa acctctgacc ccacttggca tcttgctctg   180
agcagacaca gactatgacc ttgagaagca gaatctggag actcccacac tccacagtgt   240
ccctggctga tgacctgcag tacacccctgg gatacaagct cttctcccaa agaaagcct    300 agttctccaa tctaacctca tccaggagag tgaaggacct gccattggct cctcaggtcc   360
agtgtgtaga tgagggatca gggaagagag gatgcctgct cctagaggca cagcagtttc   420
ataacctcag agaaaagctc taagccactc gtgttaatga caaatccaag agtgtgagat   480
gaagaccact ttcagtagag tgactcttct aatgcctggg aagacagtgt catcccagat   540
cgacaggtca ttatgttcac agataagaga attccagctc agcagcgcca tcaggtgact   600
gtgcaggagg caatggctgg gatgggtgtg agtcagcccc ggagccaatg agggacccta   660
```

```
gagccaaagg gaactctgcc atttgtcttg tggggttcag agaacaaac tgccccttat      720 ccactccaca ctcaggtggc actggaggct gggatgctcc atgtgacaga tgcagacatc      780
tccatgctgg aaagtcattt ccagcagcac aaagatctgg gaaatccagt ccctgttcct      840
tataaggggg gtgggcacaa tgccaaccat ctgcatccca tgtacaggat gatgtttctg      900
aaaggtgtgc atgttaccca gactgggccg gtagcatctt ccctaaaatg attaaaactg      960
tagtatacac tctggaaata tacaacagag acaaattaat acacacacac acagagagat     1020
aagctgtgag gtgatgagaa agaaagatat agaaaataga gatgaaaaga gaaacacagc     1080
aagataaaga gatgccgata aagagtgata aagat                                1115
```

<210> SEQ ID NO 40
<211> LENGTH: 50
<212> TYPE: DNA
<213> ORGANISM: Artificial Sequence
<220> FEATURE:
<223> OTHER INFORMATION: SLA-DQA-201 3' downstream sequence

<400> SEQUENCE: 40

```
gcaaatagtg aaaaattgat tttctttctc ctctgtagac ctttacgcag                  50
```

<210> SEQ ID NO 41
<211> LENGTH: 50
<212> TYPE: DNA
<213> ORGANISM: Artificial Sequence
<220> FEATURE:
<223> OTHER INFORMATION: SLA-DQA-202 5' upstream sequence

<400> SEQUENCE: 41

```
aactggcaac agaggtgtca tcataggga agtttctgat tggccaaaac                   50
```

<210> SEQ ID NO 42
<211> LENGTH: 191
<212> TYPE: DNA
<213> ORGANISM: Artificial Sequence
<220> FEATURE:
<223> OTHER INFORMATION: SLA-DQA-202 ENSSSCE00045087621

<400> SEQUENCE: 42

```
ctgacctggc agctgggctt tgggtgtctt tagagttctt tctcagctcc atcctcatca       60
ttgctctaca actccgaaga gcaagagctg agaccacctt gagaagagca tggtcccagg      120
ccgagttctg atgtgggggg ccctcgccct gaccaccgtg atgagcgcct gtggaggtga      180
agacattgcg g                                                           191
```

<210> SEQ ID NO 43
<211> LENGTH: 50
<212> TYPE: DNA
<213> ORGANISM: Artificial Sequence
<220> FEATURE:
<223> OTHER INFORMATION: SLA-DQA-202 Intron 1-2

<400> SEQUENCE: 43

```
gtgagtgcaa agccgaggga cgtggcacct tcatgctgac cccgacctag                  50
```

<210> SEQ ID NO 44
<211> LENGTH: 249
<212> TYPE: DNA
<213> ORGANISM: Artificial Sequence
<220> FEATURE:
<223> OTHER INFORMATION: SLA-DQA-202 ENSSSCE00045087536

<400> SEQUENCE: 44

```
ccgaccatgt tgcctcctat ggcttaaatg tctaccagtc ttacggtccc agcggctatt      60
atacccatga atttgatggc gacgaggaat ctacgtgga cctggagaag aaggagactg      120
tctggcggct gcctctgttt agtgaattta caagttttga cccgcagggt gcactgagga    180
atatagctac gttaaaacat aacttgaaca tcgtgactaa acgctccaac aacaccgcgg    240
ctgtcaatc                                                              249
```

<210> SEQ ID NO 45
<211> LENGTH: 50
<212> TYPE: DNA
<213> ORGANISM: Artificial Sequence
<220> FEATURE:
<223> OTHER INFORMATION: SLA-DQA-202 introns 2-3

<400> SEQUENCE: 45

```
gtatgtgttc atcattctgc ctttcaatca gtgctgtttt ctcaccacag                 50
```

<210> SEQ ID NO 46
<211> LENGTH: 279
<212> TYPE: DNA
<213> ORGANISM: Artificial Sequence
<220> FEATURE:
<223> OTHER INFORMATION: SLA-DQA-202 ENSSSCE00045087540

<400> SEQUENCE: 46

```
aggttcctga ggtgactgtg ttttccaagt ctccagtgat actgggtcag cccaacaccc      60
tcatctgtca tgtggacagc atctttcctc ctgtgatcaa catcacgtgg ttgaagaacg     120
ggcactctgt caaggttttt ctgagacca gcttcctctc caaaaatgat cattccttcc     180
tcaagatcag ttatctcacc ttcctcccctt ctgatgacga ttttatgac tgcaaagtgg    240 agcactgggg cctggataag ccacttctga aacactggg                            279
```

<210> SEQ ID NO 47
<211> LENGTH: 50
<212> TYPE: DNA
<213> ORGANISM: Artificial Sequence
<220> FEATURE:
<223> OTHER INFORMATION: SLA-DQA-202 introns 3-4

<400> SEQUENCE: 47

```
gtatggacga gttccacccc ttttggactt ctacaacctc acttttgcag                 50
```

<210> SEQ ID NO 48
<211> LENGTH: 175
<212> TYPE: DNA
<213> ORGANISM: Artificial Sequence
<220> FEATURE:
<223> OTHER INFORMATION: SLA-DQA-202 ENSSSCE00045087547

<400> SEQUENCE: 48

```
aacctgagat tccagccccc atgtcagagc tgacagagac tgtggtctgc gccctgggat      60
tgatcgtggg ccttgtgggc atcgtggtgg gcactgtctt catcattcaa ggcctgcgct    120
caggtggtcc ctctagacac caagggtcct tgtgagtcac actccagaag ggaag         175
```

<210> SEQ ID NO 49
<211> LENGTH: 50
<212> TYPE: DNA
<213> ORGANISM: Artificial Sequence
<220> FEATURE:
<223> OTHER INFORMATION: SLA-DQA-202 introns 4-5

<400> SEQUENCE: 49
gtaaggattc agatttgtca gaacccgatc tcatgtctgt cctattgcag      50

<210> SEQ ID NO 50
<211> LENGTH: 91
<212> TYPE: DNA
<213> ORGANISM: Artificial Sequence
<220> FEATURE:
<223> OTHER INFORMATION: SLA-DQA-202 ENSSSCE00045087625

<400> SEQUENCE: 50
gagcactgcc cgcctacaag agctgaagag tggatgtgct caacgaccta gaactatttt      60
ctggccaaat tcatcatata ccttctctct t      91

<210> SEQ ID NO 51
<211> LENGTH: 50
<212> TYPE: DNA
<213> ORGANISM: Artificial Sequence
<220> FEATURE:
<223> OTHER INFORMATION: SLA-DQA-202 introns 5-6

<400> SEQUENCE: 51
cctacattct tcttctcacc tcttctttct ccacggtgtc actctctctt      50

<210> SEQ ID NO 52
<211> LENGTH: 879
<212> TYPE: DNA
<213> ORGANISM: Artificial Sequence
<220> FEATURE:
<223> OTHER INFORMATION: SLA-DQA-202 ENSSSCE00045087664

<400> SEQUENCE: 52
tactcctatt gtgaatggca atgtccaccc taaggaagat gacagtgtca acacaaaacc      60 tctgaccca cttggcatct tgctctgagc agacacagac tatgaccttg agaagcagaa      120
tctggagact cccacactcc acagtgtccc tggctgatga cctgcagtac acctgggat      180 acaagctctt tctccaaaag aaagcctagt tctccaatct aacctcatcc aggagagtga      240
aggacctgcc attggctcct caggtccagt gtgtagatga gggatcaggg aagagaggat      300
gcctgctcct agaggcacag cagtttcata acctcagaga aaagctctaa gccactcgtg      360
ttaatgacaa atccaagagt gtgagatgaa gaccactttc agtagagtga ctcttctaat      420
gcctgggaag acagtgtcat cccagatcga caggtcatta tgttcacaga taagagaatt      480
ccagctcagc agcgccatca ggtgactgtg caggaggcaa tggctgggat gggtgtgagt      540
cagccccgga gccaatgagg gaccctagag ccaaagggaa ctctgccatt tgtcttgtgg      600
ggttcagaag aacaaactgc cccttatcca ctccacactc aggtggcact ggaggctggg      660
atgctccatg tgacagatgc agacatctcc atgctggaaa gtcatttcca gcagcacaaa      720
gatctgggaa atccagtccc tgttccttat aaggggggtg ggcacaatgc caaccatctg      780
catcccatgt acaggatgat gtttctgaaa ggtgtgcatg ttacccagac tgggccggta      840
gcatcttccc taaaatgatt aaaactgtag tatacactc      879

<210> SEQ ID NO 53
<211> LENGTH: 50
<212> TYPE: DNA
<213> ORGANISM: Artificial Sequence
<220> FEATURE:
<223> OTHER INFORMATION: SLA-DQA-202 3' downstream sequence

<400> SEQUENCE: 53
tggaaatata caacagagac aaattaatac acacacacac agagagataa          50

<210> SEQ ID NO 54
<211> LENGTH: 50
<212> TYPE: DNA
<213> ORGANISM: Artificial Sequence
<220> FEATURE:
<223> OTHER INFORMATION: SLA-DQA-203 5' upstream sequence

<400> SEQUENCE: 54
ctttgggtgt ctttagagtt ctttctcagc tccatcctca tcattgctct          50

<210> SEQ ID NO 55
<211> LENGTH: 124
<212> TYPE: DNA
<213> ORGANISM: Artificial Sequence
<220> FEATURE:
<223> OTHER INFORMATION: SLA-DQA-203 ENSSSCE00045087772

<400> SEQUENCE: 55
acaactccga agagcaagag ctgagaccac cttgagaaga gcatggtccc aggccgagtt          60
ctgatgtggg gggccctcgc cctgaccacc gtgatgagcg cctgtggagg tgaagacatt          120
gcgg          124

<210> SEQ ID NO 56
<211> LENGTH: 50
<212> TYPE: DNA
<213> ORGANISM: Artificial Sequence
<220> FEATURE:
<223> OTHER INFORMATION: SLA-DQA-203 introns 2-3

<400> SEQUENCE: 56
gtgagtgcaa agccgaggga cgtggcacct tcatgctgac cccgacctag          50

<210> SEQ ID NO 57
<211> LENGTH: 249
<212> TYPE: DNA
<213> ORGANISM: Artificial Sequence
<220> FEATURE:
<223> OTHER INFORMATION: SLA-DQA-203 ENSSSCE00045087536

<400> SEQUENCE: 57
ccgaccatgt tgcctcctat ggcttaaatg tctaccagtc ttacggtccc agcggctatt          60
atacccatga atttgatggc gacgaggaat tctacgtgga cctggagaag aaggagactg          120
tctggcggct gcctctgttt agtgaattta caagttttga cccgcagggt gcactgagga          180
atatagctac gttaaaacat aacttgaaca tcgtgactaa acgctccaac aacaccgcgg          240
ctgtcaatc          249

<210> SEQ ID NO 58
<211> LENGTH: 50
<212> TYPE: DNA
<213> ORGANISM: Artificial Sequence
<220> FEATURE:
<223> OTHER INFORMATION: SLA-DQA-203 introns 2-3

<400> SEQUENCE: 58
gtatgtgttc atcattctgc ctttcaatca gtgctgtttt ctcaccacag          50

<210> SEQ ID NO 59
<211> LENGTH: 279
<212> TYPE: DNA

<213> ORGANISM: Artificial Sequence
<220> FEATURE:
<223> OTHER INFORMATION: SLA-DQA-203 ENSSSCE00045087540

<400> SEQUENCE: 59

```
aggttcctga ggtgactgtg ttttccaagt ctccagtgat actgggtcag cccaacaccc      60
tcatctgtca tgtggacagc atctttcctc ctgtgatcaa catcacgtgg ttgaagaacg     120
ggcactctgt caaaggtttt tctgagacca gcttcctctc caaaaatgat cattccttcc     180
tcaagatcag ttatctcacc ttcctccctt ctgatgacga tttttatgac tgcaaagtgg     240
agcactgggg cctggataag ccacttctga aacactggg                            279
```

<210> SEQ ID NO 60
<211> LENGTH: 50
<212> TYPE: DNA
<213> ORGANISM: Artificial Sequence
<220> FEATURE:
<223> OTHER INFORMATION: SLA-DQA-203 introns 3-4

<400> SEQUENCE: 60

```
gtatggacga gttccacccc ttttggactt ctacaacctc acttttgcag                 50
```

<210> SEQ ID NO 61
<211> LENGTH: 175
<212> TYPE: DNA
<213> ORGANISM: Artificial Sequence
<220> FEATURE:
<223> OTHER INFORMATION: DLA-DQA-203 ENSSSCE00045087547

<400> SEQUENCE: 61

```
aacctgagat tccagccccc atgtcagagc tgacagagac tgtggtctgc gccctgggat      60
tgatcgtggg ccttgtgggc atcgtggtgg gcactgtctt catcattcaa ggcctgcgct     120
caggtggtcc ctctagacac caagggtcct tgtgagtcac actccagaag ggaag          175
```

<210> SEQ ID NO 62
<211> LENGTH: 50
<212> TYPE: DNA
<213> ORGANISM: Artificial Sequence
<220> FEATURE:
<223> OTHER INFORMATION: SLA-DQA-203 introns 4-5

<400> SEQUENCE: 62

```
gtaaggattc agatttgtca gaaccttttt tttttgtttt ccttttttcag                50
```

<210> SEQ ID NO 63
<211> LENGTH: 1324
<212> TYPE: DNA
<213> ORGANISM: Artificial Sequence
<220> FEATURE:
<223> OTHER INFORMATION: SLA-DQA-203 ENSSSCE00045087920

<400> SEQUENCE: 63

```
gacagctcct gcggcatatg gaagttccca ggctaggggg caaatctgag acgtagctgc      60
tagccattcc acagccatac cagatcagag cctcctacac cgcagctgac tgcaacgctg     120
gatccttaat ccacagagca aggccaggga tcaaacccgc atcctcatgg gtactagttg     180
ggttcatatc ctgctgagac acagtgggaa ctcctggaac taattcctta catggaagag     240
gactgtcaat tatttagcaa aatgaatgaa aaaagactca ctcctaaatg tgtcattttta    300
aaaatttcag ggagttccca ttgtggctca gcggcaatga atctgactag catccatgag     360
gatgcaggtt caatccctgg ccttgcccag tgggttaagg atccggtgtt gccgtgagtt     420
```

```
gtggtgtagg tcacagatgt ggctcagatc ccacattgct gtgtctgtgg ctatggcaca    480
ggctgacagc tgcagcttag ctccaattca accccagtc tgggaacttt acatttctta    540
tgtgacaaag agaccagtcc aaaaagtgcc ttattaccat acagcacttt gattttactt    600
gccccaaaaa ctagtaagct agatcccatt ttctcccatt tcctataacc agtgaaggaa    660 gaaggggta ttatttgttt tgttttacta ttgatatttc agtaacgatg aagagcttg    720 tgtaaccaag aagggctgct tactacccac tgtctatgta acagtcacaa agatgtgctc    780
agcctaaccc ccaaagagtt ctgaagcttc aagggctctt cagagttgac ccaagttatg    840
gtgggatcac aaactttaca cctctgcaat gagcagtcac tgcagctgaa ttcccttggg    900
aagtgcagta aaactggaac tgggattcaa ttccacagtc attcaaggga tctaggttat    960
gactcagggt tacaacactt catacaccat cattctcagc aatggcctcc aggcttgcag   1020
tagaaggaaa agacaaagca gacagagctt aaacttgctt ttaaattcca tcggctggta   1080
ccagtcacaa ctccaaccta acctggaggg gaagctggga gatactgggt gacattattg   1140
aaggtgagac caaatgttca tgacaagtgg gctgttctca gatacaccca tgtattttc   1200 tccaaggtat atgactacta aaactttggg attttttgtt agcaaacttg tttatatgta   1260
tttttaatta aatgatcaat aaaggattat attacccaat gaaatctggg tacaaaaaaa   1320
aaaa                                                                1324

<210> SEQ ID NO 64
<211> LENGTH: 50
<212> TYPE: DNA
<213> ORGANISM: Artificial Sequence
<220> FEATURE:
<223> OTHER INFORMATION: SLA-DQA-203 3' downstream sequence

<400> SEQUENCE: 64
gttgttccta tgaaactgtc actggaagga aagaaaaaag actctttctc                50

<210> SEQ ID NO 65
<211> LENGTH: 50
<212> TYPE: DNA
<213> ORGANISM: Artificial Sequence
<220> FEATURE:
<223> OTHER INFORMATION: SLA-DQA-204 5' upstream sequence

<400> SEQUENCE: 65
tagagaagca aaaagaaacg cagcaaaccc acatgtggag gccaggcaaa                50

<210> SEQ ID NO 66
<211> LENGTH: 535
<212> TYPE: DNA
<213> ORGANISM: Artificial Sequence
<220> FEATURE:
<223> OTHER INFORMATION: SLA-DQA-204 ENSSSCE00045088042

<400> SEQUENCE: 66
ggggcttggg ggggtagtgc ctgccagagg ggggtcacct caggagtctt cccggaagct     60
gtaactcagg aaatatggtt ggacaaatta ttagtgttgg cctcatctta tccatgagag   120
ctcagaaatt cccgccccgc ttgtccgtgg caggcataca cacctccgag atgattctca   180
tttcatcccc tccctccttt cactgagagt cccctcagct ctagtctgag aggaggcagc   240
ctcagaaccg ggggatttcc caacccctc caggcctctt caaacaaagt cttcaactgg   300
caacagaggt gtcatcatag gggaagtttc tgattggcca aaacctgacc tggcagctgg   360
```

```
gctttgggtg tctttagagt tctttctcag ctccatcctc atcattgctc tacaactccg    420
aagagcaaga gctgagacca ccttgagaag agcatggtcc caggccgagt tctgatgtgg    480
ggggccctcg ccctgaccac cgtgatgagc gcctgtggag gtgaagacat tgcgg         535
```

```
<210> SEQ ID NO 67
<211> LENGTH: 50
<212> TYPE: DNA
<213> ORGANISM: Artificial Sequence
<220> FEATURE:
<223> OTHER INFORMATION: SLA-DQA-204 introns 1-2

<400> SEQUENCE: 67
gtgagtgcaa agccgaggga cgtggcacct tcatgctgac cccgacctag               50
```

```
<210> SEQ ID NO 68
<211> LENGTH: 249
<212> TYPE: DNA
<213> ORGANISM: Artificial Sequence
<220> FEATURE:
<223> OTHER INFORMATION: SLA-DQA-204 ENSSSCE00045087536

<400> SEQUENCE: 68
ccgaccatgt tgcctcctat ggcttaaatg tctaccagtc ttacggtccc agcggctatt    60
atacccatga atttgatggc gacgaggaat tctacgtgga cctggagaag aaggagactg   120
tctggcggct gcctctgttt agtgaattta caagttttga cccgcagggt gcactgagga   180
atatagctac gttaaaacat aacttgaaca tcgtgactaa acgctccaac aacaccgcgg   240
ctgtcaatc                                                           249
```

```
<210> SEQ ID NO 69
<211> LENGTH: 50
<212> TYPE: DNA
<213> ORGANISM: Artificial Sequence
<220> FEATURE:
<223> OTHER INFORMATION: SLA-DQA-204 introns 2-3

<400> SEQUENCE: 69
gtatgtgttc atcattctgc ctttcaatca gtgctgtttt ctcaccacag               50
```

```
<210> SEQ ID NO 70
<211> LENGTH: 279
<212> TYPE: DNA
<213> ORGANISM: Artificial Sequence
<220> FEATURE:
<223> OTHER INFORMATION: SLA-DQA-204 ENSSSCE00045087540

<400> SEQUENCE: 70
aggttcctga ggtgactgtg ttttccaagt ctccagtgat actgggtcag cccaacaccc    60
tcatctgtca tgtggacagc atctttcctc ctgtgatcaa catcacgtgg ttgaagaacg   120
ggcactctgt caaaggtttt tctgagacca gcttcctctc caaaaatgat cattccttcc   180
tcaagatcag ttatctcacc ttcctcccct ctgatgacga tttttatgac tgcaaagtgg   240
agcactgggg cctggataag ccacttctga aacactggg                          279
```

```
<210> SEQ ID NO 71
<211> LENGTH: 50
<212> TYPE: DNA
<213> ORGANISM: Artificial Sequence
<220> FEATURE:
<223> OTHER INFORMATION: SLA-DQA-204 introns 3-4

<400> SEQUENCE: 71
```
gtatggacga gttccacccc ttttggactt ctacaacctc acttttgcag    50

<210> SEQ ID NO 72
<211> LENGTH: 44
<212> TYPE: DNA
<213> ORGANISM: Artificial Sequence
<220> FEATURE:
<223> OTHER INFORMATION: SLA-DQA-204 ENSSSCE00045088055

<400> SEQUENCE: 72
aacctgagat tccagccccc atgtcagagc tgacagagac tgtg    44

<210> SEQ ID NO 73
<211> LENGTH: 50
<212> TYPE: DNA
<213> ORGANISM: Artificial Sequence
<220> FEATURE:
<223> OTHER INFORMATION: SLA-DQA-204 introns 4-5

<400> SEQUENCE: 73
gtctgcgccc tgggattgat cgtgggtggg cactgtcttc atcattcaag    50

<210> SEQ ID NO 74
<211> LENGTH: 64
<212> TYPE: DNA
<213> ORGANISM: Artificial Sequence
<220> FEATURE:
<223> OTHER INFORMATION: SLA-DQA-204 ENSSSCE00045088069

<400> SEQUENCE: 74
gcctgcgctc aggtggtccc tctagacacc aagggtcctt gtgagtcaca ctccagaagg    60
gaag    64

<210> SEQ ID NO 75
<211> LENGTH: 50
<212> TYPE: DNA
<213> ORGANISM: Artificial Sequence
<220> FEATURE:
<223> OTHER INFORMATION: SLA-DQA-204 introns 5-6

<400> SEQUENCE: 75
gtaaggattc agatttgtca gaacccgatc tcatgtctgt cctattgcag    50

<210> SEQ ID NO 76
<211> LENGTH: 26
<212> TYPE: DNA
<213> ORGANISM: Artificial Sequence
<220> FEATURE:
<223> OTHER INFORMATION: SLA-DQA-204 ENSSSCE00045088082

<400> SEQUENCE: 76
gagcactgcc cgcctacaag agctga    26

<210> SEQ ID NO 77
<211> LENGTH: 50
<212> TYPE: DNA
<213> ORGANISM: Artificial Sequence
<220> FEATURE:
<223> OTHER INFORMATION: SLA-DQA-204 3' downstream sequence

<400> SEQUENCE: 77
agagtggatg tgctcaacga cctagaacta ttttctggcc aaattcatca    50

<210> SEQ ID NO 78

```
<211> LENGTH: 50
<212> TYPE: DNA
<213> ORGANISM: Artificial Sequence
<220> FEATURE:
<223> OTHER INFORMATION: SLA-DQB1-201 5' upstream sequence

<400> SEQUENCE: 78
ctacatgggc acttccacag gtttttattc tctgaagggg ggatacgaga              50

<210> SEQ ID NO 79
<211> LENGTH: 163
<212> TYPE: DNA
<213> ORGANISM: Artificial Sequence
<220> FEATURE:
<223> OTHER INFORMATION: SLA-DQB1-201 ENSSSCE00045084941

<400> SEQUENCE: 79
accactgagt gggagctgtg ttgactacca ttacttcttc gtttgccctc aattatgtct   60
gggatggtgg ctctgcggct ccccagaggc ctttggacag cggccttgac ggtgatgctg   120
gtggtgctgg gtgctccagt ggctgagggc agagactctc cac                    163

<210> SEQ ID NO 80
<211> LENGTH: 50
<212> TYPE: DNA
<213> ORGANISM: Artificial Sequence
<220> FEATURE:
<223> OTHER INFORMATION: SLA-DQB1-201 introns 1-2

<400> SEQUENCE: 80
gtaagtgcag ccaccattca ggggactgac tgacgcggat ctccccgcag              50

<210> SEQ ID NO 81
<211> LENGTH: 270
<212> TYPE: DNA
<213> ORGANISM: Artificial Sequence
<220> FEATURE:
<223> OTHER INFORMATION: SLA-DQB1-201 ENSSSCE00045085054

<400> SEQUENCE: 81
aggatttcgt gtaccagttt aagttcgagt gctacttctt caacggaacg cagcgggtgc   60
ggctcttgac cagatacatc tacaaccagg aggagcacgt gcgcttcgac agcaacgtgg   120
gggagtaccg gcggtgacc ccgctggggc ggccggacgc cgactactgg aacggccaga    180
aggacgtcct ggagcagacg cgggccgagc tggacactgt gtgcaaacac aactaccaga   240
tagaggaagg cacgaccctg cagcggcgag                                   270

<210> SEQ ID NO 82
<211> LENGTH: 50
<212> TYPE: DNA
<213> ORGANISM: Artificial Sequence
<220> FEATURE:
<223> OTHER INFORMATION: SLA-DQB1-201 introns 2-3

<400> SEQUENCE: 82
gtgagtgcct gcccgccgcc cgcggttttc ccgtctgtta ctcccctcag              50

<210> SEQ ID NO 83
<211> LENGTH: 885
<212> TYPE: DNA
<213> ORGANISM: Artificial Sequence
<220> FEATURE:
<223> OTHER INFORMATION: SLA-DQB1-201 ENSSSCE00045085455

<400> SEQUENCE: 83
```

```
tgcaacctac agtgactatc tccccatcca aggcagaggc tctaaaccac cacaacctgc      60
tggtctgtgc ggtgacagat ttctatccaa gccaggtgaa agtccagtgg ttccggaatg     120
gccaggagga gacagctggc gttgtgtcca ctcctcttat taggaatgga gactggacct     180
accaggtgct cgtgatgcta gagatgaatc tccagcgagg agatgtctac acctgccgcg     240
tggagcactc cagcctccag agccccatct tggtggagtg gcgtaagggg cagttggttt     300
tctttccctg tgggccctgc agaacagagg gcaggcagag cttcccgggt ccatcccatc     360
tcattctttg tccccgacat cactactgag ctggacatca ctgggcacat gagtgctctt     420
gcctcatagc aagggcatca ggagaatctt tatctccttg tctttccaga tacagagcga     480
tcactacata ccatgacccc agagcccagc ctaggagct  ctgcaggatt gactagtgcc     540
tggggcctta aggtctcaga ttatgaaagg agcaggatc  catttccctt ctcactcacc     600
ctcccactct gtccagggag ctattggctg gtccctcacc taggggtggt cagaatggac     660
aacggggttc ccctggcacc tctaccccct gtacctcaga ctagacttca ggcctcataa     720
aggagcacca tggggtgtgg tgacaaactc tgacatttgg gctctgctcc ccaggggcac     780
agtctgaatc tgcccagagc aagatgctga gcggtgtcgg gggcttcgtg ctggggctga     840
tcttcctcgg gctgggcctt tcatccgtc  acaggagtca gaagg                    885

<210> SEQ ID NO 84
<211> LENGTH: 50
<212> TYPE: DNA
<213> ORGANISM: Artificial Sequence
<220> FEATURE:
<223> OTHER INFORMATION: SLA-DQB1-201 introns 3-4

<400> SEQUENCE: 84
gtaaggagct ctggggaaat ggggatgacc actctctctc tcttctacag               50

<210> SEQ ID NO 85
<211> LENGTH: 372
<212> TYPE: DNA
<213> ORGANISM: Artificial Sequence
<220> FEATURE:
<223> OTHER INFORMATION: SLA-DQB1-201 ENSSSCE00045085731

<400> SEQUENCE: 85
ggctcgtgcg ctgaatcctg aagatacttt ggggttggtt tttgctcttc ttaaatgcct      60
gtctgttctt gcctggaatt cccataccc  tgccagcttg ttcctctctg aggtcagatc     120
ctacagtgac tctgatgcag tcacgagggc gcttcctgtg atccccacct caaggctctg     180
gctgtgaagc ttcttcctga actgaccca  gcgcctctgc ctgagtgcag ccagctgtgt     240
ctactcagac cacaagggat tttcctgttc ctattttccc tcaacagact gtgcaagaga     300
agcacattga aaccatttac ctggctgtag agtgcttttt ttaaaatcat aattaaacat     360
gattatgagt ta                                                         372

<210> SEQ ID NO 86
<211> LENGTH: 50
<212> TYPE: DNA
<213> ORGANISM: Artificial Sequence
<220> FEATURE:
<223> OTHER INFORMATION: SLA-DQB1-201 3' downstream sequence

<400> SEQUENCE: 86
tctgtgcacc gacccttctt aaatgggcag aggtaagaaa caatggcaga               50
```

<210> SEQ ID NO 87
<211> LENGTH: 50
<212> TYPE: DNA
<213> ORGANISM: Artificial Sequence
<220> FEATURE:
<223> OTHER INFORMATION: SLA-DQB1-202 5' upstream sequence

<400> SEQUENCE: 87
catgggcact tccacaggtt tttattctct gaagggggga tacgagaacc         50

<210> SEQ ID NO 88
<211> LENGTH: 160
<212> TYPE: DNA
<213> ORGANISM: Artificial Sequence
<220> FEATURE:
<223> OTHER INFORMATION: SLA-DQB1-202 ENSSSCE00045085952

<400> SEQUENCE: 88
actgagtggg agctgtgttg actaccatta cttcttcgtt tgccctcaat tatgtctggg    60
atggtggctc tgcggctccc cagaggcctt tggacagcgg ccttgacggt gatgctggtg   120
gtgctgggtg ctccagtggc tgagggcaga gactctccac                         160

<210> SEQ ID NO 89
<211> LENGTH: 50
<212> TYPE: DNA
<213> ORGANISM: Artificial Sequence
<220> FEATURE:
<223> OTHER INFORMATION: SLA-DQB1-202 introns 1-2

<400> SEQUENCE: 89
gtaagtgcag ccaccattca ggggactgac tgacgcggat ctccccgcag              50

<210> SEQ ID NO 90
<211> LENGTH: 270
<212> TYPE: DNA
<213> ORGANISM: Artificial Sequence
<220> FEATURE:
<223> OTHER INFORMATION: SLA-DQB1-202 ENSSSCE00045085054

<400> SEQUENCE: 90
aggatttcgt gtaccagttt aagttcgagt gctacttctt caacggaacg cagcgggtgc    60
ggctcttgac cagatacatc tacaaccagg aggagcacgt gcgcttcgac agcaacgtgg   120
gggagtaccg ggcggtgacc ccgctggggc ggccggacgc cgactactgg aacggccaga   180
aggacgtcct ggagcagacg cgggccgagc tggacactgt gtgcaaacac aactaccaga   240
tagaggaagg cacgaccctg cagcggcgag                                    270

<210> SEQ ID NO 91
<211> LENGTH: 50
<212> TYPE: DNA
<213> ORGANISM: Artificial Sequence
<220> FEATURE:
<223> OTHER INFORMATION: SLA-DQB1-202 introns 2-3

<400> SEQUENCE: 91
gtgagtgcct gcccgccgcc cgcggttttc ccgtctgtta ctcccctcag              50

<210> SEQ ID NO 92
<211> LENGTH: 282
<212> TYPE: DNA
<213> ORGANISM: Artificial Sequence
<220> FEATURE:
<223> OTHER INFORMATION: SLA-DQB1-202 ENSSSCE00045085973

<400> SEQUENCE: 92

```
tgcaacctac agtgactatc tccccatcca aggcagaggc tctaaaccac cacaacctgc      60
tggtctgtgc ggtgacagat ttctatccaa gccaggtgaa agtccagtgg ttccggaatg     120
gccaggagga gacagctggc gttgtgtcca ctcctcttat taggaatgga gactggacct    180
accaggtgct cgtgatgcta gagatgaatc tccagcgagg agatgtctac acctgccgcg    240
tggagcactc cagcctccag agccccatct tggtggagtg gc                        282
```

<210> SEQ ID NO 93
<211> LENGTH: 50
<212> TYPE: DNA
<213> ORGANISM: Artificial Sequence
<220> FEATURE:
<223> OTHER INFORMATION: SLA-DQB1-202 introns 3-4

<400> SEQUENCE: 93

```
gtaagggca gttggttttc tttccctgac atttgggctc tgctccccag                 50
```

<210> SEQ ID NO 94
<211> LENGTH: 111
<212> TYPE: DNA
<213> ORGANISM: Artificial Sequence
<220> FEATURE:
<223> OTHER INFORMATION: SLA_DQB1-202 ENSSSCE00045086264

<400> SEQUENCE: 94

```
gggcacagtc tgaatctgcc cagagcaaga tgctgagcgg tgtcggggc ttcgtgctgg     60 ggctgatctt cctcgggctg ggccttttca tccgtcacag gagtcagaag g             111
```

<210> SEQ ID NO 95
<211> LENGTH: 50
<212> TYPE: DNA
<213> ORGANISM: Artificial Sequence
<220> FEATURE:
<223> OTHER INFORMATION: SLA-DQB1-202 introns 4-5

<400> SEQUENCE: 95

```
gtaaggagct ctggggaaat ggggatgacc actctctctc tcttctacag               50
```

<210> SEQ ID NO 96
<211> LENGTH: 371
<212> TYPE: DNA
<213> ORGANISM: Artificial Sequence
<220> FEATURE:
<223> OTHER INFORMATION: SLA-DQB1-202 ENSSSCE00045086397

<400> SEQUENCE: 96

```
ggctcgtgcg ctgaatcctg aagatacttt ggggttggtt tttgctcttc ttaaatgcct    60
gtctgttctt gcctggaatt cccatacccc tgccagcttg ttcctctctg aggtcagatc   120
ctacagtgac tctgatgcag tcacgagggc gcttcctgtg atccccacct caaggctctg   180
gctgtgaagc ttcttcctga actgacccca gcgcctctgc ctgagtgcag ccagctgtgt   240
ctactcagac cacaagggat tttcctgttc ctattttccc tcaacagact gtgcaagaga   300
agcacattga aaccatttac ctggctgtag agtgcttttt ttaaaatcat aattaaacat   360
gattatgagt t                                                         371
```

<210> SEQ ID NO 97
<211> LENGTH: 50
<212> TYPE: DNA

```
<213> ORGANISM: Artificial Sequence
<220> FEATURE:
<223> OTHER INFORMATION: SLA-DQB1-202 3' downstream sequence

<400> SEQUENCE: 97
atctgtgcac cgacccttct taaatgggca gaggtaagaa acaatggcag            50

<210> SEQ ID NO 98
<211> LENGTH: 50
<212> TYPE: DNA
<213> ORGANISM: Artificial Sequence
<220> FEATURE:
<223> OTHER INFORMATION: SLA-DQB1-203 5' upstream sequence

<400> SEQUENCE: 98
ctgagtggga gctgtgttga ctaccattac ttcttcgttt gccctcaatt            50

<210> SEQ ID NO 99
<211> LENGTH: 109
<212> TYPE: DNA
<213> ORGANISM: Artificial Sequence
<220> FEATURE:
<223> OTHER INFORMATION: SLA-DQB1-203 ENSSSCE00045086523

<400> SEQUENCE: 99
atgtctggga tggtggctct gcggctcccc agaggccttt ggacagcggc cttgacggtg    60
atgctggtgg tgctgggtgc tccagtggct gagggcagag actctccac              109

<210> SEQ ID NO 100
<211> LENGTH: 50
<212> TYPE: DNA
<213> ORGANISM: Artificial Sequence
<220> FEATURE:
<223> OTHER INFORMATION: SLA-DQB1-203 introns 1-2

<400> SEQUENCE: 100
gtaagtgcag ccaccattca ggggactgac tgacgcggat ctccccgcag            50

<210> SEQ ID NO 101
<211> LENGTH: 270
<212> TYPE: DNA
<213> ORGANISM: Artificial Sequence
<220> FEATURE:
<223> OTHER INFORMATION: SLA-DQB1-203 ENSSSCE00045085054

<400> SEQUENCE: 101
aggatttcgt gtaccagttt aagttcgagt gctacttctt caacggaacg cagcgggtgc    60
ggctcttgac cagatacatc tacaaccagg aggagcacgt gcgcttcgac agcaacgtgg   120
gggagtaccg ggcggtgacc ccgctggggc ggccggacgc cgactactgg aacggccaga   180
aggacgtcct ggagcagacg cgggccgagc tggacactgt gtgcaaacac aactaccaga   240
tagaggaagg cacgaccctg cagcggcgag                                   270

<210> SEQ ID NO 102
<211> LENGTH: 50
<212> TYPE: DNA
<213> ORGANISM: Artificial Sequence
<220> FEATURE:
<223> OTHER INFORMATION: SLA-DQB1-203 introns 2-3

<400> SEQUENCE: 102
gtgagtgcct gcccgccgcc cgcggttttc ccgtctgtta ctcccctcag            50
```

```
<210> SEQ ID NO 103
<211> LENGTH: 282
<212> TYPE: DNA
<213> ORGANISM: Artificial Sequence
<220> FEATURE:
<223> OTHER INFORMATION: SLA-DQB1-203 ENSSSCE00045085973

<400> SEQUENCE: 103
tgcaacctac agtgactatc tccccatcca aggcagaggc tctaaaccac cacaacctgc      60
tggtctgtgc ggtgacagat ttctatccaa gccaggtgaa agtccagtgg ttccggaatg     120
gccaggagga gacagctggc gttgtgtcca ctcctcttat taggaatgga gactggacct     180
accaggtgct cgtgatgcta gagatgaatc tccagcgagg agatgtctac acctgccgcg     240
tggagcactc cagcctccag agccccatct tggtggagtg gc                        282

<210> SEQ ID NO 104
<211> LENGTH: 50
<212> TYPE: DNA
<213> ORGANISM: Artificial Sequence
<220> FEATURE:
<223> OTHER INFORMATION: SLA-DQB1-203 introns 3-4

<400> SEQUENCE: 104
gtaaggggca gttggttttc tttccctgac atttgggctc tgctccccag                 50

<210> SEQ ID NO 105
<211> LENGTH: 118
<212> TYPE: DNA
<213> ORGANISM: Artificial Sequence
<220> FEATURE:
<223> OTHER INFORMATION: SLA-DQB1-203 ENSSSCE00045086652

<400> SEQUENCE: 105
gggcacagtc tgaatctgcc cagagcaaga tgctgagcgg tgtcggggc ttcgtgctgg       60 ggctgatctt cctcgggctg ggccttttca tccgtcacag gagtcagaag ggtaagga      118

<210> SEQ ID NO 106
<211> LENGTH: 50
<212> TYPE: DNA
<213> ORGANISM: Artificial Sequence
<220> FEATURE:
<223> OTHER INFORMATION: SLA-DQB1-203 introns 4-5

<400> SEQUENCE: 106
gctctgggga aatggggaga cgggcggaag gagactggga tggtggtgag                 50

<210> SEQ ID NO 107
<211> LENGTH: 19
<212> TYPE: DNA
<213> ORGANISM: Artificial Sequence
<220> FEATURE:
<223> OTHER INFORMATION: SLA_DQB1-203 ENSSSCE00045086845

<400> SEQUENCE: 107
aagaaacaaa ataatctag                                                   19

<210> SEQ ID NO 108
<211> LENGTH: 50
<212> TYPE: DNA
<213> ORGANISM: Artificial Sequence
<220> FEATURE:
<223> OTHER INFORMATION: SLA-DQB1-203 3' downstream sequence

<400> SEQUENCE: 108
```

```
ggagacaatg gagtctgatt tcactgattg aaaggtagcc ccactgcaga        50
```

<210> SEQ ID NO 109
<211> LENGTH: 50
<212> TYPE: DNA
<213> ORGANISM: Artificial Sequence
<220> FEATURE:
<223> OTHER INFORMATION: SLA-DQB1-204 5' upstream sequence

<400> SEQUENCE: 109

```
ctgagtggga gctgtgttga ctaccattac ttcttcgttt gccctcaatt        50
```

<210> SEQ ID NO 110
<211> LENGTH: 109
<212> TYPE: DNA
<213> ORGANISM: Artificial Sequence
<220> FEATURE:
<223> OTHER INFORMATION: SLA-DQB1-204 ENSSSCE00045086523

<400> SEQUENCE: 110

```
atgtctggga tggtggctct gcggctcccc agaggccttt ggacagcggc cttgacggtg        60
atgctggtgg tgctgggtgc tccagtggct gagggcagag actctccac               109
```

<210> SEQ ID NO 111
<211> LENGTH: 50
<212> TYPE: DNA
<213> ORGANISM: Artificial Sequence
<220> FEATURE:
<223> OTHER INFORMATION: SLA-DQB1-204 introns 1-2

<400> SEQUENCE: 111

```
gtaagtgcag ccaccattca ggggactgac tgacgcggat ctccccgcag        50
```

<210> SEQ ID NO 112
<211> LENGTH: 270
<212> TYPE: DNA
<213> ORGANISM: Artificial Sequence
<220> FEATURE:
<223> OTHER INFORMATION: SLA-DQB1-204 ENSSSCE00045085054

<400> SEQUENCE: 112

```
aggatttcgt gtaccagttt aagttcgagt gctacttctt caacggaacg cagcgggtgc        60
ggctcttgac cagatacatc tacaaccagg aggagcacgt gcgcttcgac agcaacgtgg       120
gggagtaccg ggcggtgacc ccgctggggc ggccggacgc cgactactgg aacgccaga       180 aggacgtcct ggagcagacg cggggccgagc tggacactgt gtgcaaacac aactaccaga       240
tagaggaagg cacgaccctg cagcggcgag                                     270
```

<210> SEQ ID NO 113
<211> LENGTH: 50
<212> TYPE: DNA
<213> ORGANISM: Artificial Sequence
<220> FEATURE:
<223> OTHER INFORMATION: SLA-DQB1-204 introns 2-3

<400> SEQUENCE: 113

```
gtgagtgcct gcccgccgcc cgcggttttc ccgtctgtta ctcccctcag        50
```

<210> SEQ ID NO 114
<211> LENGTH: 282
<212> TYPE: DNA
<213> ORGANISM: Artificial Sequence
<220> FEATURE:
<223> OTHER INFORMATION: SLA-DQB1-204 ENSSSCE00045085973

<400> SEQUENCE: 114

```
tgcaacctac agtgactatc tccccatcca aggcagaggc tctaaaccac cacaacctgc      60
tggtctgtgc ggtgacagat ttctatccaa gccaggtgaa agtccagtgg ttccggaatg     120
gccaggagga gacagctggc gttgtgtcca ctcctcttat taggaatgga gactggacct    180
accaggtgct cgtgatgcta gagatgaatc tccagcgagg agatgtctac acctgccgcg    240
tggagcactc cagcctccag agccccatct tggtggagtg gc                        282
```

<210> SEQ ID NO 115
<211> LENGTH: 50
<212> TYPE: DNA
<213> ORGANISM: Artificial Sequence
<220> FEATURE:
<223> OTHER INFORMATION: SLA-DQB1-204 introns 3-4

<400> SEQUENCE: 115

```
gtaagggca gttggttttc tttccctgac atttgggctc tgctccccag                  50
```

<210> SEQ ID NO 116
<211> LENGTH: 118
<212> TYPE: DNA
<213> ORGANISM: Artificial Sequence
<220> FEATURE:
<223> OTHER INFORMATION: SLA_DQB1-204 ENSSSCE00045086652

<400> SEQUENCE: 116

```
gggcacagtc tgaatctgcc cagagcaaga tgctgagcgg tgtcggggc ttcgtgctgg      60 ggctgatctt cctcgggctg ggccttttca tccgtcacag gagtcagaag ggtaagga     118
```

<210> SEQ ID NO 117
<211> LENGTH: 50
<212> TYPE: DNA
<213> ORGANISM: Artificial Sequence
<220> FEATURE:
<223> OTHER INFORMATION: SLA-DQB1-204 introns 4-5

<400> SEQUENCE: 117

```
gctctgggga aatggggaga cgggcggaga agtttgctca gtttctatag                 50
```

<210> SEQ ID NO 118
<211> LENGTH: 37
<212> TYPE: DNA
<213> ORGANISM: Artificial Sequence
<220> FEATURE:
<223> OTHER INFORMATION: SLA-DQB1-204 ENSSSCE00045086763

<400> SEQUENCE: 118

```
gaagctcctg aggttgttcc ccagaaccag gccataa                               37
```

<210> SEQ ID NO 119
<211> LENGTH: 50
<212> TYPE: DNA
<213> ORGANISM: Artificial Sequence
<220> FEATURE:
<223> OTHER INFORMATION: SLA_DQB1-204 3' downstream sequence

<400> SEQUENCE: 119

```
ctttggtggc acctttctct gaagctggga ggaaagggtg aggtcagtgt                 50
```

<210> SEQ ID NO 120
<211> LENGTH: 50
<212> TYPE: DNA

<213> ORGANISM: Artificial Sequence
<220> FEATURE:
<223> OTHER INFORMATION: SLA-DQB1-205 5' upstream sequence

<400> SEQUENCE: 120

| cggggccggg cacggccggg cacccggctt gggcggcggg tttcaggtgg | 50 |
|---|---|

<210> SEQ ID NO 121
<211> LENGTH: 370
<212> TYPE: DNA
<213> ORGANISM: Artificial Sequence
<220> FEATURE:
<223> OTHER INFORMATION: SLA-DQB1-205 ENSSSCE00045086917

<400> SEQUENCE: 121

| atgggcccag ctggcggcgg cggacgtctc cccgcctggc cgagcggtgg cggcgtcggg | 60 |
|---|---|
| ctggcgggcg gaggcctgac tgacgcggat ctccccgcag aggatttcgt gtaccagttt | 120 |
| aagttcgagt gctacttctt caacggaacg cagcgggtgc ggctcttgac cagatacatc | 180 |
| tacaaccagg aggagcacgt gcgcttcgac agcaacgtgg gggagtaccg ggcggtgacc | 240 |
| ccgctggggc ggccggacgc cgactactgg aacggccaga aggacgtcct ggagcagacg | 300 |
| cgggccgagc tggacactgt gtgcaaacac aactaccaga tagaggaagg cacgaccctg | 360 |
| cagcggcgag | 370 |

<210> SEQ ID NO 122
<211> LENGTH: 50
<212> TYPE: DNA
<213> ORGANISM: Artificial Sequence
<220> FEATURE:
<223> OTHER INFORMATION: SLA-DQB1-205 introns 1-2

<400> SEQUENCE: 122

| gtgagtgcct gcccgccgcc cgcggttttc ccgtctgtta ctcccctcag | 50 |
|---|---|

<210> SEQ ID NO 123
<211> LENGTH: 1441
<212> TYPE: DNA
<213> ORGANISM: Artificial Sequence
<220> FEATURE:
<223> OTHER INFORMATION: SLA_DQB1-205 ENSSSCE00045087028

<400> SEQUENCE: 123

| tgcaacctac agtgactatc tccccatcca aggcagaggc tctaaaccac cacaacctgc | 60 |
|---|---|
| tggtctgtgc ggtgacagat ttctatccaa gccaggtgaa agtccagtgg ttccggaatg | 120 |
| gccaggagga gacagctggc gttgtgtcca ctcctcttat taggaatgga gactggacct | 180 |
| accaggtgct cgtgatgcta gagatgaatc tccagcgagg agatgtctac acctgccgcg | 240 |
| tggagcactc cagcctccag agcccatct tggtggagtg gcgtaagggg cagttggttt | 300 |
| tctttccctg tgggccctgc agaacagagg gcaggcagag cttcccgggt ccatcccatc | 360 |
| tcattctttg tccccgacat cactactgag ctggacatca ctgggcacat gagtgctctt | 420 |
| gcctcatagc aagggcatca ggagaatctt tatctccttg tctttccaga tacagagcga | 480 |
| tcactacata ccatgacccc agagcccagc cctaggagct ctgcaggatt gactagtgcc | 540 |
| tggggcctta aggtctcaga ttatgaaagg agcagggatc catttttcctt ctcactcacc | 600 |
| ctcccactct gtccagggag ctattggctg gtccctcacc taggggtggt cagaatggac | 660 |
| aacgggttc ccctggcacc tctacccct gtacctcaga ctagacttca ggcctcataa | 720 |
| aggagcacca tggggtgtgg tgacaaactc tgacatttgg gctctgctcc ccagggggcac | 780 |

```
agtctgaatc tgcccagagc aagatgctga gcggtgtcgg gggcttcgtg ctggggctga      840
tcttcctcgg gctgggcctt ttcatccgtc acaggagtca gaagggtaag gagctctggg      900
gaaatgggga gacgggctgt ggttgggacc gtctgcaggg aggccttgtc tctagatgag      960
ctctttcctc ctgaccgtga aaggaaggag actgggatgg tggtgagaag aaacaaaata     1020
atctagggag acaatggagt ctgatttcac tgattgaaag gtagcccac tgcagaggtg      1080 acaggtggaa tttattctag ggcttttttc tagtgacaac tctattcatt tgggaggatt     1140
ttattttaga tcacttaagg ccttgtgggt agggagggaa tatatttcca gttaagttgc     1200
ttatctcatt tcctttggg gtgagtgaga cactgtgcca tgagacattt tgtgggacct      1260
cctgggcagg taatgtttct gctctgattc caggggtt gtgggacag ggaaggagg         1320 gaggaagggg tgaggtcagt gtacctgggc gcagtggtct cattcacagc ctatttactt     1380
ctgtgggatc cagagttagg ggagaagttt gctcagtttc tataggaagc tcctgaggtt     1440
g                                                                     1441

<210> SEQ ID NO 124
<211> LENGTH: 50
<212> TYPE: DNA
<213> ORGANISM: Artificial Sequence
<220> FEATURE:
<223> OTHER INFORMATION: SLA-DQB1-205 3' downstream sequence

<400> SEQUENCE: 124
ttccccagaa ccaggccata actttggtgg cacctttctc tgaagctggg                 50

<210> SEQ ID NO 125
<211> LENGTH: 82
<212> TYPE: DNA
<213> ORGANISM: Artificial Sequence
<220> FEATURE:
<223> OTHER INFORMATION: DRA sample 11 01:01:01 Ex 1

<400> SEQUENCE: 125
atggccataa gtggagtccc tgtgctagga ttttcatca tagctgtgct gatgagcgct      60
caggaatcat gggctatcaa ag                                               82

<210> SEQ ID NO 126
<211> LENGTH: 246
<212> TYPE: DNA
<213> ORGANISM: Artificial Sequence
<220> FEATURE:
<223> OTHER INFORMATION: Sample 11 01:01:01 Ex 2

<400> SEQUENCE: 126
aagaacatgt gatcatccag gccgagttct atctgaatcc tgaccaatca ggcgagttta     60
tgtttgactt tgatggtgat gagattttcc atgtggatat ggcaaagaag gagacggtct    120
ggcggcttga agaatttgga cgatttgcca gctttgaggc tcaaggtgca ttggccaaca    180
tagctgtgga caaagccaac ctggaaatca tgacaaagcg ctccaactat actccgatca    240
ccaatg                                                               246

<210> SEQ ID NO 127
<211> LENGTH: 282
<212> TYPE: DNA
<213> ORGANISM: Artificial Sequence
<220> FEATURE:
<223> OTHER INFORMATION: Sample 11 01:01:01 Ex 3
```

<400> SEQUENCE: 127

```
tacctccaga ggtaactgtg ctcacgaaca gccctgtgga actgagagag cccaacgtcc    60
tcatctgttt catcgacaag ttcaccccac cagtggtcaa tgtcacgtgg cttcgaaatg   120
gaaaacctgt caccacagga gtgtcagaga cagtcttcct gcccagggaa gaccaccttt   180
tccgcaagtt ccactatctc cccttcctgc cctcaactga ggacgtttac gactgcaggg   240
tggagcactg gggcttggat gagcctcttc tcaagcactg gg                      282
```

<210> SEQ ID NO 128
<211> LENGTH: 155
<212> TYPE: DNA
<213> ORGANISM: Artificial Sequence
<220> FEATURE:
<223> OTHER INFORMATION: Sample 11 01:01:01 Ex 4

<400> SEQUENCE: 128

```
agtttgatgc tccaagccct ctcccagaga ctacagagaa cgtggtgtgt gccctgggcc    60
tgactgtggg tctggtgggc atcattattg ggaccatctt catcatcaag ggagtgcgca   120
aaagcaatgc agcagaacgc aggggggcctc tgtaa                              155
```

<210> SEQ ID NO 129
<211> LENGTH: 82
<212> TYPE: DNA
<213> ORGANISM: Artificial Sequence
<220> FEATURE:
<223> OTHER INFORMATION: Sample 19 01:01:02 Ex 1

<400> SEQUENCE: 129

```
atggccataa gtggagtccc tgtgctagga tttttcatca tagctgtgct gatgagcgct    60
caggaatcat gggctatcaa ag                                             82
```

<210> SEQ ID NO 130
<211> LENGTH: 246
<212> TYPE: DNA
<213> ORGANISM: Artificial Sequence
<220> FEATURE:
<223> OTHER INFORMATION: Sample 19 01:01:02 Ex 2

<400> SEQUENCE: 130

```
aagaacatgt gatcatccag gccgagttct atctgaatcc tgaccaatca ggcgagttta    60
tgtttgactt tgatggtgat gagattttcc atgtggatat ggcaaagaag gagacggtct   120
ggcggcttga agaatttgga cgatttgcca gctttgaggc tcaaggtgca ttggccaaca   180
tagctgtgga caaagccaac ctggaaatca tgacaaagcg ctccaactat actccgatca   240
ccaatg                                                              246
```

<210> SEQ ID NO 131
<211> LENGTH: 282
<212> TYPE: DNA
<213> ORGANISM: Artificial Sequence
<220> FEATURE:
<223> OTHER INFORMATION: Sample 19 01:01:02 Ex 3

<400> SEQUENCE: 131

```
tacctccaga ggtaactgtg ctcacgaaca gccctgtgga actgagagag cccaacgtcc    60
tcatctgttt catagacaag ttcaccccac cagtggtcaa tgtcacgtgg cttcgaaatg   120
gaaaacctgt caccacagga gtgtcagaga cagtcttcct gcccagggaa gaccaccttt   180
tccgcaagtt ccactatctc cccttcctgc cctcaactga ggacgtttac gactgcaggg   240
```

```
tggagcactg gggcttggat gagcctcttc tcaagcactg gg                    282
```

<210> SEQ ID NO 132
<211> LENGTH: 155
<212> TYPE: DNA
<213> ORGANISM: Artificial Sequence
<220> FEATURE:
<223> OTHER INFORMATION: Sample 19 01:01:02 Ex 4

<400> SEQUENCE: 132

```
agtttgatgc tccaagccct ctcccagaga ctacagagaa tgtggtgtgt gccctgggcc    60
tgactgtggg tctggtgggc atcattattg ggaccatctt catcatcaag ggagtgcgca   120
aaagcaatgc agcagaacgc aggggggcctc tgtaa                              155
```

<210> SEQ ID NO 133
<211> LENGTH: 246
<212> TYPE: DNA
<213> ORGANISM: Artificial Sequence
<220> FEATURE:
<223> OTHER INFORMATION: DQA1 Sample 11 05:05:01 Exon 2

<400> SEQUENCE: 133

```
ctgaccacgt cgcctcttat ggtgtaaact tgtaccagtc ttacggtccc tctggccagt    60
acacccatga atttgatgga gatgagcagt tctacgtgga cctggggagg aaggagactg   120
tctggtgttt gcctgttctc agacaattta gatttgaccc gcaatttgca ctgacaaaca   180
tcgctgtcct aaaacataac ttgaacagtc tgattaaacg ctccaactct accgctgcta   240
ccaatg                                                              246
```

<210> SEQ ID NO 134
<211> LENGTH: 249
<212> TYPE: DNA
<213> ORGANISM: Artificial Sequence
<220> FEATURE:
<223> OTHER INFORMATION: DQA1 Sample 19 01:01:01 Exon 2

<400> SEQUENCE: 134

```
ctgaccacgt tgcctcttgt ggtgtaaact tgtaccagtt ttacggtccc tctggccagt    60
acacccatga atttgatgga gatgaggagt tctacgtgga cctggagagg aaggagactg   120
cctggcggtg gcctgagttc agcaaatttg gaggttttga cccgcagggt gcactgagaa   180
acatggctgt ggcaaaacac aacttgaaca tcatgattaa acgctacaac tctaccgctg   240
ctaccaatg                                                           249
```

<210> SEQ ID NO 135
<211> LENGTH: 246
<212> TYPE: DNA
<213> ORGANISM: Artificial Sequence
<220> FEATURE:
<223> OTHER INFORMATION: DQA1 05:01:01 Exon 2

<400> SEQUENCE: 135

```
ctgaccacgt cgcctcttat ggtgtaaact tgtaccagtc ttacggtccc tctggccagt    60
acacccatga atttgatgga gatgagcagt tctacgtgga cctggggagg aaggagactg   120
tctggtgttt gcctgttctc agacaattta gatttgaccc gcaatttgca ctgacaaaca   180
tcgctgtcct aaaacataac ttgaacagtc tgattaaacg ctccaactct accgctgcta   240
ccaatg                                                              246
```

<210> SEQ ID NO 136
<211> LENGTH: 249
<212> TYPE: DNA
<213> ORGANISM: Artificial Sequence
<220> FEATURE:
<223> OTHER INFORMATION: Sample 57 01:01:01 Exon 2

<400> SEQUENCE: 136

```
ctgaccacgt tgcctcttgt ggtgtaaact tgtaccagtt ttacggtccc tctggccagt      60
acacccatga atttgatgga gatgaggagt tctacgtgga cctggagagg aaggagactg     120
cctggcggtg gcctgagttc agcaaatttg gaggttttga cccgcagggt gcactgagaa     180
acatggctgt ggcaaaacac aacttgaaca tcatgattaa acgctacaac tctaccgctg     240
ctaccaatg                                                             249
```

<210> SEQ ID NO 137
<211> LENGTH: 249
<212> TYPE: DNA
<213> ORGANISM: Artificial Sequence
<220> FEATURE:
<223> OTHER INFORMATION: DQA1 03:03:01 Exon 2

<400> SEQUENCE: 137

```
ctgaccatgt tgcctcttac ggtgtaaact tgtaccagtc ttatggtccc tctgggcagt      60
acagccatga atttgatgga gacgaggagt tctatgtgga cctggagagg aaggagactg     120
tctggcagtt gcctctgttc cgcagattta gaagatttga cccgcaattt gcactgacaa     180
acatcgctgt gctaaaacat aacttgaaca tcgtgattaa acgctccaac tctaccgctg     240
ctaccaatg                                                             249
```

<210> SEQ ID NO 138
<211> LENGTH: 246
<212> TYPE: DNA
<213> ORGANISM: Artificial Sequence
<220> FEATURE:
<223> OTHER INFORMATION: DQA1 Sample 29 05:01:01 Exon 2

<400> SEQUENCE: 138

```
ctgaccacgt cgcctcttat ggtgtaaact tgtaccagtc ttacggtccc tctggccagt      60
acacccatga atttgatgga gatgagcagt tctacgtgga cctggggagg aaggagactg     120
tctggtgttt gcctgttctc agacaattta gatttgaccc gcaatttgca ctgacaaaca     180
tcgctgtcct aaaacataac ttgaacagtc tgattaaacg ctccaactct accgctgcta     240
ccaatg                                                                246
```

<210> SEQ ID NO 139
<211> LENGTH: 249
<212> TYPE: DNA
<213> ORGANISM: Artificial Sequence
<220> FEATURE:
<223> OTHER INFORMATION: DQA1 Sample 50 01:02:01 Exon 2

<400> SEQUENCE: 139

```
ctgaccacgt tgcctcttgt ggtgtaaact tgtaccagtt ttacggtccc tctggccagt      60
acacccatga atttgatgga gatgagcagt tctacgtgga cctggagagg aaggagactg     120
cctggcggtg gcctgagttc agcaaatttg gaggttttga cccgcagggt gcactgagaa     180
acatggctgt ggcaaaacac aacttgaaca tcatgattaa acgctacaac tctaccgctg     240
ctaccaatg                                                             249
```

<210> SEQ ID NO 140
<211> LENGTH: 249
<212> TYPE: DNA
<213> ORGANISM: Artificial Sequence
<220> FEATURE:
<223> OTHER INFORMATION: DQA SLA-201 ENSSSCE00045087536

<400> SEQUENCE: 140

```
ccgaccatgt tgcctcctat ggcttaaatg tctaccagtc ttacggtccc agcggctatt      60
atacccatga atttgatggc gacgaggaat tctacgtgga cctggagaag aaggagactg     120
tctggcggct gcctctgttt agtgaattta caagttttga cccgcagggt gcactgagga     180
atatagctac gttaaaacat aacttgaaca tcgtgactaa acgctccaac aacaccgcgg     240
ctgtcaatc                                                             249
```

<210> SEQ ID NO 141
<211> LENGTH: 249
<212> TYPE: DNA
<213> ORGANISM: Artificial Sequence
<220> FEATURE:
<223> OTHER INFORMATION: DQA SLA-202 ENSSSCE00045087536 Exon 2

<400> SEQUENCE: 141

```
ccgaccatgt tgcctcctat ggcttaaatg tctaccagtc ttacggtccc agcggctatt      60
atacccatga atttgatggc gacgaggaat tctacgtgga cctggagaag aaggagactg     120
tctggcggct gcctctgttt agtgaattta caagttttga cccgcagggt gcactgagga     180
atatagctac gttaaaacat aacttgaaca tcgtgactaa acgctccaac aacaccgcgg     240
ctgtcaatc                                                             249
```

<210> SEQ ID NO 142
<211> LENGTH: 249
<212> TYPE: DNA
<213> ORGANISM: Artificial Sequence
<220> FEATURE:
<223> OTHER INFORMATION: DQA SLA-203 ENSSSCE00045087536 Exon 2

<400> SEQUENCE: 142

```
ccgaccatgt tgcctcctat ggcttaaatg tctaccagtc ttacggtccc agcggctatt      60
atacccatga atttgatggc gacgaggaat tctacgtgga cctggagaag aaggagactg     120
tctggcggct gcctctgttt agtgaattta caagttttga cccgcagggt gcactgagga     180
atatagctac gttaaaacat aacttgaaca tcgtgactaa acgctccaac aacaccgcgg     240
ctgtcaatc                                                             249
```

<210> SEQ ID NO 143
<211> LENGTH: 249
<212> TYPE: DNA
<213> ORGANISM: Artificial Sequence
<220> FEATURE:
<223> OTHER INFORMATION: DQA SLA-204 ENSSSCE00045087536 Exon 2

<400> SEQUENCE: 143

```
ccgaccatgt tgcctcctat ggcttaaatg tctaccagtc ttacggtccc agcggctatt      60
atacccatga atttgatggc gacgaggaat tctacgtgga cctggagaag aaggagactg     120
tctggcggct gcctctgttt agtgaattta caagttttga cccgcagggt gcactgagga     180
atatagctac gttaaaacat aacttgaaca tcgtgactaa acgctccaac aacaccgcgg     240
```

-continued ctgtcaatc 249

<210> SEQ ID NO 144
<211> LENGTH: 82
<212> TYPE: DNA
<213> ORGANISM: Artificial Sequence
<220> FEATURE:
<223> OTHER INFORMATION: HLA-DQA1-PT.11 05:05:01 Exon 1

<400> SEQUENCE: 144
atgatcctaa acaaagctct gatgctgggg acccttgccc tgaccaccgt gatgagcccc    60
tgtggaggtg aagacattgt gg    82

<210> SEQ ID NO 145
<211> LENGTH: 246
<212> TYPE: DNA
<213> ORGANISM: Artificial Sequence
<220> FEATURE:
<223> OTHER INFORMATION: HLA-DQA1-PT.11 05:05:01 Exon 2

<400> SEQUENCE: 145
ctgaccacgt cgcctcttat ggtgtaaact tgtaccagtc ttacggtccc tctggccagt    60
acacccatga atttgatgga gatgagcagt tctacgtgga cctggggagg aaggagactg   120
tctggtgttt gcctgttctc agacaattta gatttgaccc gcaatttgca ctgacaaaca   180
tcgctgtcct aaaacataac ttgaacagtc tgattaaacg ctccaactct accgctgcta   240
ccaatg   246

<210> SEQ ID NO 146
<211> LENGTH: 282
<212> TYPE: DNA
<213> ORGANISM: Artificial Sequence
<220> FEATURE:
<223> OTHER INFORMATION: HLA-DQA1-PT.11 05:05:01 Exon 3

<400> SEQUENCE: 146
aggttcctga ggtcacagtg ttttccaagt ctcccgtgac actgggtcag cccaacatcc    60
tcatctgtct tgtggacaac atctttcctc ctgtggtcaa catcacatgg ctgagcaatg   120
ggcactcagt cacagaaggt gtttctgaga ccagcttcct ctccaagagt gatcattcct   180
tcttcaagat cagttacctc accctcctcc cttctgctga ggagagttat gactgcaagg   240
tggagcactg gggactggac aagcctcttc tgaaacactg gg    282

<210> SEQ ID NO 147
<211> LENGTH: 155
<212> TYPE: DNA
<213> ORGANISM: Artificial Sequence
<220> FEATURE:
<223> OTHER INFORMATION: HLA-DQA1-PT.11 05:05:01 Exon 4

<400> SEQUENCE: 147
agcctgagat tccagcccct atgtcagagc tcacagagac tgtggtctgc gccctggggt    60
tgtctgtggg cctcgtgggc attgtggtgg gcactgtctt catcatccga ggcctgcgtt   120
cagttggtgc ttccagacac caagggccct tgtga    155

<210> SEQ ID NO 148
<211> LENGTH: 82
<212> TYPE: DNA
<213> ORGANISM: Artificial Sequence
<220> FEATURE:
<223> OTHER INFORMATION: HLA-DQA1-PT. 50 01:02:01 Exon 1

<400> SEQUENCE: 148

```
atgatcctaa acaaagctct gctgctgggg gccctcgctc tgaccaccgt gatgagcccc    60
tgtggaggtg aagacattgt gg                                              82
```

<210> SEQ ID NO 149
<211> LENGTH: 249
<212> TYPE: DNA
<213> ORGANISM: Artificial Sequence
<220> FEATURE:
<223> OTHER INFORMATION: HLA-DQA1-PT. 50 01:02:01 Exon 2

<400> SEQUENCE: 149

```
ctgaccacgt tgcctcttgt ggtgtaaact tgtaccagtt ttacggtccc tctggccagt    60
acacccatga atttgatgga gatgagcagt tctacgtgga cctggagagg aaggagactg   120
cctggcggtg gcctgagttc agcaaatttg gaggttttga cccgcagggt gcactgagaa   180
acatggctgt ggcaaaacac aacttgaaca tcatgattaa acgctacaac tctaccgctg   240
ctaccaatg                                                           249
```

<210> SEQ ID NO 150
<211> LENGTH: 282
<212> TYPE: DNA
<213> ORGANISM: Artificial Sequence
<220> FEATURE:
<223> OTHER INFORMATION: HLA-DQA1-PT. 50 01:02:01 Exon 3

<400> SEQUENCE: 150

```
aggttcctga ggtcacagtg ttttccaagt ctcccgtgac actgggtcag cccaacaccc    60
tcatttgtct tgtggacaac atctttcctc ctgtggtcaa catcacatgg ctgagcaatg   120
ggcagtcagt cacagaaggt gtttctgaga ccagcttcct ctccaagagt gatcattcct   180
tcttcaagat cagttacctc accttcctcc cttctgctga tgagatttat gactgcaagg   240
tggagcactg gggcctggac cagcctcttc tgaaacactg gg                      282
```

<210> SEQ ID NO 151
<211> LENGTH: 155
<212> TYPE: DNA
<213> ORGANISM: Artificial Sequence
<220> FEATURE:
<223> OTHER INFORMATION: HLA-DQA1-PT. 50  01:02:01 Exon 4

<400> SEQUENCE: 151

```
agcctgagat tccagcccct atgtcagagc tcacagagac tgtggtctgt gccctggggt    60
tgtctgtggg cctcatgggc attgtggtgg gcactgtctt catcatccaa ggcctgcgtt   120
cagttggtgc ttccagacac caagggccat tgtga                              155
```

<210> SEQ ID NO 152
<211> LENGTH: 82
<212> TYPE: DNA
<213> ORGANISM: Artificial Sequence
<220> FEATURE:
<223> OTHER INFORMATION: HLA-DQA1-PT. 57 03:03:01 Exon 1

<400> SEQUENCE: 152

```
atgatcctaa acaaagctct gatgctgggg gccctcgccc tgaccaccgt gatgagccct    60
tgtggaggtg aagacattgt gg                                              82
```

<210> SEQ ID NO 153

<211> LENGTH: 249
<212> TYPE: DNA
<213> ORGANISM: Artificial Sequence
<220> FEATURE:
<223> OTHER INFORMATION: HLA-DQA1-PT. 57 03:03:01 Exon 2

<400> SEQUENCE: 153

```
ctgaccatgt tgcctcttac ggtgtaaact tgtaccagtc ttatggtccc tctgggcagt    60
acagccatga atttgatgga gacgaggagt tctatgtgga cctggagagg aaggagactg   120
tctggcagtt gcctctgttc cgcagattta aagatttga cccgcaattt gcactgacaa    180
acatcgctgt gctaaaacat aacttgaaca tcgtgattaa acgctccaac tctaccgctg   240
ctaccaatg                                                           249
```

<210> SEQ ID NO 154
<211> LENGTH: 282
<212> TYPE: DNA
<213> ORGANISM: Artificial Sequence
<220> FEATURE:
<223> OTHER INFORMATION: HLA-DQA1-PT. 57 03:03:01 Exon 3

<400> SEQUENCE: 154

```
aggttcctga ggtcacagtg ttttccaagt ctcccgtgac actgggtcag cccaacaccc    60
tcatctgtct tgtggacaac atctttcctc ctgtggtcaa catcacctgg ctgagcaatg   120
ggcactcagt cacagaaggt gtttctgaga ccagcttcct ctccaagagt gatcattcct   180
tcttcaagat cagttacctc accttcctcc cttctgatga tgagattat gactgcaagg    240 tggagcactg gggcctggat gagcctcttc tgaaacactg gg                      282
```

<210> SEQ ID NO 155
<211> LENGTH: 155
<212> TYPE: DNA
<213> ORGANISM: Artificial Sequence
<220> FEATURE:
<223> OTHER INFORMATION: HLA-DQA1-PT. 57 03:03:01 Exon 4

<400> SEQUENCE: 155

```
agcctgagat ccaacacct atgtcagagc tcacagagac tgtggtctgc gccctggggt     60
tgtctgtggg cctcgtgggc attgtggtgg ggaccgtctt gatcatccga ggcctgcgtt   120
cagttggtgc ttccagacac caagggccct tgtga                              155
```

<210> SEQ ID NO 156
<211> LENGTH: 109
<212> TYPE: DNA
<213> ORGANISM: Artificial Sequence
<220> FEATURE:
<223> OTHER INFORMATION: HLA-DQB1-PT. 11 03:01:01 Exon 1

<400> SEQUENCE: 156

```
atgtcttgga aaaggctttt gcggatcccc ggaggccttc gggcagcaac tgttaccttg     60
atgctggcga tgctgagcac cccagtggct gagggcagag actctcccg               109
```

<210> SEQ ID NO 157
<211> LENGTH: 270
<212> TYPE: DNA
<213> ORGANISM: Artificial Sequence
<220> FEATURE:
<223> OTHER INFORMATION: HLA-DQB1-PT. 11 03:01:01 Exon 2

<400> SEQUENCE: 157

```
aggatttcgt gtaccagttt aaggccatgt gctacttcac caacgggacg gagcgcgtgc    60
```

```
gttatgtgac cagatacatc tataaccgag aggagtacgc acgcttcgac agcgacgtgg    120
aggtgtaccg ggcggtgacg ccgctggggc cgcctgacgc cgagtactgg aacagccaga    180
aggaagtcct ggagaggacc cgggcggagt tggacacggt gtgcagacac aactaccagt    240
tggagctccg cacgaccttg cagcggcgag                                     270

<210> SEQ ID NO 158
<211> LENGTH: 282
<212> TYPE: DNA
<213> ORGANISM: Artificial Sequence
<220> FEATURE:
<223> OTHER INFORMATION: HLA-DQB1-PT. 11 03:03:01 Exon 3

<400> SEQUENCE: 158
tggagcccac agtgaccatc tccccatcca ggacagaggc cctcaaccac cacaacctgc    60
tggtctgctc agtgacagat ttctatccag cccagatcaa agtccggtgg tttcggaatg    120
accaggagga gacaaccggc gttgtgtcca ccccccttat taggaacggt gactggacct    180
tccagatcct ggtgatgctg gaaatgactc cccagcatgg agacgtctac acctgccacg    240
tggagcaccc cagcctccag aaccccatca ccgtggagtg gc                       282

<210> SEQ ID NO 159
<211> LENGTH: 111
<212> TYPE: DNA
<213> ORGANISM: Artificial Sequence
<220> FEATURE:
<223> OTHER INFORMATION: HLA-DQB1-PT. 11 03:01:01 Exon 4

<400> SEQUENCE: 159
gggctcagtc tgaatctgcc cagagcaaga tgctgagtgg cattggaggc ttcgtgctgg    60
ggctcatctt cctcgggctg ggccttatta tccatcacag gagtcagaaa g            111

<210> SEQ ID NO 160
<211> LENGTH: 109
<212> TYPE: DNA
<213> ORGANISM: Artificial Sequence
<220> FEATURE:
<223> OTHER INFORMATION: HLA-DQB1-PT. 50 06:02:01 Exon 1

<400> SEQUENCE: 160
atgtcttgga agaaggcttt gcggatcccc ggagaccttc gggtagcaac tgtcaccttg    60
atgctggcga tgctgagctc cctactggct gagggcagag actctcccg               109

<210> SEQ ID NO 161
<211> LENGTH: 270
<212> TYPE: DNA
<213> ORGANISM: Artificial Sequence
<220> FEATURE:
<223> OTHER INFORMATION: HLA-DQB1-PT. 50 06:02:01 Exon 2

<400> SEQUENCE: 161
aggatttcgt gttccagttt aagggcatgt gctacttcac caacgggacg gagcgcgtgc    60
gtcttgtgac cagatacatc tataaccgag aggagtacgc gcgcttcgac agcgacgtgg    120
gggtgtaccg cgcggtgacg ccgcaggggc ggcctgatgc cgagtactgg aacagccaga    180
aggaagtcct ggaggggacc cgggcggagt tggacacggt gtgcagacac aactacgagg    240
tggcgttccg cgggatcttg cagaggagag                                     270

<210> SEQ ID NO 162
```

<211> LENGTH: 282
<212> TYPE: DNA
<213> ORGANISM: Artificial Sequence
<220> FEATURE:
<223> OTHER INFORMATION: HLA-DQB1-PT. 50 06:02:01 Exon 3

<400> SEQUENCE: 162

| tggagcccac agtgaccatc tcccatcca ggacagaggc cctcaaccac cacaacctgc | 60 |
| tggtctgctc ggtgacagat ttctatccag gccagatcaa agtccggtgg tttcggaatg | 120 |
| atcaggagga gacagccggc gttgtgtcca ccccccttat taggaatggt gactggactt | 180 |
| tccagatcct ggtgatgctg gaaatgactc cccagcgtgg agatgtctac acctgccacg | 240 |
| tggagcaccc cagcctccag agccccatca ccgtggagtg gc | 282 |

<210> SEQ ID NO 163
<211> LENGTH: 111
<212> TYPE: DNA
<213> ORGANISM: Artificial Sequence
<220> FEATURE:
<223> OTHER INFORMATION: HLA-DQB1-PT. 50 06:02:01 Exon 4

<400> SEQUENCE: 163

| gggctcagtc tgaatctgcc cagagcaaga tgctgagtgg cgttggaggc ttcgtgctgg | 60 |
| ggctgatctt ccttgggctg gccttatca tccgtcaaag gagtcagaaa g | 111 |

<210> SEQ ID NO 164
<211> LENGTH: 109
<212> TYPE: DNA
<213> ORGANISM: Artificial Sequence
<220> FEATURE:
<223> OTHER INFORMATION: HLA-DQB1-PT. 57 03:01:01 Exon 1

<400> SEQUENCE: 164

| atgtcttgga aaaaggctttt gcggatcccc ggaggccttc gggcagcaac tgttaccttg | 60 |
| atgctggcga tgctgagcac cccagtggct gagggcagag actctcccg | 109 |

<210> SEQ ID NO 165
<211> LENGTH: 270
<212> TYPE: DNA
<213> ORGANISM: Artificial Sequence
<220> FEATURE:
<223> OTHER INFORMATION: HLA-DQB1-PT. 57 03:01:01 Exon 2

<400> SEQUENCE: 165

| aggatttcgt gtaccagttt aaggccatgt gctacttcac caacgggacg gagcgcgtgc | 60 |
| gttatgtgac cagatacatc tataaccgag aggagtacgc acgcttcgac agcgacgtgg | 120 |
| aggtgtaccg ggcggtgacg ccgctggggc cgcctgacgc cgagtactgg aacagccaga | 180 |
| aggaagtcct ggagaggacc cgggcggagt tggacacggt gtgcagacac aactaccagt | 240 |
| tggagctccg cacgaccttg cagcggcgag | 270 |

<210> SEQ ID NO 166
<211> LENGTH: 164
<212> TYPE: DNA
<213> ORGANISM: Artificial Sequence
<220> FEATURE:
<223> OTHER INFORMATION: HLA-DQB1-PT. 57 03:01:01 Exon 3

<400> SEQUENCE: 166

| tgaccaggag gagacaaccg gcgttgtgtc cacccccctt attaggaacg gtgactggac | 60 |
| cttccagatc ctggtgatgc tggaaatgac tccccagcat ggagacgtct acacctgcca | 120 |

-continued cgtggagcac cccagcctcc agaacccat caccgtggag tggc    164

<210> SEQ ID NO 167
<211> LENGTH: 111
<212> TYPE: DNA
<213> ORGANISM: Artificial Sequence
<220> FEATURE:
<223> OTHER INFORMATION: HLA-DQB1-PT. 57 03:01:01 Exon 4

<400> SEQUENCE: 167
gggctcagtc tgaatctgcc cagagcaaga tgctgagtgg cattggaggc ttcgtgctgg    60
ggctcatctt cctcgggctg ggccttatta tccatcacag gagtcagaaa g    111

<210> SEQ ID NO 168
<211> LENGTH: 249
<212> TYPE: DNA
<213> ORGANISM: Artificial Sequence
<220> FEATURE:
<223> OTHER INFORMATION: HLAAlleles.Org 9.05% USA Exon 2
      DQA1*01:01:01:01

<400> SEQUENCE: 168
ctgaccacgt tgcctcttgt ggtgtaaact tgtaccagtt ttacggtccc tctggccagt    60
acacccatga atttgatgga gatgaggagt tctacgtgga cctggagagg aaggagactg    120
cctggcggtg gcctgagttc agcaaatttg gaggttttga cccgcagggt gcactgagaa    180
acatggctgt ggcaaaacac aacttgaaca tcatgattaa acgctacaac tctaccgctg    240
ctaccaatg    249

<210> SEQ ID NO 169
<211> LENGTH: 249
<212> TYPE: DNA
<213> ORGANISM: Artificial Sequence
<220> FEATURE:
<223> OTHER INFORMATION: HLAAlleles.Org 14.17% USA Exon 2
      DQA1*01:02:01:01

<400> SEQUENCE: 169
ctgaccacgt tgcctcttgt ggtgtaaact tgtaccagtt ttacggtccc tctggccagt    60
acacccatga atttgatgga gatgagcagt tctacgtgga cctggagagg aaggagactg    120
cctggcggtg gcctgagttc agcaaatttg gaggttttga cccgcagggt gcactgagaa    180
acatggctgt ggcaaaacac aacttgaaca tcatgattaa acgctacaac tctaccgctg    240
ctaccaatg    249

<210> SEQ ID NO 170
<211> LENGTH: 246
<212> TYPE: DNA
<213> ORGANISM: Artificial Sequence
<220> FEATURE:
<223> OTHER INFORMATION: HLAAlleles.Org 13.14% USA Exon 2
      DQA1*05:01:01:01

<400> SEQUENCE: 170
ctgaccacgt cgcctcttat ggtgtaaact tgtaccagtc ttacggtccc tctggccagt    60
acacccatga atttgatgga gatgagcagt tctacgtgga cctggggagg aaggagactg    120
tctggtgttt gcctgttctc agacaattta gatttgaccc gcaatttgca ctgacaaaca    180
tcgctgtcct aaaacataac ttgaacagtg tgattaaacg ctccaactct accgctgcta    240
ccaatg    246

<210> SEQ ID NO 171
<211> LENGTH: 246
<212> TYPE: DNA
<213> ORGANISM: Artificial Sequence
<220> FEATURE:
<223> OTHER INFORMATION: HLAAlleles.Org 11.08% USA Exon 2
    DQA1*02:01:01:01

<400> SEQUENCE: 171
ctgaccacgt tgcctcttac ggtgtaaact tgtaccagtc ttacggtccc tctggccagt      60
tcacccatga atttgatgga gacgaggagt tctatgtgga cctggagagg aaggagactg     120
tctggaagtt gcctctgttc acaaatttg gatttgaccc gcaatttgca ctgacaaaca     180
tcgctgtgct aaaacataac ttgaacatcc tgattaaacg ctccaactct accgctgcta     240
ccaatg                                                                246

<210> SEQ ID NO 172
<211> LENGTH: 82
<212> TYPE: DNA
<213> ORGANISM: Artificial Sequence
<220> FEATURE:
<223> OTHER INFORMATION: HLA-DRA-PT. 11 01:01:01 Exon 1

<400> SEQUENCE: 172
atggccataa gtggagtccc tgtgctagga tttttcatca tagctgtgct gatgagcgct      60
caggaatcat gggctatcaa ag                                              82

<210> SEQ ID NO 173
<211> LENGTH: 246
<212> TYPE: DNA
<213> ORGANISM: Artificial Sequence
<220> FEATURE:
<223> OTHER INFORMATION: HLA-DRA-PT. 11 01:01:01 Exon 2

<400> SEQUENCE: 173
aagaacatgt gatcatccag gccgagttct atctgaatcc tgaccaatca ggcgagttta      60
tgtttgactt tgatggtgat gagatttttc atgtggatat ggcaaagaag agacggtct     120 ggcggcttga agaatttgga cgatttgcca gctttgaggc tcaaggtgca ttggccaaca     180
tagctgtgga caaagccaac ctggaaatca tgacaaagcg ctccaactat actccgatca     240
ccaatg                                                                246

<210> SEQ ID NO 174
<211> LENGTH: 282
<212> TYPE: DNA
<213> ORGANISM: Artificial Sequence
<220> FEATURE:
<223> OTHER INFORMATION: HLA-DRA-PT. 11 01:01:01 Exon 3

<400> SEQUENCE: 174
tacctccaga ggtaactgtg ctcacgaaca gccctgtgga actgagagag cccaacgtcc      60
tcatctgttt catcgacaag ttcacccca cagtggtcaa tgtcacgtgg cttcgaaatg     120
gaaaacctgt caccacagga gtgtcagaga cagtcttcct gcccagggaa gaccacctt     180 tccgcaagtt ccactatctc cccttcctgc cctcaactga ggacgtttac gactgcaggg     240
tggagcactg gggcttggat gagcctcttc tcaagcactg gg                       282

<210> SEQ ID NO 175
<211> LENGTH: 155

-continued

```
<212> TYPE: DNA
<213> ORGANISM: Artificial Sequence
<220> FEATURE:
<223> OTHER INFORMATION: HLA-DRA-PT. 11 01:01:01 Exon 4

<400> SEQUENCE: 175
agtttgatgc tccaagccct ctcccagaga ctacagagaa cgtggtgtgt gccctgggcc    60
tgactgtggg tctggtgggc atcattattg gaccatctt catcatcaag ggagtgcgca    120
aaagcaatgc agcagaacgc aggggcctc tgtaa                              155

<210> SEQ ID NO 176
<211> LENGTH: 82
<212> TYPE: DNA
<213> ORGANISM: Artificial Sequence
<220> FEATURE:
<223> OTHER INFORMATION: HLA-DRA-PT. 50 01:02:03 Exon 1

<400> SEQUENCE: 176
atggccataa gtggagtccc tgtgctagga ttttttcatca tagctgtgct gatgagcgct    60
caggaatcat gggctatcaa ag                                            82

<210> SEQ ID NO 177
<211> LENGTH: 246
<212> TYPE: DNA
<213> ORGANISM: Artificial Sequence
<220> FEATURE:
<223> OTHER INFORMATION: HLA-DRA-PT. 50 01:02:03 Exon 2

<400> SEQUENCE: 177
aagaacatgt gatcatccag gccgagttct atctgaatcc tgaccaatca ggcgagttta    60
tgtttgactt tgatggtgat gagattttcc atgtggatat ggcaaagaag agacggtct    120 ggcggcttga agaatttgga cgatttgcca gctttgaggc tcaaggtgca ttggccaaca    180
tagctgtgga caaagccaac ctggaaatca tgacaaagcg ctccaactat actccgatca    240
ccaatg                                                              246

<210> SEQ ID NO 178
<211> LENGTH: 282
<212> TYPE: DNA
<213> ORGANISM: Artificial Sequence
<220> FEATURE:
<223> OTHER INFORMATION: HLA-DRA-PT. 50 01:02:03 Exon 3

<400> SEQUENCE: 178
tacctccaga ggtaactgtg ctcacaaaca gccctgtgga actgagagag cccaacgtcc    60
tcatctgttt catagacaag ttcacccccac cagtggtcaa tgtcacgtgg cttcgaaatg    120
gaaaacctgt caccacagga gtgtcagaga cagtcttcct gcccagggaa gaccacctt    180 tccgcaagtt ccactatctc cccttcctgc cctcaactga ggacgtttac gactgcaggg    240
tggagcactg gggcttggat gagcctcttc tcaagcactg gg                       282

<210> SEQ ID NO 179
<211> LENGTH: 155
<212> TYPE: DNA
<213> ORGANISM: Artificial Sequence
<220> FEATURE:
<223> OTHER INFORMATION: HLA-DRA-PT. 50 01:02:03 Exon 4

<400> SEQUENCE: 179
agtttgatgc tccaagccct ctcccagaga ctacagagaa cgtggtgtgt gccctgggcc    60
```
tgactgtggg tctggtgggc atcattattg ggaccatctt catcatcaag ggattgcgca    120
aaagcaatgc agcagaacgc aggggggcctc tgtaa    155

<210> SEQ ID NO 180
<211> LENGTH: 82
<212> TYPE: DNA
<213> ORGANISM: Artificial Sequence
<220> FEATURE:
<223> OTHER INFORMATION: HLA-DRA-PT. 57 01:01:01 Exon 1

<400> SEQUENCE: 180
atggccataa gtggagtccc tgtgctagga tttttcatca tagctgtgct gatgagcgct    60
caggaatcat gggctatcaa ag    82

<210> SEQ ID NO 181
<211> LENGTH: 246
<212> TYPE: DNA
<213> ORGANISM: Artificial Sequence
<220> FEATURE:
<223> OTHER INFORMATION: HLA-DRA-PT. 57 01:01:01 Exon 2

<400> SEQUENCE: 181
aagaacatgt gatcatccag gccgagttct atctgaatcc tgaccaatca ggcgagttta    60
tgtttgactt tgatggtgat gagattttcc atgtggatat ggcaaagaag gagacggtct    120
ggcggcttga agaatttgga cgatttgcca gctttgaggc tcaaggtgca ttggccaaca    180
tagctgtgga caaagccaac ctggaaatca tgacaaagcg ctccaactat actccgatca    240
ccaatg    246

<210> SEQ ID NO 182
<211> LENGTH: 282
<212> TYPE: DNA
<213> ORGANISM: Artificial Sequence
<220> FEATURE:
<223> OTHER INFORMATION: HLA-DRA-PT. 57 01:01:01 Exon 3

<400> SEQUENCE: 182
tacctccaga ggtaactgtg ctcacgaaca gccctgtgga actgagagag cccaacgtcc    60
tcatctgttt catcgacaag ttcaccccac cagtggtcaa tgtcacgtgg cttcgaaatg    120
gaaaacctgt caccacagga gtgtcagaga cagtcttcct gcccagggaa gaccacctt    180 tccgcaagtt ccactatctc cccttcctgc cctcaactga ggacgtttac gactgcaggg    240
tggagcactg gggcttggat gagcctcttc tcaagcactg gg    282

<210> SEQ ID NO 183
<211> LENGTH: 155
<212> TYPE: DNA
<213> ORGANISM: Artificial Sequence
<220> FEATURE:
<223> OTHER INFORMATION: HLA-DRA-PT. 57 01:01:01 Exon 4

<400> SEQUENCE: 183
agtttgatgc tccaagccct ctcccagaga ctacagagaa cgtggtgtgt gccctgggcc    60
tgactgtggg tctggtgggc atcattattg ggaccatctt catcatcaag ggagtgcgca    120
aaagcaatgc agcagaacgc aggggggcctc tgtaa    155

<210> SEQ ID NO 184
<211> LENGTH: 100
<212> TYPE: DNA
<213> ORGANISM: Artificial Sequence

```
<220> FEATURE:
<223> OTHER INFORMATION: HLA-DRB1-PT. 11 11:01:01 Exon 1

<400> SEQUENCE: 184
atggtgtgtc tgaggctccc tggaggctcc tgcatggcag ttctgacagt gacactgatg      60
gtgctgagct ccccactggc tttggctggg gacaccagac                          100

<210> SEQ ID NO 185
<211> LENGTH: 270
<212> TYPE: DNA
<213> ORGANISM: Artificial Sequence
<220> FEATURE:
<223> OTHER INFORMATION: HLA-DRB1-PT. 11 11;01:01 Exon 2

<400> SEQUENCE: 185
cacgtttctt ggagtactct acgtctgagt gtcatttctt caatgggacg gagcgggtgc      60
ggttcctgga cagatacttc tataaccaag aggagtacgt gcgcttcgac agcgacgtgg    120
gggagttccg ggcggtgacg gagctggggc ggcctgatga ggagtactgg aacagccaga    180
aggacttcct ggaagacagg cgggccgcgg tggacaccta ctgcagacac aactacgggg    240
ttggtgagag cttcacagtg cagcggcgag                                    270

<210> SEQ ID NO 186
<211> LENGTH: 282
<212> TYPE: DNA
<213> ORGANISM: Artificial Sequence
<220> FEATURE:
<223> OTHER INFORMATION: HLA-DRB1-PT. 11 11:01:01 Exon 3

<400> SEQUENCE: 186
tccatcctaa ggtgactgtg tatccttcaa agacccagcc cctgcagcac acaacctcc       60 tggtctgttc tgtgagtggt ttctatccag gcagcattga agtcaggtgg ttccggaatg    120
gccaggaaga aagactgggg gtggtgtcca caggcctgat ccacaatgga gactggacct    180
tccagaccct ggtgatgctg gaaacagttc ctcggagtgg agaggtttac acctgccaag    240
tggagcaccc aagcgtgaca agccctctca cagtggaatg ga                      282

<210> SEQ ID NO 187
<211> LENGTH: 111
<212> TYPE: DNA
<213> ORGANISM: Artificial Sequence
<220> FEATURE:
<223> OTHER INFORMATION: HLA-DRB1-PT. 11 11:01:01 Exon 4

<400> SEQUENCE: 187
gagcacggtc tgaatctgca cagagcaaga tgctgagtgg agtcggggc tttgtgctgg       60 gcctgctctt ccttggggcc gggctgttca tctacttcag gaatcagaaa g             111

<210> SEQ ID NO 188
<211> LENGTH: 100
<212> TYPE: DNA
<213> ORGANISM: Artificial Sequence
<220> FEATURE:
<223> OTHER INFORMATION: HLA-DRB1-PT. 50 15:01:01 Exon 1

<400> SEQUENCE: 188
atggtgtgtc tgaagctccc tggaggctcc tgcatgacag cgctgacagt gacactgatg      60
gtgctgagct ccccactggc tttgtctggg gacacccgac                          100

<210> SEQ ID NO 189
```

```
<211> LENGTH: 270
<212> TYPE: DNA
<213> ORGANISM: Artificial Sequence
<220> FEATURE:
<223> OTHER INFORMATION: HLA-DRB1-PT. 50 15:01:01 Exon 2

<400> SEQUENCE: 189
cacgtttcct gtggcagcct aagagggagt gtcatttctt caatgggacg gagcgggtgc      60
ggttcctgga cagatacttc tataaccagg aggagtccgt gcgcttcgac agcgacgtgg     120
gggagttccg gcggtgacg gagctggggc ggcctgacgc tgagtactgg aacagccaga     180
aggacatcct ggagcaggcg cgggccgcgg tggacaccta ctgcagacac aactacgggg     240
ttgtggagag cttcacagtg cagcggcgag                                     270

<210> SEQ ID NO 190
<211> LENGTH: 282
<212> TYPE: DNA
<213> ORGANISM: Artificial Sequence
<220> FEATURE:
<223> OTHER INFORMATION: HLA-DRB1-PT. 50 15:01:01 Exon 3

<400> SEQUENCE: 190
tccaacctaa ggtgactgta tatccttcaa agacccagcc cctgcagcac acaacctcc      60 tggtctgctc tgtgagtggt ttctatccag gcagcattga agtcaggtgg ttcctgaacg     120
gccaggaaga gaaggctggg atggtgtcca caggcctgat ccagaatgga gactggacct     180
tccagaccct ggtgatgctg gaaacagttc ctcgaagtgg agaggtttac acctgccaag     240
tggagcaccc aagcgtgaca agccctctca cagtggaatg ga                        282

<210> SEQ ID NO 191
<211> LENGTH: 111
<212> TYPE: DNA
<213> ORGANISM: Artificial Sequence
<220> FEATURE:
<223> OTHER INFORMATION: HLA-DRB1-PT. 50 15:01:01 Exon 4

<400> SEQUENCE: 191
gagcacggtc tgaatctgca cagagcaaga tgctgagtgg agtcgggggc tttgtgctgg      60
gcctgctctt ccttggggcc gggctgttca tctacttcag gaatcagaaa g               111

<210> SEQ ID NO 192
<211> LENGTH: 100
<212> TYPE: DNA
<213> ORGANISM: Artificial Sequence
<220> FEATURE:
<223> OTHER INFORMATION: HLA-DRB1-PT. 57 04:01:01 Exon 1

<400> SEQUENCE: 192
atggtgtgtc tgaagttccc tggaggctcc tgcatggcag ctctgacagt gacactgatg      60
gtgctgagct ccccactggc tttggctggg acacccgac                            100

<210> SEQ ID NO 193
<211> LENGTH: 270
<212> TYPE: DNA
<213> ORGANISM: Artificial Sequence
<220> FEATURE:
<223> OTHER INFORMATION: HLA-DRB1-PT. 57 04:01:01 Exon 2

<400> SEQUENCE: 193
cacgtttctt ggagcaggtt aaacatgagt gtcatttctt caacgggacg gagcgggtgc      60
ggttcctgga cagatacttc tataccaag aggagtacgt gcgcttcgac agcgacgtgg     120
```

```
gggagtaccg ggcggtgacg gagctggggc ggcctgatgc cgagtactgg aacagccaga    180
aggacctcct ggagcagaag cgggccgcgg tggacaccta ctgcagacac aactacgggg    240
ttggtgagag cttcacagtg cagcggcgag                                     270
```

<210> SEQ ID NO 194
<211> LENGTH: 282
<212> TYPE: DNA
<213> ORGANISM: Artificial Sequence
<220> FEATURE:
<223> OTHER INFORMATION: HLA-DRB1-PT. 57 04:01:01 Exon 3

<400> SEQUENCE: 194

```
tctatcctga ggtgactgtg tatcctgcaa agacccagcc cctgcagcac acaacctcc     60 tggtctgctc tgtgaatggt ttctatccag gcagcattga agtcaggtgg ttccggaacg   120
gccaggaaga gaagactggg gtggtgtcca caggcctgat ccagaatgga gactggacct   180
tccagaccct ggtgatgctg gaaacagttc ctcggagtgg agaggtttac acctgccaag   240
tggagcaccc aagcctgacg agccctctca cagtggaatg ga                      282
```

<210> SEQ ID NO 195
<211> LENGTH: 111
<212> TYPE: DNA
<213> ORGANISM: Artificial Sequence
<220> FEATURE:
<223> OTHER INFORMATION: HLA-DRB1-PT. 57 04:01:01 Exon 4

<400> SEQUENCE: 195

```
gagcacggtc tgaatctgca cagagcaaga tgctgagtgg agtcgggggc ttcgtgctgg    60
gcctgctctt ccttggggcc gggctgttca tctacttcag gaatcagaaa g            111
```

<210> SEQ ID NO 196
<211> LENGTH: 246
<212> TYPE: DNA
<213> ORGANISM: Artificial Sequence
<220> FEATURE:
<223> OTHER INFORMATION: HLA-DQA1-PT. 11 05:05:01 Exon 2

<400> SEQUENCE: 196

```
ctgaccacgt cgcctcttat ggtgtaaact tgtaccagtc ttacggtccc tctggccagt    60
acacccatga atttgatgga gatgagcagt tctacgtgga cctggggagg aaggagactg   120
tctggtgttt gcctgttctc agacaattta gatttgaccc gcaatttgca ctgacaaaca   180
tcgctgtcct aaaacataac ttgaacagtc tgattaaacg ctccaactct accgctgcta   240
ccaatg                                                              246
```

<210> SEQ ID NO 197
<211> LENGTH: 249
<212> TYPE: DNA
<213> ORGANISM: Artificial Sequence
<220> FEATURE:
<223> OTHER INFORMATION: HLA-DQA1-PT. 50 01:02:01 Exon 2

<400> SEQUENCE: 197

```
ctgaccacgt tgcctcttgt ggtgtaaact tgtaccagtt ttacggtccc tctggccagt    60
acacccatga atttgatgga gatgagcagt tctacgtgga cctggagagg aaggagactg   120
cctggcggtg gcctgagttc agcaaatttg gaggttttga cccgcagggt gcactgagaa   180
acatggctgt ggcaaaacac aacttgaaca tcatgattaa acgctacaac tctaccgctg   240
```

```
ctaccaatg                                                              249

<210> SEQ ID NO 198
<211> LENGTH: 249
<212> TYPE: DNA
<213> ORGANISM: Artificial Sequence
<220> FEATURE:
<223> OTHER INFORMATION: HLA-DQA1-PT. 57 03:03:01 Exon 2

<400> SEQUENCE: 198
ctgaccatgt tgcctcttac ggtgtaaact tgtaccagtc ttatggtccc tctgggcagt      60
acagccatga atttgatgga gacgaggagt tctatgtgga cctggagagg aaggagactg     120
tctggcagtt gcctctgttc cgcagattta aagatttga cccgcaattt gcactgacaa      180
acatcgctgt gctaaaacat aacttgaaca tcgtgattaa acgctccaac tctaccgctg     240
ctaccaatg                                                              249

<210> SEQ ID NO 199
<211> LENGTH: 270
<212> TYPE: DNA
<213> ORGANISM: Artificial Sequence
<220> FEATURE:
<223> OTHER INFORMATION: HLA-DQB1-PT. 11 03:01:01 Exon 2

<400> SEQUENCE: 199
aggatttcgt gtaccagttt aaggccatgt gctacttcac caacgggacg gagcgcgtgc      60
gttatgtgac cagatacatc tataaccgag aggagtacgc acgcttcgac agcgacgtgg     120
aggtgtaccg gcggtgacg ccgctgggc cgcctgacgc cgagtactgg aacagccaga       180
aggaagtcct ggagaggacc cgggcggagt tggacacggt gtgcagacac aactaccagt     240
tggagctccg cacgaccttg cagcggcgag                                       270

<210> SEQ ID NO 200
<211> LENGTH: 270
<212> TYPE: DNA
<213> ORGANISM: Artificial Sequence
<220> FEATURE:
<223> OTHER INFORMATION: HLA-DQB1-PT. 50 06:02:01 Exon 2

<400> SEQUENCE: 200
aggatttcgt gttccagttt aagggcatgt gctacttcac caacgggacg gagcgcgtgc      60
gtcttgtgac cagatacatc tataaccgag aggagtacgc gcgcttcgac agcgacgtgg     120
gggtgtaccg cgcggtgacg ccgcagggc ggcctgatgc cgagtactgg aacagccaga      180
aggaagtcct ggaggggacc cgggcggagt tggacacggt gtgcagacac aactacgagg     240
tggcgttccg cgggatcttg cagaggagag                                       270

<210> SEQ ID NO 201
<211> LENGTH: 270
<212> TYPE: DNA
<213> ORGANISM: Artificial Sequence
<220> FEATURE:
<223> OTHER INFORMATION: HLA-DQB1-PT. 57 03:01:01 Exon 2

<400> SEQUENCE: 201
aggatttcgt gtaccagttt aaggccatgt gctacttcac caacgggacg gagcgcgtgc      60
gttatgtgac cagatacatc tataaccgag aggagtacgc acgcttcgac agcgacgtgg     120
aggtgtaccg gcggtgacg ccgctgggc cgcctgacgc cgagtactgg aacagccaga       180
aggaagtcct ggagaggacc cgggcggagt tggacacggt gtgcagacac aactaccagt     240
```
tggagctccg cacgaccttg cagcggcgag        270

<210> SEQ ID NO 202
<211> LENGTH: 82
<212> TYPE: DNA
<213> ORGANISM: Artificial Sequence
<220> FEATURE:
<223> OTHER INFORMATION: HLA-DRA-PT. 11 01:01:01 Exon 1

<400> SEQUENCE: 202
taagccataa gtggagtccc tgtgctagga tttttcatca tagctgtgct gatgagcgct        60
caggaatcat gggctatcaa ag        82

<210> SEQ ID NO 203
<211> LENGTH: 82
<212> TYPE: DNA
<213> ORGANISM: Artificial Sequence
<220> FEATURE:
<223> OTHER INFORMATION: HLA-DRA-PT. 50 01:02:03 Exon 1

<400> SEQUENCE: 203
taagccataa gtggagtccc tgtgctagga tttttcatca tagctgtgct gatgagcgct        60
caggaatcat gggctatcaa ag        82

<210> SEQ ID NO 204
<211> LENGTH: 82
<212> TYPE: DNA
<213> ORGANISM: Artificial Sequence
<220> FEATURE:
<223> OTHER INFORMATION: HLA-DRA-PT. 57 01:01:01 Exon 1

<400> SEQUENCE: 204
taagccataa gtggagtccc tgtgctagga tttttcatca tagctgtgct gatgagcgct        60
caggaatcat gggctatcaa ag        82

<210> SEQ ID NO 205
<211> LENGTH: 100
<212> TYPE: DNA
<213> ORGANISM: Artificial Sequence
<220> FEATURE:
<223> OTHER INFORMATION: HLA-DRB1-PT. 11 11:01:01 Exon 1

<400> SEQUENCE: 205
taagtgtgtc tgaagctccc tggaggctcc tgcatgacag cgctgacagt gacactgatg        60
gtgctgagct ccccactggc tttgtctggg gacacccgac        100

<210> SEQ ID NO 206
<211> LENGTH: 100
<212> TYPE: DNA
<213> ORGANISM: Artificial Sequence
<220> FEATURE:
<223> OTHER INFORMATION: HLA-DRB1-PT. 50 15:01:01 Exon 1

<400> SEQUENCE: 206
taagtgtgtc tgaagctccc tggaggctcc tgcatgacag cgctgacagt gacactgatg        60
gtgctgagct ccccactggc tttgtctggg gacacccgac        100

<210> SEQ ID NO 207
<211> LENGTH: 100
<212> TYPE: DNA
<213> ORGANISM: Artificial Sequence
<220> FEATURE:

<223> OTHER INFORMATION: HLA-DRB1-PT. 57 04:01:01 Exon 1

<400> SEQUENCE: 207

```
taagtgtgtc tgaagttccc tggaggctcc tgcatggcag ctctgacagt gacactgatg      60
gtgctgagct ccccactggc tttggctggg gacacccgac                           100
```

<210> SEQ ID NO 208
<211> LENGTH: 92
<212> TYPE: PRT
<213> ORGANISM: Artificial Sequence
<220> FEATURE:
<223> OTHER INFORMATION: SLA-B2M-208 ENSSSCE00000185155

<400> SEQUENCE: 208

```
Arg Pro Pro Lys Val Gln Val Tyr Ser Arg His Pro Ala Glu Asn Gly
1               5                   10                  15

Lys Pro Asn Tyr Leu Asn Cys Tyr Val Ser Gly Phe His Pro Pro Gln
            20                  25                  30

Ile Glu Ile Asp Leu Leu Lys Asn Gly Glu Lys Met Asn Ala Glu Gln
        35                  40                  45

Ser Asp Leu Ser Phe Ser Lys Asp Trp Ser Phe Tyr Leu Leu Val His
    50                  55                  60

Thr Glu Phe Thr Pro Asn Ala Val Asp Gln Tyr Ser Cys Arg Val Lys
65                  70                  75                  80

His Val Thr Leu Asp Lys Pro Lys Ile Val Lys Trp
                85                  90
```

<210> SEQ ID NO 209
<211> LENGTH: 93
<212> TYPE: PRT
<213> ORGANISM: Artificial Sequence
<220> FEATURE:
<223> OTHER INFORMATION: Exon 2 B2M human ENSE00003751577

<400> SEQUENCE: 209

```
Arg Thr Pro Lys Ile Gln Val Tyr Ser Arg His Pro Ala Glu Asn Gly
1               5                   10                  15

Lys Ser Asn Phe Leu Asn Cys Tyr Val Ser Gly Phe His Pro Ser Asp
            20                  25                  30

Ile Glu Val Asp Leu Leu Lys Asn Gly Glu Arg Ile Glu Lys Val Glu
        35                  40                  45

His Ser Asp Leu Ser Phe Ser Lys Asp Trp Ser Phe Tyr Leu Leu Tyr
    50                  55                  60

Tyr Thr Glu Phe Thr Pro Thr Glu Lys Asp Glu Tyr Ala Cys Arg Val
65                  70                  75                  80

Asn His Val Thr Leu Ser Gln Pro Lys Ile Val Lys Trp
                85                  90
```

<210> SEQ ID NO 210
<211> LENGTH: 93
<212> TYPE: PRT
<213> ORGANISM: Artificial Sequence
<220> FEATURE:
<223> OTHER INFORMATION: HLA-B2M-207 ENSE00003659794

<400> SEQUENCE: 210

```
Arg Thr Pro Lys Ile Gln Val Tyr Ser Arg His Pro Ala Glu Asn Gly
1               5                   10                  15

Lys Ser Asn Phe Leu Asn Cys Tyr Val Ser Gly Phe His Pro Ser Asp
            20                  25                  30
```

```
Ile Glu Val Asp Leu Leu Lys Asn Gly Glu Arg Ile Glu Lys Val Glu
        35                  40                  45

His Ser Asp Leu Ser Phe Ser Lys Asp Trp Ser Phe Tyr Leu Leu Tyr
    50                  55                  60

Tyr Thr Glu Phe Thr Pro Thr Glu Lys Asp Glu Tyr Ala Cys Arg Val
65                  70                  75                  80

Asn His Val Thr Leu Ser Gln Pro Lys Ile Val Lys Trp
                85                  90

<210> SEQ ID NO 211
<211> LENGTH: 93
<212> TYPE: PRT
<213> ORGANISM: Artificial Sequence
<220> FEATURE:
<223> OTHER INFORMATION: HLA B2M-214 ENSE00003659794

<400> SEQUENCE: 211

Arg Thr Pro Lys Ile Gln Val Tyr Ser Arg His Pro Ala Glu Asn Gly
1               5                   10                  15

Lys Ser Asn Phe Leu Asn Cys Tyr Val Ser Gly Phe His Pro Ser Asp
            20                  25                  30

Ile Glu Val Asp Leu Leu Lys Asn Gly Glu Arg Ile Glu Lys Val Glu
        35                  40                  45

His Ser Asp Leu Ser Phe Ser Lys Asp Trp Ser Phe Tyr Leu Leu Tyr
    50                  55                  60

Tyr Thr Glu Phe Thr Pro Thr Glu Lys Asp Glu Tyr Ala Cys Arg Val
65                  70                  75                  80

Asn His Val Thr Leu Ser Gln Pro Lys Ile Val Lys Trp
                85                  90
```